(12) United States Patent
Hung et al.

(10) Patent No.: US 8,338,447 B2
(45) Date of Patent: Dec. 25, 2012

(54) PYRIDO[3,4-B]INDOLES AND METHODS OF USE

(75) Inventors: David T. Hung, Redwood City, CA (US); Andrew Asher Protter, Palo Alto, CA (US); Sarvajit Chakravarty, Mountain View, CA (US); Rajendra P. Jain, Maharashtra (IN); Sundeep Dugar, San Jose, CA (US)

(73) Assignee: Medivation Technologies, Inc., San Francisco, CA (US)

( * ) Notice: Subject to any disclaimer, the term of this patent is extended or adjusted under 35 U.S.C. 154(b) by 657 days.

(21) Appl. No.: 12/410,407

(22) Filed: Mar. 24, 2009

(65) Prior Publication Data

US 2009/0270412 A1    Oct. 29, 2009

Related U.S. Application Data

(60) Provisional application No. 61/039,056, filed on Mar. 24, 2008, provisional application No. 61/145,079, filed on Jan. 15, 2009.

(51) Int. Cl.
- *C07D 471/14* (2006.01)
- *C07D 471/22* (2006.01)
- *A61K 31/437* (2006.01)
- *A61K 31/438* (2006.01)
- *A61P 25/28* (2006.01)

(52) U.S. Cl. .......................... 514/292; 546/85
(58) Field of Classification Search ............... 546/85; 514/292

See application file for complete search history.

(56) References Cited

U.S. PATENT DOCUMENTS

| | | | |
|---|---|---|---|
| 2,642,438 | A | 6/1953 | Duschinsky |
| 4,754,038 | A | 6/1988 | Abou-Gharbia |
| 6,187,785 | B1 | 2/2001 | Zefirov et al. |
| 7,071,206 | B2 | 7/2006 | Zefirov et al. |
| 2009/0233903 | A1 | 9/2009 | Rodgers et al. |
| 2009/0239854 | A1 | 9/2009 | Hung et al. |
| 2009/0247561 | A1 | 10/2009 | Zemolka et al. |
| 2010/0022580 | A1 | 1/2010 | Hung et al. |
| 2010/0080786 | A1 | 4/2010 | Berger et al. |
| 2010/0087489 | A1 | 4/2010 | Berger et al. |
| 2010/0099667 | A1 | 4/2010 | Hung et al. |
| 2010/0152163 | A1 | 6/2010 | Hung et al. |
| 2010/0216814 | A1 | 8/2010 | Hung et al. |
| 2011/0237582 | A1 | 9/2011 | Jain et al. |
| 2011/0245272 | A1 | 10/2011 | Jain et al. |
| 2012/0136008 | A1 | 5/2012 | Jain et al. |
| 2012/0172377 | A1 | 7/2012 | Jain et al. |

FOREIGN PATENT DOCUMENTS

| | | |
|---|---|---|
| GB | 721 171 | 12/1954 |
| WO | WO-2005/031301 A2 | 4/2005 |
| WO | WO-2005/031301 A3 | 4/2005 |
| WO | WO-2005/055951 A2 | 6/2005 |
| WO | WO-2005/055951 A3 | 6/2005 |
| WO | WO-2007/007072 A1 | 1/2007 |
| WO | WO-2007/041697 A2 | 4/2007 |
| WO | WO-2007/041697 A3 | 4/2007 |
| WO | WO-2007/087425 A1 | 8/2007 |
| WO | WO-2008/036400 A2 | 3/2008 |
| WO | WO-2008-036400 A3 | 3/2008 |
| WO | WO-2008/036410 A2 | 3/2008 |
| WO | WO-2008/036410 A3 | 3/2008 |
| WO | WO-2008/051599 A2 | 5/2008 |
| WO | WO-2008/051599 A3 | 5/2008 |
| WO | WO-2008/069963 A1 | 6/2008 |
| WO | WO-2008/073231 A1 | 6/2008 |
| WO | WO-2008/147551 A1 | 12/2008 |
| WO | WO-2009/005771 A1 | 1/2009 |
| WO | WO-2009/017836 A1 | 2/2009 |
| WO | WO-2009/039420 A1 | 3/2009 |
| WO | WO-2009/039420 A9 | 3/2009 |
| WO | WO-2009/120717 A2 | 10/2009 |
| WO | WO-2009/120717 A3 | 10/2009 |

OTHER PUBLICATIONS

Abou-Gharbia, M. et al. (1987). "Psychotropic Agents: Synthesis and Antipsychotic Activity of Substituted β-Carbolines," *J. Med. Chem.* 30(6):1100-1105.

Audia, J.E. et al. (Jan. 1, 1996). "Potent, Selective Tetrahydro-β-Carboline Antagonists of the Serotonin 2B ($5HT_{2B}$) Contractile Receptor in the Rat Stomach Fundus," *Journal of Medicinal Chemistry* 39:2773-2780.

(Continued)

*Primary Examiner* — Susanna Moore
(74) *Attorney, Agent, or Firm* — Morrison & Foerster LLP

(57) ABSTRACT

This disclosure relates to new heterocyclic compounds that may be used to modulate a histamine receptor in an individual. Compounds of formula (I)

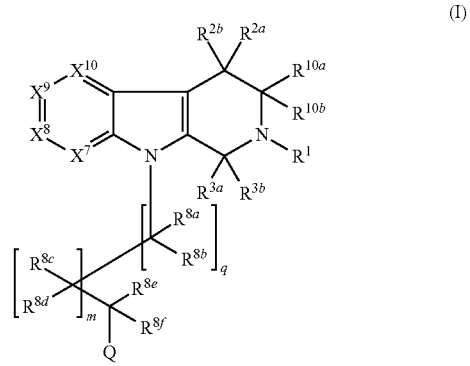

are described, as are pharmaceutical compositions comprising the compounds and methods of using the compounds in a variety of therapeutic applications, including the treatment of a cognitive disorder, psychotic disorder, neurotransmitter-mediated disorder and/or a neuronal disorder.

19 Claims, No Drawings

OTHER PUBLICATIONS

Bartolini, L. et al. (1996). "Aniracetam Restores Object Recognition Impaired by Age, Scopolamine, and Nucleus Basalis Lesions," *Pharmacology Biochemistry Behavior* 53(2):277-283.

Boess, F.G. et al. (1997). "Analysis of the Ligand Binding Site of the 5-HT$_3$ Receptor Using Site Directed Mutagenesis: Importance of Glutamate 106," *Neuropharmacology* 36(4/5):637-647.

Boksa, J. et al. (1995). "Structure-Activity Relationship Studies of CNS Agents, Part 20: 9-{ω[-(m-Chlorophenyll)-4-Piperazinyl]alkyl]-1,2,3,4-tetra-hydro-β 5-HT$_{1A\ and\ h-HT2A}$ Receptor Ligands," *Pharmazie* 50:220-221.

Bonhaus, D.W. et al. (1995). "The Pharmacology and Distribution of Human 5-Hydroxytryptamine$_{2B}$ (5-HT$_{2B}$) Receptor Gene Products: Comparison with 5-HT$_{2A}$ and 5-HT$_{2C}$ Receptors," *British Journal of Pharmacology* 115:622-628.

Brown, C.M. et al. (1990). "α$_2$-Adrenoceptor Subtypes and Imidazoline-Like Binding Sites in the Rat Brain," *Br. J. Pharmacol.* 99:803-809.

Bubber, P. et al. (May 2005, e-pub. Apr. 25, 2005). "Mitochondrial Abnormalities in Alzheimer Brain: Mechanistic Implications," *Ann Neurol.* 57(5):695-703.

Chemcats Database Accession No. 2048718668, published Feb. 9, 2009, 8 pages.

Chérn, M-S. et al. (2004, e-pub. Oct. 21, 2004). "Traceless Solid-Phase Synthesis of Carbolinones," *Journal of Combinatorial Chemistry* 6:855-858.

De Backer, M.D. et al. (Dec. 30, 1993). "Genomic Cloning, Heterologous Expression and Pharmacological Characterization of a Human Histamine H1 Receptor," *Biochemical and Biophysical Research Communications* 197(3):1601-1608.

Ennaceur, A. et al. (1988). "A New One-Trial Test for Neurobiological Studies of Memory in Rats. 1: Behavioral Data," *Behav. Brain. Res.* 31:47-59.

García-Sáinz, J.A. et al. (Jul. 31, 1992). "Species Heterogeneity of Hepatic α$_1$-Adrenoceptors: α$_{1A}$-, α$_{1B}$- and α$_{1C}$-Subtypes," *Biochemical and Biophysical Research Communications* 186(2):760-767.

Gilliland, S.L. et al. (2000, e-pub. Feb. 29, 2000). "Characterization of Dopaminergic Compounds at hD$_{2short}$, hD$_{4.2}$ and hD$_{4.7}$ Receptors in Agonist-Stimulated [$^{35}$S]GTPyS Binding Assays," *Naunyn-Schmiedeberg's Archives of Pharmacology* 361:498-504.

Grandy, D.K. et al. (Dec. 1989). "Cloning of the cDNA and Gene for a Human D$_2$ Dopamine Receptor," *Proc. Natl. Acad. Sci. USA* 86:9762-9766.

Grossman, C.J. et al. (1993). "Development of a Radioligand Binding Assay for 5-HT$_4$ Receptors in Guinea-Pig and Rat Brain," *Br. J. Pharmacol.* 109:618-624.

Hardy, J. (1996). "New Insights Into the Genetics of Alzheimer's Disease," *Annals of Medicine* 28:255-258.

Hardy, J. (1997). "Amyloid, the Presenilins and Alzheimer's Disease," *Trends Neurosci.* 20(4):154-159.

Hayes, G. et al. (1992). "Structural Subtypes of the Dopamine D2 Receptor are Functionally Distinct: Expression of the Cloned D2$_A$ and D2$_B$ Subtypes in a Heterologous Cell Line," *Mol. Endocrinol.* 6(6):920-926.

Hoyer, D. et al. (1985). "Characterization of the 5-HT$_{1B}$ Recognition Site in Rat Brain: Binding Studies with (−)[$^{125}$I] Iodocyanopindolol," *European Journal of Pharmacology* 118:1-12.

International Search Report mailed on Oct. 21, 2009, for PCT Application No. PCT/US2009/038138, filed on Mar. 24, 2009, 7 pages.

Jentsch, J.D. et al. (Aug. 15, 1997). "Enduring Cognitive Deficits and Cortical Dopamine Dysfunction in Monkeys After Long-Term Administration of Phencyclidine," *Science* 277:953-955.

Jerman, J.C. et al. (2001). "Pharmacological Characterisation of Human 5-HT$_2$ Receptor Subtypes," *European Journal of Pharmacology* 414:23-30.

Jiang, W. et al. (2003, e-pub. Dec. 12, 2002). "Potassium Superoxide as an Alternative Reagent for Winterfeldt Oxidation of β-Carbolines," *Organic Letters* 5(1):43-46, erratum (2003, e-pub. Mar. 19, 2003). *Organic Letters* 5(9):1595.

Kenny, B.A. et al. (1995). "Characterization of an α$_{1D}$-Adrenoceptor Mediating the Contractile Response of Rat Aorta to Noradrenaline," *British Journal of Pharmacology* 115:981-986.

Kikuchi, C. et al. (2002, e-pub. May 1, 2002). "2a[4-Tetrahydropyridoindo1-2-yl)butyl]tetrahydrobenzindole Derivatives: New Selective Antagonists of the 5-Hydroxytryptamine$_7$ Receptor," *J. Med. Chem.* 45(11):2197-2206.

Kindermann, S.S. et al. (2005, e-pub. May 26, 2005). "Catalytic N-Sulfonyliminium Ion-Mediated Cyclizations to α-Vinyl-Substituted Isoquinolines and β-Carbolines and Applications in Metathesis," *J. Org. Chem.* 70(14):5519-5527.

Kohen, R. et al. (1996). "Cloning, Characterization and Chromosomal Localization of a Human 5-HT$_6$ Serotonin Receptor," *J. Neurochem.* 66(1):47-56.

Martin, G.R. (1994). "Receptors for 5-Hydroxytryptamine: Current Perspectives on Classification and Nomenclature," *Neuropharmacology* 33(3/4):261-273.

May, J.A. et al. (2003). "Evaluation of the Ocular Hypotensive Response of Serotonin 5-HT$_{1A}$ and 5-HT$_2$ Receptor Ligands in Conscious Ocular Hypertenisve Cynomolgus Monkeys," *The Journal of Pharmacology and Experimental Therapeutics* 306(1):301-309.

Michel, A.D. et al. (1989). "Identification of a Single α$_1$-Adrenoceptor Corresponding to the α$_{1A}$-Subtype in Rat Submaxillary Gland," *Br. J. Pharmacol.* 98:883-889.

Miller, K et al. (1992). "Membrane-Bound and Solubilized Brain 5HT$_3$ Receptors: Improved Radioligand Binding Assays Using Bovine Area Postrema or Rat Cortex and the Radioligands $^3$H-GR65630, $^3$H-BRL43694, and $^3$H-LY278584," *Synapse* 11:58-66.

Miller, T.R. et al. (1999). "Analysis of Apparent Noncompetitive Responses to Competitive H$_1$-Histamine Receptor Antagonists in Fluorescent Imaging Plate Reader-Based Calcium Assays," *Journal of Biomolecular Screening* 4(5):249-258.

Monsma, F.J. Jr. et al. (1993). "Cloning and Expression of a Novel Serotonin Receptor with High Affinity for Tricyclic Psychotropic Drugs," *Molecular Pharmacology* 43:320-327.

Pazos, A. et al. (1985). "Mesulergine, A Selective Serotonin-2 Ligand in the Rat Cortex, Does Not Label these Receptors in Porcine and Human Cortex: Evidence for Species Differences in Brain Serotonin-2 Receptors," *European Journal of Pharmacology* 106:531-538.

Piercey, M.F. et al. (1988). "Dramatic Limbic and Cortical Effects Mediated by High Affinity PCP Receptors," *Life Sciences* 43(4):379-385.

Prichep, L.S. et al. (1994). "Quantitative EEG Correlates of Cognitive Deterioration in the Elderly," *Neurobiology of Aging* 15(1):85-90.

Reddy, P.H. et al. (2005, e-pub. Apr. 19, 2005). "Are Mitochondria Critical in the Pathogenesis of Alzheimer's Disease?" *Brain Res Rev.* 49(3):618-632.

Rees, S. et al. (Oct. 11, 1994). "Cloning and Characterisation of the Human 5-HT$_{5A}$ Serotonin Receptor," *FEBS Letters* 355:242-246.

Reisberg, B. et al. (Sep. 1982). "The Global Deterioration Scale for Assessment of Primary Degenerative Dementia," *Am. J. Psychiatry* 139(9):1136-1139.

Roth, B.L. et al. (1994). "Binding of Typical and Atypical Antipsychotic Agents to 5-Hydroxytryptamine-6 and 5-Hydroxytryptamine-7 Receptors," *J. Pharmacol. Exp. Ther.* 268(3):1403-1410.

Ruat, M. et al. (Mar. 1990). "Reversible and Irreversible Labeling and Autoradiographic Localization of the Cerebral Histamine H$_2$ Receptor Using [$^{125}$I]Iodinated Probes," *Proc. Natl. Acad. Sci. USA* 87(5):1658-1662.

Saucier, C. et al. (1997). "Identification of an Endogenous 5-Hydroxytryptamine$_{2A}$ Receptor in NIH-3T3 Cells: Agonist-Induced Down-Regulation Involves Decreases in Receptor RNA and Number," *Journal of Neurochemistry* 68(5):1998-2011.

Scali, C. et al. (1994). "Nerve Growth Factor Increases Extracellular Acetylcholine Levels in the Parietal Cortex and Hippocampus of Aged Rats and Restores Object Recognition," *Neuroscience Letters* 170:117-120.

Senogles, S.E. et al. (Mar. 15, 1990). "Specificity of Receptor-G Protein Interactions. Discrimination of $G_i$ Subtypes by the $D_2$ Dopamine Receptor in a Reconstituted System," *Journal of Biological Chemistry* 265(8):4507-4514.

Shen, Y. et al. (Aug. 25, 1993). "Molecular Cloning and Expression of a 5-Hydroxytryptamine$_7$ Serotonin Receptor Subtype," *The Journal of Biological Chemistry* 268(24):18200-18204.

Swerdlow, R.H. et al. (2002). "Mitochondria in Alzheimer's Disease," *International Review of Neurobiology* 53:341-385.

Tanzi, R.E. et al. (1996). "The Gene Defects Responsible for Familial Alzheimer's Disease," *Neurobiology of Disease* 3:159-168.

Uhlén, S. et al. (1994). "The Novel *Alpha*-2 Adrenergic RadioLigand [$^3$H]-MK912 is *Alpha*-2C Selective Among Human *Alpha*-2A, *Alpha*-2B and *Alpha*-2C Adrenoceptors," *Journal of Pharmacology and Experimental Therapeutics* 271(3):1558-1565.

Uhlén, S. et al. (1998). "[$^3$H]RS79948-197 Binding to Human, Rat, Guinea Pig and Pig $\alpha_{2A}$-, $\alpha_{2B}$- and $\alpha_{2C}$-Adrenoceptors. Comparison with MK912, RX821002, Rauwolscine and Yohimbine," *European Journal of Pharmacology* 343:93-101.

Wang, X. et al. (2007, e-pub. Sep. 21, 2007). "Insights Into Amyloid-β-Induced Mitochondrial Dysfunction in Alzheimer Disease," *Free Radical Biology & Medicine* 43:1569-1573.

Wolf, W.A. et al. (1997). "The Serotonin 5-HT$_{2C}$ Receptor is a Prominent Serotonin Receptor in Basal Ganglia: Evidence from Functional Studies on Serotonin-Mediated Phosphoinositide Hydrolysis," *Journal of Neurochemistry* 69(4):1449-1458.

Written Opinion of the International Searching Authority mailed on Oct. 21, 2009, for PCT Application No. PCT/US2009/038138, filed on Mar. 24, 2009, 12 pages.

Yanai, K. et al. (1994). "Binding Characteristics of a Histamine H$_3$-Receptor Antagonist, [$^3$H]S-Methylthioperamide: Comparison with [$^3$H](R)α-Methylhistamine Binding to Rat Tissues," *Jpn. J. Pharmacol.* 65:107-112.

Zhu, Y. et al. (2001). "Cloning, Expression, and Pharmacological Characterization of a Novel Human Histamine Receptor," *Molecular Pharmacology* 59(3):434-441.

Chilean Search Report mailed on Sep. 13, 2011, for Chilean Patent Application No. 724-09, filed on Mar. 24, 2009, 2 pages.

U.S. Appl. No. 13/498,097, internationally filed Sep. 23, 2010, by Jain et al. (Copy not attached).

U.S. Appl. No. 13/498,099, internationally filed Sep. 23, 2010, by Jain et al. (Copy not attached).

U.S. Appl. No. 13/540,472, filed Jul. 2, 2012, by Jain et al. (Copy not attached).

U.S. Appl. No. 13/579,900, internationally filed Feb. 18, 2011, by Chakravarty et al. (Copy not attached).

U.S. Appl. No. 13/579,904, internationally filed Feb. 18, 2011, by Chakravarty et al. (Copy not attached).

U.S. Appl. No. 13/579,908, internationally filed Feb. 18, 2011, by Chakravarty et al. (Copy not attached).

U.S. Appl. No. 13/579,911, internationally filed Feb. 18, 2011, by Chakravarty et al. (Copy not attached).

U.S. Appl. No. 13/579,912, internationally filed Feb. 18, 2011, by Chakravarty et al.

PYRIDO[3,4-B]INDOLES AND METHODS OF USE

CROSS-REFERENCE TO RELATED APPLICATIONS

This application claims priority to U.S. Provisional Patent Application No. 61/039,056 filed Mar. 24, 2008 and U.S. Provisional Patent Application No. 61/145,079 filed Jan. 15, 2009, the disclosures of each of which are incorporated herein by reference in their entireties.

STATEMENT OF RIGHTS TO INVENTIONS MADE UNDER FEDERALLY SPONSORED RESEARCH

Not applicable.

BACKGROUND OF THE INVENTION

Neurotransmitters such as histamine, serotonin, dopamine and norepinephrine mediate a large number of processes in the central nervous system (CNS) as well as outside the CNS. Abnormal neurotransmitter levels are associated with a wide variety of diseases and conditions including, but not limited to, Alzheimer's disease, Parkinson's Disease, autism, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases. Compounds that modulate these neurotransmitters may be useful therapeutics.

Histamine receptors belong to the superfamily of G protein-coupled seven transmembrane proteins. G protein-coupled receptors constitute one of the major signal transduction systems in eukaryotic cells. Coding sequences for these receptors, in those regions believed to contribute to the agonist-antagonist binding site, are strongly conserved across mammalian species. Histamine receptors are found in most peripheral tissue and within the central nervous system. Compounds capable of modulating a histamine receptor may find use in therapy, e.g., as antihistamines.

Dimebon is a known anti-histamine drug that has also been characterized as a neuroprotective agent useful to treat, inter alia, neurodegenerative diseases. Dimebon has been shown to inhibit the death of brain cells (neurons) in preclinical models of Alzheimer's disease and Huntington's disease, making it a novel potential treatment for these and other neurodegenerative diseases. In addition, dimebon has been shown to improve the mitochondrial function of cells in the setting of cellular stress with very high potency. For example, dimebon treatment improved mitochondrial function and increased the number of surviving cells after treatment with the cell toxin ionomycin in a dose dependent fashion. Dimebon has also been shown to promote neurite outgrowth and neurogenesis, processes important in the formation of new and/or enhanced neuronal cell connections, and evidence of dimebon's potential for use in additional diseases or conditions. See, e.g., U.S. Pat. Nos. 6,187,785 and 7,071,206 and PCT Patent Application Nos. PCT/US2004/041081, PCT/US2007/020483, PCT/US2006/039077, PCT/US2008/077090, PCT/US2007/020516, PCT/US2007/022645, PCT/US2007/002117, PCT/US2008/006667, PCT/US2007/024626, PCT/US2008/009357, PCT/US2007/024623 and PCT/US2008/008121. All references disclosed herein and throughout, such as publications, patents, patent applications and published patent applications, are incorporated herein by reference in their entireties.

Although dimebon holds great promise as a drug for the treatment of neurodegenerative diseases and/or diseases in which neurite outgrowth and/or neurogenesis may be implicated in therapy, there remains a need for new and alternative therapies for the treatment of such diseases or conditions. In addition, there remains a need for new and alternative antihistamine drugs, preferably ones in which side-effects such as drowsiness are reduced or eliminated. Compounds that exhibit enhanced and/or more desirable properties than dimebon (e.g., superior safety and efficacy) may find particular use in the treatment of at least those indications for which dimebon is believed to be advantageous. Further, compounds that exhibit a different therapeutic profile than dimebon as determined, e.g. by in vitro and/or in vivo assays, may find use in additional diseases and conditions.

BRIEF SUMMARY OF THE INVENTION

Compounds detailed herein are described as histamine receptor modulators. Compositions comprising the compounds are provided, as are kits comprising the compound as well as methods of using and making the compounds. The compounds may find use in treating neurodegenerative diseases. Compounds of the invention may also find use in treating diseases and/or conditions in which modulation of aminergic G protein-coupled receptors and/or neurite outgrowth may be implicated in therapy. Compounds disclosed herein may find use the methods disclosed herein, including use in treating, preventing, delaying the onset and/or delaying the development of a cognitive disorder, psychotic disorder, neurotransmitter-mediated disorder and/or a neuronal disorder in an individual in need thereof, such as humans.

Compounds of the formula (F) are detailed herein:

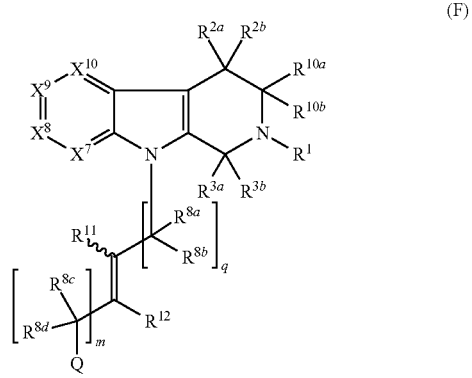

wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^1$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;

each $R^{3a}$ and $R^{3b}$ is independently H, substituted or unsubstituted $C_1$-$C_8$ alkyl, halo, cyano, nitro, hydroxyl, alkoxy, amino, substituted amino, cycloalkyl, phenyl, acylamino or acyloxy, or $R^{3a}$ and $R^{3b}$ are taken together with the carbon to which they are attached to form a cycloalkyl moiety or a carbonyl moiety;

each $X^7$, $X^8$, $X^9$ and $X^{10}$ is independently N or $CR^4$;

m and q are independently 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ and $R^{8d}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^{8(a-d)}$ to form a cycloalkyl moiety or a carbonyl moiety, or is taken together with a geminal $R^{8(a-d)}$ to form a methylene or a substituted methylene;

each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety;

$R^{11}$ and $R^{12}$ are independently H or $C_1$-$C_8$ alkyl, $C_1$-$C_8$ perhaloalkyl, carboxy, carbonylalkoxy, or are taken together with the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or are taken together to form a bond, thereby providing an acetylenyl moiety;

∿∿∿ indicates the presence of either an E or Z double bond configuration when $R^{11}$ and $R^{12}$ are independently H, $C_1$-$C_8$ alkyl, $C_1$-$C_8$ perhaloalkyl, carboxy or carbonylalkoxy; and Q is a substituted or unsubstituted aryl, substituted or unsubstituted heteroaryl, substituted or unsubstituted cycloalkyl, substituted or unsubstituted cycloalkenyl, substituted or a unsubstituted heterocyclyl, unsubstituted amino, substituted amino, alkoxy, aminoacyl, acyloxy, carbonylalkoxy, aminocarbonylalkoxy, acylamino, carboxy, cyano or alkynyl;

or a salt thereof. In one aspect, the salt is a pharmaceutically acceptable salt.

Variations of formula (F) are also described, such as where $R^1$ is unsubstituted $C_1$-$C_8$ alkyl and/or Q is phenyl or substituted phenyl and/or wherein any one or more of (i)-(xi) apply, provided that provisions (iv) and (v) are not combined, provisions (ii) and (xi) are not combined and provisions (iii) and (xi) are not combined: (i) q and m are both 0; (ii) $R^{11}$ is H; (iii) $R^{12}$ is an unsubstituted $C_1$-$C_8$alkyl; (iv) one of $R^{3a}$ and $R^{3b}$ is methyl, ethyl or phenyl and the other is H; (v) $R^{3a}$ and $R^{3b}$ are both H; (vi) $R^1$ is an unsubstituted $C_1$-$C_8$ alkyl; (vii) $X^9$ is $CR^4$ where $R^4$ is unsubstituted $C_1$-$C_8$ alkyl or halo; (viii) $X^7$, $X^8$ and $X^{10}$ are each $CR^4$ where $R^4$ is H; (ix) $R^{2a}$ and $R^{2b}$ are both H; (x) $R^{10a}$ and $R^{10b}$ are both H; and (xi) $R^{11}$ and $R^{12}$ are taken together to form a bond.

A compound of the formula (E-2) is also described:

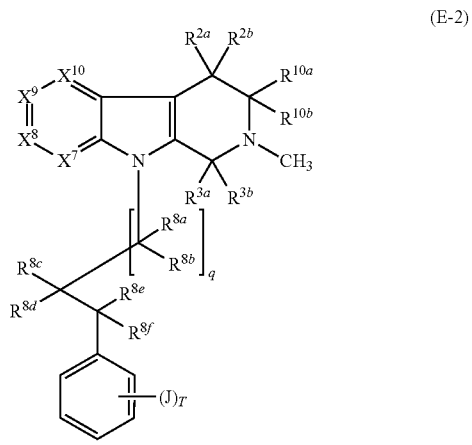

(E-2)

wherein:

each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;

each $R^{3a}$ and $R^{3b}$ is independently H, substituted or unsubstituted $C_1$-$C_8$ alkyl, halo, cyano, nitro, hydroxyl, alkoxy, amino, substituted amino, cycloalkyl, acylamino or acyloxy or $R^{3a}$ and $R^{3b}$ are taken together with the carbon to which they are attached to form a cycloalkyl moiety or a carbonyl moiety;

each $X^7$, $X^8$, $X^9$ and $X^{10}$ is independently N or $CR^4$;

q is independently 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^{8(a-f)}$ to form a cycloalkyl moiety or a carbonyl moiety, is taken together with a geminal $R^{8(a-f)}$ to form a methylene or a substituted methylene, is taken together with a vicinal $R^{8(a-f)}$ and the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or is taken together with a vicinal $R^{8(a-f)}$ to form a bond, provided that when an $R^{8(a-f)}$ is taken together with a vicinal $R^8$ to form a bond, the geminal $R^{8(a-f)}$ is other than hydroxyl;

each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety;

J is halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl and aminocarbonylamino moiety; and T is an integer from 0 to 5, or a salt thereof. In one aspect, the salt is a pharmaceutically acceptable salt.

Variations of formula (E-2) are also provided, such as when any one or more of (i)-(viii) apply, provided that only one of (ii), (iii) and (iv) applies: (i) q is 0; (ii) $R^{8c}$ and $R^{8d}$ are both H and $R^{8e}$ and $R^{8f}$ are independently H, hydroxyl or methyl; (iii) $R^{8c}$ is taken together with $R^{8e}$ to form a bond and $R^{8d}$ is taken together with $R^{8f}$ to form a bond; (iv) one of $R^{8c}$ and $R^{8d}$ is taken together with one of $R^{8a}$ and $R^{8f}$ to form a bond and the $R^{8c}$ or $R^{8d}$ that is not taken to form a bond is H and the $R^{8e}$ or $R^{8f}$ that is not taken to form a bond is H or methyl; (v) $X^9$ is $CR^4$ where $R^4$ is halo or alkyl; (vi) $X^7$, $X^8$ and $X^{10}$ are each $CR^4$ where $R^4$ is H; (vii) $R^{2a}$ and $R^{2b}$ are both H; and (viii) $R^{10a}$ and $R^{10b}$ are both H.

Compound of the formula (E-3) as also embraced:

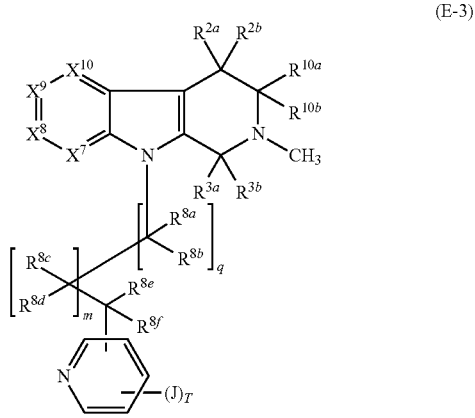

(E-3)

wherein:

each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;

each $R^{3a}$ and $R^{3b}$ is independently H, substituted or unsubstituted $C_1$-$C_8$ alkyl, halo, cyano, nitro, hydroxyl, alkoxy, amino, substituted amino, cycloalkyl, acylamino or acyloxy or $R^{3a}$ and $R^{3b}$ are taken together with the carbon to which they are attached to form a cycloalkyl moiety or a carbonyl moiety;

each $X^7$, $X^8$, $X^9$ and $X^{10}$ is independently N or $CR^4$;

m and q are independently 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^{8(a-f)}$ to form a cycloalkyl moiety or a carbonyl moiety, is taken together with a geminal $R^{8(a-f)}$ to form a methylene or a substituted methylene, is taken together with a vicinal $R^{8(a-f)}$ and the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or is taken together with a vicinal $R^{8(a-f)}$ to form a bond, provided that when an $R^{8(a-f)}$ is taken together with a vicinal $R^8$ to form a bond, the geminal $R^{8(a-f)}$ is other than hydroxyl;

each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety J is halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl and aminocarbonylamino moiety; and T is an integer from 0 to 4, or a salt thereof. In one aspect, the salt is a pharmaceutically acceptable salt.

Variations of compounds of formula (E-3) are also provided, such as when any one or more of (i)-(vi) apply, provided that provisions (i) and (ii) are not combined: (i) q is 0; (ii) m and q are each 1 and $R^{8c}$, $R^{8d}$, $R^{8e}$ and $R^{8f}$ are each H; (iii) $X^9$ is $CR^4$ where $R^4$ is halo or substituted or unsubstituted $C_1$-$C_8$ alkyl; (iv) $X^7$, $X^8$ and $X^{10}$ are each $CR^4$ where $R^4$ is H; (v) $R^{2a}$ and $R^{2b}$ are both H; and (vi) $R^{10a}$ and $R^{10b}$ are both H.

Also described are compounds of the formula (E-4):

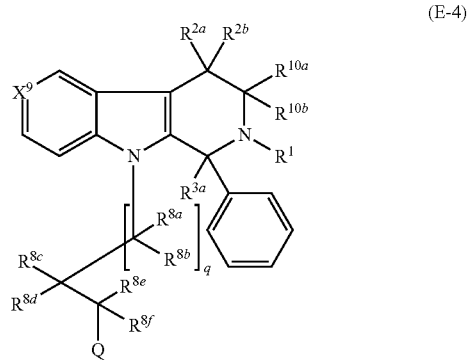

(E-4)

wherein:

$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;

each $R^{3a}$ is H, substituted or unsubstituted $C_1$-$C_8$ alkyl, halo, cyano, nitro, hydroxyl, alkoxy, amino, substituted amino, cycloalkyl, acylamino or acyloxy;

$X^9$ is N or $CR^4$;

q is 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^{8(a-f)}$ to form a cycloalkyl moiety or a carbonyl moiety, is taken together with a geminal $R^{8(a-f)}$ to form a methylene or a substituted methylene, is taken together with a vicinal $R^{8(a-f)}$ and the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or is taken together with a vicinal $R^{8(a-f)}$ to form a bond, provided that when an $R^{8(a-f)}$ is taken together with a vicinal $R^8$ to form a bond, the geminal $R^{8(a-f)}$ is other than hydroxyl;

each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety; and Q is a substituted or unsubstituted aryl, substituted or unsubstituted heteroaryl, substituted or unsubstituted cycloalkyl, substituted or unsubstituted cycloalkenyl, substituted or a unsubstituted heterocyclyl, unsubstituted amino, substituted amino, alkoxy, aminoacyl, acyloxy, carbonylalkoxy, aminocarbonylalkoxy, acylamino, carboxy, cyano or alkynyl, or a salt thereof. In one aspect, the salt is a pharmaceutically acceptable salt.

Compounds of the formula (E-5) are also provided:

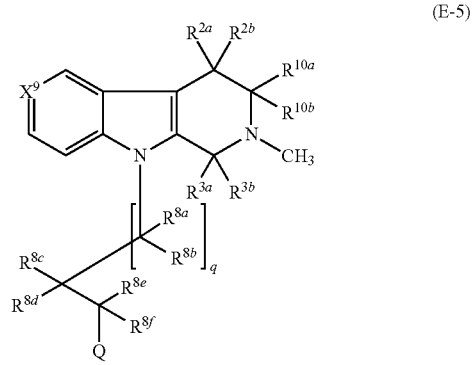

(E-5)

wherein:

each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;

$R^{3a}$ and $R^{3b}$ are independently H, substituted or unsubstituted $C_1$-$C_8$ alkyl, halo, cyano, nitro, hydroxyl, alkoxy, amino, substituted amino, cycloalkyl, acylamino, phenyl or acyloxy or $R^{3a}$ and $R^{3b}$ are taken together with the carbon to which they are attached to form a cycloalkyl moiety;

$X^9$ is $CR^4$ where $R^4$ is a substituted or unsubstituted $C_1$-$C_8$ alkyl or halo;

q is 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^{8(a-f)}$ to form a cycloalkyl moiety or a carbonyl moiety, is taken together with a geminal $R^{8(a-f)}$ to form a methylene or a substituted methylene, is taken together with a vicinal $R^{8(a-f)}$ and the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or is taken together with a vicinal $R^{8(a-f)}$ to form a bond, provided that when an $R^{8(a-f)}$ is taken together with a vicinal $R^8$ to form a bond, the geminal $R^{8(a-f)}$ is other than hydroxyl;

each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety; and Q is a substituted or unsubstituted aryl, substituted or unsubstituted heteroaryl, substituted or unsubstituted cycloalkyl, substituted or unsubstituted cycloalkenyl, substituted or a unsubstituted heterocyclyl, unsubstituted amino, substituted amino, alkoxy, aminoacyl, acyloxy, carbonylalkoxy, aminocarbonylalkoxy, acylamino, carboxy, cyano or alkynyl;

or a salt thereof. In one aspect, the salt is a pharmaceutically acceptable salt.

Variations of compounds of formula (E-5) are also detailed herein, such as when any one or more of (i)-(vi) apply, provided that provisions (iv) and (v) are not combined: (i) $X^9$ is $CR^4$ where $R^4$ is an unsubstituted $C_1$-$C_8$ alkyl or halo; (ii) $R^{3a}$ and $R^{3b}$ are independently H or unsubstituted $C_1$-$C_8$ alkyl; (iii) $R^{2a}$, $R^{2b}$, $R^{10a}$ and $R^{10b}$ are each H; (iv) $R^{8c}$ and $R^{8d}$ are taken together to form a carbonyl; (v) one of $R^{8c}$ and $R^{8d}$ is taken together with one of $R^{8e}$ and $R^{8f}$ to form a bond and the $R^{8c}$ or $R^{8d}$ that is not taken to form a bond is H and the $R^{8e}$ or $R^{8f}$ that is not taken to form a bond is a substituted or unsubstituted $C_1$-$C_8$ alkyl; and (vi) Q is a substituted or unsubstituted aryl or substituted or unsubstituted heteroaryl.

Compounds of the formula (E-6) are provided:

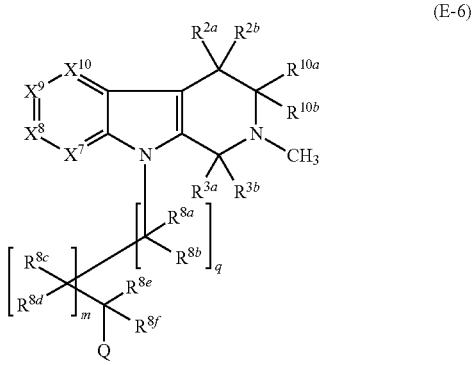

(E-6)

wherein:
each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;

$R^{3a}$ and $R^{3b}$ are independently H, substituted or unsubstituted $C_1$-$C_8$ alkyl, halo, cyano, nitro, hydroxyl, alkoxy, amino, substituted amino, cycloalkyl, phenyl, acylamino or acyloxy or $R^{3a}$ and $R^{3b}$ are taken together with the carbon to which they are attached to form a cycloalkyl moiety;

each $X^7$, $X^8$ and $X^{10}$ is independently N or $CR^4$;

$X^9$ is N or $CR^4$ where $R^4$ is halo or a substituted or unsubstituted $C_1$-$C_8$ alkyl;

m and q are independently 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^{8(a-f)}$ to form a cycloalkyl moiety or a carbonyl moiety, is taken together with a geminal $R^{8(a-f)}$ to form a methylene or a substituted methylene, is taken together with a vicinal $R^{8(a-f)}$ and the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or is taken together with a vicinal $R^{8(a-f)}$ to form a bond, provided that when an $R^{8(a-f)}$ is taken together with a vicinal $R^8$ to form a bond, the geminal $R^{8(a-f)}$ is other than hydroxyl;

each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety;

Q comprises a substituted phenyl, unsubstituted phenyl, substituted pyridyl or unsubstituted pyridyl moiety, or a salt thereof. In one aspect, the salt is a pharmaceutically acceptable salt.

Variations of compounds of the formula (E-6) are detailed herein, such as when any one or more of (i)-(ix) apply, provided that when one of provisions (iv), (v) or (vi) apply, only one of provisions (iv), (v) or (vi) applies: (i) $X^9$ is $CR^4$ where $R^4$ is an unsubstituted $C_1$-$C_8$ alkyl or halo; (ii) $R^{3a}$ and $R^{3b}$ are independently H, phenyl or unsubstituted $C_1$-$C_8$ alkyl; (iii) $R^{2a}$, $R^{2b}$, $R^{10a}$ and $R^{10b}$ are each H; (iv) m is 1 and $R^{8c}$ and $R^{8d}$ are taken together to form a carbonyl; (v) m is 1 and one of $R^{8c}$ and $R^{8d}$ is taken together with one of $R^{8e}$ and $R^{8f}$ to form a bond and the $R^{8c}$ or $R^{8d}$ that is not taken to form a bond is H and the $R^{8e}$ or $R^{8f}$ that is not taken to form a bond is a substituted or unsubstituted $C_1$-$C_8$ alkyl or H; (vi) m is 1 and $R^{8c}$ is taken together with $R^{8e}$ to form a bond and $R^{8d}$ is taken together with $R^{8f}$ to form a bond; (vii) q is 0; (viii) $X^7$, $X^8$ and $X^{10}$ are each $CR^4$ where $R^4$ is H; and (ix) Q is a substituted or unsubstituted phenyl or pyridyl moiety.

Compounds of the formula (E-7) are also embraced:

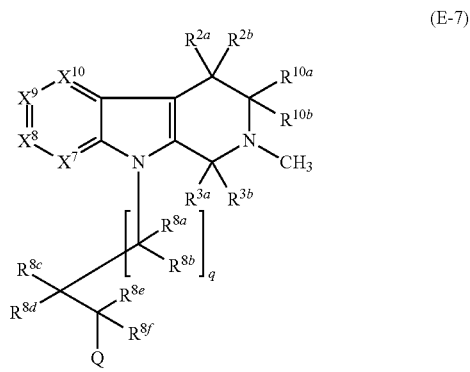

(E-7)

wherein:
each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;

$R^{3a}$ and $R^{3b}$ are independently H, substituted or unsubstituted $C_1$-$C_8$ alkyl, halo, cyano, nitro, hydroxyl, alkoxy, amino, substituted amino, cycloalkyl, phenyl, acylamino or acyloxy or $R^{3a}$ and $R^{3b}$ are taken together with the carbon to which they are attached to form a cycloalkyl moiety;

each $X^7$, $X^8$, $X^9$ and $X^{10}$ is independently N or $CR^4$;

q is 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^{8(a-f)}$ to form a cycloalkyl moiety or a carbonyl moiety, is taken together with a geminal $R^{8(a-f)}$ to form a methylene or a substituted methylene, is taken together with a vicinal $R^{8(a-f)}$ and the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or is taken together with a vicinal $R^{8(a-f)}$ to form a bond, provided that when an $R^{8(a-f)}$ is taken together with a vicinal $R^8$ to form a bond, the geminal $R^{8(a-f)}$ is other than hydroxyl;

each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety;

Q is an unsubstituted cycloalkyl, substituted cycloalkyl, unsubstituted heterocyclyl or substituted heterocyclyl moiety, or a salt thereof. In one aspect, the salt is a pharmaceutically acceptable salt.

Variations of compounds of the formula (E-7) are also provided, such as when any one or more of (i)-(viii) applies, provided that provisions (iv) and (v) are not combined: (i) $X^9$ is $CR^4$ where $R^4$ is H, an unsubstituted $C_1$-$C_8$ alkyl or halo; (ii) $R^{3a}$ and $R^{3b}$ are each H; (iii) $R^{2a}$, $R^{2b}$, $R^{10a}$ and $R^{10b}$ are each H; (iv) $R^{8e}$ and $R^{8f}$ are taken together to form a carbonyl; (v) $R^{8c}$, $R^{8d}$, $R^{8e}$ and $R^{8f}$ are each H; (vi) q is 0; (vii) $X^7$, $X^8$ and $X^{10}$ are each $CR^4$ where $R^4$ is H; and (viii) Q is a substituted or unsubstituted cyclopentyl, cyclohexyl, piperidinyl or piperazinyl moiety.

Further compounds include those of the formula (E-8):

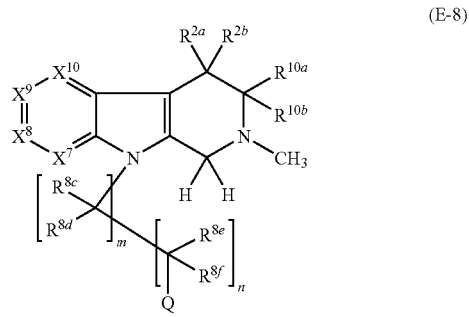

(E-8)

wherein:

each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;

each $X^7$, $X^8$, $X^9$ and $X^{10}$ is independently N or $CR^4$;

m is 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^{8(a-f)}$ to form a cycloalkyl moiety or a carbonyl moiety, is taken together with a geminal $R^{8(a-f)}$ to form a methylene or a substituted methylene, is taken together with a vicinal $R^{8(a-f)}$ and the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or is taken together with a vicinal $R^{8(a-f)}$ to form a bond, provided that when an $R^{8(a-f)}$ is taken together with a vicinal $R^8$ to form a bond, the geminal $R^{8(a-f)}$ is other than hydroxyl;

each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety;

Q is unsubstituted amino, substituted amino, alkoxy, aminoacyl, acyloxy, carbonylalkoxy, aminocarbonylalkoxy, acylamino, carboxy, cyano or alkynyl, or a salt thereof. In one aspect, the salt is a pharmaceutically acceptable salt.

Additional compounds are provided, including compounds of the formula (E) as detailed herein and any variation thereof.

The invention also includes all salts of compounds referred to herein, such as pharmaceutically acceptable salts. The invention also includes any or all of the stereochemical forms, including any enantiomeric or diastereomeric forms, of the compounds described. Unless stereochemistry is explicitly indicated in a chemical structure or name, the structure or name is intended to embrace all possible stereoisomers of a compound depicted. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

The invention is also directed to pharmaceutical compositions comprising a compound of the invention and a pharmaceutically acceptable carrier or excipient. Kits comprising a compound of the invention and instructions for use are also embraced by this invention. Compounds as detailed herein or a pharmaceutically acceptable salt thereof are also provided for the manufacture of a medicament for the treatment of a cognitive disorder, psychotic disorder, neurotransmitter-mediated disorder or a neuronal disorder.

In one aspect, compounds of the invention are used to treat, prevent, delay the onset and/or delay the development of any one or more of the following: cognitive disorders, psychotic disorders, neurotransmitter-mediated disorders and/or neuronal disorders in individuals in need thereof, such as humans. In one variation, compounds of the invention are used to treat, prevent, delay the onset and/or delay the development of diseases or conditions for which the modulation of an aminergic G protein-coupled receptor is believed to be or is beneficial. In one variation, compounds of the invention are used to treat, prevent, delay the onset and/or delay the development of any one or more of diseases or conditions for which neurite outgrowth and/or neurogenesis and/or neurotrophic effects are believed to be or are beneficial. In another variation, compounds of the invention are used to treat, prevent, delay the onset and/or delay the development of diseases or conditions for which the modulation of an aminergic G protein-coupled receptor and neurite outgrowth and/or neurogenesis and/or neurotrophic effects are believed to be or are beneficial. In one variation, the disease or condition is a cognitive disorder, psychotic disorder, neurotransmitter-mediated disorder and/or a neuronal disorder.

In another aspect, compounds of the invention are used to improve cognitive function and/or reduce psychotic effects in an individual, comprising administering to an individual in need thereof an amount of a compound described herein or a pharmaceutically acceptable salt thereof effective to improve cognitive function and/or reduce psychotic effects.

In a further aspect, compounds of the invention are used to stimulate neurite outgrowth and/or promote neurogenesis and/or enhance neurotrophic effects in an individual comprising administering to an individual in need thereof an amount of a compound described herein or a pharmaceutically acceptable salt thereof effective to stimulate neurite outgrowth and/or to promote neurogenesis and/or to enhance neurotrophic effects. Synapse loss is associated with a variety of neurodegenerative diseases and conditions including Alzheimer's disease, Huntington's disease, Parkinson's disease, amyotrophic lateral sclerosis, stroke, head trauma and spinal cord injury. Compounds of the invention that stimulate neurite outgrowth may have a benefit in these settings.

In another aspect, compounds described herein are used to modulate an aminergic G protein-coupled receptor comprising administering to an individual in need thereof an amount of a compound described herein or a pharmaceutically acceptable salt thereof effective to modulate an aminergic G protein-coupled receptor. In one variation, a compound of the invention modulates at least one of the following receptors: adrenergic receptor (e.g., α1D, α2A and/or α2B), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, at least two of the following receptors are modulated: adrenergic receptor (e.g., α1D, α2A and/or α2B), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, at least three of the following receptors are modulated: adrenergic receptor (e.g., α1D, α2A and/or α2B), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, each of the following receptors is modulated: adrenergic receptor (e.g., α1D, α2A and/or α2B), serotonin receptor (e.g., 5-HT2A, 5-HT2C, 5-HT6 and/or 5-HT7), dopamine receptor (e.g., D2L) and histamine receptor (e.g., H1, H2 and/or H3). In another variation, at least one of the following receptors is modulated: α1D, α2A, α2B, 5-HT2A, 5-HT2C, 5-HT6, 5-HT7, D2L, H1, H2 and H3. In another variation, at least two or three or four or five or six or seven or eight or nine or ten or eleven of the following receptors are modulated: α1D, α2A, α2B, 5-HT2A, 5-HT2C, 5-HT6, 5-HT7, D2L, H1, H2 and H3. In a particular variation, at least dopamine receptor D2L is modulated. In another particular variation, at least dopamine receptor D2L and serotonin receptor 5-HT2A are modulated. In a further particular variation, at least adrenergic receptors α1D, α2A, α2B and serotonin receptor 5-HT6 are modulated. In another particular variation, at least adrenergic receptors α1D, α2A, α2B, serotonin receptor 5-HT6 and one or more of serotonin receptor 5-HT7, 5-HT2A, 5-HT2C and histamine receptor H1 and H2 are modulated. In a further particular variation, histamine receptor H1 is modulated. In another variation, compounds of the invention exhibit any receptor modulation activity detailed herein and further stimulate neurite outgrowth and/or neurogenesis and/or enhance neurotrophic effects.

The invention is also directed to pharmaceutical compositions comprising a compound of the invention and a pharmaceutically acceptable carrier or excipient. Kits comprising a compound of the invention and instructions for use are also embraced by this invention.

DETAILED DESCRIPTION OF THE INVENTION

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

As used herein, the term "adrenergic receptor modulator" intends and encompasses a compound that binds to or inhibits binding of a ligand to an adrenergic receptor or reduces or eliminates or increases or enhances or mimics an activity of an adrenergic receptor. As such, an "adrenergic receptor modulator" encompasses both an adrenergic receptor antagonist and an adrenergic receptor agonist. In some aspects, the adrenergic receptor modulator binds to or inhibits binding to a ligand to an α1-adrenergic receptor (e.g., α1A, α1B and/or α1D) and/or a α2-adrenergic receptor (e.g., α2A, α2B and/or α2C) and/or reduces or eliminates or increases or enhances or mimics an activity of a α1-adrenergic receptor (e.g., α1A, α1B and/or α1D) and/or a α2-adrenergic receptor (e.g., α2A, α2B and/or α2C) in a reversible or irreversible manner. In some aspects, the adrenergic receptor modulator inhibits binding of a ligand by at least about or about any one of 10%, 20%, 30%, 40%, 50%, 60%, 70%, 80%, 90%, 95% or 100% as determined in the assays described herein. In some aspects, the adrenergic receptor modulator reduces an activity of an adrenergic receptor by at least or about any of 10%, 20%, 30%, 40%, 50%, 60%, 70%, 80%, 90%, 95% or 100% as compared to the corresponding activity in the same subject prior to treatment with the adrenergic receptor modulator or compared to the corresponding activity in other subjects not receiving the adrenergic receptor modulator. In some aspects, the adrenergic receptor modulator enhances an activity of an adrenergic receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the adrenergic receptor modulator or compared to the corresponding activity in other subjects not receiving the adrenergic receptor modulator. In some aspects, the adrenergic receptor modulator is capable of binding to the active site of an adrenergic receptor (e.g., a binding site for a ligand). In some embodiments, the adrenergic receptor modulator is capable of binding to an allosteric site of an adrenergic receptor.

As used herein, the term "dopamine receptor modulator" intends and encompasses a compound that binds to or inhibits binding of a ligand to a dopamine receptor or reduces or eliminates or increases or enhances or mimics an activity of a dopamine receptor. As such, a "dopamine receptor modulator" encompasses both a dopamine receptor antagonist and a dopamine receptor agonist. In some aspects, the dopamine receptor modulator binds to or inhibits binding of a ligand to a dopamine-1 (D1) and/or a dopamine-2 (D2) receptor or reduces or eliminates or increases or enhances or mimics an activity of a dopamine-1 (D1) and/or a dopamine-2 (D2) receptor in a reversible or irreversible manner. Dopamine D2 receptors are divided into two categories, D2L and D2S, which are formed from a single gene by differential splicing. D2L receptors have a longer intracellular domain than D2S.

In some embodiments, the dopamine receptor modulator inhibits binding of a ligand by at least about or about any one of 10%, 20%, 30%, 40%, 50%, 60%, 70%, 80%, 90%, 95% or 100% as determined in the assays described herein. In some embodiments, the dopamine receptor modulator reduces an activity of a dopamine receptor by at least about or about any of 10%, 20%, 30%, 40%, 50%, 60%, 70%, 80%, 90%, 95% or 100% as compared to the corresponding activity in the same subject prior to treatment with the dopamine receptor modulator or compared to the corresponding activity in other subjects not receiving the dopamine receptor modulator. In some embodiments, the dopamine receptor modulator enhances an activity of a dopamine receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the dopamine receptor modulator or compared to the corresponding activity in other subjects not receiving the dopamine receptor modulator. In some embodiments, the dopamine receptor modulator is capable of binding to the active site of a dopamine receptor (e.g., a binding site for a ligand). In some embodiments, the dopamine receptor modulator is capable of binding to an allosteric site of a dopamine receptor.

As used herein, the term "serotonin receptor modulator" intends and encompasses a compound that binds to or inhibits binding of a ligand to a serotonin receptor or reduces or eliminates or increases or enhances or mimics an activity of a serotonin receptor. As such, a "serotonin receptor modulator" encompasses both a serotonin receptor antagonist and a serotonin receptor agonist. In some embodiments, the serotonin receptor modulator binds to or inhibits binding of a ligand to a 5-HT1A and/or a 5-HT1B and/or a 5-HT2A and/or a 5-HT2B and/or a 5-HT2C and/or a 5-HT3 and/or a 5-HT4 and/or a 5-HT6 and/or a 5-HT7 receptor or reduces or eliminates or increases or enhances or mimics an activity of a 5-HT1A and/or a 5-HT1B and/or a 5-HT2A and/or a 5-HT2B and/or a 5-HT2C and/or a 5-HT3 and/or a 5-HT4 and/or a 5-HT6 and/or a 5-HT7 receptor in a reversible or irreversible manner. In some embodiments, the serotonin receptor modulator inhibits binding of a ligand by at least about or about any one of 10%, 20%, 30%, 40%, 50%, 60%, 70%, 80%, 90%, 95% or 100% as determined in the assays described herein. In some embodiments, the serotonin receptor modulator reduces an activity of a serotonin receptor by at least about or about any of 10%, 20%, 30%, 40%, 50%, 60%, 70%, 80%, 90%, 95% or 100% as compared to the corresponding activity in the same subject prior to treatment with the serotonin receptor modulator or compared to the corresponding activity in other subjects not receiving the serotonin receptor modulator. In some embodiments, the serotonin receptor modulator enhances an activity of a serotonin receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the serotonin receptor modulator or compared to the corresponding activity in other subjects not receiving the serotonin receptor modulator. In some embodiments, the serotonin receptor modulator is capable of binding to the active site of a serotonin receptor (e.g., a binding site for a ligand). In some embodiments, the serotonin receptor modulator is capable of binding to an allosteric site of a serotonin receptor.

As used herein, the term "histamine receptor modulator" intends and encompasses a compound that reduces or eliminates or increases or enhances an activity of a histamine receptor. As such, a "histamine receptor modulator" encompasses both a histamine receptor antagonist and a histamine receptor agonist. In some embodiments, the histamine receptor modulator reduces or eliminates or increases or enhances an activity of a histamine receptor in a reversible or irreversible manner. In some embodiments, the histamine receptor modulator reduces an activity of a histamine receptor by at least or about any of 10%, 20%, 30%, 40%, 50%, 60%, 70%, 80%, 90%, 95% or 100% as compared to the corresponding activity in the same individual prior to treatment with the histamine receptor modulator or compared to the corresponding activity in like individuals not receiving the histamine receptor modulator. In some embodiments, the histamine receptor modulator enhances an activity of a histamine receptor by at least or about any of 10%, 20%, 30%, 40%, 50%, 60%, 70%, 80%, 90%, 95% or 100 or 200% or 300% or 400% or 500% or more as compared to the corresponding activity in the same individual prior to treatment with the histamine receptor modulator or compared to the corresponding activity in like individuals not receiving the histamine receptor modulator. In some embodiments, the histamine receptor modulator is capable of binding to the active site of a histamine receptor (e.g., a binding site for a ligand). In some embodiments, the histamine receptor modulator is capable of binding to an allosteric site of a histamine receptor.

Unless clearly indicated otherwise, "an individual" as used herein intends a mammal, including but not limited to a human. An individual includes but is not limited to human, bovine, primate, equine, canine, feline, porcine, and ovine animals. Thus, the invention finds use in both human medicine and in the veterinary context, including use in agricultural animals and domestic pets. The individual may be a human who has been diagnosed with or is suspected of having a cognitive disorder, a psychotic disorder, a neurotransmitter-mediated disorder and/or a neuronal disorder. The individual may be a human who exhibits one or more symptoms associated with a cognitive disorder, a psychotic disorder, a neurotransmitter-mediated disorder and/or a neuronal disorder. The individual may be a human who has a mutated or abnormal gene associated with a cognitive disorder, a psychotic disorder, a neurotransmitter-mediated disorder and/or a neuronal disorder. The individual may be a human who is genetically or otherwise predisposed to developing a cognitive disorder, a psychotic disorder, a neurotransmitter-mediated disorder and/or a neuronal disorder.

As used herein, "treatment" or "treating" is an approach for obtaining a beneficial or desired result, such as a clinical result.

For purposes of this invention, beneficial or desired clinical results include, but are not limited to, alleviation of a symptom and/or diminishment of the extent of a symptom and/or preventing a worsening of a symptom associated with a disease or condition. In one variation, beneficial or desired clinical results include, but are not limited to, alleviation of a symptom and/or diminishment of the extent of a symptom and/or preventing a worsening of a symptom associated with a cognitive disorder, a psychotic disorder, a neurotransmitter-mediated disorder and/or a neuronal disorder. Preferably, treatment of a disease or condition with a compound of the invention or a pharmaceutically acceptable salt thereof is accompanied by no or fewer side effects than are associated with currently available therapies for the disease or condition and/or improves the quality of life of the individual.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of Alzheimer's disease is a method that reduces probability of disease development in a given time frame and/or reduces extent of the disease in a given time frame, when compared to not using the method. Such comparisons are typically based on clinical studies, using a statistically significant number of subjects. For example, Alzheimer's disease development can be detected using standard clinical techniques, such as routine neurological examination, patient interview, neuroimaging, detecting alterations of levels of specific proteins in the serum or cerebrospinal fluid (e.g., amyloid peptides and Tau), computerized tomography (CT) or magnetic resonance imaging (MRI). Similar techniques are known in the art for other diseases and conditions. Development may also refer to disease progression that may be initially undetectable and includes occurrence, recurrence and onset.

As used herein, an "at risk" individual is an individual who is at risk of developing a cognitive disorder, a psychotic disorder, a neurotransmitter-mediated disorder and/or a neuronal disorder that can be treated with a compound of the invention. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). These risk factors include, but are not limited to, age, sex, race, diet, history of previous disease, presence of precursor disease, genetic (i.e., hereditary) considerations, and environmental exposure. For example, individuals at risk for Alzheimer's disease include, e.g., those having relatives who have experienced this disease and those whose risk is determined by analysis of genetic or biochemical markers. Genetic markers of risk for Alzheimer's disease include mutations in the APP gene, particularly mutations at position 717 and positions 670 and 671 referred to as the Hardy and Swedish mutations, respectively (Hardy, *Trends Neurosci.*, 20:154-9, 1997). Other markers of risk are mutations in the presenilin genes (e.g., PS1 or PS2), ApoE4 alleles, family history of Alzheimer's disease, hypercholesterolemia and/or atherosclerosis. Other such factors are known in the art for other diseases and conditions.

As used herein, the term "pro-cognitive" includes but is not limited to an improvement of one or more mental processes such as memory, attention, perception and/or thinking, which may be assessed by methods known in the art.

As used herein, the term "neurotrophic" effects includes but is not limited to effects that enhance neuron function such as growth, survival and/or neurotransmitter synthesis.

As used herein, the term "cognitive disorders" refers to and intends diseases and conditions that are believed to involve or be associated with or do involve or are associated with progressive loss of structure and/or function of neurons, including death of neurons, and where a central feature of the disorder may be the impairment of cognition (e.g., memory, attention, perception and/or thinking). These disorders include pathogen-induced cognitive dysfunction, e.g. HIV associated cognitive dysfunction and Lyme disease associated cognitive dysfunction. Examples of cognitive disorders include Alzheimer's Disease, Huntington's Disease, Parkinson's Disease, schizophrenia, amyotrophic lateral sclerosis (ALS), autism, mild cognitive impairment (MCI), stroke, traumatic brain injury (TBI) and age-associated memory impairment (AAMI).

As used herein, the term "psychotic disorders" refers to and intends mental diseases or conditions that are believed to cause or do cause abnormal thinking and perceptions. Psychotic disorders are characterized by a loss of reality which may be accompanied by delusions, hallucinations (perceptions in a conscious and awake state in the absence of external stimuli which have qualities of real perception, in that they are vivid, substantial, and located in external objective space), personality changes and/or disorganized thinking. Other common symptoms include unusual or bizarre behavior, as well as difficulty with social interaction and impairment in carrying out the activities of daily living. Exemplary psychotic disorders are schizophrenia, bipolar disorders, psychosis, anxiety and depression.

As used herein, the term "neurotransmitter-mediated disorders" refers to and intends diseases or conditions that are believed to involve or be associated with or do involve or are associated with abnormal levels of neurotransmitters such as histamine, serotonin, dopamine, norepinephrine or impaired function of aminergic G protein-coupled receptors. Exemplary neurotransmitter-mediated disorders include spinal cord injury, diabetic neuropathy, allergic diseases and diseases involving geroprotective activity such as age-associated hair loss (alopecia), age-associated weight loss and age-associated vision disturbances (cataracts). Abnormal neurotransmitter levels are associated with a wide variety of diseases and conditions including, but not limited to Alzheimer's disease, Parkinson's Disease, autism, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases.

As used herein, the term "neuronal disorders" refers to and intends diseases or conditions that are believed to involve, or be associated with, or do involve or are associated with neuronal cell death and/or impaired neuronal function or decreased neuronal function. Exemplary neuronal indications include neurodegenerative diseases and disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder, adjuvant chemotherapy, traumatic brain injury (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety or depression.

As used herein, the term "neuron" represents a cell of ectodermal embryonic origin derived from any part of the nervous system of an animal. Neurons express well-characterized neuron-specific markers, including neurofilament proteins, NeuN (Neuronal Nuclei marker), MAP2, and class III tubulin. Included as neurons are, for example, hippocampal, cortical, midbrain dopaminergic, spinal motor, sensory, sympathetic, septal cholinergic, and cerebellar neurons.

As used herein, the term "neurite outgrowth" or "neurite activation" refers to the extension of existing neuronal processes (e.g., axons and dendrites) and the growth or sprouting of new neuronal processes (e.g., axons and dendrites). Neurite outgrowth or neurite activation may alter neural connectivity, resulting in the establishment of new synapses or the remodeling of existing synapses.

As used herein, the term "neurogenesis" refers to the generation of new nerve cells from undifferentiated neuronal progenitor cells, also known as multipotential neuronal stem cells. Neurogenesis actively produces new neurons, astrocytes, glia, Schwann cells, oligodendrocytes and/or other neural lineages. Much neurogenesis occurs early in human development, though it continues later in life, particularly in certain localized regions of the adult brain.

As used herein, the term "neural connectivity" refers to the number, type, and quality of connections ("synapses") between neurons in an organism. Synapses form between neurons, between neurons and muscles (a "neuromuscular junction"), and between neurons and other biological structures, including internal organs, endocrine glands, and the like. Synapses are specialized structures by which neurons transmit chemical or electrical signals to each other and to non-neuronal cells, muscles, tissues, and organs. Compounds that affect neural connectivity may do so by establishing new synapses (e.g., by neurite outgrowth or neurite activation) or by altering or remodeling existing synapses. Synaptic remodeling refers to changes in the quality, intensity or type of signal transmitted at particular synapses.

As used herein, the term "neuropathy" refers to a disorder characterized by altered function and/or structure of motor, sensory, and autonomic neurons of the nervous system, initiated or caused by a primary lesion or other dysfunction of the nervous system. Patterns of peripheral neuropathy include polyneuropathy, mononeuropathy, mononeuritis multiplex and autonomic neuropathy. The most common form is (symmetrical) peripheral polyneuropathy, which mainly affects the feet and legs. A radiculopathy involves spinal nerve roots, but if peripheral nerves are also involved the term radiculoneuropathy is used. The form of neuropathy may be further broken down by cause, or the size of predominant fiber involvement, e.g. large fiber or small fiber peripheral neuropathy. Central neuropathic pain can occur in spinal cord injury, multiple sclerosis, and some strokes, as well as fibromyalgia. Neuropathy may be associated with varying combinations of weakness, autonomic changes and sensory changes. Loss of muscle bulk or fasciculations, a particular fine twitching of muscle may also be seen. Sensory symptoms encompass loss of sensation and "positive" phenomena including pain. Neuropathies are associated with a variety of disorders, including diabetes (e.g., diabetic neuropathy), fibromyalgia, multiple sclerosis, and herpes zoster infection, as well as with spinal cord injury and other types of nerve damage.

As used herein, the term "Alzheimer's disease" refers to a degenerative brain disorder characterized clinically by progressive memory deficits, confusion, behavioral problems, inability to care for oneself, gradual physical deterioration and, ultimately, death. Histologically, the disease is characterized by neuritic plaques, found primarily in the association cortex, limbic system and basal ganglia. The major constituent of these plaques is amyloid beta peptide (Aβ), which is the cleavage product of beta amyloid precursor protein (βAPP or APP). APP is a type I transmembrane glycoprotein that contains a large ectopic N-terminal domain, a transmembrane domain and a small cytoplasmic C-terminal tail. Alternative splicing of the transcript of the single APP gene on chromosome 21 results in several isoforms that differ in the number of amino acids. Aβ appears to have a central role in the neuropathology of Alzheimer's disease. Familial forms of the disease have been linked to mutations in APP and the presenilin genes (Tanzi et al., 1996, *Neurobiol. Dis.*, 3:159-168; Hardy, 1996, *Ann. Med.*, 28:255-258). Diseased-linked mutations in these genes result in increased production of the 42-amino acid form of Aβ, the predominant form found in amyloid plaques. Mitochondrial dysfunction has also been reported to be an important component of Alzheimer's disease (Bubber et al., Mitochondrial abnormalities in Alzheimer brain: Mechanistic Implications, *Ann Neurol.*, 2005, 57(5), 695-703; Wang et al., Insights into amyloid-β-induced mitochondrial dysfunction in Alzheimer disease, *Free Radical Biology & Medicine*, 2007, 43, 1569-1573; Swerdlow et al., Mitochondria in Alzheimer's disease, *Int. Rev. Neurobiol.*, 2002, 53, 341-385; and Reddy et al., Are mitochondria critical in the pathogenesis of Alzheimer's disease?, *Brain Res Rev.* 2005, 49(3), 618-32). It has been proposed that mitochondrial dysfunction has a causal relationship with neuronal function (including neurotransmitter synthesis and secretion) and viability. Compounds which stabilize mitochondria may therefore have a beneficial impact on Alzheimer's patients.

As used herein, the term "Huntington's disease" refers to a fatal neurological disorder characterized clinically by symptoms such as involuntary movements, cognition impairment or loss of cognitive function and a wide spectrum of behavioral disorders. Common motor symptoms associated with Huntington's disease include chorea (involuntary writhing and spasming), clumsiness, and progressive loss of the abilities to walk, speak (e.g., exhibiting slurred speech) and swallow. Other symptoms of Huntington's disease can include cognitive symptoms such as loss of intellectual speed, attention and short-term memory and/or behavioral symptoms that can span the range of changes in personality, depression, irritability, emotional outbursts and apathy. Clinical symptoms typically appear in the fourth or fifth decade of life. Huntington's disease is a devastating and often protracted illness, with death usually occurring approximately 10-20 years after the onset of symptoms. Huntington's disease is inherited through a mutated or abnormal gene encoding an abnormal protein called the mutant huntingtin protein; the mutated huntingtin protein produces neuronal degeneration in many different regions of the brain. The degeneration focuses on neurons located in the basal ganglia, structures deep within the brain that control many important functions including coordinating movement, and on neurons on the outer surface of the brain or cortex, which controls thought, perception and memory.

"Amyotrophic lateral sclerosis" or "ALS" is used herein to denote a progressive neurodegenerative disease that affects upper motor neurons (motor neurons in the brain) and/or lower motor neurons (motor neurons in the spinal cord) and results in motor neuron death. As used herein, the term "ALS" includes all of the classifications of ALS known in the art, including, but not limited to classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking), Progressive Muscular Atrophy (PMA, typically affecting only the lower motor neurons) and familial ALS (a genetic version of ALS).

The term "Parkinson's disease" as used herein refers to any medical condition wherein an individual experiences one or more symptoms associated with Parkinson's disease, such as without limitation one or more of the following symptoms: rest tremor, cogwheel rigidity, bradykinesia, postural reflex impairment, symptoms having good response to 1-dopa treatment, the absence of prominent oculomotor palsy, cerebellar or pyramidal signs, amyotrophy, dyspraxia and/or dysphasia. In a specific embodiment, the present invention is utilized for the treatment of a dopaminergic dysfunction-related disorder. In a specific embodiment, the individual with Parkinson's disease has a mutation or polymorphism in a synuclein, parkin or NURR1 nucleic acid that is associated with Parkinson's disease. In one embodiment, the individual with Parkinson's disease has defective or decreased expression of a nucleic acid or a mutation in a nucleic acid that regulates the development and/or survival of dopaminergic neurons.

As used herein, the term "canine cognitive dysfunction syndrome," or "CCDS" refers to an age-related deterioration of mental function typified by multiple cognitive impairments that affect an afflicted canine's ability to function normally. The decline in cognitive ability that is associated with CCDS cannot be completely attributed to a general medical condition such as neoplasia, infection, sensory impairment, or organ failure. Diagnosis of CCDS in canines, such as dogs, is generally a diagnosis of exclusion, based on thorough behavior and medical histories and the presence of clinical symptoms of CCDS that are unrelated to other disease processes. Owner observation of age-related changes in behavior is a practical means used to detect the possible onset of CCDS in aging domestic dogs. A number of laboratory cognitive tasks may be used to help diagnose CCDS, while blood counts, chemistry panels and urinalysis can be used to rule out other underlying diseases that could mimic the clinical symptoms of CCDS. Symptoms of CCDS include memory loss, which in domestic dogs may be manifested by disorientation and/or confusion, decreased or altered interaction with family members and/or greeting behavior, changes in sleep-wake cycle, decreased activity level, and loss of house training or frequent, inappropriate elimination. A canine suffering from CCDS may exhibit one or more of the following clinical or behavioral symptoms: decreased appetite, decreased awareness of surroundings, decreased ability to recognize familiar places, people or other animals, decreased hearing, decreased ability to climb up and down stairs, decreased tolerance to being alone, development of compulsive behavior or repetitive behaviors or habits, circling, tremors or shaking, disorientation, decreased activity level, abnormal sleep wake cycles, loss of house training, decreased or altered responsiveness to family members, and decreased or altered greeting behavior. CCDS can dramatically affect the health and well-being of an afflicted canine. Moreover, the companionship offered by a pet with CCDS can become less rewarding as the severity of the disease increases and its symptoms become more severe.

As used herein, the term "age-associated memory impairment" or "AAMI" refers to a condition that may be identified as GDS stage 2 on the global deterioration scale (GDS) (Reisberg, et al. (1982) *Am. J. Psychiatry* 139: 1136-1139) which differentiates the aging process and progressive degenerative dementia in seven major stages. The first stage of the GDS is one in which individuals at any age have neither subjective complaints of cognitive impairment nor objective evidence of impairment. These GDS stage 1 individuals are considered normal. The second stage of the GDS applies to those generally elderly persons who complain of memory and cognitive functioning difficulties such as not recalling names as well as they could five or ten years previously or not recalling where they have placed things as well as they could five or ten years previously. These subjective complaints appear to be very common in otherwise normal elderly individuals. AAMI refers to persons in GDS stage 2, who may differ neurophysiologically from elderly persons who are normal and free of subjective complaints, i.e., GDS stage 1. For example, AAMI subjects have been found to have more electrophysiologic slowing on a computer analyzed EEG than GDS stage 1 elderly persons (Prichep, John, Ferris, Reisberg, et al. (1994) *Neurobiol. Aging* 15: 85-90).

As used herein, the term "mild cognitive impairment" or "MCI" refers to a type of cognitive disorder characterized by a more pronounced deterioration in cognitive functions than is typical for normal age-related decline. As a result, elderly or aged patients with MCI have greater than normal difficulty performing complex daily tasks and learning, but without the inability to perform normal social, everyday, and/or professional functions typical of patients with Alzheimer's disease, or other similar neurodegenerative disorders eventually resulting in dementia. MCI is characterized by subtle, clinically manifest deficits in cognition, memory, and functioning, amongst other impairments, which are not of sufficient magnitude to fulfill criteria for diagnosis of Alzheimer's disease or other dementia. MCI also encompasses injury-related MCI, defined herein as cognitive impairment resulting from certain types of injury, such as nerve injury (i.e., battlefield injuries, including post-concussion syndrome, and the like), neurotoxic treatment (i.e., adjuvant chemotherapy resulting in "chemo brain" and the like), and tissue damage resulting from physical injury or other neurodegeneration, which is separate and distinct from mild cognitive impairment resulting from stroke, ischemia, hemorrhagic insult, blunt force trauma, and the like.

As used herein, the term "traumatic brain injury" or "TBI" refers to a brain injury caused by a sudden trauma, such as a blow or jolt or a penetrating head injury, which disrupts the function or damages the brain. Symptoms of TBI can range from mild, moderate to severe and can significantly affect many cognitive (deficits of language and communication, information processing, memory, and perceptual skills), physical (ambulation, balance, coordination, fine motor skills, strength, and endurance), and psychological skills.

"Neuronal death mediated ocular disease" intends an ocular disease in which death of the neuron is implicated in whole or in part. The disease may involve death of photoreceptors. The disease may involve retinal cell death. The disease may involve ocular nerve death by apoptosis. Particular neuronal death mediated ocular diseases include but are not limited to macular degeneration, glaucoma, retinitis pigmentosa, congenital stationary night blindness (Oguchi disease), childhood onset severe retinal dystrophy, Leber congenital amaurosis, Bardet-Biedle syndrome, Usher syndrome, blindness from an optic neuropathy, Leber's hereditary optic neuropathy, color blindness and Hansen-Larson-Berg syndrome.

As used herein, the term "macular degeneration" includes all forms and classifications of macular degeneration known in the art, including, but not limited to diseases that are characterized by a progressive loss of central vision associated with abnormalities of Bruch's membrane, the choroid, the neural retina and/or the retinal pigment epithelium. The term thus encompasses disorders such as age-related macular degeneration (ARMD) as well as rarer, earlier-onset dystrophies that in some cases can be detected in the first decade of life. Other maculopathies include North Carolina macular dystrophy, Sorsby's fundus dystrophy, Stargardt's disease, pattern dystrophy, Best disease, and Malattia Leventinese.

As used herein, the term "autism" refers to a brain development disorder that impairs social interaction and communication and causes restricted and repetitive behavior, typically appearing during infancy or early childhood. The cognitive and behavioral defects are thought to result in part from altered neural connectivity. Autism encompasses related disorders sometimes referred to as "autism spectrum disorder," as well as Asperger syndrome and Rett syndrome.

As used herein, the term "nerve injury" or "nerve damage" refers to physical damage to nerves, such as avulsion injury (i.e., where a nerve or nerves have been torn or ripped) or spinal cord injury (i.e., damage to white matter or myelinated fiber tracts that carry sensation and motor signals to and from the brain). Spinal cord injury can occur from many causes, including physical trauma (i.e., car accidents, sports injuries, and the like), tumors impinging on the spinal column, developmental disorders, such as spina bifida, and the like.

As used herein, the term "myasthenia gravis" or "MG" refers to a non-cognitive neuromuscular disorder caused by immune-mediated loss of acetylcholine receptors at neuromuscular junctions of skeletal muscle. Clinically, MG typically appears first as occasional muscle weakness in approximately two-thirds of patients, most commonly in the extraocular muscles. These initial symptoms eventually worsen, producing drooping eyelids (ptosis) and/or double vision (diplopia), often causing the patient to seek medical attention. Eventually, many patients develop general muscular weakness that may fluctuate weekly, daily, or even more frequently. Generalized MG often affects muscles that control facial expression, chewing, talking, swallowing, and breathing; before recent advances in treatment, respiratory failure was the most common cause of death.

As used herein, the term "Guillain-Barré syndrome" refers to a non-cognitive disorder in which the body's immune system attacks part of the peripheral nervous system. The first symptoms of this disorder include varying degrees of weakness or tingling sensations in the legs. In many instances the weakness and abnormal sensations spread to the arms and upper body. These symptoms can increase in intensity until certain muscles cannot be used at all and, when severe, the patient is almost totally paralyzed. In these cases the disorder is life threatening—potentially interfering with breathing and, at times, with blood pressure or heart rate—and is considered a medical emergency. Most patients, however, recover from even the most severe cases of Guillain-Barré syndrome, although some continue to have a certain degree of weakness.

As used herein, the term "multiple sclerosis" or "MS" refers to an autoimmune condition in which the immune system attacks the central nervous system (CNS), leading to demyelination of neurons. It may cause numerous symptoms, many of which are non-cognitive, and often progresses to physical disability. MS affects the areas of the brain and spinal cord known as the white matter. White matter cells carry signals between the grey matter areas, where the processing is done, and the rest of the body. More specifically, MS destroys oligodendrocytes which are the cells responsible for creating and maintaining a fatty layer, known as the myelin sheath, which helps the neurons carry electrical signals. MS results in a thinning or complete loss of myelin and, less frequently, the cutting (transection) of the neuron's extensions or axons. When the myelin is lost, the neurons can no longer effectively conduct their electrical signals. Almost any neurological symptom can accompany the disease. MS takes several forms, with new symptoms occurring either in discrete attacks (relapsing forms) or slowly accumulating over time (progressive forms). Most people are first diagnosed with relapsing-remitting MS but develop secondary-progressive MS (SPMS) after a number of years. Between attacks, symptoms may go away completely, but permanent neurological problems often persist, especially as the disease advances.

As used herein, the term "schizophrenia" refers to a chronic, mental disorder characterized by one or more positive symptoms (e.g., delusions and hallucinations) and/or negative symptoms (e.g., blunted emotions and lack of interest) and/or disorganized symptoms (e.g., disorganized thinking and speech or disorganized perception and behavior). Schizophrenia as used herein includes all forms and classifications of schizophrenia known in the art, including, but not limited to catatonic type, hebephrenic type, disorganized type, paranoid type, residual type or undifferentiated type schizophrenia and deficit syndrome and/or those described in American Psychiatric Association: *Diagnostic and Statistical Manual of Mental Disorders*, Fourth Edition, Washington D.C., 2000 or in International Statistical Classification of Diseases and Related Health Problems, or otherwise known to those of skill in the art.

As used herein "geroprotective activity" or "geroprotector" means a biological activity that slows down ageing and/or prolongs life and/or increases or improves the quality of life via a decrease in the amount and/or the level of intensity of pathologies or conditions that are not life-threatening but are associated with the aging process and which are typical for elderly people. Pathologies or conditions that are not life-threatening but are associated with the aging process include such pathologies or conditions as loss of sight (cataract), deterioration of the dermatohairy integument (alopecia), and an age-associated decrease in weight due to the death of muscular and/or fatty cells.

As used herein "allergic disease" refers to a disorder of the immune system which is characterized by excessive activation of mast cells and basophils and production of IgE immunoglobulins, resulting in an extreme inflammatory response. It represents a form of hypersensitivity to an environmental substance known as allergen and is an acquired disease. Common allergic reactions include eczema, hives, hay fever, asthma, food allergies, and reactions to the venom of stinging insects such as wasps and bees. Allergic reactions are accompanied by an excessive release of histamines, and can thus be treated with antihistaminic agents.

As used herein, by "combination therapy" is meant a therapy that includes two or more different compounds. Thus, in one aspect, a combination therapy comprising a compound detailed herein and anther compound is provided. In some variations, the combination therapy optionally includes one or more pharmaceutically acceptable carriers or excipients, non-pharmaceutically active compounds, and/or inert substances. In various embodiments, treatment with a combination therapy may result in an additive or even synergistic (e.g., greater than additive) result compared to administration of a single compound of the invention alone. In some embodiments, a lower amount of each compound is used as part of a combination therapy compared to the amount generally used for individual therapy. Preferably, the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a compound in a combination therapy than the amount generally used for individual compound or therapy. Preferably, the use of a small amount of compound results in a reduction in the number, severity, frequency, and/or duration of one or more side-effects associated with the compound.

As used herein, the term "effective amount" intends such amount of a compound of the invention which in combination with its parameters of efficacy and toxicity, as well as based on the knowledge of the practicing specialist should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc "directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Alkyl" refers to and includes saturated linear, branched, or cyclic univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, tert-butyl and cyclobutyl; "propyl" includes n-propyl, iso-propyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclohexyl, or multiple rings, such as adamantyl. A cycloalkyl comprising more than one ring may be fused, spiro or bridged, or combinations thereof. In fused ring systems, one or more of the rings can be aryl or heteroaryl. A cycloalkyl having more than one ring where at least one ring is aromatic may be connected to the parent structure at either a non-aromatic ring position or at an aromatic ring position. In one variation, a cycloalkyl having more than one ring where at least one ring is aromatic is connected to the parent structure at a non-aromatic ring position. A preferred cycloalkyl is a saturated cyclic hydrocarbon having from 3 to 13 annular carbon atoms. A more preferred cycloalkyl is a saturated cyclic hydrocarbon having from 3 to 7 annular carbon atoms (a "$C_3$-$C_7$ cycloalkyl"). Examples of cycloalkyl groups include adamantyl, decahydronaphthalenyl, cyclopropyl, cyclobutyl, cyclopentyl and the like.

"Alkylene" refers to the same residues as alkyl, but having bivalency. Examples of alkylene include ethylene (—$CH_2CH_2$—) and propylene (—$CH_2CH_2CH_2$—).

"Alkenyl" refers to an unsaturated hydrocarbon group having at least one site of olefinic unsaturation (i.e., having at least one moiety of the formula C═C) and preferably having from 2 to 10 carbon atoms and more preferably 2 to 8 carbon atoms. Examples of alkenyl include but are not limited to —$CH_2$—CH═CH—$CH_3$ and —$CH_2$—$CH_2$-cyclohexenyl, where the ethyl group of the later example can be attached to the cyclohexenyl moiety at any available position on the ring.

"Alkynyl" refers to an unsaturated hydrocarbon group having at least one site of acetylenic unsaturation (i.e., having at least one moiety of the formula C≡C) and preferably having from 2 to 10 carbon atoms and more preferably 3 to 8 carbon atoms.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkenyl" refers to alkenyl group having from 1 to 5 substituents s including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkynyl" refers to alkynyl groups having from 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted heterocyclyl, substituted or unsubstituted aralkyl, aminosulfonyl, sulfonylamino, sulfonyl, oxo, carbonylalkylenealkoxy and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Substituted heterocyclic" or "substituted heterocyclyl" refers to a heterocycle group which is substituted with from 1 to 3 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like. In one variation, a substituted heterocycle is a heterocycle substituted with an additional ring, wherein the additional ring may be aromatic or non-aromatic.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic carbocyclic group having from 2 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Substituted aryl" refers to an aryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted heteroaryl" refers to a heteroaryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Aralkyl" refers to a residue in which an aryl moiety is attached to an alkyl residue and wherein the aralkyl group may be attached to the parent structure at either the aryl or the alkyl residue. Preferably, an aralkyl is connected to the parent structure via the alkyl moiety. A "substituted aralkyl" refers to a residue in which an aryl moiety is attached to a substituted alkyl residue and wherein the aralkyl group may be attached to the parent structure at either the aryl or the alkyl residue.

"Alkoxy" refers to the group alkyl-O—, which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. Similarly, alkenyloxy refers to the group "alkenyl-O—" and alkynyloxy refers to the group "alkynyl-O—". "Substituted alkoxy" refers to the group substituted alkyl-O.

"Unsubstituted amino" refers to the group —NH$_2$.

"Substituted amino" refers to the group —NR$_a$R$_b$, where either (a) each R$_a$ and R$_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, provided that both R$_a$ and R$_b$ groups are not H; or (b) R$_a$ and R$_b$ are joined together with the nitrogen atom to form a heterocyclic or substituted heterocyclic ring.

"Acylamino" refers to the group —C(O)NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic or R$_a$ and R$_b$ groups can be joined together with the nitrogen atom to form a heterocyclic or substituted heterocyclic ring.

"Aminocarbonylalkoxy" refers to the group —NR$_a$C(O)OR$_b$ where each R$_a$ and R$_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclic.

"Aminoacyl" refers to the group —NR$_a$C(O)R$_b$ where each R$_a$ and R$_b$ group is independently selected from the group consisting of H, alkyl, substituted alkyl, substituted alkenyl, alkynyl, substituted alkynyl, aryl, substituted aryl, heteroaryl, substituted heteroaryl, heterocyclic or substituted heterocyclic. Preferably, R$_a$ is H or alkyl.

"Aminosulfonyl" refers to the groups —NRSO$_2$-alkyl, —NRSO$_2$ substituted alkyl, —NRSO$_2$-alkenyl, —NRSO$_2$-substituted alkenyl, —NRSO$_2$-alkynyl, —NRSO$_2$-substituted alkynyl, —NRSO$_2$-aryl, —NRSO$_2$-substituted aryl, —NRSO$_2$-heteroaryl, —NRSO$_2$-substituted heteroaryl, —NRSO$_2$-heterocyclic, and —NRSO$_2$-substituted heterocyclic, where R is H or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the groups —SO$_2$NH$_2$, —SO$_2$NR-alkyl, —SO$_2$NR-substituted alkyl, —SO$_2$NR-alkenyl, —SO$_2$NR-substituted alkenyl, —SO$_2$NR-alkynyl, —SO$_2$NR-substituted alkynyl, —SO$_2$NR-aryl, —SO$_2$NR-substituted aryl, —SO$_2$NR-heteroaryl, —SO$_2$NR-substituted heteroaryl, —SO$_2$NR-heterocyclic, and —SO$_2$NR-substituted heterocyclic, where R is H or alkyl, or —SO$_2$NR$_2$, where the two R groups are taken together and with the nitrogen atom to which they are attached to form a heterocyclic or substituted heterocyclic ring.

"Sulfonyl" refers to the groups —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic.

"Carbonylalkylenealkoxy" refers to the group —C(=O)—(CH$_2$)$_n$—OR where R is a substituted or unsubstituted alkyl and n is an integer from 1 to 100, more preferably n is an integer from 1 to 10 or 1 to 5.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." A preferred perhaloalkyl group is trifluoroalkyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

"Carbonyl" refers to the group C=O.

"Cyano" refers to the group —CN.

"Oxo" refers to the moiety =O.

"Nitro" refers to the group —NO$_2$.

"Thioalkyl" refers to the groups —S-alkyl.

"Alkylsulfonylamino" refers to the groups —R$^1$SO$_2$NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, or the R$_a$ and R$_b$ groups can be joined together with the nitrogen atom to form a heterocyclic or substituted heterocyclic ring and R$^1$ is an alkyl group.

"Carbonylalkoxy" refers to as used herein refers to the groups —C(O)O-alkyl, —C(O)O-substituted alkyl, —C(O)O-aryl, —C(O)O-substituted aryl, —C(O)O-alkenyl, —C(O)O-substituted alkenyl, —C(O)O-alkynyl, —C(O)O-substituted alkynyl, —C(O)O-heteroaryl, —C(O)O-substituted heteroaryl, —C(O)O-heterocyclic or —C(O)O-substituted heterocyclic.

"Geminal" refers to the relationship between two moieties that are attached to the same atom. For example, in the residue —CH$_2$—CHR$^1$R$^2$, R$^1$ and R$^2$ are geminal and R$^1$ may be referred to as a geminal R group to R$^2$ "Vicinal" refers to the relationship between two moieties that are attached to adjacent atoms. For example, in the residue —CHR$^1$—CH$_2$R$^2$, R$^1$ and R$^2$ are vicinal and R$^1$ may be referred to as a vicinal R group to R$^2$ A composition of "substantially pure" compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure S compound means that the composition contains no more than 15% or no more than 10% or no more than 5% or no more than 3% or no more than 1% of the R form of the compound.

Compounds of the Invention

Compounds according to the invention are detailed herein, including in the Brief Summary of the Invention and the appended claims. The invention includes the use of all of the compounds described herein, including any and all stereoisomers, salts and solvates of the compounds described as histamine receptor modulators.

The invention embraces compounds of the formula (I):

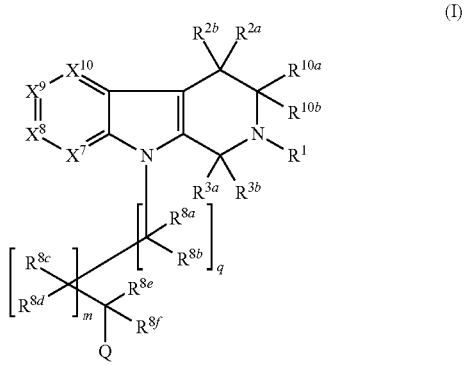

(I)

wherein:

R$^1$ is H, hydroxyl, nitro, cyano, halo, substituted or unsubstituted C$_1$-C$_8$ alkyl, substituted or unsubstituted C$_2$-C$_8$ alkenyl, substituted or unsubstituted C$_2$-C$_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, C$_1$-C$_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each R$^{2a}$ and R$^{2b}$ is independently H, substituted or unsubstituted C$_1$-C$_8$ alkyl, halo, cyano, hydroxyl, alkoxy, nitro or R$^{2a}$ and R$^{2b}$ are taken together to form a carbonyl moiety;

each R$^{3a}$ and R$^{3b}$ is independently H, substituted or unsubstituted C$_1$-C$_8$ alkyl, halo, cyano, nitro, hydroxyl, alkoxy, unsubstituted amino, substituted amino, cycloalkyl, acylamino or acyloxy or R$^{3a}$ and R$^{3b}$ are taken together to form a carbonyl moiety;

each X$^7$, X$^8$, X$^9$ and X$^{10}$ is independently N or CR$^4$;

m and q are independently 0 or 1;

each R$^4$ is independently H, hydroxyl, nitro, cyano, halo, C$_1$-C$_8$ perhaloalkyl, substituted or unsubstituted C$_1$-C$_8$ alkyl, substituted or unsubstituted C$_2$-C$_8$ alkenyl, substituted or unsubstituted C$_2$-C$_8$ alkynyl, substituted or unsubstituted aryl, substituted or unsubstituted heteroaryl, C$_1$-C$_8$ perhaloalkoxy, C$_1$-C$_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each R$^{8a}$, R$^{8b}$, R$^{8c}$, R$^{8d}$, R$^{8e}$ and R$^{8f}$ is independently H, hydroxyl, C$_1$-C$_8$ alkyl or is taken together with the carbon to which it is attached and a geminal R$_8$ to form a cycloalkyl moiety or a carbonyl moiety;

each R$^{10a}$ and R$^{10b}$ is independently H, halo, a substituted or unsubstituted C$_1$-C$_8$ alkyl, hydroxyl, alkoxyl or R$^{10a}$ and R$^{10b}$ are taken together to form a carbonyl;

Q is a substituted or unsubstituted aryl, substituted or unsubstituted heteroaryl, substituted or unsubstituted C$_{3-8}$ cycloalkyl, substituted or unsubstituted C$_{3-8}$ cycloalkenyl, substituted or a substituted unsubstituted heterocyclyl, unsubstituted amino, substituted amino, alkoxy, aminoacyl, acyloxy, carbonylalkoxy, aminocarbonylalkoxy or acylamino, provided that the compound is other than a compound in Table 1, or a salt or solvate thereof.

In one embodiment, compounds are of the formula (I) provided the compound is other than a compound in Table 1 or Table 1a.

Compounds of the general formula (I) are described as new histamine receptor modulators. Compounds of the invention may also find use in treating neurodegenerative diseases.

In another variation, the invention embraces compounds of the formula (I) or any variation herein, including any compound listed in Table 1 or a salt or solvate herein. In another variation, the invention embraces compounds of the formula (I) or any variation herein, including any compound listed in Table 1a or a salt or solvate herein. In a particular variation, the invention embraces methods of using compounds of the formula (I) or any variation herein, including any compound listed in Table 1 or a salt or solvate herein as detailed herein. In a particular variation, the invention embraces methods of using compounds of the formula (I) or any variation herein, including any compound listed in Table 1a or a salt or solvate herein as detailed herein.

TABLE 1

| No. | Compound Name |
|---|---|
| 1x | 9H-Pyrido[3,4-b]indole-9-carboxylic acid, 1,2,3,4-tetrahydro-4-hydroxy-3-(2-methylpropyl)-2-(2-propen-1-yl)-, 1,1-dimethylethyl ester, (3S,4S)- |
| 2x | 2H-Pyrido[3,4-b]indole-2-carboxamide, 1,3,4,9-tetrahydro-N-1H-indazol-3-yl-9-[2-(4-morpholinyl)ethyl]- |
| 4x | 1H-Pyrido[3,4-b]indole, 2,3,4,9-tetrahydro-9-(methoxymethyl)-2-[(2E)-1-oxo-2,4-pentadienyl]-1-(2-propenyl)-, (1R)- |
| 6x | 9H-Pyrido[3,4-b]indole-9-acetic acid, 1,2,3,4-tetrahydro-2-[(phenylmethoxy)carbonyl]-, 1,1-dimethylethyl ester |
| 7x | 1H-Pyrido[3,4-b]indole, 2,3,4,9-tetrahydro-9-(phenylmethyl)-2-[2-(2-pyridinyl)ethyl]- |
| 9x | 1H-Pyrido[3,4-b]indol-1-one, 6-butyl-2,9-bis[(4-fluorophenyl)methyl]-2,3,4,9-tetrahydro- |
| 10x | 1H-Pyrido[3,4-b]indol-1-one, 6-chloro-2,9-bis(4-chlorobenzoyl)-2,3,4,9-tetrahydro- |
| 11x | 1H-Pyrido[3,4-b]indole, 9-[3-[4-(3-chlorophenyl)-1-piperazinyl]propyl]-2,3,4,9-tetrahydro-2-[3-(3-pyridinyl)propyl]- |

TABLE 1-continued

| No. | Compound Name |
|---|---|
| 12x | 1H-Pyrido[3,4-b]indole, 2-[2,3:4,6-bis-O-(1-methylethylidene)-alpha-L-xylo-2-hexulofuranosonoyl]-9-(ethoxymethyl)-2,3,4,9-tetrahydro-1-methyl-, (1R)- |
| 13x | 1H-Pyrido[3,4-b]indole, 2,3,4,9-tetrahydro-2-(4-hydroxybenzoyl)-9-[(4-hydroxyphenyl)methyl]- |
| 15x | 1H-Pyrido[3,4-b]indole-1-acetonitrile, 2-(2-bromo-1-oxobutyl)-2,3,4,9-tetrahydro-9-(methoxymethyl)-, [S-(R*,R*)]- |
| 16x | 1H-Pyrido[3,4-b]indole, 3-ethyl-2,3,4,9-tetrahydro-9-[2-(6-methyl-3-pyridinyl)ethyl]- |
| 17x | 1H-Pyrido[3,4-b]indol-1-one, 2-butyl-2,3,4,9-tetrahydro-6-(methylsulfonyl)-9-(phenylmethyl)- |
| 18x | 1H-Pyrido[3,4-b]indole, 6-chloro-9-(4-chlorobenzoyl)-2,3,4,9-tetrahydro-2-(trifluoroacetyl)- |
| 21x | 1H-Pyrido[3,4-b]indole, 2,3,4,9-tetrahydro-2-(2-hydroxy-4-methylbenzoyl)-9-[(4-hydroxyphenyl)methyl]- |
| 23x | 4H-Pyrido[3,4-b]indol-4-one, 1-ethyl-1,2,3,9-tetrahydro-9-(phenylmethyl)- |
| 24x | 1H-Pyrido[3,4-b]indol-1-carbonitrile, 2-benzoyl-2,3,4,9-tetrahydro-1,9-bis(phenylmethyl)- |
| 25x | 1H-Pyrido[3,4-b]indol-1-one, 6-bromo-9-[(4-bromophenyl)methyl]-2,3,4,9-tetrahydro-2-(phenylmethyl)- |
| 26x | 9H-Pyrido[3,4-b]indole-9-carboxylic acid, 1,2,3,4-tetrahydro-2-[5-(methoxycarbonyl)-2-pyrimidinyl]-, 1,1-dimethylethyl ester |
| 27x | 1H-Pyrido[3,4-b]indole, 2-acetyl-2,3,4,9-tetrahydro-9-[2-[4-(2-methoxyphenyl)-1-piperazinyl]ethyl]- |
| 30x | Benz[cd]indol-2(1H)-one, 2a,3,4,5-tetrahydro-2a-[4-[1,3,4,9-tetrahydro-9-(methoxymethyl)-2H-pyrido[3,4-b]indol-2-yl]butyl]- |
| 32x | 1H-Pyrido[3,4-b]indol-1-one, 2-acetyl-2,3,4,9-tetrahydro-6-hydroxy-9-(2-piperidinoethyl)- |
| 34x | 1H-Pyrido[3,4-b]indol-1-one, 9-[3-(cyclopentylamino)-2-hydroxypropyl]-2,3,4,9-tetrahydro-2-methyl- |
| 35x | 1H-Pyrido[3,4-b]indole-2,9-dicarboxylic acid, 3,4-dihydro-1-[4-(phenylmethoxy)butyl]-, 9-(1,1-dimethylethyl) 2-methyl ester |
| 42x | 9H-Pyrido[3,4-b]indole-9-carboxylic acid, 1,2,3,4-tetrahydro-3-(1-methylethyl)-4-oxo-2-(2-propen-1-yl)-, 1,1-dimethylethyl ester, (3S)- |
| 43x | 1H-Pyrido[3,4-b]indole, 2,3,4,9-tetrahydro-9-(2-methoxyethyl)- |
| 45x | 9H-Pyrido[3,4-b]indole-9-acetic acid, 1,2,3,4-tetrahydro-2-(4-hydroxybenzoyl)-, methyl ester |
| 46x | 1H-Pyrido[3,4-b]indole-2,9-dicarboxylic acid, 3,4-dihydro-1-(2-oxoethyl)-,9-(1,1-dimethylethyl) 2-(phenylmethyl) ester, (1S)- |
| 47x | 2H-Pyrido[3,4-b]indole-2-carboxylic acid, 1,3,4,9-tetrahydro-9-(phenylmethyl)-, 1,1-dimethylethyl ester |
| 48x | 4-Piperidinol, 4-(4-chlorophenyl)-1-[3-[1,2,3,4-tetrahydro-2-[2-(2-pyridinyl)ethyl]-9H-pyrido[3,4-b]indol-9-yl]propyl]- |
| 50x | 1H-Pyrido[3,4-b]indol-1-one, 6-butyl-2,3,4,9-tetrahydro-2,9-bis[(4-methylphenyl)methyl]- |
| 51x | 1H-Pyrido[3,4-b]indol-1-one, 6-chloro-2,9-bis[(4-chlorophenyl)methyl]-2,3,4,9-tetrahydro- |
| 52x | 1H-Pyrido[3,4-b]indole, 2,3,4,9-tetrahydro-9-[3-[4-(2-methoxyphenyl)-1-piperazinyl]propyl]- |
| 53x | 1H-Pyrido[3,4-b]indole, 2-[2,3:4,6-bis-O-(1-methylethylidene)-alpha-L-xylo-2-hexulofuranosonoyl]-9-(ethoxymethyl)-2,3,4,9-tetrahydro-1-(2-phenylethyl)-, (1R)- |
| 54x | 1H-Pyrido[3,4-b]indole, 2,3,4,9-tetrahydro-2-(2-hydroxybenzoyl)-9-[(4-hydroxyphenyl)methyl]- |
| 56x | 1H-Pyrido[3,4-b]indole-1-acetonitrile, 2-[(2R)-2-bromo-1-oxobutyl]-2,3,4,9-tetrahydro-9-(methoxymethyl)-, (1S)- |
| 57x | 1H-Pyrido[3,4-b]indole, 3-heptyl-2,3,4,9-tetrahydro-9-[2-(6-methyl-3-pyridinyl)ethyl]- |
| 58x | 1H-Pyrido[3,4-b]indol-1-one, 9-[(4-bromophenyl)methyl]-2,3,4,9-tetrahydro-6-(methylsulfonyl)-2-(phenylmethyl)- |
| 59x | 1H-Pyrido[3,4-b]indole, 6-chloro-2,3,4,9-tetrahydro-9-(2-methoxybenzoyl)-2-(trifluoroacetyl)- |
| 65x | 1H-Pyrido[3,4-b]indole-1-carbonitrile, 2-(4-chloro-1-oxobutyl)-2,3,4,9-tetrahydro-9-(phenylmethyl)- |
| 66x | 1H-Pyrido[3,4-b]indol-1-one, 6-bromo-2-[(4-fluorophenyl)methyl]-2,3,4,9-tetrahydro-9-[(4-methylphenyl)methyl]- |
| 67x | 9H-Pyrido[3,4-b]indole-9-carboxylic acid, 1,2,3,4-tetrahydro-2-[5-(3-methoxy-3-oxopropyl)-2-pyrimidinyl]-, 1,1-dimethylethyl ester |
| 71x | 9H-Pyrido[3,4-b]indole-9-carboxamide, N,N-diethyl-1,2,3,4-tetrahydro-2-[4-(1,2,4,5-tetrahydro-2-oxobenz[cd]indol-2a(3H)-yl)butyl]- |
| 74x | 1H-Pyrido[3,4-b]indole-4-acetaldehyde, 2,3,4,9-tetrahydro-2-[(4-methylphenyl)sulfonyl]-9-(phenylmethyl)-, (4R)- |
| 75x | 9H-Pyrido[3,4-b]indole-9-carboxylic acid, 1,2,3,4-tetrahydro-3-[(1S)-1-methylpropyl]-4-oxo-, 1,1-dimethylethyl ester, (3S)- |
| 76x | 9H-Pyrido[3,4-b]indole-9-carboxylic acid, 1,2,3,4-tetrahydro-1-(4-hydroxybutyl)-2-methyl-, 1,1-dimethylethyl ester |
| 81x | 1H-Pyrido[3,4-b]indole, 2,3,4,9-tetrahydro-9-(2-isopropoxyethyl)-3-methyl- |
| 83x | 1H-Pyrido[3,4-b]indol-1-one, 2,9-bis[(4-fluorophenyl)methyl]-2,3,4,9-tetrahydro-6-methoxy- |
| 84x | 1H-Pyrido[3,4-b]indole, 9-benzyl-2,3,4,9-tetrahydro-1-methyl- |
| 86x | 1H-Pyrido[3,4-b]indole, 9-[(4-aminophenyl)methyl]-2,3,4,9-tetrahydro-2-(4-hydroxybenzoyl)- |
| 88x | 2H-Pyrido[3,4-b]indole-2-butanoic acid, 1,3,4,9-tetrahydro-gamma-oxo-9-(phenylmethyl)-1-(tricyclo[3.3.1.13,7]dec-1-ylmethyl)-, phenylmethyl ester |
| 91x | 1H-Pyrido[3,4-b]indol-1-one, 9-[(4-bromophenyl)methyl]-6-butyl-2,3,4,9-tetrahydro-2-(phenylmethyl)- |
| 92x | 1H-Pyrido[3,4-b]indol-1-one, 2,9-dibenzoyl-6-chloro-2,3,4,9-tetrahydro- |
| 93x | 1H-Pyrido[3,4-b]indole, 2,3,4,9-tetrahydro-9-[2-[4-(2-methoxyphenyl)-1-piperazinyl]ethyl]-2-(1-oxo-2-propenyl)- |
| 95x | 1H-Pyrido[3,4-b]indole, 2-[(6-amino-3-pyridinyl)carbonyl]-2,3,4,9-tetrahydro-9-[(4-hydroxyphenyl)methyl]- |
| 98x | 1H-Pyrido[3,4-b]indole, 2,3,4,9-tetrahydro-3-(2-methylpropyl)-9-[2-(6-methyl-3-pyridinyl)ethyl]- |
| 99x | 1H-Pyrido[3,4-b]indole, 2,3,4,9-tetrahydro-2-benzoyl-6-(methylsulfonyl)-9-(phenylmethyl)- |
| 100x | 1H-Pyrido[3,4-b]indole, 6-chloro-2,3,4,9-tetrahydro-9-(1-naphthalenylcarbonyl)-2-(trifluoroacetyl)- |
| 101x | 1H-Pyrido[3,4-b]indol-1-one, 2-acetyl-9-[3-[4-(3-chlorophenyl)-1-piperazinyl]propyl]-2,3,4,9-tetrahydro- |
| 103x | 2H-Pyrido[3,4-b]indole-2-carboxylic acid, 9-[(4-fluorophenyl)methyl]-1,3,4,9-tetrahydro-, phenylmethyl ester |
| 105x | 2H-Pyrido[3,4-b]indole-2-ethanol, 1,3,4,9-tetrahydro-1-methyl-beta-phenyl-9-(phenylmethyl)-, [S-(R*,S*)]- |
| 107x | 1H-Pyrido[3,4-b]indol-1-one, 2,3,4,9-tetrahydro-2,9-bis[(4-methylphenyl)methyl]-6-(trifluoromethoxy)- |
| 109x | 1H-Pyrido[3,4-b]indol-1-one, 9-[3-(1,1-dioxido-3-oxo-1,2-benzisothiazol-2(3H)-yl)-2-hydroxypropyl]-2,3,4,9-tetrahydro-2-methyl- |
| 112x | 2H-Pyrido[3,4-b]indole-2-carboxylic acid, 1,3,4,9-tetrahydro-9-[(methylamino)carbonyl]-, 1,1-dimethylethyl ester |
| 116x | 9H-Pyrido[3,4-b]indole-9-carboxylic acid, 1,2,3,4-tetrahydro-4-hydroxy-3-methyl-4-(phenylmethyl)-, 1,1-dimethylethyl ester, (3S,4S)- |
| 117x | 1H-Pyrido[3,4-b]indole, 2-(benzoyl-d5)-9-[(4-fluorophenyl)methyl]-2,3,4,9-tetrahydro- |
| 121x | Benzeneacetamide, alpha-cyclopentyl-N-(2-hydroxy-1-phenylethyl)-4-[(1,2,3,4-tetrahydro-2-methyl-1-oxo-9H-pyrido[3,4-b]indol-9-yl)methyl]- |
| 122x | 1H-Pyrido[3,4-b]indole, 9-(2-tert-butoxyethyl)-2,3,4,9-tetrahydro-3-methyl- |
| 124x | 1H-Pyrido[3,4-b]indol-1-one, 2,9-bis[(4-bromophenyl)methyl]-2,3,4,9-tetrahydro-6-methoxy- |
| 126x | 1H-Pyrido[3,4-b]indol-1-one, 2,3,4,9-tetrahydro-9-[2-hydroxy-3-[(4-methylphenyl)amino]propyl]-2-methyl- |
| 127x | 1H-Pyrido[3,4-b]indole, 2,3,4,9-tetrahydro-9-[(4-hydroxyphenyl)methyl]-2-(4-methylbenzoyl)- |
| 129x | 9H-Pyrido[3,4-b]indole-9-carboxylic acid, 1,2,3,4-tetrahydro-3-(1-methylethyl)-4-oxo-2-(phenylsulfonyl)-, 1,1-dimethylethyl ester, (3S)- |
| 131x | 1H-Pyrido[3,4-b]indol-1-one, 2,3,4,9-tetrahydro-6-methoxy-2,9-bis(phenylmethyl)- |
| 132x | 1H-Pyrido[3,4-b]indol-1-one, 6-butyl-2,3,4,9-tetrahydro-2-(2-propen-1-yl)-9-[[4-(trifluoromethyl)phenyl]methyl]- |
| 133x | 2H-Pyrido[3,4-b]indole-2-carboxylic acid, 9-benzoyl-1,3,4,9-tetrahydro-, ethyl ester |
| 134x | 1H-Pyrido[3,4-b]indole, 2-benzoyl-2,3,4,9-tetrahydro-9-[2-[4-(2-methoxyphenyl)-1-piperazinyl]ethyl]- |
| 136x | 1H-Pyrido[3,4-b]indole, 2-(4-chlorobenzoyl)-2,3,4,9-tetrahydro-9-[(4-hydroxyphenyl)methyl]- |
| 138x | 1H-Pyrido[3,4-b]indole, 2,3,4,9-tetrahydro-9-(methoxymethyl)-2-(1-naphthalenylcarbonyl)-1-(2,4-pentadienyl)-, [S-(E)]- |
| 139x | 1H-Pyrido[3,4-b]indole, 2,3,4,9-tetrahydro-6-methoxy-9-[2-(6-methyl-3-pyridinyl)ethyl]-3-propyl- |
| 140x | 1H-Pyrido[3,4-b]indol-1-one, 9-[(4-chlorophenyl)methyl]-2,3,4,9-tetrahydro-2-(1-methylethyl)-6-(methylsulfonyl)-' |
| 141x | 1H-Pyrido[3,4-b]indole, 6-chloro-2,3,4,9-tetrahydro-9-(phenylmethyl)-2-(trifluoroacetyl)- |

TABLE 1-continued

| No. | Compound Name |
|---|---|
| 142x | 9H-Pyrido[3,4-b]indole-9-carboxylic acid, 2-[[3-bromo-1-[(1,1-dimethylethoxy)carbonyl]-1H-indol-2-yl]methyl]-3-(butoxymethyl)-1,2,3,4-tetrahydro-4-oxo-, 1,1-dimethylethyl ester, (3S)- |
| 143x | 1H-Pyrido[3,4-b]indole, 2,3,4,9-tetrahydro-6-methoxy-9-(2-naphthalenylcarbonyl)- |
| 146x | 1H-Pyrido[3,4-b]indole-1-propanoic acid, 2,3,4,9-tetrahydro-2-methyl-9-(phenylmethyl)-, methyl ester |
| 147x | 1H-Pyrido[3,4-b]indole, 2,3,4,9-tetrahydro-9-(methoxymethyl)-1-methyl- |
| 148x | 1H-Pyrido[3,4-b]indol-1-one, 2,3,4,9-tetrahydro-2-propyl-6-(trifluoromethoxy)-9-[[4-(trifluoromethyl)phenyl]methyl]- |
| 149x | 5-Pyrimidinecarboxylic acid, 2-[1,3,4,9-tetrahydro-9-(phenylmethyl)-2H-pyrido[3,4-b]indol-2-yl]-, methyl ester |
| 150x | 2H-Pyrido[3,4-b]indole-2-propionic acid, 9-benzyl-1-(carboxymethyl)-1,3,4,9-tetrahydro-, diethyl ester |
| 153x | 9H-Pyrido[3,4-b]indole-9-acetic acid, 1,2,3,4-tetrahydro-2-[4-(1,2,4,5-tetrahydro-2-oxobenz[cd]indol-2a(3H)-yl)butyl]-, methyl ester |
| 156x | 1H-Pyrido[3,4-b]indole, 2-(4-butylbenzoyl)-9-(4-hydroxyphenyl)methyl-2,3,4,9-tetrahydro- |
| 157x | 9H-Pyrido[3,4-b]indole-9-carboxylic acid, 1,2,3,4-tetrahydro-4-hydroxy-3-[(1S)-1-methylpropyl]-4-(2-propen-1-yl)-, 1,1-dimethylethyl ester,(3S,4S)- |
| 158x | 1H-Pyrido[3,4-b]indol-1-one, 2,3,4,9-tetrahydro-9-[2-hydroxy-3-[[(tetrahydro-2-furanyl)methyl]amino]propyl]-2-methyl- |
| 161x | 9H-Pyrido[3,4-b]indole-9-acetamide, 1,2,3,4-tetrahydro- |
| 162x | Benzeneacetic acid, alpha-cyclopentyl-4-[(1,2,3,4-tetrahydro-2-methyl-1-oxo-9H-pyrido[3,4-b]indol-9-yl)methyl]-, 1,1-dimethylethyl ester |
| 163x | 2H-Pyrido[3,4-b]indole-2-carboxaldehyde, 1-ethyl-1,3,4,9-tetrahydro-4-oxo-9-(phenylmethyl)- |
| 165x | 1H-Pyrido[3,4-b]indol-1-one, 9-[(4-bromophenyl)methyl]-2-butyl-2,3,4,9-tetrahydro-6-methoxy- |
| 166x | 9H-Pyrido[3,4-b]indole-9-carboxylic acid, 1,2,3,4-tetrahydro-1-(1-methylethyl)-, 1,1-dimethylethyl ester, (1S)- |
| 167x | 1H-Pyrido[3,4-b]indol-1-one, 2,3,4,9-tetrahydro-9-[2-hydroxy-3-(4-morpholinyl)propyl]-2-methyl- |
| 168x | 1H-Pyrido[3,4-b]indole, 2,3,4,9-tetrahydro-2-(3-hydroxybenzoyl)-9-[(4-hydroxyphenyl)methyl]- |
| 171x | 1H-Pyrido[3,4-b]indol-1-one, 2-acetyl-2,3,4,9-tetrahydro-1-methyl-9-[(pentafluorophenyl)methyl]- |
| 172x | 1H-Pyrido[3,4-b]indol-1-ol, 9-[2-(dimethylamino)ethyl]-2,3,4,9-tetrahydro-7-methoxy- |
| 174x | 1H-Pyrido[3,4-b]indole, 6-chloro-2,3,4,9-tetrahydro-9-(4-nitrobenzoyl)-2-(trifluoroacetyl)- |
| 175x | 1H-Pyrido[3,4-b]indole, 2,3,4,9-tetrahydro-9-[3-(1-piperidinyl)propyl]-2-[3-(4-pyridinyl)propyl]- |
| 177x | 1H-Pyrido[3,4-b]indole, 2,3,4,9-tetrahydro-2-(4-hydroxybenzoyl)-9-[[4-(trifluoromethyl)phenyl]methyl]- |
| 179x | 1H-Pyrido[3,4-b]indole, 2,3,4,9-tetrahydro-9-(methoxymethyl)-2-(1-oxo-2-butenyl)-1-(4-oxo-2-butenyl)-, (E,E)- |
| 180x | 9H-Pyrido[3,4-b]indole-9-propanamine, 1,2,3,4-tetrahydro-N,N,1-trimethyl- |
| 181x | 1H-Pyrido[3,4-b]indol-1-one, 6-bromo-2,9-bis[(4-bromophenyl)methyl]-2,3,4,9-tetrahydro- |
| 182x | 2H-Pyrido[3,4-b]indole-2-propanoic acid, 9-[(1,1-dimethylethoxy)carbonyl]-1,3,4,9-tetrahydro-7-hydroxy-, 1,1-dimethylethyl ester |
| 183x | Phenol, 4-[(1,2,3,4-tetrahydro-9H-pyrido[3,4-b]indol-9-yl)methyl]- |
| 189x | 1H-Pyrido[3,4-b]indol-1-one, 6-chloro-2,9-bis[(4-fluorophenyl)methyl]-2,3,4,9-tetrahydro- |
| 191x | 1H-Pyrido[3,4-b]indol-1-one, 2,3,4,9-tetrahydro-2-methyl-3-[[(4-methylphenyl)thio]methyl]-9-(phenylmethyl)-, (3S) |
| 197x | 1H-Pyrido[3,4-b]indol-1-one, 9-benzyl-6-chloro-2-[3-(dimethylamino)propyl]-2,3,4,9-tetrahydro- |
| 199x | 1H-Pyrido[3,4-b]indole, 9-benzyl-2,3,4,9-tetrahydro-2-methyl- |
| 201x | 9H-Pyrido[3,4-b]indole-9-carboxylic acid, 1,2,3,4-tetrahydro-,2,2,2-trichloroethyl ester |
| 203x | 1H-Pyrido[3,4-b]indole, 2-[2-(3,4-dimethoxyphenyl)ethyl]-2,3,4,9-tetrahydro-6-methoxy-9-(4-nitrobenzoyl)- |
| 204x | 1H-Pyrido[3,4-b]indol-1-one, 2,3,4,9-tetrahydro-3-methyl-2,9-bis(phenylmethyl)- |
| 206x | 1H-Pyrido[3,4-b]indol-1-one, 2,3,4,9-tetrahydro-6-methoxy-2-propyl-9-[[4-(trifluoromethyl)phenyl]methyl]- |
| 208x | 1H-Pyrido[3,4-b]indol-1-one, 2,3,4,9-tetrahydro-9-[2-hydroxy-3-(1-piperidinyl)propyl]-2-methyl- |
| 209x | 1H-Pyrido[3,4-b]indole, 2-(3,5-dichloro-2-hydroxybenzoyl)-2,3,4,9-tetrahydro-9-[(4-hydroxyphenyl)methyl]- |
| 212x | 1H-Pyrido[3,4-b]indol-1-one, 9-(2-aminoethyl)-2,3,4,9-tetrahydro-6-methoxy-2-methyl- |
| 213x | 1H-Pyrido[3,4-b]indole, 3-butyl-2,3,4,9-tetrahydro-1-methyl-9-[2-(6-methyl-3-pyridinyl)ethyl]- |
| 214x | 1H-Pyrido[3,4-b]indol-1-one, 2,3,4,9-tetrahydro-6-(methylsulfonyl)-2,9-bis[[4-(trifluoromethyl)phenyl]methyl]- |
| 215x | 1H-Pyrido[3,4-b]indole, 6-chloro-2,3,4,9-tetrahydro-2-(trifluoroacetyl)-9-[2-(trifluoromethyl)benzoyl]- |
| 218x | 1H-Pyrido[3,4-b]indole, 2-(5-chloro-2-hydroxybenzoyl)-2,3,4,9-tetrahydro-9-[(4-hydroxyphenyl)methyl]- |
| 220x | 1H-Pyrido[3,4-b]indole, 2-acetyl-2,3,4,9-tetrahydro-9-(phenylmethyl)- |
| 221x | 1H-Pyrido[3,4-b]indole-1-carbonitrile, 2-benzoyl-2,3,4,9-tetrahydro-9-(phenylmethyl)- |
| 222x | 1H-Pyrido[3,4-b]indol-1-one, 6-bromo-2,3,4,9-tetrahydro-2,9-bis[(4-methylphenyl)methyl]- |
| 224x | 1H-Pyrido[3,4-b]indole, 2,3,4,9-tetrahydro-9-[3-(1-piperidinyl)propyl]-2-[2-(2-pyridinyl)ethyl]- |
| 227x | 2H-Pyrido[3,4-b]indole-2-carboxylic acid, 1,3,4,9-tetrahydro-9-(methoxymethyl)-, 1,1-dimethylethyl ester |
| 229x | 9H-Pyrido[3,4-b]indole-9-ethanamine, 1,2,3,4-tetrahydro-N,N,3-trimethyl- |
| 230x | 1H-Pyrido[3,4-b]indol-1-one, 9-[(4-bromophenyl)methyl]-6-chloro-2,3,4,9-tetrahydro-2-(phenylmethyl)- |
| 231x | 9H-Pyrido[3,4-b]indole-9-carboxylic acid, 1,2,3,4-tetrahydro-2-[5-[(1E)-3-methoxy-3-oxo-1-propenyl]-2-pyrimidinyl]-, 1,1-dimethylethyl ester |
| 232x | 1H-Pyrido[3,4-b]indol-1-one, 2,3,4,9-tetrahydro-9-[2-hydroxy-3-[4-(2-hydroxyethyl)-1-piperazinyl]propyl]-2-methyl- |
| 235x | 9H-Pyrido[3,4-b]indole-9-acetamide, 1,2,3,4-tetrahydro-N,N-dimethyl- |
| 238x | 1H-Pyrido[3,4-b]indol-1-one, 9-benzyl-2,3,4,9-tetrahydro-6-methoxy-2-[3-(1-pyrrolidinyl)propyl]- |
| 239x | 9H-Pyrido[3,4-b]indole-9-carboxylic acid, 1,2,3,4-tetrahydro-4-hydroxy-3-methyl-2-(2-propen-1-yl)-, 1,1-dimethylethyl ester, (3S,4S)- |
| 240x | 1H-Pyrido[3,4-b]indol-1-one, 2,3,4,9-tetrahydro-9-[2-hydroxy-3-[(2-hydroxyethyl)amino]propyl]-2-methyl- |
| 241x | 1H-Pyrido[3,4-b]indole-2,9-dicarboxylic acid, 3,4-dihydro-4-(2-oxo-2-phenylethyl)-, bis(1,1-dimethylethyl) ester |
| 242x | 9H-Pyrido[3,4-b]indole-9-carboxylic acid, 1,2,3,4-tetrahydro-2-[[(2R)-4-methyl-2-[(4R)-2-oxo-4-(phenylmethyl)-3-oxazolidinyl]pentyl]sulfonyl]-,2,2,2-trichloroethyl ester |
| 243x | 9H-Pyrido[3,4-b]indole-9-carboxamide, 1,2,3,4-tetrahydro-N-methyl- |
| 244x | 9H-Pyrido[3,4-b]indole-9-carboxylic acid, 2-acetyl-1,2,3,4-tetrahydro-6-methoxy-1-methylene-, ethyl ester |
| 247x | 1H-Pyrido[3,4-b]indol-1-one, 2,9-bis[(4-bromophenyl)methyl]-6-butyl-2,3,4,9-tetrahydro- |
| 248x | 1H-Pyrido[3,4-b]indol-1-one, 2,9-dibenzoyl-6-bromo-2,3,4,9-tetrahydro- |
| 249x | 1H-Pyrido[3,4-b]indol-1-one, 2,3,4,9-tetrahydro-9-[2-hydroxy-3-[(4-methoxyphenyl)amino]propyl]-2-methyl- |
| 250x | Benzeneacetamide, alpha-cyclopentyl-N-[(1R)-2-hydroxy-1-phenylethyl]-4-[(1,2,3,4-tetrahydro-2-methyl-1-oxo-9H-pyrido[3,4-b]indol-9-yl)methyl]- |
| 254x | 1H-Pyrido[3,4-b]indole, 3-butyl-2,3,4,9-tetrahydro-9-[2-(2-pyridinyl)ethyl]- |
| 255x | 1H-Pyrido[3,4-b]indol-1-one, 2,3,4,9-tetrahydro-6-(methylsulfonyl)-2-propyl-9-[[4-(trifluoromethyl)phenyl]methyl]- |
| 256x | 1H-Pyrido[3,4-b]indol-1-one, 6-chloro-9-(2-chlorobenzoyl)-2,3,4,9-tetrahydro-2-(trifluoroacetyl)- |
| 259x | 1H-Pyrido[3,4-b]indole, 2-(3,5-dichloro-4-hydroxybenzoyl)-9-[(4-fluorophenyl)methyl]-2,3,4,9-tetrahydro- |
| 262x | 1H-Pyrido[3,4-b]indole-1-carbonitrile, 2-benzoyl-2,3,4,9-tetrahydro-1-methyl-9-(phenylmethyl)- |
| 263x | 1H-Pyrido[3,4-b]indol-1-one, 6-bromo-2,9-bis[(2-fluorophenyl)methyl]-2,3,4,9-tetrahydro- |
| 265x | 1H-Pyrido[3,4-b]indole, 2-(cyclohexylcarbonyl)-2,3,4,9-tetrahydro-9-[3-[4-(2-methoxyphenyl)-1-piperazinyl]propyl]- |
| 268x | 2H-Pyrido[3,4-b]indole-2-carboxylic acid, 9-(2-amino-2-oxoethyl)-1,3,4,9-tetrahydro-, 1,1-dimethylethyl ester |
| 270x | 1H-Pyrido[3,4-b]indol-1-one, 2,3,4,9-tetrahydro-2-phenyl-9-(phenylmethyl)- |
| 271x | 1H-Pyrido[3,4-b]indol-1-one, 6-chloro-2,3,4,9-tetrahydro-9-[(4-nitrophenyl)methyl]-2-(phenylmethyl)- |
| 272x | 1H-Pyrido[3,4-b]indol-1-one, 9-[3-(azepan-1-yl)-2-hydroxypropyl]-2,3,4,9-tetrahydro-2-methyl- |

TABLE 1-continued

| No. | Compound Name |
|---|---|
| 276x | 2H-Pyrido[3,4-b]indole-2-carboxylic acid, 9-[2-(acetyloxy)ethyl]-1,3,4,9-tetrahydro-, 1,1-dimethylethyl ester |
| 279x | 1H-Pyrido[3,4-b]indole, 2-acetyl-9-[3-(dimethylamino)propyl]-2,3,4,9-tetrahydro-6-methoxy- |
| 280x | 1H-Pyrido[3,4-b]indol-1-one, 9-[3-[(4-chlorophenyl)amino]-2-hydroxypropyl]-2,3,4,9-tetrahydro-2-methyl- |
| 282x | Propanedioic acid, [2-[9-[(1,1-dimethylethoxy)carbonyl]-2,3,4,9-tetrahydro-2-(2-iodo-2-butenyl)-1H-pyrido[3,4-b]indol-1-yl]ethylidene]-, dimethylester |
| 283x | 2H-Pyrido[3,4-b]indole-2-carboxylic acid, 9-[[(2S)-1-[[4-(1,1-dimethylpropyl)phenyl]sulfonyl]-2-pyrrolidinyl]carbonyl]-1,3,4,9-tetrahydro-1-(2-propenyl)-, 2,2,2-trichloroethyl ester, (1R)- |
| 284x | 1H-Pyrido[3,4-b]indole-2,9-dicarboxylic acid, 3,4-dihydro-1-(2-oxoethyl)-,9-(1,1-dimethylethyl) 2-(phenylmethyl) ester, (1R)- |
| 285x | 9H-Pyrido[3,4-b]indole-9-acetic acid, 1,2,3,4-tetrahydro-,1,1-dimethylethyl ester |
| 286x | 1H-Pyrido[3,4-b]indole, 9-[(4-fluorophenyl)methyl]-2,3,4,9-tetrahydro-2-[2-(2-pyridinyl)ethyl]- |
| 288x | 1H-Pyrido[3,4-b]indol-1-one, 6-butyl-2,3,4,9-tetrahydro-2,9-bis[(4-nitrophenyl)methyl]- |
| 289x | 2H-Pyrido[3,4-b]indole-2-carboxylic acid, 6-bromo-9-[(4-chlorophenyl)methyl]-1,3,4,9-tetrahydro-1,1-dimethyl-, ethyl ester |
| 290x | 1H-Pyrido[3,4-b]indol-1-one, 2,3,4,9-tetrahydro-6-methoxy-9-(phenylmethyl)-2-[3-(1-piperidinyl)propyl]- |
| 291x | 1H-Pyrido[3,4-b]indole, 2-[2,3:4,6-bis-O-(1-methylethylidene)-alpha-L-xylo-2-hexulofuranosonoyl]-9-(ethoxymethyl)-2,3,4,9-tetrahydro-1-(2-propenyl)-, (1R)- |
| 292x | 1H-Pyrido[3,4-b]indole, 2-benzoyl-2,3,4,9-tetrahydro-9-[(4-hydroxyphenyl)methyl]- |
| 295x | 1H-Pyrido[3,4-b]indole, 3-heptyl-2,3,4,9-tetrahydro-6-methoxy-9-[2-(6-methyl-3-pyridinyl)ethyl]- |
| 296x | 1H-Pyrido[3,4-b]indol-1-one, 9-[(4-bromophenyl)methyl]-2,3,4,9-tetrahydro-6-(methylsulfonyl)-2-propyl- |
| 297x | 1H-Pyrido[3,4-b]indole, 9-(2-bromobenzoyl)-6-chloro-2,3,4,9-tetrahydro-2-(trifluoroacetyl)- |
| 298x | 1H-Pyrido[3,4-b]indole, 2-benzoyl-2,3,4,9-tetrahydro-9-[3-[4-(2-methoxyphenyl)-1-piperazinyl]propyl]- |
| 303x | 1H-Pyrido[3,4-b]indole-1-carbonitrile, 2-benzoyl-1,9-bis[(4-bromophenyl)methyl]-2,3,4,9-tetrahydro- |
| 304x | 1H-Pyrido[3,4-b]indol-1-one, 6-bromo-9-[(4-fluorophenyl)methyl]-2,3,4,9-tetrahydro-2-(phenylmethyl)- |
| 305x | 9H-Pyrido[3,4-b]indole-9-carboxylic acid, 1,2,3,4-tetrahydro-2-[5-(hydroxymethyl)-2-pyrimidinyl]-, 1,1-dimethylethyl ester |
| 306x | 1H-Pyrido[3,4-b]indole, 2,3,4,9-tetrahydro-9-[3-[4-(2-methoxyphenyl)-1-piperazinyl]propyl]-2-(phenylacetyl)- |
| 309x | 9H-Pyrido[3,4-b]indole-9-acetamide, 1,2,3,4-tetrahydro-2-[4-(1,2,4,5-tetrahydro-2-oxobenz[cd]indol-2a(3H)-yl)butyl]- |
| 313x | 9H-Pyrido[3,4-b]indole-9-carboxylic acid, 4-ethyl-1,2,3,4-tetrahydro-4-hydroxy-3-(1-methylethyl)-2-(phenylsulfonyl)-, 1,1-dimethylethyl ester,(3S,4S)- |
| 314x | 1H-Pyrido[3,4-b]indole-2,9-dicarboxylic acid, 3,4-dihydro-1-(4-oxobutyl)-,9-(1,1-dimethylethyl) 2-methyl ester |
| 320x | 1H-Pyrido[3,4-b]indole, 9-[3-(dimethylamino)propyl]-2,3,4,9-tetrahydro-6-methoxy-2-methyl- |
| 321x | 9H-Pyrido[3,4-b]indole-9-carboxylic acid, 1,2,3,4-tetrahydro-3-(2-methylpropyl)-4-oxo-2-(2-propen-1-yl)-, 1,1-dimethylethyl ester, (3S)- |
| 322x | 1H-Pyrido[3,4-b]indole, 2,3,4,9-tetrahydro-9-[2-(4-morpholinyl)ethyl]- |
| 323x | 2,6-Octadien-1-ol, 8-[2,3,4,9-tetrahydro-9-(methoxymethyl)-1H-pyrido[3,4-b]indol-1-yl]-, acetate (ester), (2E,6E)- |
| 324x | 1H-Pyrido[3,4-b]indole, 2,3,4,9-tetrahydro-2-(4-hydroxybenzoyl)-9-(phenylmethyl)- |
| 326x | 2H-Pyrido[3,4-b]indole-2-carboxamide, 1,3,4,9-tetrahydro-N-(3-methylphenyl)-9-(phenylmethyl)- |
| 329x | 1H-Pyrido[3,4-b]indol-1-one, 6-butyl-2,3,4,9-tetrahydro-2,9-bis(phenylmethyl)- |
| 330x | 1H-Pyrido[3,4-b]indol-1-one, 6-chloro-2,3,4,9-tetrahydro-2,9-bis(4-methoxybenzoyl)- |
| 333x | 1H-Pyrido[3,4-b]indole, 2-(1H-benzimidazol-5-ylcarbonyl)-2,3,4,9-tetrahydro-9-[(4-hydroxyphenyl)methyl]- |
| 336x | 1H-Pyrido[3,4-b]indole, 3-hexyl-2,3,4,9-tetrahydro-9-[2-(6-methyl-3-pyridinyl)ethyl]- |
| 337x | 1H-Pyrido[3,4-b]indol-1-one, 9-[(4-chlorophenyl)methyl]-2,3,4,9-tetrahydro-6-(methylsulfonyl)-2-(phenylmethyl)- |
| 338x | 1H-Pyrido[3,4-b]indole, 6-chloro-2,3,4,9-tetrahydro-9-(3-methoxybenzoyl)-2-(trifluoroacetyl)- |
| 339x | 9H-Pyrido[3,4-b]indole-9-propanamine, 1,2,3,4-tetrahydro-N,N-dimethyl-2-[3-(4-pyridinyl)propyl]- |
| 341x | 2H-Pyrido[3,4-b]indole-2-carboxylic acid, 1,3,4,9-tetrahydro-9-[[4-(trifluoromethyl)phenyl]methyl]-, phenylmethyl ester |
| 343x | 1H-Pyrido[3,4-b]indole, 2,3,4,9-tetrahydro-1-methyl-9-(phenylmethyl)-, (S)- |
| 345x | 1H-Pyrido[3,4-b]indol-1-one, 2,3,4,9-tetrahydro-2,9-bis(phenylmethyl)-6-(trifluoromethoxy)- |
| 346x | 5-Pyrimidinecarboxylic acid, 2-[1,3,4,9-tetrahydro-9-[2-(1-pyrrolidinyl)ethyl]-2H-pyrido[3,4-b]indol-2-yl]-, methyl ester |
| 347x | 1H-Pyrido[3,4-b]indole, 9-[2-[4-(3-chlorophenyl)-1-piperazinyl]ethyl]-2,3,4,9-tetrahydro- |
| 350x | 9H-Pyrido[3,4-b]indole-9-carboxamide, 1,2,3,4-tetrahydro-2-[4-(1,2,4,5-tetrahydro-2-oxobenz[cd]indol-2a(3H)-yl)butyl]- |
| 353x | 9H-Pyrido[3,4-b]indole-9-carboxylic acid, 1,2,3,4-tetrahydro-6-methoxy-2,4,4-trimethyl-1-oxo-, 1,1-dimethylethyl ester |
| 354x | 9H-Pyrido[3,4-b]indole-9-carboxylic acid, 1,2,3,4-tetrahydro-3-(2-methylpropyl)-4-oxo-, 1,1-dimethylethyl ester, (3S)- |
| 355x | 9H-Pyrido[3,4-b]indole-9-carboxylic acid, 1,2,3,4-tetrahydro-2-[(4-methylphenyl)sulfonyl]-1-(4-oxobutyl)-, 1,1-dimethylethyl ester |
| 360x | 1H-Pyrido[3,4-b]indole, 2,3,4,9-tetrahydro-9-(2-isobutoxyethyl)-3-methyl- |
| 361x | 9H-Pyrido[3,4-b]indole-9-propanamine, N,N-diethyl-1,2,3,4-tetrahydro-6-methoxy- |
| 362x | 1H-Pyrido[3,4-b]indol-1-one, 2,3,4,9-tetrahydro-6-methoxy-2,9-bis[[4-(trifluoromethyl)phenyl]methyl]- |
| 364x | 1H-Pyrido[3,4-b]indole, 9-([1,1'-biphenyl]-4-ylcarbonyl)-2,3,4,9-tetrahydro-6-methoxy-2-methyl- |
| 365x | 1H-Pyrido[3,4-b]indole, 2,3,4,9-tetrahydro-2-(4-hydroxybenzoyl)-9-[[4-(methylsulfonyl)phenyl]methyl]- |
| 366x | 9H-Pyrido[3,4-b]indole-9-carboxamide, 1,2,3,4-tetrahydro-N,N-dimethyl-2-[4-[(2aS)-1,2,4,5-tetrahydro-4-oxobenz[cd]indol-2a(3H)-yl]butyl]- |
| 367x | 9H-Pyrido[3,4-b]indole-9-carboxylic acid, 1,2,3,4-tetrahydro-3-methyl-4-oxo-2-(phenylsulfonyl)-, 1,1-dimethylethyl ester, (3S)- |
| 369x | 1H-Pyrido[3,4-b]indole, 9,9'-methylenebis[2,3,4,9-tetrahydro-2-methyl- |
| 370x | 1H-Pyrido[3,4-b]indol-1-one, 6-butyl-9-[(3-fluorophenyl)methyl]-2,3,4,9-tetrahydro-2-(2-propen-1-yl)- |
| 371x | 1H-Pyrido[3,4-b]indole, 9-benzoyl-6-chloro-2,3,4,9-tetrahydro-2-(trifluoroacetyl)- |
| 372x | 1H-Pyrido[3,4-b]indole-1-acetic acid, 2,3,4,9-tetrahydro-9-(phenylmethyl)-, ethyl ester |
| 373x | 9H-Pyrido[3,4-b]indole-9-carboxamide, 1,2,3,4-tetrahydro-N,N-dimethyl- |
| 374x | 1H-Pyrido[3,4-b]indole, 2,3,4,9-tetrahydro-9-[(4-hydroxyphenyl)methyl]-2-[4-(methylamino)benzoyl]- |
| 376x | 1H-Pyrido[3,4-b]indole, 2,3,4,9-tetrahydro-9-(methoxymethyl)-1-(2,4-pentadienyl)-, [S-(E)]- |
| 377x | 1H-Pyrido[3,4-b]indole, 2,3,4,9-tetrahydro-6-methyl-3-(3-methylbutyl)-9-[2-(6-methyl-3-pyridinyl)ethyl]- |
| 378x | 1H-Pyrido[3,4-b]indol-1-one, 9-[(4-chlorophenyl)methyl]-2,3,4,9-tetrahydro-6-(methylsulfonyl)-2-propyl- |
| 379x | 1H-Pyrido[3,4-b]indole, 6-chloro-2,3,4,9-tetrahydro-9-(2-naphthalenylcarbonyl)-2-(trifluoroacetyl)- |
| 380x | 9H-Pyrido[3,4-b]indole-9-carboxylic acid, 2-[(2-bromophenyl)methyl]-1,2,3,4-tetrahydro-3-methyl-4-oxo-, 1,1-dimethylethyl ester, (3S)- |
| 386x | 1H-Pyrido[3,4-b]indol-1-one, 2,3,4,9-tetrahydro-6-(trifluoromethoxy)-2,9-bis[[4-(trifluoromethyl)phenyl]methyl]- |
| 387x | 5-Pyrimidinecarboxylic acid, 2-[1,3,4,9-tetrahydro-9-[2-(4-morpholinyl)ethyl]-2H-pyrido[3,4-b]indol-2-yl]- |
| 388x | 1H-Pyrido[3,4-b]indol-1-one, 9-[3-(benztriazol-1(1H)-yl)-2-hydroxypropyl]-2,3,4,9-tetrahydro-2-methyl- |
| 391x | 9H-Pyrido[3,4-b]indole-9-carboxamide, 1,2,3,4-tetrahydro-N-methyl-2-[4-(1,2,4,5-tetrahydro-2-oxobenz[cd]indol-2a(3H)-yl)butyl]- |
| 394x | 1H-Pyrido[3,4-b]indol-1-one, 9-[3-(3,5-dimethyl-1H-pyrazol-1-yl)-2-hydroxypropyl]-2,3,4,9-tetrahydro-2-methyl- |
| 395x | 9H-Pyrido[3,4-b]indole-9-carboxylic acid, 1,2,3,4-tetrahydro-4-hydroxy-3-methyl-4-(2-propen-1-yl)-, 1,1-dimethylethyl ester, (3S,4S)- |
| 396x | 1H-Pyrido[3,4-b]indole, 2-(4-bromobenzoyl)-9-[(4-cyanophenyl)methyl]-2,3,4,9-tetrahydro- |
| 399x | 9H-Pyrido[3,4-b]indole-9-carboxylic acid, 1,2,3,4-tetrahydro-, methyl ester |
| 400x | Benzeneacetamide, alpha-cyclopentyl-N-(phenylmethyl)-4-[(1,2,3,4-tetrahydro-2-methyl-1-oxo-9H-pyrido[3,4-b]indol-9-yl)methyl]- |

TABLE 1-continued

| No. | Compound Name |
|---|---|
| 403x | 1H-Pyrido[3,4-b]indol-1-one, 9-[(4-bromophenyl)methyl]-2,3,4,9-tetrahydro-6-methoxy-2-(phenylmethyl)- |
| 405x | 1H-Pyrido[3,4-b]indol-1-one, 9-[3-(di-2-propenylamino)-2-hydroxypropyl]-2,3,4,9-tetrahydro-2-methyl- |
| 406x | 1H-Pyrido[3,4-b]indole, 2-(2,4-dichlorobenzoyl)-2,3,4,9-tetrahydro-9-[(4-hydroxyphenyl)methyl]- |
| 410x | 1H-Pyrido[3,4-b]indol-1-one, 2,3,4,9-tetrahydro-2-methyl-9-(phenylmethyl)- |
| 411x | 1H-Pyrido[3,4-b]indol-1-one, 2,3,4,9-tetrahydro-6-(methylthio)-2,9-bis(phenylmethyl)- |
| 412x | 1H-Pyrido[3,4-b]indole-2,9-dicarboxylic acid, 3,4-dihydro-, 2-ethyl9-phenyl ester |
| 413x | 1H-Pyrido[3,4-b]indole, 9-[3-[4-(3-chlorophenyl)-1-piperazinyl]propyl]-2,3,4,9-tetrahydro-2-[2-(2-pyridinyl)ethyl]- |
| 415x | 1H-Pyrido[3,4-b]indole, 2-(3,5-dichloro-4-hydroxybenzoyl)-2,3,4,9-tetrahydro-9-[(4-hydroxyphenyl)methyl]- |
| 417x | 1H-Pyrido[3,4-b]indole, 2,3,4,9-tetrahydro-9-(methoxymethyl)-2-(1-oxo-2,4-pentadienyl)-1-(2-propenyl)-, [S-(E)]- |
| 418x | 1H-Pyrido[3,4-b]indole, 2,3,4,9-tetrahydro-6-methyl-9-[2-(6-methyl-3-pyridinyl)ethyl]-3-propyl- |
| 419x | 1H-Pyrido[3,4-b]indol-1-one, 2-butyl-9-[(4-chlorophenyl)methyl]-2,3,4,9-tetrahydro-6-(methylsulfonyl)- |
| 420x | 1H-Pyrido[3,4-b]indole, 2,3,4,9-tetrahydro-9-[2-hydroxy-3-(10H-phenothiazin-10-yl)propyl]-2-methyl- |
| 421x | 9H-Pyrido[3,4-b]indole-9-carboxylic acid, 2-[(3-bromo-2-thienyl)methyl]-1,2,3,4-tetrahydro-3-(1-methylethyl)-4-oxo-, 1,1-dimethylethyl ester,(3S)- |
| 422x | 1H-Pyrido[3,4-b]indole, 2,3,4,9-tetrahydro-6-methoxy-9-(2-naphthalenylmethyl)- |
| 425x | 1H-Pyrido[3,4-b]indole-1-propanal, 2,3,4,9-tetrahydro-2-methyl-9-(phenylmethyl)- |
| 426x | 1H-Pyrido[3,4-b]indole, 2,3,4,9-tetrahydro-9-(methoxymethyl)-1-(2-methylpropyl)- |
| 427x | 1H-Pyrido[3,4-b]indol-1-one, 6-chloro-2,3,4,9-tetrahydro-9-[(4-methylphenyl)methyl]-2-(phenylmethyl)- |
| 428x | 5-Pyrimidinecarboxylic acid, 2-[1,3,4,9-tetrahydro-9-(phenylmethyl)-2H-pyrido[3,4-b]indol-2-yl]- |
| 429x | Benzoic acid, 3,4,5-trimethoxy-, 3-(1,2,3,4-tetrahydro-9H-pyrido[3,4-b]indol-9-yl)propyl ester |
| 432x | 2H-Pyrido[3,4-b]indole-2-carboxylic acid, 1,3,4,9-tetrahydro-9-[2-(methylamino)-2-oxoethyl]-, 1,1-dimethylethyl ester |
| 435x | 1H-Pyrido[3,4-b]indol-1-one, 9-benzyl-2-[2-(dimethylamino)ethyl]-2,3,4,9-tetrahydro-6-methoxy- |
| 436x | 9H-Pyrido[3,4-b]indole-9-carboxylic acid, 4-(3-buten-1-yl)-1,2,3,4-tetrahydro-4-hydroxy-3-methyl-, 1,1-dimethylethyl ester, (3S,4S)- |
| 437x | 1H-Pyrido[3,4-b]indole, 9-(3-aminopropyl)-2,3,4,9-tetrahydro- |
| 438x | 1H-Pyrido[3,4-b]indole-2,9-dicarboxylic acid, 3,4-dihydro-4-methylene-1-oxo-, bis(1,1-dimethylethyl) ester |
| 439x | 9H-Pyrido[3,4-b]indole-9-carboxylic acid, 2-[[2-carboxy-2-[1-[(phenylmethoxy)carbonyl]-4-piperidinyl]ethyl]sulfonyl]-1,2,3,4-tetrahydro-, 9-(2,2,2-trichloroethyl) ester |
| 441x | Benzeneacetic acid, alpha-cyclopentyl-4-[(1,2,3,4-tetrahydro-2-methyl-1-oxo-9H-pyrido[3,4-b]indol-9-yl)methyl]- |
| 442x | 1H-Pyrido[3,4-b]indole, 2,3,4,9-tetrahydro-2,9-bis(phenylmethyl)- |
| 444x | 1H-Pyrido[3,4-b]indol-1-one, 2-butyl-2,3,4,9-tetrahydro-6-methoxy-9-[[4-(trifluoromethyl)phenyl]methyl]- |
| 445x | 9H-Pyrido[3,4-b]indole-9-carboxylic acid, 1,2,3,4-tetrahydro-1-(phenylmethyl)-, 1,1-dimethylethyl ester, (1S)- |
| 446x | 1H-Pyrido[3,4-b]indol-1-one, 2,3,4,9-tetrahydro-9-[2-hydroxy-3-(2-methyl-1H-benzimidazol-1-yl)propyl]-2-methyl- |
| 447x | 1H-Pyrido[3,4-b]indole, 2,3,4,9-tetrahydro-9-[(4-hydroxyphenyl)methyl]-2-(4-methoxybenzoyl)- |
| 449x | 1H-Pyrido[3,4-b]indole-2,9-dicarboxylic acid, 3,4-dihydro-4-oxo-, bis(1,1-dimethylethyl)ester |
| 451x | 1H-Pyrido[3,4-b]indole, 2,3,4,9-tetrahydro-9-[2-(6-methyl-3-pyridinyl)ethyl]-3-methyl- |
| 452x | 1H-Pyrido[3,4-b]indol-1-one, 2,9-bis[(4-bromophenyl)methyl]-2,3,4,9-tetrahydro-6-(methylsulfonyl)- |
| 453x | 1H-Pyrido[3,4-b]indole, 6-chloro-9-(3-cyanobenzoyl)-2,3,4,9-tetrahydro-2-(trifluoroacetyl)- |
| 456x | Benzoic acid, 4-[[1,2,3,4-tetrahydro-2-(4-hydroxybenzoyl)-9H-pyrido[3,4-b]indol-9-yl]methyl]-, methyl ester |
| 458x | 1H-Pyrido[3,4-b]indole, 2,3,4,9-tetrahydro-9-(phenylmethyl)- |
| 459x | 9H-Pyrido[3,4-b]indole-9-propanamine, 1-ethyl-1,2,3,4-tetrahydro-N,N-dimethyl- |
| 460x | 1H-Pyrido[3,4-b]indol-1-one, 6-bromo-2,3,4,9-tetrahydro-2,9-bis[[4-(trifluoromethyl)phenyl]methyl]- |
| 462x | 1H-Pyrido[3,4-b]indole, 2-acetyl-2,3,4,9-tetrahydro-9-[3-[4-(2-methoxyphenyl)-1-piperazinyl]propyl]- |
| 468x | 1H-Pyrido[3,4-b]indol-1-one, 6-chloro-2,3,4,9-tetrahydro-2,9-bis(phenylmethyl)- |
| 470x | 1H-Pyrido[3,4-b]indol-1-one, 2-ethyl-2,3,4,9-tetrahydro-3-[[(4-methylphenyl)thio]methyl]-9-(phenylmethyl)-, (3S)- |
| 473x | 9H-Pyrido[3,4-b]indole-9-acetamide, 1,2,3,4-tetrahydro-N-methyl-2-[4-(1,2,4,5-tetrahydro-2-oxobenz[cd]indol-2a(3H)-yl)butyl]- |
| 478x | 9H-Pyrido[3,4-b]indole-9-ethanol, 1,2,3,4-tetrahydro-,3,4,5-trimethoxybenzoate |
| 480x | 9H-Pyrido[3,4-b]indole-9-carboxylic acid, 1,2,3,4-tetrahydro-2-[[[tetrahydro-4-(methoxycarbonyl)-2H-pyran-4-yl]methyl]sulfonyl]-,2,2,2-trichloroethyl ester |
| 481x | 9H-Pyrido[3,4-b]indole-9-carboxamide, 1,2,3,4-tetrahydro- |
| 483x | 1H-Pyrido[3,4-b]indol-1-one, 2,3,4,9-tetrahydro-2,9-bis(phenylmethyl)- |
| 485x | 1H-Pyrido[3,4-b]indol-1-one, 2,3,4,9-tetrahydro-6-methoxy-2-(phenylmethyl)-9-[[4-(trifluoromethyl)phenyl]methyl]- |
| 486x | 1H-Pyrido[3,4-b]indol-1-one, 6-bromo-2,9-bis(3-chlorobenzoyl)-2,3,4,9-tetrahydro- |
| 487x | 1H-Pyrido[3,4-b]indol-1-one, 9-[3-(4,5-diphenyl-1H-imidazol-1-yl)-2-hydroxypropyl]-2,3,4,9-tetrahydro-2-methyl- |
| 488x | 1H-Pyrido[3,4-b]indole, 2,3,4,9-tetrahydro-2-(4-hydroxy-3,5-dimethylbenzoyl)-9-[(4-hydroxyphenyl)methyl]- |
| 492x | 1H-Pyrido[3,4-b]indole, 3-butyl-2,3,4,9-tetrahydro-9-[2-(6-methyl-3-pyridinyl)ethyl]- |
| 493x | 1H-Pyrido[3,4-b]indol-1-one, 2,3,4,9-tetrahydro-6-(methylsulfonyl)-2,9-bis(phenylmethyl)- |
| 494x | 1H-Pyrido[3,4-b]indole, 6-chloro-2,3,4,9-tetrahydro-2-(trifluoroacetyl)-9-[2-(trifluoromethoxy)benzoyl]- |
| 495x | 1H-Pyrido[3,4-b]indole, 2,3,4,9-tetrahydro-9-[2-[4-(2-methoxyphenyl)-1-piperazinyl]ethyl]- |
| 497x | 1H-Pyrido[3,4-b]indole, 9-[(4-fluorophenyl)methyl]-2,3,4,9-tetrahydro-2-(4-hydroxybenzoyl)- |
| 498x | 1H-Pyrido[3,4-b]indole, 2-(4-cyanobenzoyl)-9-[(3-cyanophenyl)methyl]-2,3,4,9-tetrahydro- |
| 500x | 1H-Pyrido[3,4-b]indole-1-carbonitrile, 2-[2-(chloromethyl)benzoyl]-2,3,4,9-tetrahydro-9-(phenylmethyl)- |
| 501x | 1H-Pyrido[3,4-b]indol-1-one, 6-bromo-2,9-bis[(3-fluorophenyl)methyl]-2,3,4,9-tetrahydro- |
| 503x | Benzoic acid, 4-[(1,2,3,4-tetrahydro-9H-pyrido[3,4-b]indol-9-yl)methyl]-,methyl ester |
| 506x | 2H-Pyrido[3,4-b]indole-2-carboxylic acid, 9-[(dimethyl-amino)carbonyl]-1,3,4,9-tetrahydro-, 1,1-dimethylethyl ester |
| 508x | 2-Butenoic acid, 3-methoxy-4-[2,3,4,9-tetrahydro-2,9-bis(phenylmethyl)-1H-pyrido[3,4-b]indol-1-yl]-, methyl ester |
| 509x | 1H-Pyrido[3,4-b]indol-1-one, 6-chloro-2,3,4,9-tetrahydro-9-[(4-methylphenyl)methyl]-2-propyl- |
| 510x | 1H-Pyrido[3,4-b]indol-1-one, 9-[3-(4-bromo-3,5-dimethyl-1H-pyrazol-1-yl)-2-hydroxypropyl]-2,3,4,9-tetrahydro-2-methyl- |
| 511x | 1H-Pyrido[3,4-b]indol-1-one, 9-[3-[bis(2-hydroxyethyl)amino]-2-hydroxypropyl]-2,3,4,9-tetrahydro-2-methyl- |
| 518x | 9H-Pyrido[3,4-b]indole-9-carboxylic acid, 1,2,3,4-tetrahydro-4-hydroxy-3-(1-methylethyl)-2-(2-propen-1-yl)-, 1,1-dimethylethyl ester, (3S,4S)- |
| 519x | 2H-Pyrido[3,4-b]indole-2-carboxamide, 1,3,4,9-tetrahydro-N-1H-indazol-3-yl-9-(2-methoxyethyl)- |
| 521x | 1H-Pyrido[3,4-b]indole-2,9-dicarboxylic acid, 3,4-dihydro-,2-(1,1-dimethylethyl) 9-(2,2,2-trichloroethyl) ester |
| 523x | Propanedioic acid, [2-[9-[(1,1-dimethylethoxy)carbonyl]-2,3,4,9-tetrahydro-2-(2-iodo-2-butenyl)-1H-pyrido[3,4-b]indol-1-yl]ethyl]-, dimethyl ester,(Z)- |
| 526x | 1H-Pyrido[3,4-b]indol-1-one, 6-butyl-2,3,4,9-tetrahydro-2,9-bis[[4-(trifluoromethyl)phenyl]methyl]- |
| 527x | 1H-Pyrido[3,4-b]indol-1-one, 6-chloro-2,3,4,9-tetrahydro-2,9-bis(3-methoxybenzoyl)- |
| 528x | 1H-Pyrido[3,4-b]indole, 9-[3-[4-(3-chlorophenyl)-1-piperazinyl]propyl]-2,3,4,9-tetrahydro- |
| 529x | 1H-Pyrido[3,4-b]indole, 2-[2,3,4,6-bis-O-(1-methylethylidene)-alpha-L-xylo-2-hexulofuranosonoyl]-9-(ethoxymethyl)-2,3,4,9-tetrahydro- |
| 530x | 1H-Pyrido[3,4-b]indole, 2-benzoyl-2,3,4,9-tetrahydro-9-[[4-(phenylmethoxy)phenyl]methyl]- |
| 533x | 1H-Pyrido[3,4-b]indole, 3-butyl-2,3,4,9-tetrahydro-9-[2-(4-pyridinyl)ethyl]- |
| 534x | 1H-Pyrido[3,4-b]indol-1-one, 2,3,4,9-tetrahydro-6-(methylsulfonyl)-9-(phenylmethyl)-2-propyl- |

TABLE 1-continued

| No. | Compound Name |
|---|---|
| 535x | 1H-Pyrido[3,4-b]indole, 6-chloro-9-(3-chlorobenzoyl)-2,3,4,9-tetrahydro-2-(trifluoroacetyl)- |
| 538x | 1H-Pyrido[3,4-b]indole, 2-(3-chloro-4-hydroxybenzoyl)-2,3,4,9-tetrahydro-9-[[4-(trifluoromethyl)phenyl]methyl]- |
| 540x | 2H-Pyrido[3,4-b]indole-2-carboxaldehyde, 1,3,4,9-tetrahydro-4-oxo-9-(phenylmethyl)- |
| 542x | 1H-Pyrido[3,4-b]indol-1-one, 6-bromo-2,3,4,9-tetrahydro-9-(phenylmethyl)-2-propyl- |
| 547x | 9H-Pyrido[3,4-b]indole-9-carboxylic acid, 1,2,3,4-tetrahydro-2-[4-(1,2,4,5-tetrahydro-2-oxobenz[cd]indol-2a(3H)-yl)butyl]-, methyl ester |
| 549x | 2H-Pyrido[3,4-b]indole-2-carboxaldehyde, 1,3,4,9-tetrahydro-1-oxo-9-(phenylmethyl)- |
| 550x | 1H-Pyrido[3,4-b]indol-1-one, 6-chloro-2,3,4,9-tetrahydro-2,9-bis[(4-nitrophenyl)methyl]- |
| 552x | 1H-Pyrido[3,4-b]indol-1-one, 2,3,4,9-tetrahydro-9-[2-hydroxy-3-[(phenylmethyl)amino]propyl]-2-methyl- |
| 555x | 9H-Pyrido[3,4-b]indole-9-ethanol, 1,2,3,4-tetrahydro-, acetate (ester) |
| 559x | 9H-Pyrido[3,4-b]indole-9-carboxylic acid, 1,2,3,4-tetrahydro-3-methyl-4-oxo-2-(2-propen-1-yl)-, 1,1-dimethylethyl ester, (3S)- |
| 562x | 2H-Pyrido[3,4-b]indole-2-carboxylic acid, 9-[[(2S)-1-[[4-(1,1-dimethylpropyl)phenyl]sulfonyl]-2-pyrrolidinyl]carbonyl]-1,3,4,9-tetrahydro-1-(2-propenyl)-, 2,2,2-trichloroethyl ester, (1S)- |
| 563x | 1H-Pyrido[3,4-b]indole-2,9-dicarboxylic acid, 1-[[(4R)-3-ethyltetrahydro-2-(4-methoxyphenoxy)-6-oxo-2H-pyran-4-yl]methyl]-3,4-dihydro-,9-(1,1-dimethylethyl) 2-(phenylmethyl) ester, (1R)- |
| 564x | 9H-Pyrido[3,4-b]indole-9-acetic acid, 1,2,3,4-tetrahydro-2-[[(3-methylphenyl)amino]carbonyl]-, 1,1-dimethylethyl ester |
| 565x | 1-Butanone, 1-[4-(1,1-dimethylethyl)phenyl]-4-[9-[(4-fluorophenyl)methyl]-1,3,4,9-tetrahydro-2H-pyrido[3,4-b]indol-2-yl]- |
| 567x | 1H-Pyrido[3,4-b]indol-1-one, 6-butyl-2,9-bis[(4-chlorophenyl)methyl]-2,3,4,9-tetrahydro- |
| 568x | 1H-Pyrido[3,4-b]indole-2,9-dicarboxylic acid, 6-chloro-3,4-dihydro-,diethyl ester |
| 569x | 9H-Pyrido[3,4-b]indole-9-propanamine, 1,2,3,4-tetrahydro-N,N-dimethyl-2-[3-(3-pyridinyl)propyl]- |
| 570x | 1H-Pyrido[3,4-b]indole, 2-[2,3:4,6-bis-O-(1-methylethylidene)-alpha-L-xylo-2-hexulofuranosonoyl]-9-(ethoxymethyl)-2,3,4,9-tetrahydro-1-phenylmethyl)-, (1R)- |
| 571x | 1H-Pyrido[3,4-b]indole, 2-(1,3-benzodioxol-5-ylcarbonyl)-2,3,4,9-tetrahydro-9-[(4-hydroxyphenyl)methyl]- |
| 573x | 1H-Pyrido[3,4-b]indole-1-acetonitrile, 2,3,4,9-tetrahydro-9-(methoxymethyl)-, (S)- |
| 574x | 1H-Pyrido[3,4-b]indole, 3-heptyl-2,3,4,9-tetrahydro-6-methyl-9-[2-(6-methyl-3-pyridinyl)ethyl]- |
| 575x | 1H-Pyrido[3,4-b]indol-1-one, 2-[(4-bromophenyl)methyl]-2,3,4,9-tetrahydro-6-(methylsulfonyl)-9-(phenylmethyl)- |
| 576x | 1H-Pyrido[3,4-b]indole, 9-(3-bromobenzoyl)-6-chloro-2,3,4,9-tetrahydro-2-(trifluoroacetyl)- |
| 577x | 1H-Pyrido[3,4-b]indole, 2,3,4,9-tetrahydro-9-[2-[4-(2-methoxyphenyl)-1-piperazinyl]ethyl]-2-(phenylacetyl)- |
| 579x | 2H-Pyrido[3,4-b]indole-2-carboxylic acid, 1,3,4,9-tetrahydro-9-[[4-(phenylmethoxy)phenyl]methyl]-, phenylmethyl ester |
| 582x | 1H-Pyrido[3,4-b]indole-1-carbonitrile, 1,1'-[1,4-phenylene-bis(methylene)]bis[2-benzoyl-2,3,4,9-tetrahydro-9-(phenylmethyl)- |
| 583x | 1H-Pyrido[3,4-b]indol-1-one, 6-bromo-2,3,4,9-tetrahydro-9-[(4-methylphenyl)methyl]-2-(phenylmethyl)- |
| 584x | 9H-Pyrido[3,4-b]indole-9-carboxylic acid, 2-(5-formyl-2-pyrimidinyl)-1,2,3,4-tetrahydro-, 1,1-dimethylethyl ester |
| 588x | 2H-Pyrido[3,4-b]indole-2-carboxylic acid, 9-[(diethyl-amino)carbonyl]-1,3,4,9-tetrahydro-, 1,1-dimethylethyl ester |
| 592x | 9H-Pyrido[3,4-b]indole-9-carboxylic acid, 1,2,3,4-tetrahydro-3-methyl-4-oxo-, 1,1-dimethylethyl ester, (3S)- |
| 593x | 9H-Pyrido[3,4-b]indole-9-carboxylic acid, 1,2,3,4-tetrahydro-1-(4-hydroxybutyl)-2-[(4-methylphenyl)sulfonyl]-, 1,1-dimethylethyl ester |
| 599x | 1H-Pyrido[3,4-b]indole, 2-benzyl-9-[3-(dimethylamino)propyl]-2,3,4,9-tetrahydro-6-methoxy- |
| 600x | 1H-Pyrido[3,4-b]indol-1-one, 2,3,4,9-tetrahydro-6-methoxy-2,9-bis[(4-methylphenyl)methyl]- |
| 601x | 1H-Pyrido[3,4-b]indole, 9-(2-dimethylaminoethyl)-2,3,4,9-tetrahydro-1,2-dimethyl- |
| 603x | 1H-Pyrido[3,4-b]indole, 2,3,4,9-tetrahydro-2-(4-hydroxybenzoyl)-9-[(3-hydroxyphenyl)methyl]- |
| 607x | 1H-Pyrido[3,4-b]indole-1-acetic acid, 9-benzyl-2,3,4,9-tetrahydro-, ethyl ester |
| 608x | 1H-Pyrido[3,4-b]indol-1-one, 6-butyl-2,9-bis[(3-fluorophenyl)methyl]-2,3,4,9-tetrahydro- |
| 609x | 1H-Pyrido[3,4-b]indol-1-one, 6-chloro-2,9-bis(2-chlorobenzoyl)-2,3,4,9-tetrahydro- |
| 610x | 1H-Pyrido[3,4-b]indole, 2-acetyl-9-[2-[4-(3-chlorophenyl)-1-piperazinyl]ethyl]-2,3,4,9-tetrahydro- |
| 611x | 1H-Pyrido[3,4-b]indole, 2,3,4,9-tetrahydro-9-(methoxymethyl)- |
| 612x | 1H-Pyrido[3,4-b]indole, 2-[(1,6-dihydro-6-oxo-3-pyridin-yl)carbonyl]-2,3,4,9-tetrahydro-9-[(4-hydroxyphenyl)methyl]- |
| 614x | 1H-Pyrido[3,4-b]indole, 2,3,4,9-tetrahydro-9-(methoxymethyl)-1-(2-propenyl)-, (S)- |
| 615x | 1H-Pyrido[3,4-b]indole, 2,3,4,9-tetrahydro-6-methyl-3-(2-methylpropyl)-9-[2-(6-methyl-3-pyridinyl)ethyl]- |
| 616x | 1H-Pyrido[3,4-b]indol-1-one, 2-[(4-chlorophenyl)methyl]-2,3,4,9-tetrahydro-6-(methylsulfonyl)-9-(phenylmethyl)- |
| 617x | 1H-Pyrido[3,4-b]indole, 6-chloro-2,3,4,9-tetrahydro-9-(4-methoxybenzoyl)-2-(trifluoroacetyl)- |
| 622x | 2H-Pyrido[3,4-b]indole-2-ethanol, 1,3,4,9-tetrahydro-1-methyl-beta-phenyl-9-(phenylmethyl)-, [R-(R*,R*)]- |
| 624x | 1H-Pyrido[3,4-b]indol-1-one, 2,9-bis[(4-bromophenyl)methyl]-2,3,4,9-tetrahydro-6-(trifluoromethoxy)- |
| 625x | 5-Pyrimidinecarboxylic acid, 2-[1,3,4,9-tetrahydro-9-[2-(1-piperidinyl)ethyl]-2H-pyrido[3,4-b]indol-2-yl]- |
| 626x | 1H-Pyrido[3,4-b]indole, 2-(cyclohexylcarbonyl)-2,3,4,9-tetrahydro-9-[2-[4-(2-methoxyphenyl)-1-piperazinyl]ethyl]- |
| 629x | 2H-Pyrido[3,4-b]indole-2-carboxylic acid, 9-(aminocarbonyl)-1,3,4,9-tetrahydro-, 1,1-dimethylethyl ester |
| 630x | 9H-Pyrido[3,4-b]indole-9-propanoic acid, 2-[(1,1-dimethylethoxy)carbonyl]-1,2,3,4-tetrahydro-, ethyl ester |
| 631x | 1H-Pyrido[3,4-b]indole, 2,3,4,9-tetrahydro-9-(methoxymethyl)-1-(phenylmethyl)-, (S)- |
| 633x | 9H-Pyrido[3,4-b]indole-9-carboxylic acid, 4-(1,1-dimethylethyl)-1,2,3,4-tetrahydro-4-hydroxy-3-methyl-, 1,1-dimethylethyl ester, (3S,4S)- |
| 634x | 1H-Pyrido[3,4-b]indole, 2-(4-chlorobenzoyl)-9-[(4-cyanophenyl)methyl]-2,3,4,9-tetrahydro- |
| 639x | 1H-Pyrido[3,4-b]indole, 9-(2-butoxyethyl)-2,3,4,9-tetrahydro-3-methyl- |
| 640x | 9H-Pyrido[3,4-b]indole-9-propanamine, 2-acetyl-N,N-diethyl-1,2,3,4-tetrahydro-6-methoxy- |
| 641x | 1H-Pyrido[3,4-b]indol-1-one, 2-benzoyl-9-[(4-bromophenyl)methyl]-2,3,4,9-tetrahydro-6-methoxy- |
| 642x | 1H-Pyrido[3,4-b]indole, 9-benzyl-2,3,4,9-tetrahydro-1,2-dimethyl- |
| 643x | 2H-Pyrido[3,4-b]indole-2-carboxaldehyde, 1,3,4,9-tetrahydro-9-[(4-methoxyphenyl)methyl]-4-oxo- |
| 644x | Benzoic acid, 4-[[1,2,3,4-tetrahydro-2-(4-hydroxybenzoyl)-9H-pyrido[3,4-b]indol-9-yl]methyl]- |
| 645x | 9H-Pyrido[3,4-b]indole-9-acetamide, 1,2,3,4-tetrahydro-N-methyl-2-[4-[(2aS)-1,2,4,5-tetrahydro-2-oxobenz[cd]indol-2a(3H)-yl]butyl]- |
| 646x | 9H-Pyrido[3,4-b]indole-9-carboxylic acid, 1,2,3,4-tetrahydro-3-(1-methylpropyl)-4-oxo-2-(phenylsulfonyl)-, 1,1-dimethylethyl ester, [S-(R*,R*)]- |
| 648x | 1H-Pyrido[3,4-b]indole, 2,3,4,9-tetrahydro-2-methyl-6-[(1,2,3,4-tetrahydro-2-methyl-9H-pyrido[3,4-b]indol-9-yl)methyl]- |
| 649x | 1H-Pyrido[3,4-b]indol-1-one, 6-butyl-9-[(4-chlorophenyl)methyl]-2,3,4,9-tetrahydro-2-(2-propen-1-yl)- |
| 650x | 9H-Pyrido[3,4-b]indole-9-carboxylic acid, 6-chloro-1,2,3,4-tetrahydro-2-(trifluoroacetyl)-, phenyl ester |
| 651x | 1H-Pyrido[3,4-b]indole, 2,3,4,9-tetrahydro-9-[3-(1-piperidinyl)propyl]-2-[3-(3-pyridinyl)propyl]- |
| 653x | 1H-Pyrido[3,4-b]indole, 2-(4-aminobenzoyl)-2,3,4,9-tetrahydro-9-[(4-hydroxyphenyl)methyl]- |
| 655x | 1H-Pyrido[3,4-b]indole, 2,3,4,9-tetrahydro-9-(methoxymethyl)-2-(1-naphthalenylcarbonyl)-1-(2-propenyl)-, (S)- |
| 656x | 1H-Pyrido[3,4-b]indole, 2,3,4,9-tetrahydro-3-(3-methylbutyl)-9-[2-(6-methyl-3-pyridinyl)ethyl]- |
| 657x | 1H-Pyrido[3,4-b]indol-1-one, 9-[(4-bromophenyl)methyl]-2,3,4,9-tetrahydro-2-(1-methylethyl)-6-(methylsulfonyl)- |
| 658x | 2H-Pyrido[3,4-b]indole-2-carboxylic acid, 6-chloro-1,3,4,9-tetrahydro-9-(phenylmethyl)-, ethyl ester |
| 659x | 9H-Pyrido[3,4-b]indole-9-carboxylic acid, 2-[[3-bromo-1-[(1,1-dimethylethoxy)carbonyl]-1H-indol-2-yl]methyl]-1,2,3,4-tetrahydro-3-(hydroxymethyl)-4-oxo-, 1,1-dimethylethyl ester, (3S)- |
| 661x | 2H-Pyrido[3,4-b]indole-2-carboxylic acid, 1,3,4,9-tetrahydro-9-[[4-(methoxycarbonyl)phenyl]methyl]-, phenylmethyl ester |
| 663x | 1H-Pyrido[3,4-b]indole-1-propanoic acid, 2,3,4,9-tetrahydro-2-methyl-9-(phenylmethyl)- |

TABLE 1-continued

| No. | Compound Name |
|---|---|
| 665x | 1H-Pyrido[3,4-b]indol-1-one, 2,9-bis[(4-fluorophenyl)methyl]-2,3,4,9-tetrahydro-6-(trifluoromethoxy)- |
| 667x | 1H-Pyrido[3,4-b]indol-1-one, 9-benzyl-2-[3-(dimethylamino)propyl]-2,3,4,9-tetrahydro-6-methoxy- |
| 670x | 9H-Pyrido[3,4-b]indole-9-acetic acid, 2-[(1,1-dimethylethoxy)carbonyl]-1,2,3,4-tetrahydro-, methyl ester |
| 673x | 1H-pyrido[1,2-a][1,5]diazocin-8(2H)-one, 3-(3-(2-methyl-1-oxo-3,4-dihydro-1H-pyrido[3,4-b]indol-9(2H)-yl)-2-hydroxypropyl)-1,5-methano-3,4,5,6-tetrahydro-, (1R,5S)- |
| 674x | 9H-Pyrido[3,4-b]indole-9-carboxylic acid, 1,2,3,4-tetrahydro-4-hydroxy-3-(1-methylethyl)-4-(2-propen-1-yl)-, 1,1-dimethylethyl ester, (3S,4S)- |
| 675x | 1H-Pyrido[3,4-b]indole, 9-(2-butynyl)-2-(4-chlorobenzoyl)-2,3,4,9-tetrahydro- |
| 679x | Benzeneacetamide, alpha-cyclopentyl-N-(2-hydroxy-1-phenylethyl)-4-[(1,2,3,4-tetrahydro-2-methyl-1-oxo-9H-pyrido[3,4-b]indol-9-yl)methyl]-,[R—(R*,R*)]- |
| 680x | 1H-Pyrido[3,4-b]indol-1,3(2H)-dione, 4,9-dihydro-2-methyl-9-(phenylmethyl)- |
| 681x | 1H-Pyrido[3,4-b]indol-1-one, 9-benzyl-2-[2-(dimethylamino)ethyl]-2,3,4,9-tetrahydro- |
| 682x | 1H-Pyrido[3,4-b]indol-1-one, 9-[(4-bromophenyl)methyl]-2,3,4,9-tetrahydro-6-methoxy-2-propyl- |
| 683x | 9H-Pyrido[3,4-b]indole-9-carboxylic acid, 1,2,3,4-tetrahydro-1-methyl-,1,1-dimethylethyl ester, (1S)- |
| 684x | 1H-Pyrido[3,4-b]indole, 9-[(4-fluorophenyl)methyl]-2,3,4,9-tetrahydro- |
| 685x | Benzoic acid, 4-[[1,3,4,9-tetrahydro-9-[(4-hydroxyphenyl)methyl]-2H-pyrido[3,4-b]indol-2-yl]carbonyl]-, methyl ester |
| 688x | 1H-Pyrido[3,4-b]indole, 2-acetyl-2,3,4,9-tetrahydro-9-[(pentafluorophenyl)methyl]- |
| 689x | 1H-Pyrido[3,4-b]indol-1-ol, 9-[2-(dimethylamino)ethyl]-2,3,4,9-tetrahydro- |
| 690x | 1H-Pyrido[3,4-b]indol-1-one, 2,9-bis[(4-bromophenyl)methyl]-2,3,4,9-tetrahydro-6-(methylthio)- |
| 691x | 1H-Pyrido[3,4-b]indole, 6-chloro-2,3,4,9-tetrahydro-9-(3-nitrobenzoyl)-2-(trifluoroacetyl)- |
| 694x | 1H-Pyrido[3,4-b]indole, 2-(3-chloro-4-hydroxybenzoyl)-2,3,4,9-tetrahydro-9-[(4-hydroxyphenyl)methyl]- |
| 696x | 9H-Pyrido[3,4-b]indole-9-carboxylic acid, 1,2,3,4-tetrahydro-2-(1-oxo-2-butenyl)-1-(4-oxo-2-butenyl)-, methyl ester, (E,E)- |
| 697x | 9H-Pyrido[3,4-b]indole-9-propanamine, 1,2,3,4-tetrahydro-N,N-dimethyl- |
| 698x | 1H-Pyrido[3,4-b]indol-1-one, 6-bromo-2,3,4,9-tetrahydro-2,9-bis(phenylmethyl)- |
| 700x | 9H-Pyrido[3,4-b]indole-9-carboxylic acid, 1,2,3,4-tetrahydro-3-(1-methylethyl)-4-oxo-, 1,1-dimethylethyl ester, (3S)- |
| 702x | 1H-Pyrido[3,4-b]indole, 2,3,4,9-tetrahydro-2,3-dimethyl-4-phenyl-9-(phenylmethyl)- |
| 704x | 1H-Pyrido[3,4-b]indole, 1-[2-(1,3-dioxolan-2-yl)ethyl]-2,3,4,9-tetrahydro-2-methyl-9-(phenylmethyl)- |
| 706x | 1H-Pyrido[3,4-b]indol-1-one, 2,9-bis[(4-bromophenyl)methyl]-6-chloro-2,3,4,9-tetrahydro- |
| 708x | 1H-Pyrido[3,4-b]indol-1-one, 2,3,4,9-tetrahydro-2-methyl-9-(3-phenylpropyl)- |
| 711x | 9H-Pyrido[3,4-b]indole-9-acetamide, 1,2,3,4-tetrahydro-N-methyl- |
| 715x | 9H-Pyrido[3,4-b]indole-9-carboxylic acid, 4-(3-buten-1-yl)-1,2,3,4-tetrahydro-4-hydroxy-3-(1-methylethyl)-, 1,1-dimethylethyl ester, (3S,4S)- |
| 716x | 1H-Pyrido[3,4-b]indole, 9-benzyl-2,3,4,9-tetrahydro-2-p-tolylsulfonyl- |
| 717x | 2H-Pyrido[3,4-b]indole-2-carboxylic acid, 1,3,4,9-tetrahydro-1-(1-methylethyl)-9-(phenylmethyl)-, (1R,2S,5R)-5-methyl-2-(1-methyl-1-phenylethyl)cyclohexyl ester, (1S)- |
| 719x | 9H-Pyrido[3,4-b]indole-9-carboxamide, N,N-diethyl-1,2,3,4-tetrahydro- |
| 720x | Benzeneacetamide, alpha-cyclopentyl-N-(2-hydroxy-1-phenylethyl)-4-[(1,2,3,4-tetrahydro-2-methyl-1-oxo-9H-pyrido[3,4-b]indol-9-yl)methyl]-,[R-(R*,S*)]- |
| 721x | 1H-Pyrido[3,4-b]indole, 2,3,4,9-tetrahydro-2-methyl-9-(phenylmethyl)- |
| 722x | 1H-Pyrido[3,4-b]indol-1-one, 9-benzyl-2,3,4,9-tetrahydro-6-methoxy-2-(3-piperidinopropyl)- |
| 723x | 1H-Pyrido[3,4-b]indol-1-one, 2-butyl-2,3,4,9-tetrahydro-6-methoxy-9-(phenylmethyl)- |
| 725x | 1H-Pyrido[3,4-b]indol-1-one, 9-[3-[[2-(3,4-dimethoxyphenyl)ethyl]amino]-2-hydroxypropyl]-2,3,4,9-tetrahydro-2-methyl- |
| 726x | 1H-Pyrido[3,4-b]indole, 2,3,4,9-tetrahydro-2-(4-hydroxy-3-methylbenzoyl)-9-[(4-hydroxyphenyl)methyl]- |
| 728x | 1H-Pyrido[3,4-b]indole-2,9-dicarboxylic acid, 3,4-dihydro-4-hydroxy-4-propyl-, bis(1,1-dimethylethyl) ester |
| 730x | 1H-Pyrido[3,4-b]indole, 2,3,4,9-tetrahydro-9-[2-(6-methyl-3-pyridinyl)ethyl]-3-propyl- |
| 731x | 1H-Pyrido[3,4-b]indol-1-one, 2,3,4,9-tetrahydro-2,9-bis[(4-methylphenyl)methyl]-6-(methylsulfonyl)- |
| 732x | 1H-Pyrido[3,4-b]indole, 6-chloro-9-(4-cyanobenzoyl)-2,3,4,9-tetrahydro-2-(trifluoroacetyl)- |
| 733x | 9H-Pyrido[3,4-b]indole-9-carboxylic acid, 1-ethyl-1,2,3,4-tetrahydro-2-propyl-, methyl ester |
| 735x | 1H-Pyrido[3,4-b]indole, 2-(4-chloro-2-hydroxybenzoyl)-2,3,4,9-tetrahydro-9-[(4-hydroxyphenyl)methyl]- |
| 738x | 1H-Pyrido[3,4-b]indol-1-one, 2-butyl-2,3,4,9-tetrahydro-9-(phenylmethyl)- |
| 739x | 1H-Pyrido[3,4-b]indol-1-one, 6-bromo-2,3,4,9-tetrahydro-2,9-bis[(4-nitrophenyl)methyl]- |
| 744x | Benz[cd]indol-2(1H)-one, 2a,3,4,5-tetrahydro-2a-[4-[1,3,4,9-tetrahydro-9-(phenylmethyl)-2H-pyrido[3,4-b]indol-2-yl]butyl]- |
| 746x | 1H-Pyrido[3,4-b]indol-1-one, 2,9-bis[2-(dimethylamino)ethyl]-2,3,4,9-tetrahydro-6-methoxy- |
| 747x | 1H-Pyrido[3,4-b]indol-1-one, 2-[(4-bromophenyl)methyl]-6-chloro-2,3,4,9-tetrahydro-9-[(4-methylphenyl)methyl]- |
| 749x | 1H-Pyrido[3,4-b]indol-1-one, 9-[3-(diethylamino)-2-hydroxypropyl]-2,3,4,9-tetrahydro-2-methyl- |
| 752x | 2H-Pyrido[3,4-b]indole-2-carboxylic acid, 9-[2-(dimethylamino)-2-oxoethyl]-1,3,4,9-tetrahydro-, 1,1-dimethylethyl ester |
| 755x | 1H-Pyrido[3,4-b]indol-1-one, 6-chloro-2-[2-(diethylamino)ethyl]-2,3,4,9-tetrahydro-9-phenethyl- |
| 756x | 9H-Pyrido[3,4-b]indole-9-carboxylic acid, 1,2,3,4-tetrahydro-4-hydroxy-3-(1-methylethyl)-2-(phenylsulfonyl)-, 1,1-dimethylethyl ester, (3S,4S)- |
| 757x | 1H-Pyrido[3,4-b]indole, 9-(2-ethoxyethyl)-2,3,4,9-tetrahydro-3-methyl- |
| 758x | 1H-Pyrido[3,4-b]indole-2,9-dicarboxylic acid, 4-[2-(4-chlorophenyl)-2-oxoethyl]-3,4-dihydro-, bis(1,1-dimethylethyl) ester |
| 759x | 9H-Pyrido[3,4-b]indole-9-carboxylic acid, 2-[[3-(1,1-dimethylethoxy)-3-oxo-2-[1-[(phenylmethoxy)carbonyl]-4-piperidinyl]propyl]sulfonyl]-1,2,3,4-tetrahydro-, 2,2,2-trichloroethyl ester |
| 761x | 4H-Pyrido[3,4-b]indole-4-one, 1,2,3,9-tetrahydro-9-(phenylmethyl)- |
| 762x | 1H-Pyrido[3,4-b]indole, 2,3,4,9-tetrahydro-9-(methoxymethyl)-1-[(3-methoxyphenyl)methyl]-, (S)- |
| 764x | 1H-Pyrido[3,4-b]indol-1-one, 2-[(4-bromophenyl)methyl]-2,3,4,9-tetrahydro-6-methoxy-9-(phenylmethyl)- |
| 765x | 1H-Pyrido[3,4-b]indol-1-one, 6-chloro-2,9-bis(3-chlorobenzoyl)-2,3,4,9-tetrahydro- |
| 767x | 1H-Pyrido[3,4-b]indole, 2-(2,4-dihydroxy-3,6-dimethylbenzoyl)-2,3,4,9-tetrahydro-9-[(4-hydroxyphenyl)methyl]- |
| 770x | 1H-Pyrido[3,4-b]indol-1-one, 9-[2-[bis(phenylmethyl)amino]ethyl]-2,3,4,9-tetrahydro-6-methoxy-2-methyl- |
| 771x | 1H-Pyrido[3,4-b]indole, 2,3,4,9-tetrahydro-3-(1-methylpropyl)-9-[2-(6-methyl-3-pyridinyl)ethyl]- |
| 772x | 1H-Pyrido[3,4-b]indol-1-one, 2,3,4,9-tetrahydro-9-[(4-methylphenyl)methyl]-6-(methylsulfonyl)-2-propyl- |
| 773x | 1H-Pyrido[3,4-b]indole, 6-chloro-2,3,4,9-tetrahydro-2-(trifluoroacetyl)-9-[3-(trifluoromethoxy)benzoyl]- |
| 774x | 1H-Pyrido[3,4-b]indole, 2,3,4,9-tetrahydro-9-[[4-(trifluoromethyl)phenyl]methyl]- |
| 776x | 1H-Pyrido[3,4-b]indole, 2-(3-chloro-4-hydroxybenzoyl)-9-[(4-fluorophenyl)methyl]-2,3,4,9-tetrahydro- |
| 779x | 1H-Pyrido[3,4-b]indole-1-carbonitrile, 2,9-dibenzoyl-2,3,4,9-tetrahydro- |
| 780x | 1H-Pyrido[3,4-b]indol-1-one, 6-bromo-2,9-bis[(4-fluorophenyl)methyl]-2,3,4,9-tetrahydro- |
| 782x | 1H-Pyrido[3,4-b]indole, 2,3,4,9-tetrahydro-9-[3-[4-(2-methoxyphenyl)-1-piperazinyl]propyl]-2-(1-oxo-2-propenyl)- |
| 785x | 9H-Pyrido[3,4-b]indole-9-carboxamide, 1,2,3,4-tetrahydro-N,N-dimethyl-2-[4-(1,2,4,5-tetrahydro-2-oxobenz[cd]indol-2a(3H)-yl)butyl]- |
| 788x | 1H-Pyrido[3,4-b]indol-1-one, 6-fluoro-2,3,4,9-tetrahydro-2,9-bis(phenylmethyl)- |
| 789x | 1H-Pyrido[3,4-b]indol-1-one, 2,3,4,9-tetrahydro-9-[2-hydroxy-3-(1-pyrrolidinyl)propyl]-2-methyl- |
| 793x | 9H-Pyrido[3,4-b]indole-9-acetamide, 1,2,3,4-tetrahydro-N,N-dimethyl-2-[4-(1,2,4,5-tetrahydro-2-oxobenz[cd]indol-2a(3H)-yl)butyl]- |

TABLE 1A

| No | Name |
|---|---|
| 450z | 9H-Pyrido[3,4-b]indole-9-acetic acid, 2-[(4-fluorophenyl)sulfonyl]-1,2,3,4-tetrahydro- |
| 451z | 1H-Pyrido[3,4-b]indole, 2,3,4,9-tetrahydro-1-phenyl-9-(phenylmethyl)-,(S)-(9CI) |
| 452z | 9H-Pyrido[3,4-b]indole-9-propanoic acid, 2-[(1,1-dimethylethoxy)carbonyl]-1,2,3,4-tetrahydro- |
| 453z | 2H-Pyrido[3,4-b]indole-2-ethanol, 1,3,4,9-tetrahydro-beta,1-diphenyl-9-(phenylmethyl)-, [S-(R*,S*)]-(9CI) |
| 454z | 9H-Pyrido[3,4-b]indole-9-acetic acid, 2-[(1,1-dimethylethoxy)carbonyl]-1,2,3,4-tetrahydro- |
| 455z | 9H-Pyrido[3,4-b]indole-9-acetic acid, 1,2,3,4-tetrahydro-2-(phenylsulfonyl)- |
| 456z | 1H-Pyrido[3,4-b]indole-5-carboxylic acid, 2,3,4,9-tetrahydro-4-oxo-2,9-bis(phenylmethyl)-, methyl ester |
| 457z | 1H-Pyrido[3,4-b]indol-1-one, 9-[3-(dimethylamino)propyl]-2,3,4,9-tetrahydro- |
| 458z | 1H-Pyrido[3,4-b]indol-1-one, 6-chloro-9-[3-(dimethylamino)propyl]-2,3,4,9-tetrahydro- |
| 459z | 1H-Pyrido[3,4-b]indol-1-one, 6-chloro-2,3,4,9-tetrahydro-9-[3-(4-methyl-1-piperazinyl)propyl]- |
| 460z | 1H-Pyrido[3,4-b]indol-1-one, 2,3,4,9-tetrahydro-6-(phenylmethoxy)-9-[2-(1-piperidinyl)ethyl]- |
| 461z | 1H-Pyrido[3,4-b]indol-1-one, 9-[3-(butylamino)propyl]-6-chloro-2,3,4,9-tetrahydro- |
| 462z | 1H-Pyrido[3,4-b]indol-1-one, 9-[2-(dimethylamino)ethyl]-2,3,4,9-tetrahydro-6-methoxy- |
| 463z | 1H-Pyrido[3,4-b]indol-1-one, 6-chloro-9-[2-(diethylamino)ethyl]-2,3,4,9-tetrahydro- |
| 464z | 1H-Pyrido[3,4-b]indol-1-one, 6-chloro-2,3,4,9-tetrahydro-9-[3-[4-(2-hydroxyethyl)-1-piperazinyl]propyl]- |
| 465z | 1H-Pyrido[3,4-b]indol-1-one, 9-[3-(dimethylamino)propyl]-2,3,4,9-tetrahydro-7-methoxy- |
| 466z | 1H-Pyrido[3,4-b]indol-1-one, 9-[3-(dimethylamino)propyl]-2,3,4,9-tetrahydro-6-methoxy- |
| 467z | 1H-Pyrido[3,4-b]indol-1-one, 9-[3-(dimethylamino)propyl]-2,3,4,9-tetrahydro-6-(phenylmethoxy)- |
| 468z | 1H-Pyrido[3,4-b]indol-1-one, 2,3,4,9-tetrahydro-9-(2-oxo-2-phenylethyl)-6-(phenylmethoxy)- |
| 469z | 1H-Pyrido[3,4-b]indol-1-one, 6-chloro-2,3,4,9-tetrahydro-9-[3-(1-piperidinyl)propyl]- |
| 470z | 1H-Pyrido[3,4-b]indol-1-one, 9-[2-(diethylamino)ethyl]-2,3,4,9-tetrahydro-6-(phenylmethoxy)- |
| 471z | 1H-Pyrido[3,4-b]indol-1-one, 2,3,4,9-tetrahydro-6-methoxy-9-[3-(1-pyrrolidinyl)propyl]- |
| 472z | 1H-Pyrido[3,4-b]indol-1-one, 9-[2-(dimethylamino)ethyl]-2,3,4,9-tetrahydro-6-hydroxy- |
| 473z | 1H-Pyrido[3,4-b]indol-1-one, 9-[3-(diethylamino)propyl]-2,3,4,9-tetrahydro-6-methoxy- |
| 474z | 1H-Pyrido[3,4-b]indol-1-one, 2,3,4,9-tetrahydro-6-methoxy-9-[3-(1-piperidinyl)propyl]- |
| 475z | 9H-Pyrido[3,4-b]indole-9-acetamide, 1,2,3,4-tetrahydro-1-oxo-N-phenyl- |
| 476z | 1H-Pyrido[3,4-b]indol-1-one, 2,3,4,9-tetrahydro-6-hydroxy-9-[2-(1-piperidinyl)ethyl]- |
| 477z | 1H-Pyrido[3,4-b]indol-1-one, 2,3,4,9-tetrahydro-6-methoxy-9-[3-(4-morpholinyl)propyl]- |
| 478z | 1H-Pyrido[3,4-b]indol-1-one, 9-[2-(dimethylamino)-1-methylethyl]-2,3,4,9-tetrahydro-6-(phenylmethoxy)- |
| 479z | 1H-Pyrido[3,4-b]indole-2,9-dipropanenitrile,3,4-dihydro-7-methoxy-1-methyl- |
| 480z | 1H-Pyrido[3,4-b]indol-1-one, 9-[3-(dimethylamino)propyl]-2,3,4,9-tetrahydro-6-methyl- |
| 481z | 1H-Pyrido[3,4-b]indol-1-one, 9-[(4-fluorophenyl)methyl]-2,3,4,9-tetrahydro-6-methoxy- |
| 482z | 1H-Pyrido[3,4-b]indol-1-one, 6-acetyl-9-[2-(dimethylamino)ethyl]-2,3,4,9-tetrahydro- |
| 483z | 1H-Pyrido[3,4-b]indol-1-one, 2,3,4,9-tetrahydro-6-methoxy-9-[(4-methylphenyl)methyl]- |
| 484z | 1H-Pyrido[3,4-b]indole-6-carboxylic acid,9-[3-(dimethylamino)propyl]-2,3,4,9-tetrahydro-1-oxo-, ethyl ester |
| 485z | 1H-Pyrido[3,4-b]indol-1-one, 9-[(4-bromophenyl)methyl]-2,3,4,9-tetrahydro-6-methoxy- |
| 486z | 1H-Pyrido[3,4-b]indol-1-one, 2,3,4,9-tetrahydro-6-methoxy-9-[(4-nitrophenyl)methyl]- |
| 487z | 1H-Pyrido[3,4-b]indol-1-one, 9-[(4-chlorophenyl)methyl]-2,3,4,9-tetrahydro-6-methoxy- |
| 488z | 1H-Pyrido[3,4-b]indol-1-one, 2,3,4,9-tetrahydro-6-methoxy-9-[[4-(trifluoromethyl)phenyl]methyl]- |
| 489z | 1H-Pyrido[3,4-b]indol-1-one, 6-bromo-9-[3-(dimethylamino)propyl]-2,3,4,9-tetrahydro- |
| 490z | 1H-Pyrido[3,4-b]indol-1-one, 9-[(4-bromophenyl)methyl]-6-butyl-2,3,4,9-tetrahydro- |
| 491z | 1H-Pyrido[3,4-b]indol-1-one, 9-[3-(dimethylamino)propyl]-6-fluoro-2,3,4,9-tetrahydro- |
| 492z | 1H-Pyrido[3,4-b]indol-1-one, 6-butyl-2,3,4,9-tetrahydro-9-[[4-(trifluoromethyl)phenyl]methyl]- |
| 493z | 2H-Pyrido[3,4-b]indole-2-carboxylic acid,9-(cyanomethyl)-1,3,4,9-tetrahydro-, 1,1-dimethylethyl ester |
| 494z | 1H-Pyrido[3,4-b]indol-1-one, 2,3,4,9-tetrahydro-9-(phenylmethyl)- |
| 495z | 1H-Pyrido[3,4-b]indol-1-one, 6-butyl-9-[(4-chlorophenyl)methyl]-2,3,4,9-tetrahydro- |
| 496z | 9H-Pyrido[3,4-b]indole-9-acetamide, 1,2,3,4-tetrahydro-6-methoxy-N-[4-(1-methylethoxy)phenyl]-1-oxo- |
| 497z | 9H-Pyrido[3,4-b]indole-9-acetonitrile,1,2,3,4-tetrahydro-2-[4-(1,2,4,5-tetrahydro-2-oxobenz[cd]indol-2a(3H)-yl)butyl]- |
| 498z | 1H-Pyrido[3,4-b]indol-1-one, 6-acetyl-9-[3-(dimethylamino)propyl]-2,3,4,9-tetrahydro- |
| 499z | 1H-Pyrido[3,4-b]indol-1-one, 6-butyl-9-[(3-fluorophenyl)methyl]-2,3,4,9-tetrahydro- |
| 500z | 1H-Pyrido[3,4-b]indol-1-one, 9-[2-(2,3-dihydro-1H-indol-1-yl)-2-oxoethyl]-2,3,4,9-tetrahydro-6-methoxy- |
| 501z | 1H-Pyrido[3,4-b]indol-1-one, 9-[3-(dimethylamino)propyl]-2,3,4,9-tetrahydro-8-(trifluoromethyl)- |
| 502z | 1H-Pyrido[3,4-b]indol-1-one, 6-butyl-2,3,4,9-tetrahydro-9-[(4-nitrophenyl)methyl]- |
| 503z | 1H-Pyrido[3,4-b]indol-1-one, 6-bromo-2,3,4,9-tetrahydro-9-(phenylmethyl)- |
| 504z | 1H-Pyrido[3,4-b]indol-1-one, 6-butyl-9-[(4-fluorophenyl)methyl]-2,3,4,9-tetrahydro- |
| 505z | 1H-Pyrido[3,4-b]indol-1-one, 6-bromo-2,3,4,9-tetrahydro-9-(2-methoxyethyl)- |
| 506z | 1H-Pyrido[3,4-b]indol-1-one, 6-butyl-2,3,4,9-tetrahydro-9-[(4-methylphenyl)methyl]- |
| 507z | 9H-Pyrido[3,4-b]indole-9-carboxylic acid,6-bromo-1,2,3,4-tetrahydro-1-oxo-, 1,1-dimethylethyl ester |
| 508z | 1H-Pyrido[3,4-b]indol-1-one, 6-bromo-9-[(4-bromophenyl)methyl]-2,3,4,9-tetrahydro- |
| 509z | 9H-Pyrido[3,4-b]indole-9-acetic acid, 6-bromo-1,2,3,4-tetrahydro-1-oxo-,methyl ester |
| 510z | 1H-Pyrido[3,4-b]indol-1-one, 8-chloro-9-[3-(dimethylamino)propyl]-2,3,4,9-tetrahydro- |
| 511z | 1H-Pyrido[3,4-b]indol-1-one, 6-bromo-2,3,4,9-tetrahydro-9-[[4-(trifluoromethyl)phenyl]methyl]- |
| 512z | 9H-Pyrido[3,4-b]indole-9-acetic acid, 6-bromo-1,2,3,4-tetrahydro-1-oxo- |
| 513z | 1H-Pyrido[3,4-b]indol-1-one, 6-bromo-2,3,4,9-tetrahydro-9-[(4-nitrophenyl)methyl]- |
| 514z | 9H-Pyrido[3,4-b]indole-9-acetamide, 6-bromo-1,2,3,4-tetrahydro-1-oxo- |
| 515z | 1H-Pyrido[3,4-b]indol-1-one, 6-bromo-2,3,4,9-tetrahydro-9-[(4-methylphenyl)methyl]- |
| 516z | 1H-Pyrido[3,4-b]indol-1-one, 6-bromo-2,3,4,9-tetrahydro-9-(2-methoxyacetyl)- |
| 517z | 1H-Pyrido[3,4-b]indol-1-one, 9-[3-(dimethylamino)propyl]-2,3,4,9-tetrahydro-6-(trifluoromethyl)- |
| 518z | 1H-Pyrido[3,4-b]indol-1-one, 6-bromo-9-[(3-fluorophenyl)methyl]-2,3,4,9-tetrahydro- |
| 519z | 1H-Pyrido[3,4-b]indol-1-one, 9-[2-(acetyloxy)acetyl]-6-bromo-2,3,4,9-tetrahydro- |
| 520z | 1H-Pyrido[3,4-b]indol-1-one, 6-bromo-9-[(2-fluorophenyl)methyl]-2,3,4,9-tetrahydro- |
| 521z | 1H-Pyrido[3,4-b]indol-1-one, 6-bromo-9-(cyclohexylcarbonyl)-2,3,4,9-tetrahydro- |
| 522z | 1H-Pyrido[3,4-b]indol-1-one, 6-bromo-9-[(4-fluorophenyl)methyl]-2,3,4,9-tetrahydro- |
| 523z | 1H-Pyrido[3,4-b]indol-1-one, 9-[2-(3,4-dihydro-2(1H)-isoquinolinyl)ethyl]-2,3,4,9-tetrahydro- |
| 524z | 1H-Pyrido[3,4-b]indole-6-sulfonamide,9-[2-(diethylamino)ethyl]-2,3,4,9-tetrahydro-N,N-dimethyl-1-oxo- |
| 525z | 1H-Pyrido[3,4-b]indol-1-one, 2,3,4,9-tetrahydro-9-[(4-methylphenyl)methyl]-6-(methylthio)- |
| 526z | 1H-Pyrido[3,4-b]indol-1-one, 2,3,4,9-tetrahydro-9-[2-[4-(2-methoxyphenyl)-1-piperazinyl]ethyl]- |
| 527z | 1H-Pyrido[3,4-b]indol-1-one, 6-chloro-9-[3-(dimethylamino)-2-methylpropyl]-2,3,4,9-tetrahydro- |

TABLE 1A-continued

| No | Name |
|---|---|
| 528z | 1H-Pyrido[3,4-b]indol-1-one, 2,3,4,9-tetrahydro-9-[(4-methylphenyl)methyl]-6-(methylsulfonyl)- |
| 529z | 1H-Pyrido[3,4-b]indol-1-one, 2,3,4,9-tetrahydro-9-[2-[4-(2-pyrimidinyl)-1-piperazinyl]ethyl]- |
| 530z | 1H-Pyrido[3,4-b]indol-1-one, 2,3,4,9-tetrahydro-6-(trifluoromethoxy)-9-[[4-(trifluoromethyl)phenyl]methyl]- |
| 531z | 1H-Pyrido[3,4-b]indol-1-one, 9-[3-(3,4-dihydro-2(1H)-isoquinolinyl)propyl]-2,3,4,9-tetrahydro- |
| 532z | 1H-Pyrido[3,4-b]indol-1-one, 6-chloro-2,3,4,9-tetrahydro-9-[2-methyl-3-(1-piperidinyl)propyl]- |
| 533z | 1H-Pyrido[3,4-b]indol-1-one, 9-[(4-fluorophenyl)methyl]-2,3,4,9-tetrahydro-6-(trifluoromethoxy)- |
| 534z | 1H-Pyrido[3,4-b]indol-1-one, 2,3,4,9-tetrahydro-9-[3-[4-(2-methoxyphenyl)-1-piperazinyl]propyl]- |
| 535z | 1H-Pyrido[3,4-b]indol-1-one, 2,3,4,9-tetrahydro-6-(methylthio)-9-[[4-(trifluoromethyl)phenyl]methyl]- |
| 536z | 1H-Pyrido[3,4-b]indol-1-one, 2,3,4,9-tetrahydro-9-[3-[4-(2-pyrimidinyl)-1-piperazinyl]propyl]- |
| 537z | 1H-Pyrido[3,4-b]indol-1-one, 2,3,4,9-tetrahydro-6-(methylsulfonyl)-9-[[4-(trifluoromethyl)phenyl]methyl]- |
| 538z | 1H-Pyrido[3,4-b]indol-1-one, 9-[2-(dimethylamino)ethyl]-2,3,4,9-tetrahydro- |
| 539z | 1H-Pyrido[3,4-b]indol-1-one, 2,3,4,9-tetrahydro-6-(methylsulfonyl)-9-(phenylmethyl)- |
| 540z | 1H-Pyrido[3,4-b]indole-6-carbonitrile,2,3,4,9-tetrahydro-9-[2-methyl-3-(1-piperidinyl)propyl]-1-oxo- |
| 541z | 1H-Pyrido[3,4-b]indol-1-one, 9-[(4-bromophenyl)methyl]-6-chloro-2,3,4,9-tetrahydro- |
| 542z | 1H-Pyrido[3,4-b]indol-1-one, 9-[2-(dimethylamino)ethyl]-2,3,4,9-tetrahydro-7-methoxy- |
| 543z | 1H-Pyrido[3,4-b]indol-1-one, 6-chloro-2,3,4,9-tetrahydro-9-[(4-methylphenyl)methyl]- |
| 544z | 1H-Pyrido[3,4-b]indol-1-one, 9-[3-[4-(3-chlorophenyl)-1-piperazinyl]propyl]-2,3,4,9-tetrahydro- |
| 545z | 1H-Pyrido[3,4-b]indol-1-one, 6-chloro-9-[(4-fluorophenyl)methyl]-2,3,4,9-tetrahydro- |
| 546z | 1H-Pyrido[3,4-b]indol-1-one, 2,3,4,9-tetrahydro-6-methoxy-9-(phenylmethyl)- |
| 547z | 1H-Pyrido[3,4-b]indol-1-one, 6-chloro-2,3,4,9-tetrahydro-9-(phenylmethyl)- |
| 548z | 1H-Pyrido[3,4-b]indol-1-one, 5-acetyl-2,3,4,9-tetrahydro-6-methoxy-9-(phenylmethyl)- |
| 549z | 1H-Pyrido[3,4-b]indol-1-one, 8-chloro-9-[3-(dimethylamino)propyl]-2,3,4,9-tetrahydro-5-(trifluoromethyl)- |
| 550z | 1H-Pyrido[3,4-b]indol-1-one, 6-chloro-2,3,4,9-tetrahydro-9-[[4-(trifluoromethyl)phenyl]methyl]- |
| 551z | 1H-Pyrido[3,4-b]indol-1-one, 9-[2-(dimethylamino)ethyl]-2,3,4,9-tetrahydro-3-methyl- |
| 552z | 1H-Pyrido[3,4-b]indol-1-one, 6-fluoro-2,3,4,9-tetrahydro-9-(phenylmethyl)- |
| 553z | 1H-Pyrido[3,4-b]indol-1-one, 9-[3-(dimethylamino)propyl]-2,3,4,9-tetrahydro-6-nitro- |
| 554z | 1H-Pyrido[3,4-b]indole-6-carbonitrile,9-[3-(dimethylamino)-2-methylpropyl]-2,3,4,9-tetrahydro-1-oxo- |
| 555z | 1H-Pyrido[3,4-b]indole-6-carbonitrile,9-[3-(dimethylamino)propyl]-2,3,4,9-tetrahydro-1-oxo- |
| 556z | 1H-Pyrido[3,4-b]indol-1-one, 6-acetyl-2,3,4,9-tetrahydro-9-(phenylmethyl)- |
| 557z | 1H-Pyrido[3,4-b]indole-6-carboxylic acid,2,3,4,9-tetrahydro-1-oxo-9-(phenylmethyl)-, ethyl ester |
| 558z | Benzeneacetamide, alpha-cyclopentyl-N-(phenylmethyl)-4-[(1,2,3,4-tetrahydro-1-oxo-9H-pyrido[3,4-b]indol-9-yl)methyl]- |
| 559z | 1H-Pyrido[3,4-b]indol-1-one, 9-[2-[4-(3-chlorophenyl)-1-piperazinyl]ethyl]-2,3,4,9-tetrahydro- |
| 560z | Benzeneacetamide, alpha-cyclopentyl-N-(2-hydroxy-1-phenylethyl)-4-[(1,2,3,4-tetrahydro-1-oxo-9H-pyrido[3,4-b]indol-9-yl)methyl]- |
| 561z | Benzeneacetamide, alpha-cyclopentyl-N-(2-hydroxy-1-phenylethyl)-4-[(1,2,3,4-tetrahydro-5,7-dimethyl-1-oxo-9H-pyrido[3,4-b]indol-9-yl)methyl]- |
| 562z | Benzeneacetamide, alpha-cyclopentyl-N-(phenylmethyl)-4-[(1,2,3,4-tetrahydro-5,7-dimethyl-1-oxo-9H-pyrido[3,4-b]indol-9-yl)methyl]- |
| 563z | 9H-Pyrido[3,4-b]indole-9-carboxylic acid,1,2,3,4-tetrahydro-6-methoxy-4,4-dimethyl-1-oxo-, 1,1-dimethylethyl ester |
| 564z | Benzeneacetic acid, alpha-cyclopentyl-4-[(1,2,3,4-tetrahydro-1-oxo-9H-pyrido[3,4-b]indol-9-yl)methyl]-, 1,1-dimethylethyl ester |
| 565z | Benzeneacetic acid, alpha-cyclopentyl-4-[(1,2,3,4-tetrahydro-5,7-dimethyl-1-oxo-9H-pyrido[3,4-b]indol-9-yl)methyl]-, 1,1-dimethylethylester |
| 566z | Benzeneacetic acid, alpha-cyclopentyl-4-[(1,2,3,4-tetrahydro-1-oxo-9H-pyrido[3,4-b]indol-9-yl)methyl]- |
| 567z | Benzeneacetic acid, alpha-cyclopentyl-4-[(1,2,3,4-tetrahydro-5,7-dimethyl-1-oxo-9H-pyrido[3,4-b]indol-9-yl)methyl]- |
| 568z | 1H-Pyrido[3,4-b]indol-1-one, 9-(2-aminoethyl)-2,3,4,9-tetrahydro-6-methoxy- |
| 569z | 1H-Pyrido[3,4-b]indol-1-one, 9-[2-(diethylamino)ethyl]-2,3,4,9-tetrahydro-6-hydroxy- |
| 570z | 1H-Pyrido[3,4-b]indol-1-one, 9-(2-aminoethyl)-6-cyclohexyl-2,3,4,9-tetrahydro- |
| 571z | 1H-Pyrido[3,4-b]indol-1-one, 9-[2-(cyclohexylamino)ethyl]-2,3,4,9-tetrahydro-6-methoxy- |
| 572z | 1H-Pyrido[3,4-b]indol-1-one, 6-cyclohexyl-9-[2-(dimethylamino)ethyl]-2,3,4,9-tetrahydro- |
| 573z | 1H-Pyrido[3,4-b]indol-1-one, 9-[2-(dimethylamino)-1-methylethyl]-2,3,4,9-tetrahydro-6-hydroxy- |
| 574z | 1H-Pyrido[3,4-b]indol-1-one, 9-[3-(dimethylamino)propyl]-2,3,4,9-tetrahydro-6-hydroxy- |
| 575z | 1H-Pyrido[3,4-b]indol-1-one, 9-[2-(dimethylamino)ethyl]-2,3,4,9-tetrahydro-6-(phenylmethoxy)- |
| 576z | 9H-Pyrido[3,4-b]indole-9-acetamide,1,2,3,4-tetrahydro-6-methoxy-1-oxo-N-phenyl- |
| 577z | 1H-Pyrido[3,4-b]indol-1-one, 9-[2-[bis(phenylmethyl)amino]ethyl]-2,3,4,9-tetrahydro-6-methoxy- |
| 578z | 1H-Pyrido[3,4-b]indol-1-one, 9-[2-[bis(phenylmethyl)amino]ethyl]-6-cyclohexyl-2,3,4,9-tetrahydro- |
| 579z | 1H-Pyrido[3,4-b]indol-1-one, 2,3,4,9-tetrahydro-6-methoxy-9-[2-[(phenylmethyl)amino]ethyl]- |
| 580z | 1H-Pyrido[3,4-b]indol-1-one, 6-[2-(diethylamino)ethoxy]-9-[2-(diethylamino)ethyl]-2,3,4,9-tetrahydro- |
| 581z | 9H-Pyrido[3,4-b]indole-9-acetic acid,alpha-ethyl-1,2,3,4-tetrahydro-1-oxo-6-(phenylmethoxy)-, ethyl ester |
| 582z | 9H-Pyrido[3,4-b]indole-9-acetonitrile,2-(2,5-dioxo-1-phenyl-3-pyrrolidinyl)-1,2,3,4-tetrahydro- |
| 583z | (1R,3S)-benzyl 2-acetyl-9-benzyl-6-methyl-1-((1-adamantyl)methyl)-2,3,4,9-tetrahydro-1H-pyrido[3,4-b]indole-3-carboxylate |
| 584z | 1H-Pyrido[3,4-b]indol-1-one, 2,3,4,9-tetrahydro-8-methyl-2-phenyl-9-(phenylmethyl)- |
| 585z | 1H-Pyrido[3,4-b]indol-1-one, 6-bromo-2-butyl-2,3,4,9-tetrahydro-9-(phenylmethyl)- |
| 586z | 9H-Pyrido[3,4-b]indole-9-acetic acid,1,2,3,4-tetrahydro-2-methyl-6-nitro-1-oxo-, methyl ester |
| 587z | 9H-Pyrido[3,4-b]indole-9-acetic acid,1,2,3,4-tetrahydro-6,8-dimethyl-1-oxo-2-phenyl- |
| 588z | 1H-Pyrido[3,4-b]indol-1-one, 2-butyl-2,3,4,9-tetrahydro-6-nitro-9-(phenylmethyl)- |
| 589z | 9H-Pyrido[3,4-b]indole-9-acetic acid,1,2,3,4-tetrahydro-2-methyl-8-nitro-1-oxo- |
| 590z | 9H-Pyrido[3,4-b]indole-9-acetic acid, 2-butyl-1,2,3,4-tetrahydro-1-oxo-,methyl ester |
| 591z | 9H-Pyrido[3,4-b]indole-9-acetic acid,1,2,3,4-tetrahydro-7,8-dimethyl-1-oxo-2-phenyl-, methyl ester |
| 592z | 1H-Pyrido[3,4-b]indol-1-one, 2-butyl-2,3,4,9-tetrahydro-8-nitro-9-(2-phenylethyl)- |
| 593z | 9H-Pyrido[3,4-b]indole-9-acetic acid,6-bromo-1,2,3,4-tetrahydro-2-methyl-1-oxo- |
| 594z | 1H-Pyrido[3,4-b]indol-1-one, 2,3,4,9-tetrahydro-2,5,8-trimethyl-9-(phenylmethyl)- |
| 595z | 9H-Pyrido[3,4-b]indole-9-carboxylic acid,2-[[4-chloro-3-(3-chloro-5-cyanophenoxy)-2-fluorophenyl]methyl]-1,2,3,4-tetrahydro-6-methoxy-1-oxo-, 1,1-dimethylethyl ester |
| 596z | 1H-Pyrido[3,4-b]indole-1-propanoic acid,2,3,4,9-tetrahydro-3-(methoxycarbonyl)-2-(1-methylethyl)-9-(phenylmethyl)- |
| 597z | 2-cyclopentyl-N-((R)-2-hydroxy-1-phenylethyl)-2-(4-((2,5,7-trimethyl-1-oxo-3,4-dihydro-1H-pyrido[3,4-b]indol-9(2H)-yl)methyl)phenyl)acetamide |
| 598z | 1H-Pyrido[3,4-b]indol-1-one, 2,3,4,9-tetrahydro-8-nitro-2-phenyl-9-(2-phenylethyl)- |
| 599z | 1H-Pyrido[3,4-b]indol-1-one, 2-butyl-2,3,4,9-tetrahydro-6-nitro-9-(2-phenylethyl)- |
| 600z | 9H-Pyrido[3,4-b]indole-9-acetic acid,6-fluoro-1,2,3,4-tetrahydro-2-methyl-1-oxo- |
| 601z | 1H-Pyrido[3,4-b]indol-1-one, 2-butyl-2,3,4,9-tetrahydro-9-(2-phenylethyl)- |
| 602z | 9H-Pyrido[3,4-b]indole-9-acetic acid,1,2,3,4-tetrahydro-1-oxo-2-phenyl-6-sulfo-, 9-methyl ester |
| 603z | 9H-Pyrido[3,4-b]indole-9-acetic acid,2-butyl-6-fluoro-1,2,3,4-tetrahydro-1-oxo- |

TABLE 1A-continued

| No | Name |
|---|---|
| 604z | 9H-Pyrido[3,4-b]indole-9-acetic acid,1,2,3,4-tetrahydro-6-methyl-1-oxo-2-phenyl-, methyl ester |
| 605z | 9H-Pyrido[3,4-b]indole-9-acetic acid,2-butyl-1,2,3,4-tetrahydro-5,8-dimethyl-1-oxo-, methyl ester |
| 606z | 9H-Pyrido[3,4-b]indole-9-acetic acid, 2-butyl-1,2,3,4-tetrahydro-1-oxo- |
| 607z | 1H-Pyrido[3,4-b]indol-1-one, 2,3,4,9-tetrahydro-2,8-dimethyl-9-(phenylmethyl)- |
| 608z | 1H-Pyrido[3,4-b]indole-2,9-dicarboxylic acid,1-[3-carboxy-1-(2-carboxyethyl)-1-ethylpropyl]-3,4-dihydro-,2,9-bis(1,1-dimethylethyl) ester |
| 609z | 9H-Pyrido[3,4-b]indole-9-acetic acid,8-carboxy-1,2,3,4-tetrahydro-1-oxo-2-phenyl-, 9-methyl ester |
| 610z | 1H-Pyrido[3,4-b]indol-1-one, 2-butyl-2,3,4,9-tetrahydro-5,8-dimethyl-9-(2-phenylethyl)- |
| 611z | 9H-Pyrido[3,4-b]indole-9-acetic acid,2-butyl-1,2,3,4-tetrahydro-8-methyl-1-oxo-, methyl ester |
| 612z | 1H-Pyrido[3,4-b]indol-1-one, 2,3,4,9-tetrahydro-6-methoxy-2-methyl-9-(phenylmethyl)- |
| 613z | 1H-Pyrido[3,4-b]indol-1-one, 6-bromo-2-butyl-2,3,4,9-tetrahydro-9-(2-phenylethyl)- |
| 614z | 1H-Pyrido[3,4-b]indol-1-one, 2,3,4,9-tetrahydro-6-methoxy-2-phenyl-9-(phenylmethyl)- |
| 615z | 9H-Pyrido[3,4-b]indole-9-acetic acid,2-butyl-8-carboxy-1,2,3,4-tetrahydro-1-oxo- |
| 616z | 9H-Pyrido[3,4-b]indole-9-acetic acid,8-carboxy-1,2,3,4-tetrahydro-1-oxo-2-phenyl- |
| 617z | 1H-Pyrido[3,4-b]indol-1-one, 2,3,4,9-tetrahydro-7,8-dimethyl-2-phenyl-9-(phenylmethyl)- |
| 618z | 9H-Pyrido[3,4-b]indole-9-acetic acid,2-butyl-1,2,3,4-tetrahydro-6,8-dimethyl-1-oxo- |
| 619z | 1H-Pyrido[3,4-b]indol-1-one, 2,3,4,9-tetrahydro-2,7,8-trimethyl-9-(2-phenylethyl)- |
| 620z | 1H-Pyrido[3,4-b]indole-1-acetic acid,9-[(1,1-dimethylethoxy)carbonyl]-2,3,4,9-tetrahydro-2-propyl-, methyl ester |
| 621z | 9H-Pyrido[3,4-b]indole-9-acetic acid,1,2,3,4-tetrahydro-6-methyl-1-oxo-2-phenyl- |
| 622z | 9H-Pyrido[3,4-b]indole-9-acetic acid,2-butyl-1,2,3,4-tetrahydro-7,8-dimethyl-1-oxo-, methyl ester |
| 623z | 9H-Pyrido[3,4-b]indole-9-acetic acid,2-butyl-1,2,3,4-tetrahydro-7,8-dimethyl-1-oxo- |
| 624z | 2-(2-butyl-7,8-dimethyl-1-oxo-3,4-dihydro-1H-pyrido[3,4-b]indol-9(2H)-yl)acetic acid |
| 625z | 1H-Pyrido[3,4-b]indol-1-one, 2-butyl-2,3,4,9-tetrahydro-6,8-dimethyl-9-(2-phenylethyl)- |
| 626z | 1H-Pyrido[3,4-b]indole-8-carboxylic acid,2,3,4,9-tetrahydro-1-oxo-2-phenyl-9-(2-phenylethyl)- |
| 627z | 9H-Pyrido[3,4-b]indole-9-acetic acid,6-bromo-1,2,3,4-tetrahydro-2-methyl-1-oxo-, methyl ester |
| 628z | 1H-Pyrido[3,4-b]indol-1-one, 2,3,4,9-tetrahydro-2-methyl-8-nitro-9-(phenylmethyl)- |
| 629z | 1H-Pyrido[3,4-b]indol-1-one, 2,3,4,9-tetrahydro-6-methyl-2-phenyl-9-(2-phenylethyl)- |
| 630z | 1H-Pyrido[3,4-b]indol-1-one, 2-butyl-2,3,4,9-tetrahydro-8-nitro-9-(phenylmethyl)- |
| 631z | 9H-Pyrido[3,4-b]indole-9-acetic acid,1,2,3,4-tetrahydro-2-methyl-8-nitro-1-oxo-, methyl ester |
| 632z | 9H-Pyrido[3,4-b]indole-9-acetic acid,2-(2,5-dioxo-1-phenyl-3-pyrrolidinyl)-1,2,3,4-tetrahydro-, ethyl ester |
| 633z | 9H-Pyrido[3,4-b]indole-9-acetic acid,2-butyl-1,2,3,4-tetrahydro-6-nitro-1-oxo-, methyl ester |
| 634z | 9-benzyl-2-butyl-1-oxo-2,3,4,9-tetrahydro-1H-pyrido[3,4-b]indole-8-carboxylic acid |
| 635z | 9H-Pyrido[3,4-b]indole-9-acetic acid,6-carboxy-1,2,3,4-tetrahydro-2-methyl-1-oxo-, 9-methyl ester |
| 636z | 9H-Pyrido[3,4-b]indole-9-acetic acid,2-butyl-1,2,3,4-tetrahydro-6,8-dimethyl-1-oxo-, methyl ester |
| 637z | 9H-Pyrido[3,4-b]indole-9-acetic acid,8-fluoro-1,2,3,4-tetrahydro-2-methyl-1-oxo- |
| 638z | 1H-Pyrido[3,4-b]indol-1-one, 8-fluoro-2,3,4,9-tetrahydro-2-methyl-9-(2-phenylethyl)- |
| 639z | 1H-Pyrido[3,4-b]indol-1-one, 2,3,4,9-tetrahydro-5,8-dimethyl-2-phenyl-9-(2-phenylethyl)- |
| 640z | 1H-Pyrido[3,4-b]indol-1-one, 2-butyl-8-fluoro-2,3,4,9-tetrahydro-9-(2-phenylethyl)- |
| 641z | 9H-Pyrido[3,4-b]indole-9-acetic acid,1,2,3,4-tetrahydro-6-methoxy-2-methyl-1-oxo- |
| 642z | 9H-Pyrido[3,4-b]indole-9-carboxylic acid,2-[(2E,4E)-5-(benzoyloxy)-2,4-pentadien-1-yl]-1,2,3,4-tetrahydro-1-(2-hydroxyethyl)-, phenylmethyl ester, (1S)- |
| 643z | 9H-Pyrido[3,4-b]indole-9-carboxylic acid,1,2,3,4-tetrahydro-6-methoxy-1-oxo-, 1,1-dimethylethyl ester |
| 644z | (1R,3S)-benzyl 1-(1-adamantyl)-9-(2-chlorobenzyl)-2,3,4,9-tetrahydro-1H-pyrido[3,4-b]indole-3-carboxylate |
| 645z | 1H-Pyrido[3,4-b]indol-1-one, 6-fluoro-2,3,4,9-tetrahydro-2-phenyl-9-(2-phenylethyl)- |
| 646z | 1H-Pyrido[3,4-b]indol-1-one, 2-butyl-6-fluoro-2,3,4,9-tetrahydro-9-(2-phenylethyl)- |
| 647z | 9H-Pyrido[3,4-b]indole-9-acetic acid,1,2,3,4-tetrahydro-2,8-dimethyl-1-oxo- |
| 648z | 9H-Pyrido[3,4-b]indole-9-acetic acid,2-butyl-1,2,3,4-tetrahydro-6-methoxy-1-oxo-, methyl ester |
| 649z | 9H-Pyrido[3,4-b]indole-9-acetic acid,1,2,3,4-tetrahydro-8-nitro-1-oxo-2-phenyl-, methyl ester |
| 650z | 1H-Pyrido[3,4-b]indole-6-sulfonic acid,2,3,4,9-tetrahydro-1-oxo-2-phenyl-9-(2-phenylethyl)- |
| 651z | 2-methyl-1-oxo-9-phenethyl-2,3,4,9-tetrahydro-1H-pyrido[3,4-b]indole-8-carboxylic acid |
| 652z | 9H-Pyrido[3,4-b]indole-9-acetic acid,6-fluoro-1,2,3,4-tetrahydro-1-oxo-2-phenyl-, methyl ester |
| 653z | 1H-Pyrido[3,4-b]indol-1-one, 8-fluoro-2,3,4,9-tetrahydro-2-methyl-9-(phenylmethyl)- |
| 654z | 1H-Pyrido[3,4-b]indole-2,9-dicarboxylic acid,1-[[(4R)-3-ethyltetrahydro-2-[(4-methoxyphenyl)methoxy]-6-oxo-2H-pyran-4-yl]methyl]-3,4-dihydro-, 9-(1,1-dimethylethyl) 2-(phenylmethyl) ester,(1R)- |
| 655z | 9H-Pyrido[3,4-b]indole-9-acetic acid,1,2,3,4-tetrahydro-6,8-dimethyl-1-oxo-2-phenyl-, methyl ester |
| 656z | 9H-Pyrido[3,4-b]indole-9-acetic acid,1,2,3,4-tetrahydro-1-oxo-2-phenyl-6-sulfo- |
| 657z | 9H-Pyrido[3,4-b]indole-9-acetic acid,1,2,3,4-tetrahydro-2-methyl-1-oxo-6-sulfo- |
| 658z | 1H-Pyrido[3,4-b]indol-1-one, 6-bromo-2,3,4,9-tetrahydro-2-methyl-9-(phenylmethyl)- |
| 659z | 9H-Pyrido[3,4-b]indole-9-acetic acid,1,2,3,4-tetrahydro-8-methyl-1-oxo-2-phenyl-, methyl ester |
| 660z | 1H-Pyrido[3,4-b]indol-1-one, 6-fluoro-2,3,4,9-tetrahydro-2-phenyl-9-(phenylmethyl)- |
| 661z | 2-methyl-1-oxo-9-phenethyl-2,3,4,9-tetrahydro-1H-pyrido[3,4-b]indole-6-sulfonic acid |
| 662z | 9H-Pyrido[3,4-b]indole-9-acetic acid,1,2,3,4-tetrahydro-8-nitro-1-oxo-2-phenyl- |
| 663z | 9H-Pyrido[3,4-b]indole-9-acetic acid,2-butyl-6-carboxy-1,2,3,4-tetrahydro-1-oxo- |
| 664z | 1H-Pyrido[3,4-b]indol-1-one, 2,3,4,9-tetrahydro-2-methyl-8-nitro-9-(2-phenylethyl)- |
| 665z | 1-(benzyloxycarbonyl)-4-((9-((2,2,2-trichloroethoxy)carbonyl)-3,4-dihydro-1H-pyrido[3,4-b]indol-2(9H)-ylsulfonyl)methyl)piperidine-4-carboxylic acid |
| 666z | 9H-Pyrido[3,4-b]indole-9-acetic acid, 1,2,3,4-tetrahydro-1-oxo-2-phenyl-,methyl ester |
| 667z | 1H-Pyrido[3,4-b]indole-6-carboxylic acid,2,3,4,9-tetrahydro-1-oxo-2-phenyl-9-(phenylmethyl)- |
| 668z | 9H-Pyrido[3,4-b]indole-9-acetic acid,2-butyl-1,2,3,4-tetrahydro-8-nitro-1-oxo- |
| 669z | 1H-Pyrido[3,4-b]indol-1-one, 2,3,4,9-tetrahydro-2-methyl-6-nitro-9-(2-phenylethyl)- |
| 670z | 9H-Pyrido[3,4-b]indole-9-acetic acid,6-fluoro-1,2,3,4-tetrahydro-1-oxo-2-phenyl- |
| 671z | 1H-Pyrido[3,4-b]indol-1-one, 6-bromo-2,3,4,9-tetrahydro-2-phenyl-9-(2-phenylethyl)- |
| 672z | 9H-Pyrido[3,4-b]indole-9-acetic acid,8-carboxy-1,2,3,4-tetrahydro-2-methyl-1-oxo-, 9-methyl ester |
| 673z | 1H-Pyrido[3,4-b]indol-1-one, 2,3,4,9-tetrahydro-2,7,8-trimethyl-9-(phenylmethyl)- |
| 674z | 1H-Pyrido[3,4-b]indol-1-one, 2,3,4,9-tetrahydro-6-methyl-2-phenyl-9-(phenylmethyl)- |
| 675z | 1H-Pyrido[3,4-b]indol-1-one, 2-butyl-2,3,4,9-tetrahydro-6,8-dimethyl-9-(phenylmethyl)- |
| 676z | 9H-Pyrido[3,4-b]indole-9-acetic acid,1,2,3,4-tetrahydro-2,7,8-trimethyl-1-oxo-, methyl ester |
| 677z | (1R,3S)-benzyl 2-acetyl-9-benzyl-6-fluoro-1-((1-adamantyl)methyl)-2,3,4,9-tetrahydro-1H-pyrido[3,4-b]indole-3-carboxylate |
| 678z | 9H-Pyrido[3,4-b]indole-9-acetic acid,1,2,3,4-tetrahydro-7,8-dimethyl-1-oxo-2-phenyl- |

TABLE 1A-continued

| No | Name |
|---|---|
| 679z | 1H-Pyrido[3,4-b]indol-1-one, 8-fluoro-2,3,4,9-tetrahydro-2-phenyl-9-(phenylmethyl)- |
| 680z | 1H-Pyrido[3,4-b]indol-1-one, 2-butyl-2,3,4,9-tetrahydro-5,8-dimethyl-9-(phenylmethyl)- |
| 681z | 9H-Pyrido[3,4-b]indole-9-acetic acid,1,2,3,4-tetrahydro-2,5,8-trimethyl-1-oxo-, methyl ester |
| 682z | 9H-Pyrido[3,4-b]indole-9-acetic acid,6-carboxy-1,2,3,4-tetrahydro-1-oxo-2-phenyl- |
| 683z | 9-benzyl-2-butyl-1-oxo-2,3,4,9-tetrahydro-1H-pyrido[3,4-b]indole-6-carboxylic acid |
| 684z | 9H-Pyrido[3,4-b]indole-9-acetic acid,1,2,3,4-tetrahydro-2,6-dimethyl-1-oxo- |
| 685z | 1H-Pyrido[3,4-b]indol-1-one, 2,3,4,9-tetrahydro-2,8-dimethyl-9-(2-phenylethyl)- |
| 686z | 1H-Pyrido[3,4-b]indole-6-carboxylic acid,2,3,4,9-tetrahydro-1-oxo-2-phenyl-9-(2-phenylethyl)- |
| 687z | 1H-Pyrido[3,4-b]indol-1-one, 2-butyl-2,3,4,9-tetrahydro-6-methyl-9-(2-phenylethyl)- |
| 688z | 9H-Pyrido[3,4-b]indole-9-acetic acid, 1,2,3,4-tetrahydro-2-methyl-1-oxo- |
| 689z | Methanone, phenyl[(1R)-1,2,3,4-tetrahydro-1-methyl-9H-pyrido[3,4-b]indol-9-yl]- |
| 690z | 9H-Pyrido[3,4-b]indole-9-acetic acid,1,2,3,4-tetrahydro-2-[4-(1,2,4,5-tetrahydro-2-oxobenz[cd]indol-2a(3H)-yl)butyl]- |
| 691z | (S)-2-((S)-4-amino-2-(16-((2S,3S)-1-(2-carbamoyl-3,4-dihydro-1H-pyrido[3,4-b]indol-9(2H)-yl)-3-methyl-1-oxopentan-2-ylamino)-16-oxohexadecanamido)-4-oxobutanamido)-3-phenylpropanoic acid |
| 692z | 1H-Pyrido[3,4-b]indol-1-one, 2,3,4,9-tetrahydro-8-methyl-2-phenyl-9-(2-phenylethyl)- |
| 693z | 1H-Pyrido[3,4-b]indol-1-one, 2-butyl-2,3,4,9-tetrahydro-8-methyl-9-(2-phenylethyl)- |
| 694z | 9H-Pyrido[3,4-b]indole-9-acetic acid,1,2,3,4-tetrahydro-2,8-dimethyl-1-oxo-, methyl ester |
| 695z | 9H-Pyrido[3,4-b]indole-9-acetic acid,6-bromo-2-butyl-1,2,3,4-tetrahydro-1-oxo-, methyl ester |
| 696z | 1H-Pyrido[3,4-b]indol-1-one, 2-butyl-8-fluoro-2,3,4,9-tetrahydro-9-(phenylmethyl)- |
| 697z | 9H-Pyrido[3,4-b]indole-9-acetic acid,1,2,3,4-tetrahydro-2,5,8-trimethyl-1-oxo- |
| 698z | 9H-Pyrido[3,4-b]indole-9-acetic acid,2-butyl-1,2,3,4-tetrahydro-8-methyl-1-oxo- |
| 699z | 9H-Pyrido[3,4-b]indole-9-acetic acid,1,2,3,4-tetrahydro-6-nitro-1-oxo-2-phenyl-, methyl ester |
| 700z | 9H-Pyrido[3,4-b]indole-9-acetic acid,1,2,3,4-tetrahydro-2,6,8-trimethyl-1-oxo- |
| 701z | 1H-Pyrido[3,4-b]indol-1-one, 2,3,4,9-tetrahydro-2-methyl-6-nitro-9-(phenylmethyl)- |
| 702z | 2-butyl-1-oxo-9-phenethyl-2,3,4,9-tetrahydro-1H-pyrido[3,4-b]indole-6-carboxylic acid |
| 703z | 9H-Pyrido[3,4-b]indole-9-acetic acid,1,2,3,4-tetrahydro-2,7,8-trimethyl-1-oxo- |
| 704z | 9-benzyl-2-methyl-1-oxo-2,3,4,9-tetrahydro-1H-pyrido[3,4-b]indole-8-carboxylic acid |
| 705z | 1H-Pyrido[3,4-b]indole-8-carboxylic acid,2,3,4,9-tetrahydro-1-oxo-2-phenyl-9-(phenylmethyl)- |
| 706z | 9H-Pyrido[3,4-b]indole-9-acetic acid,2-butyl-8-fluoro-1,2,3,4-tetrahydro-1-oxo- |
| 707z | 9H-Pyrido[3,4-b]indole-9-acetic acid,6-bromo-1,2,3,4-tetrahydro-1-oxo-2-phenyl- |
| 708z | 9H-Pyrido[3,4-b]indole-9-acetic acid,2-butyl-6-fluoro-1,2,3,4-tetrahydro-1-oxo-, methyl ester |
| 709z | 9H-Pyrido[3,4-b]indole-9-acetic acid,2-butyl-1,2,3,4-tetrahydro-6-nitro-1-oxo- |
| 710z | 1H-Pyrido[3,4-b]indol-1-one, 6-fluoro-2,3,4,9-tetrahydro-2-methyl-9-(2-phenylethyl)- |
| 711z | 9H-Pyrido[3,4-b]indole-9-acetic acid,8-fluoro-1,2,3,4-tetrahydro-1-oxo-2-phenyl-, methyl ester |
| 712z | 2-butyl-1-oxo-9-phenethyl-2,3,4,9-tetrahydro-1H-pyrido[3,4-b]indole-6-sulfonic acid |
| 713z | 9H-Pyrido[3,4-b]indole-9-acetic acid,6-bromo-2-butyl-1,2,3,4-tetrahydro-1-oxo- |
| 714z | 1H-Pyrido[3,4-b]indol-1-one, 2,3,4,9-tetrahydro-6-methoxy-2-methyl-9-(2-phenylethyl)- |
| 715z | 2-butyl-1-oxo-9-phenethyl-2,3,4,9-tetrahydro-1H-pyrido[3,4-b]indole-8-carboxylic acid |
| 716z | 1H-Pyrido[3,4-b]indol-1-one, 2,3,4,9-tetrahydro-6-methoxy-2-phenyl-9-(2-phenylethyl)- |
| 717z | 9H-Pyrido[3,4-b]indole-9-acetic acid,2-butyl-1,2,3,4-tetrahydro-5,8-dimethyl-1-oxo- |
| 718z | 9-benzyl-2-methyl-1-oxo-2,3,4,9-tetrahydro-1H-pyrido[3,4-b]indole-6-sulfonic acid |
| 719z | 1H-Pyrido[3,4-b]indol-1-one, 6-bromo-2,3,4,9-tetrahydro-2-phenyl-9-(phenylmethyl)- |
| 720z | 1H-Pyrido[3,4-b]indole-1-acetic acid,9-[(1,1-dimethylethoxy)carbonyl]-2,3,4,9- tetrahydro-6-methoxy-2-[(4-methylphenyl)sulfonyl]-, ethyl ester |
| 721z | 9H-Pyrido[3,4-b]indole-9-acetic acid,1,2,3,4-tetrahydro-6-nitro-1-oxo-2-phenyl- |
| 722z | 9H-Pyrido[3,4-b]indole-9-acetic acid,2-butyl-6-carboxy-1,2,3,4-tetrahydro-1-oxo-, 9-methyl ester |
| 723z | 9-benzyl-2-butyl-1-oxo-2,3,4,9-tetrahydro-1H-pyrido[3,4-b]indole-6-sulfonic acid |
| 724z | 9H-Pyrido[3,4-b]indole-9-acetic acid,1,2,3,4-tetrahydro-2-methyl-1-oxo-6-sulfo-, 9-methyl ester |
| 725z | 2-butyl-9-(2-methoxy-2-oxoethyl)-1-oxo-2,3,4,9-tetrahydro-1H-pyrido[3,4-b]indole-6-sulfonic acid |
| 726z | 1H-Pyrido[3,4-b]indol-1-one, 2,3,4,9-tetrahydro-6,8-dimethyl-2-phenyl-9-(2-phenylethyl)- |
| 727z | 9H-Pyrido[3,4-b]indole-9-acetic acid, 1,2,3,4-tetrahydro-2-methyl-1-oxo-,methyl ester |
| 728z | 1H-Pyrido[3,4-b]indol-1-one, 2,3,4,9-tetrahydro-2,6-dimethyl-9-(phenylmethyl)- |
| 729z | 1H-Pyrido[3,4-b]indol-1-one, 2,3,4,9-tetrahydro-6-nitro-2-phenyl-9-(2-phenylethyl)- |
| 730z | 1H-Pyrido[3,4-b]indol-1-one, 2-butyl-2,3,4,9-tetrahydro-8-methyl-9-(phenylmethyl)- |
| 731z | 9H-Pyrido[3,4-b]indole-9-acetic acid,1,2,3,4-tetrahydro-2,6-dimethyl-1-oxo-, methyl ester |
| 732z | 9H-Pyrido[3,4-b]indole-9-propanenitrile,2-(2,5-dioxo-1-phenyl-3-pyrrolidinyl)-1,2,3,4-tetrahydro- |
| 733z | 9H-Pyrido[3,4-b]indole-9-acetic acid,2-[4-(1,3-dihydro-1,3-dioxo-2H-isoindol-2-yl)butyl]-1,2,3,4-tetrahydro- |
| 734z | 9H-Pyrido[3,4-b]indole-9-acetic acid,2-butyl-1,2,3,4-tetrahydro-6-methyl-1-oxo-, methyl ester |
| 735z | 1H-Pyrido[3,4-b]indol-1-one, 2-butyl-2,3,4,9-tetrahydro-6-methyl-9-(phenylmethyl)- |
| 736z | 9H-Pyrido[3,4-b]indole-9-acetic acid,8-fluoro-1,2,3,4-tetrahydro-2-methyl-1-oxo-, methyl ester |
| 737z | 9H-Pyrido[3,4-b]indole-9-acetic acid,2-butyl-8-carboxy-1,2,3,4-tetrahydro-1-oxo-, 9-methyl ester |
| 738z | 9H-Pyrido[3,4-b]indole-9-acetic acid,1,2,3,4-tetrahydro-5,8-dimethyl-1-oxo-2-phenyl-, methyl ester |
| 739z | 9H-Pyrido[3,4-b]indole-9-acetic acid,6-carboxy-1,2,3,4-tetrahydro-2-methyl-1-oxo- |
| 740z | 1H-Pyrido[3,4-b]indol-1-one, 6-bromo-2,3,4,9-tetrahydro-2-methyl-9-(2-phenylethyl)- |
| 741z | 9H-Pyrido[3,4-b]indole-9-acetic acid,6-carboxy-1,2,3,4-tetrahydro-1-oxo-2-phenyl-, 9-methyl ester |
| 742z | 1H-Pyrido[3,4-b]indol-1-one, 2-butyl-2,3,4,9-tetrahydro-7,8-dimethyl-9-(2-phenylethyl)- |
| 743z | 9H-Pyrido[3,4-b]indole-9-acetic acid,8-carboxy-1,2,3,4-tetrahydro-2-methyl-1-oxo- |
| 744z | 9-benzyl-2-methyl-1-oxo-2,3,4,9-tetrahydro-1H-pyrido[3,4-b]indole-6-carboxylic acid |
| 745z | Methanone, (3,4-dichloro-2-hydroxyphenyl)[1,3,4,9-tetrahydro-9-[(4-hydroxyphenyl)methyl]-2H-pyrido[3,4-b]indol-2-yl]- |
| 746z | (1R,3S)-3-benzyl 2-methyl 9-(2-chlorobenzyl)-1-(1-adamantyl)-3,4-dihydro-1H-pyrido[3,4-b]indole-2,3(9H)-dicarboxylate |
| 747z | 1H-Pyrido[3,4-b]indol-1-one, 2,3,4,9-tetrahydro-7,8-dimethyl-2-phenyl-9-(2-phenylethyl)- |
| 748z | 1H-Pyrido[3,4-b]indole-6-sulfonic acid,2,3,4,9-tetrahydro-1-oxo-2-phenyl-9-(phenylmethyl)- |
| 749z | 9H-Pyrido[3,4-b]indole-9-acetic acid,1,2,3,4-tetrahydro-2-methyl-6-nitro-1-oxo- |
| 750z | 1H-Pyrido[3,4-b]indol-1-one, 2,3,4,9-tetrahydro-2,6,8-trimethyl-9-(phenylmethyl)- |
| 751z | 9H-Pyrido[3,4-b]indole-9-acetic acid,6-bromo-1,2,3,4-tetrahydro-1-oxo-2-phenyl-, methyl ester |
| 752z | 1H-Pyrido[3,4-b]indol-1-one, 2,3,4,9-tetrahydro-6,8-dimethyl-2-phenyl-9-(phenylmethyl)- |
| 753z | 1H-Pyrido[3,4-b]indol-1-one, 2,3,4,9-tetrahydro-2,6,8-trimethyl-9-(2-phenylethyl)- |
| 754z | 9H-Pyrido[3,4-b]indole-9-acetic acid,1,2,3,4-tetrahydro-8-methyl-1-oxo-2-phenyl- |

TABLE 1A-continued

| No | Name |
|---|---|
| 755z | 9H-Pyrido[3,4-b]indole-9-acetic acid,2-butyl-1,2,3,4-tetrahydro-8-nitro-1-oxo-, methyl ester |
| 756z | 9H-Pyrido[3,4-b]indole-9-acetic acid,2-butyl-1,2,3,4-tetrahydro-6-methoxy-1-oxo- |
| 757z | 1H-Pyrido[3,4-b]indol-1-one, 2,3,4,9-tetrahydro-2,6-dimethyl-9-(2-phenylethyl)- |
| 758z | 9H-Pyrido[3,4-b]indole-9-acetic acid,1,2,3,4-tetrahydro-6-methoxy-1-oxo-2-phenyl-, methyl ester |
| 759z | 1H-Pyrido[3,4-b]indol-1-one, 2,3,4,9-tetrahydro-5,8-dimethyl-2-phenyl-9-(phenylmethyl)- |
| 760z | 9H-Pyrido[3,4-b]indole-9-acetic acid,2-butyl-1,2,3,4-tetrahydro-6-methyl-1-oxo- |
| 761z | 1H-Pyrido[3,4-b]indol-1-one, 2,3,4,9-tetrahydro-2-methyl-9-(2-phenylethyl)- |
| 762z | 9H-Pyrido[3,4-b]indole-9-acetic acid, 1,2,3,4-tetrahydro-1-oxo-2-phenyl- |
| 763z | 1H-Pyrido[3,4-b]indol-1-one, 2,3,4,9-tetrahydro-2-phenyl-9-(2-phenylethyl)- |
| 764z | 9H-Pyrido[3,4-b]indole-9-acetic acid,1,2,3,4-tetrahydro-2,6,8-trimethyl-1-oxo-, methyl ester |
| 765z | 9H-Pyrido[3,4-b]indole-9-acetic acid,1,2,3,4-tetrahydro-5,8-dimethyl-1-oxo-2-phenyl- |
| 766z | 1H-Pyrido[3,4-b]indol-1-one, 2,3,4,9-tetrahydro-8-nitro-2-phenyl-9-(phenylmethyl)- |
| 767z | 2-(2-butyl-1-oxo-6-sulfo-3,4-dihydro-1H-pyrido[3,4-b]indol-9(2H)-yl)acetic acid |
| 768z | 1H-Pyrido[3,4-b]indole-1-acetic acid,9-[(1,1-dimethylethoxy)carbonyl]-2,3,4,9-tetrahydro-2-[(4-methylphenyl)sulfonyl]-, ethyl ester |
| 769z | (1R,3S)-benzyl 2-acetyl-9-(4-fluorobenzyl)-1-(1-adamantyl)-2,3,4,9-tetrahydro-1H-pyrido[3,4-b]indole-3-carboxylate |
| 770z | 9H-Pyrido[3,4-b]indole-9-acetic acid,1,2,3,4-tetrahydro-6-methoxy-1-oxo-2-phenyl- |
| 771z | 1H-Pyrido[3,4-b]indol-1-one, 2,3,4,9-tetrahydro-6-nitro-2-phenyl-9-(phenylmethyl)- |
| 772z | 1H-Pyrido[3,4-b]indol-1-one, 2,3,4,9-tetrahydro-2,5,8-trimethyl-9-(2-phenylethyl)- |
| 773z | 9H-Pyrido[3,4-b]indole-9-acetic acid,8-fluoro-1,2,3,4-tetrahydro-1-oxo-2-phenyl- |
| 774z | 1H-Pyrido[3,4-b]indol-1-one, 2-butyl-2,3,4,9-tetrahydro-7,8-dimethyl-9-(phenylmethyl)- |
| 775z | 9H-Pyrido[3,4-b]indole-9-acetic acid,1,2,3,4-tetrahydro-6-methoxy-2-methyl-1-oxo-, methyl ester |
| 776z | 1H-Pyrido[3,4-b]indol-1-one, 6-fluoro-2,3,4,9-tetrahydro-2-methyl-9-(phenylmethyl)- |
| 777z | 1H-Pyrido[3,4-b]indol-1-one, 8-fluoro-2,3,4,9-tetrahydro-2-phenyl-9-(2-phenylethyl)- |
| 778z | 1H-Pyrido[3,4-b]indol-1-one, 2-butyl-6-fluoro-2,3,4,9-tetrahydro-9-(phenylmethyl)- |
| 779z | 9H-Pyrido[3,4-b]indole-9-acetic acid,6-fluoro-1,2,3,4-tetrahydro-2-methyl-1-oxo-, methyl ester |
| 780z | 9H-Pyrido[3,4-b]indole-9-carboxylic acid,2-[(2E,4E)-5-(benzoyloxy)-2,4-pentadien-1-yl]-1,2,3,4-tetrahydro-1-[(2E)-4-methoxy-4-oxo-2-buten-1-yl]-, phenylmethyl ester, (1S)- |
| 781z | (1-(2,2-difluorobenzo[d][1,3]dioxol-5-yl)-3,4-dihydro-1H-pyrido[3,4-b]indole-2,9-diyl)bis((5-(3-(dihydroxyamino)phenyl)furan-2-yl)methanone) |
| 782z | 1H-Pyrido[3,4-b]indole, 1-(1,3-benzodioxol-5-yl)-2,3,4,9-tetrahydro-2-[5-[4-(methylsulfonyl)-2-nitrophenyl]-2-pyrimidinyl]-9-[2-(1-pyrrolidinyl)ethyl]- |
| 783z | 9H-Pyrido[3,4-b]indole-9-ethanamine, 1-(1,3-benzodioxol-5-yl)-2-[[5-(4-chloro-2-nitrophenyl)-2-furanyl]carbonyl]-1,2,3,4-tetrahydro-N,N-dimethyl- |
| 784z | 9H-Pyrido[3,4-b]indole-9-ethanamine, 1-(1,3-benzodioxol-5-yl)-2-(benzo[b]thien-2-ylcarbonyl)-1,2,3,4-tetrahydro-N,N-dimethyl- |
| 785z | 9H-Pyrido[3,4-b]indole-9-ethanamine, 1-(1,3-benzodioxol-5-yl)-2-[[5-[2-chloro-5-(trifluoromethyl)phenyl]-2-furanyl]carbonyl]-1,2,3,4-tetrahydro-N,N-dimethyl- |
| 786z | 9H-Pyrido[3,4-b]indole-9-propanoic acid, 1-(1,3-benzodioxol-5-yl)-1,2,3,4-tetrahydro-2-[[5-[3-(trifluoromethyl)phenyl]-2-furanyl]carbonyl]-, methyl ester |
| 787z | 9H-Pyrido[3,4-b]indole-9-ethanamine, 1-(1,3-benzodioxol-5-yl)-2-[[5-(4-chlorophenyl)-2-methyl-3-furanyl]carbonyl]-1,2,3,4-tetrahydro-N,N-dimethyl- |
| 788z | 1H-Pyrido[3,4-b]indole, 1-(1,3-benzodioxol-5-yl)-2,3,4,9-tetrahydro-9-(2-pyridinylmethyl)-2-[[5-[3-(trifluoromethyl)phenyl]-2-furanyl]carbonyl]- |
| 789z | 9H-Pyrido[3,4-b]indole-9-ethanamine, 1-(1,3-benzodioxol-5-yl)-1,2,3,4-tetrahydro-N,N-dimethyl-2-[(5-phenyl-2-furanyl)carbonyl]- |
| 790z | 1H-Pyrido[3,4-b]indole, 1-(1,3-benzodioxol-5-yl)-2,3,4,9-tetrahydro-9-[2-(1-pyrrolidinyl)ethyl]-2-[[5-[3-(trifluoromethyl)phenyl]-2-furanyl]carbonyl]- |
| 791z | 9H-Pyrido[3,4-b]indole-9-acetic acid, 1-(1,3-benzodioxol-5-yl)-1,2,3,4-tetrahydro-2-[[5-(3-nitrophenyl)-2-furanyl]carbonyl]- |
| 792z | 9H-Pyrido[3,4-b]indole-9-ethanamine, 1-(1,3-benzodioxol-5-yl)-1,2,3,4-tetrahydro-N,N-dimethyl-2-[5-(2-pyridinyl)-2-pyrimidinyl]- |
| 793z | 9H-Pyrido[3,4-b]indole-9-ethanamine, 1-(1,3-benzodioxol-5-yl)-1,2,3,4-tetrahydro-N,N-dimethyl-2-[[5-[3-(trifluoromethyl)phenyl]-2-furanyl]carbonyl]- |
| 794z | 9H-Pyrido[3,4-b]indole-9-ethanamine, 1-(1,3-benzodioxol-5-yl)-1,2,3,4-tetrahydro-2-[5-(4-methoxyphenyl)-2-pyrimidinyl]-N,N-dimethyl- |
| 795z | 9H-Pyrido[3,4-b]indole-9-ethanamine, 1-(1,3-benzodioxol-5-yl)-1,2,3,4-tetrahydro-N,N-dimethyl-2-[[5-(3-nitrophenyl)-2-furanyl]carbonyl]- |
| 796z | 9H-Pyrido[3,4-b]indole-9-ethanamine, 1-(1,3-benzodioxol-5-yl)-2-(2-benzoxazolyl)-1,2,3,4-tetrahydro-N,N-dimethyl- |
| 797z | 9H-Pyrido[3,4-b]indole-9-ethanamine, 1-(1,3-benzodioxol-5-yl)-1,2,3,4-tetrahydro-N,N-dimethyl-2-[[5-(2-nitrophenyl)-2-furanyl]carbonyl]- |
| 798z | 9H-Pyrido[3,4-b]indole-9-propanamine, 1-(1,3-benzodioxol-5-yl)-1,2,3,4-tetrahydro-N,N-dimethyl-2-[[5-[3-(trifluoromethyl)phenyl]-2-furanyl]carbonyl]- |
| 799z | 9H-Pyrido[3,4-b]indole-9-acetic acid, 1-(1,3-benzodioxol-5-yl)-1,2,3,4-tetrahydro-2-[[5-[3-(trifluoromethyl)phenyl]-2-furanyl]carbonyl]-, methyl ester |
| 800z | 9H-Pyrido[3,4-b]indole-9-ethanamine, 1-(1,3-benzodioxol-5-yl)-1,2,3,4-tetrahydro-N,N-dimethyl-2-(1-naphthalenylcarbonyl)- |
| 801z | 1H-Pyrido[3,4-b]indole, 1-(1,3-benzodioxol-5-yl)-2,3,4,9-tetrahydro-9-[2-(4-morpholinyl)ethyl]-2-[[5-[3-(trifluoromethyl)phenyl]-2-furanyl]carbonyl]- |
| 802z | 9H-Pyrido[3,4-b]indole-9-acetic acid, 1-(1,3-benzodioxol-5-yl)-1,2,3,4-tetrahydro-2-[[5-[3-(trifluoromethyl)phenyl]-2-furanyl]carbonyl]- |
| 803z | 9H-Pyrido[3,4-b]indole-9-ethanamine, 1-(1,3-benzodioxol-5-yl)-2-(2-benzothiazolyl)-1,2,3,4-tetrahydro-N,N-dimethyl- |
| 804z | 9H-Pyrido[3,4-b]indole-9-ethanamine, 1-(1,3-benzodioxol-5-yl)-2-[[5-(1,1-dimethylethyl)-2-furanyl]carbonyl]-1,2,3,4-tetrahydro-N,N-dimethyl- |
| 805z | 1H-Pyrido[3,4-b]indole-2,9-dicarboxylic acid, 3,4-dihydro-1-(1H-indol-3-yl)-, diethyl ester |
| 806z | 1H-Pyrido[3,4-b]indole, 1-(1,3-benzodioxol-5-yl)-2,3,4,9-tetrahydro-2-[5-(4-methoxyphenyl)-2-pyrimidinyl]-9-[2-(1-pyrrolidinyl)ethyl]- |
| 807z | 9H-Pyrido[3,4-b]indole-9-ethanamine, 1-(1,3-benzodioxol-5-yl)-2-[[5-(4-chlorophenyl)-2-furanyl]carbonyl]-1,2,3,4-tetrahydro-N,N-dimethyl- |
| 808z | 9H-Pyrido[3,4-b]indole-9-ethanamine, 1-(1,3-benzodioxol-5-yl)-1,2,3,4-tetrahydro-N,N-dimethyl-2-[(5-nitro-2-benzofuranyl)carbonyl]- |
| 809z | 9H-Pyrido[3,4-b]indole-9-ethanamine, 1-(1,3-benzodioxol-5-yl)-1,2,3,4-tetrahydro-N,N-dimethyl-2-[[5-(4-methyl-2-nitrophenyl)-2-furanyl]carbonyl]- |
| 810z | 1H-Pyrido[3,4-b]indole, 1-(1,3-benzodioxol-5-yl)-2,3,4,9-tetrahydro-9-(4-pyridinylmethyl)-2-[[5-[3-(trifluoromethyl)phenyl]-2-furanyl]carbonyl]- |
| 811z | 9H-Pyrido[3,4-b]indole-9-acetic acid, 1-(1,3-benzodioxol-5-yl)-1,2,3,4-tetrahydro-2-[[5-(3-nitrophenyl)-2-furanyl]carbonyl]-, methyl ester |
| 812z | 9H-Pyrido[3,4-b]indole-9-ethanamine, 1-(1,3-benzodioxol-5-yl)-2-(2-benzofuranylcarbonyl)-1,2,3,4-tetrahydro-N,N-dimethyl- |
| 813z | 9H-Pyrido[3,4-b]indole-9-propanoic acid, 1-(1,3-benzodioxol-5-yl)-1,2,3,4-tetrahydro-2-[[5-[3-(trifluoromethyl)phenyl]-2-furanyl]carbonyl]- |
| 814z | 9H-Pyrido[3,4-b]indole-9-ethanamine, 1-(1,3-benzodioxol-5-yl)-2-[5-(3,4-dimethoxyphenyl)-2-pyrimidinyl]-1,2,3,4-tetrahydro-N,N-dimethyl- |
| 815z | 9H-Pyrido[3,4-b]indole-9-ethanamine, 1-(1,3-benzodioxol-5-yl)-N,N-diethyl-1,2,3,4-tetrahydro-2-[[5-[3-(trifluoromethyl)phenyl]-2-furanyl]carbonyl]- |
| 816z | 9H-Pyrido[3,4-b]indole-9-ethanamine, 1-(1,3-benzodioxol-5-yl)-2-[5-(4-chlorophenyl)-2-pyrimidinyl]-1,2,3,4-tetrahydro-N,N-dimethyl- |
| 817z | 9H-Pyrido[3,4-b]indole-9-ethanamine, 1-(1,3-benzodioxol-5-yl)-1,2,3,4-tetrahydro-N,N-dimethyl-2-[[5-(4-nitrophenyl)-2-furanyl]carbonyl]- |

TABLE 1A-continued

| No | Name |
|---|---|
| 818z | 1H-Pyrido[3,4-b]indole, 1-(2,2-difluoro-1,3-benzodioxol-5-yl)-2,3,4,9-tetrahydro-2,9-bis[[5-(3-nitrophenyl)-2-furanyl]carbonyl]- |
| 819z | 1H-Pyrido[3,4-b]indole, 1-(2,2-difluoro-1,3-benzodioxol-5-yl)-2,3,4,9-tetrahydro-2,9-bis[[5-[3-(trifluoromethyl)phenyl]-2-furanyl]carbonyl]- |

In one variation, the compound is of the formula (I) wherein $R^1$ is other than a substituted or unsubstituted aryl, substituted or unsubstituted heteroaryl, an aryloxy or an aralkyl. In one variation the compound is of the formula (I) wherein $R^4$ is other than a substituted or unsubstituted aryl.

In another variation, the invention embraces compounds of the formula (I) or any variation herein, including any compound listed in Table 1 or a salt or solvate herein. In a particular variation, the invention embraces methods of using compounds of the formula (I) or any variation herein, including any compound listed in Table 1 or a salt or solvate herein as detailed herein.

In one variation, the invention embraces a compound of formula (I) wherein at least one of $X^7$, $X^8$, $X^9$ and $X^{10}$ is other than CH, provided that the compound is other than a compound of No. 9x, 10x, 17x, 18x, 25x, 32x, 50x, 51x, 58x, 59x, 66x, 83x, 91x, 92x, 99x, 100x, 107x, 124x, 131x, 132x, 139x, 140x, 141x, 143x, 148x, 165x, 172x, 174x, 181x, 182x, 189x, 197x, 203x, 206x, 212x, 214x, 215x, 222x, 230x, 238x, 244x, 247x, 248x, 255x, 256x, 263x, 271x, 279x, 288x, 289x, 290x, 295x, 296x, 297x, 304x, 320x, 329x, 330x, 337x, 338x, 345x, 353x, 361x, 362x, 364x, 370x, 371x, 377x, 378x, 379x, 386x, 403x, 411x, 418x, 419x, 422x, 427x, 435x, 444x, 452x, 453x, 460x, 468x, 485x, 486x, 493x, 494x, 501x, 509x, 526x, 527x, 534x, 535x, 542x, 550x, 567x, 568x, 574x, 575x, 576x, 583x, 599x, 600x, 608x, 609x, 615x, 616x, 617x, 624x, 640x, 641x, 649x, 650x, 657x, 658x, 665x, 667x, 682x, 690x, 691x, 698x, 706x, 722x, 723x, 731x, 732x, 739x, 746x, 747x, 755x, 764x, 765x, 770x, 772x, 773x, 780x or 788x in Table 1, or a salt or solvate thereof.

In one variation, the invention embraces a compound of formula (I), provided: (i) when m=q=0, Q is other than phenyl, naphthyl and substituted phenyl; and (ii) that the compound is other than a compound of No. 1x, 2x, 4x, 6x, 11x, 12x, 15x, 16x, 26x, 27x, 30x, 32x, 34x, 35x, 42x, 43x, 45x, 46x, 48x, 52x, 53x, 56x, 57x, 67x, 71x, 75x, 76x, 81x, 93x, 98x, 101x, 109x, 112x, 116x, 122x, 126x, 129x, 134x, 138x, 139x, 142x, 147x, 153x, 157x, 158x, 161x, 166x, 167x, 172x, 175x, 179x, 180x, 182x, 201x, 208x, 212x, 213x, 224x, 227x, 229x, 231x, 232x, 235x, 239x, 240x, 241x, 242x, 243x, 244x, 249x, 254x, 265x, 268x, 272x, 276x, 279x, 280x, 282x, 283x, 284x, 285x, 291x, 295x, 298x, 305x, 306x, 309x, 313x, 314x, 320x, 321x, 322x, 323x, 336x, 339x, 346x, 347x, 350x, 353x, 354x, 355x, 360x, 361x, 366x, 367x, 369x, 373x, 376x, 377x, 380x, 387x, 388x, 391x, 394x, 395x, 399x, 405x, 412x, 413x, 417x, 418x, 420x, 421x, 426x, 429x, 432x, 436x, 437x, 438x, 439x, 445x, 446x, 449x, 451x, 459x, 462x, 473x, 478x, 480x, 481x, 487x, 492x, 495x, 506x, 510x, 511x, 518x, 519x, 521x, 523x, 528x, 529x, 533x, 547x, 552x, 555x, 559x, 562x, 563x, 564x, 568x, 569x, 570x, 573x, 574x, 577x, 584x, 588x, 592x, 593x, 599x, 601x, 610x, 611x, 614x, 615x, 625x, 626x, 629x, 630x, 631x, 633x, 639x, 640x, 645x, 646x, 650x, 651x, 655x, 656x, 659x, 670x, 673x, 674x, 675x, 683x, 689x, 696x, 697x, 700x, 708x, 711x, 715x, 719x, 725x, 728x, 730x, 733x, 746x, 749x, 752x, 755x, 756x, 757x, 758x, 759x, 762x, 770x, 771x, 782x, 785x, 789x or 793x in Table 1, or a salt or solvate thereof.

In one variation, the invention embraces a compound of formula (I), provided: (i) when q=0, $CR^{3a}R^{3b}$ is not C=O; and (ii) that the compound is other than a compound of No. 1x, 2x, 4x, 6x, 7x, 1x, 12x, 13x, 15x, 16x, 18x, 21x, 23x, 24x, 26x, 27x, 30x, 35x, 42x, 43x, 45x, 46x, 47x, 48x, 52x, 53x, 54x, 56x, 57x, 59x, 65x, 67x, 71x, 74x, 75x, 76x, 81x, 84x, 86x, 88x, 93x, 95x, 98x, 100x, 101x, 103x, 105x, 112x, 116x, 117x, 122x, 127x, 129x, 133x, 134x, 136x, 138x, 139x, 141x, 142x, 143x, 146x, 147x, 149x, 150x, 153x, 156x, 157x, 161x, 163x, 166x, 168x, 171x, 172x, 174x, 175x, 177x, 179x, 180x, 182x, 183x, 199x, 201x, 203x, 209x, 213x, 215x, 218x, 220x, 221x, 224x, 227x, 229x, 231x, 235x, 239x, 241x, 242x, 243x, 244x, 254x, 256x, 259x, 262x, 265x, 268x, 276x, 279x, 282x, 283x, 284x, 285x, 286x, 289x, 291x, 292x, 295x, 297x, 298x, 303x, 305x, 306x, 309x, 313x, 314x, 320x, 321x, 322x, 323x, 324x, 326x, 333x, 336x, 338x, 339x, 341x, 343x, 346x, 347x, 350x, 354x, 355x, 360x, 361x, 364x, 365x, 366x, 367x, 369x, 371x, 372x, 373x, 374x, 376x, 377x, 379x, 380x, 387x, 391x, 395x, 396x, 399x, 406x, 412x, 413x, 415x, 417x, 418x, 421x, 422x, 425x, 426x, 428x, 429x, 432x, 436x, 437x, 439x, 442x, 445x, 447x, 449x, 451x, 453x, 456x, 458x, 459x, 462x, 473x, 478x, 480x, 481x, 488x, 492x, 494x, 495x, 497x, 498x, 500x, 503x, 506x, 508x, 518x, 519x, 521x, 523x, 528x, 529x, 530x, 533x, 535x, 538x, 540x, 547x, 555x, 559x, 562x, 563x, 564x, 565x, 568x, 569x, 570x, 571x, 573x, 574x, 576x, 577x, 579x, 582x, 584x, 588x, 592x, 593x, 599x, 601x, 603x, 607x, 610x, 611x, 612x, 614x, 615x, 617x, 622x, 625x, 626x, 629x, 630x, 631x, 633x, 634x, 639x, 640x, 642x, 643x, 644x, 645x, 646x, 648x, 650x, 651x, 653x, 655x, 656x, 658x, 659x, 661x, 663x, 670x, 674x, 675x, 683x, 684x, 685x, 688x, 689x, 691x, 694x, 696x, 697x, 700x, 702x, 704x, 711x, 715x, 716x, 717x, 719x, 721x, 726x, 728x, 730x, 732x, 733x, 735x, 744x, 752x, 756x, 757x, 758x, 759x, 761x, 762x, 767x, 771x, 773x, 774x, 776x, 779x, 782x, 785x or 793x in Table 1, or a salt or solvate thereof.

In one variation, the invention embraces a compound of formula (I) wherein at least one of $X^7$, $X^8$, $X^9$ and $X^{10}$ is not CH, provided: (i) when q=0, $CR^{3a}R^{3b}$ is not C=O; and (ii) that the compound is other than a compound of No. 18x, 59x, 100x, 139x, 141x, 143x, 172x, 174x, 182x, 203x, 215x, 244x, 256x, 279x, 289x, 295x, 297x, 320x, 338x, 361x, 364x, 371x, 377x, 379x, 418x, 422x, 453x, 494x, 535x, 568x, 574x, 576x, 599x, 615x, 617x, 640x, 650x, 658x, 691x, 732x or 773x in Table 1, or a salt or solvate thereof.

In one variation, the invention embraces a compound of formula (I), wherein at least one of $X^7$, $X^8$, $X^9$ and $X^{10}$ is not CH, provided: (i) when m=q=0, Q is other than phenyl, naphthyl and substituted phenyl; and (ii) that the compound is other than a compound of No. 32x, 139x, 172x, 182x, 212x, 244x, 279x, 295x, 320x, 353x, 361x, 377x, 418x, 568x, 574x, 599x, 615x, 640x, 650x, 746x, 755x or 770x in Table 1, or a salt or solvate thereof.

In one variation, the invention embraces a compound of formula (I) wherein at least one of $X^7$, $X^8$, $X^9$ and $X^{10}$ is not CH, provided: (i) when q=0, $CR^{3a}R^{3b}$ is not C=O; (ii) when m=q=0, Q is other than phenyl, naphthyl and substituted phenyl; and (iii) that the compound is other than a compound of No. 182x, 244x, 568x, 650x, 139x, 172x, 295x, 377x, 418x, 574x, 615x, 279x, 320x, 361x, 599x or 640x in Table 1, or a salt or solvate thereof.

In another variation, the invention embraces a compound of formula (I) wherein at least one of $X^7$, $X^8$, $X^9$ and $X^{10}$ is not CH, provided: (i) when q=0, $CR^{3a}R^{3b}$ is not C=O; and the compound conforms to one of provisions (ii) and (iii): (ii) when m=q=0, Q is other than phenyl, naphthyl, substituted phenyl, alkoxy and phenoxy; (iii) when $CR^{8c}R^{8d}$ is $CH_2$, Q is other than $Me_2N$ and $Et_2N$, and $R^{10a}$ and $R^{10b}$ are other than $C_3$-$C_7$ alkyl.

In yet another variation, the invention embraces a compound of formula (I) wherein at least one of $X^7$, $X^8$, $X^9$ and $X^{10}$ is not CH, provided: (i) when q=0, $CR^{3a}R^{3b}$ is not C=O; and the compound conforms to one of provisions (ii)-(iv): (ii) when q, m, $R^{8a}$, $R^{8b}$, $R^{8c}$, $R^{8d}$, $R^{8e}$ and $R^{8f}$ are taken together to form —$CH_2$— or C=O, Q is other than phenyl, naphthyl, substituted phenyl, alkoxy and phenoxy; (iii) when q, m, $R^{8a}$, $R^{8b}$, $R^{8c}$, $R^{8d}$, $R^{8e}$ and $R^{8f}$ are taken together to form —$CH_2CH_2$—, $R^1$ is other than H; (iv) when q, m, $R^{8a}$, $R^{8b}$, $R^{8c}$, $R^{8d}$, $R^{8e}$ and $R^{8f}$ are taken together to form —$CH_2CH_2CH_2$—, Q is other than $Me_2N$ and $Et_2N$; or a salt or solvate thereof.

In one variation, a compound of the invention is of the formula (I) where: $R^1$ is a substituted or unsubstituted $C_1$-$C_8$ alkyl, acyl, acyloxy, carbonylalkoxy, substituted or unsubstituted heterocyclyl or substituted or unsubstituted aryl; each $R^{2a}$ and $R^{2b}$ is independently H, methyl, fluoro or $R^{2a}$ and $R^{2b}$ are taken together to form a carbonyl moiety; each $R^{3a}$ and $R^{3b}$ is independently H or fluoro; and each $R^{10a}$ and $R^{10b}$ is independently H, halo, hydroxyl or methyl or $R^{10a}$ and $R^{10b}$ are taken together to form a carbonyl. This variation of formula (I) is referred to herein as formula "(Ia)". All variations referring to formula (I), where applicable, may apply equally to any of formula (A)-(D) the same as if each and every variation were specifically and individually listed.

In one variation, the invention embraces a compound of formula (Ia), provided that the compound is other than a compound of No. 6x, 7x, 11x, 13x, 18x, 21x, 27x, 30x, 45x, 47x, 48x, 54x, 59x, 71x, 86x, 93x, 95x, 100x, 101x, 103x, 112x, 117x, 127x, 133x, 134x, 136x, 141x, 153x, 156x, 168x, 174x, 175x, 177x, 182x, 199x, 203x, 209x, 215x, 218x, 220x, 224x, 227x, 256x, 259x, 265x, 268x, 276x, 279x, 286x, 292x, 297x, 298x, 306x, 309x, 320x, 324x, 333x, 338x, 339x, 341x, 350x, 364x, 365x, 366x, 369x, 371x, 374x, 379x, 391x, 396x, 406x, 412x, 413x, 415x, 432x, 442x, 447x, 453x, 456x, 462x, 473x, 488x, 494x, 497x, 498x, 506x, 521x, 529x, 530x, 535x, 538x, 547x, 565x, 568x, 569x, 571x, 576x, 577x, 579x, 588x, 599x, 603x, 610x, 612x, 617x, 626x, 629x, 630x, 634x, 640x, 644x, 645x, 648x, 650x, 651x, 653x, 658x, 661x, 670x, 675x, 685x, 688x, 691x, 694x, 721x, 726x, 732x, 735x, 744x, 752x, 767x, 773x, 776x, 782x, 785x or 793x in Table 1, or a salt or solvate thereof. In another variation, e.g., in any of the methods detailed herein, the compound may be of formula (Ia), including any suitable compound in Table 1, such as any compound of Table 1 listed in this paragraph.

In another variation, the invention embraces a compound of formula (Ia), provided: (i) at least one of $X^7$, $X^8$, $X^9$ and $X^{10}$ is not CH; and the compound conforms to one of provisions (ii) and (iii): (ii) when m=q=0, Q is other than phenyl, naphthyl, substituted phenyl, alkoxy and phenoxy; (iii) when q, m, $R^{8a}$, $R^{8b}$, $R^{8c}$, $R^{8d}$, $R^{8e}$ and $R^{8f}$ are taken together to form —$CH_2CH_2CH_2$—, Q is other than $Me_2N$ and $Et_2N$; or a salt or solvate thereof.

In another variation, the invention embraces compounds of the formula (A):

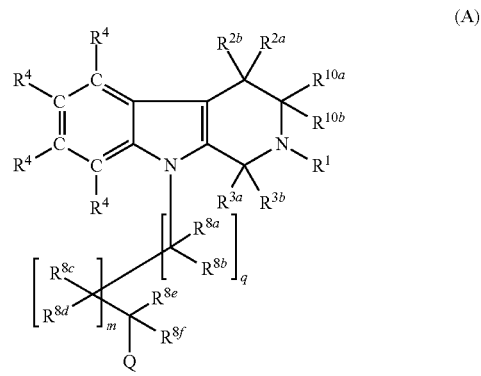

(A)

wherein:
$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, hydroxyl, alkoxy, cyano, nitro or $R^{2a}$ and $R^{2b}$ are taken together to form a carbonyl moiety;

each $R^{3a}$ and $R^{3b}$ is independently H, substituted or unsubstituted $C_1$-$C_8$ alkyl, halo, cyano, nitro, hydroxyl, alkoxy, unsubstituted amino, substituted amino, cycloalkyl, acylamino or acyloxy or $R^{3a}$ and $R^{3b}$ are taken together to form a carbonyl moiety;

m and q are independently 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl or is taken together with the carbon to which it is attached and a geminal $R_8$ to form a cycloalkyl moiety or a carbonyl moiety;

each $R^{10a}$ and $R^{10b}$ is independently H, halo, a substituted or unsubstituted $C_1$-$C_8$ alkyl, hydroxyl, alkoxyl or $R^{10a}$ and $R^{10b}$ are taken together to form a carbonyl; and Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or a unsubstituted heterocyclyl, unsubstituted amino, substituted amino, alkoxy, aminoacyl, acyloxy, carbonylalkoxy, aminocarbonylalkoxy or acylamino,
provided that the compound is other than a compound in Table 1,
or a salt or solvate thereof.

In one embodiment, a compound is of the formula (A) provided that the compound is other than a compound in Table 1 or Table 1a.

In another variation, e.g., in any of the methods detailed herein, the compound may be of formula (A), including any suitable compounds in Table 1. In another variation, e.g., in any of the methods detailed herein, the compound may be of formula (A), including any suitable compounds in Table 1a.

In one variation, the invention embraces a compound of formula (A) wherein at least one $R^4$ is other than H, provided: (i) when q=0, $CR^{3a}R^{3b}$ is not C=O, and the compound conforms to one of provisions (ii) and (iii): (ii) when m=q=0, Q is other than phenyl, naphthyl, substituted phenyl, alkoxy and phenoxy; (iii) when $CR^{8c}R^{8d}$ is $CH_2$, Q is other than $Me_2N$ and $Et_2N$, and $R^{10a}$ and $R^{10b}$ are other than $C_3$-$C_7$ alkyl, or a salt or solvate thereof.

In one variation, the invention embraces a compound of formula (A) wherein at least one $R^4$ is other than H, provided: (i) when q=0, $CR^{3a}R^{3b}$ is not C=O; and the compound conforms to one of provisions (ii)-(iv): (ii) when q, m, $R^{8a}$, $R^{8b}$, $R^{8c}$, $R^{8d}$, $R^{8e}$ and $R^{8f}$ are taken together to form —$CH_2$— or C=O, Q is other than phenyl, naphthyl, substituted phenyl, alkoxy and phenoxy; (iii) when q, m, $R^{8a}$, $R^{8b}$, $R^{8c}$, $R^{8d}$, $R^{8e}$ and $R^{8f}$ are taken together to form —$CH_2CH_2$—, $R^1$ is other than H; (iv) when q, m, $R^{8a}$, $R^{8b}$, $R^{8c}$, $R^{8d}$, $R^{8e}$ and $R^{8f}$ are taken together to form —$CH_2CH_2CH_2$—, Q is other than $Me_2N$ and $Et_2N$; or a salt or solvate thereof.

The invention also embraces compound of the formula (B):

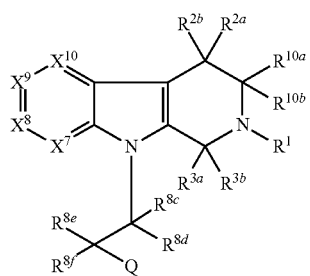

(B)

wherein:
$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, hydroxyl, alkoxy, cyano, nitro or $R^{2a}$ and $R^{2b}$ are taken together to form a carbonyl moiety;

each $R^{3a}$ and $R^{3b}$ is independently H, substituted or unsubstituted $C_1$-$C_8$ alkyl, halo, cyano, nitro, hydroxyl, alkoxy, unsubstituted amino, substituted amino, cycloalkyl, acylamino or acyloxy or $R^{3a}$ and $R^{3b}$ are taken together to form a carbonyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8c}$, $R^{8d}$, $R^{8e}$ and $R^{8f}$ is independently H, hydroxyl, $C_1$-$C_8$ alkyl or is taken together with the carbon to which it is attached and a geminal $R_8$ to form a cycloalkyl moiety or a carbonyl moiety;

each $R^{10a}$ and $R^{10b}$ is independently H, halo, a substituted or unsubstituted $C_1$-$C_8$ alkyl, hydroxyl, alkoxyl or $R^{10a}$ and $R^{10b}$ are taken together to form a carbonyl; and Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or a unsubstituted heterocyclyl, amino, substituted amino, alkoxy, aminoacyl, acyloxy, carbonylalkoxy, aminocarbonylalkoxy or acylamino, provided that the compound is other than a compound of No. 2x, 6x, 16x, 27x, 32x, 43x, 45x, 57x, 81x, 93x, 98x, 122x, 134x, 139x, 153x, 161x, 172x, 212x, 213x, 229x, 235x, 254x, 268x, 276x, 285x, 295x, 309x, 322x, 336x, 346x, 347x, 360x, 377x, 387x, 418x, 432x, 451x, 473x, 478x, 492x, 495x, 519x, 533x, 555x, 564x, 574x, 577x, 601x, 610x, 615x, 625x, 626x, 630x, 639x, 645x, 656x, 670x, 689x, 711x, 730x, 746x, 752x, 755x, 757x, 770x, 771x or 793x in Table 1, or a salt or solvate thereof.

In one embodiment, a compound is of the formula (B) provided that the compound is other than a compound in Table 1 or Table 1a.

In another variation, e.g., in any of the methods detailed herein, the compound may be of formula (B), including any suitable compound in Table 1, such as any compound of Table 1 listed hereinabove, or a salt or solvate thereof. In another variation, e.g., in any of the methods detailed herein, the compound may be of formula (B), including any suitable compound in Table 1a, such as any compound of Table 1a listed hereinabove, or a salt or solvate thereof.

In another variation, the compound is of the formula (B) where Q is a substituted or unsubstituted $C_{3-8}$ cycloalkyl, substituted or unsubstituted $C_{3-8}$ cycloalkenyl, or substituted or a unsubstituted heterocyclyl, or a salt or solvate thereof. In one variation, the compound is of the formula (B) or any variation thereof detailed herein, where Q is a carbocycle, such as a 5, 6 or 7 membered carbocycle. In one variation, the compound is of the formula (B) or any variation thereof detailed herein, where Q is a heterocycle, such as a 5, 6 or 7 membered carbocycle.

In another variation, the compound is of the formula (B) where Q is a substituted or unsubstituted aryl or a substituted or unsubstituted heteroaryl, or a salt or solvate thereof. In another variation, the compound is of the formula (B) where Q is substituted or unsubstituted heteroaryl, such as a 5, 6 or 7 membered heteroaryl. In one variation, the compound is of the formula (B) where Q is a substituted or unsubstituted aryl, such as a 5, 6 or 7 membered aryl, or a salt or solvate thereof.

In one variation, the invention embraces a compound of formula (B), provided: (i) at least one of $X^7$, $X^8$, $X^9$ and $X^{10}$ is not CH; (ii) $CR^{3a}R^{3b}$ is not C=O or CHOH; and (iii) $R^{10a}$ and $R^{10b}$ are other than $C_3$-$C_7$ alkyl, or a salt or solvate thereof.

In one variation, the invention embraces a compound of formula (B), provided: (i) at least one of $X^7$, $X^8$, $X^9$ and $X^{10}$ is not CH; (ii) $CR^{3a}R^{3b}$ is not C=O; and (iii) $R^1$ is other than H, or a salt or solvate thereof.

The invention also embraces compounds of the formula (C):

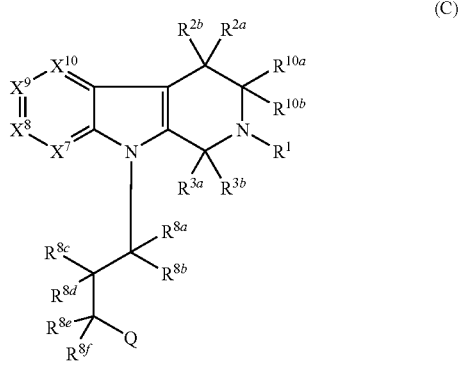

(C)

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, hydroxyl, alkoxy, cyano, nitro or $R^{2a}$ and $R^{2b}$ are taken together to form a carbonyl moiety;

each $R^{3a}$ and $R^{3b}$ is independently H, substituted or unsubstituted $C_1$-$C_8$ alkyl, halo, cyano, nitro, hydroxyl, alkoxy, unsubstituted amino, substituted amino, cycloalkyl, acylamino or acyloxy or $R^{3a}$ and $R^{3b}$ are taken together to form a carbonyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl or is taken together with the carbon to which it is attached and a geminal $R_8$ to form a cycloalkyl moiety or a carbonyl moiety;

each $R^{10a}$ and $R^{10b}$ is independently H, halo a substituted or unsubstituted $C_1$-$C_8$ alkyl, hydroxyl, alkoxyl or $R^{10a}$ and $R^{10b}$ are taken together to form a carbonyl; and Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or a unsubstituted heterocyclyl, amino, substituted amino, alkoxy, aminoacyl, acyloxy, carbonylalkoxy, aminocarbonylalkoxy or acylamino;

provided that the compound is other than a compound of No. 1x, 34x, 48x, 52x, 101x, 109x, 126x, 158x, 167x, 175x, 180x, 208x, 224x, 232x, 240x, 249x, 265x, 272x, 279x, 280x, 298x, 306x, 320x, 339x, 361x, 388x, 394x, 405x, 413x, 420x, 429x, 437x, 446x, 459x, 462x, 487x, 510x, 511x, 528x, 552x, 569x, 599x, 630x, 640x, 651x, 673x, 697x, 708x, 725x, 749x, 782x or 789x in Table 1, or a salt or solvate thereof.

In one embodiment, a compound is of the formula (C) provided that the compound is other than a compound in Table 1 or Table 1a.

In another variation, e.g., in any of the methods detailed herein, the compound may be of formula (C), including any suitable compound in Table 1, such as any compound of Table 1 listed hereinabove, or a salt or solvate thereof. In another variation, e.g., in any of the methods detailed herein, the compound may be of formula (C), including any suitable compound in Table 1a, such as any compound of Table 1a listed hereinabove, or a salt or solvate thereof.

In another variation, the compound is of the formula (C) where Q is a substituted or unsubstituted $C_{3-8}$ cycloalkyl, substituted or unsubstituted $C_{3-8}$ cycloalkenyl, or substituted or a unsubstituted heterocyclyl, or a salt or solvate thereof. In one variation, the compound is of the formula (C) where Q is a carbocycle, such as a 5, 6 or 7 membered carbocycle. In another variation, the compound is of the formula (C) where Q is a heterocycle, such as a 5, 6 or 7 membered heterocycle.

In another variation, the compound is of the formula (C) where Q is a substituted or unsubstituted aryl, such as a 5, 6 or 7 membered aryl group. In another variation, the compound is of the formula (C) where Q is a substituted or unsubstituted heteroaryl, such as a 5, 6 or 7 membered heteroaryl group.

In one variation, the invention embraces a compound of formula (C) wherein at least one of $X^7$, $X^8$, $X^9$ and $X^{10}$ is not CH, provided: when $R^{8a}$, $R^{8b}$, $R^{8c}$, $R^{8d}$, $R^{8e}$ and $R^{8f}$ each H, Q is other than $Me_2N$ and $Et_2N$, or a salt or solvate thereof.

The invention also embraces compounds of the formula (D):

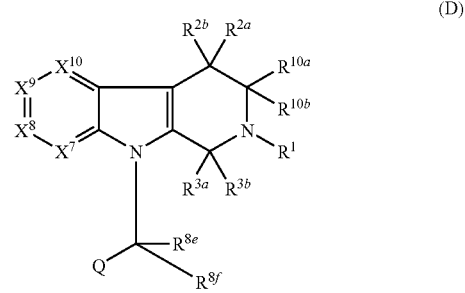

(D)

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, hydroxyl, alkoxy, cyano, nitro or $R^{2a}$ and $R^{2b}$ are taken together to form a carbonyl moiety;

each $R^{3a}$ and $R^{3b}$ is independently H, substituted or unsubstituted $C_1$-$C_8$ alkyl, halo, cyano, nitro, hydroxyl, alkoxy, unsubstituted amino, substituted amino, cycloalkyl, acylamino or acyloxy or $R^{3a}$ and $R^{3b}$ are taken together to form a carbonyl moiety;

each $X^7$, $X^8$, $X^9$ and $X^{10}$ is independently N or $CR^4$;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, carbonylalkoxy, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8e}$ and $R^{8f}$ is independently H, hydroxyl, $C_1$-$C_8$ alkyl or is taken together with the carbon to which it is attached and a geminal $R_8$ to form a cycloalkyl moiety or a carbonyl moiety;

each $R^{10a}$ and $R^{10b}$ is independently H, halo, a substituted or unsubstituted $C_1$-$C_8$ alkyl, hydroxyl, alkoxyl or $R^{10a}$ and $R^{10b}$ are taken together to form a carbonyl; and Q is a substituted or unsubstituted aryl, substituted or unsubstituted heteroaryl, substituted or unsubstituted $C_{3-8}$ cycloalkyl, substituted or unsubstituted $C_{3-8}$ cycloalkenyl, substituted or a unsubstituted heterocyclyl, unsubstituted amino, substituted amino, alkoxy, aminoacyl, acyloxy, carbonylalkoxy, aminocarbonylalkoxy or acylamino;

provided that the compound is other than a compound of No. 1x, 4x, 6x, 7x, 9x, 10x, 12x, 13x, 15x, 17x, 18x, 21x, 23x, 24x, 25x, 26x, 30x, 35x, 42x, 45x, 46x, 47x, 50x, 51x, 53x, 54x, 56x, 58x, 59x, 65x, 66x, 67x, 71x, 74x, 75x, 76x, 83x, 84x, 86x, 88x, 91x, 92x, 95x, 99x, 100x, 103x, 105x, 107x, 112x, 116x, 117x, 121x, 124x, 127x, 129x, 131x, 132x, 133x, 136x, 138x, 140x, 141x, 142x, 143x, 146x, 147x, 148x, 149x, 150x, 153x, 156x, 157x, 161x, 162x, 163x, 165x, 166x, 168x, 171x, 174x, 177x, 179x, 181x, 182x, 183x, 189x, 191x, 197x, 199x, 201x, 203x, 204x, 206x, 209x, 214x, 215x, 218x, 220x, 221x, 222x, 227x, 230x, 231x, 235x, 238x, 239x, 241x, 242x, 243x, 244x, 247x, 248x, 250x, 255x, 256x, 259x, 262x, 263x, 268x, 270x, 271x, 282x, 283x, 284x, 285x, 286x, 288x, 289x, 290x, 291x, 292x, 296x, 297x, 303x, 304x, 305x, 309x, 313x, 314x, 321x, 323x, 324x, 326x, 329x, 330x, 333x, 337x, 338x, 341x, 343x, 345x, 350x, 353x, 354x, 355x, 362x, 364x, 365x, 366x, 367x, 369x, 370x, 371x, 372x, 373x, 374x, 376x, 378x, 379x, 380x, 386x, 391x, 395x, 396x, 399x, 400x, 403x, 406x, 410x, 411x, 412x, 415x, 417x, 419x, 421x, 422x, 425x, 426x, 427x, 428x, 432x, 435x, 436x, 438x, 439x, 441x, 442x, 444x, 445x, 447x, 449x, 452x, 453x, 456x, 458x, 460x, 468x, 470x, 473x, 480x, 481x, 483x, 485x, 486x, 488x, 493x, 494x, 497x, 498x, 500x, 501x, 503x, 506x, 508x, 509x, 518x, 521x, 523x, 526x, 527x, 529x, 530x, 534x, 535x, 538x, 540x, 542x, 547x, 549x, 550x, 559x, 562x, 563x, 564x, 565x, 567x, 568x, 570x, 571x, 573x, 575x, 576x, 579x, 582x, 583x, 584x, 588x, 592x, 593x, 600x, 603x, 607x, 608x, 609x, 611x, 612x, 614x, 616x, 617x, 622x, 624x, 629x, 631x, 633x, 634x, 641x, 642x, 643x, 644x, 645x, 646x, 648x, 649x, 650x, 653x, 655x, 657x, 658x, 659x, 661x, 663x, 665x, 667x, 670x, 674x, 675x, 679x, 680x, 681x, 682x, 683x, 684x, 685x, 688x, 690x, 691x, 694x, 696x, 698x, 700x, 702x, 704x, 706x, 711x, 715x, 716x, 717x, 719x, 720x, 721x, 722x, 723x, 726x, 728x, 731x, 732x, 733x, 735x, 738x, 739x, 744x, 747x, 752x, 756x, 758x, 759x, 761x, 762x, 764x, 765x, 767x, 772x, 773x, 774x, 776x, 779x, 780x, 785x, 788x or 793x in Table 1, or a salt or solvate thereof.

In one embodiment, a compound is of the formula (D) provided that the compound is other than a compound in Table 1 or Table 1a.

In another variation, e.g., in any of the methods detailed herein, the compound may be of formula (D), including any suitable compound in Table 1, such as any compound of Table 1 listed hereinabove, or a salt or solvate thereof. In another variation, e.g., in any of the methods detailed herein, the compound may be of formula (D), including any suitable compound in Table 1a, such as any compound of Table 1a listed hereinabove, or a salt or solvate thereof.

In another variation, the compound is of the formula (D) where Q is substituted or unsubstituted $C_{3-8}$ cycloalkyl, substituted or unsubstituted $C_{3-8}$ cycloalkenyl, or substituted or a unsubstituted heterocyclyl, or a salt or solvate thereof. In one variation, the compound is of the formula (D) where Q is a carbocycle or a heterocycle, such as a 5, 6 or 7 membered carbocycle or heterocycle.

In still another variation, the compound is of the formula (D) where Q is substituted or unsubstituted aryl or a substituted or unsubstituted heteroaryl or a salt or solvate thereof.

In one variation, the invention embraces a compound of formula (D) provided: (i) at least one of $X^7$, $X^8$, $X^9$ and $X^{10}$ is not CH; and (ii) Q is other than phenyl, naphthyl, substituted phenyl, alkoxy and phenoxy, or a salt or solvate thereof.

In one variation, the compound is of the formula (E):

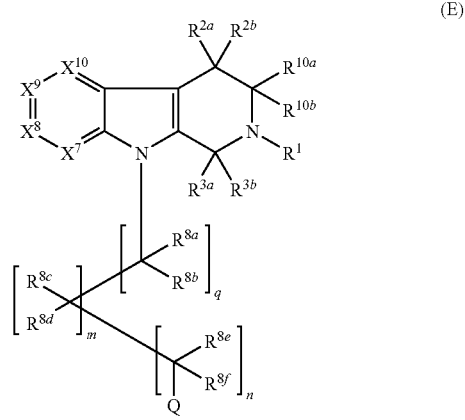

(E)

where:
$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;

each $R^{3a}$ and $R^{3b}$ is independently H, substituted or unsubstituted $C_1$-$C_8$ alkyl, halo, cyano, nitro, hydroxyl, alkoxy, amino, substituted amino, cycloalkyl, acylamino or acyloxy or $R^{3a}$ and $R^{3b}$ are taken together with the carbon to which they are attached to form a cycloalkyl moiety or a carbonyl moiety;

each $X^7$, $X^8$, $X^9$ and $X^{10}$ is independently N or $CR^4$;

m and q are independently 0 or 1;

n is 1 or 0, provided that n is 0 only when Q is a substituted heterocycle wherein the substituted heterocycle is a lactam;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^{8(a\text{-}f)}$ to form a cycloalkyl moiety or a carbonyl moiety, is taken together with a geminal $R^{8(a\text{-}f)}$ to form a methylene or a substituted methylene, is taken together with a vicinal $R^{8(a\text{-}f)}$ and the carbon atoms to which they are attached to form a substituted or unsubstituted $C_{3\text{-}8}$ cycloalkyl, substituted or unsubstituted $C_{3\text{-}8}$ cycloalkenyl or substituted or unsubstituted heterocyclyl moiety or is taken together with a vicinal $R^{8(a\text{-}f)}$ to form a bond, provided that when an $R^{8(a\text{-}f)}$ is taken together with a vicinal $R^8$ to form a bond, the geminal $R^{8(a\text{-}f)}$ is other than hydroxyl;

each $R^{10a}$ and $R^{10b}$ is independently H, halo, a substituted or unsubstituted $C_1$-$C_8$ alkyl, hydroxyl, alkoxy, cyano or nitro, or $R^{10a}$ and $R^{10b}$ are taken together with the carbon to which they are attached to form a cycloalkyl moiety or a carbonyl moiety;

Q is a substituted or unsubstituted aryl, substituted or unsubstituted heteroaryl, substituted or unsubstituted cycloalkyl, substituted or unsubstituted cycloalkenyl, substituted or a unsubstituted heterocyclyl, unsubstituted amino, substituted amino, alkoxy, aminoacyl, acyloxy, carbonylalkoxy, aminocarbonylalkoxy, acylamino, carboxy, cyano or alkynyl;

provided that the compound is other than a compound listed in Table 1 or a salt or solvate thereof. In another variation the compound is of the formula (E) provided that the compound is other than a compound listed in Table 1 or Table 1A.

In another variation, the compounds of the invention, and methods of using the compounds and administering the compounds as detailed herein, encompass any of the compounds of formula (E), including those listed in Table 1 or Table 1A or a salt thereof.

In one embodiment, "alkyl" refers to and includes saturated linear, branched, or cyclic univalent hydrocarbon structures and combinations thereof provided that when the alkyl is a cyclic alkyl having more than one ring, all rings are saturated rings. In this embodiment, which may be applied as a further variation in each instance in which the term "alkyl" (e.g., "substituted alkyl," "unsubstituted alkyl" and "$C_1$-$C_8$ alkyl") is used herein (including but not limited to compounds of the formula E or any variation thereof), a cyclic alkyl having more than one ring in which a first ring is fused to a second or subsequent ring cannot have an aryl or heteroaryl group as the second or subsequent ring. Particular alkyl groups of this embodiment are those having 1 to 20 carbon atoms. More particular alkyl groups of this embodiment are those having 1 to 8 carbon atoms.

In one embodiment of formula (E) or any variation thereof detailed herein, each $R^{3a}$ and $R^{3b}$ is independently H, substituted or unsubstituted $C_1$-$C_8$ alkyl, cycloalkyl or acylamino or $R^{3a}$ and $R^{3b}$ are taken together with the carbon to which they are attached to form a cycloalkyl moiety or a carbonyl moiety and each $R^{10a}$ and $R^{10b}$ is independently H, a substituted or unsubstituted $C_1$-$C_8$ alkyl, or $R^{10a}$ and $R^{10b}$ are taken together with the carbon to which they are attached to form a cycloalkyl moiety or a carbonyl moiety.

In one variation, the compound is of the formula (E) where $R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy. In another variation, the compound is of the formula (E) where $R^1$ is substituted or unsubstituted $C_1$-$C_8$ alkyl or acyl. In a further variation, the compound is of the formula (E) where $R^1$ is unsubstituted $C_1$-$C_8$ alkyl. Where applicable, any variation of formula (E) detailed herein may in additional variations be further defined by the $R^1$ moieties of this paragraph.

In one variation, the compound is of the formula (E) where q is 0; m and n are each 1; $R^1$ is methyl; $X^7$, $X^8$ and $X^{10}$ are each $CR^4$ where $R^4$ is H; and $X^9$ is $CR^4$ where $R^4$ is Cl. In one such variation, the compound is further defined by Q being a substituted aryl or substituted heteroaryl or $R^{8c}$, $R^{8d}$, $R^{8e}$ and $R^{8f}$ each being H. In another such variation, the compound is further defined by Q being a substituted aryl or substituted heteroaryl and $R^{8c}$, $R^{8d}$, $R^{8e}$ and $R^{8f}$ each being H. In a further such variation, Q is a substituted phenyl or substituted pyridyl group. When Q is a pyridyl group it may be bound to the carbon bearing $R^{8e}$ and $R^{8f}$ at any available ring position (e.g., Q can be a 4-pyridyl, 3-pyridyl, 2-pyridyl, etc.). The substituted aryl (e.g., substituted phenyl) or substituted heteroaryl (e.g., substituted pyridyl) in one aspect is substituted with 1 to 5 substituents independently selected from halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl and aminocarbonylamino moiety. In one such variation, Q is a phenyl or pyridyl substituted with at least one substituted or unsubstituted $C_1$-$C_8$alkyl (e.g., methyl) or halo (e.g., fluoro) moiety. Q may also be substituted with a single moiety, e.g., 4-fluorophenyl or 6-methyl-3-pyridyl. In a particular variation, the compound is of the formula (E) where q is 0; m and n are each 1; $R^{8c}$, $R^{8d}$, $R^{8e}$ and $R^{8f}$ are each H; $R^1$ is methyl; $X^7$, $X^8$ and $X^{10}$ are each $CR^4$ where $R^4$ is H; $X^9$ is $CR^4$ where $R^4$ is Cl; and Q is a phenyl or pyridyl moiety substituted with a substituted or unsubstituted $C_1$-$C_8$alkyl or halo group.

In another variation, the compound is of the formula (E) where q is 0; m and n are each 1; $R^{8c}$, $R^{8d}$, $R^{8e}$ and $R^{8f}$ are each H; $X^9$ is $CR^4$ where $R^4$ is Cl; and $R^{3a}$ and $R^{3b}$ are each H or substituted or unsubstituted $C_1$-$C_8$alkyl. In one such variation, the compound is further defined by Q being a substituted aryl or substituted heteroaryl or $R^1$ being methyl. In another such variation, the compound is further defined by Q being a substituted aryl or substituted heteroaryl and $R^1$ being methyl. When Q is a substituted aryl or substituted heteroaryl, it may be a moiety as defined in the paragraph immediately above and include a phenyl or pyridyl group substituted with a substituted or unsubstituted $C_1$-$C_8$alkyl (e.g., methyl) or halo (e.g., fluoro) group. In one such variation, one of $R^{3a}$ and $R^{3b}$ is substituted or unsubstituted $C_1$-$C_8$alkyl (e.g., a $C_1$-$C_4$ alkyl such as methyl or ethyl) and the other is H. In another such variation, $R^{3a}$ and $R^{3b}$ are both H. In one aspect, the compound is of the formula (E) where q is 0; m and n are each 1; $R^{8c}$, $R^{8d}$, $R^{8e}$ and $R^{8f}$ are each H; $R^1$ is methyl; $X^7$, $X^8$ and $X^{10}$ are each $CR^4$ where $R^4$ is H; and $R^{3a}$ and $R^{3b}$ are each H or unsubstituted $C_1$-$C_8$alkyl.

In another variation, the compound is of the formula (E) where q is 0; m and n are each 1; $R^{8c}$, $R^{8d}$, $R^{8e}$ and $R^{8f}$ are each H; $R^1$ is methyl, at least one of $R^{3a}$ and $R^{3b}$ is substituted or unsubstituted $C_1$-$C_8$alkyl and Q is a substituted aryl or substituted heteroaryl. In one variation, the compound is further defined by $X^9$ being $CR^4$ where $R^4$ is halo (e.g., chloro) and/or $X^7$, $X^8$ and $X^{10}$ each being $CR^4$ where $R^4$ is H. Q may be a substituted aryl or substituted heteroaryl moiety as detailed in the paragraphs immediately above and include a phenyl or pyridyl group substituted with a substituted or unsubstituted $C_1$-$C_8$alkyl (e.g., methyl), halo (e.g., fluoro) or perhaloalkyl (e.g., $CF_3$) group. In one such variation, one of $R^{3a}$ and $R^{3b}$ is substituted or unsubstituted $C_1$-$C_8$alkyl (in one variation, one of $R^{3a}$ and $R^{3b}$ is a $C_1$-$C_4$ alkyl such as methyl or ethyl) and the other is H. In another such variation, $R^{3a}$ and $R^{3b}$ are both H. In a particular variation, the compound is of the formula (E) where q is 0; m and n are each 1; $R^{8c}$, $R^{8d}$, $R^{8e}$ and $R^{8f}$ are each H; $R^1$ is methyl, one of $R^{3a}$ and $R^{3b}$ is substituted or unsubstituted $C_1$-$C_8$alkyl and the other is H and Q is a 4-fluorophenyl or 6-methyl-3-pyridyl group. In one aspect, the compound is of the formula (E) where q is 0; m and n are each 1; $R^{8c}$, $R^{8d}$, $R^{8e}$ and $R^{8f}$ are each H; $R^1$ is methyl, $R^{3a}$ and $R^{3b}$ are both H and Q is a substituted aryl (e.g., a substituted phenyl such as 4-fluorophenyl).

In one variation, the compound is of the formula (E) where q, m and n are each 1; $R^{8a}$, $R^{8b}$, $R^{8c}$, $R^{8d}$, $R^{8e}$ and $R^{8f}$ (collectively "$R^{8a-f}$") are each H; $X^9$ is $CR^4$ where $R^4$ is Cl and at least one of (i)-(iii) applies: (i) $R^1$ is substituted or unsubstituted $C_1$-$C_8$alkyl; (ii) $R^{3a}$ and $R^{3b}$ are each H; and (iii) Q is a substituted or unsubstituted aryl or a substituted or unsubstituted heteroaryl. In one variation, the compound is of the formula (E) where q, m and n are each 1; $R^{8a-f}$ are each H; $X^9$ is $CR^4$ where $R^4$ is Cl and at least two of (i)-(iii) apply. In another variation, the compound is of the formula (E) where q, m and n are each 1; $R^{8a-f}$ are each H; $X^9$ is $CR^4$ where $R^4$ is Cl and all of (i)-(iii) apply. In a particular variation of any of the foregoing in which (iii) applies, Q in one aspect is an unsubstituted aryl, such as phenyl.

In one variation, the compound is of the formula (E) where q, m and n are each 1; $R^{8a-f}$ are each H; Q is a substituted or unsubstituted phenyl and $R^{3a}$ and $R^{3b}$ are both H. Q in a particular variation is unsubstituted phenyl. In one aspect, the compound of the foregoing variations is further defined by $X^9$ being $CR^4$ where $R^4$ is halo (e.g., chloro).

In another variation, the compound is of the formula (E) where q, m and n are each 1; $R^{8a-f}$ are each H; $R^1$ is methyl and (i) $X^9$ is $CR^4$ where $R^4$ is halo or substituted or unsubstituted $C_1$-$C_8$alkyl and/or (ii) Q is a substituted or unsubstituted aryl or a substituted or unsubstituted heteroaryl. In one such variation, $X^9$ is $CR^4$ where $R^4$ is halo. In another such variation, Q is unsubstituted aryl. In a particular such variation, $X^9$ is $CR^4$ where $R^4$ is halo (e.g., chloro) and Q is an unsubstituted aryl (e.g., phenyl).

In another variation, the compound is of the formula (E) where q is 0; m and n are both 1; $R^{3a}$ and $R^{3b}$ are both H and $R^1$ is methyl. In one variation, the compound is further defined by applying one or more of (i)-(iv): (i) $X^9$ is $CR^4$ where $R^4$ is halo (e.g., chloro) or substituted or unsubstituted $C_1$-$C_8$alkyl (e.g., methyl); (ii) $R^{8c}$ and $R^{8d}$ are taken together to form a carbonyl moiety; (iii) one of $R^{8e}$ and $R^{8f}$ is hydroxyl and the other is H or methyl; and (iv) Q is a substituted or unsubstituted phenyl. In one such variation, (i) and (ii) apply. In another variation, (i) and (ii) and (iv) apply. In a further variation, (i) and (iii) apply. In still a further variation, (i), (iii) and (iv) apply.

In another variation, the compound is of the formula (E) where q is 0; m and n are both 1; $R^1$ is methyl; $R^{3a}$ and $R^{3b}$ are both H and Q comprises a phenyl or pyridyl moiety. In one such variation, Q is phenyl or substituted phenyl. In another such variation, Q is a phenyl substituted with one halo or one substituted or unsubstituted alkyl moiety. The phenyl may be substituted with one halo moiety such as fluoro or may be substituted with one substituted or unsubstituted alkyl moiety, e.g., a $C_1$-$C_4$ alkyl such as methyl. For example, in one variation, Q may be phenyl, 2-fluorophenyl, 4-fluorophenyl, 2-methylphenyl or 4-methylphenyl. In yet another variation, Q is a disubstituted phenyl wherein the phenyl is substituted with at least two moieties selected from halo and alkoxy. For example, in this variation, Q may be 3,4-difluorophenyl, 3,4-dichlorophenyl, 3-fluoro-4-methoxyphenyl. In still another variation, Q is a substituted pyridyl moiety, such as 6-methyl-3-pyridyl. In a particular variation, the compound is of the formula (E) where q is 0; m and n are both 1; $R^1$ is methyl; $R^{3a}$ and $R^{3b}$ are both H and Q is phenyl, phenyl substituted with one halo moiety or one alkyl moiety or substituted pyridyl. In a more particular variation, the compound of any of the these variations is further defined by one of $R^{8c}$ and $R^{8d}$ being taken together with one of $R^{8e}$ and $R^{8f}$ to form a bond and the $R^{8c}$, $R^{8d}$, $R^{8e}$ and $R^{8f}$ that are not taken to form a bond is H or methyl (thus providing an alkene moiety). In a particular such variation, $R^{8c}$ and $R^{8d}$ are taken together with one of $R^{8e}$ and $R^{8f}$ to form a bond and the $R^{8c}$, $R^{8d}$, $R^{8e}$ and $R^{8f}$ that are not taken to form a bond are H or methyl. In one aspect, the compound is of the formula (E) where q is 0; m and n are both 1; $R^1$ is methyl; $R^{3a}$ and $R^{3b}$ are both H; one of $R^{8c}$ and $R^{8d}$ being taken together with one of $R^{8e}$ and $R^{8f}$ to form a bond and the $R^{8c}$ or $R^{8d}$ that is not taken to form a bond is H and the $R^{8e}$ or $R^{8f}$ that is not taken to form a bond is methyl. In a further such variation, the compound is of the formula (E) where q is 0; m and n are both 1; $R^1$ is methyl; $R^{3a}$ and $R^{3b}$ are both H; Q comprises a phenyl or pyridyl moiety; one of $R^{8c}$ and $R^{8d}$ being taken together with one of $R^{8e}$ and $R^{8f}$ to form a bond and the $R^{8c}$ or $R^{8d}$ that is not taken to form a bond is H and the $R^{8e}$ or $R^{8f}$ that is not taken to form a bond is methyl.

In another variation, the compound is of the formula (E) where q is 0, m and n are both 1, $R^{8c}$ and $R^{8d}$ are taken together to form a carbonyl and $R^1$ is methyl. In one such variation the compound is further defined by any one or more of (i)-(iv): (i) $R^{8e}$ and $R^{8f}$ are both H; (ii) Q is a substituted phenyl; (iii) $X^9$ is $CR^4$ where $R^4$ is substituted or unsubstituted $C_1$-$C_8$alkyl or halo; and (iv) one of $R^{3a}$ and $R^{3b}$ is substituted or unsubstituted $C_1$-$C_8$alkyl, phenyl or H and the other is H. Where more than one (i)-(iv) applies, they may be combined in any manner, e.g., (i) and (ii); (i) and (iv); (ii), (iii) and (iv), (i), (ii), (iii) and (iv), etc. In one variation, Q is a phenyl substituted with a halo group, e.g., 2-fluorophenyl and 2-chlorophenyl. In one variation, $X^9$ is $CR^4$ where $R^4$ is methyl or chloro. In a particular variation, the compound is of the formula (E) where q is 0, m and n are both 1, $R^{8c}$ and $R^{8d}$ are taken together to form a carbonyl; $R^1$ is methyl; $X^9$ is $CR^4$ where $R^4$ is methyl or chloro; and Q is a substituted phenyl.

In another variation, the compound is of the formula (E) where q is 0, m and n are each 1 and one of $R^{8e}$ and $R^{8f}$ is hydroxyl. In one such variation the compound is further defined by any one or more of (i)-(vii): (i) the $R^{8e}$ or $R^{8f}$ that is not hydroxyl is methyl or H; (ii) $R^1$ is substituted or unsubstituted $C_1$-$C_8$alkyl (which in one variation is an unsubstituted $C_1$-$C_4$ alkyl such as methyl); (iii) $X^9$ is $CR^4$ where $R^4$ is substituted or unsubstituted $C_1$-$C_8$alkyl (e.g., methyl) or halo (e.g., chloro); (iv) $X^7$, $X^8$ and $X^{10}$ are each $CR^4$ where $R^4$ is H; (v) $R^{2a}$ and $R^{2b}$ are both H; (vi) $R^{10a}$ and $R^{10b}$ are both H; and (vii) Q is a substituted or unsubstituted phenyl or a substituted or unsubstituted pyridyl. In one such variation, (vii) applies and Q is an unsubstituted phenyl or phenyl substituted with a halo or substituted or unsubstituted $C_1$-$C_8$alkyl group. Where more than one (i)-(vii) applies, they may be combined in any manner and/or number. For example, in one variation, all of (i)-(vii) apply and in another, any one or two or three or more of (i)-(iv) apply. In one variation, (iii) applies and $X^9$ is $CR^4$ where $R^4$ is methyl or chloro. In another variation, both (iii) and (vii) apply, and in a particular aspect, $X^9$ is $CR^4$ where $R^4$ is methyl or chloro and Q is phenyl or 2- or 4-substituted phenyl wherein the substituent is methyl or fluoro. In a particular variation, the compound is of the formula (E) where q is 0, m and n are each 1, one of $R^{8e}$ and $R^{8f}$ is hydroxyl and the other is H or methyl and Q is phenyl or a phenyl substituted with a halo or substituted or unsubstituted alkyl moiety.

In one variation, the compound is of the formula (E) wherein $X^9$ is $CR^4$ where $R^4$ is halo or substituted or unsubstituted $C_1$-$C_8$alkyl; $R^1$ is methyl and at least one of $R^{3a}$ and $R^{3b}$ is ethyl, methyl or phenyl. In one such variation, $X^9$ is $CR^4$ where $R^4$ is chloro or methyl. In one aspect, the compound is further defined by one or more of (i)-(iv): (i) q is 0; (ii) m and n are each 1; (iii) each $R^{(8a\text{-}f)}$ is H, when present; (iv) Q is substituted phenyl or substituted pyridyl. Where more than one (i)-(iv) applies, they may be combined in any manner and/or number. For example, in one variation, all of (i)-(iv) apply and in another, any one or two or three of (i)-(iv) apply. In one variation, all of (i)-(iv) apply and Q is an unsubstituted alkyl-substituted pyridyl (e.g., 6-methyl-3-pyridyl) or a halo-substituted phenyl (e.g., 4-fluorophenyl). In another variation, the compound is of the formula (E) wherein $X^9$ is $CR^4$ where $R^4$ is halo or substituted or unsubstituted $C_1$-$C_8$alkyl; $R^1$ is methyl; at least one of $R^{3a}$ and $R^{3b}$ is ethyl, methyl or phenyl and one of $R^{8c}$ and $R^{8d}$ is taken together with one of $R^{8e}$ and $R^{8f}$ to form a bond and the $R^{8c}$ or $R^{8d}$ that is not taken to form a bond is H and the $R^{8e}$ or $R^{8f}$ that is not taken to form a bond is substituted or unsubstituted $C_1$-$C_8$alkyl (e.g., in one variation, the moiety is an unsubstituted $C_1$-$C_4$ alkyl such as methyl). In this variation, the compound may be further defined by any one or more of (v)-(vii): (v) one of $R^{3a}$ and $R^{3b}$ is methyl and the other is H; (vi) $X^9$ is $CR^4$ where $R^4$ is chloro or methyl; and (vii) Q is a mono- or di-halo-substituted phenyl (e.g., 2- or 4-fluorophenyl; 2- or 4-chlorophenyl; 2,4-dichlorophenyl; 2,4-difluorophenyl; 3,4-dichlorophenyl and 3,4-difluorophenyl). In one such variation, each of (v)-(vii) applies.

In another variation, the compound is of the formula (E) wherein m and n are both 1 and Q is a substituted phenyl. In one such variation, q is also 1. In another such variation, q is 0. When Q is a substituted phenyl, the substituent or substituents may be positioned at any available phenyl ring position. For example, singly- or mono-substituted phenyl groups may be substituted at the ortho, meta or para-position of the phenyl group. Any available phenyl ring substitution pattern is suitable for di- or tri-substituted phenyl groups (e.g., at the ortho and para positions, at two ortho positions, at two meta positions, at the meta and para positions, at the ortho, meta and para positions, at two ortho and the para position, at two ortho and a meta position, or at two meta and a para or ortho position). In one aspect, Q is a mono-substituted phenyl wherein the substituent is halo or substituted or unsubstituted alkyl. In another aspect, Q is a di-substituted phenyl wherein both substituents are halo. In a further aspect, Q is a di-substituted phenyl wherein one substituent is halo and the other substituent is alkoxy. Q in one variation is a phenyl substituted with 1 to 5 moieties where each substituent is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino moiety. In another variation, Q is a phenyl substituted with at least one substituted or unsubstituted alkyl (e.g., methyl), alkoxy (e.g., methoxy) or halo (e.g., chloro or fluoro) moiety. In still another variation, Q is a phenyl substituted with at least two halo moieties, which may be the same or different. In another such variation, Q is a phenyl substituted with one halo moiety and one alkoxy moiety. Q in one variation is 2-fluorophenyl, 4-fluorophenyl, 4-chlorophenyl, 4-methylphenyl, 2,4-dichlorophenyl, 3,4-difluorophenyl, 3,4-dichlorophenyl or 3-fluoro-4-methoxyphenyl. In still another aspect, the compound is according to the foregoing variations wherein the compound is further defined by any one or more of (i)-(vi): (i) $R^1$ is substituted or unsubstituted $C_1$-$C_8$alkyl (e.g., methyl); (ii) $X^7$, $X^8$ and $X^{10}$ are each $CR^4$ where $R^4$ is H; (iii) one of $R^{8e}$ and $R^{8f}$ is hydroxyl and the other is H or methyl; (iv) one of $R^{8c}$ and $R^{8d}$ is taken together with one of $R^{8e}$ and $R^{8f}$ to form a bond and the $R^{8c}$ or $R^{8d}$ that is not taken to form a bond is H and the $R^{8e}$ or $R^{8f}$ that is not taken to form a bond is a substituted or unsubstituted $C_1$-$C_8$alkyl (e.g., methyl); (v) q is 0; and (vi) $R^{3a}$ and $R^{3b}$ are independently H, methyl, ethyl or phenyl. Where more than one (i)-(vi) applies, they may be combined in any manner and/or number, provided that provisions (iii) and (iv) are not combined. For example, in one variation, all of (i)-(iii), (v) and (vi) apply and in another, any one or two or three or four or five of (i)-(vi) apply provided that (iii) and (iv) are not combined.

In another variation, the compound is of the formula (E) wherein Q is a substituted 3-pyridyl (e.g., 6-methyl-3-pyridyl); m and n are each 1 and $R^{8c}$, $R^{8d}$, $R^{8e}$, $R^{8f}$ are each H; $R^{10a}$ and $R^{10b}$ are both H. In one such variation, the compound is further defined by any one or more of: (i) $R^1$ is substituted or unsubstituted $C_1$-$C_8$alkyl (e.g., methyl), (ii) $X^9$ is $CR^4$ where $R^4$ is substituted or unsubstituted $C_1$-$C_8$alkyl (e.g., methyl) or halo (e.g., chloro); (iii) $X^7$, $X^8$ and $X^{10}$ are each $CR^4$ where $R^4$ is H; (iv) $R^{1a}$ and $R^{1b}$ are both H; and (v) q is 0.

In another variation, the compound is of the formula (E) wherein q and m are 0; n is 1 and Q is alkynyl. In a further variation, the compound is of the formula (E) where q and m are 0; n is 1; Q is alkynyl where the alkynyl moiety is acetylenyl. In a further variation, the compound is of the formula (E) wherein q and m are 0; n is 1; Q is alkynyl and $R^1$ is substituted or unsubstituted $C_1$-$C_8$alkyl (e.g., methyl). Such compounds may be further defined by one or more of (i)-(v): (i) $X^9$ being $CR^4$ where $R^4$ is halo (e.g., chloro) or substituted or unsubstituted $C_1$-$C_8$alkyl (e.g., methyl); (ii) $X^7$, $X^8$ and $X^{10}$ are each $CR^4$ where $R^4$ is H; (iii) $R^{2a}$ and $R^{2b}$ are both H; (iv) $R^{10a}$ and $R^{10b}$ are both H; (v) $R^{1a}$ and $R^{3b}$ are both H. Where more than one (i)-(v) apply, they may be combined in any manner and/or number. For example, in one variation, all of (i)-(v) apply and in another, any 1 or any 2 or any 3 or any 4 of (i)-(v) apply.

In one such variation, Q is a substituted heterocyclyl wherein the substituted heterocyclyl group is a substituted or unsubstituted lactam, q, m and n are each 0 and the compound is of the formula (E-1):

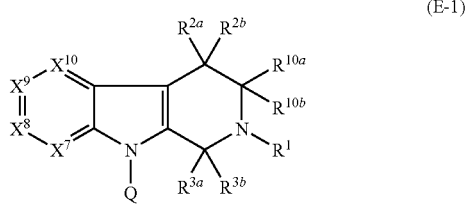

(E-1)

or a salt thereof,
wherein $R^1$, $R^{2a}$, $R^{2b}$, $R^{3a}$, $R^{3b}$, $R^{10a}$, $R^{10b}$, $X^7$, $X^8$, $X^9$ and $X^{10}$ are as defined for formula (E).

In certain variations of formula (E-1), Q is of the formula:

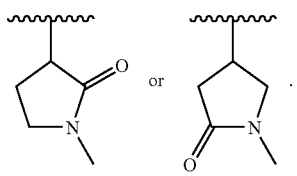

In another variation the compound is of the formula (E-1) wherein $R^1$, $R^{2a}$, $R^{2b}$, $R^{3a}$, $R^{3b}$, $R^{10a}$, $R^{10b}$, $X^7$, $X^8$, $X^9$ and $X^{10}$ are as defined for formula (E) and Q is a substituted or unsubstituted $C_3$-$C_7$ cycloalkyl, e.g., in one variation Q is

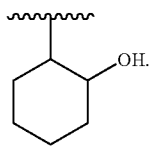

In another variation of formula (E), Q is a phenyl or substituted phenyl; $R^1$ is methyl; m and n are both 1; $R^{3a}$ and $R^{3b}$ are independently H, ethyl, methyl or phenyl and the compound is of the formula (E-2):

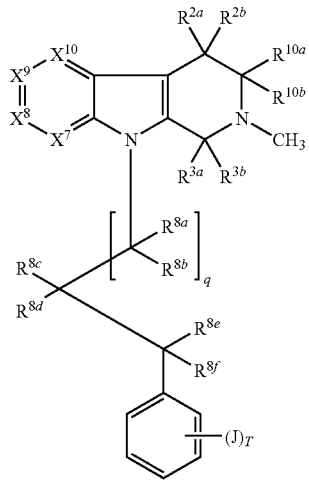

(E-2)

wherein q, $R^{2a}$, $R^{2b}$, $R^{3a}$, $R^{3b}$, $R^{8a}$, $R^{8b}$, $R^{8c}$, $R^{8d}$, $R^{8e}$, $R^{8f}$, $R^{10a}$, $R^{10b}$, $X^7$, $X^8$, $X^9$ and $X^{10}$ are as defined for formula (E);

J is halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl and aminocarbonylamino moiety; and T is an integer from 0 to 5.

In another such variation, the compound is of the formula (E-2) and is further defined by any one or more of (i)-(viii), provided that only one of (ii), (iii) and (iv) applies: (i) q is 0; (ii) $R^{8c}$ and $R^{8d}$ are both H and $R^{8e}$ and $R^{8f}$ are independently H, hydroxyl or methyl; (iii) $R^{8c}$ is taken together with $R^{8e}$ to form a bond and $R^{8d}$ is taken together with $R^{8f}$ to form a bond, such that a triple bond exists between the carbons bearing such $R^8$ groups; (iv) one of $R^{8c}$ and $R^{8d}$ is taken together with one of $R^{8e}$ and $R^{8f}$ to form a bond and the $R^{8c}$ or $R^{8d}$ that is not taken to form a bond is H and the $R^{8e}$ or $R^{8f}$ that is not taken to form a bond is H or methyl; (v) $X^9$ is $CR^4$ where $R^4$ is halo (e.g., chloro) or substituted or unsubstituted $C_1$-$C_8$alkyl (e.g., methyl); (vi) $X^7$, $X^8$ and $X^{10}$ are each $CR^4$ where $R^4$ is H; (vii) $R^{2a}$ and $R^{2b}$ are both H; and (viii) $R^{10a}$ and $R^{10b}$ are both H. Where more than one of (i)-(viii) applies, they may be combined in any manner and/or number, provided that only one of (ii), (iii) and (iv) applies. In a particular variation, the compound is of the formula (E-2), or a variation thereof where any one or more of (i)-(viii) apply (provided that only one of (ii), (iii) and (iv) applies), where J is halo, perhaloalkyl, alkoxy or a substituted or unsubstituted $C_1$-$C_8$ alkyl and T is an integer from 1 to 2.

In another variation, $R^1$ is methyl; Q is a pyridyl or substituted pyridyl; $R^{3a}$ and $R^{3b}$ are independently H, ethyl, methyl or phenyl and the compound is of the formula (E-3):

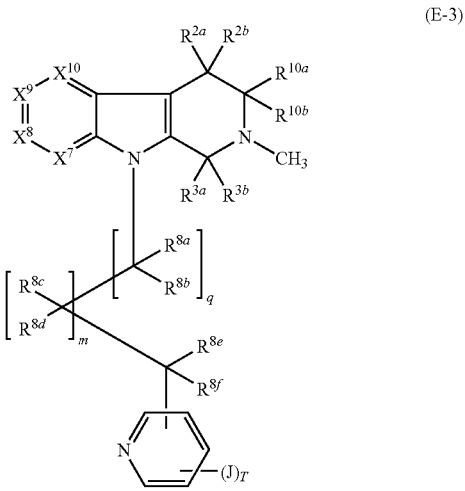

(E-3)

wherein q, m, $R^{2a}$, $R^{2b}$, $R^{3a}$, $R^{3b}$, $R^{8a}$—, $R^{8b}$, $R^{8c}$, $R^{8d}$, $R^{8e}$, $R^{8f}$, $R^{10a}$, $R^{10b}$, $X^7$, $X^8$, $X^9$ and $X^{10}$ are as defined for formula (E);

J is halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl and aminocarbonylamino moiety; and T is an integer from 0 to 4.

In one such variation, the compound is of the formula (E-3) and is further defined by any one or more of (i)-(vi): (i) q is 0; (ii) m and q are each 1 and $R^{8c}$, $R^{8d}$, $R^{8e}$ and $R^{8f}$ are each H; (iii) $X^9$ is $CR^4$ where $R^4$ is halo (e.g., chloro) or substituted or unsubstituted $C_1$-$C_8$alkyl (e.g., methyl); (iv) $X^7$, $X^8$ and $X^{10}$ are each $CR^4$ where $R^4$ is H; (v) $R^{2a}$ and $R^{2b}$ are both H; and (vi) $R^{10a}$ and $R^{10b}$ are both H. Where more than one of (i)-(vi) apply, they may be combined in any manner and/or number. The pyridyl ring may be attached to the parent structure at any available position, e.g., the pyridyl may be a 2-pyridyl, 3-pyridyl or 4-pyridyl group. In addition, when T is greater than 0, the J substituents may be bound to the pyridyl ring at any ring position. In one instance, T is 1 and the pyridyl is a 3-pyridyl group where the J moiety is bound at any available ring position. In a particular variation, the compound is of the formula (E-3), or a variation thereof, including where any one or more of (i)-(vi) apply, where J is substituted or unsubstituted $C_1$-$C_8$alkyl and T is an integer from 1 to 2. In a particular such variation, J is methyl and T is 1, e.g., to provide a 6-methyl-3-pyridyl.

In another variation, $R^{3b}$ is phenyl, $X^7$, $X^8$ and $X^{10}$ are each $CR^4$ where $R^4$ is H, m and n are each 1 and the compound is of the formula (E-4):

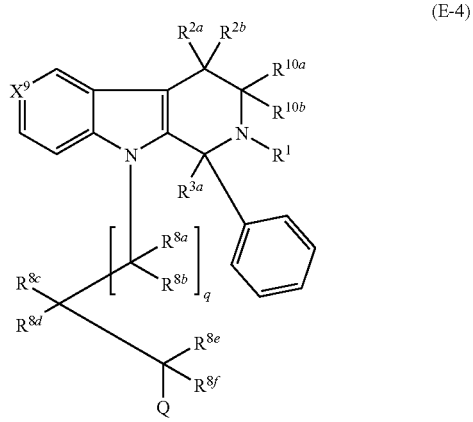

(E-4)

wherein q, m, $R^{2a}$, $R^{2b}$, $R^{3a}$, $R^{3b}$, $R^{8a}$, $R^{8b}$, $R^{8c}$, $R^{8d}$, $R^{8e}$, $R^{8f}$, $R^{10a}$, $R^{10b}$, and $X^9$ are as defined for formula (E). In one such variation, the compound is of the formula (E-4) and is further defined by any one or more of (i)-(vi), provided that provisions (iv) and (v) are not combined: (i) $X^9$ is $CR^4$ where $R^4$ is other than H (e.g., when $R^4$ is substituted or unsubstituted $C_1$-$C_8$alkyl); (ii) $R^1$ is substituted or unsubstituted $C_1$-$C_8$ alkyl; (iii) q is 0; (iv) $R^{8c}$ and $R^{8d}$ are taken together to form a carbonyl; (v) one of $R^{8c}$ and $R^{8d}$ is taken together with one of $R^{8e}$ and $R^{8f}$ to form a bond and the $R^{8c}$ or $R^{8d}$ that is not taken to form a bond is H and the $R^{8e}$ or $R^{8f}$ that is not taken to form a bond is substituted or unsubstituted $C_1$-$C_8$alkyl; and (vi) Q is a substituted phenyl. Where more than one of (i)-(vi) apply, they may be combined in any manner and/or number provided that (iv) and (v) are not combined.

In another variation, $R^1$ is methyl, $X^7$, $X^8$ and $X^{10}$ are each $CR^4$ where $R^4$ is H, m and n are each 1 and the compound is of the formula (E-5):

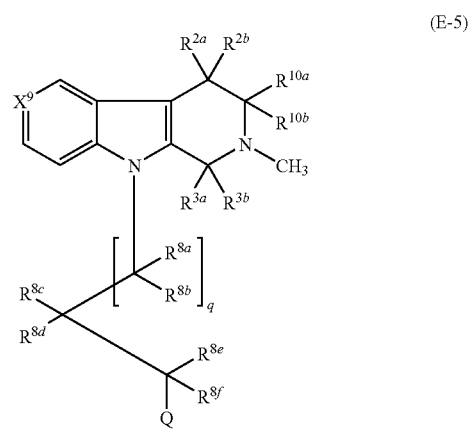

(E-5)

wherein:
$R^{3a}$ and $R^{3b}$ are independently H, substituted or unsubstituted $C_1$-$C_8$ alkyl, halo, cyano, nitro, hydroxyl, alkoxy, amino, substituted amino, cycloalkyl, acylamino, phenyl or acyloxy or $R^{3a}$ and $R^{3b}$ are taken together with the carbon to which they are attached to form a cycloalkyl moiety;
$X^9$ is $CR^4$ where $R^4$ is a substituted or unsubstituted $C_1$-$C_8$ alkyl or halo; and
$R^{2a}$, $R^{2b}$, $R^{8a}$, $R^{8b}$, $R^{8c}$, $R^{8d}$, $R^{8e}$, $R^{8f}$, $R^{10a}$, $R^{10b}$ are as defined for formula (E).

In one such variation, the compound is of the formula (E-5) and is further defined by any one or more of (i)-(vi) provided that provisions (iv) and (v) are not combined: (i) $X^9$ is $CR^4$ where $R^4$ is an unsubstituted $C_1$-$C_8$ alkyl (e.g., methyl) or halo (e.g., chloro); (ii) $R^{3a}$ and $R^{3b}$ are independently H or unsubstituted $C_1$-$C_8$ alkyl; (iii) $R^{2a}$, $R^{2b}$, $R^{10a}$ and $R^{10b}$ are each H; (iv) $R^{8c}$ and $R^{8d}$ are taken together to form a carbonyl; (v) one of $R^{8c}$ and $R^{8d}$ is taken together with one of $R^{8e}$ and $R^{8f}$ to form a bond and the $R^{8c}$ or $R^{8d}$ that is not taken to form a bond is H and the $R^{8e}$ or $R^{8f}$ that is not taken to form a bond is substituted or unsubstituted $C_1$-$C_8$alkyl; and (vi) Q is a substituted or unsubstituted aryl or substituted or unsubstituted heteroaryl. Where more than one of (i)-(vi) apply, they may be combined in any manner and/or number provided that (iv) and (v) are not combined.

In one variation, $R^1$ is methyl, n is 1 and the compound is of the formula (E-6):

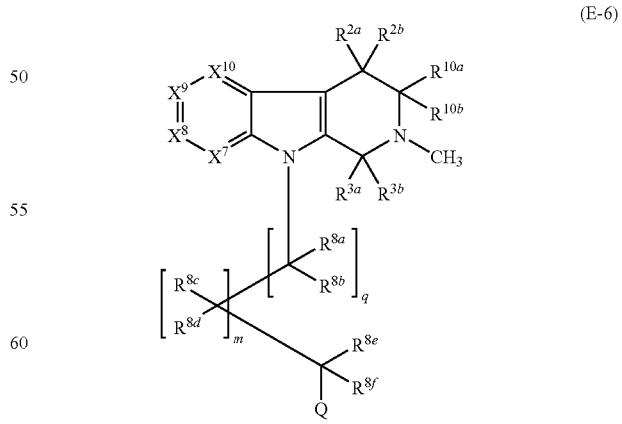

(E-6)

wherein:
$R^{3a}$ and $R^{3b}$ are independently H, substituted or unsubstituted $C_1$-$C_8$ alkyl, halo, cyano, nitro, hydroxyl, alkoxy, amino, substituted amino, cycloalkyl, phenyl, acylamino or acyloxy or $R^{3a}$ and $R^{3b}$ are taken together with the carbon to which they are attached to form a cycloalkyl moiety;

$X^9$ is N or $CR^4$ where $R^4$ is halo or a substituted or unsubstituted $C_1$-$C_8$ alkyl;

Q comprises a substituted phenyl, unsubstituted phenyl, substituted pyridyl or unsubstituted pyridyl moiety; and q, m, $X^7$, $X^8$, $X^{10}$, $R^{2a}$, $R^{2b}$, $R^{8a}$, $R^{8b}$, $R^{8c}$, $R^{8d}$, $R^{8e}$, $R^{8f}$, $R^{10a}$, $R^{10b}$ are as defined for formula (E).

In one such variation, the compound is of the formula (E-6) and is further defined by any one or more of (i)-(ix), provided that provisions (iv), (v) and (vi) are not combined in any manner: (i) $X^9$ is $CR^4$ where $R^4$ is an unsubstituted $C_1$-$C_8$ alkyl (e.g., methyl) or halo (e.g., chloro); (ii) $R^{3a}$ and $R^{3b}$ are independently H, phenyl or unsubstituted $C_1$-$C_8$ alkyl; (iii) $R^{2a}$, $R^{2b}$, $R^{10a}$ and $R^{10b}$ are each H; (iv) m is 1 and $R^{8c}$ and $R^{8d}$ are taken together to form a carbonyl; (v) m is 1 and one of $R^{8c}$ and $R^{8d}$ is taken together with one of $R^{8e}$ and $R^{8f}$ to form a bond and the $R^{8c}$ or $R^{8d}$ that is not taken to form a bond is H and the $R^{8e}$ or $R^{8f}$ that is not taken to form a bond is alkyl or H; (vi) m is 1 and $R^{8c}$ is taken together with $R^{8e}$ to form a bond and $R^{8d}$ is taken together with $R^{8f}$ to form a bond, such that a triple bond is provided; (vii) q is 0; (viii) $X^7$, $X^8$ and $X^{10}$ are each $CR^4$ where $R^4$ is H; (ix) Q is a substituted or unsubstituted phenyl or pyridyl moiety. Where more than one of (i)-(ix) apply, they may be combined in any manner and/or number provided that provisions (iv), (v) and (vi) are not combined.

In one variation, $R^1$ is methyl, m and n are both 1 and the compound is of the formula (E-7):

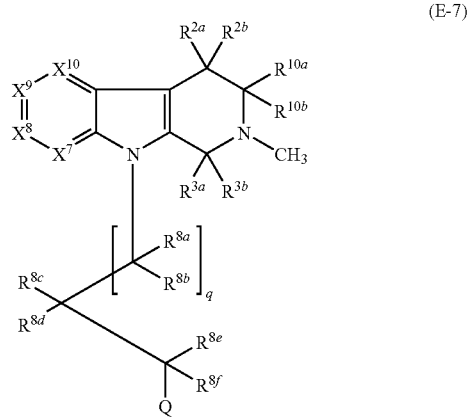

(E-7)

wherein:

$R^{3a}$ and $R^{3b}$ are independently H, substituted or unsubstituted $C_1$-$C_8$ alkyl, halo, cyano, nitro, hydroxyl, alkoxy, amino, substituted amino, cycloalkyl, phenyl, acylamino or acyloxy or $R^{3a}$ and $R^{3b}$ are taken together with the carbon to which they are attached to form a cycloalkyl moiety;

Q is an unsubstituted cycloalkyl, substituted cycloalkyl, unsubstituted heterocyclyl or substituted heterocyclyl moiety; and q, $X^7$, $X^8$, $X^9$, $X^{10}$, $R^{2a}$, $R^{2b}$, $R^{8a}$, $R^{8b}$, $R^{8c}$, $R^{8d}$, $R^{8e}$, $R^{8f}$, $R^{10a}$, $R^{10b}$ are as defined for formula (E).

In one such variation, the compound is of the formula (E-7) and is further defined by any one or more of (i)-(viii) provided that provisions (iv) and (v) are not combined: (i) $X^9$ is $CR^4$ where $R^4$ is H, an unsubstituted $C_1$-$C_8$ alkyl (e.g., methyl) or halo (e.g., chloro); (ii) $R^{3a}$ and $R^{3b}$ are each H (iii) $R^{2a}$, $R^{2b}$, $R^{10a}$ and $R^{10b}$ are each H; (iv) $R^{8e}$ and $R^{8f}$ are taken together to form a carbonyl; (v) $R^{8c}$, $R^{8d}$, $R^{8e}$ and $R^{8f}$ are each H; (vi) q is 0; (vii) $X^7$, $X^8$ and $X^{10}$ are each $CR^4$ where $R^4$ is H; (viii) Q is a substituted or unsubstituted cyclopentyl, cyclohexyl, piperidinyl or piperazinyl moiety. Where more than one of (i)-(viii) apply, they may be combined in any manner and/or number provided that provisions (iv) and (v) are not combined.

In one variation, q is 0, n is 1, $R^1$ is methyl, $R^{3a}$ and $R^{3b}$ are both H and the compound is of the formula (E-8):

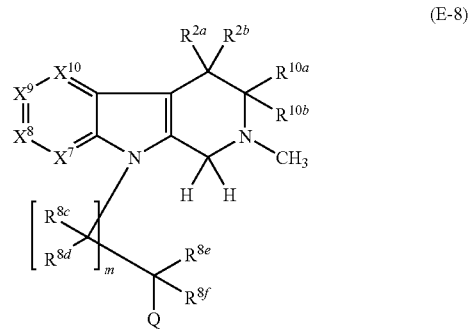

(E-8)

wherein:

Q is unsubstituted amino, substituted amino, alkoxy, aminoacyl, acyloxy, carbonylalkoxy, aminocarbonylalkoxy, acylamino, carboxy, cyano or alkynyl; and m, n, $X^7$, $X^8$, $X^9$, $X^{10}$, $R^{2a}$, $R^{2b}$, $R^{8c}$, $R^{8d}$, $R^{8e}$, $R^{8f}$, $R^{10a}$, $R^{10b}$ are as defined for formula (E). In one such variation, the compound is of the formula (E-8) and is further defined by any one or more of (i)-(v): (i) $R^{2a}$ and $R^{2b}$ are both H; (ii) $R^{10a}$ and $R^{10b}$ are both H; (iii) $R^{8e}$ and $R^{8f}$ are taken together to form a carbonyl; (iv) $X^9$ is $CR^4$ where $R^4$ is H, halo or unsubstituted $C_1$-$C_8$ alkyl; and (v) $R^{8c}$ and $R^{8d}$ are both H. Where more than one of (i)-(v) apply, they may be combined in any manner and/or number. In a particular variation of formula (E-8), $R^{8e}$ and $R^{8f}$ are taken together to form a carbonyl when Q is unsubstituted amino, substituted amino or alkoxy.

In one variation, the compound is of the formula (F):

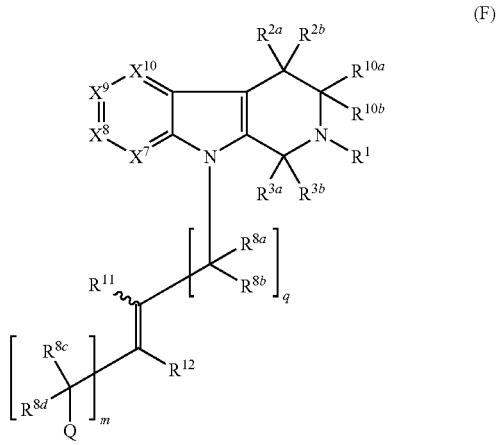

(F)

wherein:

$R^1$ is H, hydroxyl, nitro, cyano, halo, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thiol, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;

each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;

each $R^{3a}$ and $R^{3b}$ is independently H, substituted or unsubstituted $C_1$-$C_8$ alkyl, halo, cyano, nitro, hydroxyl, alkoxy, amino, substituted amino, cycloalkyl, phenyl, acylamino or acyloxy, or $R^{3a}$ and $R^{3b}$ are taken together with the carbon to which they are attached to form a cycloalkyl moiety or a carbonyl moiety;

each $X^7$, $X^8$, $X^9$ and $X^{10}$ is independently N or $CR^4$;

m and q are independently 0 or 1;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8a}$, $R^{8b}$, $R^{8c}$ and $R^{8d}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^{8(a-d)}$ to form a cycloalkyl moiety or a carbonyl moiety, or is taken together with a geminal $R^{8(a-d)}$ to form a methylene or a substituted methylene;

each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety;

$R^{11}$ and $R^{12}$ are independently H or $C_1$-$C_8$ alkyl, $C_1$-$C_8$ perhaloalkyl, carboxy, carbonylalkoxy, or are taken together with the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or are taken together to form a bond, thereby providing an acetylenyl moiety;

∿∿∿ indicates the presence of either an E or Z double bond configuration when $R^{11}$ and $R^{12}$ are independently H, $C_1$-$C_8$ alkyl, $C_1$-$C_8$ perhaloalkyl, carboxy or carbonylalkoxy;

Q is a substituted or unsubstituted aryl, substituted or unsubstituted heteroaryl, substituted or unsubstituted cycloalkyl, substituted or unsubstituted cycloalkenyl, substituted or a unsubstituted heterocyclyl, unsubstituted amino, substituted amino, alkoxy, aminoacyl, acyloxy, carbonylalkoxy, aminocarbonylalkoxy, acylamino, carboxy, cyano or alkynyl.

In one variation, the compound is of the formula (F) where q is 0, ∿∿∿ indicates an E double bond configuration, $R^{11}$ is H and $R^{12}$ is $C_1$-$C_8$ alkyl. In one variation, the compound is of the formula (F) where q is 0, ∿∿∿ indicates a Z double bond configuration, $R^{11}$ is H and $R^{12}$ is $C_1$-$C_8$ alkyl.

In one variation, the compound is of the formula (F) where Q is a phenyl or substituted phenyl. When Q is a phenyl or substituted phenyl in one aspect it is substituted with 1 to 5 substituents. When Q is a substituted phenyl, the substituent or substituents may be positioned at any available phenyl ring position. For example, singly- or mono-substituted phenyl groups may be substituted at the ortho, meta or para-position of the phenyl group. Any available phenyl ring substitution pattern is suitable for di- or tri-substituted phenyl groups (e.g., at the ortho and para positions, at two ortho positions, at two meta positions, at the meta and para positions, at the ortho, meta and para positions, at two ortho and the para position, at two ortho and a meta position, or at two meta and a para or ortho position). In one aspect, Q is a mono-substituted phenyl wherein the substituent is halo (e.g., 2-chlorophenyl, 2-fluorophenyl, 4-chlorophenyl and 4-fluorophenyl). In another aspect, Q is a di-substituted phenyl wherein both substituents are halo (e.g., 3,4-difluorophenyl, 3,4-dichlorophenyl and 2,4-dichlorophenyl). In a further aspect, Q is a di-substituted phenyl wherein one substituent is halo and the other substituent is alkoxy (e.g., 3-fluoro-4-methoxyphenyl). In one variation, Q is unsubstituted phenyl. In still another aspect, the compound is according to the foregoing variations is further defined by any one or more of (i)-(xi), provided that (iv) and (v) are not combined, (ii) and (xi) are not combined and (iii) and (xi) are not combined: (i) q and m are both 0; (ii) $R^{11}$ is H; (iii) $R^{12}$ is an unsubstituted alkyl (e.g., a $C_1$-$C_8$ alkyl such as methyl); (iv) one of $R^{3a}$ and $R^{3b}$ is methyl, ethyl or phenyl and the other is H; (v) $R^{3a}$ and $R^{3b}$ are both H; (vi) $R^1$ is alkyl (e.g., a $C_1$-$C_4$ alkyl such as methyl); (vii) $X^9$ is $CR^4$ where $R^4$ is unsubstituted alkyl (e.g., methyl) or halo (e.g., chloro); (viii) $X^7$, $X^8$ and $X^{10}$ are each $CR^4$ where $R^4$ is H; (ix) $R^{2a}$ and $R^{2b}$ are both H; (x) $R^{10a}$ and $R^{10b}$ are both H; (xi) $R^{11}$ and $R^{12}$ are taken together to form a bond, thereby providing an acetylenyl moiety. Where more than one (i)-(xi) apply, they may be combined in any manner and/or number, provided that provisions (iv) and (iv) are not combined, provisions (ii) and (xi) are not combined and provisions (iii) and (xi) are not combined. In a particular variation, provision (iii) applies ($R^{12}$ is an unsubstituted alkyl) and the double bond of compound (F) is in the "E" configuration. In another variation, provision (iii) applies ($R^{12}$ is an unsubstituted alkyl) and the double bond of compound (F) is in the "Z" configuration.

In a particular variation, the compound is of the formula (F) where Q is unsubstituted phenyl and $R^{11}$ and $R^{12}$ are both H. In a more particular variation, the compound is further defined by each of provisions (i), (v)-(x): (i) q and m are both 0; (v) $R^{3a}$ and $R^{3b}$ are both H; (vi) $R^1$ is alkyl (e.g., a $C_1$-$C_4$ alkyl such as methyl); (vii) $X^9$ is $CR^4$ where $R^4$ is unsubstituted alkyl (e.g., methyl) or halo (e.g., chloro); (viii) $X^7$, $X^8$ and $X^{10}$ are each $CR^4$ where $R^4$ is H; (ix) $R^{2a}$ and $R^{2b}$ are both H; and (x) $R^{10a}$ and $R^{10b}$ are both H.

In a particular variation, the compound is of the formula (F) where Q is a substituted phenyl and $R^1$ and $R^{12}$ are both methyl. In a more particular variation, the compound is further defined by each of provisions (i), (ii), (vii)-(x): (i) q and m are both 0; (ii) $R^{11}$ is H; (vii) $X^9$ is $CR^4$ where $R^4$ is unsubstituted alkyl (e.g., methyl) or halo (e.g., chloro); (viii) $X^7$, $X^8$ and $X^{10}$ are each $CR^4$ where $R^4$ is H; (ix) $R^{2a}$ and $R^{2b}$ are both H; and (x) $R^{10a}$ and $R^{10b}$ are both H. In an even more particular variation, the compound is of the formula (F) where Q is a substituted phenyl, $R^{11}$ and $R^{12}$ are both methyl, each of provisions (i), (ii) and (vii)-(x) apply and provision (iv) also applies: (iv) one of $R^{3a}$ and $R^{3b}$ is methyl, ethyl or phenyl and the other is H. In still another particular variation, the compound is of the formula (F) where Q is a substituted phenyl, $R^{11}$ and $R^{12}$ are both methyl, each of provisions (i), (ii) and (vii)-(x) apply and provision (v) also applies: (v) $R^{3a}$ and $R^{3b}$ are both H.

In one variation of formula (F), q and m are 0, $R^{11}$ and $R^{12}$ are independently H, $C_1$-$C_8$ alkyl, $C_1$-$C_8$ perhaloalkyl, carboxy or carbonylalkoxy and the compound is of the formula (F-1):

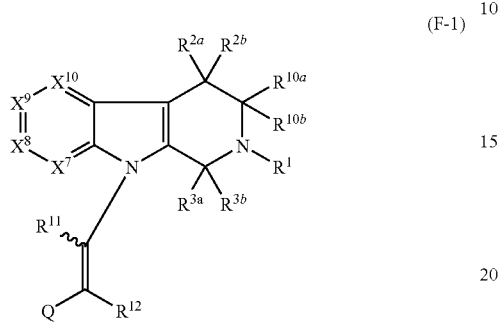

or a salt thereof,
wherein $R^1$, $R^{2a}$, $R^{2b}$, $R^{3a}$, $R^{3b}$, $R^{10a}$, $R^{10b}$, $X^7$, $X^8$, $X^9$, $X^{10}$ and Q are as defined for formula (F).

In one variation, the compound is of the formula (F-1) where ∿ indicates an E double bond configuration, $R^{11}$ is H and $R^{12}$ is $C_1$-$C_8$ alkyl. In one variation, the compound is of the formula (F-1) where ∿ indicates a Z double bond configuration, $R^{11}$ is H and $R^{12}$ is $C_1$-$C_8$ alkyl.

In one variation, the compound is of the formula (F-1) wherein Q is a substituted phenyl group, such as those described for formula (F) above, including but not limited to, mono-substituted phenyl wherein the substituent is halo (e.g., 2-chlorophenyl, 2-fluorophenyl, 4-chlorophenyl and 4-fluorophenyl) and di-substituted phenyl wherein both substituents are halo (e.g., 3,4-difluorophenyl, 3,4-dichlorophenyl and 2,4-dichlorophenyl) or when one substituent is halo and the other is alkoxy (e.g., 3-fluoro-4-methoxyphenyl). A compound of formula (F-1) where Q is a substituted phenyl may be further defined by any one or more of (i)-(vi): (i) $R^{11}$ is H; (ii) $R^{12}$ is an unsubstituted alkyl (e.g., a $C_1$-$C_8$ alkyl such as methyl); (iii) $X^9$ is $CR^4$ where $R^4$ is halo (e.g., chloro) or alkyl (e.g., methyl); (iv) $X^7$, $X^8$ and $X^{10}$ are each $CR^4$ where $R^4$ is H; (v) $R^{2a}$ and $R^{2b}$ are both H; and (vi) $R^{10a}$ and $R^{10b}$ are both H. Where more than one (i)-(vi) applies, they may be combined in any manner and/or number. In one variation, the compound is of the formula (F-1) where Q is a substituted phenyl and all of provisions (i)-(vi) apply.

In a particular variation of formula (F-1), $R^{11}$ is H and Q is a substituted or unsubstituted aryl or heteroaryl e.g., a substituted or unsubstituted phenyl or pyridyl. In a more particular variation of formula (F-1), $R^{11}$ is H, $R^{12}$ is H or methyl and Q is a substituted or unsubstituted aryl or heteroaryl. Examples of substituted or unsubstituted phenyl or pyridyl Q groups include, but are not limited to, 3-pyridyl, 4-pyridyl, 4-methoxyphenyl, 4-chlorophenyl, 4-fluorophenyl, 3-fluoro-4-methoxylphenyl, 3,4-dichlorophenyl, 3,4-difluorophenyl, 4-methyl-3-pyridyl, 4-fluorophenyl and 2-methyl-5-pyrimidyl.

In another variation of formula (F), q and m are 0, $R^{11}$ and $R^{12}$ are taken together to form a bond and the compound is of the formula (F-2):
or a salt thereof, (F-2)

wherein $R^1$, $R^{2a}$, $R^{2b}$, $R^{3a}$, $R^{3b}$, $R^{10a}$, $R^{10b}$, $X^7$, $X^8$, $X^9$, $X^{10}$ and Q are as defined for formula (F). In one variation of (F-2), Q is a substituted or unsubstituted aryl, substituted or unsubstituted heteroaryl, substituted or unsubstituted cycloalkyl, substituted or unsubstituted cycloalkenyl or substituted or unsubstituted heterocyclyl.

In a particular variation of (F-2), Q is a substituted or unsubstituted aryl or heteroaryl, e.g., a substituted or unsubstituted phenyl or pyridyl. Examples of Q include, but are not limited to, 4-methoxyphenyl, 4-chlorophenyl, 4-fluorophenyl, 3-fluoro-4-methoxyphenyl, 3,4-dichlorophenyl, 3,4-difluorophenyl, 3-pyridyl, 4-pyridyl, 4-trifluoromethyl-3-pyridyl and 4-methyl-3-pyridyl.

In a further variation of (F-2), Q is a substituted phenyl. In one aspect, the compound of formula (F-2) where Q is a substituted phenyl, including but not limited to, mono-substituted phenyl wherein the substituent is halo (e.g., 2-chlorophenyl, 2-fluorophenyl, 4-chlorophenyl and 4-fluorophenyl) and di-substituted phenyl wherein both substituents are halo (e.g., 3,4-difluorophenyl, 3,4-dichlorophenyl and 2,4-dichlorophenyl) or when one substituent is halo and the other is alkoxy (e.g., 3-fluoro-4-methoxyphenyl). The compound of formula (F-2) where Q is a substituted phenyl may be further defined by one or more of (i)-(v): (i) one of $R^{3a}$ and $R^{3b}$ is methyl, ethyl or phenyl and the other is H; (ii) $X^9$ is $CR^4$ where $R^4$ is halo (e.g., chloro) or alkyl (e.g., methyl); (iii) $X^7$, $X^8$ and $X^{10}$ are each $CR^4$ where $R^4$ is H; (iv) $R^{2a}$ and $R^{2b}$ are both H; and (v) $R^{10a}$ and $R^{10b}$ are both H. Where more than one (i)-(v) apply, they may be combined in any manner and/or number. In one variation, the compound is of the formula (F-2) where Q is a substituted phenyl and all of provisions (i)-(v) apply.

In one variation, compounds of the formula (G) are provided:

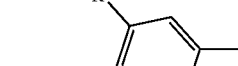

where $R^3$ is H, methyl, ethyl or phenyl; $R^4$ is methyl or chloro; Y is CH or N; $R^9$ is fluoro, chloro or methoxy; T is 0, 1 or 2 and each $R^{8a}$, $R^{8b}$, $R^{8c}$ and $R^{8d}$ is independently H, hydroxyl, methyl, is taken together with the carbon to which it is attached and a geminal $R^{8(a-d)}$ to form a carbonyl moiety or is taken together with a vicinal $R^{8(a-d)}$ to form a bond, or a pharmaceutically acceptable salt thereof. In one embodiment, the compound is of the formula (G) where $R^3$ is H. In another embodiment, the compound is of the formula (G) where each $R^{8a}$, $R^{8b}$, $R^{8c}$ and $R^{8d}$ is independently H, hydroxyl, methyl. In another embodiment, the compound is of the formula (G) where $R^{8b}$ is taken together with $R^{8d}$ to form a bond and $R^{8a}$ and $R^{8c}$ are independently H or methyl. In another embodiment, the compound is of the formula (G) where $R^3$ is H and Y is CH. In another embodiment, the compound is of the formula (G) where $R^3$ is H and Y is N. In another embodiment, the compound is of the formula (G) where $R^3$ is H, Y is N and T is 1.

Any formula detailed herein, where applicable, in one variation has each $R^{2a}$ and $R^{2b}$ independently selected from H, substituted or unsubstituted $C_1$-$C_8$ alkyl, halo, cyano, nitro, hydroxyl, alkoxy, unsubstituted amino, substituted amino, cycloalkyl, acylamino or acyloxy or $R^{2a}$ and $R^{2b}$ are taken together to form a cycloalkyl moiety or a carbonyl moiety. It is understood that by "where applicable" it is intended that such $R^{2a}$ and $R^{2b}$ moieties be a variation if the formula encompasses such a structure.

Any formula detailed herein, where applicable, in one variation has each $R^{3a}$, $R^{3b}$, $R^{10a}$, $R^{10b}$ independently selected from H, hydroxyl, alkoxyl or substituted or unsubstituted $C_1$-$C_8$ alkyl. It is understood that by "where applicable" it is intended that such $R^{3a}$, $R^{3b}$, $R^{10a}$, $R^{10b}$ moieties be a variation if the formula encompasses such a structure.

In one variation, compounds of the formula (H-1) are provided:

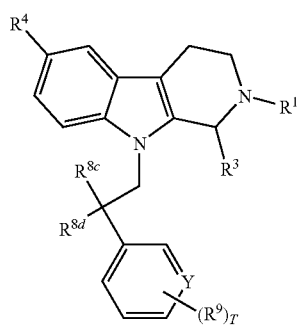

(H-1)

where $R^1$ is $CH_3$; $R^3$ is H, $CH_3$, ethyl or phenyl; $R^4$ is $CH_3$ or Cl; $R^{8c}$ and $R^{8d}$ are independently H, OH or $CH_3$; $R^9$ is H, F, Cl or $OCH_3$ and T is 1 or 2. In one embodiment, the structure is of the formula (H-1) where $R^3$ is H.

In another variation, compounds of the formula (H-2) are provided:

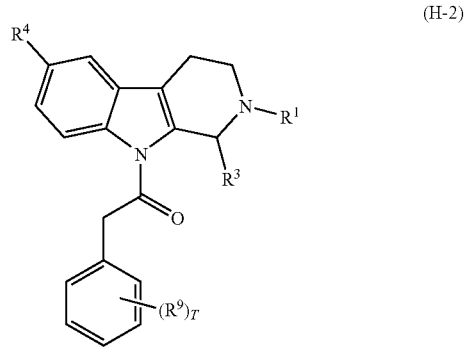

(H-2)

where $R^1$ is $CH_3$; $R^3$ is H, $CH_3$, ethyl or phenyl; $R^4$ is $CH_3$ or Cl; $R^9$ is H, F, Cl or $OCH_3$ and T is 1 or 2. In one embodiment of formula (H-2), $R^3$ is H.

In another variation, compounds of the formula (H-3) are provided:

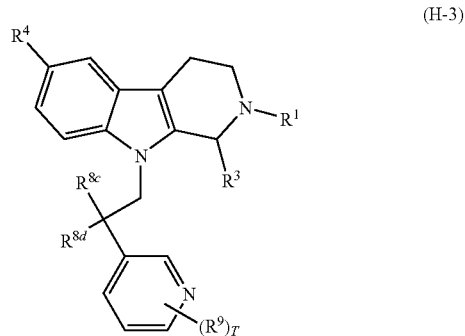

(H-3)

where $R^1$ is $CH_3$; $R^3$=H, $CH_3$, ethyl or phenyl; $R^4$ is $CH_3$ or Cl; $R^{8a}$ and $R^{8d}$ are independently H, OH or $CH_3$; $R^9$ is H, F, Cl or $OCH_3$ and T is 1 or 2. In one embodiment of formula H-3, $R^3$ is H.

In another variation, compounds of the formula (H-4) are provided:

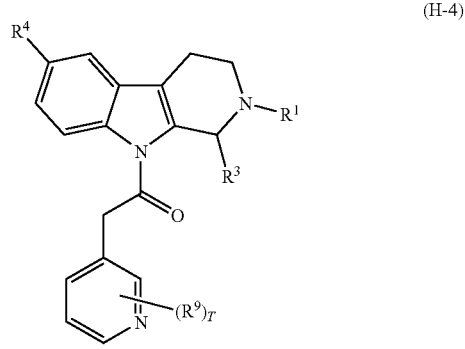

(H-4)

where $R^1$ is $CH_3$; $R^3$ is H, $CH_3$, ethyl or phenyl; $R^4$ is $CH_3$ or Cl; $R^9$ is H, F, Cl or $OCH_3$ and T is 1 or 2. In one embodiment of formula (H-4), $R^3$ is H.

In another variation, compounds of the formula (H-5) are provided:

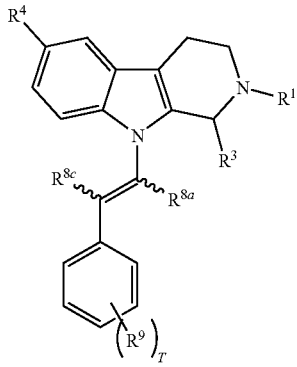
(H-5)

where $R^1$ is $CH_3$; $R^3$ is H, $CH_3$, ethyl or phenyl; $R^4$ is $CH_3$ or Cl; $R^{8a}$ and $R^{8c}$ are independently H, $CH_3$ or $R^{8a}$ and $R^{8c}$ together form a bond; $R^9$ is H, F, Cl or $OCH_3$ and T is 1 or 2. In one embodiment of formula H-5, $R^3$=H.

In another variation, compounds of the formula (H-6) are provided:

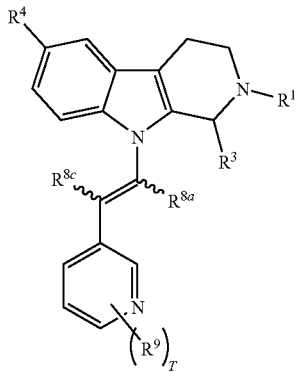
(H-6)

where $R^1$ is $CH_3$; $R^3$ is H, $CH_3$, ethyl or phenyl; $R^4$ is $CH_3$ or Cl; $R^{8a}$ and $R^{8c}$ are independently H, $CH_3$ or $R^{8a}$ and $R^{8c}$ together form a bond; $R^9$ is H, F, Cl or $OCH_3$ and T is 1 or 2. In one embodiment of formula H-6, $R^3$ is H.

In a particular embodiment, the compound is of the formula (I), (E), (F) or (Ia) where $X^7$, $X^8$, $X^9$ and $X^{10}$ are $CR^4$. In another embodiment, the compound is of the formula (I), (E), (F) or (Ia) where at least one of $X^7$, $X^8$, $X^9$ and $X^{10}$ is N. Another variation provides a compound of the formula (I), (E), (F) or (Ia) where at least two of $X^7$, $X^8$, $X^9$ and $X^{10}$ are N. A further variation provides a compound of the formula (I), (E), (F) or (Ia) where 2 of $X^7$, $X^8$, $X^9$ and $X^{10}$ are N and 2 of $X^7$, $X^8$, $X^9$ and $X^{10}$ are $CR^4$. A compound of the formula (I), (E), (F) or (Ia) where 1 of $X^7$, $X^8$, $X^9$ and $X^{10}$ is N and 3 of $X^7$, $X^8$, $X^9$ and $X^{10}$ are $CR^4$ is also embraced by this invention.

In another variation, a compound of the invention is of the formula (I), (E), (F) or (Ia) where $X^7$, $X^8$, $X^9$ and $X^{10}$ are taken together to provide an aromatic moiety selected from the following structures:

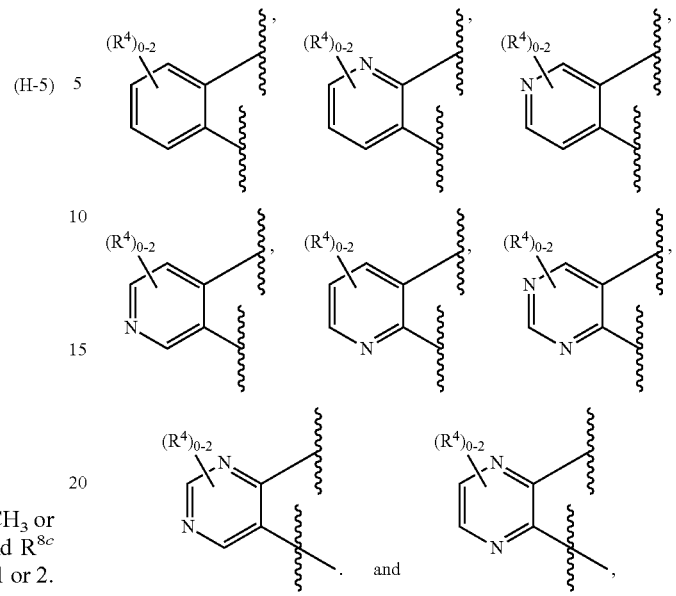

where each $R^4$ is as defined for formula (I) or (Ia); or in a particular variation, where each $R^4$ is independently hydroxyl, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, substituted or unsubstituted heterocyclyl, substituted or unsubstituted aralkyl, thioalkyl, substituted or unsubstituted amino, alkylsulfonylamino or acyl; or in still a further variation, where $R^4$ is independently halo, unsubstituted $C_1$-$C_4$ alkyl or $C_1$-$C_4$ perhaloalkyl. In another variation, each $R^4$ is independently halo or an unsubstituted $C_1$-$C_8$ alkyl. In one embodiment, the foregoing rings are substituted with an $(R^4)_1$ substituent, such that that aromatic moiety is substituted is a single $R^4$ group, which in one variation is halo or unsubstituted $C_1$-$C_8$ alkyl. In one such variation, the foregoing rings have $(R^4)_0$ substituents, such that that aromatic moiety is unsubstituted and contains no $R^4$ groups. In a further variation, the compound is of the formula (B), (C), (D), (E-1), (E-2), (E-3), (E-6), (E-7), (E-8), (F), (F-1) or (F2) where $X^7$, $X^8$, $X^9$ and $X^{10}$ are taken together to provide an aromatic moiety selected from the foregoing structures of this paragraph.

In another variation, a compound of the invention is of the formula (I), (E), (F) or (Ia) where $X^7$, $X^8$, $X^9$ and $X^{10}$ are taken together to provide an aromatic moiety selected from the following structures:

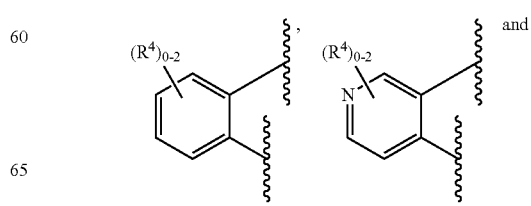

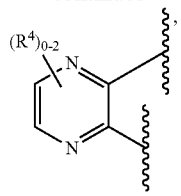

where each R⁴ is as defined for formula (I) or (Ia); or in a particular variation, where each R⁴ is independently alkyl, perhaloalkyl or halo or in an even more particular variation, where each R⁴ is independently methyl, trifluoromethyl, chloro or fluoro. In one embodiment, the foregoing rings are substituted with an (R⁴)₁ substituent, such that that aromatic moiety is substituted is a single R⁴ group, which in one variation is halo or unsubstituted C₁-C₈ alkyl. In one such variation, the foregoing rings have (R⁴)₀ substituents, such that that aromatic moiety is unsubstituted and contains no R⁴ groups. In a further variation, the compound is of the formula (B), (C), (D), (E-1), (E-2), (E-3), (E-6), (E-7), (E-8), (F), (F-1) or (F2) where X⁷, X⁸, X⁹ and X¹⁰ are taken together to provide an aromatic moiety selected from the foregoing structures of this paragraph.

In a further variation, the compound is of the formula (I), (Ia), (B), (C), (D), (E), (E-1), (E-2), (E-3), (E-6), (E-7), (E-8), (F), (F-1) or (F2) where X⁷, X⁸, X⁹ and X¹⁰ are taken together to provide a structure of the following formulae, where R⁴ may be as defined in any variation hereinabove:

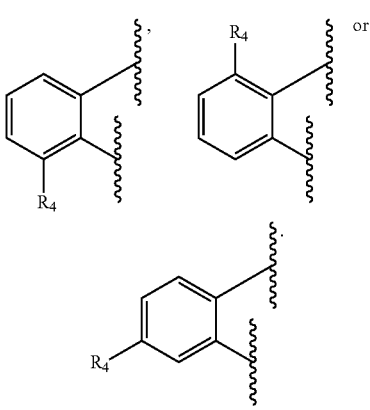

In one such variation, R⁴ is halo or an unsubstituted C₁-C₈ alkyl.

In still a further variation, a compound of the invention is of the formula (I), (E), (F) or (Ia) where X⁷, X⁸, X⁹ and X¹⁰ are taken together provide an aromatic moiety selected from the following structures:

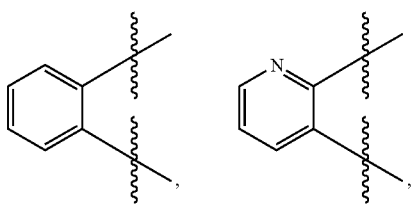

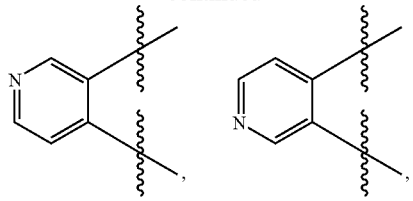

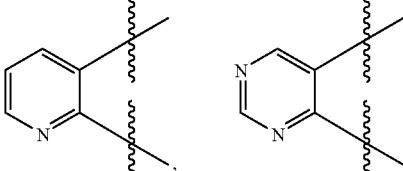

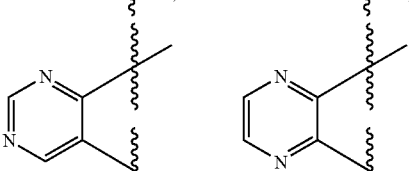

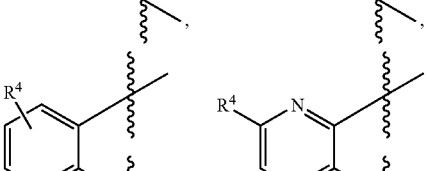

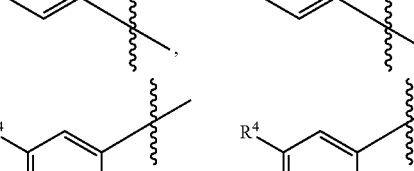

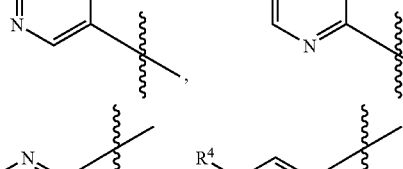

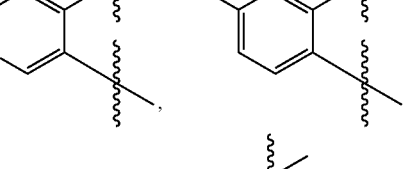

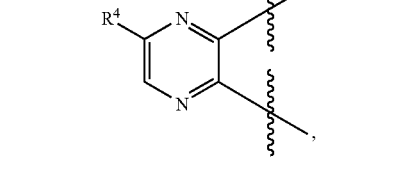

and

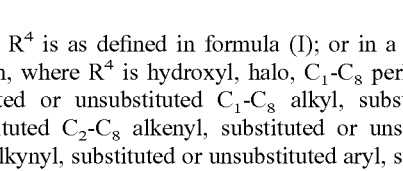

wherein R⁴ is as defined in formula (I); or in a particular variation, where R⁴ is hydroxyl, halo, C₁-C₈ perhaloalkyl, substituted or unsubstituted C₁-C₈ alkyl, substituted or unsubstituted C₂-C₈ alkenyl, substituted or unsubstituted C₂-C₈ alkynyl, substituted or unsubstituted aryl, substituted or unsubstituted heteroaryl, C₁-C₈ perhaloalkoxy, C₁-C₈ alkoxy, substituted or unsubstituted heterocyclyl, substituted or unsubstituted aralkyl, thioalkyl, substituted or unsubstituted amino, alkylsulfonylamino or acyl; or in still a further variation, where each R⁴ is independently halo, unsubstituted C₁-C₄ alkyl or C₁-C₄ perhaloalkyl. In another variation, R⁴ is halo or unsubstituted C₁-C₈ alkyl. In still a further variation, the compound is of the formula (B), (C), (D), (E-1), (E-2), (E-3), (E-6), (E-7), (E-8), (F), (F-1) or (F2) where $X^7$, $X^8$, $X^9$ and $X^{10}$ are taken together to provide an aromatic moiety selected from the foregoing structures of this paragraph. In yet another variation, the compound is of the formula (I), (B), (C), (D), (E), (F), (Ia), (E-1), (E-2), (E-3), (E-6), (E-7), (E-8), (F), (F-1) or (F2) where $X^7$, $X^8$, $X^9$ and $X^{10}$ are taken together to provide a structure of the formula:

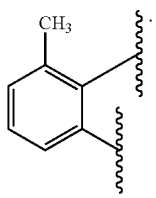

In still a further variation, a compound of the invention is of the formula (I), (E), (F) or (Ia) where $X^7$, $X^8$, $X^9$ and $X^{10}$ are taken together provide an aromatic moiety selected from the following structures:

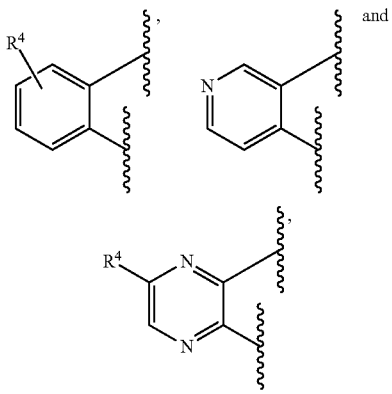

wherein $R^4$ is as defined in formula (I) or in any particular variation herein, such as when each $R^4$ is independently alkyl or halo or in an even more particular variation, where each $R^4$ is independently methyl, chloro, iodo or fluoro. In still a further variation, the compound is of the formula (B), (C), (D), (E-1), (E-2), (E-3), (E-6), (E-7), (E-8), (F), (F-1) or (F2) where $X^7$, $X^8$, $X^9$ and $X^{10}$ are taken together to provide an aromatic moiety selected from the foregoing structures of this paragraph.

In yet another variation, a compound of the invention is of the formula (I), (E), (F) or (Ia) where $X^7$, $X^8$, $X^9$ and $X^{10}$ are taken together provide an aromatic moiety selected from the following structures:

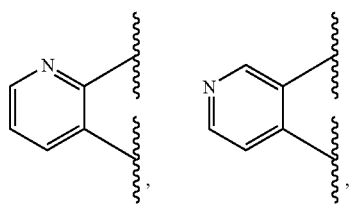

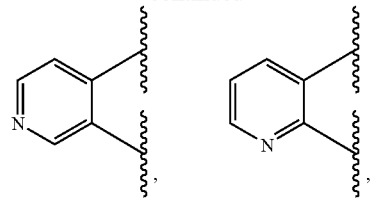

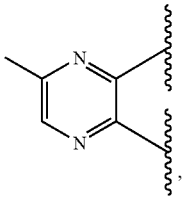

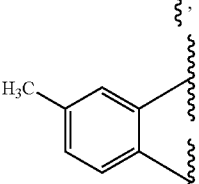

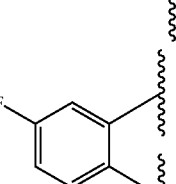

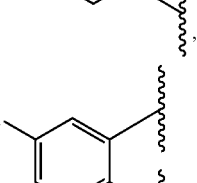

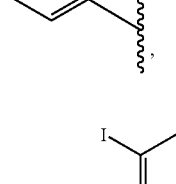

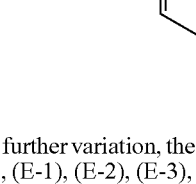

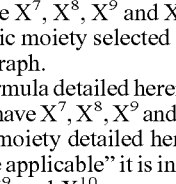

and

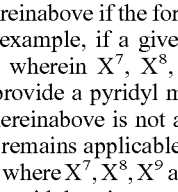

In still a further variation, the compound is of the formula (B), (C), (D), (E-1), (E-2), (E-3), (E-6), (E-7), (E-8), (F), (F-1) or (F2) where $X^7$, $X^8$, $X^9$ and $X^{10}$ are taken together to provide an aromatic moiety selected from the foregoing structures of this paragraph.

Any formula detailed herein, where applicable, may in one variation have $X^7$, $X^8$, $X^9$ and $X^{10}$ taken together to provide an aromatic moiety detailed herein above. It is understood that by "where applicable" it is intended that in one variation such $X^7$, $X^8$, $X^9$ and $X^{10}$ groups are taken together to provide a moiety hereinabove if the formula encompasses such a structure. For example, if a given formula does not encompass structures wherein $X^7$, $X^8$, $X^9$ and $X^{10}$ groups are taken together provide a pyridyl moiety, then a pyridyl moiety as detailed hereinabove is not applicable to that particular formula, but remains applicable to formulae that do encompass structures where $X^7$, $X^8$, $X^9$ and $X^{10}$ groups are taken together provide a pyridyl moiety.

In another embodiment, a compound of the invention is of the formula (I), (E) or (F), wherein $X^7$-$X^{10}$ are as defined in formula (I) or as detailed in any variation herein, where $R^1$ is H, substituted or unsubstituted $C_1$-$C_8$ alkyl, acyl, acyloxy, carbonylalkoxy, substituted or unsubstituted heterocyclyl, substituted or unsubstituted aryl, substituted or unsubstituted heteroaryl, substituted or unsubstituted aralkyl. In a further embodiment, a compound of the invention is of the formula (I), (E) or (F), wherein $X^7$-$X^{10}$ are as defined in formula (I) or as detailed in any variation herein, where $R^1$ is a substituted or unsubstituted $C_1$-$C_8$ alkyl, acyl, acyloxy, carbonylalkoxy, substituted or unsubstituted heterocyclyl or substituted or unsubstituted aryl. In a particular variation, a compound of the invention is of the formula (I), (E) or (F), wherein $X^7$-$X^{10}$ are as defined in formula (I) or as detailed in any variation herein, where $R^1$ is methyl, ethyl, cyclopropyl, propylate, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In another variation, the compound of the invention is of the formula (I), (E) or (F), where $X^7$-$X^{10}$ and $R^1$ are as defined in formula (I) or as detailed in any variation herein, where $R^{2a}$ and $R^{2b}$ are independently H, substituted or unsubstituted $C_1$-$C_8$ alkyl, halo, cyano, nitro or $R^{2a}$ and $R^{2b}$ are taken together to form a carbonyl moiety and each $R^{3a}$ and $R^{3b}$ is independently H, substituted or unsubstituted $C_1$-$C_8$ alkyl, halo, cyano, nitro, hydroxyl, alkoxy, unsubstituted amino, substituted amino, cycloalkyl, acylamino or acyloxy. In another variation, the compound of the invention is of the formula (I), (E) or (F), where $X^7$-$X^{10}$ and $R^1$ are as defined in formula (I) or as detailed in any variation herein, where each $R^{2a}$ and $R^{2b}$ is independently H, unsubstituted $C_1$-$C_8$ alkyl, halo or $R^{2a}$ and $R^{2b}$ are taken together to form a carbonyl moiety and each $R^{3a}$ and $R^{3b}$ is independently H, unsubstituted $C_1$-$C_8$ alkyl, halo or $R^{3a}$ and $R^{3b}$ are taken together to form a carbonyl moiety. In still a further variation, the compound of the invention is of the formula (I), (E) or (F), where $X^7$-$X^{10}$ and $R^1$ are as defined in formula (I) or as detailed in any variation herein, where each $R^{2a}$ and $R^{2b}$ is independently H, unsubstituted $C_1$-$C_8$ alkyl, halo or $R^{2a}$ and $R^{2b}$ are taken together to form a carbonyl moiety; and each $R^{3a}$ and $R^{3b}$ is independently H, unsubstituted $C_1$-$C_8$ alkyl, halo or $R^{3a}$ and $R^{3b}$ are taken together to form a carbonyl moiety. The invention also embraces compounds of the invention according to formula (I), where $X^7$-$X^{10}$ and $R^1$ are as defined in formula (I) or as detailed in any variation herein, where each $R^{2a}$ and $R^{2b}$ is independently H, methyl, halo or $R^{2a}$ and $R^{2b}$ are taken together to form a carbonyl moiety and each $R^{3a}$ and $R^{3b}$ is independently H, methyl, halo or $R^{3a}$ and $R^{3b}$ are taken together to form a carbonyl moiety. The invention further embraces compounds of the invention according to formula (I), where $X^7$-$X^{10}$ and $R^1$ are as defined in formula (I) or as detailed in any variation herein, where each of $R^{2a}$, $R^{2b}$, $R^{3a}$ and $R^{3b}$ is H. In one variation, a compound of the invention is of the formula (I), (E) or (F) where $X^7$-$X^{10}$ and $R^1$ are as defined in formula (I) or as detailed in any variation herein, where at least one of $R^{2a}$, $R^{2b}$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety. In another variation, a compound of the invention is of the formula (I), (E) or (F) where $X^7$-$X^{10}$ and $R^1$ are as defined in formula (I) or as detailed in any variation herein, where at least two of $R^{2a}$, $R^{2b}$, $R^{3a}$ and $R^{3b}$ is a substituted or unsubstituted $C_1$-$C_8$ alkyl, halo, cyano, nitro or is taken together with a geminal $R^2$ or $R^3$ to form a carbonyl moiety. In yet another variation, a compound of the invention is of the formula (I), (E) or (F) where $X^7$-$X^{10}$ and $R^1$ are as defined in formula (I) or as detailed in any variation herein, where at least one of $R^{2a}$, $R^{2b}$, $R^{3a}$ and $R^{3b}$ is fluoro or methyl or is taken together with a geminal $R^2$ or $R^3$ to form a carbonyl moiety. In still another variation, a compound of the invention is of the formula (I), (E) or (F) where $X^7$-$X^{10}$ and $R^1$ are as defined in formula (I) or as detailed in any variation herein, where either $R^{2a}$ and $R^{2b}$ or $R^{3a}$ and $R^{3b}$ are each methyl or fluoro (e.g., both $R^{2a}$ and $R^{2b}$ are methyl or one is fluoro and one is methyl) or are taken together to form a carbonyl moiety. In one variation, $R^{2a}$ and $R^{2b}$ are taken together to form a carbonyl moiety. In another variation, at least one of $R^{2a}$ and $R^{2b}$ is hydroxyl or alkoxy. In a particular variation, each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl. In another variation, each $R^{2a}$ and $R^{2b}$ is independently H, substituted or unsubstituted $C_1$-$C_8$ alkyl, halo, cyano, nitro or $R^{2a}$ and $R^{2b}$ are taken together to form a carbonyl.

The invention also embraces compounds according to formula (I), where $X^7$-$X^{10}$, $R^1$, $R^{2a}$, $R^{2b}$, $R^{3a}$ and $R^{3b}$ are as defined in formula (I) or as detailed in any variation herein, where each $R^{10a}$ and $R^{10b}$ is independently H, halo, an unsubstituted $C_1$-$C_8$ alkyl, hydroxyl or $R^{10a}$ and $R^{10b}$ are taken together to form a carbonyl. Also embraced are compounds according to formula (I), where $X^7$-$X^{10}$, $R^1$, $R^{2a}$, $R^{2b}$, $R^{3a}$ and $R^{3b}$ are as defined in formula (I) or as detailed in any variation herein, where each $R^{10a}$ and $R^{10b}$ is independently H, halo, an unsubstituted $C_1$-$C_4$ alkyl, hydroxyl or $R^{10a}$ and $R^{10b}$ are taken together to form a carbonyl. In another variation, a compound of the invention is of the formula (I), (E) or (F), where $X^7$-$X^{10}$, $R^1$, $R^{2a}$, $R^{2b}$, $R^{3a}$ and $R^{3b}$ are as defined in formula (I) or as detailed in any variation herein, where each $R^{10a}$ and $R^{10b}$ is independently H, bromo, methyl, hydroxyl or $R^{10a}$ and $R^{10b}$ are taken together to form a carbonyl. In yet another variation, a compound of the invention is of the formula (I), (E) or (F), where $X^7$-$X^{10}$, $R^1$, $R^{2a}$, $R^{2b}$, $R^{3a}$ and $R^{3b}$ are as defined in formula (I) or as detailed in any variation herein, where at least one of $R^{10a}$ and $R^{1b}$ is an unsubstituted $C_1$-$C_8$ alkyl, hydroxyl, halo or $R^{1a}$ and $R^{1b}$ are taken together to form a carbonyl. In still a further variation, a compound of the invention is of the formula (I), (E) or (F), where $X^7$-$X^{10}$, $R^1$, $R^{2a}$, $R^{2b}$, $R^{3a}$ and $R^{3b}$ are as defined in formula (I) or as detailed in any variation herein, where at least one of $R^{10a}$ and $R^{10b}$ is methyl, bromo, hydroxyl or $R^{10a}$ and $R^{10b}$ are taken together to form a carbonyl. In another variation, a compound of the invention is of the formula (I), (E) or (F), where $X^7$-$X^{10}$, $R^1$, $R^{2a}$, $R^{2b}$, $R^{3a}$ and $R^{3b}$ are as defined in formula (I) or as detailed in any variation herein, where both $R^{10a}$ and $R^{10b}$ are methyl. In another variation, a compound of the invention is of the formula (I), (E) or (F), where $X^7$-$X^{10}$, $R^1$, $R^{2a}$, $R^{2b}$, $R^{3a}$ and $R^{3b}$ are as defined in formula (I) or as detailed in any variation herein, where $R^{10a}$ and $R^{10b}$ are taken together to form a carbonyl. In another variation, a compound of the invention is of the formula (I), (E) or (F), where $X^7$-$X^{10}$, $R^1$, $R^{2a}$, $R^{2b}$, $R^{3a}$ and $R^{3b}$ are as defined in formula (I) or as detailed in any variation herein, where $R^{1a}$ is H and $R^{10b}$ is methyl. In another variation, a compound of the invention is of the formula (I), (E) or (F), where $X^7$-$X^{10}$, $R^1$, $R^{2a}$, $R^{2b}$, $R^{3a}$ and $R^{3b}$ are as defined in formula (I) or as detailed in any variation herein, where $R^{1a}$ is H and $R^{10b}$ is bromo. When the carbon of formula (I) bearing $R^{10a}$ and $R^{10b}$ is optically active, it may be in the S or R configuration and compositions comprising substantially pure R or S compound or mixtures thereof in any amount are embraced by this invention.

In a particular variation, a compound of the invention is of the formula (I), (E) or (F) where $R^{2a}$, $R^{2b}$, $R^1$, $R^{10a}$, $R^{10b}$, $R^{3a}$ and $R^{3b}$ are taken together to form a ring selected from the structures:

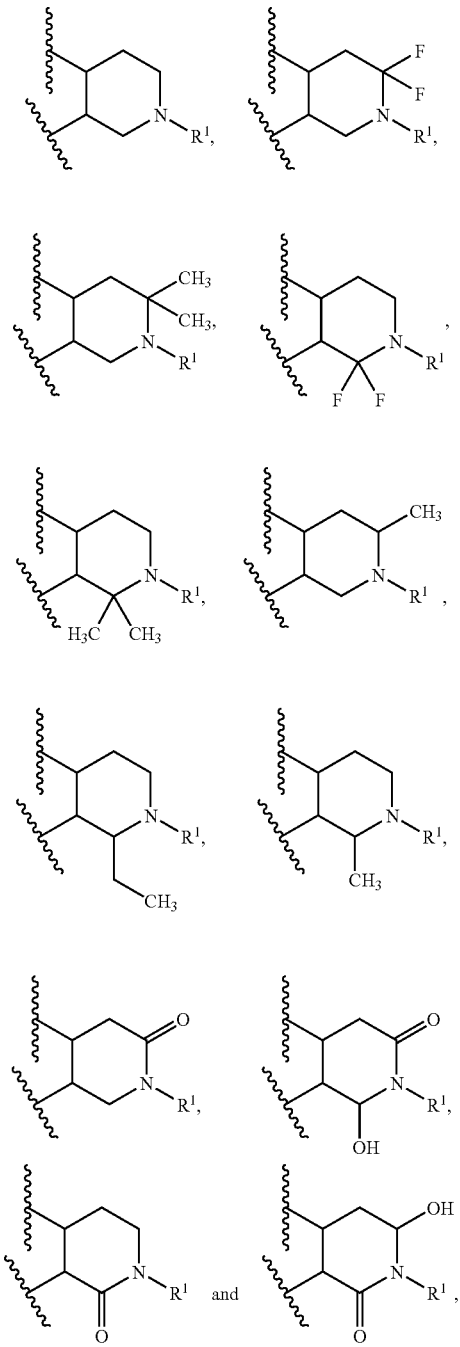

where $R^1$ in the structures above is as defined for formula (I) or any particular variation detailed herein. In a particular variation, $R^1$ of the immediately preceding structures is $CH_3$. In another particular variation, $R^1$ of the immediately preceding structures is H. In another variation, a compound of the invention is of the formula (I), (E) or (F) where $R^{2a}$, $R^{2b}$, $R^1$, $R^{10a}$, $R^{10b}$, $R^{3a}$ and $R^{3b}$ are taken together to form a ring of the structure:

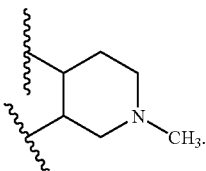

In still another variation, a compound of the invention is of the formula (I), (E) or (F) where $R^{2a}$, $R^{2b}$, $R^1$, $R^{10a}$, $R^{10b}$, $R^{3a}$ and $R^{3b}$ are taken together to form a ring of the structure:

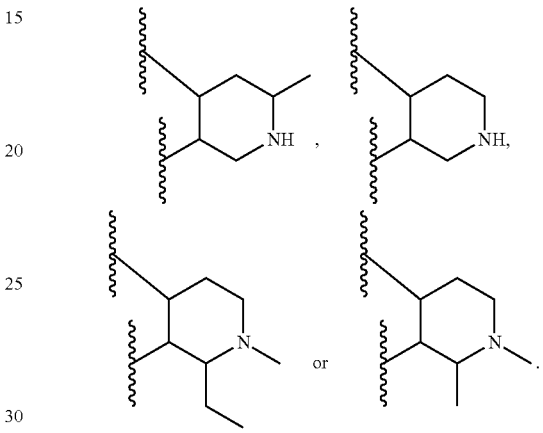

In a further variation, the compound is of the formula (A), (B), (C), (D), (E-1), (F-1) or (F2) where $R^{2a}$, $R^{2b}$, $R^1$, $R^{10a}$, $R^{10b}$, $R^{3a}$ and $R^{3b}$ are taken together to provide a moiety selected from the foregoing structures of this paragraph. In a further variation and where applicable, $R^1$ is $CH_3$, the compound is of the formula (E-2), (E-3), (E-5), (E-6), (E-7) or (E-8) where $R^{2a}$, $R^{2b}$, $R^1$, $R^{10a}$, $R^{10b}$, $R^{3a}$ and $R^{3b}$ are taken together to provide a moiety selected from the foregoing structures of this paragraph. In such a variation, it is understood that where applicable intends that only structures conforming to the $R^{2a}$, $R^{2b}$, $R^1$, $R^{10a}$, $R^{10b}$, $R^{3a}$ and $R^{3b}$ requirements for each formula are embraced (e.g., where a formula does not allow for $R^{3a}$ and $R^{3b}$ to be combined to form a carbonyl, such structures of this paragraph are not encompassed as a variation for such a structure).

Any formula detailed herein, where applicable, may in one variation have $R^{2a}$, $R^{2b}$, $R^1$, $R^{10a}$, $R^{10b}$, $R^{3a}$ and $R^{3b}$ taken together to provide a moiety detailed herein above. It is understood that by "where applicable" it is intended that in one variation such $R^{2a}$, $R^{2b}$, $R^1$, $R^{10a}$, $R^{10b}$, $R^{3a}$ and $R^{3b}$ groups are taken together to provide a moiety hereinabove if the formula encompasses such a structure. For example, if a given formula does not encompass structures wherein $R^{2a}$, $R^{2b}$, $R^1$, $R^{10a}$, $R^{10b}$, $R^{3a}$ and $R^{3b}$ are taken together provide a

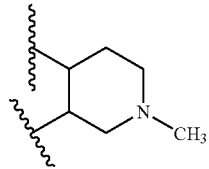

moiety, then a

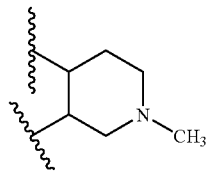

moiety as detailed hereinabove is not applicable to that particular formula, but remains applicable to formulae that do encompass structures where $R^{2a}$, $R^{2b}$, $R^1$, $R^{10a}$, $R^{10b}$, $R^{3a}$ and $R^{3b}$ are taken together provide a

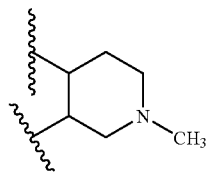

moiety.

Compounds of the formulae (IIa), (IIb), (IIc), (IId), (IIe), (IIf), (IIg) and (IIh) are also embraced by this invention:

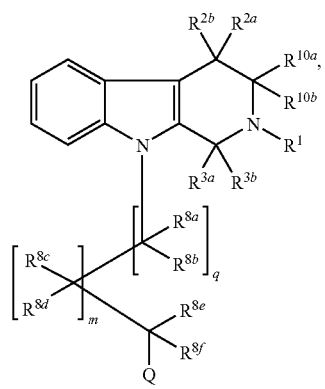

(IIa)

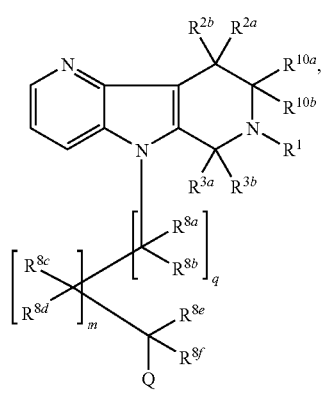

(IIb)

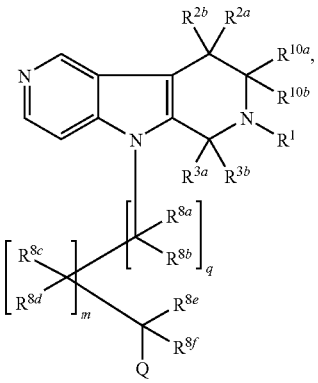

(IIc)

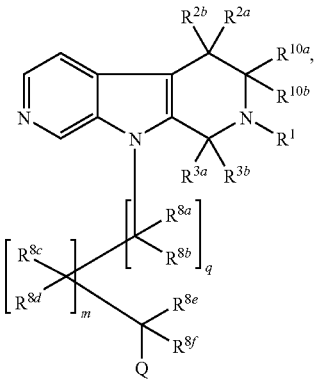

(IId)

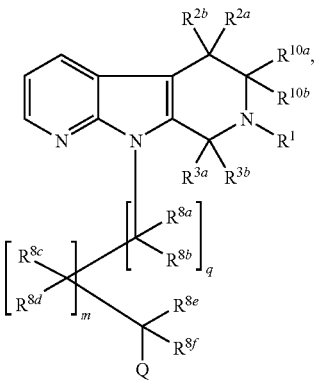

(IIe)

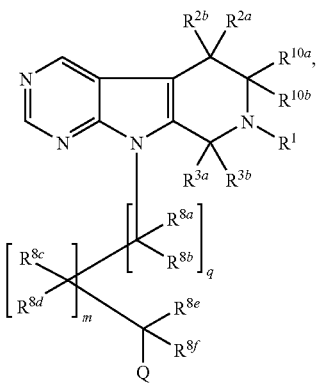

(IIf)

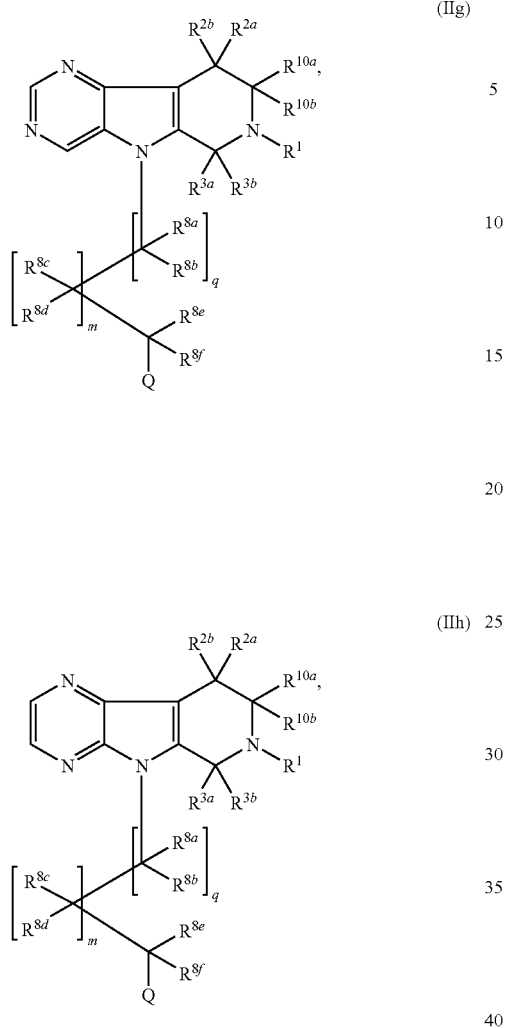

(IIg)

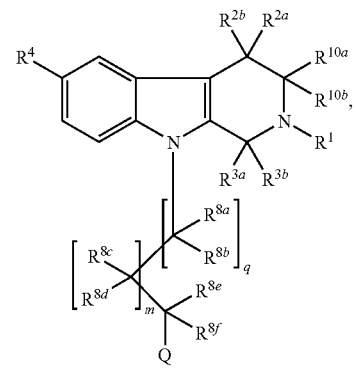

(IIIa)

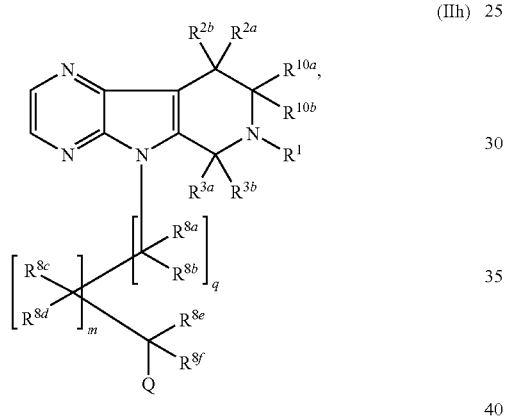

(IIh)

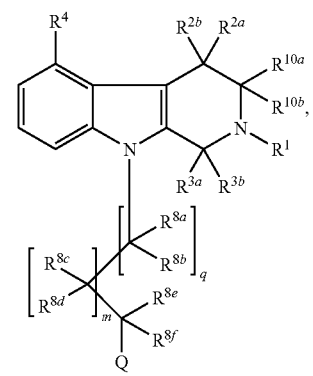

(IIIb)

where in each of (IIa), (IIb), (IIc), (IId), (IIe), (IIf), (IIg) and (IIh), $R^1$, $R^{2a}$, $R^{2b}$, $R^{3a}$, $R^{3b}$, $R^{10a}$, $R^{10b}$, $R^{8a}$-$R^{8f}$, m, q and Q are as described for formula (I) or any applicable variation thereof. In a particular variation, a compound of the invention is of the formula (IIb), (IIc), (IId) or (IIe) and where $R^{2a}$, $R^{2b}$, $R^{10a}$, $R^{10b}$, $R^{3a}$ and $R^{3b}$ are H and where $R^1$ is an alkyl moiety such as methyl. Where applicable, in each of (IIa), (IIb), (IIc), (IId), (IIe), (IIf), (IIg) and (IIh), $R^1$, $R^{2a}$, $R^{2b}$, $R^{3a}$, $R^{3b}$, $R^{10a}$, $R^{10b}$, $R^{8a}$-$R^{8f}$, m, q and Q may also be as described for any formulae or any applicable variation thereof detailed herein, including but not limited to formulae (A)-(F).

In one embodiment, the invention embraces a compound of any one of formula (IIb), (IIc), (IId), (IIe), (IIf), (IIg) and (IIh) wherein $R^1$, $R^{2a}$, $R^{2b}$, $R^{3a}$, $R^{3b}$, $R^{10a}$, $R^{10b}$, $R^{8a}$-$R^{8f}$, m, q and Q are as described for formula (I) or any applicable variation thereof, or a salt or solvate thereof.

Compounds of the formulae (IIIa), (IIIb), (IIIc), (IIId), (IIIe), (IIIf), (IIIg), (IIIh), (IIIi), (IIIj), (IIIk), (IIIl), (IIIm), (IIIn) and (IIIo) are further embraced this invention:

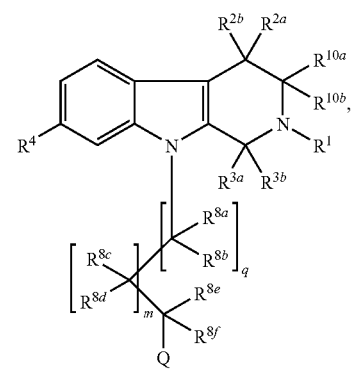

(IIIc)

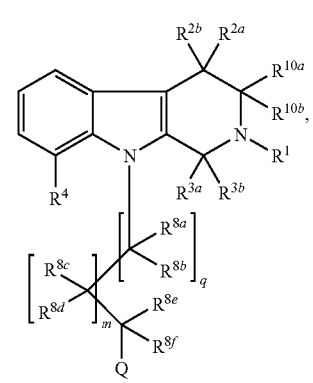

(IIId)

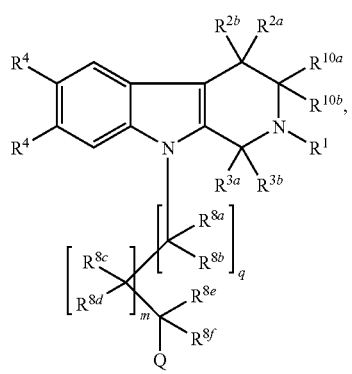
(IIIe)
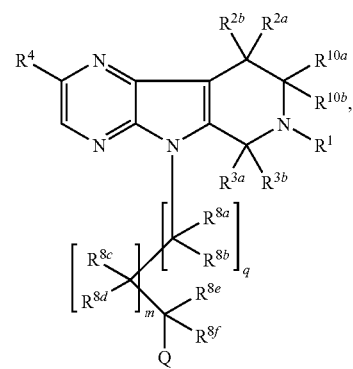
(IIIi)
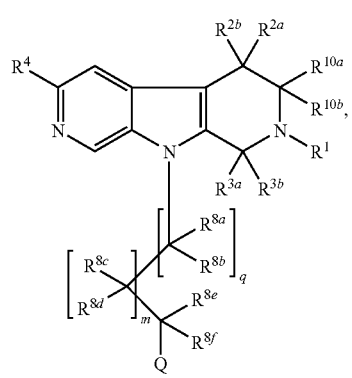
(IIIf)
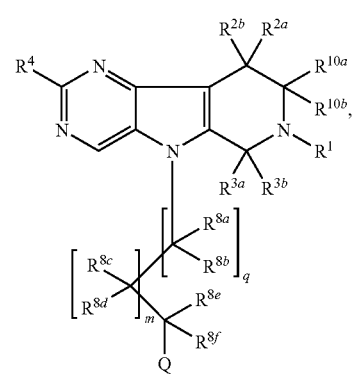
(IIIj)
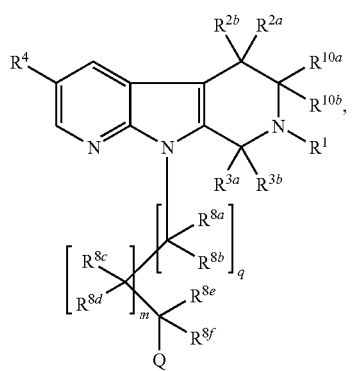
(IIIg)
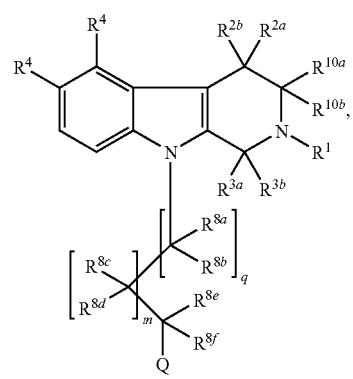
(IIIk)
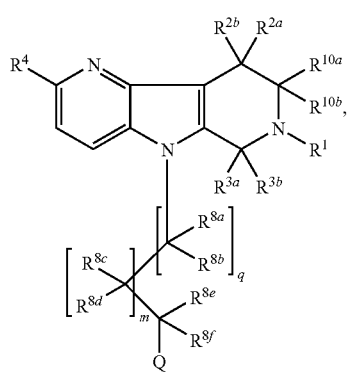
(IIIh)
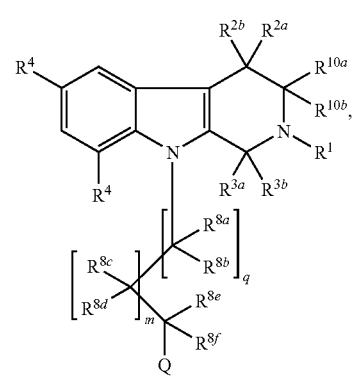
(IIIl)

-continued

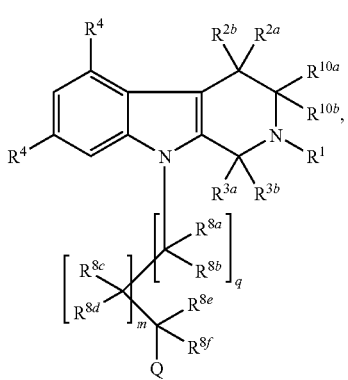
(IIIm)

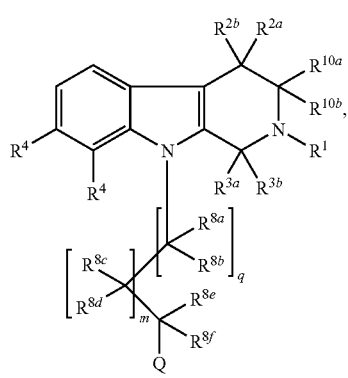
(IIIn)

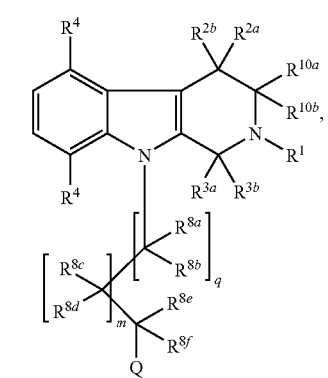
(IIIo)

where in each of (IIIa), (IIIb), (IIIc), (IIId), (IIIe), (IIIf), (IIIg), (IIIh), (IIIi), (IIIj), (IIIk), (IIIl), (IIIm), (IIIn) and (IIIo), $R^1$, $R^4$, $R^{2a}$, $R^{2b}$, $R^{3a}$, $R^{3b}$, $R^{10a}$, $R^{10b}$, $R^{8a}$-$R^{8f}$, m, q and Q are as described for formula (I) or any applicable variation thereof. Where applicable, in each of (IIIa)-(IIIi), $R^1$, $R^{2a}$, $R^{2b}$, $R^{3a}$, $R^{3b}$, $R^{10a}$, $R^{10b}$, $R^{8a}$-$R^{8f}$, m, q and Q may also be as described for any formulae or any applicable variation thereof detailed herein, including but not limited to formulae (A)-(F). In a particular variation, a compound of the invention is of the formula (IIIa), (IIIb), (IIIc) or (IIId) and where $R^{2a}$, $R^{2b}$, $R^{10a}$, $R^{10b}$, $R^{3a}$ and $R^{3b}$ are H and where $R^1$ is an alkyl moiety such as methyl.

In one variation, the invention embraces a compound of formula (IIIa), where $R^4$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl, provided: (i) when q=0, $CR^{3a}R^{3b}$ is not C=O; and the compound conforms to one of provisions (ii)-(iv): (ii) when q, m, $R^{8a}$, $R^{8b}$, $R^{8c}$, $R^{8d}$, $R^{8e}$ and $R^{8f}$ are taken together to form —CH$_2$— or C=O, Q is other than phenyl, naphthyl, substituted phenyl, alkoxy and phenoxy; (iii) when q, m, $R^{8a}$, $R^{8b}$, $R^{8c}$, $R^{8d}$, $R^{8e}$ and $R^{8f}$ are taken together to form —CH$_2$CH$_2$—, $R^{10a}$ and $R^{10b}$ are other than $C_3$-$C_7$ alkyl; (iv) when q, m, $R^{8a}$, $R^{8b}$, $R^{8c}$, $R^{8d}$, $R^{8e}$ and $R^{8f}$ are taken together to form —CH$_2$CH$_2$CH$_2$—, Q is other than Me$_2$N and Et$_2$N; or a salt or solvate thereof.

In another variation, the invention embraces a compound of formula (IIa), where $R^4$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl, provided: (i) when q=0, $CR^3R^{3b}$ is not C=O; and the compound conforms to one of provisions (ii)-(iv): (ii) when q, m, $R^{8a}$, $R^{8b}$, $R^{8c}$, $R^{8d}$, $R^{8e}$ and $R^{8f}$ are taken together to form —CH$_2$— or C=O, Q is other than phenyl, naphthyl, substituted phenyl, alkoxy and phenoxy; (iii) when q, m, $R^{8a}$, $R^{8b}$, $R^{8c}$, $R^{8d}$, $R^{8e}$ and $R^{8f}$ are taken together to form —CH$_2$CH$_2$—, $R^1$ is other than H; (iv) when q, m, $R^{8a}$, $R^{8b}$, $R^{8c}$, $R^{8d}$, $R^{8e}$ and $R^{8f}$ are taken together to form —CH$_2$CH$_2$CH$_2$—, Q is other than Me$_2$N and Et$_2$N; or a salt or solvate thereof.

In one variation, the invention embraces a compound of formula (IIb), where $R^4$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl, or a salt or solvate thereof.

In one variation, the invention embraces a compound of formula (IIIc), where $R^4$ is nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_2$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl, or a salt or solvate thereof.

In one variation, the invention embraces a compound of formula (IIId), where $R^4$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl, or a salt or solvate thereof.

In one variation, the invention embraces a compound of formula (IIIe), provided: (i) at least one $R^4$ is other than H; (ii) when q=0, $CR^{3a}R^{3b}$ is not C=O; and the compound conforms to one of provisions (iii) and (iv): (iii) when m=q=0, Q is other than phenyl, naphthyl, substituted phenyl, alkoxy and phenoxy; (iv) when $CR^{8c}R^{8d}$ is $CH_2$, Q is other than $Me_2N$ and $Et_2N$, and $R^{10a}$ and $R^{10b}$ are other than $C_3$-$C_7$ alkyl; or a salt or solvate thereof.

In another variation, the invention embraces a compound of formula (IIIe) wherein at least one $R^4$ is other than H, provided: (i) when q=0, $CR^{3a}R^{3b}$ is not C=O; and the compound conforms to one of provisions (ii)-(iv): (ii) when q, m, $R^{8a}$, $R^{8b}$, $R^{8c}$, $R^{8d}$, $R^{8e}$ and $R^{8f}$ are taken together to form —$CH_2$— or C=O, Q is other than phenyl, naphthyl, substituted phenyl, alkoxy and phenoxy; (iii) when q, m, $R^{8a}$, $R^{8b}$, $R^{8c}$, $R^{8d}$, $R^{8e}$ and $R^{8f}$ are taken together to form —$CH_2CH_2$—, $R^1$ is other than H; (iv) when q, m, $R^{8a}$, $R^{8b}$, $R^{8c}$, $R^{8d}$, $R^{8e}$ and $R^{8f}$ are taken together to form —$CH_2CH_2CH_2$—, Q is other than $Me_2N$ and $Et_2N$; or a salt or solvate thereof.

In one embodiment, the invention embraces a compound of any one of formula (IIIf), (IIIg), (IIIh), (IIIi), (IIIj), (IIIk), (IIIl), (IIIm), (IIIn) and (IIIo) wherein $R^1$, $R^{2a}$, $R^{2b}$, $R^{3a}$, $R^{3b}$, $R^{10a}$, $R^{10b}$, $R^{8a}$-$R^{8f}$, m, q and Q are as described for formula (I) or any applicable variation thereof, or a salt or solvate thereof.

Compounds of the formulae (IVa), (IVb), (IVc), (IVd), (IVe), (IVf), (IVg), (IVh), (IVi), (IVj), (IVk), (IVl), (IVm), (IVn), (IVo) and (IVp) are further embraced by this invention:

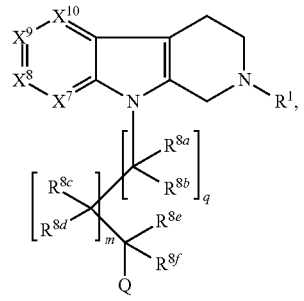
(IVa)

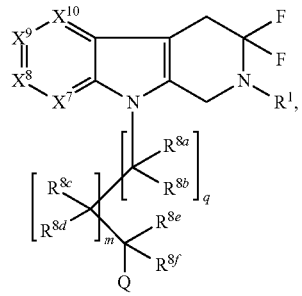
(IVb)

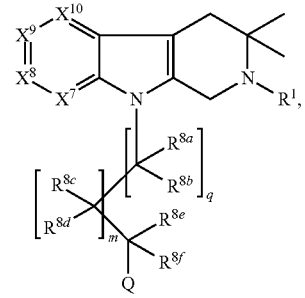
(IVc)

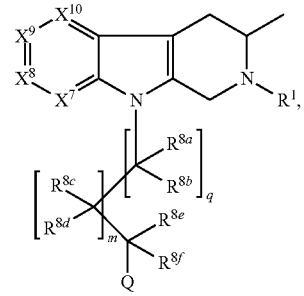
(IVd)

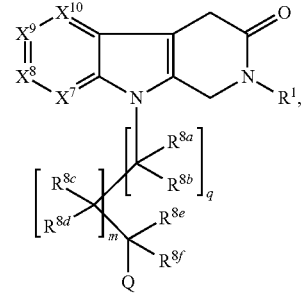
(IVe)

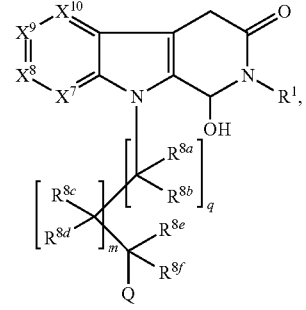
(IVf)

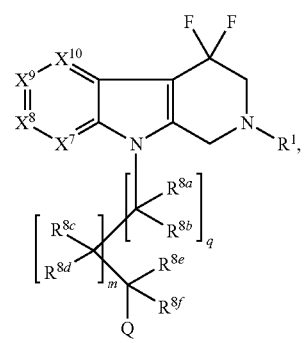
(IVg)

103
-continued (IVh)
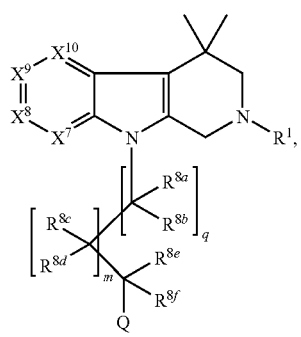

(IVi)
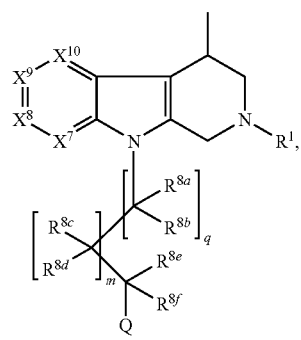

(IVj)
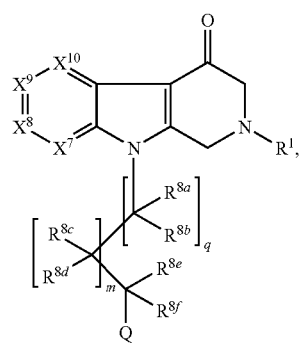

(IVk)
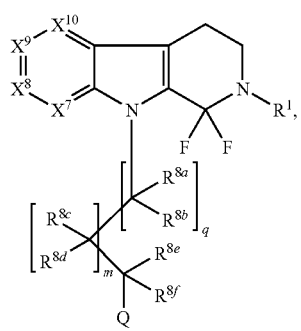

(IVl)
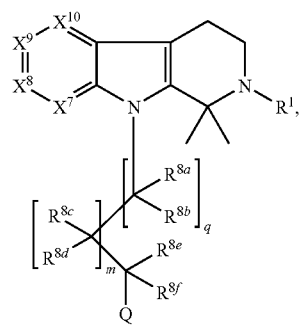

104
-continued (IVm)
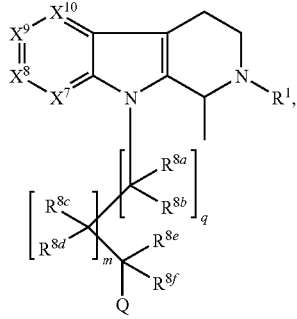

(IVn)
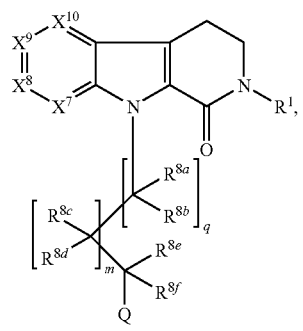

(IVo)
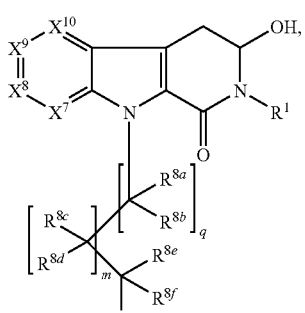

(IVp)
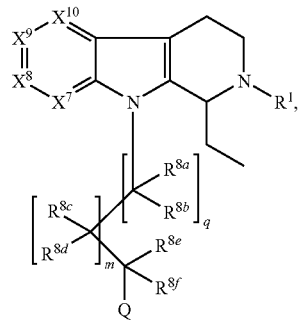

where in each of (IVa), (IVb), (IVc), (IVd), (IVe), (IVf), (IVg), (IVh), (IVi), (IVj), (IVk), (IVl), (IVm), (IVn), (IVo) and (IVp), $R^1$, $X^7$, $X^8$, $X^9$, $X^{10}$, $R^{8a}$-$R^{8f}$, m, q and Q are as described for formula (I) or any applicable variation thereof. Where applicable, in each of (IVa)-(IVo), $R^1$, $X^7$, $X^8$, $X^9$, $X^{10}$, $R^{8a}$-$R^{8f}$, m, q and Q may also be as described for any formulae or any applicable variation thereof detailed herein, including but not limited to formulae (A)-(F). In a particular variation, a compound of the invention is of the formula (IVa) and where $R^1$ is an alkyl moiety such as methyl.

In one variation, the invention embraces a compound of formula (IVa), provided: (i) at least one of $X^7$, $X^8$, $X^9$ and $X^{10}$ is not CH; and the compound conforms to one of provisions (ii) and (iii): (ii) when q, m, $R^{8a}$, $R^{8b}$, $R^{8c}$, $R^{8d}$, $R^{8e}$ and $R^{8f}$ are taken together to form —CH$_2$— or C(═O), Q is other than phenyl, naphthyl, substituted phenyl, alkoxy and phenoxy; (iii) when q, m, $R^{8a}$, $R^{8b}$, $R^{8c}$, $R^{8d}$, $R^{8e}$ and $R^{8f}$ are taken together to form —CH$_2$CH$_2$CH$_2$—, Q is other than Me$_2$N and Et$_2$N, or a salt or solvate thereof.

In one variation, the invention embraces a compound of formula (IVd), provided that the compound is other that a compound of No. 81x, 122x, 229x, 360x, 451x, 639x or 757x in Table 1, or a salt or solvate thereof. In another variation, e.g., in any of the methods detailed herein, the compound may be of formula (IVd), including any suitable compound in Table 1, such as any compound of Table 1 listed in this paragraph.

In one variation, the invention embraces a compound of formula (IVd) wherein at least one of $X^7$, $X^8$, $X^9$ and $X^{10}$ is not CH, or a salt or solvate thereof.

In one variation, the invention embraces a compound of formula (IVj), provided that the compound is other that a compound of No. 449x, 540x, 643x or 761x in Table 1, or a salt or solvate thereof. In another variation, e.g., in any of the methods detailed herein, the compound may be of formula (IVj), including compound Nos. 449x, 540x, 643x and 761x in Table 1.

In one variation, the invention embraces a compound of formula (IVj) wherein at least one of $X^7$, $X^8$, $X^9$ and $X^{10}$ is not CH, or a salt or solvate thereof. In another variation, the invention embraces a compound of formula (IVj), provided: when q, m, $R^{8a}$, $R^{8b}$, $R^{8c}$, $R^{8d}$, $R^{8e}$ and $R^{8f}$ are taken together to form —CH$_2$— or C(═O), Q is other than phenyl, substituted phenyl and alkoxy.

In one variation, the invention embraces a compound of formula (IVl), provided that the compound is other than compound No. 289x in Table 1, or a salt or solvate thereof. In another variation, e.g., in any of the methods detailed herein, the compound may be of formula (IVl), including compound No. 289x in Table 1.

In one variation, the invention embraces a compound of formula (IVl), provided: when q, m, $R^{8a}$, $R^{8b}$, $R^{8c}$, $R^{8d}$, $R^{8e}$ and $R^{8f}$ are taken together to form —CH$_2$—, Q is other than substituted phenyl, or a salt or solvate thereof.

In one variation, the invention embraces a compound of formula (IVn), provided: (i) at least one of $X^7$, $X^8$, $X^9$ and $X^{10}$ is not CH; and (ii) when q, m, $R^{8a}$, $R^{8b}$, $R^{8c}$, $R^{8d}$, $R^{8e}$ and $R^{8f}$ are taken together to form —CH$_2$—, C═O or —CH$_2$CH$_2$—, Q is other than phenyl, naphthyl, substituted phenyl and amino, or a salt or solvate thereof.

The invention also embraces compounds of the formulae (Va)-(Vzf):

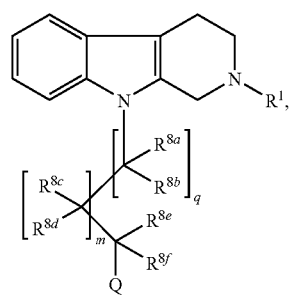

(Va)

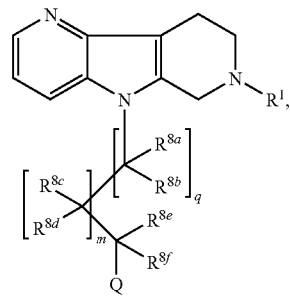

(Vb)

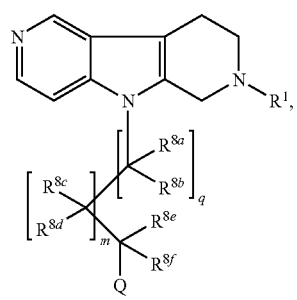

(Vc)

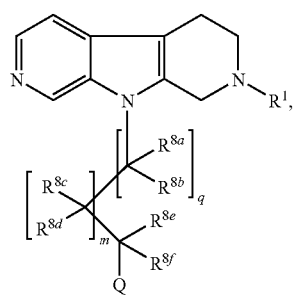

(Vd)

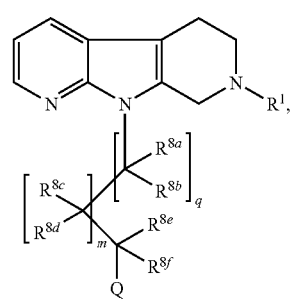

(Ve)

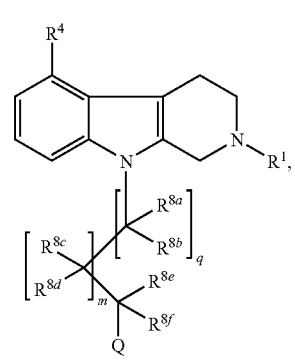

(Vf)

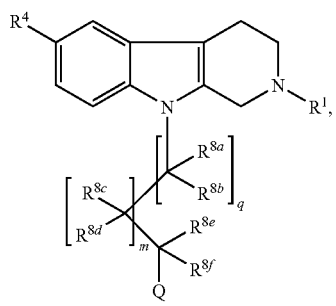 (Vg)
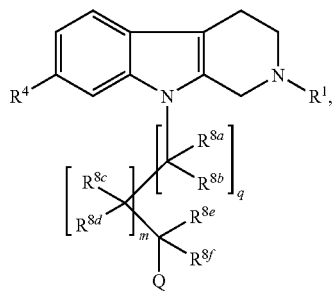 (Vh)
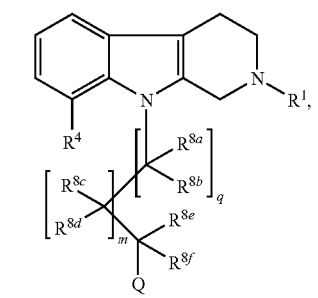 (Vi)
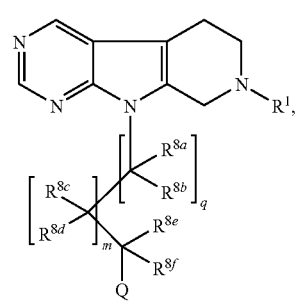 (Vj)
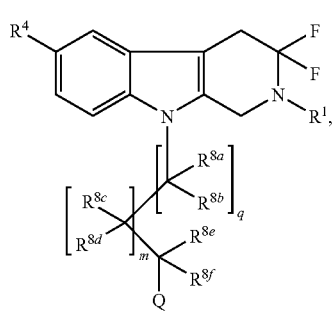 (Vk)
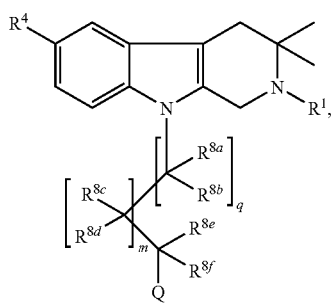 (Vl)
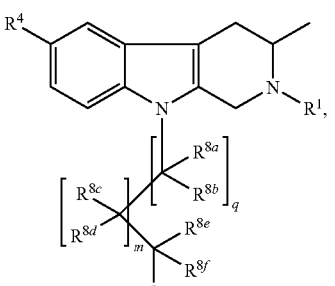 (Vm)
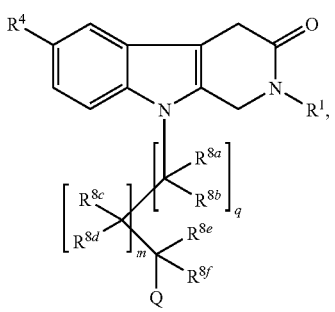 (Vn)
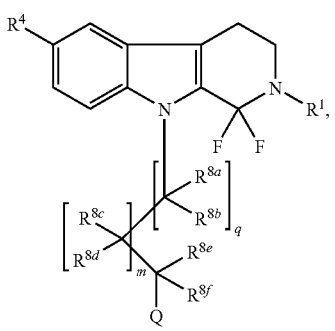 (Vo)
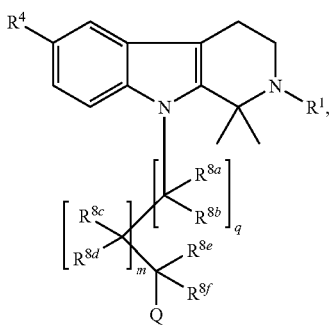 (Vp)

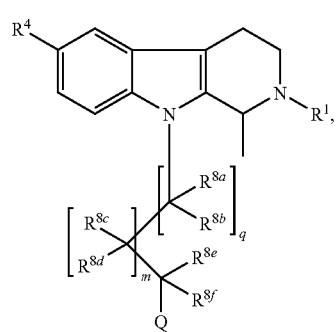 (Vq)
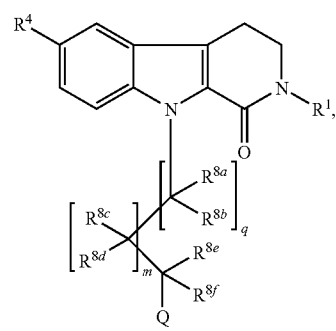 (Vr)
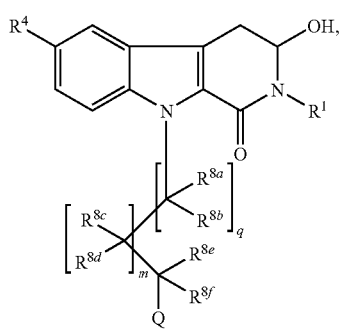 (Vs)
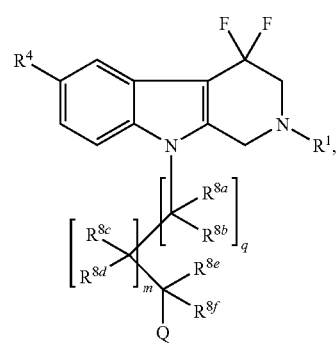 (Vt)
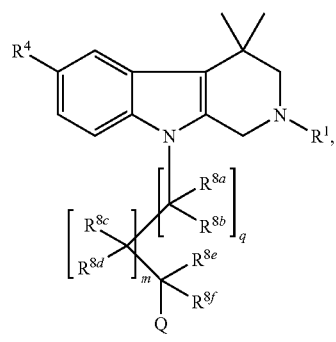 (Vu)
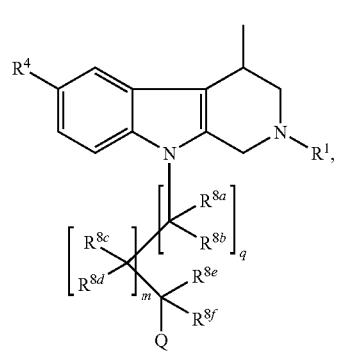 (Vv)
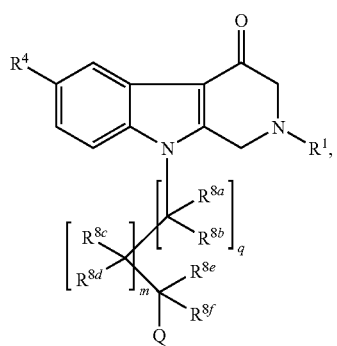 (Vw)
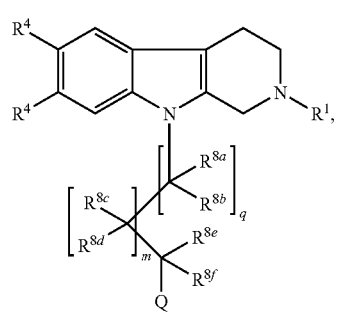 (Vx)
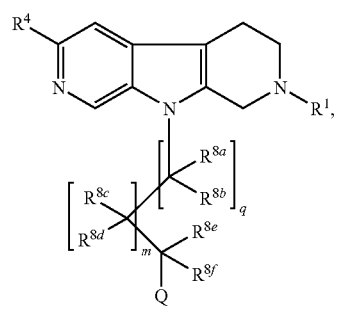 (Vy)
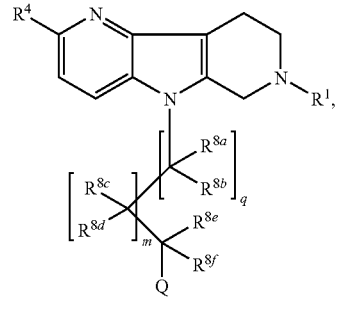 (Vz)

(Vza) 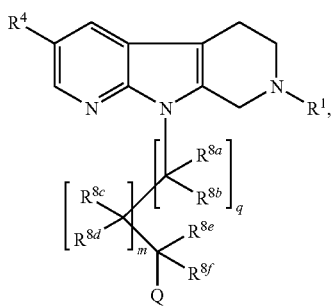

(Vzb) 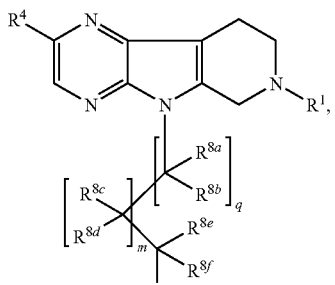

(Vzc) 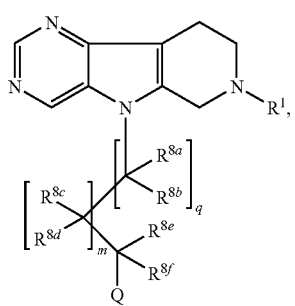

(Vzd) 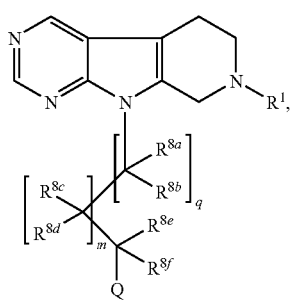

(Vze) 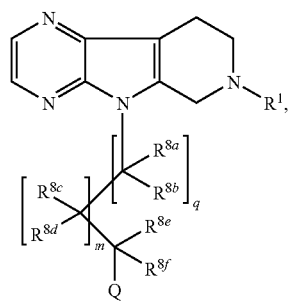

(Vzf) 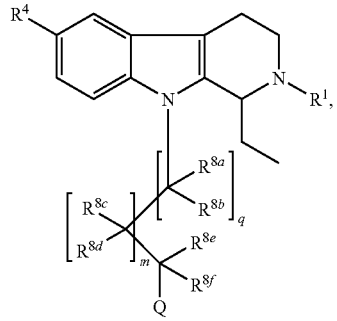

where in each of (Va)-(Vzf), $R^1$, $R^4$, $R^{8a}$-$R^{8f}$, m, q and Q are as described for formula (I) or any applicable variation thereof. Where applicable, in each of (Va)-(Vzf), $R^1$, $R^{8a}$-$R^{8f}$, m, q and Q may also be as described for any formulae or any applicable variation thereof detailed herein, including but not limited to formulae (A)-(F). In a particular variation, a compound of the invention is of the formula (Vb), (Vc), (Vd), (Ve), (Vf), (Vg), (Vh) or (vi) and where $R^4$ is an alkyl moiety such as methyl.

In one variation, the invention embraces a compound of formula (Vf), where $R^4$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl, or a salt or solvate thereof.

In one variation, the invention embraces a compound of formula (Vg), wherein $R^4$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl; provided: (i) when q, m, $R^{8a}$, $R^{8b}$, $R^{8c}$, $R^{8d}$, $R^{8e}$ and $R^{8f}$ are taken together to form —$CH_2$— or C=O, Q is other than phenyl, naphthyl, substituted phenyl, alkoxy and phenoxy; or (ii) when q, m, $R^{8a}$, $R^{8b}$, $R^{8c}$, $R^{8d}$, $R^{8e}$ and $R^{8f}$ are taken together to form —$CH_2CH_2CH_2$—, Q is other than $Me_2N$ and $Et_2N$, or a salt or solvate thereof.

In one variation, the invention embraces a compound of formula (Vh), wherein $R^4$ is nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl, or a salt or solvate thereof.

In one variation, the invention embraces a compound of formula (vi), wherein $R^4$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl, or a salt or solvate thereof.

In one variation, the invention embraces a compound of formula (Vm), provided that the compound is other that a compound of No. 81x, 122x, 229x, 360x, 451x, 639x or 757x in Table 1, or a salt or solvate thereof. In another variation, e.g., in any of the methods detailed herein, the compound may be of formula (Vm), including any suitable compound in Table 1, such as any compound of Table 1 listed in this paragraph.

In one variation, the invention embraces a compound of formula (Vm), wherein $R^4$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl, or a salt or solvate thereof.

In one variation, the invention embraces a compound of formula (Vp), provided that the compound is other than compound No. 289x in Table 1, or a salt or solvate thereof. In another variation, e.g., in any of the methods detailed herein, the compound may be of formula (Vp), including compound No. 289x in Table 1.

In one variation, the invention embraces a compound of formula (Vp), provided: when q, m, $R^{8a}$, $R^{8b}$, $R^{8c}$, $R^{8d}$, $R^{8e}$ and $R^{8f}$ are taken together to form —$CH_2$—, Q is other than substituted phenyl, or a salt or solvate thereof.

In one variation, the invention embraces a compound of formula (Vr), wherein $R^4$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl; provided: when q, m, $R^{8a}$, $R^{8b}$, $R^{8c}$, $R^{8d}$, $R^{8e}$ and $R^{8f}$ are taken together to form —$CH_2$—, C=O or —$CH_2CH_2$—, Q is other than phenyl, naphthyl, substituted phenyl and amino, or a salt or solvate thereof.

In one variation, the invention embraces a compound of formula (Vw), provided that the compound is other that a compound of No. 449x, 540x, 643x or 761x in Table 1, or a salt or solvate thereof. In another variation, e.g., in any of the methods detailed herein, the compound may be of formula (Vw), including compound Nos. 449x, 540x, 643x and 761x in Table 1.

In one variation, the invention embraces a compound of formula (Vw), wherein $R^4$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl, or a salt or solvate thereof.

In one variation, the invention embraces a compound of formula (Vx), wherein $R^4$ is hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl); provided: (i) when q, m, $R^{8a}$, $R^{8b}$, $R^{8c}$, $R^{8d}$, $R^{8e}$ and $R^{8f}$ are taken together to form —$CH_2$— or C(=O), Q is other than phenyl, naphthyl, substituted phenyl, alkoxy and phenoxy; or (ii) when q, m, $R^{8a}$, $R^{8b}$, $R^{8c}$, $R^{8d}$, $R^{8e}$ and $R^{8f}$ are taken together to form —$CH_2CH_2CH_2$—, Q is other than $Me_2N$ and $Et_2N$, or a salt or solvate thereof.

In one embodiment, the invention embraces a compound of any one of formula (Vb), (Vc), (Vd), (Ve), (Vy), (Vz), (Vza), (Vzb), (Vzc), (Vzd) and (Vze) wherein $R^1$, $R^{2a}$, $R^{2b}$, $R^{3a}$, $R^{3b}$, $R^{10a}$, $R^{10b}$, $R^{8a}$-$R^{8f}$, m, q and Q are as described for formula (I) or any applicable variation thereof, or a salt or solvate thereof.

In one variation, a compound of the invention is of the formula (I) or (Ia) or any variation of the foregoing detailed herein, or is of any one of the formulae (IIa)-(IIh), (IIIa)-(IIIo), (IVa)-(IVp) or (Va)-(Vzf), where each $R^{8a}$, $R^{8b}$, $R^{8c}$, $R^{8d}$, $R^{8e}$ and $R^{8f}$ is independently H, hydroxyl, unsubstituted $C_1$-$C_4$ alkyl or is taken together with the carbon to which it is attached and a geminal $R^{8(a-f)}$ to form a cycloalkyl moiety. In one variation, a compound of the invention is of the formula (I) or (Ia) or any variation of the foregoing detailed herein, or is of any one of the formulae (IIa)-(IIh), (IIIa)-(IIIo), (IVa)-(IVp) or (Va)-(Vzf), where at least one of $R^{8a}$, $R^{8b}$, $R^{8c}$, $R^{8d}$, $R^{8e}$ and $R^{8f}$ is taken together with the carbon to which it is attached and a geminal $R^{8(a-f)}$ to form a carbonyl moiety. In another variation, a compound of the invention is of the formula (I) or (Ia) or any variation of the foregoing detailed herein, or is of any one of the formulae (IIa)-(IIh), (IIIa)-(IIIo), (IVa)-(IVp) or (Va)-(Vzf), where each $R^{8a}$, $R^{8b}$, $R^{8c}$, $R^{8d}$, $R^{8e}$ and $R^{8f}$ is independently H, hydroxyl, methyl or is taken together with the carbon to which it is attached and a geminal $R^{8(a-f)}$ to form a cyclopropyl moiety. In yet another variation, a compound of the invention is of the formula (I) or (Ia) or any variation of the foregoing detailed herein, or is any one of the formulae (IIa)-(IIh), (IIIa)-(IIIo), (IVa)-(IVp) or (Va)-(Vzf), where wherein q is 0 and m is 1. The invention also embraces a compound of the invention according to formula (I) or (Ia) or any variation of the foregoing detailed herein, or a compound according to any one of the formulae (IIa)-(IIh), (IIIa)-(IIIo), (IVa)-(IVp) or (Va)-(Vzf), where q and m are both 0. The invention further embraces a compound according to formula (I) or (Ia) or any variation of the foregoing detailed herein, or a compound according to any one of the formulae (IIa)-(IIh), (IIIa)-(IIIo), (IVa)-(IVp) or (Va)-(Vzf), where q, m, $R^{8a}$, $R^{8b}$, $R^{8c}$, $R^{8d}$, $R^{8e}$ and $R^{8f}$ are taken together to form a moiety selected from the group consisting of: —$CH_2$—, —$CH_2CH_2$—, —$CH_2CH_2CH_2$—, —$CH_2$—C(H)(OH)—, —C(H)(OH)—$CH_2$—, —$CH_2$—C(OH)($CH_3$)—, —C(OH)($CH_3$)—$CH_2$—, —$CH_2$—C(H)($CH_3$)—, —C(H)($CH_3$)—$CH_2$—, —$CH_2$—C($CH_3$)($CH_3$)—, —C($CH_2CH_2$)—$CH_2$— and —$CH_2$—C($CH_2CH_2$)—.

The invention embraces a compound according to formula (I), (A), (B), (C), (D) or (E) or any variation thereof detailed herein, or a compound according to any one of the formulae (IIa)-(IIh), (IIIa)-(IIIo), (IVa)-(IVp) or (Va)-(Vzf), where each $R^{8a}$, $R^{8b}$, $R^{8c}$, $R^{8d}$, $R^{8e}$ and $R^{8f}$ where present, is independently H, hydroxyl, $C_1$-$C_8$ alkyl, $C_1$-$C_8$ perhaloalkyl, carboxy, carbonylalkoxy, is taken together with the carbon to which it is attached and a geminal $R^8$ to form a cycloalkyl moiety or a carbonyl moiety, is taken together with a geminal $R^8$ to form a methylene or a substituted methylene, is taken together with a vicinal $R^8$ and the carbon atoms to which they are attached to form a substituted or unsubstituted $C_{3-8}$ cycloalkyl, substituted or unsubstituted $C_{3-8}$ cycloalkenyl or substituted or unsubstituted heterocyclyl moiety or is taken together with a vicinal $R^{8(a-f)}$ to form a bond, provided that when an $R^8$ is taken together with a vicinal $R^{8(a-f)}$ to form a bond, the geminal $R^{8(a-f)}$ is other than hydroxyl. In one variation, a compound of the invention is of the formula (I), (A), (B), (C), (D) or (E) or any variation thereof detailed herein, or a compound according to any one of the formulae (IIa)-(IIh), (IIIa)-(IIIo), (IVa)-(IVp) or (Va)-(Vzf), where each $R^{8a}$, $R^{8b}$, $R^{8c}$, $R^{8d}$, $R^{8e}$ and $R^{8f}$ where present, is independently H, hydroxyl, unsubstituted $C_1$-$C_4$ alkyl or is taken together with the carbon to which it is attached and a geminal $R^8$ to form a cycloalkyl moiety. In one variation, a compound of the invention is of the formula (I), (A), (B), (C), (D) or (E) or any variation thereof detailed herein, or a compound according to any one of the formulae (IIa)-(IIh), (IIIa)-(IIIo), (IVa)-(IVp) or (Va)-(Vzf), where at least one of $R^{8a}$, $R^{8b}$, $R^{8c}$, $R^{8d}$, $R^{8e}$ and $R^{8f}$ is taken together with the carbon to which it is attached and a geminal $R^{8(a-f)}$ to form a carbonyl moiety. In another variation, a compound of the invention is of the formula (I), (A), (B), (C), (D) or (E) or any variation thereof detailed herein, or a compound according to any one of the formulae (IIa)-(IIh), (IIIa)-(IIIo), (IVa)-(IVp) or (Va)-(Vzf), where each $R^{8a}$, $R^{8b}$, $R^{8c}$, $R^{8d}$, $R^{8e}$ and $R^{8f}$ is independently H, hydroxyl, methyl or is taken together with the carbon to which it is attached and a geminal $R^{8(a-f)}$ to form a cyclopropyl moiety. In one variation, a compound of the invention is of the formula (I), (A), (B), (C), (D) or (E) or any variation thereof detailed herein, or a compound according to any one of the formulae (IIa)-(IIh), (IIIa)-(IIIo), (IVa)-(IVp) or (Va)-(Vzf), where at least one of $R^{8a}$, $R^{8b}$, $R^{8c}$, $R^{8d}$, $R^{8e}$ and $R^{8f}$ is taken together with a geminal $R^8$ to form a methylene ($CH_2$=) or a substituted methylene such as $CH_3CH$= or the like. In another variation, a compound of the invention is of the formula (I), (A), (B), (C), (D) or (E) or any variation thereof detailed herein, or a compound according to any one of the formulae (IIa)-(IIh), (IIIa)-(IIIo), (IVa)-(IVp) or (Va)-(Vzf), where at least one of $R^{8ab}$, $R^{8c}$, $R^{8d}$, $R^{8e}$ and $R^{8f}$ is taken together with a vicinal $R^{8(a-f)}$ to form a bond, where the resultant double bond is in E- or Z-configuration. In one variation, a compound of the invention is of the formula (I), (A), (B), (C), (D) or (E) or any variation thereof detailed herein, or a compound according to any one of the formulae (IIa)-(IIh), (IIIa)-(IIIo), (IVa)-(IVp) or (Va)-(Vzf), where at least one of $R^{8a}$, $R^{8b}$, $R^{8c}$, $R^{8d}$, $R^{8e}$ and $R^{8f}$ is taken together with a vicinal $R^{8(a-f)}$ and the carbons to which they are attached to form a substituted or unsubstituted $C_{3-8}$ cycloalkyl, substituted or unsubstituted $C_{3-8}$ cycloalkenyl or substituted or unsubstituted heterocyclyl moiety. In one variation, a compound of the invention is of the formula (I), (A), (B), (C), (D) or (E) or any variation thereof detailed herein, or a compound according to any one of the formulae (IIa)-(IIh), (IIIa)-(IIIo), (IVa)-(IVp) or (Va)-(Vzf), where at least one of $R^{8a}$, $R^{8b}$, $R^{8c}$, $R^{8d}$, $R^{8e}$ and $R^{8f}$ is taken together with a vicinal $R^{8(a-f)}$ and the carbons to which they are attached to form a $C_{3-8}$ cycloalkyl. In one variation, a compound of the invention is of the formula (I), (A), (B), (C), (D) or (E) or any variation thereof detailed herein, or a compound according to any one of the formulae (IIa)-(IIh), (IIIa)-(IIIo), (IVa)-(IVp) or (Va)-(Vzf), where $R^{8c}$, $R^{8d}$ and the carbon to which they are attached are taken together with two other $R^{8(a-f)}$ groups that are geminal to each other and the carbon to which they are attached to form a $C_{3-8}$ cycloalkenyl. In yet another variation, a compound of the invention is of the formula (I), (A), (B), (C), (D) or (E) or any variation thereof detailed herein, or a compound according to any one of the formulae (IIa)-(IIh), (IIIa)-(IIIo), (IVa)-(IVp) or (Va)-(Vzf), where wherein q is 0 and m is 1. The invention also embraces a compound of the invention according to formula (I), (A), (B), (C), (D) or (E) or any variation thereof detailed herein, or a compound according to any one of the formulae (IIa)-(IIh), (IIIa)-(IIIo), (IVa)-(IVp) or (Va)-(Vzf), where q and m are both 0.

The invention further embraces a compound according to formula (I), (A), (B), (C), (D) or (E) or any variation thereof detailed herein, or a compound according to any one of the formulae (IIa)-(IIh), (IIIa)-(IIIo), (IVa)-(IVp) or (Va)-(Vzf), where q, m, $R^{8a}$, $R^{8b}$, $R^{8c}$, $R^{8d}$, $R^{8e}$ and $R^{8f}$ are taken together to form a moiety selected from the group consisting of the structures:

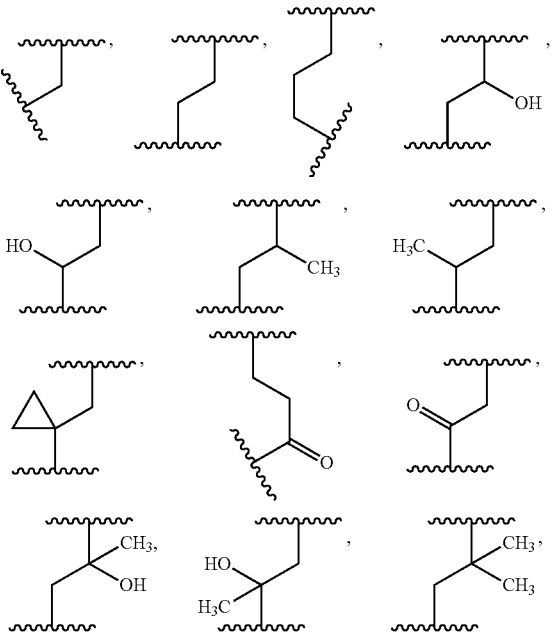

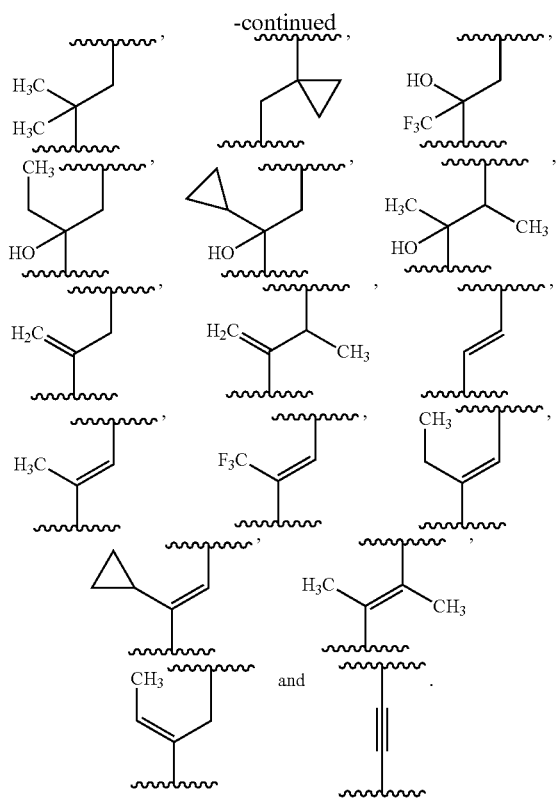

In a further variation and where applicable, a compound of the formulae detailed herein is provided where q, m, $R^{8a}$, $R^{8b}$, $R^{8c}$, $R^{8d}$, $R^{8e}$ and $R^{8f}$ are taken together to form a moiety of the formula:

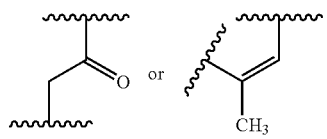

When the above structures are applied to formula (E) or any variation thereof, it is understood that q, m, n, $R^{8a}$, $R^{8b}$, $R^{8c}$, $R^{8d}$, $R^{8e}$ and $R^{8f}$ where applicable are taken together to form the foregoing moieitites, including but not limited to, the structures of this paragraph. Likewise, any formula detailed herein, where applicable, may in one variation have q, m, n, $R^{8a}$, $R^{8b}$, $R^{8c}$, $R^{8d}$, $R^{8e}$ and $R^{8f}$, if present, taken together to form a moiety as detailed herein above, including but not limited to, the structures of this paragraph. It is understood that by "where applicable" it is intended that in one variation such q, m, n, $R^{8a}$, $R^{8b}$, $R^{8c}$, $R^{8d}$, $R^{8e}$ and $R^{8f}$ groups, if present, are taken together to provide a moiety hereinabove if the formula encompasses such a structure. For example, if a given formula does not encompass structures wherein q, m, n, $R^{8a}$, $R^{8b}$, $R^{8c}$, $R^{8d}$, $R^{8e}$ and $R^{8f}$ groups, if present, are taken together to provide a —CH$_2$CH$_2$-moiety, then a —CH$_2$CH$_2$-moiety as detailed hereinabove is not applicable to that particular formula, but remains applicable to formulae that do encompass structures where q, m, n, $R^{8a}$, $R^{8b}$, $R^{8c}$, $R^{8d}$, $R^{8e}$ and $R^{8f}$ groups, if present, are taken together to provide a —CH$_2$CH$_2$-moiety.

The invention further embraces a compound according to formula (I), (A), (B), (C), (D) or (E) or any variation thereof detailed herein, or a compound according to any one of the formulae (IIa)-(IIh), (IIIa)-(IIIo), (IVa)-(IVp) or (Va)-(Vzf), where $R^{8c}$, $R^{8d}$ and the carbon to which they are attached are taken together with $R^{8e}$, $R^{8f}$ and the carbon to which they are attached or $R^{8a}$, $R^{8b}$ and the carbon to which they are attached to form a moiety selected from the group consisting of the structures, each of which may be optionally substituted, where each $R^8$ is independently H, hydroxyl, $C_1$-$C_8$ alkyl, $C_1$-$C_8$ perhaloalkyl, carboxy or carbonylalkoxy:

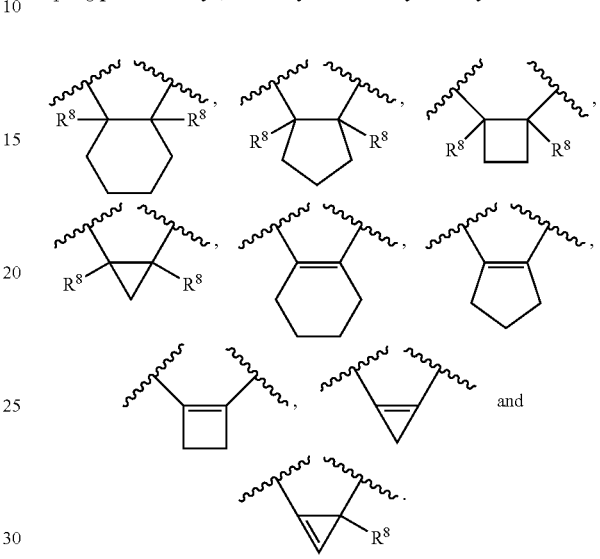

In another variation, a compound of the invention is of the formula (I), (E), (F) or (Ia) or any variation of the foregoing detailed herein, or a compound according to any one of the formulae (IIIa)-(IIIo), (IVa)-(IVp) or (Va)-(Vzf), where each $R^4$ is independently H, halo, substituted or unsubstituted $C_1$-$C_8$ alkyl, $C_1$-$C_8$ perhaloalkyl, substituted or unsubstituted heterocyclyl or a substituted or unsubstituted aryl. In yet another variation, a compound of the invention is of the formula (I), (E), (F) or (Ia) or any variation of the foregoing detailed herein, or a compound according to any one of the formulae (IIIa)-(IIIo), (IVa)-(IVp) or (Va)-(Vzf), where each $R^4$ is independently H or a substituted or unsubstituted $C_1$-$C_8$ alkyl. In still another variation, a compound of the invention is of the formula (I), (E), (F) or (Ia) or any variation of the foregoing detailed herein, or a compound according to any one of the formulae (IIIa)-(IIIo), (IVa)-(IVp) or (Va)-(Vzf), where each $R^4$ is H. The invention also embraces compounds of the formula (I), (E), (F) or (Ia) or any variation of the foregoing detailed herein, or a compound according to any one of the formulae (IIIa)-(IIIo), (IVa)-(IVp) or (Va)-(Vzf), where each $R^4$ is independently H, halo, unsubstituted $C_1$-$C_4$ alkyl, $C_1$-$C_4$ perhaloalkyl or a substituted or unsubstituted aryl. The invention further embraces compounds of the formula (I), (E), (F) or (Ia) or any variation of the foregoing detailed herein, or a compound according to any one of the formulae (IIIa)-(IIIo), (IVa)-(IVp) or (Va)-(Vzf) where each $R^4$ is independently H, halo, methyl, perfluoromethyl or cyclopropyl.

The invention also embraces compounds of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is a substituted or unsubstituted aryl, substituted or unsubstituted heteroaryl, which may be but is not limited to a substituted or unsubstituted pyridyl, phenyl, pyrimidinyl, pyrazinyl, imidazolyl, furanyl, pyrrolyl or thiophenyl group. In one variation, a compound of the invention is of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is a substituted or unsubstituted phenyl or pyridyl group. In a particular variation, Q is a phenyl or pyridyl group substituted with at least one methyl group. In another variation, a compound of the invention is of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety. In still another variation, a compound of the invention is of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is a substituted or unsubstituted $C_{3-8}$ cycloalkyl or a substituted or unsubstituted heterocyclyl. In yet another variation, a compound of the invention is of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is a substituted or unsubstituted pyridyl, phenyl, pyrazinyl, piperazinyl, pyrrolidinyl or thiomorpholinyl group. In a particular variation, Q is a pyridyl, phenyl, pyrazinyl, piperazinyl, pyrrolidinyl or thiomorpholinyl group substituted with at least one methyl or halo group. In one variation, a compound of the invention is of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is an unsubstituted $C_{3-8}$ cycloalkyl or an unsubstituted heterocyclyl. In another variation, a compound of the invention is of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is a substituted or unsubstituted cyclohexyl, morpholinyl, piperazinyl, thiomorpholinyl, cyclopentyl or pyrrolidinyl moiety. In yet another variation, a compound of the invention is of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is a substituted cyclohexyl, morpholinyl, piperazinyl, thiomorpholinyl, cyclopentyl or pyrrolidinyl moiety substituted with at least one carbonyl, hydroxymethyl, methyl or hydroxyl group.

In still another variation, a compound of the invention is of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is a moiety selected from the structures:

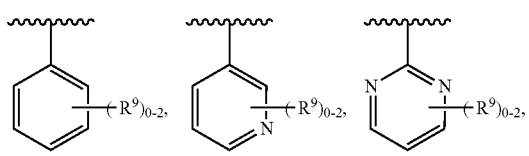

-continued

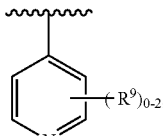

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In one variation, Q is substituted with two $R^9$ groups. In a further variation, Q is selected from the aromatic structures detailed where the residue has the moiety $(R^9)_0$ such that Q either contains no $R^9$ functionality or a moiety of the formula N—$R^9$.

In still another variation, a compound of the invention is of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is a moiety selected from the structures:

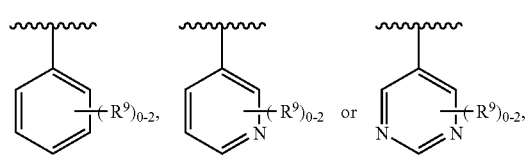

wherein each $R^9$ is independently alkyl, perhaloalkyl or halo.

In another variation, a compound of the invention is of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is a moiety selected from the structures:

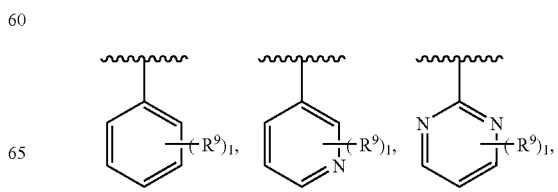

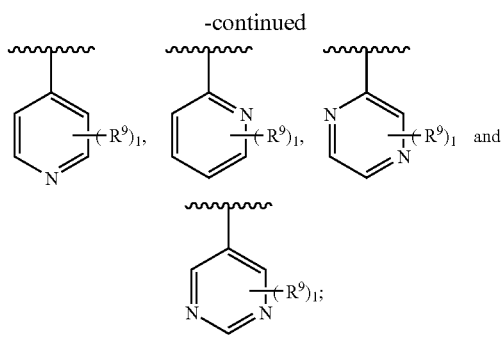

and wherein $R^9$ is connected to Q ortho or para to the position at which Q is connected to the carbon bearing $R^{8e}$ and $R^{8f}$. In a particular variation, Q is a structure of the formula:

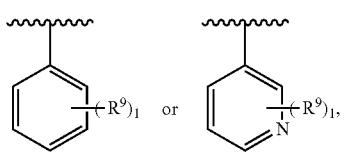

and $R^9$ is connected to Q para to the position at which Q is connected to the carbon bearing $R^{8e}$ and $R^{8f}$. In another particular variation, Q is a structure of the formula

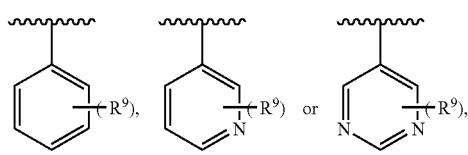

where each $R^9$ is independently alkyl, perhaloalkyl or halo.

In another variation, a compound of the invention is of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is a moiety selected from the structures:

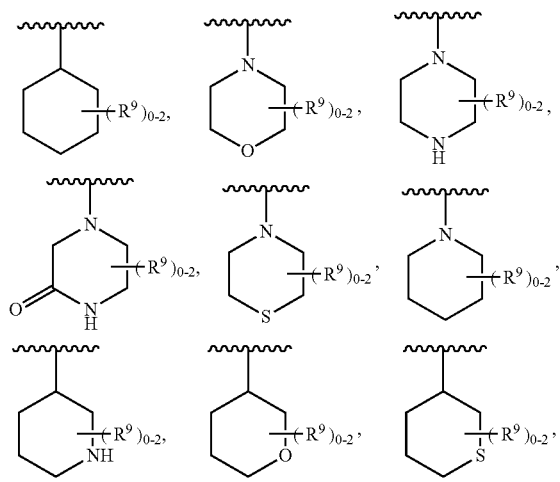

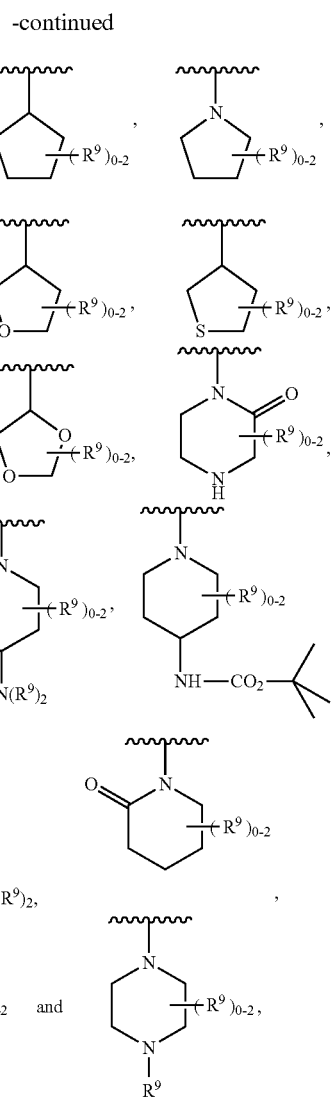

wherein each $R^9$ is independently a halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, alkoxy, substituted or unsubstituted amino, acylamino, sulfonylamino, sulfonyl, carbonyl, aminoacyl or aminocarbonylamino. In one variation, Q is substituted with no more than one $R^9$ group. In another variation, Q is substituted with only one $R^9$ group. In yet another variation, Q is substituted with two $R^9$ groups. In a particular variation, Q is selected from the carbocyclic and heterocyclic structures detailed where the residue has the moiety $(R^9)_0$ such that Q either contains no $R^9$ functionality or a moiety of the formula N—$R^9$.

In any structure or variation detailed herein containing an $R^9$ group, in one variation, each $R^9$ is independently a substituted or unsubstituted $C_1$-$C_4$ alkyl, halo, trifluoromethyl or hydroxyl. In another variation, each $R^9$ is independently methyl, —$CH_2OH$, isopropyl, halo, trifluoromethyl or hydroxyl.

In another variation, a compound of the invention is of the formula (I) or (Ia) or any variation of the foregoing detailed herein, or a compound according to any one of the formulae (IIa)-(IIh), (IIIa)-(IIIo), (IVa)-(IVp) or (Va)-(Vzf) where Q is a moiety selected from the structures:

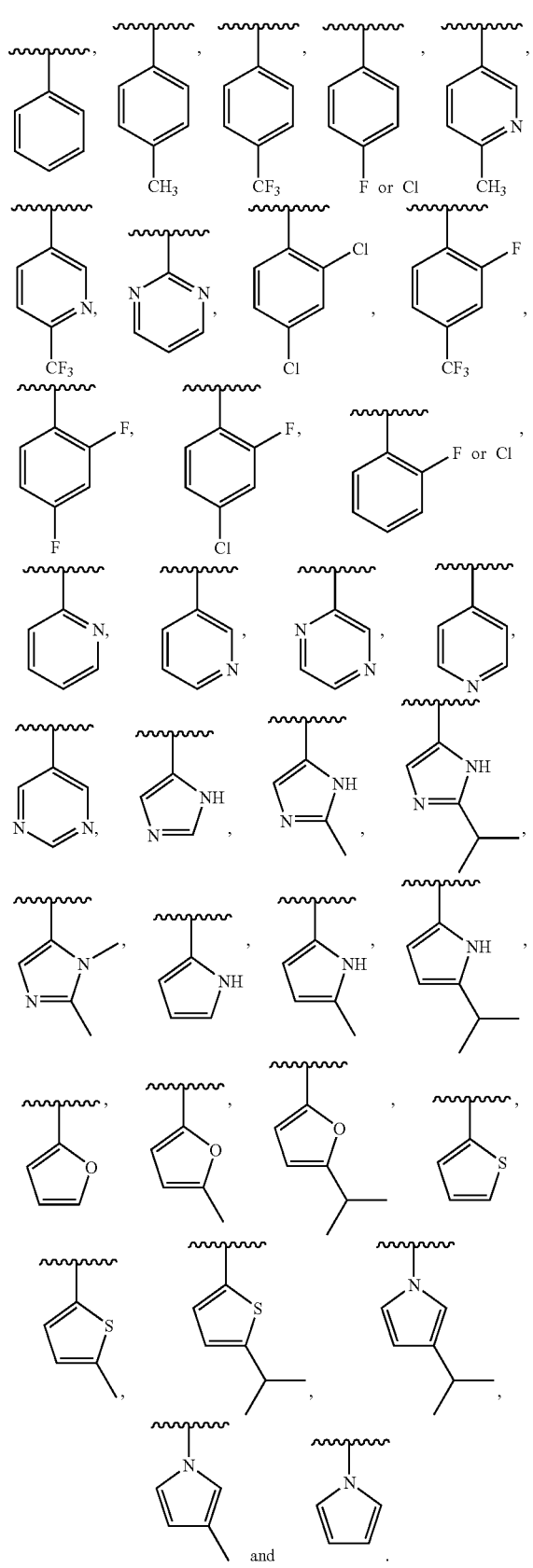

detailed herein, or a compound according to any one of the formulae (IIa)-(IIh), (IIIa)-(IIIo), (IVa)-(IVp) or (Va)-(Vzf) where Q is a moiety of the structure:

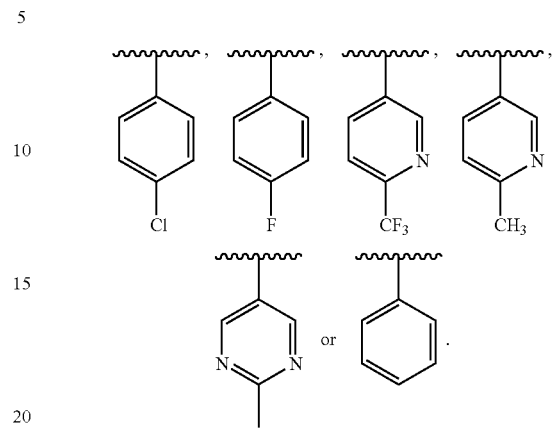

In another variation, a compound of the invention is of the formula (I) or (Ia) or any variation of the foregoing detailed herein, or a compound according to any one of the formulae (IIa)-(IIh), (IIIa)-(IIIo), (IVa)-(IVp) or (Va)-(Vzf) where Q is a moiety selected from the structures:

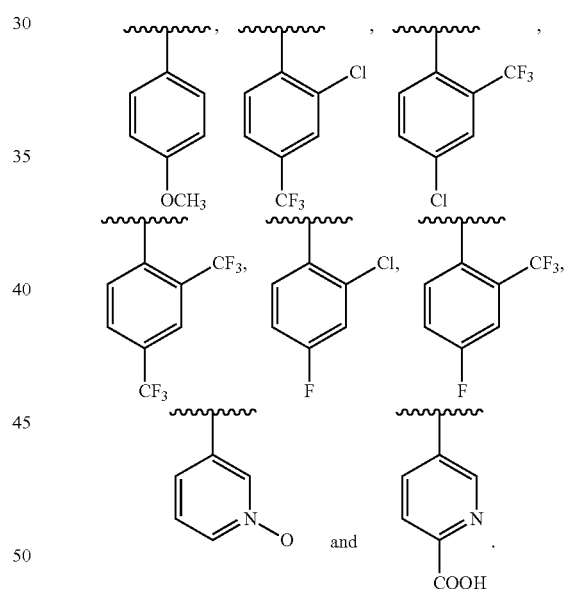

In yet another variation, a compound of the invention is of the formula (I) or (Ia) or any variation of the foregoing detailed herein, or a compound according to any one of the formulae (IIa)-(IIh), (IIIa)-(IIIo), (IVa)-(IVp) or (Va)-(Vzf) where Q is a moiety selected from the structures:

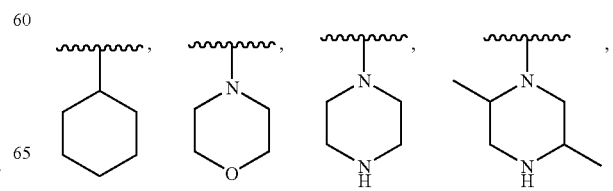

In yet another variation, a compound of the invention is of the formula (I) or (Ia) or any variation of the foregoing

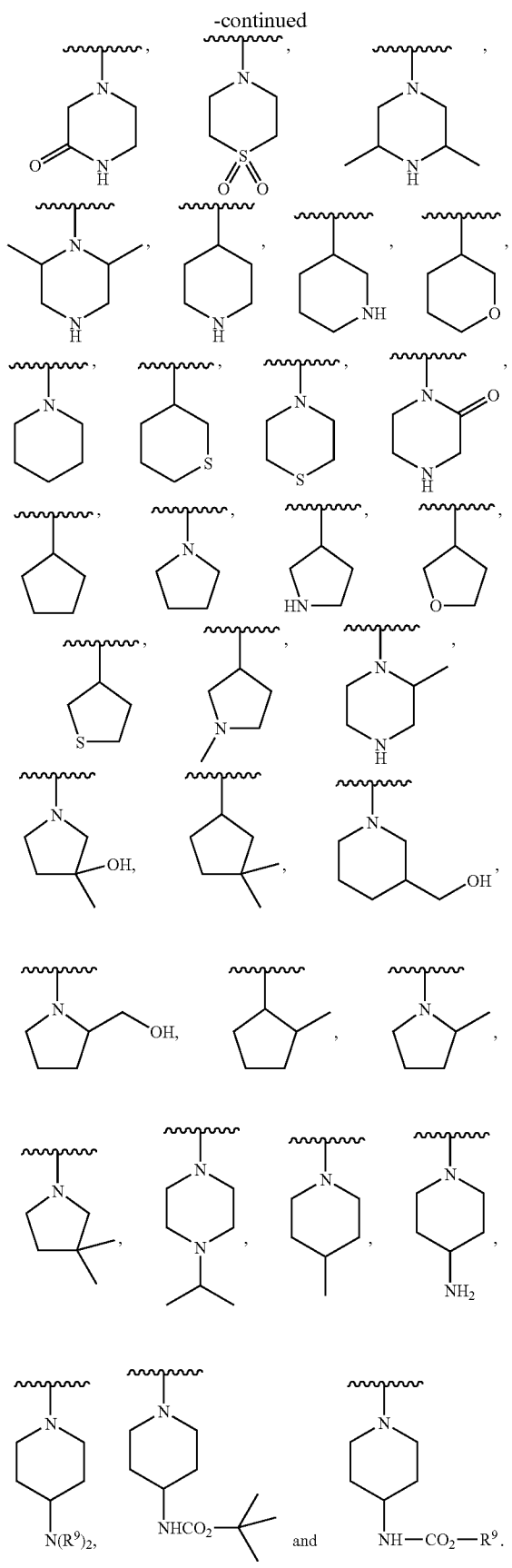

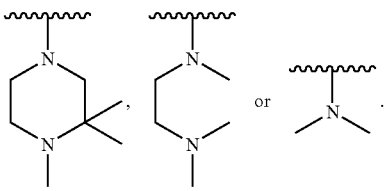

In yet another variation, a compound is of any formula detailed herein and, where applicable, Q is In yet another variation, a compound of the invention is of the formula (I) or (Ia) or any variation of the foregoing detailed herein, or a compound according to any one of the formulae (IIa)-(IIh), (IIIa)-(IIIo), (IVa)-(IVp) or (Va)-(Vzf) where Q is a moiety selected from the structures:

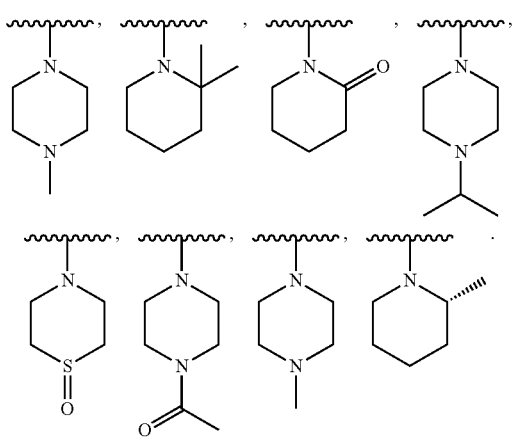

In another variation, a compound of the invention is of a formulae detailed herein, e.g., formula, (I), (A), (B), (C), (D), (E) or (F) or any variation of the foregoing detailed herein, or a compound according to any one of the formulae (IIa)-(IIh), (IIIa)-(IIIo), (IVa)-(IVp) or (Va)-(Vzf) where Q is a 6-membered ring heteroaryl or substituted heteroaryl selected from the structures:

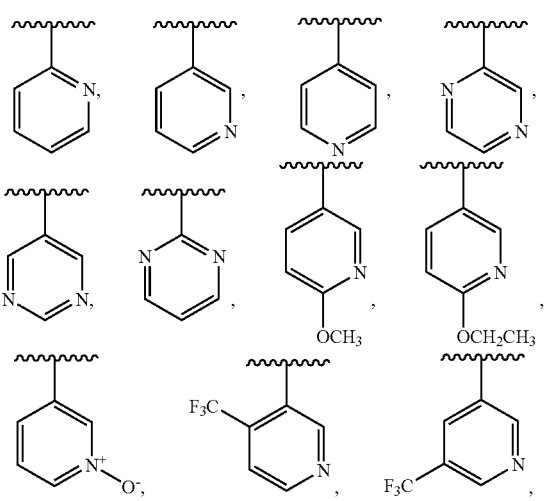

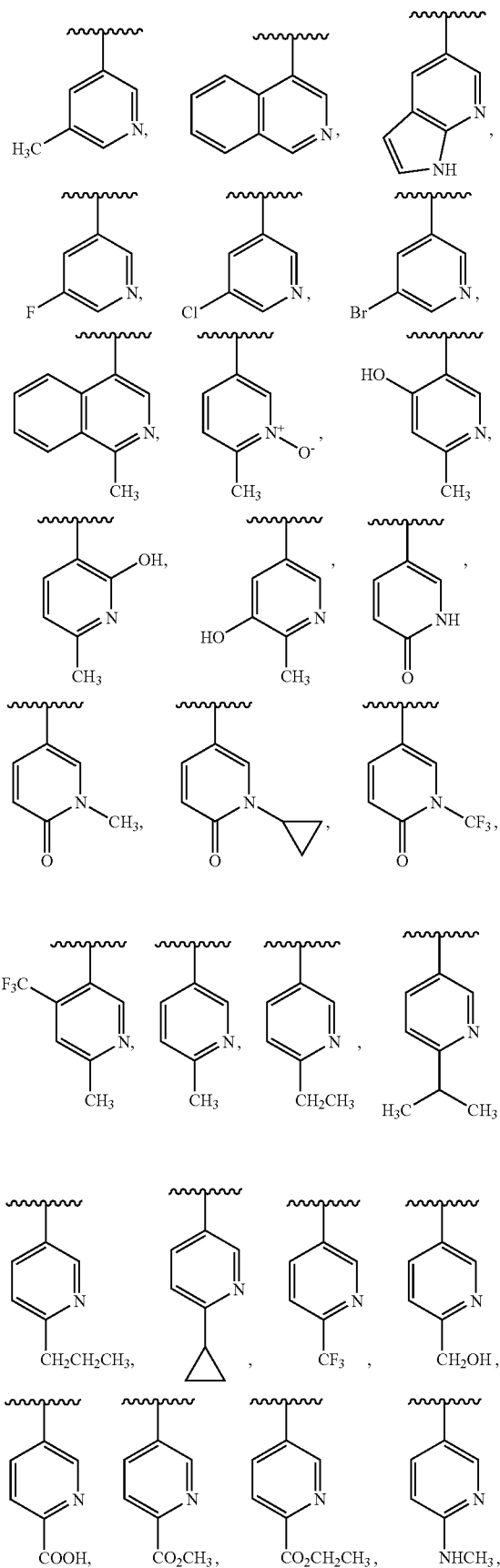
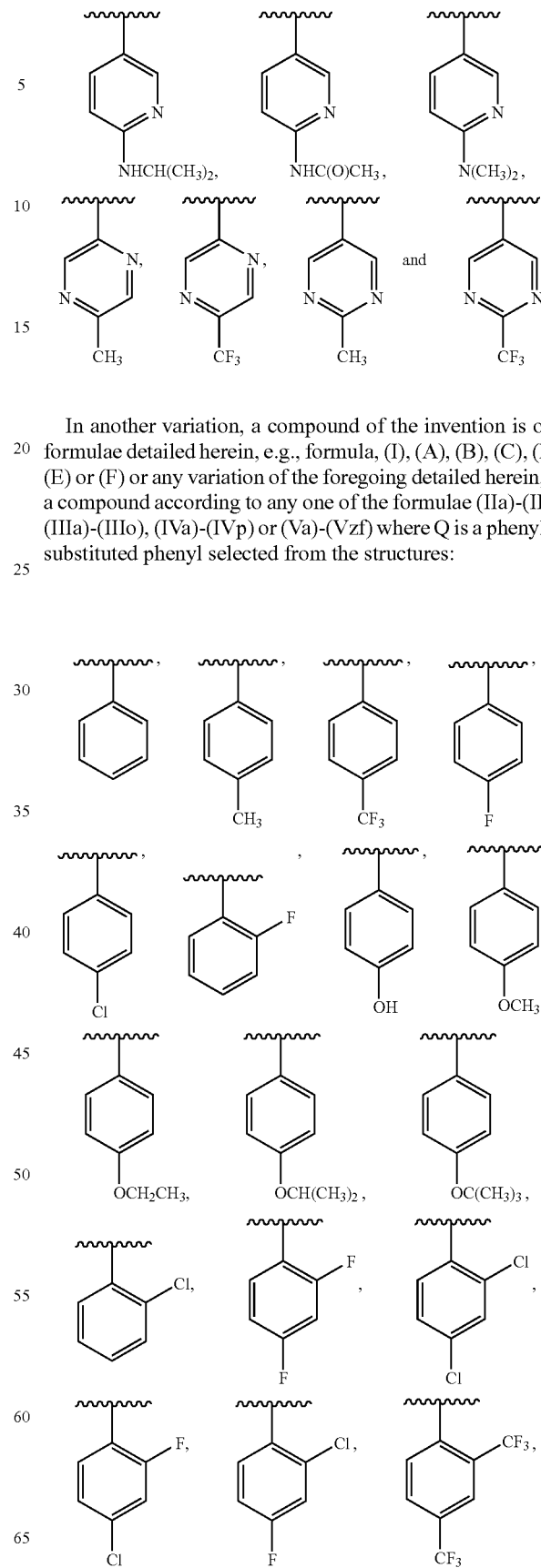
In another variation, a compound of the invention is of a formulae detailed herein, e.g., formula, (I), (A), (B), (C), (D), (E) or (F) or any variation of the foregoing detailed herein, or a compound according to any one of the formulae (IIa)-(IIh), (IIIa)-(IIIo), (IVa)-(IVp) or (Va)-(Vzf) where Q is a phenyl or substituted phenyl selected from the structures:

-continued
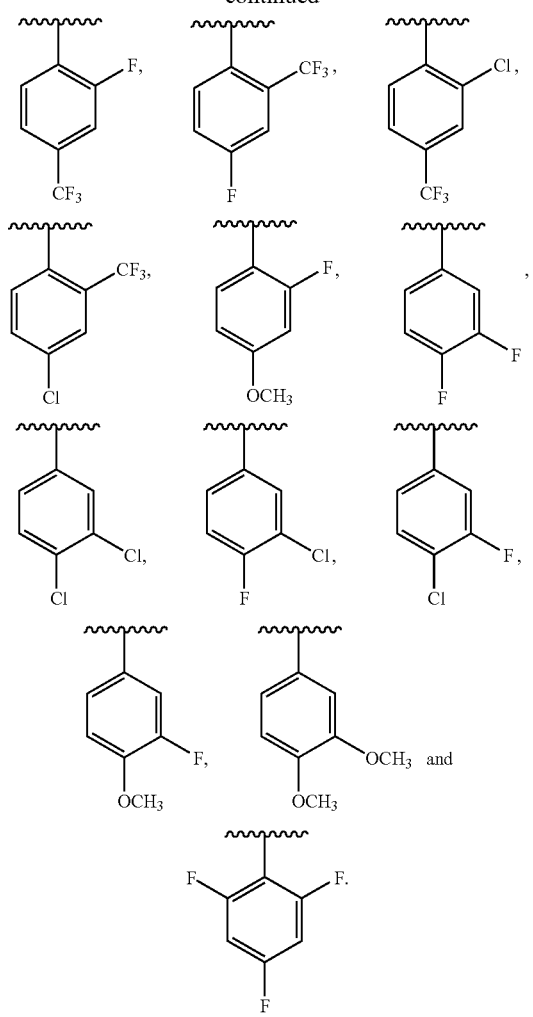
In another variation, a compound of the invention is of a formulae detailed herein, e.g., formula, (I), (A), (B), (C), (D), (E) or (F) or any variation of the foregoing detailed herein, or a compound according to any one of the formulae (IIa)-(IIh), (IIIa)-(IIIo), (IVa)-(IVp) or (Va)-(Vzf) where Q is a 5-membered ring heteroaryl or substituted heteroaryl selected from the structures:
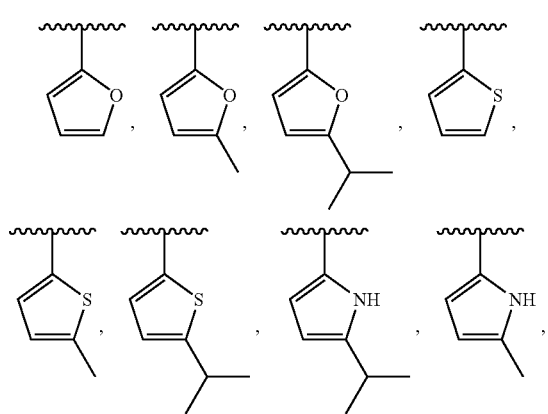
-continued
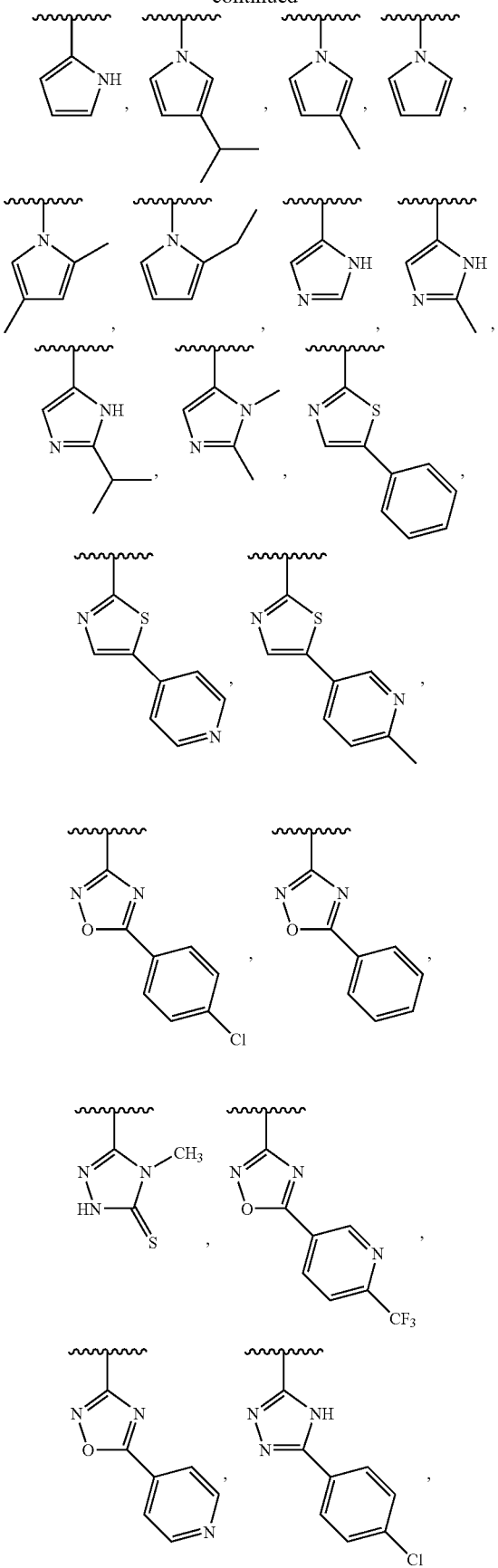

-continued

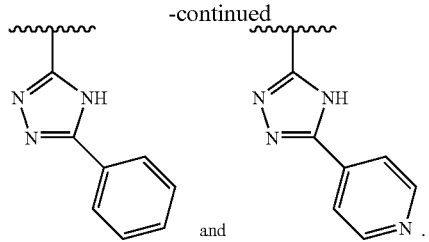

and

In another variation, a compound of the invention is of a formulae detailed herein, e.g., formula, (I), (A), (B), (C), (D), (E) or (F) or any variation of the foregoing detailed herein, or a compound according to any one of the formulae (IIa)-(IIh), (IIIa)-(IIIo), (IVa)-(IVp) or (Va)-(Vzf) where Q is a 5-membered ring substituted or unsubstituted cycloalkyl or heterocyclyl selected from the structures:

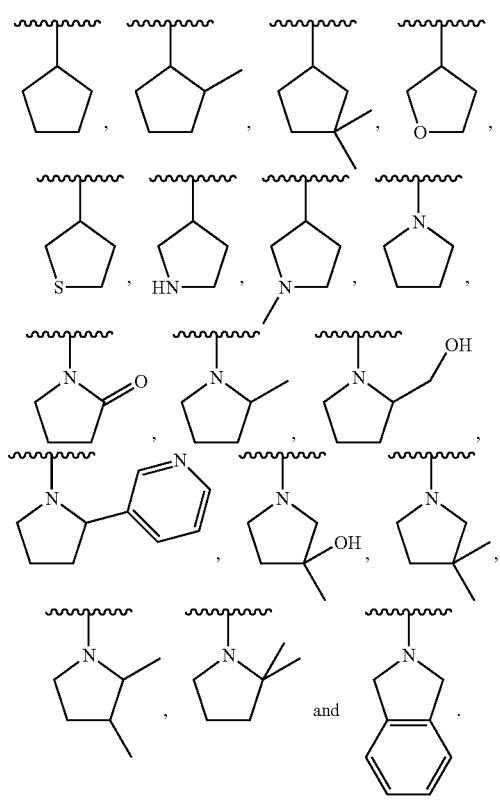

and

In another variation, a compound of the invention is of a formulae detailed herein, e.g., formula, (I), (A), (B), (C), (D), (E) or (F) or any variation of the foregoing detailed herein, or a compound according to any one of the formulae (IIa)-(IIh), (IIIa)-(IIIo), (IVa)-(IVp) or (Va)-(Vzf) where Q is a 6-membered ring substituted or unsubstituted cycloalkyl or heterocyclyl selected from the structures:

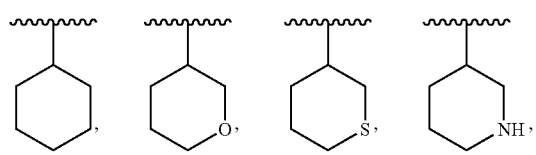

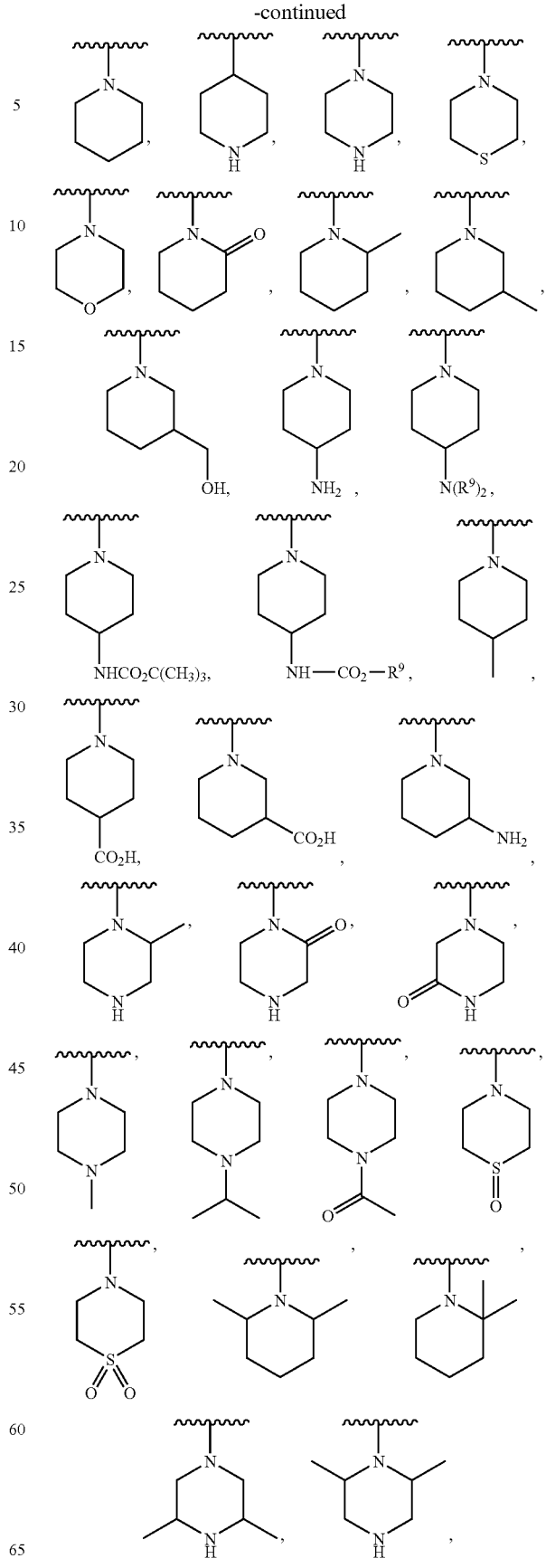

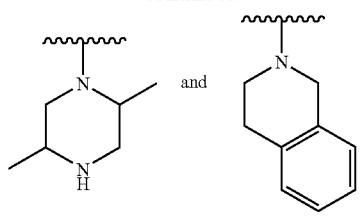

In another variation, a compound of the invention is of the formula (I) or (Ia) or any variation of the foregoing detailed herein, or a compound according to any one of the formulae (IIa)-(IIh), (IIIa)-(IIIo), (IVa)-(IVp) or (Va)-(Vzf) where Q is an unsubstituted amino, substituted amino, alkoxy, aminoacyl, acyloxy, carbonylalkoxy, aminocarbonylalkoxy or acylamino moiety. In a particular variation, Q is an unsubstituted amino. In another variation, Q is substituted amino of the formula —N($C_1$-$C_8$alkyl)$_2$ such as the moiety —N(Me)$_2$-N(CH$_3$)(CH$_2$CH$_3$). In another variation, Q is a substituted amino of the formula —N(H)(cycloalkyl or substituted cycloalkyl), such as a moiety of the formula:

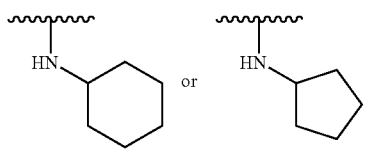

In another variation, Q is a substituted amino of the formula —N(H)(aryl or substituted aryl), such as a moiety of the formula:

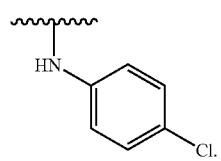

In a particular variation, Q is an amino or substituted amino and $R^{8e}$ and $R^{8f}$ are taken together to form a carbonyl moiety. In yet another variation, Q is an acylamino moiety. In still another variation, Q is an acylamino moiety and $R^{8e}$ and $R^{8f}$ are both hydrogen.

In another variation, Q is an alkoxy group of the formula —O—$C_1$-$C_8$alkyl, such as the moiety —O—CH$_2$CH$_3$. In yet another variation, Q is an alkoxy group and $R^{8e}$ and $R^{8f}$ are taken together to form a carbonyl moiety. In still a further variation, Q is a carbonylalkoxy moiety. In yet another variation, Q is a carbonylalkoxy moiety and $R^{8e}$ and $R^{8f}$ are both hydrogen.

In still another variation, Q is an acyloxy, aminocarbonylalkoxy or acylamino moiety. In one variation, Q is an acyloxy, aminocarbonylalkoxy or acylamino moiety and $R^{8e}$ and $R^{8f}$ are both hydrogen.

In one variation, Q is a moiety selected from the structures:

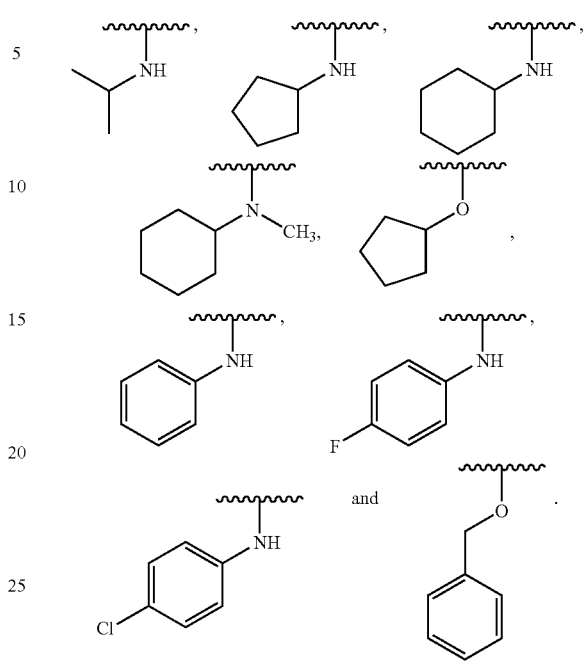

The invention also embraces compounds of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is an aminoacyl moiety. In one variation, Q is an aminoacyl group where at least one of $R_a$ and $R_b$ is H, such as when Q is of the formula —NHC(O)$R_b$. In one variation, Q is an aminoacyl moiety selected from the group consisting of: —NHC(O)-heterocyclyl, —NHC(O)-substituted heterocyclyl, —NHC(O)-alkyl, —NHC(O)-cycloalkyl, —NHC(O)-alkaryl and —NHC(O)-substituted aryl. In another variation, Q is an aminoacyl moiety selected from the group consisting of: —NHC(O)—$C_5$-$C_7$heterocyclyl, —NHC(O)—$C_1$-$C_6$alkyl, —NHC(O)—$C_3$-$C_7$cycloalkyl, —NHC(O)—$C_1$-$C_3$alkaryl and —NHC(O)-substituted phenyl. In a particular variation, Q is a moiety of the formula:

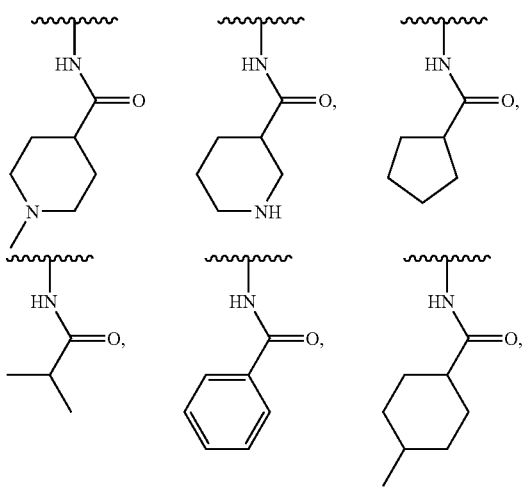

-continued

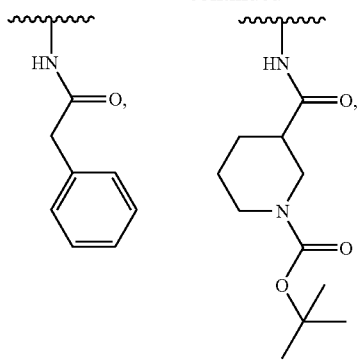

In one variation, a compound of the invention is of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is acyloxy.

In one variation, a compound of the invention is of the formula (I), (E), (F) or (Ia) or any variation of the foregoing detailed herein, or a compound according to any one of the formulae (IIa)-(IIh), (IIIa)-(IIIo), (IVa)-(IVp) or (Va)-(Vzf) where Q is a carbonylalkoxy moiety. In one variation, Q is a carbonylalkoxy moiety of the formula —C(O)—O—R$^1$ where R is H, alkyl, substituted alkyl or alkaryl. In one variation, Q is carbonylalkoxy moiety of the formula —C(O)—O—C$_1$-C$_6$alkyl. In a particular variation, Q is a carbonylalkoxy moiety of the formula —C(O)—O—C$_2$H$_5$. In one variation, Q is a carbonylalkoxy moiety selected from the group consisting of: —C(O)—O—C$_1$-C$_{10}$alkyl, —C(O)—O—C$_1$-C$_3$alkaryl, —C(O)—O—C$_1$-C$_3$ substituted alkyl and —C(O)—OH. In another variation, Q is —C(O)—O—C$_1$-C$_6$alkyl. In a particular variation, Q is a moiety of the formula:

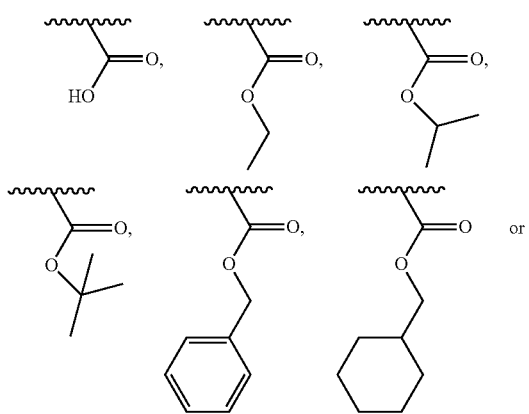

-continued

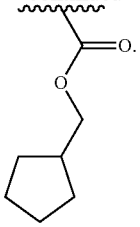

In yet another variation, a compound is of any formula detailed herein and, where applicable, Q is

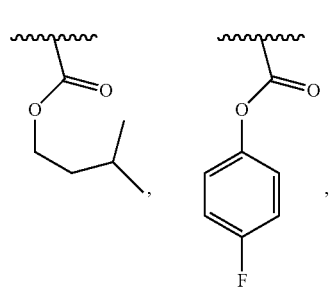

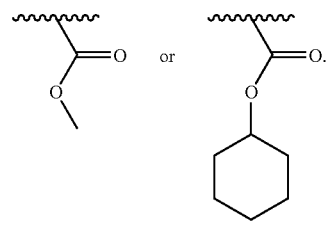

In another variation, a compound of the invention is of the formula (I), (E), (F) or (Ia) or any variation of the foregoing detailed herein, or a compound according to any one of the formulae (IIa)-(IIf), (IIIa)-(IIIi), (Iva)-(IVk) or (Va)-(Vzv) where Q is an aminocarbonylalkoxy moiety. In one variation, Q is an aminocarbonylalkoxy moiety of the formula —NHC(O)—O—R$_b$. In another variation, Q is an aminocarbonylalkoxy moiety of the formula —NHC(O)—O—R$_b$ where R$_b$ is a substituted alkyl group. In a particular variation, Q is a moiety of the formula —NH—C(O)—O—CH$_2$—C(Cl)$_3$.

The invention also embraces compounds of the formula (I), (E), (F) or (Ia) or any variation of the foregoing detailed herein, or a compound according to any one of the formulae (IIa)-(IIf), (IIIa)-(IIIi), (Iva)-(IVk) or (Va)-(Vzv) where Q is an acylamino moiety. In one variation, Q is an acylamino group where at least one of R$_a$ and R$_b$ is H, such as when Q is of the formula —C(O)N(H)(R$_b$). In another variation, Q is an acylamino group where both R$_a$ and R$_b$ alkyl. In one variation, Q is an acylamino moiety selected from the group consisting of: —C(O)—N(H)(alkyl), —C(O)—N(alkyl)$_2$, —C(O)—N(H)(alkaryl) and —C(O)—N(H)(aryl). In another variation, Q is an acylamino moiety selected from the group consisting of: —C(O)—N(H)$_2$, —C(O)—N(H)(C$_1$-C$_8$alkyl), —C(O)—N(C$_1$-C$_6$alkyl)$_2$ and —C(O)—N(H)(C$_1$-C$_3$alkaryl). In a particular variation, Q is a moiety of the formula:

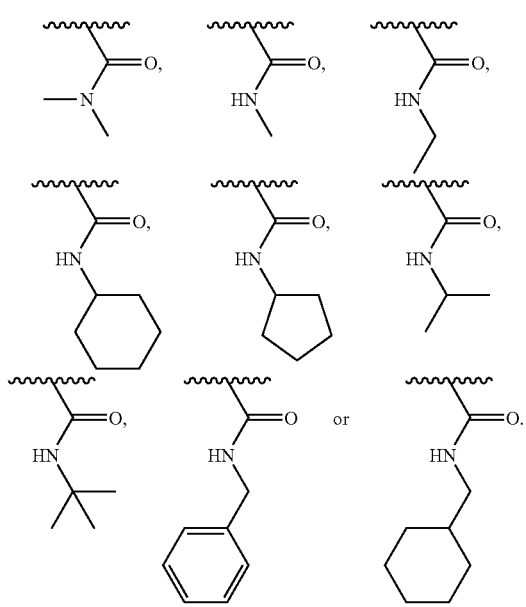

In yet another variation, a compound is of any formula detailed herein and, where applicable, Q is alkynyl and is of the formula:

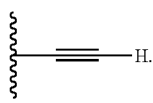

Any formula detailed herein, where applicable, may in one variation have as Q the moieties detailed herein above. It is understood that by "where applicable" it is intended that such Q moieties be a variation if the formula encompasses such a structure. For example, if a given formula does not encompass structures wherein Q is a phenyl moiety, then a phenyl moiety is not applicable to that particular formula, but remains applicable to formulae that do encompass structures where Q is a phenyl moiety.

In a further variation, a compound of the invention is of the formula (I), (E) or (F) where $R^1$ is an unsubstituted alkyl, $R^{2a}$, $R^{3a}$, $R^{3b}$, $R^{10}$ is H, each $X^7$, $X^8$, $X^9$ and $X^{10}$ is independently N or CH, each $R^{8a}$, $R^{8b}$, $R^{8c}$, $R^{8d}$, $R^{8e}$ and $R^{8f}$ is independently H or hydroxyl, and Q is a substituted or unsubstituted aryl, substituted or unsubstituted heteroaryl, including but not limited to a substituted or unsubstituted phenyl or pyridyl group. Where Q is a substituted phenyl or pyridyl group, in one variation it is substituted with at least one methyl group.

In yet a further variation, a compound of the invention is of the formula (I), (E) or (F) where $R^1$ is a substituted or unsubstituted $C_1$-$C_8$ alkyl, acyl, acyloxy, carbonylalkoxy, substituted or unsubstituted heterocyclyl, substituted or unsubstituted aryl; $R^2$ is H, unsubstituted $C_1$-$C_8$ alkyl or halo; each $R^{3a}$ and $R^{3b}$ is independently H or halo; each $X^7$, $X^8$, $X^9$ and $X^{10}$ is $CR^4$, where $R^4$ is as defined in formula (I) or in a particular variation, $R^4$ is H, halo, pyridyl, methyl or trifluoromethyl; $R^{10}$ is H, and Q is a substituted or unsubstituted aryl, substituted or unsubstituted heteroaryl, including but not limited to a substituted or unsubstituted pyridyl, phenyl, pyrimidinyl, pyrazinyl, imidazolyl, furanyl, pyrrolyl or thiophenyl group. In a particular variation, Q is a pyridyl, phenyl, pyrimidinyl, pyrazinyl, imidazolyl, furanyl, pyrrolyl or thiophenyl group substituted with at least one substituted or unsubstituted $C_1$-$C_8$ alkyl, halo or perhaloalkyl moiety. In one variation, a compound of the variation detailed herein is provided wherein $R^1$ is propylate, methyl, ethyl, cyclopropyl, trifluoromethyl, isopropyl, tert-butyl, sec-butyl, 2-methylbutyl, propanal, 1-methyl-2-hydroxyethyl, 2-hydroxyethanal, 2-hydroxyethyl, 2-hydroxypropyl, 2-hydroxy-2-methylpropyl, cyclobutyl, cyclopentyl, cyclohexyl, substituted phenyl, piperidin-4-yl, hydroxycyclopent-3-yl, hydroxycyclopent-2-yl, hydroxycycloprop-2-yl, 1-hydroxy-1-methylcycloprop-2-yl, or 1-hydroxy-1,2,2-trimethyl-cycloprop-3-yl.

In still a further variation, a compound of the invention is of the formula (I), (E) or (F) where $R^1$ is a substituted or unsubstituted $C_1$-$C_8$ alkyl; each $R^{2a}$, $R^{3a}$ and $R^{3b}$ is independently H or halo; each $R^4$ is independently H, halo, $C_1$-$C_8$ perhaloalkyl, substituted or a unsubstituted $C_1$-$C_8$ alkyl; each $R^{8a}$, $R^{8b}$, $R^{8c}$, $R^{8d}$, $R^{8e}$ and $R^{8f}$ is H; and Q is a substituted or unsubstituted cyclohexyl, morpholinyl, piperazinyl, thiomorpholinyl, cyclopentyl or pyrrolidinyl moiety. The invention also embraces a compound of the formula (I), (E) or (F) where $R^1$ is a methyl; at least one of $X^7$, $X^8$, $X^9$ and $X^{10}$ is $CR^4$, and each $R^4$ is independently H, halo, methyl or trifluoromethyl. The invention embraces compounds where Q in any variation detailed is substituted with at least one carbonyl, hydroxymethyl, methyl or hydroxyl group.

In a particular variation, the compound is of the formula (I), (E) or (F) where $R^1$ is a substituted or unsubstituted $C_1$-$C_8$ alkyl; $R^2$ is H, a substituted or unsubstituted $C_1$-$C_8$ alkyl; $R^{3a}$ and $R^{3b}$ are both H; each $R^4$ is independently H, halo or substituted or unsubstituted $C_1$-$C_8$ alkyl; each $R^{8a}$, $R^{8b}$, $R^{8c}$, $R^{8d}$, $R^{8e}$ and $R^{8f}$ is H; $R^{10}$ is H, halo, a substituted or unsubstituted $C_1$-$C_8$ alkyl, hydroxyl, alkoxyl. In one aspect of this variation, Q may be a substituted or unsubstituted pyridyl, phenyl, pyrazinyl, piperazinyl, pyrrolidinyl or thiomorpholinyl group. In another aspect of this variation, Q is a pyridyl, phenyl, pyrazinyl, piperazinyl, pyrrolidinyl or thiomorpholinyl group substituted with at least one methyl or halo group. In yet another aspect of this variation, $X^7$, $X^8$, $X^9$ and $X^{10}$ are $CR^4$ and each $R^4$ is independently H, halo or methyl.

In another variation, a compound of the invention is of the formula (I), (E) or (Ia) or any variation of the foregoing detailed herein, or a compound according to any one of the formulae (IIa)-(IIh), (IIIa)-(IIIo), (IVa)-(IVp) or (Va)-(Vzf) where q, m, Q and $R^{8a}$-$R^{8f}$ are taken together to form a moiety of the structure:

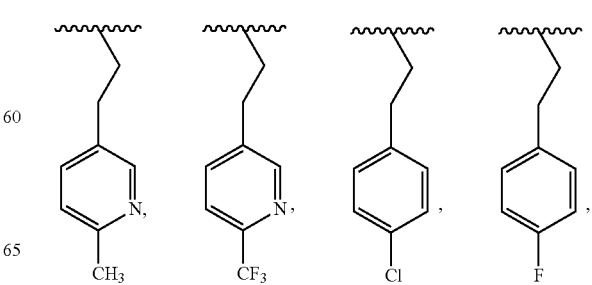

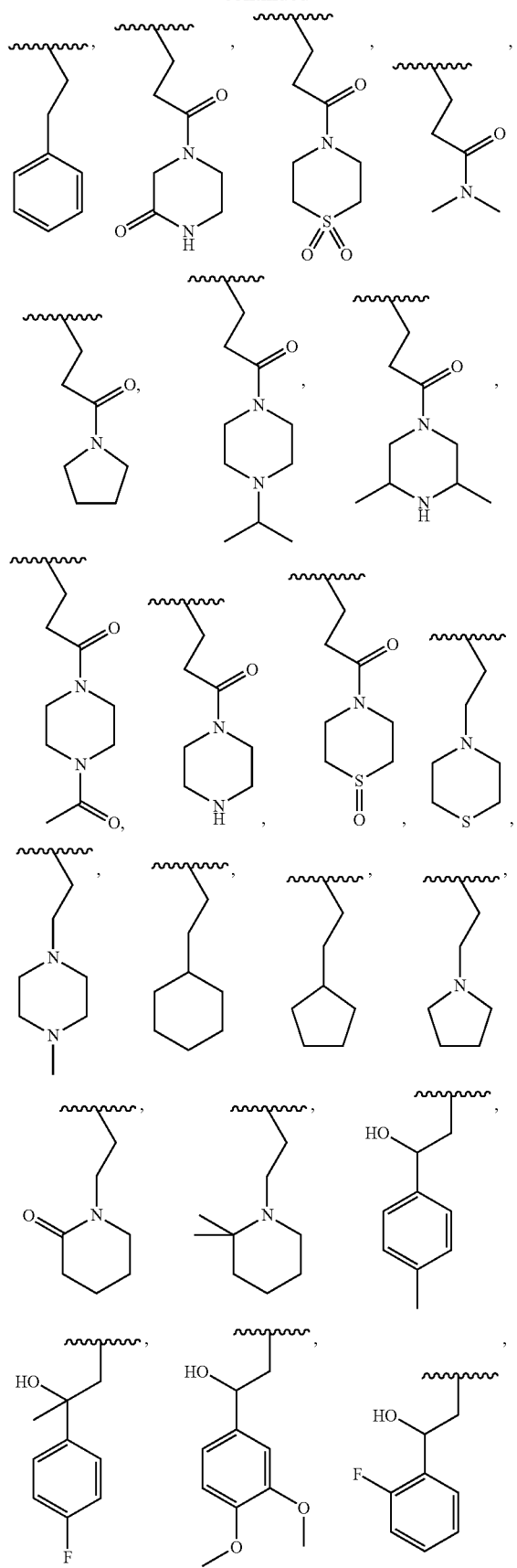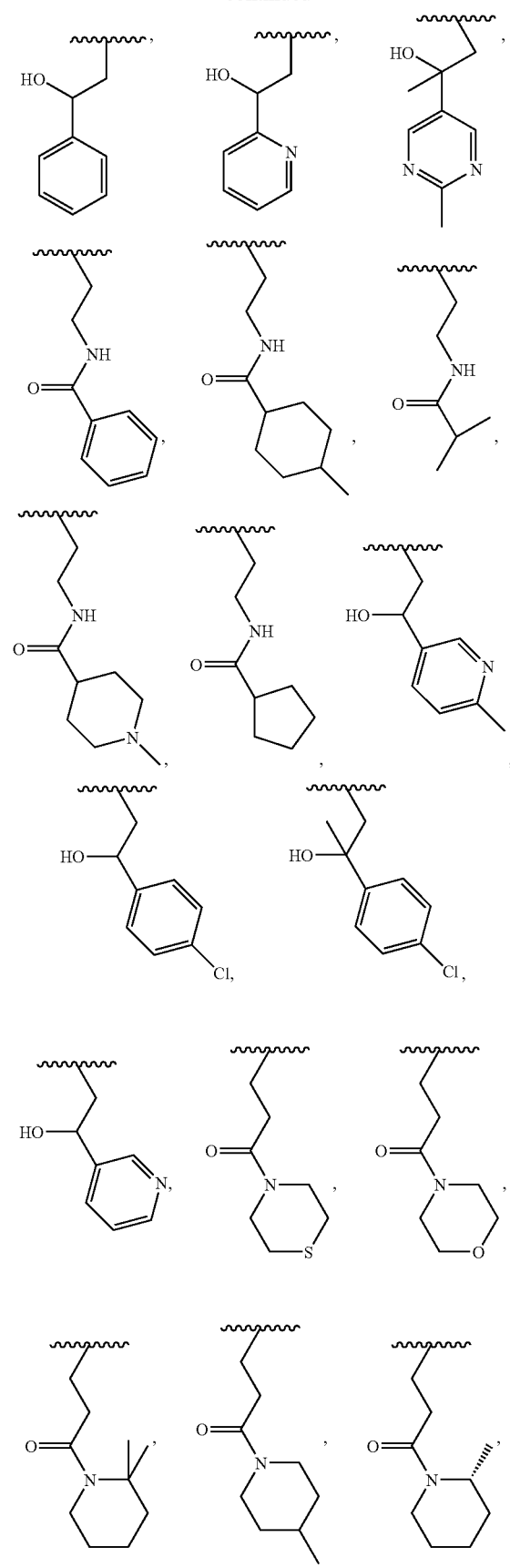

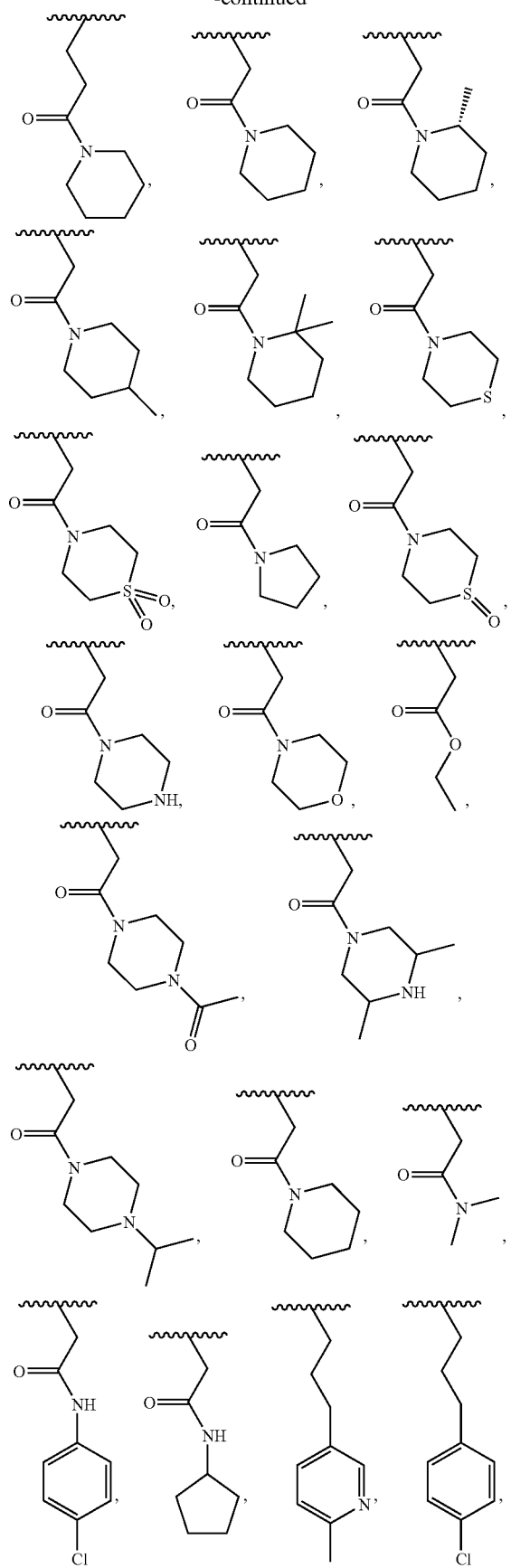
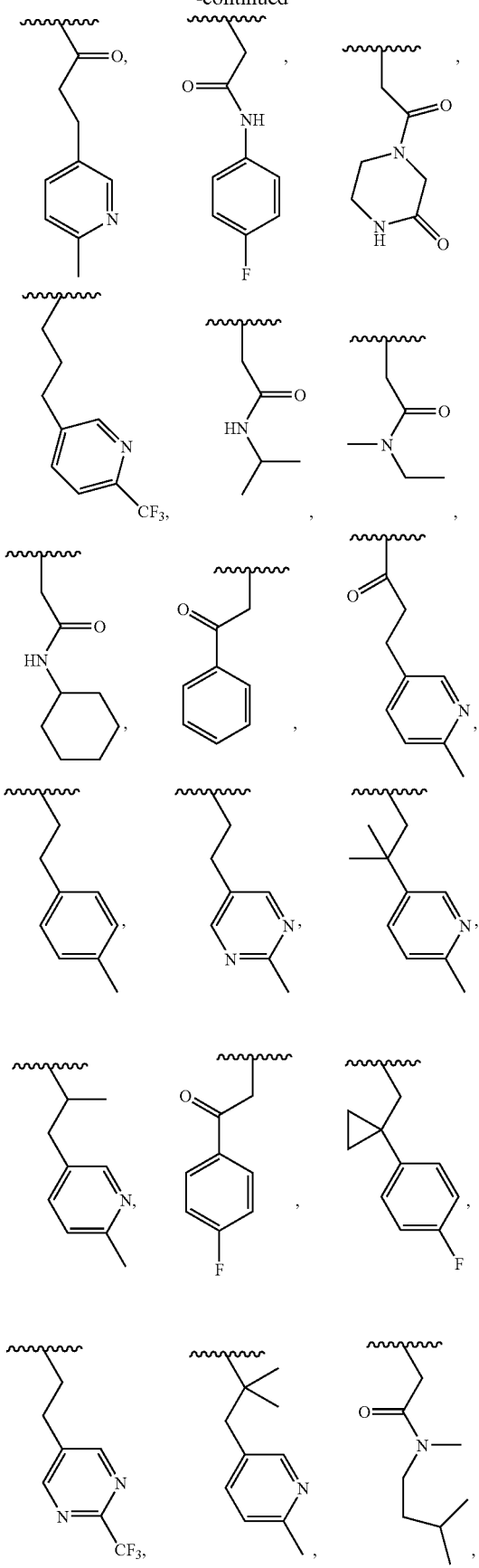

-continued
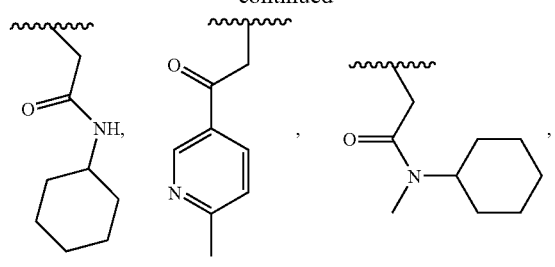
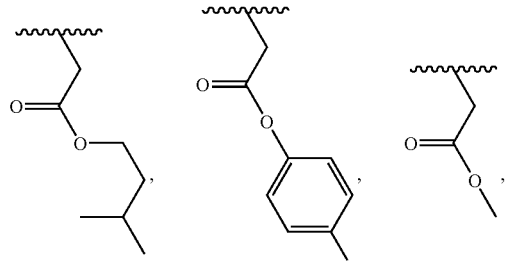
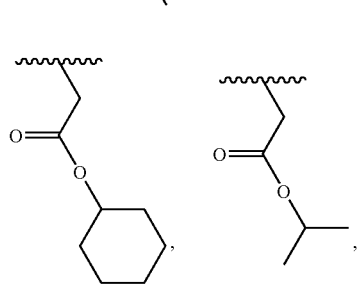
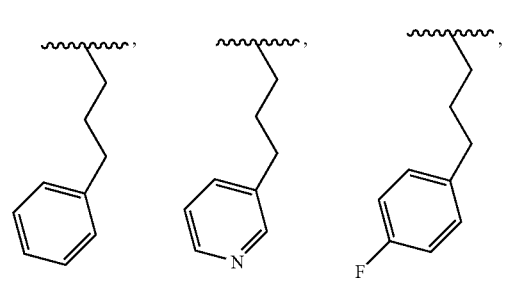
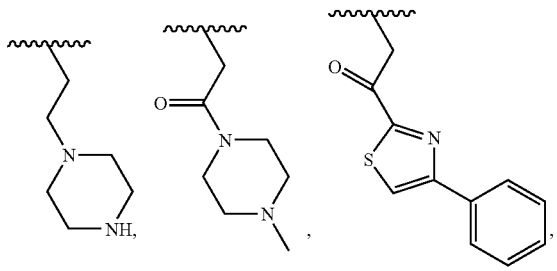
-continued
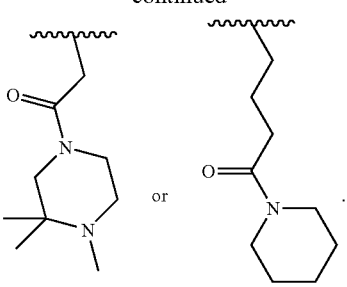
In another variation, a compound of the invention is of the formula (E) or (F) or any applicable variation of the foregoing detailed herein, where q, m, n, Q, $R^{8a}$-$R^{8f}$, $R^{11}$ and $R^{12}$ where applicable are taken together to form a moiety of the structure:
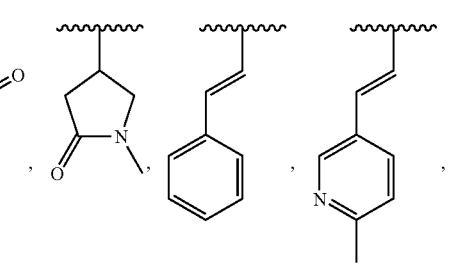
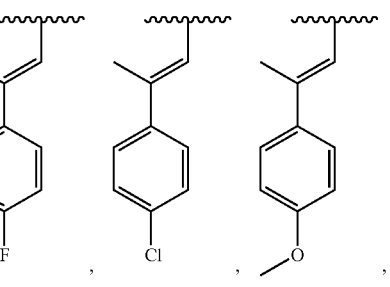
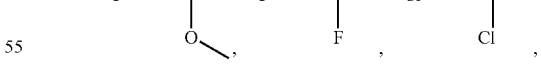
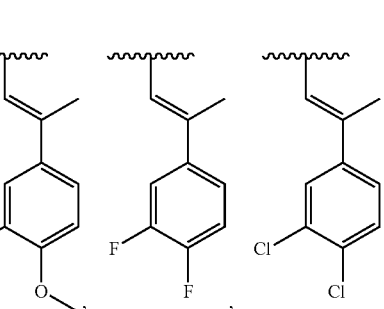
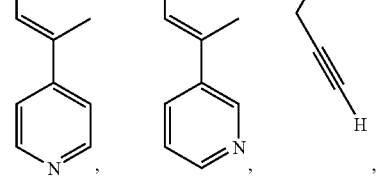

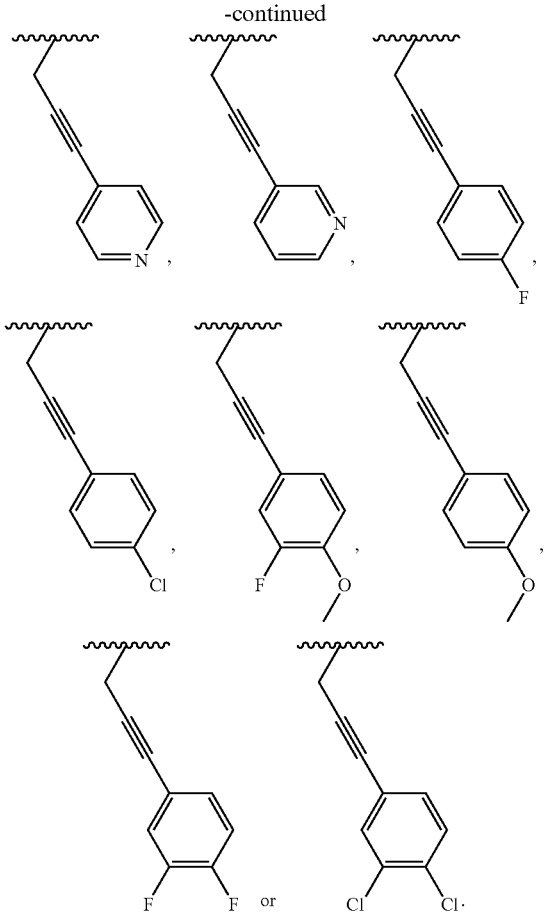

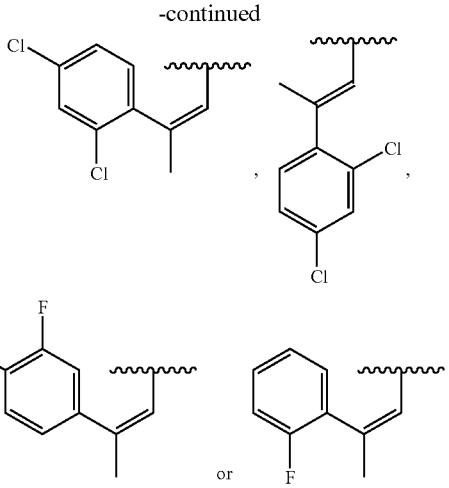

Examples of compounds according to the invention are depicted in Table 2. The compounds depicted may be present as salts even if salts are not depicted and it is understood that the invention embraces all salts and solvates of the compounds depicted here, as well as the non-salt and non-solvate form of the compound, as is well understood by the skilled artisan.

TABLE 2

Representative Compounds According to the Invention.

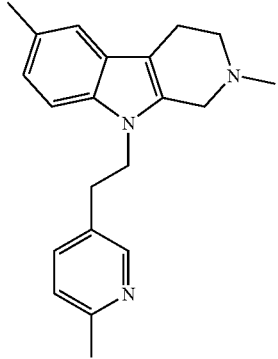

In another variation, any formula detailed herein, where applicable, may in one variation have q, m, n, Q, $R^{8a}$-$R^{8f}$, $R^{11}$ and $R^{12}$ where applicable taken together to form a moiety of the structure:

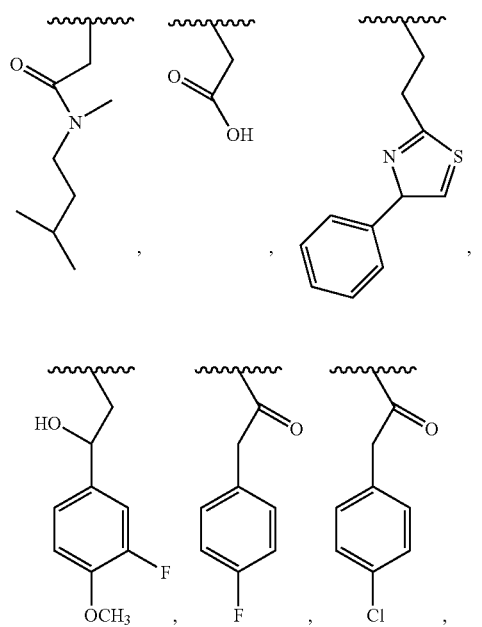

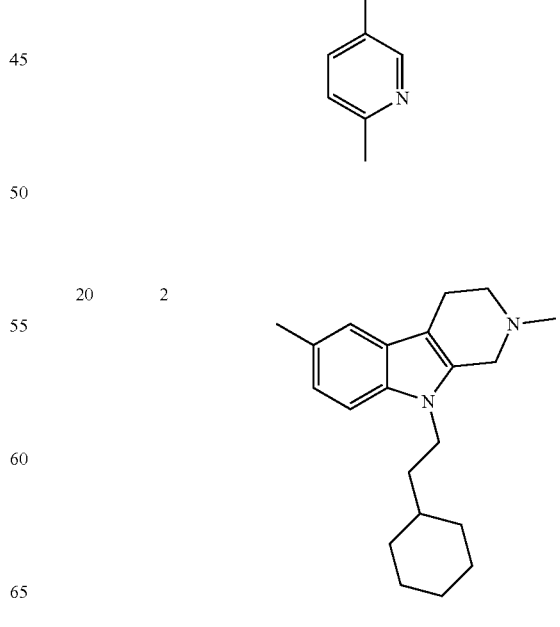

TABLE 2-continued

Representative Compounds According to the Invention.

| Ex. # | Comp. # | Structure |
|---|---|---|
| 21 | 3 | 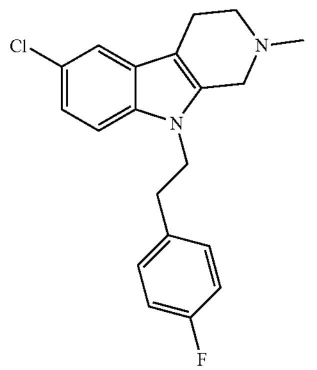 |
| 22 | 4 | 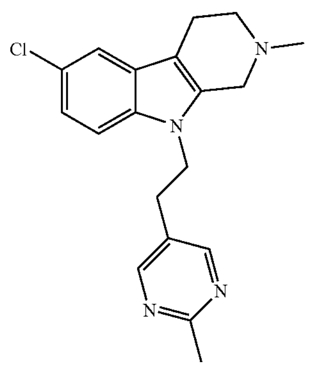 |
| 23 | 5 | 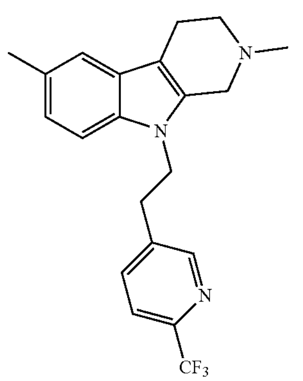 |
| 24 | 6 | 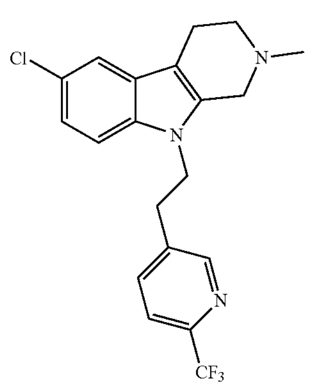 |
| 25 | 7 | |
| 26 | 8 | |
| 27 | 9 | |
| 28 | 10 | |

TABLE 2-continued
Representative Compounds According to the Invention.
| Ex. # | Comp. # | Structure |
|---|---|---|
| 29 | 11 | 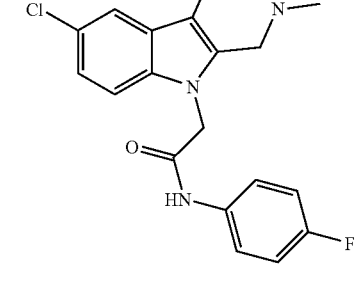 |
| 30 | 12 | 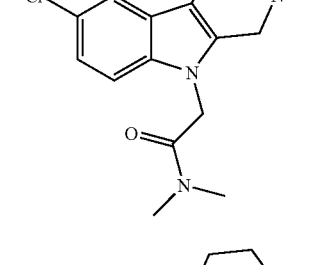 |
| 31 | 13 | 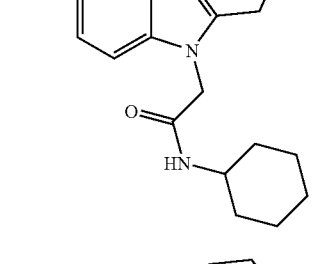 |
| 32 | 14 | 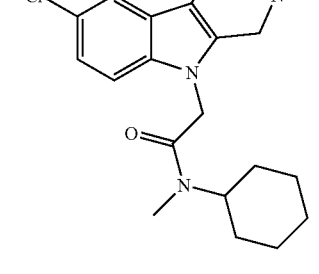 |
| 33 | 15 | 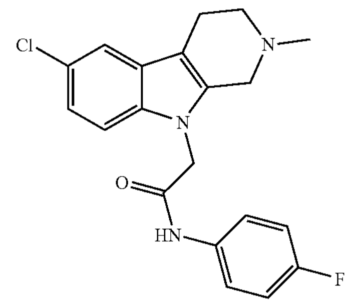 |
| 34 | 16 | 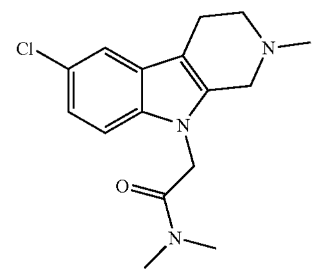 |
| 35 | 17 | 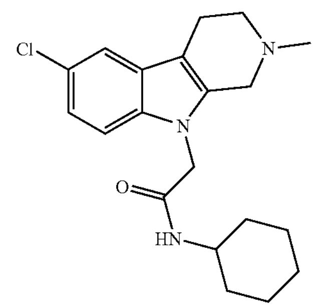 |
| 36 | 18 | 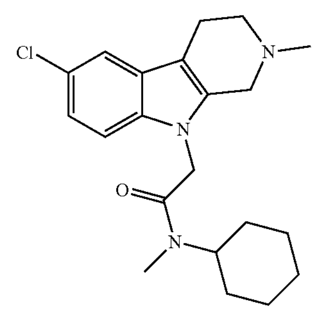 |
| 37 | 19 | 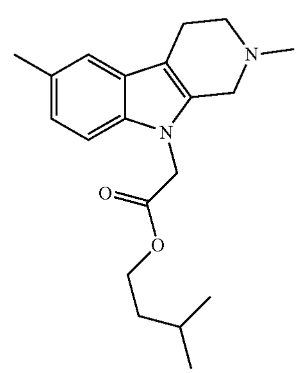 |
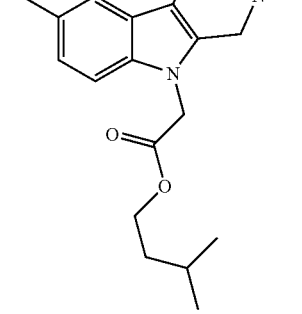

TABLE 2-continued

Representative Compounds According to the Invention.

| Ex. # | Comp. # | Structure |
|---|---|---|
| 38 | 20 | (structure) |
| 39 | 21 | (structure) |
| 40 | 22 | (structure) |
| 41 | 23 | (structure) |
| 42 | 24 | (structure) |
| 43 | 25 | (structure) |
| 44 | 26 | (structure) |
| 45 | 27 | (structure) |
| 46 | 28 | (structure) |
| 47 | 29 | (structure) |

TABLE 2-continued
Representative Compounds According to the Invention.
| Ex. # | Comp. # | Structure |
|---|---|---|
| 48 | 30 | 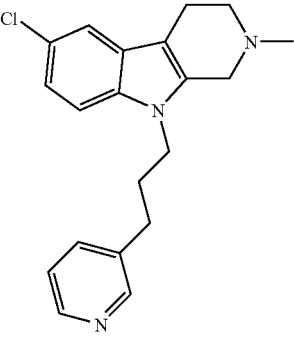 |
| 49 | 31 | 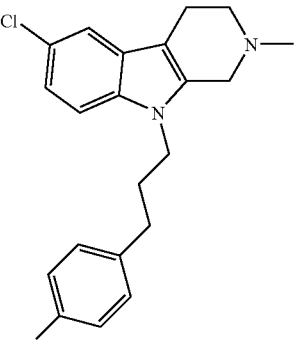 |
| 50 | 32 | 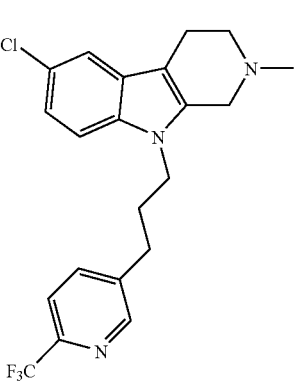 |
| 51 | 33 | 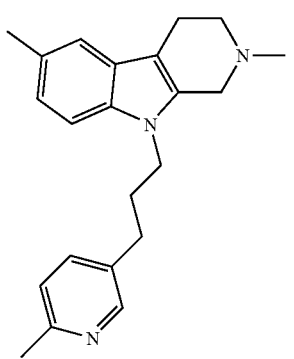 |
| 52 | 34 | 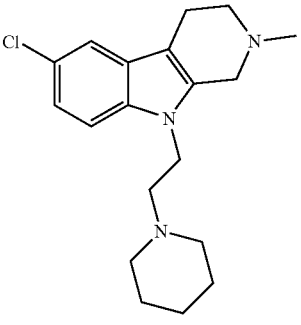 |
| 53 | 35 | 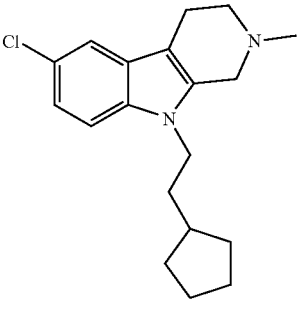 |
| 54 | 36 | 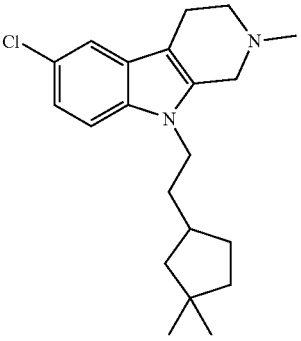 |
| 55 | 37 | 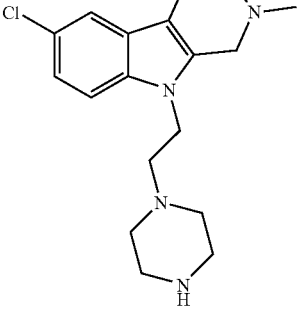 |

TABLE 2-continued

Representative Compounds According to the Invention.

| Ex. # | Comp. # | Structure |
|---|---|---|
| 56 | 38 | 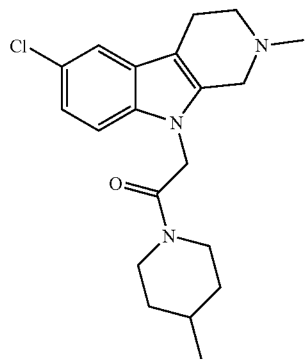 |
| 57 | 39 | 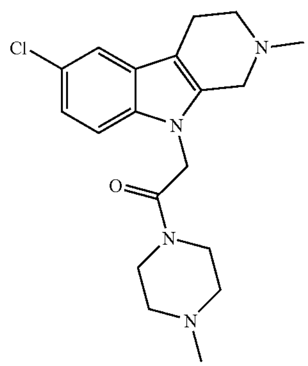 |
| 58 | 40 | 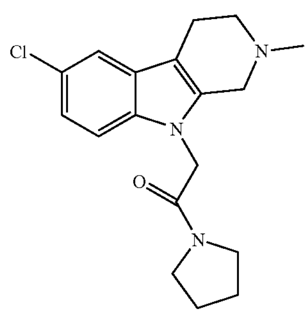 |
| 59 | 41 | 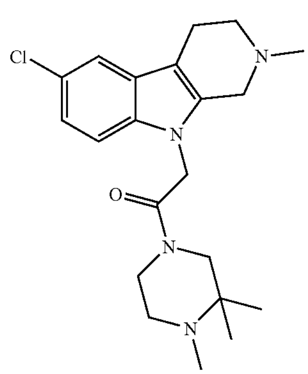 |
| 60 | 42 | |
| 61 | 43 | |
| 62 | 44 | |
| 63 | 45 | |

TABLE 2-continued

Representative Compounds According to the Invention.

| Ex. # | Comp. # | Structure |
|---|---|---|
| 64 | 46 | |
| 145 | 47 | |
| 145 | 48 | |
| 145 | 49 | |
| 145 | 50 | |
| 145 | 51 | |
| 94 | 52 | 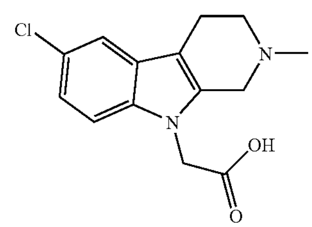 |
| 95 | 53 | 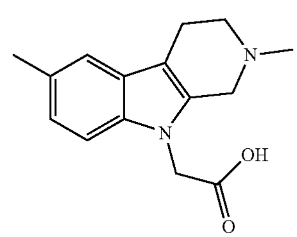 |
| 81 | 54 | 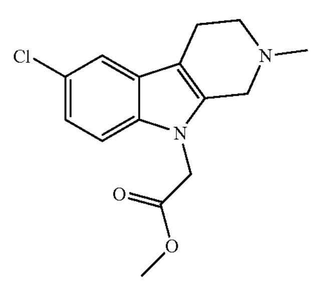 |

TABLE 2-continued
Representative Compounds According to the Invention.
| Ex. # | Comp. # | Structure |
|---|---|---|
| 69 | 55 | 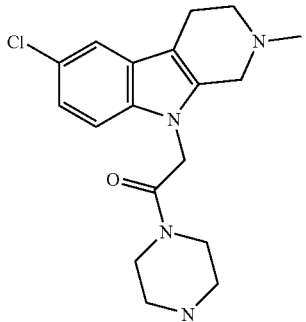 |
| 82 | 56 | 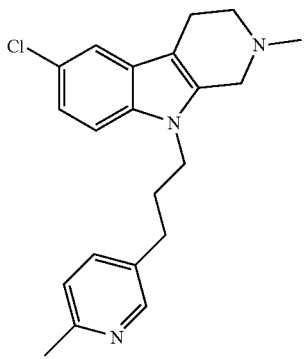 |
| 75 | 57 | 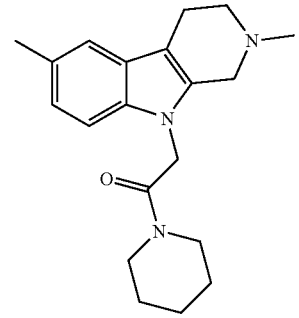 |
| 87 | 58 | 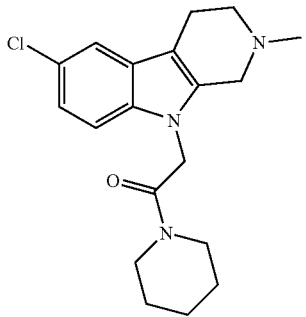 |
| 83 | 59 | 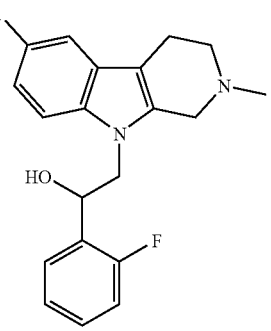 |
| 84 | 60 | 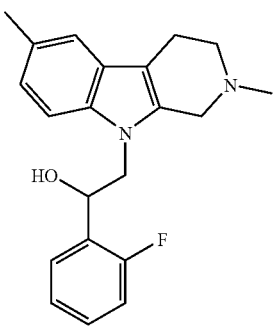 |
| 85 | 61 | 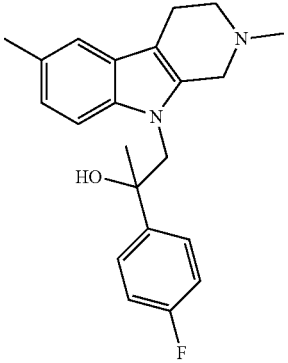 |
| 86 | 62 | 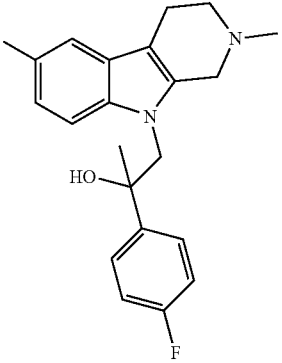 |

TABLE 2-continued
Representative Compounds According to the Invention.
| Ex. # | Comp. # | Structure |
|---|---|---|
| 145 | 63 | 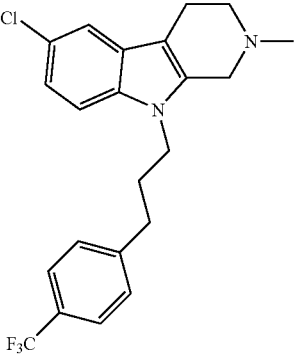 |
| 76 | 64 | 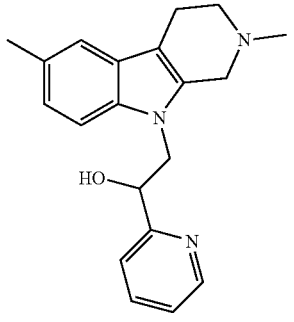 |
| 77 | 65 | 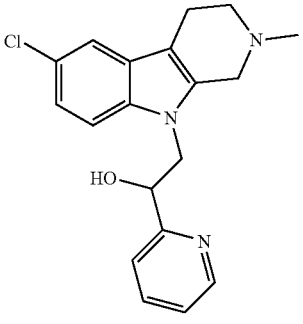 |
| 78 | 66 | 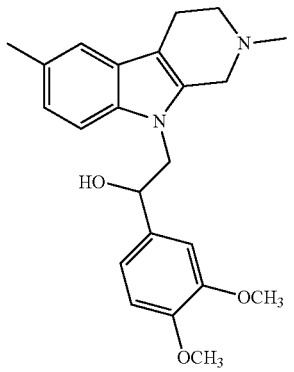 |
| 79 | 67 | 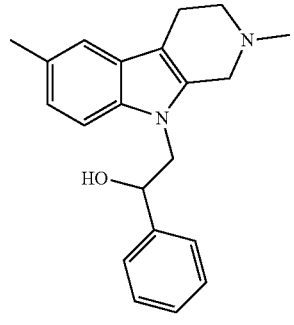 |
| 145 | 68 | 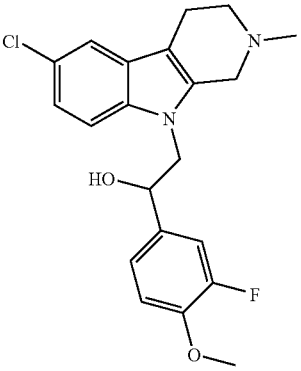 |
| 145 | 69 | 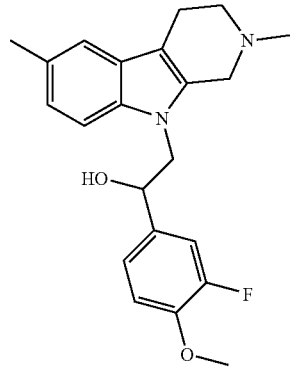 |
| 71 | 70 | 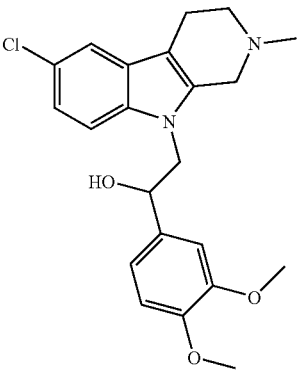 |

TABLE 2-continued

Representative Compounds According to the Invention.

| Ex. # | Comp. # | Structure |
|---|---|---|
| 70 | 71 | (6-chloro-2-methyl-tetrahydro-β-carboline N-CH2-CH(OH)-phenyl) |
| 72 | 72 | (6-methyl-2-methyl-tetrahydro-β-carboline N-CH2-CH(OH)-(3-methylphenyl)) |
| 145 | 73 | (6-chloro-2-methyl-tetrahydro-β-carboline N-CH2-CH(OH)-(4-methylphenyl)) |
| 145 | 74 | (6-methyl-2-methyl-tetrahydro-β-carboline N-CH2-C(O)-phenyl) |
| 145 | 75 | (6-methyl-2-methyl-tetrahydro-β-carboline N-CH2-C(O)-(4-fluorophenyl)) |
| 145 | 76 | (6-methyl-2-methyl-tetrahydro-β-carboline N-CH2-C(O)-(6-methylpyridin-3-yl)) |
| 90 | 77 | (6-chloro-1-ethyl-2-methyl-tetrahydro-β-carboline N-CH2-CH2-(6-methylpyridin-3-yl)) |
| 91 | 78 | (6-chloro-1-ethyl-2-methyl-tetrahydro-β-carboline N-CH2-CH2-(4-fluorophenyl)) |

TABLE 2-continued

Representative Compounds According to the Invention.

| Ex. # | Comp. # | Structure |
|---|---|---|
| 68 | 79 | 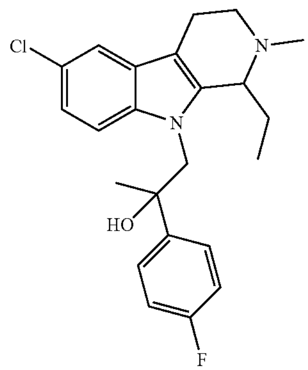 |
| 92 | 80 | 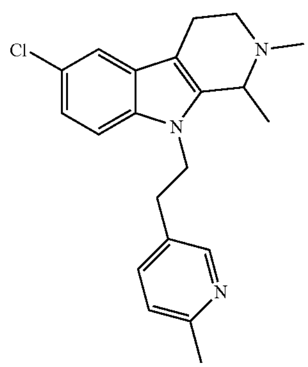 |
| 67 | 81 | 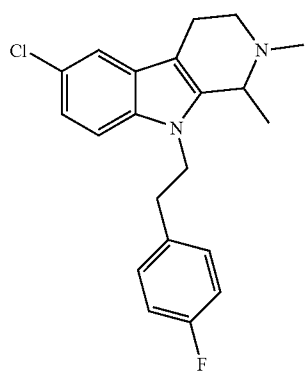 |
| 89 | 82 | 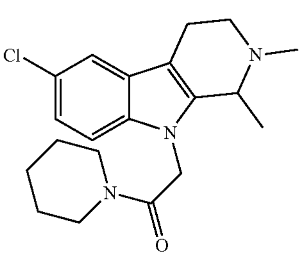 |
| 88 | 83 | 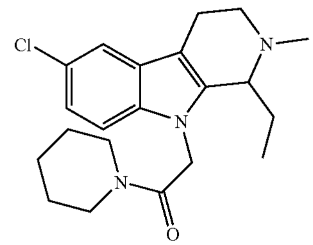 |
| 145 | 84 | |
| 145 | 85 | |
| 93 | 86 | 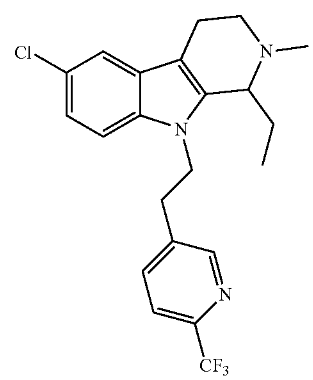 |
| 145 | 87 | |

TABLE 2-continued
Representative Compounds According to the Invention.
| Ex. # | Comp. # | Structure |
|---|---|---|
| 145 | 88 | 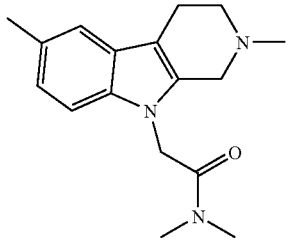 |
| 145 | 89 | 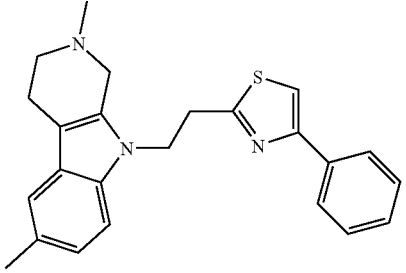 |
| 74 | 90 | 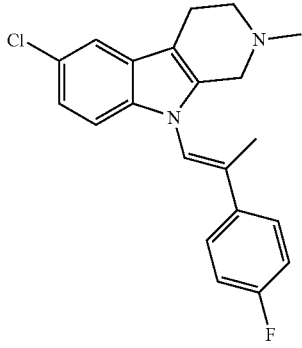 |
| 80 | 91 | 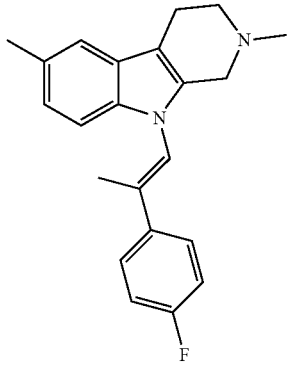 |
| 66 | 92 | 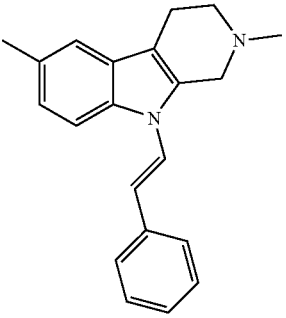 |
| 145 | 93 | 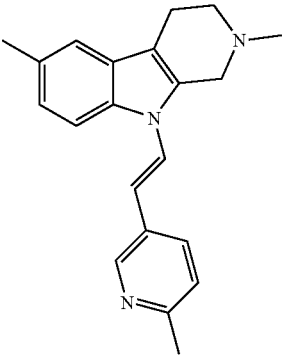 |
| 145 | 94 | 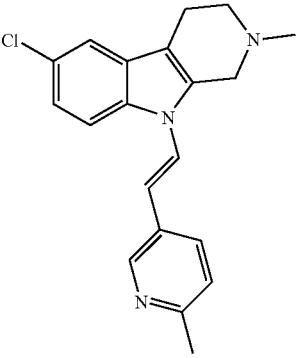 |
| 145 | 95 | 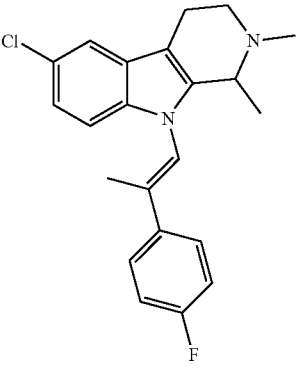 |

TABLE 2-continued

Representative Compounds According to the Invention.

| Ex. # | Comp. # | Structure |
|---|---|---|
| 145 | 96 | |
| 110 | 97 | 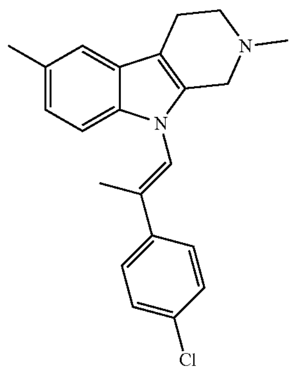 |
| 111 | 98 | 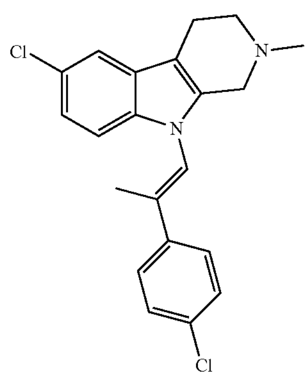 |
| 112 | 99 | 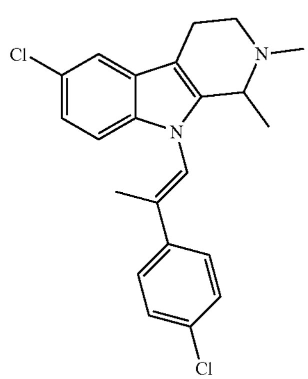 |
| 113 | 100 | |
| 145 | 101 | |
| 145 | 102 | |
| 145 | 103 | |

TABLE 2-continued

Representative Compounds According to the Invention.

| Ex. # | Comp. # | Structure |
|---|---|---|
| 145 | 104 | |
| 145 | 105 | |
| 116 | 106 | 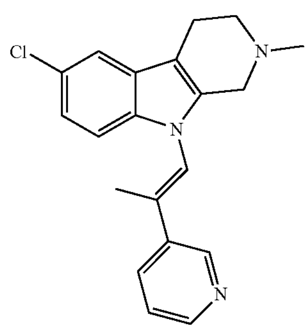 |
| 117 | 107 | 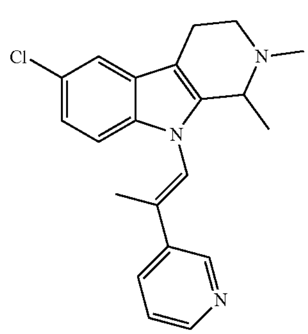 |
| 114 | 108 | 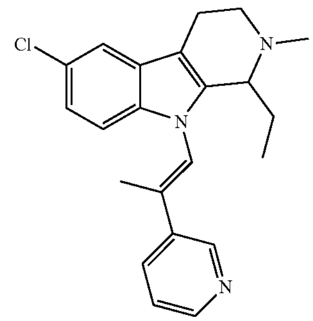 |
| 102 | 109 | 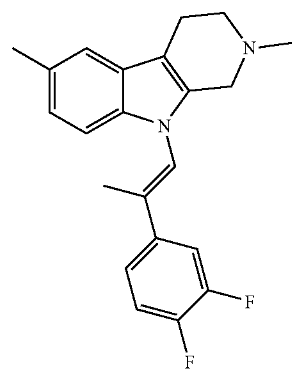 |
| 103 | 110 | 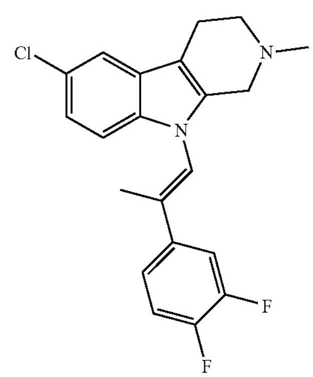 |
| 98 | 111 | 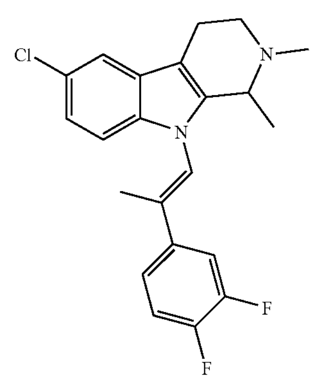 |

TABLE 2-continued

Representative Compounds According to the Invention.

| Ex. # | Comp. # | Structure |
|---|---|---|
| 97 | 112 | (6-Cl tetrahydro-β-carboline, N-methyl piperidine, N-ethyl, propenyl-3,4-difluorophenyl) |
| 115 | 113 | (6-methyl tetrahydro-β-carboline, N-methyl piperidine, propenyl-3,4-dichlorophenyl) |
| 96 | 114 | (6-Cl tetrahydro-β-carboline, N-methyl piperidine, propenyl-3,4-dichlorophenyl) |
| 105 | 115 | (6-Cl tetrahydro-β-carboline, N-methyl piperidine, N-methyl, propenyl-3,4-dichlorophenyl) |
| 104 | 116 | (6-Cl tetrahydro-β-carboline, N-methyl piperidine, N-ethyl, propenyl-3,4-dichlorophenyl) |
| 118 | 117 | (6-methyl tetrahydro-β-carboline, N-methyl piperidine, propenyl-4-methoxyphenyl) |
| 119 | 118 | (6-Cl tetrahydro-β-carboline, N-methyl piperidine, propenyl-4-methoxyphenyl) |
| 120 | 119 | (6-Cl tetrahydro-β-carboline, N-methyl piperidine, N-methyl, propenyl-4-methoxyphenyl) |

TABLE 2-continued

Representative Compounds According to the Invention.

| Ex. # | Comp. # | Structure |
|---|---|---|
| 121 | 120 | 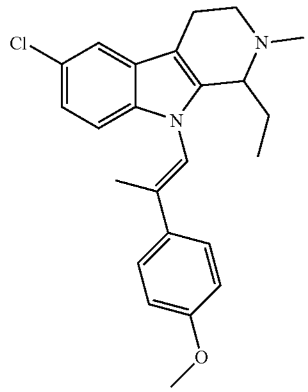 |
| 99 | 121 | 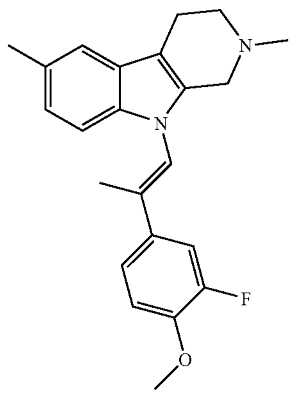 |
| 100 | 122 | 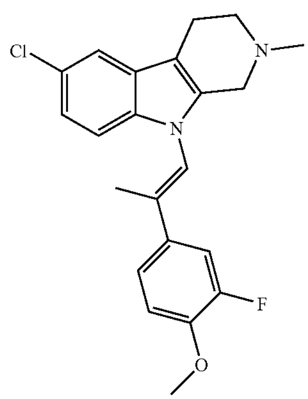 |
| 122 | 123 | 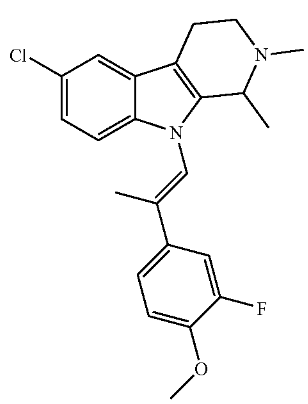 |
| 123 | 124 | |
| 65, 73 | 125 | |
| 145 | 126 | |
| 145 | 127 | |

TABLE 2-continued
Representative Compounds According to the Invention.
| Ex. # | Comp. # | Structure |
|---|---|---|
| 106 | 128 | 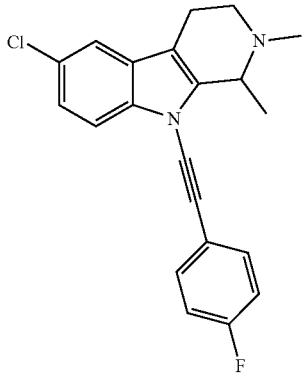 |
| 101 | 129 | 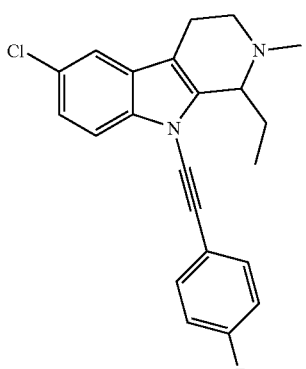 |
| 107 | 130 | 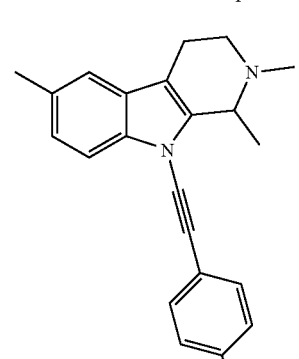 |
| 145 | 131 | 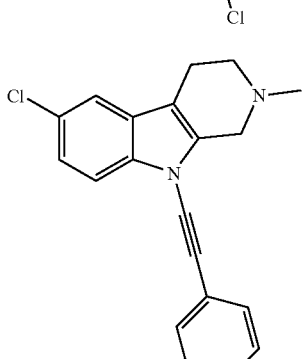 |
| 108 | 132 | 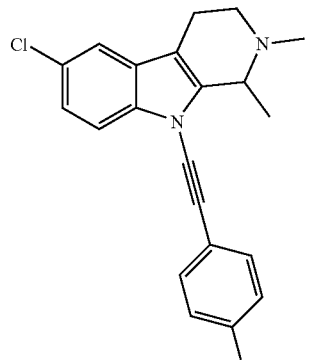 |
| 145 | 133 | 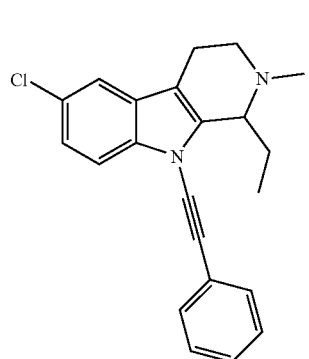 |
| 145 | 134 | 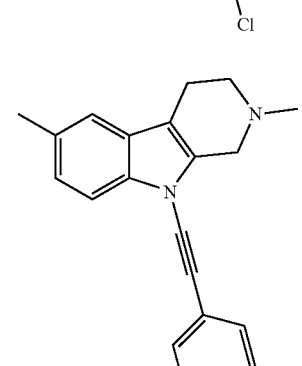 |
| 145 | 135 | 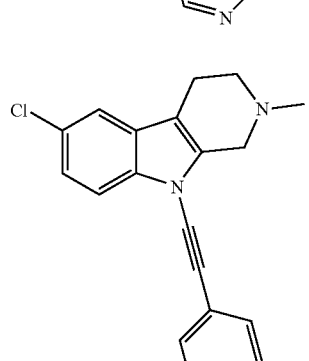 |

TABLE 2-continued

Representative Compounds According to the Invention.

| Ex. # | Comp. # | Structure |
|---|---|---|
| 145 | 136 | |
| 145 | 137 | |
| 145 | 138 | |
| 145 | 139 | |
| 145 | 140 | |
| 145 | 141 | |
| 145 | 142 | |
| 145 | 143 | |

TABLE 2-continued

Representative Compounds According to the Invention.

| Ex. # | Comp. # | Structure |
|---|---|---|
| 145 | 144 | (structure) |
| 145 | 145 | (structure) |
| 145 | 146 | (structure) |
| 145 | 147 | (structure) |
| 145 | 148 | (structure) |
| 145 | 149 | (structure) |
| 145 | 150 | (structure) |
| 145 | 151 | (structure) |

TABLE 2-continued
Representative Compounds According to the Invention.
| Ex. # | Comp. # | Structure |
|---|---|---|
| 145 | 152 | 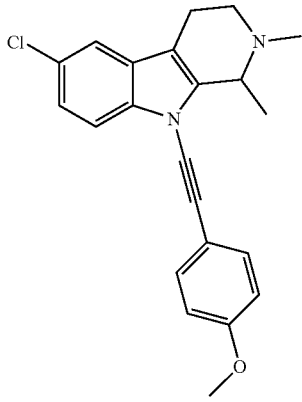 |
| 145 | 153 | 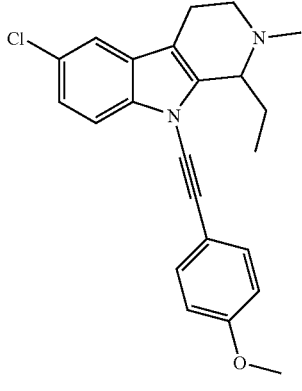 |
| 145 | 154 | 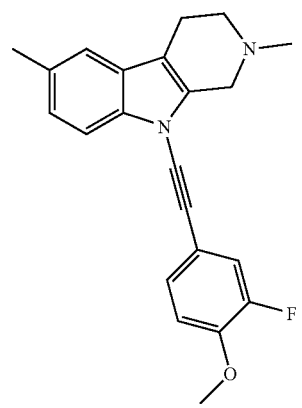 |
| 109 | 155 | 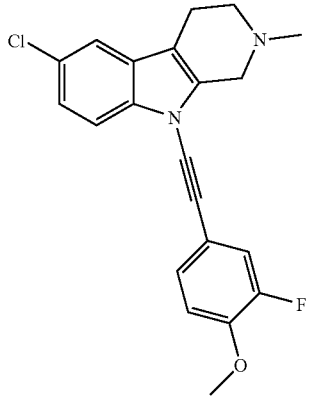 |
| 145 | 156 | 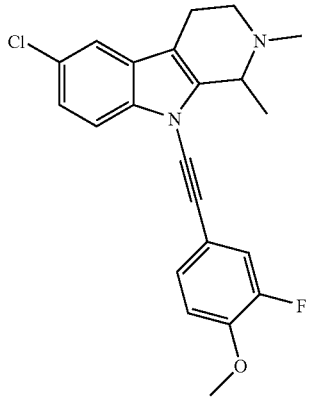 |
| 145 | 157 | 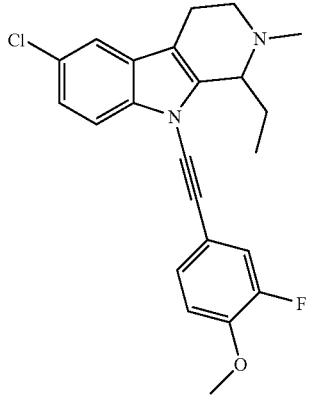 |
| 145 | 158 | 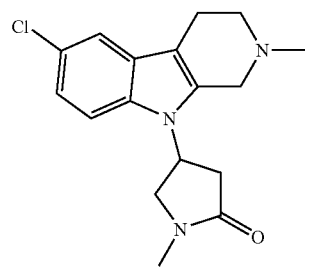 |

TABLE 2-continued

Representative Compounds According to the Invention.

| Ex. # | Comp. # | Structure |
|---|---|---|
| 124 | 159 | 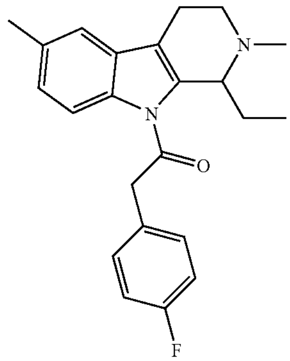 |
| 125 | 160 | 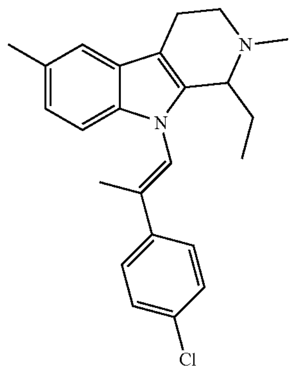 |
| 126 | 161 | 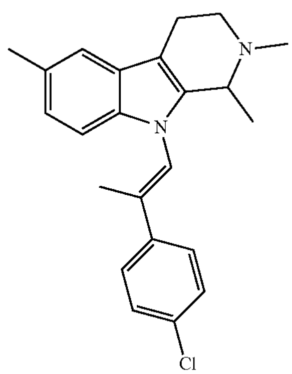 |
| 127 | 162 | 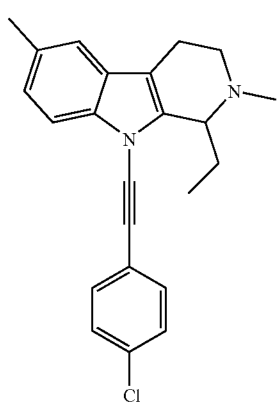 |
| 128 | 163 | |
| 129 | 164 | |
| 130 | 165 | |
| 131 | 166 | |

TABLE 2-continued

Representative Compounds According to the Invention.

| Ex. # | Comp. # | Structure |
|---|---|---|
| 132 | 167 | 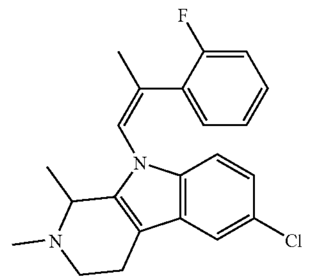 |
| 133 | 168 | 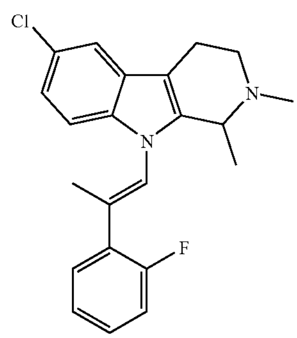 |
| 134 | 169 | 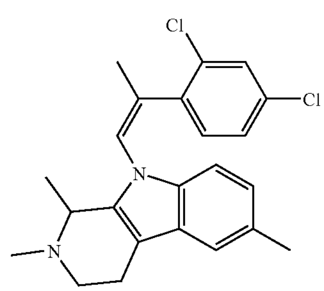 |
| 135 | 170 | 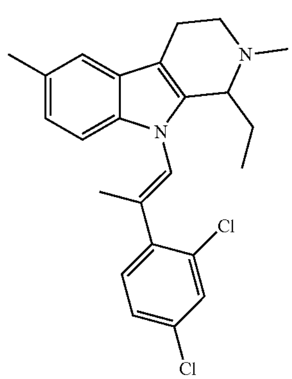 |
| 136 | 171 | 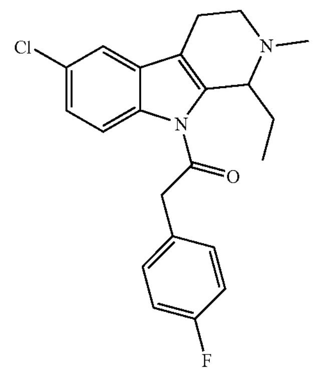 |
| 137 | 172 | 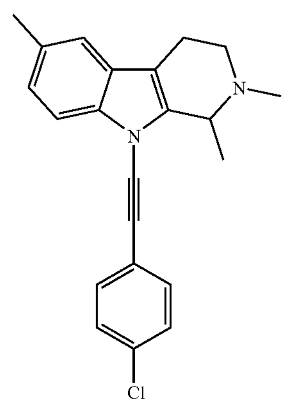 |
| 138 | 173 | 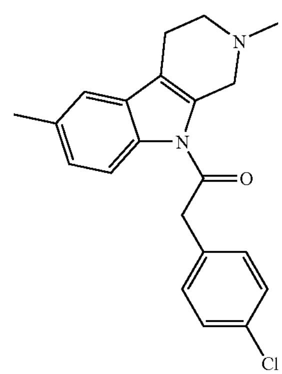 |
| 139 | 174 | 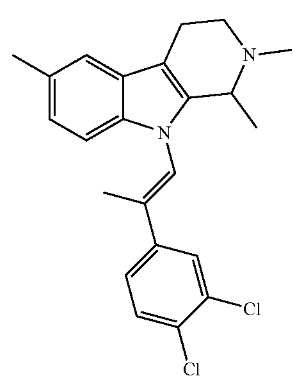 |

TABLE 2-continued

Representative Compounds According to the Invention.

| Ex. # | Comp. # | Structure |
|---|---|---|
| 140 | 175 | 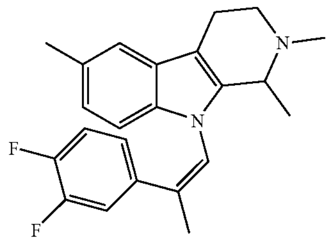 |
| 141 | 176 | 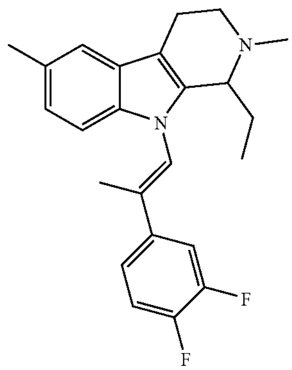 |
| 142 | 177 | 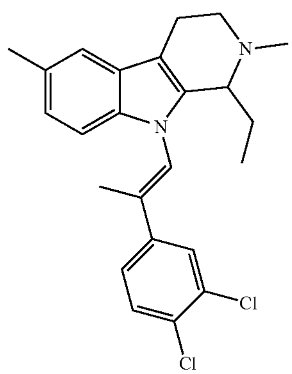 |
| 143 | 178 | 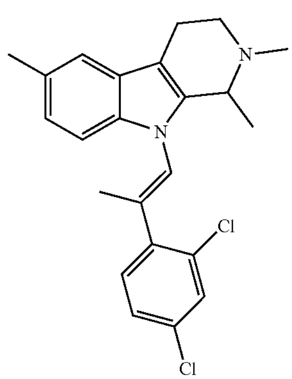 |
| 145 | 179 | |
| 145 | 180 | |
| 145 | 181 | |
| 145 | 182 | |

TABLE 2-continued

Representative Compounds According to the Invention.

| Ex. # | Comp. # | Structure |
|---|---|---|
| 145 | 183 | 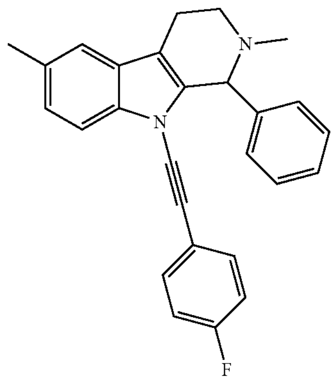 |
| 144 | 184 | 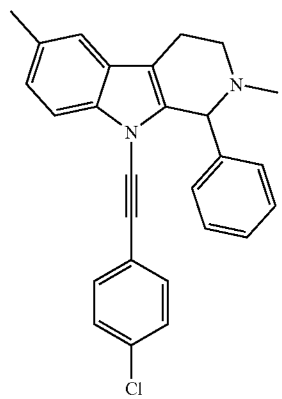 |

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. Pharmaceutical compositions according to the invention may take a form suitable for oral, buccal, parenteral, nasal, topical or rectal administration, or a form suitable for administration by inhalation.

Compounds of the invention, such as compounds of the formula 1, including compounds listed in Table 1, may be used in a method of modulating a histamine receptor.

In one variation, the compounds herein are synthetic compounds prepared for administration to an individual. In another variation, compositions are provided containing a compound in substantially pure form. In another variation, the invention embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

General Description of Biological Assays

The binding properties of compounds disclosed herein to a panel of aminergic G protein-coupled receptors including adrenergic receptors, dopamine receptors, serotonin receptors, histamine receptors and an imidazoline receptor may be determined. Binding properties may be assessed by methods known in the art, such as competitive binding assays. In one variation, compounds are assessed by the binding assays detailed herein. Compounds disclosed herein may also be tested in cell-based assays or in in vivo models for further characterization. In one aspect, compounds disclosed herein are of any formula detailed herein and further display one or more of the following characteristics: inhibition of binding of a ligand to an adrenergic receptor (e.g., $\alpha$1D, $\alpha$2A and $\alpha$2B), inhibition of binding of a ligand to a serotonin receptor (e.g., 5-HT2A, 5-HT2C, 5-HT6 and 5-HT7), inhibition of binding of a ligand to a dopamine receptor (e.g., D2L), and inhibition of binding of a ligand to a histamine receptor (e.g., H1, H2 and H3); agonist/antagonist activity to a serotonin receptor (e.g., 5-HT2A, 5-HT6); agonist/antagonist activity to a dopamine receptor (e.g., D2L, D2S); agonist/antagonist activity to a histamine receptor (e.g., H1); activity in a neurite outgrowth assay; efficacy in a preclinical model of memory dysfunction associated with cholinergic dysfunction/hypofunction; and efficacy in a preclinical model of schizophrenia.

In one variation, inhibition of binding of a ligand to a receptor is measured in the assays described herein. In another variation, inhibition of binding of a ligand is measured in an assay known in the art. In one variation, binding of a ligand to a receptor is inhibited by at least about 80% as determined in a suitable assay known in the art such as the assays described herein. In one variation, binding of a ligand to a receptor is inhibited by greater than about any one of 80%, 85%, 90%, 95%, 100%, or between about 85-95% or between about 90-100% as determined in a suitable assay known in the art such as the assays described herein. In one variation, binding of a ligand to a receptor is inhibited by at least about 80%±20% as determined in an assay known in the art.

In one variation, a compound of the invention inhibits binding of a ligand to at least one receptor and as many as eleven as detailed herein (e.g. $\alpha$1D, $\alpha$2A, $\alpha$2B, 5-HT2A, 5-HT2C, 5-HT6, 5-HT7, D2L, H1, H2, H3). In one variation, a compound of the invention inhibits binding of a ligand to at least one and as many as eleven receptors detailed herein and further displays agonist or antagonist activity to one or more receptors detailed herein (e.g., serotonin receptor 5-HT2A, serotonin receptor 5-HT6, dopamine receptor D2L, and dopamine receptor D2S, histamine receptor H1) as measured in the assays described herein. In one variation, agonist response of serotonin receptor 5-HT2A is inhibited by compounds of the invention by at least about any one of 50%, 50%, 70%, 80%, 90%, 100%, 110%, 120%, 130%, 140%, 150% as determined in a suitable assay such as the assay described herein.

In one variation, a compound of the invention displays the above described neurotransmitter receptor binding profile i.e. inhibits binding of a ligand to at least one receptor and as many as eleven as detailed herein and further stimulates neurite outgrowth, e.g. as measured by the assays described herein. Certain compounds of the invention showed activity in neurite outgrowth assays using primary neurons in culture (see Example 11B). Data is presented indicating that a compound of the invention has activity comparable in magnitude to that of naturally occurring prototypical neurotrophic proteins such as brain derived neurotrophic factor (BDNF) and nerve growth factor (NGF). Notably, neurite outgrowth plays a critical part of new synaptogenesis, which is beneficial for the treatment of neuronal disorders. In one variation, neurite outgrowth is observed with a potency of about 1 µM as measured in a suitable assay known in the art such as the assays described herein. In another variation, neurite outgrowth is observed with a potency of about 500 nM. In a further variation, neurite outgrowth is observed with a potency of about 50 nM. In another variation, neurite outgrowth is observed with a potency of about 5 nM.

In another variation, a compound of the invention inhibits binding of a ligand to at least one receptor and as many as eleven as detailed herein, further displays agonist or antagonist activity to one or more receptors detailed herein and further stimulates neurite outgrowth.

In a further variation, a compound of the invention inhibits binding of a ligand to at least one and as many as eleven receptors as detailed herein and/or display the above described neurotransmitter receptor binding profile and further shows efficacy in a preclinical model of memory dysfunction associated with cholinergic dysfunction/hypofunction, i.e. shows pro-cognitive effects in a preclinical model of memory dysfunction. As H1 antagonism may contribute to sedation, weight gain and reduced cognition, low affinity (less than about 80% inhibition of binding of Pyrilamine at 1 µM in the assay described herein) for this receptor may be associated with pro-cognitive effects and a more desirable side effect profile. Furthermore, compounds of the invention with increased potency as a 5-HT6 antagonist may have cognition-enhancing effects as serotonin acting through this receptor may impair memory.

In another variation, a compound of the invention inhibits at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction and further displays agonist or antagonist activity to one or more receptors detailed herein.

In a further variation, a compound of the invention inhibits binding of a ligand to at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction and further stimulates neurite outgrowth.

In another variation, a compound of the invention inhibits at least one and as many as eleven receptors as detailed herein, further shows efficacy in a preclinical model of memory dysfunction associated with cholinergic dysfunction/hypofunction i.e. shows pro-cognitive effects in a preclinical model of memory dysfunction, further displays agonist or antagonist activity to one or more receptor detailed herein and further stimulates neurite outgrowth.

In a further variation, a compound of the invention inhibits binding of a ligand to at least one and as many as eleven receptors and further possesses anti-psychotic effects as measured in a preclinical model of schizophrenia, i.e., shows efficacy in a preclinical model of schizophrenia.

In another variation, a compound of the invention inhibits binding of a ligand to at least one and as many as eleven receptors, further shows efficacy in a preclinical model of schizophrenia and further displays agonist or antagonist activity to one or more receptors detailed herein.

In a further variation, a compound of the invention inhibits binding of a ligand to at least one and as many as eleven receptors, further shows efficacy in a preclinical model of schizophrenia and further stimulates neurite outgrowth.

In a further variation, a compound of the invention inhibits binding of a ligand to at least one and as many as eleven receptors, further shows efficacy in a preclinical model of memory dysfunction associated with cholinergic dysfunction/hypofunction such as enhancement of memory retention and reduction of memory impairment, and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein and further shows efficacy in a preclinical model of memory dysfunction associated with cholinergic dysfunction/hypofunction such as enhancement of memory retention and reduction of memory impairment.

In another variation, a compound of the invention inhibits binding of a ligand to at least one and as many as eleven receptors, further shows efficacy in a preclinical model of schizophrenia, further stimulates neurite outgrowth and further shows efficacy in a preclinical model of memory dysfunction associated with cholinergic dysfunction/hypofunction such as enhancement of memory retention and reduction of memory impairment.

In a further variation, a compound of the invention inhibits binding to at least one and as many as eleven receptors detailed herein, further displays agonist or antagonist activity to one or more receptors detailed herein, further stimulates neurite outgrowth and further shows efficacy in a preclinical model of schizophrenia.

In another variation, a compound of the invention inhibits binding of a ligand to at least one and as many as eleven receptors, further shows efficacy in a preclinical model of schizophrenia, further displays agonist or antagonist activity to one or more receptors detailed herein, further stimulates neurite outgrowth and further shows efficacy in a preclinical model of memory dysfunction associated with cholinergic dysfunction/hypofunction such as enhancement of memory retention and reduction of memory impairment.

In another variation, a compound of the invention stimulates neurite outgrowth. In another variation, a compound of the invention shows efficacy in a preclinical model of schizophrenia and further stimulates neurite outgrowth. In another variation, a compound of the invention stimulates neurite outgrowth and further shows efficacy in a preclinical model of memory dysfunction associated with cholinergic dysfunction/hypofunction such as enhancement of memory retention and reduction of memory impairment. In another variation, a compound of the invention shows efficacy in a preclinical model of schizophrenia, further stimulates neurite outgrowth and further shows efficacy in a preclinical model of memory dysfunction associated with cholinergic dysfunction/hypofunction such as enhancement of memory retention and reduction of memory impairment.

In one aspect, compounds of the invention inhibit binding of a ligand to adrenergic receptors α1D, α2A, α2B and inhibit binding of a ligand to serotonin receptor 5-HT6. In another variation, compounds of the invention inhibit binding of a ligand to adrenergic receptors α1D, α2A, α2B, to serotonin receptor 5-HT6 and to any one or more of the following receptors: serotonin receptor 5-HT7, 5-HT2A and 5-HT2C. In another variation, compounds of the invention inhibit binding of a ligand to adrenergic receptors α1D, α2A, α2B, to serotonin receptor 5-HT6 and to any one or more of the following receptors: serotonin receptor 5-HT7, 5-HT2A and 5-HT2C and further show weak inhibition of binding of a ligand to histamine receptor H1 and/or H2. In one variation, compounds of the invention that also display strong inhibition of binding of a ligand to the serotonin receptor 5-HT7 are particularly desired. In another variation, compounds of the invention inhibit binding of a ligand to adrenergic receptors α1D, α2A, α2B, to serotonin receptor 5-HT6 and further show weak inhibition of binding of a ligand to histamine receptor H1 and/or H2. Weak inhibition of binding of a ligand to the histamine H1 receptor is permitted as agonists of this receptor have been implicated in stimulating memory as well as weight gain. In one variation, binding to histamine receptor H1 is inhibited by less than about 80%. In another variation, binding of a ligand to histamine receptor H1 is inhibited by less than about any of 75%, 70%, 65%, 60%, 55%, or 50% as determined by a suitable assay known in the art such as the assays described herein.

In another variation, compounds of the invention inhibit binding of a ligand to dopamine receptor D2L. In another variation, compounds of the invention inhibit binding of a ligand to dopamine receptor D2L and to serotonin receptor 5-HT2A. In another variation, compounds of the invention inhibit binding of a ligand to histamine receptor H1. In certain aspects, compounds of the invention further show one or more of the following properties: strong inhibition of binding of a ligand to the serotonin 5-HT7 receptor, strong inhibition of binding of a ligand to the serotonin 5-HT2A receptor, strong inhibition of binding of a ligand to the serotonin 5-HT2C receptor, weak inhibition of binding of a ligand to the histamine H1 receptor, weak inhibition of binding of ligands to the histamine H2 receptor, and antagonist activity to serotonin receptor 5-HT2A.

In one variation, compounds of the invention show any of the receptor binding aspects detailed herein and further display agonist/antagonist activity to one or more of the following receptors: serotonin receptor 5-HT2A, serotonin receptor 5-HT6, dopamine receptor D2L, dopamine receptor D2S and histamine receptor H1. In one variation, compounds of the invention show any of the receptor binding aspects detailed herein and further stimulate neurite outgrowth. In one variation, compounds of the invention show any of the receptor binding aspects detailed herein and further show efficacy in a preclinical model of memory dysfunction associated with cholinergic dysfunction/hypofunction. In one variation, compounds of the invention show any of the receptor binding aspects detailed herein and further show efficacy in a preclinical model of schizophrenia. In one variation, compounds of the invention show any of the receptor binding aspects detailed herein and further show efficacy in any one or more of agonist/antagonist assays (e.g., to serotonin receptor 5-HT2A, 5-HT6, dopamine receptor D2L, dopamine receptor D2S and histamine receptor H1), neurite outgrowth, a preclinical model of memory dysfunction associated with cholinergic dysfunction/hypofunction and a preclinical model of schizophrenia.

In some aspects, compounds of the invention inhibit binding of a ligand to adrenergic receptors α1D, α2A, α2B, serotonin receptor 5-HT6 and dopamine receptor D2L by at least about 80% as determined in a suitable assay known in the art such as the assays described herein. In one variation binding is inhibited by at least about 80% as measured in a suitable assay such as the assays described herein. In one variation, binding of a ligand to a receptor is inhibited by greater than about any one of 80%, 85%, 90%, 95%, 100%, or between about 85% and about 95%, or between about 90% and about 100% as determined in a suitable assay known in the art such as the assays described herein.

In some aspects, compounds of the invention display the above described neurotransmitter receptor binding profile and further show antipsychotic effects. It is recognized that compounds of the invention have binding profiles similar to compounds with antipsychotic activity. In addition, compounds of the invention might possess the cognitive enhancing properties of dimebon and thus add to the beneficial pharmacology profile of these antipsychotic molecules. In one variation, compounds of the invention display the above described neurotransmitter receptor binding profile and further show pro-cognitive effects in a preclinical model of memory dysfunction such as enhancement of memory retention and reduction of memory impairment due to cholinergic hypofunction in preclinical animal models. In another variation, compounds of the invention display the above described neurotransmitter receptor binding profile and do not show pro-cognitive effects in a preclinical model of memory dysfunction, learning and memory.

In one variation, compounds of the invention demonstrate pro-cognitive effects in a preclinical model of memory dysfunction, learning and memory. In a further variation, compounds of the invention possess anti-psychotic effects in a preclinical model of schizophrenia. In a further variation, compounds of the invention demonstrate pro-cognitive effects in a preclinical model of memory dysfunction, learning and memory and further possess anti-psychotic effects in a preclinical model of schizophrenia.

Overview of the Methods

The compounds described herein may be used to treat, prevent, delay the onset and/or delay the development of cognitive disorders, psychotic disorders, neurotransmitter-mediated disorders and/or neuronal disorders in individuals, such as humans. In one aspect, the compounds described herein may be used to treat, prevent, delay the onset and/or delay the development of a cognitive disorder. In another aspect, the compounds described herein may be used to treat, prevent, delay the onset and/or delay the development of a psychotic disorder. In yet another aspect, the compounds described herein may be used to treat, prevent, delay the onset and/or delay the development of a neurotransmitter-mediated disorders disorder. In one embodiment, the neurotransmitter-mediated disorder includes spinal cord injury, diabetic neuropathy, allergic diseases (including food allergies) and diseases involving geroprotective activity such as age-associated hair loss (alopecia), age-associated weight loss and age-associated vision disturbances (cataracts). In another variation, the neurotransmitter-mediated disorder includes spinal cord injury, diabetic neuropathy, fibromyalgia and allergic diseases (including food allergies). In still another embodiment, the neurotransmitter-mediated disorder includes Alzheimer's disease, Parkinson's Disease, autism, Guillain-Barré syndrome, mild cognitive impairment, multiple sclerosis, stroke and traumatic brain injury. In yet another embodiment, the neurotransmitter-mediated disorder includes schizophrenia, anxiety, bipolar disorders, psychosis and depression. In another aspect, the compounds described herein may be used to treat, prevent, delay the onset and/or delay the development of a neuronal disorder. In one aspect, the compounds described herein may also be used to treat, prevent, delay the onset and/or delay the development of cognitive disorders, psychotic disorders, neurotransmitter-mediated disorders and/or neuronal disorders for which the modulation of an aminergic G protein-coupled receptor is believed to be or is beneficial.

The invention also provides methods of improving cognitive functions and/or reducing psychotic effects comprising administering to an individual in need thereof an amount of a compound of the invention or a pharmaceutically acceptable salt thereof effective to improve cognitive functions and/or reduce psychotic effects.

The invention also provides methods of stimulating neurite outgrowth and/or promoting neurogenesis and/or enhancing neurotrophic effects in an individual comprising administering to an individual in need thereof an amount of a compound of the invention or a pharmaceutically acceptable salt thereof effective to stimulate neurite outgrowth and/or to promote neurogenesis and/or to enhance neurotrophic effects.

The invention further encompasses methods of modulating an aminergic G protein-coupled receptor comprising administering to an individual in need thereof an amount of a compound of the invention or a pharmaceutically acceptable salt thereof effective to modulate an aminergic G protein-coupled receptor.

It is to be understood that methods described herein also encompass methods of administering compositions comprising the compounds of the invention.

Methods for Treating, Preventing, Delaying the Onset, and/or Delaying the Development Cognitive Disorders, Psychotic Disorders, Neurotransmitter-Mediated Disorders and/or Neuronal Disorders In one aspect, the invention provides methods for treating, preventing, delaying the onset, and/or delaying the development of cognitive disorders, psychotic disorders, neurotransmitter-mediated disorders and/or neuronal disorders for which the modulation of an aminergic G protein-coupled receptor is believed to be or is beneficial, the method comprising administering to an individual in need thereof a compound of the invention. In some variations, modulation of adrenergic receptor α1D, α2A, α2B, serotonin receptor 5-HT2A, 5-HT6, 5HT7, histamine receptor H1 and/or H2 is expected to be or is beneficial for the cognitive disorders, psychotic disorders, neurotransmitter-mediated disorders and/or neuronal disorders. In some variations, modulation of adrenergic receptor α1D, α2A, α2B and a serotonin receptor 5-HT6 receptor is expected to be or is beneficial for the cognitive disorders, psychotic disorders, neurotransmitter-mediated disorders and/or neuronal disorders. In some variations, modulation of adrenergic receptor α1D, α2A, α2B, and a serotonin receptor 5-HT6 receptor and modulation of one or more of the following receptors serotonin 5-HT7, 5-HT2A, 5-HT2C and histamine H1 and H2 is expected to be or is beneficial for the cognitive disorders, psychotic disorders, neurotransmitter-mediated disorders and/or neuronal disorders. In some variations, modulation of dopamine receptor D2L is expected to be or is beneficial for the cognitive disorders, psychotic disorders, neurotransmitter-mediated disorders and/or neuronal disorders. In certain variations, modulation of a dopamine D2L receptor and serotonin receptor 5-HT2A is expected to be or is beneficial for the cognitive disorders, psychotic disorders, neurotransmitter-mediated disorders and/or neuronal disorders. In some variations, the cognitive disorders, psychotic disorders, neurotransmitter-mediated disorders and/or neuronal disorders are treated, prevented and/or their onset or development is delayed by administering a compound of the invention.

Methods to Improve Cognitive Functions and/or Reduce Psychotic Effects

The invention provides methods for improving cognitive functions by administering a compound of the invention to an individual in need thereof. In some variations, modulation of one or more of adrenergic receptor α1D, α2A, α2B, serotonin receptor 5-HT2A, 5-HT6, 5HT7, histamine receptor H1 and/or H2 is desirable or expected to be desirable to improve cognitive functions. In some variations modulation of α1D, α2A, α2B adrenergic receptors and a serotonin 5-HT6 receptor is desirable or expected to be desirable to improve cognitive functions. In some variations, modulation of α1D, α2A, α2B adrenergic receptors and serotonin receptor 5-HT6 and modulation of one or more of the following receptors: serotonin receptor 5-HT7, 5-HT2A, 5-HT2C and histamine receptor H1 and H2, is desirable or expected to be desirable to improve cognitive functions. In another aspect, the invention encompasses methods to reduce psychotic effects by administering a compound of the invention to an individual in need thereof. In some embodiments, modulation of a dopamine D2L receptor is expected to be or is desirable to reduce psychotic effects. In some embodiments, modulation of a dopamine D2L receptor and a serotonin 5-HT2A receptor is expected to be or is desirable to reduce psychotic effects. In some variations, a compound of the invention is administered to an individual in need thereof.

Methods to Stimulate Neurite Outgrowth, Promote Neurogenesis and/or Enhance Neurotrophic Effects In a further aspect, the invention provides methods of stimulating neurite outgrowth and/or enhancing neurogenesis and/or enhancing neurotrophic effects comprising administering a compound of the invention or pharmaceutically acceptable salt thereof under conditions sufficient to stimulate neurite outgrowth and/or to enhance neurogenesis and/or enhance neurotrophic effects to an individual in need thereof. In some variations, a compound of the invention stimulates neurite outgrowth at a potency of about 1 µM as measured in a suitable assay such as the assays described herein. In some variations, a compound of the invention stimulates neurite outgrowth at a potency of about 500 nM as measured in a suitable assay such as the assays described herein. In some variations, a compound of the invention stimulates neurite outgrowth at a potency of about 50 nM as measured in a suitable assay such as the assays described herein. In some variations, a compound of the invention stimulates neurite outgrowth at a potency of about 5 nM as measured in a suitable assay such as the assays described herein.

Methods to Modulate an Aminergic G Protein-Coupled Receptor

The invention further contemplates methods for modulating the activity of an aminergic G-protein-coupled receptor comprising administering a compound of the invention or pharmaceutically acceptable salt thereof under conditions sufficient to modulate the activity of an aminergic G protein-coupled receptor. In some variations, the aminergic G protein-coupled receptor is a α1D, α2A, α2B adrenergic receptor and a serotonin 5-HT6 receptor. In some variations, the aminergic G protein-coupled receptor is a α1D, α2A, α2B adrenergic receptor and a serotonin 5-HT6 and 5-HT7 receptor. In some variations, the aminergic G protein-coupled receptor is a α1D, α2A, α2B adrenergic receptor, a serotonin 5-HT6 and one or more of the following receptors: serotonin 5-HT-7,5-HT2A and 5-HT2C and histamine H1 and H2 receptor. In some variations, the aminergic G protein-coupled receptor is a dopamine D2L receptor. In some variations, the aminergic G protein-coupled receptor is a dopamine D2L receptor and a serotonin 5-HT2A receptor. In some variations, the aminergic G protein-coupled receptor is a histamine H1 receptor.

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to formula (I) or a variation thereof unless otherwise indicated.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

The following abbreviations are used herein: thin layer chromatography (TLC); Hour (h); Ethanol (EtOH); dimethylsulfoxide (DMSO); N,N-dimethylformamide (DMF); trifluoroacetic acid (TFA); tetrahydrofuran (THF); Normal (N); aqueous (aq.); methanol (MeOH); dichloromethane (DCM); Retention factor (Rf).

General methods of preparing compounds according to the invention are depicted in exemplified methods below. Other compounds of the invention may be prepared by similar methods. For example, Scheme Ib is an exemplified synthesis of the method detailed in Scheme Ia but other compounds of the invention may be prepared by similar methods.

A method of synthesizing an intermediate used in the synthesis of compounds of the invention is shown as General Methods 1-15.

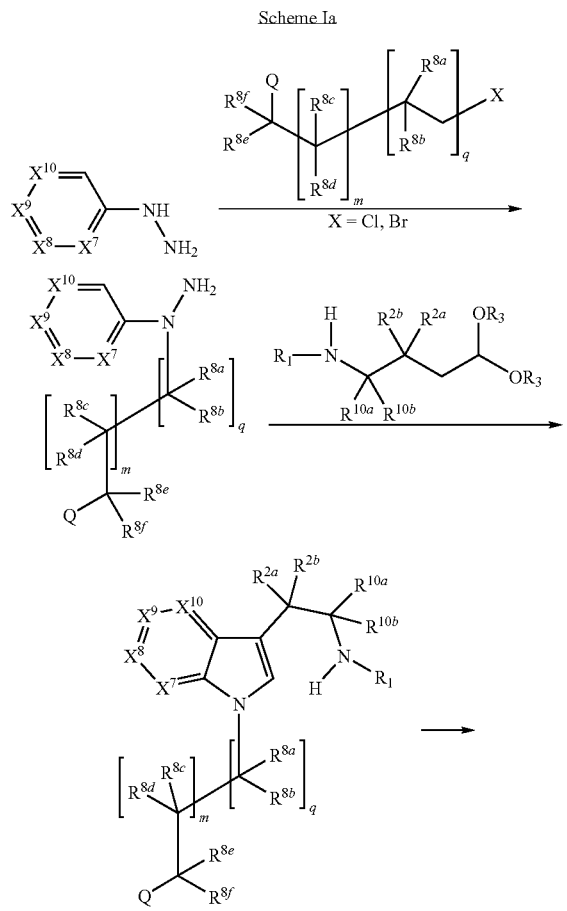

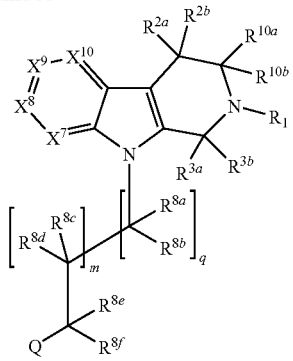

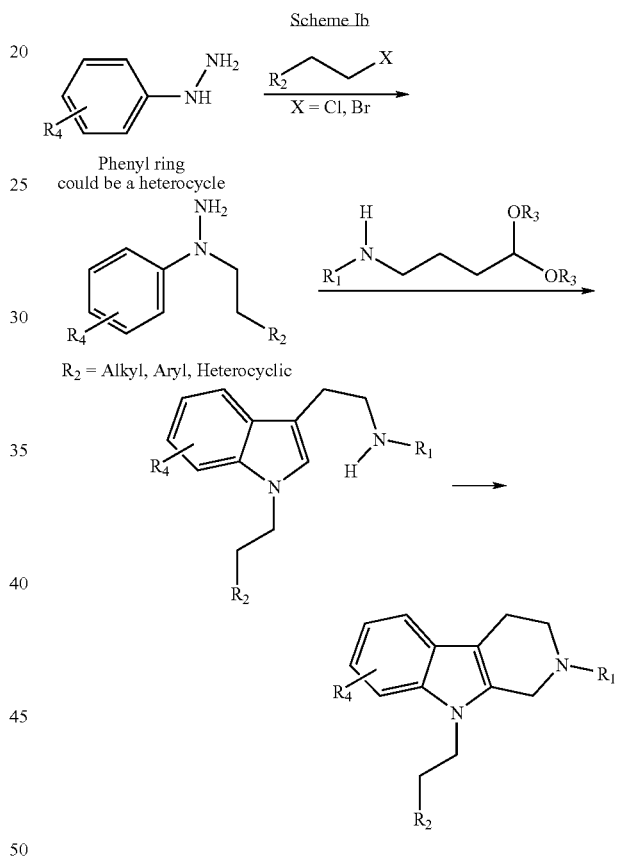

General Method 1

Arylhydrazine hydrochloride (1 equiv) is mixed with triethylamine (3 equiv) and alkyl halide (1 equiv) at 25° C. The reaction mixture is stirred at RT for 1 h and subsequently heated at 90° C. until completion of the reaction as determined by TLC and LC-MS (approx for 16 h). Reaction mixture is concentrated under reduced pressure, diluted with water and extracted with ethyl acetate. The combined organic layer is dried (Na$_2$SO$_4$) and concentrated to obtain crude product which is purified by column chromatography (silica gel, 100-200 mesh, eluent: ethyl acetate-hexanes gradient).

General Method 2

Arylhydrazine hydrochloride (1 equiv) is added to a vigorously stirred mixture of tetra-n-butylammonium chloride (0.05 equiv) in 50% aqueous sodium hydroxide (1 mL/mmol of arylhydrazine hydrochloride) followed by alkyl halide (1.1 equiv). The mixture is heated at 60° C. (oil bath temp.) for 6 h. After cooling to room temperature, water is added and the mixture is extracted with chloroform. The total extract is dried (sodium sulfate) and evaporated in vacuo to furnish crude product that is purified by column chromatography (silica gel, 100-200 mesh, eluent: eluent: ethyl acetate-hexanes gradient or dichloromethane).

General Method 3

The hydrazine derivative (1 equiv) is converted into the corresponding HCl salt and dissolved in water. The appropriate acetal (1 equiv) is added and the mixture is heated at 0-90° C. for 3-6 h. The reaction mixture is cooled to RT, and saturated aqueous $NaHCO_3$ is added. The product is extracted with ethyl acetate. Concentration of the combined organic layers under vacuum yields crude product that is purified by chromatography on silica gel to obtain the product.

General Method 4

A solution of appropriate tryptamine derivative (1 equiv), formaldehyde (1 equiv) in acetonitrile containing 5% TFA (8-10 mL/mmol) is stirred at reflux for 15 min-2 h. The reaction mixture is cooled to 25° C., concentrated under reduced pressure and partitioned between ethyl acetate and satd. aqueous $NaHCO_3$. The organic layer is dried over sodium sulfate, evaporated under reduced pressure and the residue is purified by silica gel chromatography to obtain the product.

General Method 5

A mixture of appropriate carboline derivative with side chain carboxylate ester (1 equiv) and NaOH (3N, 5 folds w/v) in ethanol (5 folds w/v) is stirred at 50° C. for 3 h after which it is cooled to RT and neutralized with conc. HCl. The solvent is removed under reduced pressure to obtain corresponding crude carboxylic acid. The resulting crude product is purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 6

A mixture of appropriate carboline derivative with side chain carboxylic acid (1 equiv) is stirred with appropriate alcohol (1 equiv), EDCI-HCl (1 equiv) and triethylamine (1 equiv) in dichloromethane for 12-16 h. The reaction mixture is evaporated under vacuo to obtain the crude ester that is purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 7

A mixture of appropriate carboline derivative with side chain carboxylic acid (1 equiv) is stirred with appropriate amine (1 equiv), EDCI-HCl (1 equiv) and triethylamine (1 equiv) in dichloromethane for 12-16 h. The reaction mixture is evaporated in vacuo to obtain the crude amide that is purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 8

Carboline derivative (1 equiv), epoxide derivative (4-7.5 equiv) and NaH (3 equiv) are heated in DMF (3 mL/mmol) at 120° C. for 16 h. The contents are quenched by methanol and evaporated to dryness. The resulting crude product is purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 9

Appropriate carboline (1 equiv) is dissolved in NMP (0.6 mL/mmol). Powdered KOH (3.5 equiv) is added to this solution, and the reaction mixture is stirred for 10 min at 25° C. Appropriate vinylpyridine derivative (1.1 equiv) is added and the reaction mixture is heated in sealed tube at 45° C. for 30 min. The reaction is monitored by LCMS. After this period, the reaction mixture is cooled to 25° C. and diluted with satd. aqueous NaCl (5 mL). The product is extracted with ethyl acetate. The combined organic layer is dried over anhydrous sodium sulfate and evaporated under reduced pressure. The resulting crude product is purified by silica gel chromatography (100-200 mesh or 230-400 mesh) using methanol-dichloromethane gradient, by neutral alumina using ethyl acetate-hexane gradient, and/or by reverse-phase chromatography (C-18, 500 mm×50 mm, Mobile Phase A=0.05% TFA in water, B=0.05% TFA in acetonitrile, Gradient: 10% B to 80% B in 30 min, injection vol. 5 mL).

General Method 10

A solution of 4% aqueous sulfuric acid (5 mL) is heated to 50° C. over 30-60 min. Nitrogen is bubbled through the solution as it is heated to displace dissolved air. The hydrazine derivative (1 mmol) is added to the heated mixture, and the solid is allowed to dissolve. The appropriate acetal (1.2 mmol) is then added as a stream over 30 min, and this mixture is heated at reflux for 2 h. The reaction mixture is cooled to rt, and 30% aqueous ammonium hydroxide (0.5 mL) is added drop wise maintaining the temperature at 25-30° C. The product is extracted with ethyl acetate. Concentration of the combined organic layers under vacuum yield a crude product that is purified by chromatography on silica gel using ethyl acetate: ethanol: $NH_4OH$ 7:3:1.

General Method 11

A mixture of appropriate tryptamine derivative (1.0 mmol), formaldehyde (1.0 mmol) and TFA (0.15 mL) in acetonitrile (3 mL) is stirred at 25° C. for 20 h. The solution is quenched with saturated aqueous $NaHCO_3$ solution. The organic layer is separated, washed with brine and dried with $MgSO_4$. The solvent is removed under reduced pressure. Flash chromatography (10% $CH_3OH/CH_2Cl_2$) allowed isolation of product as thick oil.

Scheme II

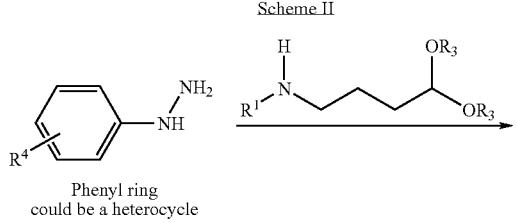

Phenyl ring could be a heterocycle

-continued

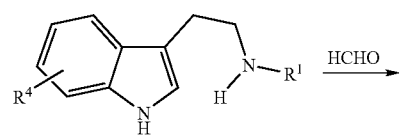

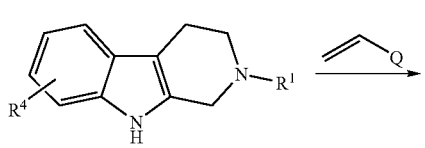

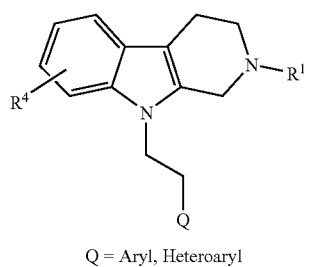

Q = Aryl, Heteroaryl

Scheme II(a)

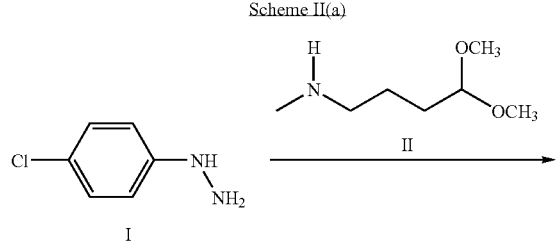

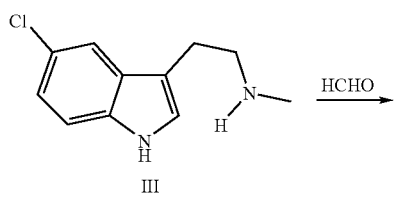

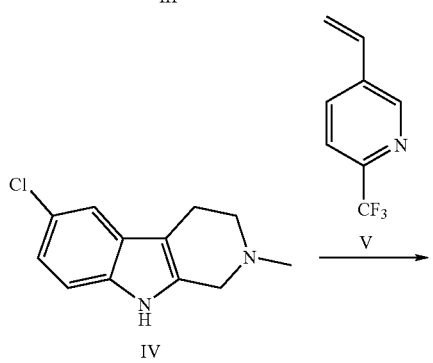

-continued

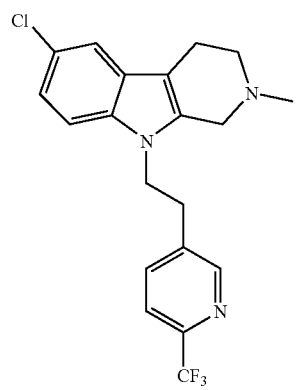

Compound 6

General Method 12

General method for the preparation of compounds using Scheme II, as exemplified for the synthesis of Compound 6 (Scheme II(a), Example 24): A suitably substituted phenyl hydrazine is reacted with a 4 carbon protected amino acetal or aldehyde (U.S. Pat. No. 2,642,438) to generate a substituted 3-(2-aminoethyl)indole. This 3-(2-aminoethyl)indole can then be reacted with formaldehyde, under standard Pictet Spingler reaction conditions (Org. Lett. 2003, 5 (1), 43-46) to give an N-unsubstituted β-carboline. This β-carboline can then be reacted with aryl and/or heteroaryl groups bearing a vinyl substituent to install the side chain denoted by Q in synthetic scheme II.

Scheme III

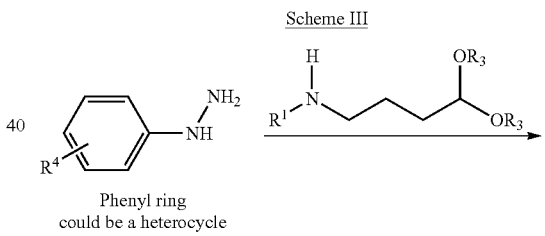

Phenyl ring could be a heterocycle

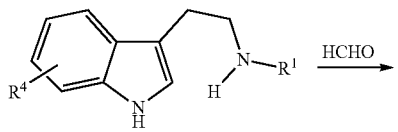

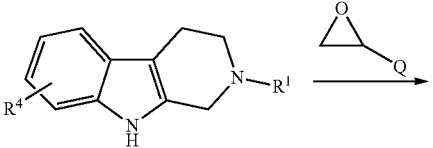

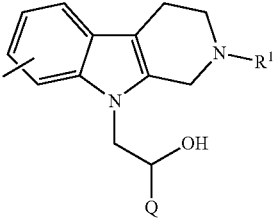

Q = Aryl, Heteroaryl

205

Scheme III(a)

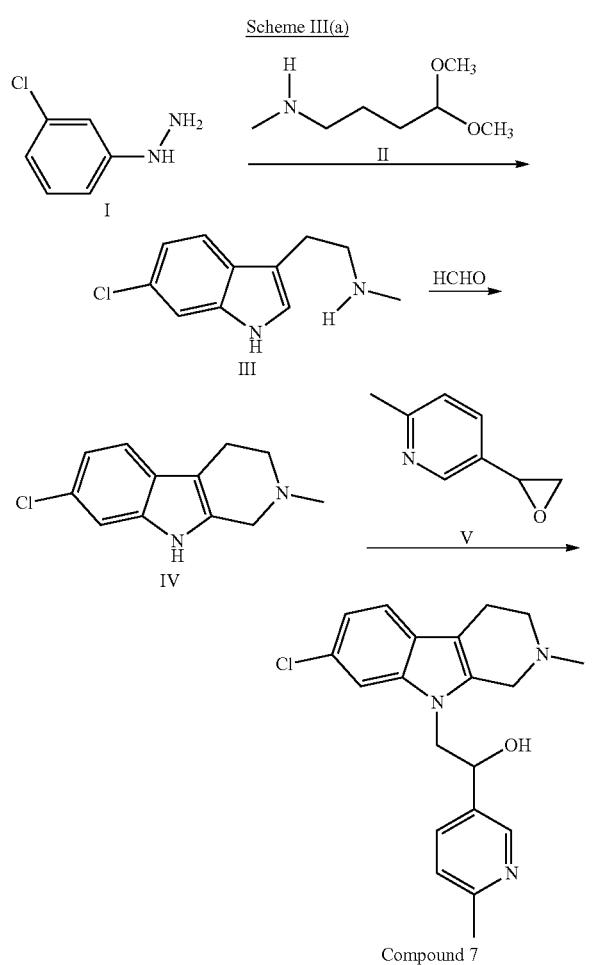

Compound 7

General Method 13

General method for the preparation of compounds using Scheme III as exemplified for the synthesis of Compound 7 (Scheme III(a), Example 25): A suitably substituted phenyl hydrazine is reacted with a 4 carbon protected amino acetal or aldehyde (U.S. Pat. No. 2,642,438) to generate a substituted 3-(2-aminoethyl)indole. This 3-(2-aminoethyl)indole can then be reacted with formaldehyde, under standard Pictet Spingler reaction conditions (U.S. Pat. No. 2,642,438) to give an N-unsubstituted β-carboline. This β-carboline can then be reacted with aryl and/or heteroaryl styrene oxides (carboline, aryl/heteroaryl oxide, NaH, DMF, 120° C.) to install the side chain denoted by Q in synthetic scheme III.

Scheme IV

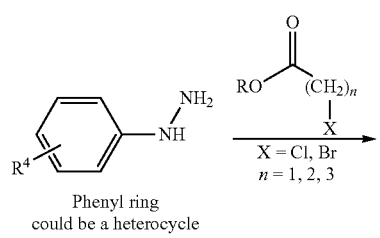

Phenyl ring could be a heterocycle

206

-continued

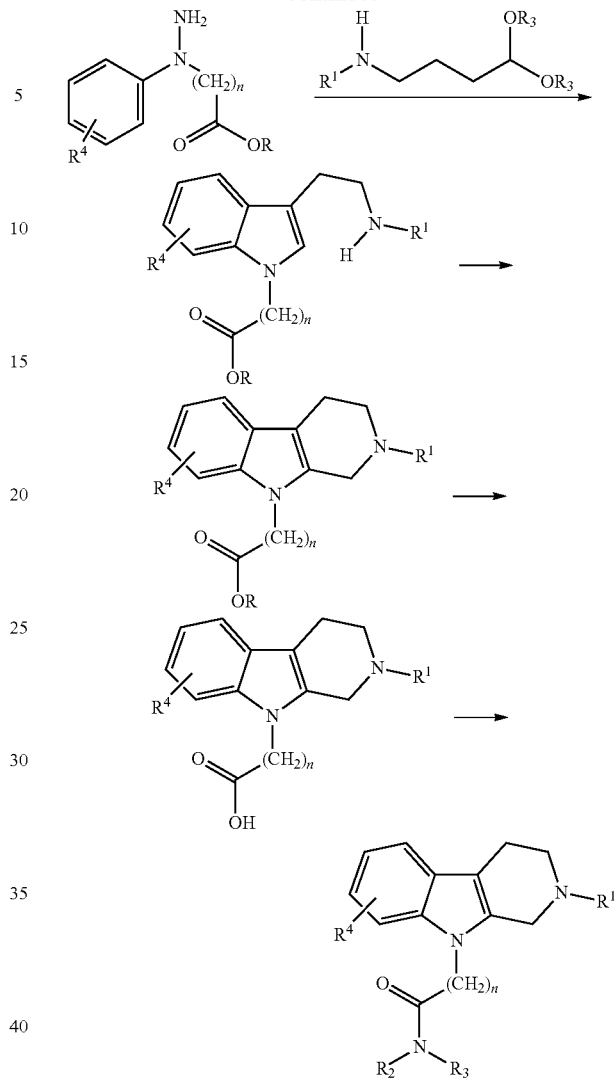

$R_2$ = H, Alkyl, Aryl, Heterocyclic
$R_3$ = H, Alkyl, Aryl, Heterocyclic

Scheme IV(a)

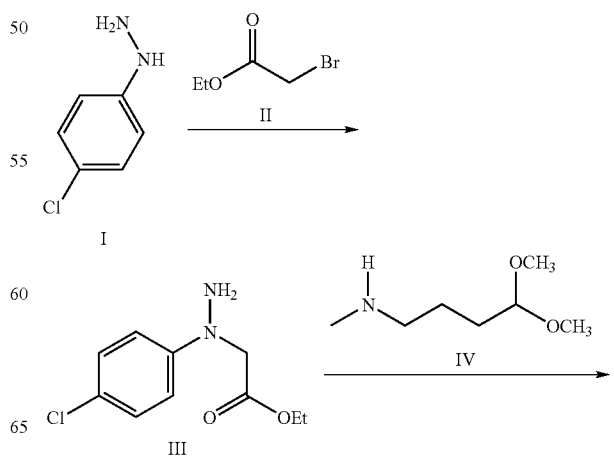

-continued

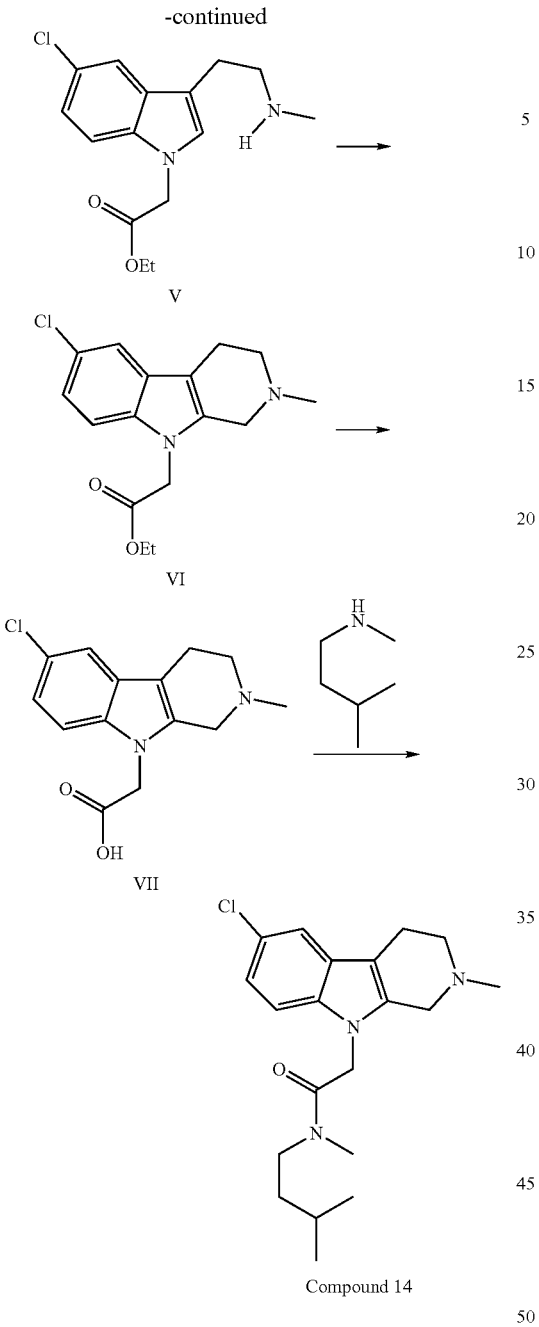

V

VI

VII

Compound 14

General Method 14

General method for the preparation of compounds using Scheme IV as exemplified for the synthesis of Compound 14 (Scheme IV(a), Example 32): A suitably substituted phenyl hydrazine is reacted with an alkyl halide bearing an ester functionality, followed by a reaction with a 4 carbon protected amino acetal or aldehyde (U.S. Pat. No. 2,642,438) to generate a substituted 3-(2-aminoethyl)indole. This 3-(2-aminoethyl)indole can then be reacted with formaldehyde, under standard Pictet Spingler reaction conditions (U.S. Pat. No. 2,642,438) to give an N-substituted β-carboline. This β-carboline is then treated with base to affect the hydrolysis of the ester functionality leading to the generation of a free acid. This acid can then be reacted with an alkyl, aryl and/or heteroaryl primary or secondary amine (carboline derivative with side chain carboxylic acid, appropriate primary or secondary amine, EDCI and triethylamine in dichloromethane for 12-16 h) to install the side chain denoted by $R_2$ and $R_3$ in Scheme IV.

Scheme V

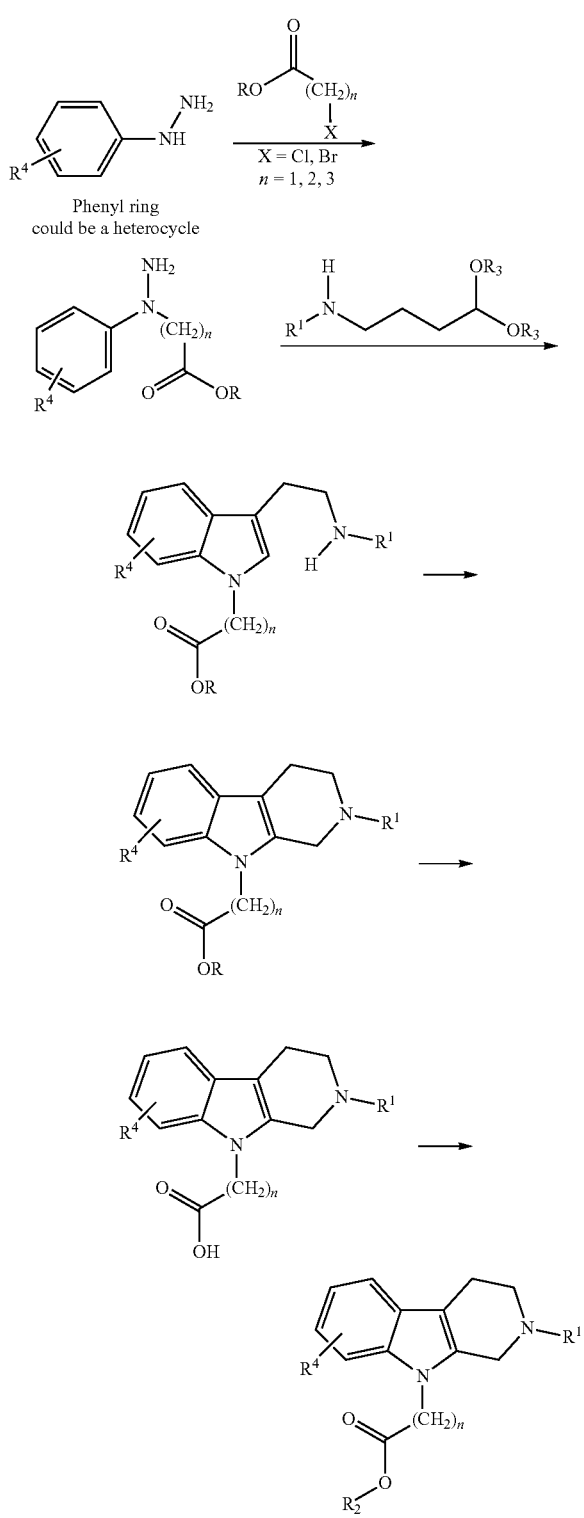

$R_2$ = H, Alkyl, Aryl, Heterocyclic

Scheme V(a)

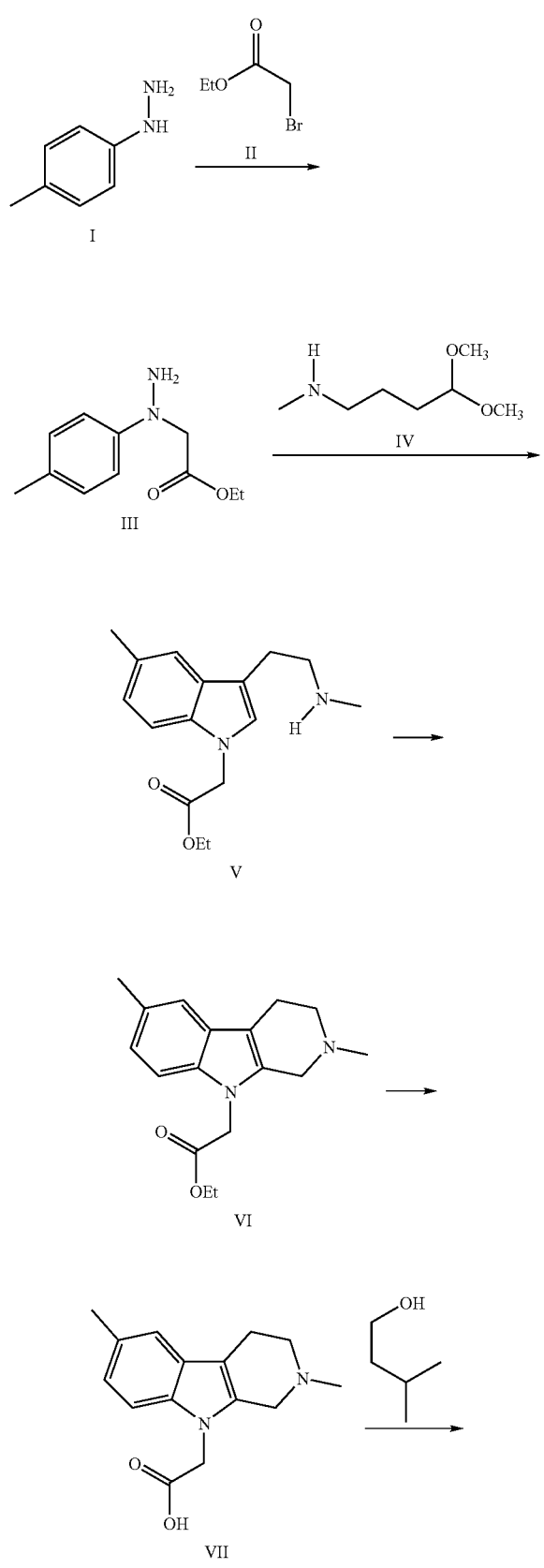

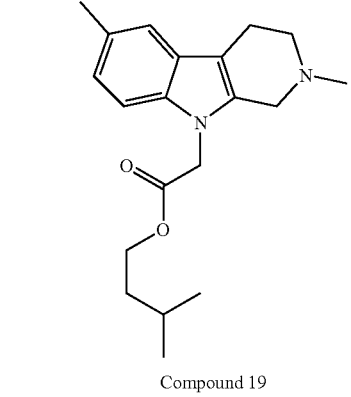

Compound 19

General Method 15

General method for the preparation of compounds using Scheme V as exemplified for the synthesis of Compound 19 (Scheme V(a), Example 37): A suitably substituted phenyl hydrazine is reacted with an alkyl halide bearing an ester functionality, followed by a reaction with a 4 carbon protected amino acetal or aldehyde (U.S. Pat. No. 2,642,438) to generate a substituted 3-(2-aminoethyl)indole. This 3-(2-aminoethyl)indole can then be reacted with formaldehyde, under standard Pictet Spingler reaction conditions (U.S. Pat. No. 2,642,438) to give an N-substituted β-carboline. This β-carboline is then treated with base to affect the hydrolysis of the ester functionality leading to the generation of a free acid. This acid can then be reacted with an alkyl, aryl and/or heteroaryl primary alcohol (carboline derivative with side chain carboxylic acid, appropriate alcohol, EDCI and triethylamine in dichloromethane for 12-16 h) to install the side chain denoted by $R_2$ in Scheme V.

General Method 16

Appropriate carboline (1 equiv, 84 mg, 0.34 mmol) is dissolved in DMF (15 mL/mmol). To this solution is added CuI (10 mol %, 6 mg, 0.034 mmol), L-proline (20 mol %, 8 mg, 0.068 mmol), $K_3PO_4$ (2 equiv). The reaction mixture is stirred for 10 min at room temperature followed by addition of 4-(1-bromoprop-1-en-2-yl)-2-fluoro-1-methoxybenzene (1.2 equiv). The reaction mixture is heated at 80° C. for 18 h. Solvent is evaporated under reduced pressure, the residue is diluted with brine and extracted with ethyl acetate. Organic layer is dried over $Na_2SO_4$, and concentrated under reduced pressure. The crude product is purified by silica gel chromatography.

General Method 17

Appropriate beta-carboline (1 equiv.) is mixed with $CuSO_4 \cdot 5H_2O$ (20 mol %), 1,10-phenanthroline (0.4 equiv), $K_3PO_4$ (2 equiv) and appropriate vinyl bromide (1.1 equiv) in toluene (5 ml). The reaction mixture is purged with nitrogen and heated at 80° C. for 16 h. The reaction mixture is filtered through Celite and Celite bed is rinsed with dichloromethane. Combined organic layer is concentrated under reduced pressure and the residue is purified by silica gel chromatography (100-200 mesh) eluting with 60-80% ethyl acetate in hexane to obtain the product.

General Methods for HPLC Analysis

Column: Phenomenex Gemini C18, 50 mm×4.6 mm.
Mobile Phase A: Acetonitrile, B: 10 mM Ammonium Acetate in Water.
Column Temp: 40° C.
Flow Rate: 1 ml/min.

Gradient: 20% A, 0.3 min hold, 20% A to 90% A 0.3-4.0 min, 90% A hold 1 min, 5.03-7.00 min 20% A.

The methods detailed above may be adapted as known by those of skill in the art. Particular examples of each General Method are provided in the Examples below.

The following Examples are provided to illustrate but not limit the invention.

All references disclosed herein are incorporated by reference in their entireties.

EXAMPLES

Example 1

Preparation of 1-(4-chlorophenyl)-1-(2-(2-methylpyrimidin-5-yl)ethyl)hydrazine

The preparation of title compound is carried out by General Method 2 using 4-chlorophenyl hydrazine hydrochloride and 5-(2-bromoethyl)-2-methylpyrimidine.

Example 2

Preparation of 1-(2-(6-(trifluoromethyl)pyridin-3-yl)ethyl)-1-p-tolylhydrazine

The preparation of title compound is carried out by General Method 2 using 4-chlorophenyl hydrazine hydrochloride and 5-(2-bromoethyl)-2-(trifluoromethyl)pyridine.

Example 3

Preparation of 1-(4-chlorophenyl)-1-(2-(piperidin-1-yl)ethyl)hydrazine

The preparation of title compound is carried out by General Method 2 using 4-chlorophenyl hydrazine hydrochloride and 1-(2-chloroethyl)piperidine hydrochloride.

Example 4

Preparation of 1-(4-chlorophenyl)-1-(2-cyclopentylethyl)hydrazine

The preparation of title compound is carried out by General Method 2 using 4-chlorophenyl hydrazine hydrochloride and (2-bromoethyl)cyclopentane.

Example 5

Preparation of 1-(4-chlorophenyl)-1-(2-(3,3-dimethylcyclopentyl)ethyl)hydrazine

The preparation of title compound is carried out by General Method 2 using 4-chlorophenyl hydrazine hydrochloride and 3-(2-chloroethyl)-1,1-dimethylcyclopentane.

Example 6

Preparation of 2-(1-(4-chlorophenyl)hydrazinyl)-1-(4-methylpiperidin-1-yl)ethanone The preparation of title compound is carried out by General Method 2 using 4-chlorophenyl hydrazine hydrochloride and 2-chloro-1-(4-methylpiperidin-1-yl)ethanone.

Example 7

Preparation of 2-(1-(4-chlorophenyl)hydrazinyl)-N-isopentyl-N-methylacetamide

The preparation of title compound is carried out by General Method 2 using 4-chlorophenyl hydrazine hydrochloride and 2-bromo-N-isopentyl-N-methylacetamide.

Example 8

Preparation of 1-(4-chlorophenyl)-1-(prop-2-ynyl)hydrazine

The preparation of title compound is carried out by General Method 2 using 4-chlorophenyl hydrazine hydrochloride and propargyl bromide.

Example 9

Preparation of 1-(4-chlorophenyl)-1-(3-phenylpropyl)hydrazine

The preparation of title compound is carried out by General Method 2 using 4-chlorophenyl hydrazine hydrochloride and 1-(3-bromopropyl)benzene.

Example 10

Preparation of 2-(5-chloro-1-(2-(2-methylpyrimidin-5-yl)ethyl)-1H-indol-3-yl)-N-methylethanamine The title compound is prepared by General Method 3 using 1-(4-chlorophenyl)-1-(2-(2-methylpyrimidin-5-yl)ethyl)hydrazine and 4,4-dimethoxy-N-methylbutan-1-amine.

Example 11

Preparation of 2-(1-(2-(6-(trifluoromethyl)pyridin-3-yl)ethyl)-5-methyl-1H-indol-3-yl)-N-methylethanamine The title compound is prepared by General Method 10 using 1-(2-(6-(trifluoromethyl)pyridin-3-yl)ethyl)-1-p-tolylhydrazine (Example 2) and 4,4-dimethoxy-N-methylbutan-1-amine.

Example 12

Preparation of 2-(5-chloro-1-(2-(piperidin-1-yl)ethyl)-1H-indol-3-yl)-N-methylethanamine The title compound is prepared by General Method 10 using 1-(4-chlorophenyl)-1-(2-(piperidin-1-yl)ethyl)hydrazine (Example 3) and 4,4-dimethoxy-N-methylbutan-1-amine.

Example 13

Preparation of 2-(5-chloro-1-(2-cyclopentylethyl)-1H-indol-3-yl)-N-methylethanamine The title compound is prepared by General Method 10 using 1-(4-chlorophenyl)-1-(2-cyclopentylethyl)hydrazine (Example 4) and 4,4-dimethoxy-N-methylbutan-1-amine.

Example 14

Preparation of 2-(5-chloro-1-(2-(3,3-dimethylcyclopentyl)ethyl)-1H-indol-3-yl)-N-methylethanamine The title compound is prepared by General Method 10 using 1-(4-chlorophenyl)-1-(2-(3,3-dimethylcyclopentyl)ethyl)hydrazine (Example 5) and 4,4-dimethoxy-N-methylbutan-1-amine.

Example 15

Preparation of 2-(5-chloro-3-(2-(methylamino)ethyl)-1H-indol-1-yl)-1-(4-methylpiperidin-1-yl)ethanone The title compound is prepared by General Method 10 using 2-(1-(4-chlorophenyl)hydrazinyl)-1-(4-methylpiperidin-1-yl)ethanone (Example 6) and 4,4-dimethoxy-N-methylbutan-1-amine.

Example 16

Preparation of 2-(5-chloro-3-(2-(methylamino)ethyl)-1H-indol-1-yl)-N-isopentyl-N-methylacetamide The title compound is prepared by General Method 10 using 2-(1-(4-chlorophenyl)hydrazinyl)-N-isopentyl-N-methylacetamide (Example 7) and 4,4-dimethoxy-N-methylbutan-1-amine.

Example 17

Preparation of 2-(5-chloro-1-(prop-2-ynyl)-1H-indol-3-yl)-N-methylethanamine

The title compound is prepared by General Method 10 using 1-(4-chlorophenyl)-1-(prop-2-ynyl)hydrazine (Example 8) and 4,4-dimethoxy-N-methylbutan-1-amine.

Example 18

Preparation of 2-(5-chloro-1-(3-phenylpropyl)-1H-indol-3-yl)-N-methylethanamine

The title compound is prepared by General Method 10 using 1-(4-chlorophenyl)-1-(3-phenylpropyl)hydrazine (Example 9) and 4,4-dimethoxy-N-methylbutan-1-amine.

Example 19a

Preparation of 2,3,4,9-tetrahydro-2,6-dimethyl-9-(2-(6-methylpyridin-3-yl)ethyl)-1H-pyrido[3,4-b]indole. (Compound 1, Scheme I)

The title compound was prepared by following General Methods 1, 3 and 4.

(A) 1-(2-(6-methylpyridin-3-yl)ethyl)-1-p-tolylhydrazine

The title compound was prepared by General Method 1. Triethylamine (13.0 mL, 94.5 mmol) was added dropwise to p-tolylhydrazine hydrochloride (5.0 g, 31.5 mmol) over a period of 5-10 min. The reaction mixture was stirred for additional 10 min. 5-(2-bromoethyl)-2-methylpyridine (6.3 g, 31.5 mmol) was added dropwise at 25° C. over a period of 10-15 min. The reaction mixture was stirred at RT for 1 h and the subsequently heated at 90° C. for 2-3 h at which point the reaction was found complete by TLC and LC-MS. Reaction mixture was concentrated under reduced pressure and diluted with water (50 mL) and extracted with ethyl acetate (100 mL×2). The organic layer was separated, dried ($Na_2SO_4$) and concentrated to obtain crude product as dark brown oil (16.7 g). Purification of crude product by column chromatography (silica gel, 100-200 mesh, eluent: 0-40% ethyl acetate-Hexane) furnished 1.92 g of pure product as brown liquid. Yield: 25%.

(B) N-methyl-2-(5-methyl-1-(2-(6-methylpyridin-3-yl)ethyl)-1H-indol-3-yl)ethanamine The title compound was prepared by General Method 3. 1-(2-(6-methylpyridin-3-yl)ethyl)-1-p-tolylhydrazine (250 mg) was suspended in water (2 mL) and 28% aqueous HCl (0.135 mL) was added. 4,4-diethoxy-N-methylbutan-1-amine (0.18 g) was added to the resulting solution and the reaction mixture was heated to 60-80° C. and an additional 28% HCl (0.135 mL) was added and the reaction mixture was heated for additional 3 h. The reaction mixture was concentrated under reduced pressure and the residue was purified by silica gel chromatography (eluent EtOAc/EtOH/$NH_3$: 7/3/1) to obtain the product.

(C) 2,3,4,9-tetrahydro-2,6-dimethyl-9-(2-(6-methylpyridin-3-yl)ethyl)-1H-pyrido[3,4-b]indole (Compound 1)

The title compound was prepared by General Method 4. 150 mg of N-methyl-2-(5-methyl-1-(2-(6-methylpyridin-3-yl)ethyl)-1H-indol-3-yl)ethanamine was dissolved in acetonitrile (4 mL) containing 5% TFA and the reaction mixture was heated to reflux. 37% aqueous formaldehyde (0.04 mL) was added and the reflux was continued for additional 1.5 h. The reaction mixture was cooled to 25° C., concentrated under reduced pressure and partitioned between ethyl acetate and satd. Aqueous $NaHCO_3$. The organic layer was dried over sodium sulfate, evaporated under reduced pressure and the residue was purified by silica gel chromatography (eluent Methanol: aqueous $NH_3$, 95:5) to obtain the product. The free base was converted into its dihydrochloride salt by treatment of dioxane-HCl. $^1$H NMR (DMSO) δ 11.7 (bs, 1H), 8.6 (s, 1H), 8.3 (d, 1H), 7.7 (d, 1H), 7.3 (d, 1H), 7.25 (s, 1H), 6.9 (d, 1H), 4.8 (m, 1H), 4.4 (m, 1H), 4.35 (t, 2H), 3.7 (bs, 1H), 3.55 (s, 3H), 3.5 (m, 1H), 3.4 (bs, 1H), 3.1 (t, 2H), 3.05 (bs, 1H), 2.65 (3, 3H), 2.35 (s, 3H). MS m/z observed 320. HPLC RT 3.63 min.

Example 19b

Preparation of Compound 1

N-methyl-2-(5-methyl-1-(2-(6-methylpyridin-3-yl)ethyl)-1H-indol-3-yl)ethanamine (150 mg) was dissolved in acetonitrile (4 mL) containing 5% TFA and the reaction mixture was refluxed. 37% aqueous formaldehyde (0.04 mL) was added and the reaction mixture was refluxed for additional 1.5 h, cooled to 25° C., concentrated under reduced pressure and partitioned between ethyl acetate and saturated aqueous $NaHCO_3$. The organic layer was dried over sodium sulfate, evaporated under reduced pressure and the residue was purified by silica gel chromatography (eluent Methanol: aqueous $NH_3$, 95:5) to obtain 2,3,4,9-tetrahydro-2,6-dimethyl-9-(2-

(6-methylpyridin-3-yl)ethyl)-1H-pyrido[3,4-b]indole. The free base was converted into its dihydrochloride salt by treatment of dioxane-HCl. $^1$H NMR (DMSO): 11.7 (bs, 1H), 8.6 (s, 1H), 8.3 (d, 1H), 7.7 (d, 1H), 7.3 (d, 1H), 7.25 (s, 1H), 6.9 (d, 1H), 4.8 (m, 1H), 4.4 (m, 1H), 4.35 (t, 2H), 3.7 (bs, 1H), 3.55 (s, 3H), 3.5 (m, 1H), 3.4 (bs, 1H), 3.1 (t, 2H), 3.05 (bs, 1H), 2.65 (s, 3H), 2.35 (s, 3H).

Example 20a

Preparation of 9-(2-cyclohexylethyl)-2,3,4,9-tetrahydro-2,6-dimethyl-1H-pyrido[3,4-b]indole (Compound 2, Scheme I)

The title compound was prepared by following General Methods 2, 3 and 4.

(A) 1-(2-cyclohexylethyl)-1-p-tolylhydrazine

The title compound was prepared by General Method 2. p-tolylhydrazine hydrochloride (0.96 g, 6.0 mmol) was added to a vigorously stirred mixture of tetra-n-butylammonium chloride (84 mg, 0.3 mmol) in 50% aqueous sodium hydroxide (6 mL) followed by 2-cyclohexylethyl bromide (1.26 g, 6.6 mmol). The mixture was heated at 60° C. (oil bath temp.) for 6 h. After cooling to room temperature, water (20-30 mL) was added and the mixture extracted with chloroform (3×10 mL). The total extract was dried (sodium sulfate), evaporated in vacuo to give a dark oil (1.49 g) which was chromatographed (45 g of silica gel, eluted with dichloromethane) to give the product as a yellow-orange oil (0.68 g, 2.93 mmol, 48.8%).

(B) 2-(1-(2-cyclohexylethyl)-5-methyl-1H-indol-3-yl)-N-methylethanamine

The title compound was prepared by General Method 3. A solution of 1-(2-cyclohexylethyl)-1-p-tolylhydrazine (0.15 g) in water (1 mL) and conc. HCl (0.18 mL) was heated to 60° C. EtOH (1 mL) was added followed by 4,4-diethoxy-N-methylbutan-1-amine (0.12 g) and the temperature was raised to 90° C. Conc. HCl (0.1 mL) was added and the heating was continued for an additional 6 h after which the reaction mixture was cooled and stirred at 25° C. for 12 h. The reaction mixture was concentrated under reduced pressure and the residue was purified by silica gel chromatography (eluent EtOAc/EtOH/NH$_3$: 9/1/0.1) to obtain 79 mg of product.

(C) 9-(2-cyclohexylethyl)-2,3,4,9-tetrahydro-2,6-dimethyl-1H-pyrido[3,4-b]indole (Compound 2)

The title compound was prepared by General Method 4. 2-(1-(2-cyclohexylethyl)-5-methyl-1H-indol-3-yl)-N-methylethanamine (72 mg) was dissolved in acetonitrile (2 mL) containing 5% TFA and the reaction mixture was heated to reflux. 37% aqueous formaldehyde (0.02 mL) was added and the reflux was continued for additional 2 h. The reaction mixture was cooled to 25° C., concentrated under reduced pressure and partitioned between ethyl acetate and satd. Aqueous NaHCO$_3$. The organic layer was dried over sodium sulfate, evaporated under reduced pressure and the residue was purified by silica gel chromatography (eluent EtOAc/EtOH/NH$_3$: 9/1/0.1) to obtain 52 mg of product. The free base was converted into its oxalate salt by treatment of oxalic acid (1 equiv) in anhydrous THF. $^1$H NMR (DMSO) δ 7.5 (d, 1H), 7.4 (s, 1H), 6.9 (d, 1H), 4.3 (bs, 2H), 4.0 (t, 2H), 3.6 (bs, 2H), 2.8 (m, 5H), 2.3 (s, 3H), 1.8-0.7 (m, 13H). MS m/z observed 311. HPLC RT 5.93 min.

Example 20b

Preparation of Compound 2

2-(1-(2-cyclohexylethyl)-5-methyl-1H-indol-3-yl)-N-methylethanamine (72 mg, 0.23 mmol) was dissolved in acetonitrile (2 mL) containing 5% TFA and the reaction mixture was refluxed. 37% aqueous formaldehyde (0.02 mL) was added to the reaction mixture and refluxed for additional 2 h, cooled to 25° C., concentrated under reduced pressure and partitioned between ethyl acetate and saturated aqueous NaHCO$_3$. The organic layer was dried over sodium sulfate, evaporated under reduced pressure and the residue was purified by silica gel chromatography (eluent EtOAc/EtOH/NH$_3$: 9/1/0.1) to obtain 9-(2-cyclohexylethyl)-2,3,4,9-tetrahydro-2,6-dimethyl-1H-pyrido[3,4-b]indole (52 mg). The free base was converted into its oxalate salt by treatment of oxalic acid (1 equiv) in anhydrous THF. $^1$H NMR (DMSO): 7.5 (d, 1H), 7.4 (s, 1H), 6.9 (d, 1H), 4.3 (bs, 2H), 4.0 (t, 2H), 3.6 (bs, 2H), 2.8 (m, 5H), 2.3 (s, 3H), 1.8-0.7 (m, 13H).

Example 21a

Preparation of 9-(4-fluorophenethyl)-6-chloro-2,3,4,9-tetrahydro-2-methyl-1H-pyrido[3,4-b]indole (Compound 3, Scheme I)

The title compound was prepared by following General Methods 2, 3 and 4.

(A) 1-(4-fluorophenethyl)-1-(4-chlorophenyl)hydrazine

The title compound was prepared by General Method 2. 4-chlorophenylhydrazine hydrochloride (2.2 g) was added to a vigorously stirred mixture of tetra-n-butylammonium chloride (200 mg) in 50% aqueous sodium hydroxide (12 mL) followed by 4-fluorophenethyl bromide (2.5 g). The mixture was heated at 75-80° C. (oil bath temp.) for 3.5 h. After cooling to room temperature, water was added and the mixture extracted with chloroform and the chloroform layer was washed with brine. The combined extract was dried (sodium sulfate), evaporated in vacuo to give a dark oil which was chromatographed over silica gel, eluting with chloroform followed by recrystallization from cyclohexane to obtain 750 mg of product.

(B) 2-(1-(4-fluorophenethyl)-5-chloro-1H-indol-3-yl)-N-methylethanamine

The title compound was prepared by General Method 3. 1-(4-fluorophenethyl)-1-(4-chlorophenyl)hydrazine (500 mg) was converted into its hydrochloride salt by dissolving in ethyl acetate and treatment of dioxane-HCl. The salt was dissolved in ethanol/water (1/1; 4 mL)) and was heated to 60° C. 4,4-diethoxy-N-methylbutan-1-amine (0.35 g) was added and the temperature was raised to 70-80° C. 28% aqueous HCl (0.24 mL) was added and the heating was continued for 40 min. Additional amount of 4,4-diethoxy-N-methylbutan-1-amine (0.3 g) and % aqueous HCl (0.3 mL) was added and heating was continued for additional 3 h after which the reaction mixture was cooled and stirred at 25° C. for 12 h. The reaction mixture was concentrated under reduced pressure and the residue was purified by silica gel chromatography (eluent EtOAc/EtOH/NH3: 7/3/1) to obtain 600 mg of product.

(C) 9-(4-fluorophenethyl)-6-chloro-2,3,4,9-tetrahydro-2-methyl-1H-pyrido[3,4-b]indole (Compound 3)

The title compound was prepared by General Method 4. 2-(1-(4-fluorophenethyl)-5-chloro-1H-indol-3-yl)-N-methylethanamine (600 mg) was dissolved in acetonitrile (10 mL) containing 5% TFA and the reaction mixture was heated to reflux. 37% aqueous formaldehyde (0.17 mL) was added and the reflux was continued for 15-20 min. The reaction mixture was cooled to 25° C., concentrated under reduced pressure and partitioned between ethyl acetate and satd. Aqueous NaHCO$_3$. The organic layer was dried over sodium sulfate, evaporated under reduced pressure and the residue was purified by silica gel chromatography (eluent 6% methanol-chloroform) to obtain 170 mg of product. The free base was converted into its HCl salt by treatment of HCL-ether. $^1$H NMR (CDCl$_3$) δ 13.1 (s, 1H), 7.25-7.1 (m, 3H), 6.8 (m, 2H), 6.7 (m, 2H), 4.4 (m, 1H), 4.2 (m, 1H), 3.9 (m, 1H), 3.4 (m, 1H), 3.2-3.0 (m, 3H), 2.8 (m, 3H), 2.6 (s, 3H). MS m/z observed 343. HPLC RT 5.16 min.

Example 21b

Preparation of Compound 3

2-(1-(4-fluorophenethyl)-5-chloro-1H-indol-3-yl)-N-methylethanamine (600 mg) was dissolved in acetonitrile (10 mL) containing 5% TFA and the reaction mixture was refluxed. 37% aqueous formaldehyde (0.17 mL) was added and the reaction mixture was refluxed for an additional for 15-20 min, cooled to 25° C., concentrated under reduced pressure and partitioned between ethyl acetate and saturated aqueous NaHCO$_3$. The organic layer was dried over sodium sulfate, evaporated under reduced pressure and the residue was purified by silica gel chromatography (eluent 6% methanol-chloroform) to yield the product (170 mg). The free base was converted into its HCl salt by treatment of HCl-ether. $^1$H NMR (CDCl$_3$): 13.1 (s, 1H), 7.25-7.1 (m, 3H), 6.8 (m, 2H), 6.7 (m, 2H), 4.4 (m, 1H), 4.2 (m, 1H), 3.9 (m, 1H), 3.4 (m, 1H), 3.2-3.0 (m, 3H), 2.8 (m, 3H), 2.6 (s, 3H).

Example 22

Preparation of 6-chloro-2,3,4,9-tetrahydro-2-methyl-9-(2-(2-methylpyrimidin-5-yl)ethyl)-1H-pyrido[3,4-b]indole (Compound 4, Scheme I/II)

Approach A.
The title compound is prepared by following General Methods 1, 3 and 4 using 4-chlorophenylhydrazine hydrochloride, 5-(2-bromoethyl)-2-methylpyrimidine, and triethylamine (General Method 1), 3,1-(4-chlorophenyl)-1-(2-(2-methylpyrimidin-5-yl)ethyl)hydrazine (Example 1) and 4,4-diethoxy-N-methylbutan-1-amine (General Method 3) and 2-(5-chloro-1-(2-(2-methylpyrimidin-5-yl)ethyl)-1H-indol-3-yl)-N-methylethanamine (Example 10), formaldehyde and TFA in acetonitrile (General Method 4).
Approach B
The title compound is prepared by following General Methods 3, 4 and 9 by using 4-chlorophenylhydrazine hydrochloride and 4,4-diethoxy-N-methylbutan-1-amine (General Method 3), 2-(5-chloro-1H-indol-3-yl)-N-methylethanamine, formaldehyde and TFA in acetonitrile (General Method 4) and 6-chloro-2,3,4,9-tetrahydro-2-methyl-1H-pyrido[3,4-b]indole and 2-methyl-5-vinylpyrimidine (General Method 9).

Example 23a

Preparation of 9-(2-(6-(trifluoromethyl)pyridin-3-yl)ethyl)-2,3,4,9-tetrahydro-2,6-dimethyl-1H-pyrido[3,4-b]indole (Compound 5, Scheme I/II)

Approach A
The title compound is prepared by following General Methods 1, 3 and 4 using p-tolylhydrazine hydrochloride, 5-(2-bromoethyl)-2-(trifluoromethyl)pyridine, and triethylamine (General Method 1), 1-(2-(6-(trifluoromethyl)pyridin-3-yl)ethyl)-1-p-tolylhydrazine (Example 2) and 4,4-diethoxy-N-methylbutan-1-amine (General Method 3) and 2-(1-(2-(6-(trifluoromethyl)pyridin-3-yl)ethyl)-5-methyl-1H-indol-3-yl)-N-methylethanamine (Example 11), formaldehyde and TFA in acetonitrile (General Method 4).
Approach B
The title compound is prepared by following General Methods 3, 4 and 9 by using p-tolylhydrazine hydrochloride and 4,4-diethoxy-N-methylbutan-1-amine (General Method 3), N-methyl-2-(5-methyl-1H-indol-3-yl)ethanamine, formaldehyde and TFA in acetonitrile (General Method 4) and 2,3,4,9-tetrahydro-2,6-dimethyl-1H-pyrido[3,4-b]indole and 2-(trifluoromethyl)-5-vinylpyridine (General Method 9).

Example 23b

Preparation of Compound 5

A mixture of 2,6-dimethyl-2,3,4,9-tetrahydro-1H-β-carboline (50 mg, 0.25 mmol), 2-trifluoromethyl-5-vinyl pyridine (48 mg, 0.27 mmol) and potassium hydroxide (49 mg, 0.87 mmol) in N-methyl-2-pyrrolidinone (0.3 mL) was heated to 45° C. for 1 h. The reaction mixture was cooled; brine (2 mL) was added followed by extraction with ethyl acetate (3×5 mL). The combined organic layer was dried over MgSO$_4$, filtered and concentrated under reduced pressure to obtain a brown oil which was purified by column chromatography (silica gel, eluent: dichloromethane followed by 2-8% methanol in dichloromethane) to yield a dark yellow semi-solid (40 mg). The semisolid was dissolved in dichloromethane (2 mL) and washed with water (0.5 mL), filtered through a Varian drying tube and washed with dichloromethane (3×2 mL). The combined organic phase was concentrated under reduced pressure to give a yellow solid (18.5 mg). The free base was converted to the hydrochloride by dissolving the product in methanol (4 mL) and 2M hydrochloride in diethyl ether (0.5 mL) was added. The solution was concentrated under reduced pressure. The residue was triturated with diethyl ether and decanted (2×7 mL) and the solvent removed under reduced pressure to yield 9-(2-(6-(trifluoromethyl)pyridin-3-yl)ethyl)-2,3,4,9-tetrahydro-2,6-dimethyl-1H-pyrido[3,4-b]indole (17 mg, 15%). $^1$H NMR (CD$_3$OD): 8.4 (s, 1H), 7.67-7.9 (m, 2H), 7.4 (s, 1H), 7.2 (d, 1H), 7.0 (d, 1H) 4.5 (bs, 4H), 3.7 (bs, 2H), 3.1-3.3 (m, 7H), 2.5 (s, 3H).

Example 24

Preparation of 6-chloro-9-(2-(6-(trifluoromethyl)pyridin-3-yl)ethyl)-2,3,4,9-tetrahydro-2-methyl-1H-pyrido[3,4-b]indole (Compound 6, Scheme I/II)

Approach A
The title compound is prepared by following General Methods 1, 3 and 4 using 4-chlorophenylhydrazine hydrochloride, 5-(2-bromoethyl)-2-(trifluoromethyl)pyridine, and triethylamine (General Method 1), 1-(4-chlorophenyl)-1-(2-(6-(trifluoromethyl)pyridin-3-yl)ethyl)hydrazine and 4,4-diethoxy-N-methylbutan-1-amine (General Method 3) and 2-(5-chloro-1-(2-(6-(trifluoromethyl)pyridin-3-yl)ethyl)-1H-indol-3-yl)-N-methylethanamine, formaldehyde and TFA in acetonitrile (General Method 4).

Approach B

The title compound is prepared by following General Methods 3, 4 and 9 by using 4-chlorophenylhydrazine hydrochloride and 4,4-diethoxy-N-methylbutan-1-amine (General Method 3), 2-(5-chloro-1H-indol-3-yl)-N-methylethanamine, formaldehyde and TFA in acetonitrile (General Method 4) and 6-chloro-2,3,4,9-tetrahydro-2-methyl-1H-pyrido[3,4-b]indole and 2-(trifluoromethyl)-5-vinylpyridine (General Method 9).

Approach C

Method for the synthesis of compound 6 [6-chloro-2-methyl-9-(2-(6-(trifluoromethyl)pyridin-3-yl)ethyl)-2,3,4,9-tetrahydro-1H-pyrido[3,4-b]indole]: (4-chlorophenyl)hydrazine is reacted with 4,4-dimethoxy-N-methylbutan-1-amine (Phytochemistry 1985, 24 (8), 1653-1656) to generate 2-(5-chloro-1H-indol-3-yl)-N-methylethanamine which upon treatment with formaldehyde, under standard Pictet Spingler reaction conditions (U.S. Pat. No. 2,642,438) gives 6-chloro-2-methyl-2,3,4,9-tetrahydro-1H-pyrido[3,4-b]indole. The further reaction of this unsubstituted β-carboline with 2-(trifluoromethyl)-5-vinylpyridine gives the desired compound [6-chloro-2-methyl-9-(2-(6-(trifluoromethyl)pyridin-3-yl)ethyl)-2,3,4,9-tetrahydro-1H-pyrido[3,4-b]indole], compound 6. After the successful synthesis of the compound, purification can be achieved using standard normal phase or reverse phase methods.

Example 25

Preparation of 2-(7-chloro-1,2,3,4-tetrahydro-2-methylpyrido[3,4-b]indol-9-yl)-1-(6-methylpyridin-3-yl)ethanol (Compound 7, Scheme III)

Approach A

The title compound is prepared by following General Methods 3, 4 and 8 by using 3-chlorophenylhydrazine hydrochloride and 4,4-diethoxy-N-methylbutan-1-amine (General Method 3), 2-(6-chloro-1H-indol-3-yl)-N-methylethanamine, formaldehyde and TFA in acetonitrile (General Method 4) and 7-chloro-2,3,4,9-tetrahydro-2-methyl-1H-pyrido[3,4-b]indole, 2-methyl-5-(oxiran-2-yl)pyridine and NaH (General Method 8).

Approach B

Method for the preparation of compound 7 [[2-(7-chloro-2-methyl-3,4-dihydro-1H-pyrido[3,4-b]indol-9(2H)-yl)-1-(6-methylpyridin-3-yl)ethanol]: (3-chlorophenyl)hydrazine is reacted with 4,4-dimethoxy-N-methylbutan-1-amine (put in the references for this) to generate 2-(6-chloro-1H-indol-3-yl)-N-methylethanamine, which upon treatment with formaldehyde, under standard Pictet Spingler reaction conditions (insert the reference for this) gives 7-chloro-2-methyl-2,3,4,9-tetrahydro-1H-pyrido[3,4-b]indole. The further reaction of this unsubstituted β-carboline with 2-methyl-5-(oxiran-2-yl)pyridine (carboline, aryl/heteroaryl oxide, NaH, DMF, 120° C.) gives the desired compound 2-(7-chloro-2-methyl-3,4-dihydro-1H-pyrido[3,4-b]indol-9(2H)-yl)-1-(6-methylpyridin-3-yl)ethanol, compound 7. After the successful synthesis of the compound, purification can be achieved using standard normal phase or reverse phase methods.

Example 26

Preparation of 6-aza-2,3,4,9-tetrahydro-2-methyl-9-(2-methyl-2-(6-methylpyridin-3-yl)propyl)-1H-pyrido[3,4-b]indole (Compound 8, Scheme I/II)

The title compound is prepared by following General Methods 1, 3 and 4 by using 1-(pyridin-4-yl)hydrazine hydrochloride, 5-(1-bromo-2-methylpropan-2-yl)-2-methylpyridine, and triethylamine (General Method 1), 1-(2-methyl-2-(6-methylpyridin-3-yl)propyl)-1-(pyridin-4-yl)hydrazine and 4,4-diethoxy-N-methylbutan-1-amine (General Method 3) and N-methyl-2-(1-(2-methyl-2-(6-methylpyridin-3-yl)propyl)-1H-pyrrolo[3,2-c]pyridin-3-yl)ethanamine, formaldehyde and TFA in acetonitrile (General Method 4)

Example 27

Preparation of 5-aza-2,3,4,9-tetrahydro-2-methyl-9-(1-(6-methylpyridin-3-yl)propan-2-yl)-1H-pyrido[3,4-b]indole (Compound 9, Scheme I/II)

The title compound is prepared by following General Methods 3, 4 and 9 by using 1-(pyridin-3-yl)hydrazine hydrochloride and 4,4-diethoxy-N-methylbutan-1-amine (General Method 3), N-methyl-2-(1H-pyrrolo[3,2-b]pyridin-3-yl)ethanamine, formaldehyde and TFA in acetonitrile (General Method 4) and 5-aza-2,3,4,9-tetrahydro-2-methyl-1H-pyrido[3,4-b]indole and 2-methyl-5-(prop-1-enyl)pyridine (General Method 9).

Example 28

Preparation of 6-chloro-9-((1-(4-fluorophenyl)cyclopropyl)methyl)-2,3,4,9-tetrahydro-2-methyl-1H-pyrido[3,4-b]indole (Compound 10, Scheme I/II)

The title compound is prepared by following General Methods 1, 3 and 4 by) using 4-chlorophenylhydrazine hydrochloride, 1-(1-(bromomethyl)cyclopropyl)-4-fluorobenzene, and triethylamine (General Method 1), 1-(4-chlorophenyl)-1-((1-(4-fluorophenyl)cyclopropyl)methyl)hydrazine and 4,4-diethoxy-N-methylbutan-1-amine (General Method 3) and 2-(5-chloro-1-((1-(4-fluorophenyl)cyclopropyl)methyl)-1H-indol-3-yl)-N-methylethanamine, formaldehyde and TFA in acetonitrile (General Method 4).

Example 29

Preparation of 6-chloro-9-(2-(2-(trifluoromethyl)pyrimidin-5-yl)ethyl)-2,3,4,9-tetrahydro-2-methyl-1H-pyrido[3,4-b]indole (Compound 11, Scheme I/II)

Approach A

The title compound is prepared by following General Methods 1, 3 and 4 using 4-chlorophenylhydrazine hydrochloride, 5-(2-bromoethyl)-2-(trifluoromethyl)pyrimidine, and triethylamine (General Method 1), 1-(4-chlorophenyl)-1-(2-(2-(trifluoromethyl)pyrimidin-5-yl)ethyl)hydrazine and 4,4-diethoxy-N-methylbutan-1-amine (General Method 3) and 2-(5-chloro-1-(2-(2-(trifluoromethyl)pyrimidin-5-yl)ethyl)-1H-indol-3-yl)-N-methylethanamine, formaldehyde and TFA in acetonitrile (General Method 4).

Approach B

The title compound is prepared by following General Methods 3, 4 and 9 by using 4-chlorophenylhydrazine hydrochloride and 4,4-diethoxy-N-methylbutan-1-amine (General Method 3), 2-(5-chloro-1H-indol-3-yl)-N-methylethanamine, formaldehyde and TFA in acetonitrile (General Method 4) and 6-chloro-2,3,4,9-tetrahydro-2-methyl-1H-pyrido[3,4-b]indole and 2-(trifluoromethyl)-5-vinylpyrimidine (General Method 9).

Example 30

Preparation of 5-aza-2,3,4,9-tetrahydro-2-methyl-9-(2-methyl-1-(6-methylpyridin-3-yl)propan-2-yl)-1H-pyrido[3,4-b]indole (Compound 12, Scheme I/II)

The title compound is prepared by following General Methods 3, 4 and 9 by using 1-(pyridin-3-yl)hydrazine hydrochloride and 4,4-diethoxy-N-methylbutan-1-amine (General Method 3), N-methyl-2-(1H-pyrrolo[3,2-b]pyridin-3-yl)ethanamine, formaldehyde and TFA in acetonitrile (General Method 4) and 5-aza-2,3,4,9-tetrahydro-2-methyl-1H-pyrido[3,4-b]indole and 2-methyl-5-(2-methylprop-1-enyl)pyridine (General Method 9).

Example 31

Preparation of 2-(8-fluoro-1,2,3,4-tetrahydro-2-methylpyrido[3,4-b]indol-9-yl)-1-(6-methylpyridin-3-yl)ethanol (Compound 13, Scheme III)

The title compound is prepared by following General Methods 3, 4 and 8 by using 2-fluorophenylhydrazine hydrochloride and 4,4-diethoxy-N-methylbutan-1-amine (General Method 3), 2-(7-fluoro-1H-indol-3-yl)-N-methylethanamine, formaldehyde and TFA in acetonitrile (General Method 4) and 8-fluoro-2,3,4,9-tetrahydro-2-methyl-1H-pyrido[3,4-b]indole, 2-methyl-5-(oxiran-2-yl)pyridine and NaH (General Method 8).

Example 32a

Preparation of 2-(6-chloro-1,2,3,4-tetrahydro-2-methylpyrido[3,4-b]indol-9-yl)-N-isopentyl-N-methylacetamide (Compound 14, Scheme IV)

Compound 14 was prepared according to a general method detailed herein.
Approach A
The title compound is prepared by following General Methods 1, 3, 4, 5 and 7 by using 4-chlorophenylhydrazine hydrochloride, ethyl bromoacetate, and triethylamine (General Method 1), ethyl 2-(1-(4-chlorophenyl)hydrazinyl)acetate and 4,4-diethoxy-N-methylbutan-1-amine (General Method 3), ethyl 2-(5-chloro-3-(2-(methylamino)ethyl)-1H-indol-1-yl)acetate, formaldehyde and TFA in acetonitrile (General Method 4), ethyl 2-(6-chloro-1,2,3,4-tetrahydro-2-methylpyrido[3,4-b]indol-9-yl)acetate and NaOH (General Method 5), and 2-(6-chloro-1,2,3,4-tetrahydro-2-methylpyrido[3,4-b]indol-9-yl)acetic acid, N,3-dimethylbutan-1-amine and EDCI (General Method 7).
Approach B
Method for the preparation of compound 14 [2-(6-chloro-2-methyl-3,4-dihydro-1H-pyrido[3,4-b]indol-9(2H)-yl)-N-isopentyl-N-methylacetamide]: (4-chlorophenyl)hydrazine is alkylated with ethyl 2-bromoacetate to give the substituted phenylhydrazine ethyl 2-(1-(4-chlorophenyl)hydrazinyl)acetate (III). The reaction of III with 4,4-dimethoxy-N-methylbutan-1-amine gives the indole derivative ethyl 2-(5-chloro-3-(2-(methylamino)ethyl)-1H-indol-1-yl)acetate (V). Effecting the indole to standard Pictet Spingler conditions with formaldehyde gives the β-carboline intermediate (VI) ethyl 2-(6-chloro-2-methyl-3,4-dihydro-1H-pyrido[3,4-b]indol-9(2H)-yl)acetate. Following treatment of VI with base the acid (VIII) 2-(6-chloro-2-methyl-3,4-dihydro-1H-pyrido[3,4-b]indol-9(2H)-yl)acetic acid is obtained. The treatment of this acid under standard peptide coupling conditions with N,3-dimethylbutan-1-amine gives compound 152-(6-chloro-2-methyl-3,4-dihydro-1H-pyrido[3,4-b]indol-9(2H)-yl)-N-isopentyl-N-methylacetamide. After the successful synthesis of the compound, purification can be achieved using standard normal phase or reverse phase methods.

Example 32b

Preparation of Compound 14

2-[5-Chloro-3-(2-methylamino-ethyl)-indol-1-yl]-N-methyl-N-(3-methyl-butyl)-acetamide (220 mg, 0.63 mmol) in 5% trifluoroacetic acid in acetonitrile (4 mL) was heated to 70° C. 37% aqueous formaldehyde (0.08 mL) was added to the reaction and refluxed for additional 30 min, cooled and concentrated under reduced pressure. The resulting residue was dissolved in chloroform and washed with saturated aqueous sodium hydrogen carbonate and brine. The organic layer was dried (MgSO$_4$), filtered and concentrated under reduced pressure to give a residue (120 mg). This was purified using the Waters Preparative HPLC to yield the product (41.5 mg, 28%). The free base was converted to the hydrochloride by dissolving the product in methanol (3 mL) and 2M hydrochloride in diethyl ether (1 mL) was added. The solution was concentrated under reduced pressure. The oil was triturated with diethyl ether and the solvent removed under reduced pressure to yield a buff solid (40 mg). $^1$H NMR (CD$_3$OD): 7.6 (s, 1H), 7.5 (d, 1H), 7.25 (d, 1H), 5.25 (bs, 2H), 4.5 (bs, 2H), 3.7 (m, 2H), 3.6 (t, 2H), 3.5 (t, 2H), 3.4 (s, 3H), 3.2 (s, 3H), 1.7-1.5 (m, 3H), 1.0 (d, 6H).

Example 33a

Preparation of 2-(6-chloro-1,2,3,4-tetrahydro-2-methylpyrido[3,4-b]indol-9-yl)-N-(4-fluorophenyl)acetamide (Compound 15, Scheme IV)

The title compound is prepared by following General Methods 1, 3, 4, 5 and 7 by using 4-chlorophenylhydrazine hydrochloride, ethyl bromoacetate, and triethylamine (General Method 1), ethyl 2-(1-(4-chlorophenyl)hydrazinyl)acetate and 4,4-diethoxy-N-methylbutan-1-amine (General Method 3), ethyl 2-(5-chloro-3-(2-(methylamino)ethyl)-1H-indol-1-yl)acetate, formaldehyde and TFA in acetonitrile (General Method 4), ethyl 2-(6-chloro-1,2,3,4-tetrahydro-2-methylpyrido[3,4-b]indol-9-yl)acetate and NaOH (General Method 5), and 2-(6-chloro-1,2,3,4-tetrahydro-2-methylpyrido[3,4-b]indol-9-yl)acetic acid, 4-fluoroaniline and EDCI (General Method 7).

Example 33b

Preparation of Compound 15

2-(6-chloro-1,2,3,4-tetrahydro-2-methylpyrido[3,4-b]indol-9-yl)acetic acid (0.1 g, 0.39 mmol) was dissolved in dichloromethane (4 mL) and was cooled to 0° C., using an ice-bath; oxalyl chloride (0.04 mL, 0.43 mmol) was added drop-wise to the reaction mixture. Catalytic amount (1 drop) of dimethyl formamide was added and the reaction mixture was stirred for 1 h at room temperature. Excess oxalyl chloride was distilled away under reduced pressure. A solution of 4-fluoroaniline (0.042 g, 0.43 mmol) in dichloromethane (2 mL) and 4-dimethylaminopyridine (0.017 g, 0.143 mmol) was added to the residue under nitrogen at room temperature and the reaction mass was stirred for 30 min. The reaction mixture was quenched with water and neutralized with 10% $NaHCO_3$, extracted with dichloromethane (2×10 mL). The combined organic layer was dried over sodium sulfate and concentrated by rotary evaporation to obtain 2-(6-chloro-1,2,3,4-tetrahydro-2-methylpyrido[3,4-b]indol-9-yl)-N-(4-fluorophenyl)acetamide (6 mg) after purification by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL). 1 H NMR (DMSO): 11.4 (s, 1H), 10.6 (s, 1H), 7.6 (m, 3H), 7.4 (d, 1H), 7.3-7.1 (m, 3H), 5.1 and 4.9 (d, 2H), 4.4 (q, 2H), 4.1-3.9 (bs, 2H), 3.5 (s, 3H), 3.2-3.1 (m, 2H).

Example 34a

Preparation of 2-(6-chloro-1,2,3,4-tetrahydro-2-methylpyrido[3,4-b]indol-9-yl)-N,N-dimethylacetamide (Compound 16, Scheme IV)

The title compound is prepared by following General Methods 1, 3, 4, 5 and 7 by using 4-chlorophenylhydrazine hydrochloride, ethyl bromoacetate, and triethylamine (General Method 1), ethyl 2-(1-(4-chlorophenyl)hydrazinyl)acetate and 4,4-diethoxy-N-methylbutan-1-amine (General Method 3), ethyl 2-(5-chloro-3-(2-(methylamino)ethyl)-1H-indol-1-yl)acetate, formaldehyde and TFA in acetonitrile (General Method 4), ethyl 2-(6-chloro-1,2,3,4-tetrahydro-2-methylpyrido[3,4-b]indol-9-yl)acetate and NaOH (General Method 5), and 2-(6-chloro-1,2,3,4-tetrahydro-2-methylpyrido[3,4-b]indol-9-yl)acetic acid, N,N-dimethylamine and EDCI (General Method 7).

Example 34b

Preparation of Compound 16

6-chloro-2-methyl-2,3,4,9-tetrahydro-1H-pyrido[3,4-b]indole (100 mg, 0.5 mmol), was dissolved in N,N-dimethylformamide. CuI (0.009 g, 0.05 mmol), L-proline (0.011 g, 0.091 mmol) and $K_3PO_4$ (0.194 g, 0.91 mmol) was added to the solution and stirred for 10 min. at room temperature, followed by drop-wise addition of 2-chloro-N,N-dimethylacetamide (0.066 g, 0.55 mmol) and stirred at 90° C. for 12 h. After completion of the reaction, the reaction mixture was filtered through Celite, N,N-dimethylformamide was evaporated under reduced pressure and extracted with ethyl acetate. The combined organic layer was dried over $Na_2SO_4$, and concentrated under reduced pressure to yield 2-(6-chloro-2-methyl-3,4-dihydro-1H-pyrido[3,4-b]indol-9(2H)-yl)-N,N-dimethylacetamide as TFA salt (9 mg) after purification by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL). 1H NMR ($CD_3OD$): 10.9 (bs, 1H), 7.65 (s, 1H), 7.38 (d, 1H), 7.19 (d, 1H), 5.1-5.2 (m, 2H), 4.55 (s, 2H), 4.2-4.3 (m, 2H), 3.83-4.1 (m, 2H), 3.25 (s, 3H), 3.19-3.25 (m, 3H), 3.0 (s, 3H).

Example 35a

Preparation of 2-(6-chloro-1,2,3,4-tetrahydro-2-methylpyrido[3,4-b]indol-9-yl)-N-cyclohexylacetamide (Compound 17, Scheme IV)

The title compound is prepared by following General Methods 1, 3, 4, 5 and 7 by using 4-chlorophenylhydrazine hydrochloride, ethyl bromoacetate, and triethylamine (General Method 1), ethyl 2-(1-(4-chlorophenyl)hydrazinyl)acetate and 4,4-diethoxy-N-methylbutan-1-amine (General Method 3), ethyl 2-(5-chloro-3-(2-(methylamino)ethyl)-1H-indol-1-yl)acetate, formaldehyde and TFA in acetonitrile (General Method 4), ethyl 2-(6-chloro-1,2,3,4-tetrahydro-2-methylpyrido[3,4-b]indol-9-yl)acetate and NaOH (General Method 5), and 2-(6-chloro-1,2,3,4-tetrahydro-2-methylpyrido[3,4-b]indol-9-yl)acetic acid, cyclohexaneamine and EDCI (General Method 7).

Example 35b

Preparation of Compound 17

6-chloro-2-methyl-2,3,4,9-tetrahydro-1H-pyrido[3,4-b]indole (100 mg, 0.5 mmol), was dissolved in N,N-dimethylformamide. CuI (0.009 g, 0.05 mmol), L-proline (0.011 g, 0.091 mmol) and $K_3PO_4$ (0.194 g, 0.91 mmol) was added to the solution and stirred for 10 min. at room temperature, followed by drop-wise addition of 2-chloro-N-cyclohexylacetamide (0.096 g, 0.55 mmol) and stirred at 90° C. for 12 h. After completion of the reaction, the reaction mixture filtered through Celite, N,N-dimethylformamide was evaporated under reduced pressure and extracted with ethyl acetate. The combined organic layer was dried over $Na_2SO_4$, and concentrated under reduced pressure to yield 2-(6-chloro-2-methyl-3,4-dihydro-1H-pyrido[3,4-b]indol-9(2H)-yl)-N-cyclohexylacetamide) as TFA salt (40 mg) after purification by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL). 1 H NMR (DMSO-D6): 11.25 (bs, 1H), 8.43 (bs, 1H), 7.6 (s, 1H), 7.41 (d, 1H), 7.18 (d, 1H), 4.8-5.9 (m, 2H), 4.1-4.2 (m, 2H), 3.82-3.0 (m, 2H), 3.25 (s, 3H), 2.92-3.2 (m, 3H), 1.5-1.8 (m, 6H), 1.15-1.29 (m, 4H).

Example 36a

Preparation of 2-(6-chloro-1,2,3,4-tetrahydro-2-methylpyrido[3,4-b]indol-9-yl)-N-cyclohexyl-N-methylacetamide (Compound 18, Scheme IV)

The title compound is prepared by following General Methods 1, 3, 4, 5 and 7 by using 4-chlorophenylhydrazine hydrochloride, ethyl bromoacetate, and triethylamine (General Method 1), ethyl 2-(1-(4-chlorophenyl)hydrazinyl)acetate and 4,4-diethoxy-N-methylbutan-1-amine (General Method 3), ethyl 2-(5-chloro-3-(2-(methylamino)ethyl)-1H-indol-1-yl)acetate, formaldehyde and TFA in acetonitrile (General Method 4), ethyl 2-(6-chloro-1,2,3,4-tetrahydro-2-methylpyrido[3,4-b]indol-9-yl)acetate and NaOH (General Method 5), and 2-(6-chloro-1,2,3,4-tetrahydro-2-methylpyrido[3,4-b]indol-9-yl)acetic acid, N-methylcyclohexylamine and EDCI (General Method 7).

Example 36b

Preparation of Compound 18

2-(6-chloro-2-methyl-3,4-dihydro-1H-pyrido[3,4-b]indol-9(2H)-yl)acetic acid (50 mg, 0.18 mmol) was dissolved in dichloromethane (3 mL) and cooled to 0° C. Oxalyl chloride (0.027 g, 0.22 mmol) was added drop-wise followed by catalytic amount of N,N-dimethylformamide, and the reaction mixture was stirred at RT for 1 h. Oxalyl chloride was evaporated under reduced pressure to obtain the corresponding acid chloride. A solution of N-methylcyclohexanamine (0.025 g, 0.22 mmol) and 4-dimethylaminopyridine (26 mg, 0.22 mmol) in dichloromethane (previously stirred at RT for 1 h) was added drop-wise to the acid chloride. The progress of the reaction was monitored by LCMS. After completion of the reaction, the reaction mixture was quenched with ice water and extracted with dichloromethane. The organic layer was dried over anhydrous sodium sulfate, evaporated under reduced pressure and purified by reverse phase chromatography to yield 2-(6-chloro-2-methyl-3,4-dihydro-1H-pyrido[3,4-b]indol-9(2H)-yl)-N-cyclohexyl-N-methylacetamide as TFA salt (2.4 mg). $^1$H NMR (DMSO): 7.6 (s, 1H), 7.4 (d, 1H), 7.15 (d, 1H), 5.15 (d, 1H), 4.95 (d, 1H), 4.65 (s, 1H), 4.50 (s, 1H), 4.3 (m, 1H), 4.1 (m, 1H), 3.9 (m, 1H), 3.1 (m, 2H), 3.35 (s, 3H), 2.8 (s, 3H), 1.9-1.1 (m, 10H).

Example 37

Preparation of isopentyl 2-(1,2,3,4-tetrahydro-2,6-dimethylpyrido[3,4-b]indol-9-yl)acetate (Compound 19, Scheme V)

Approach A

The title compound is prepared by following General Methods 1, 3, 4, 5 and 6 by using p-tolylhydrazine hydrochloride, ethyl bromoacetate, and triethylamine (General Method 1), ethyl 2-(1-(4-methylphenyl)hydrazinyl)acetate and 4,4-diethoxy-N-methylbutan-1-amine (General Method 3), ethyl 2-(5-methyl-3-(2-(methylamino)ethyl)-1H-indol-1-yl)acetate, formaldehyde and TFA in acetonitrile (General Method 4), ethyl 2-(6-methyl-1,2,3,4-tetrahydro-2-methylpyrido[3,4-b]indol-9-yl)acetate and NaOH (General Method 5), and 2-(6-methyl-1,2,3,4-tetrahydro-2-methylpyrido[3,4-b]indol-9-yl)acetic acid, 3-methylbutan-1-ol and EDCI (General Method 6).

Approach B

Method for the preparation of compound 19 [isopentyl 2-(2,6-dimethyl-3,4-dihydro-1H-pyrido[3,4-b]indol-9(2H)-yl)acetate]: p-tolylhydrazine is alkylated with ethyl 2-bromoacetate to give the substituted phenylhydrazine, ethyl 2-(1-p-tolylhydrazinyl)acetate (III). The reaction of III with 4,4-dimethoxy-N-methylbutan-1-amine gives the indole derivative ethyl 2-(5-methyl-3-(2-(methylamino)ethyl)-1H-indol-1-yl)acetate (V). Effecting the indole to standard Pictet Spingler conditions with formaldehyde gives the 1-carboline intermediate (VI) ethyl 2-(2,6-dimethyl-3,4-dihydro-1H-pyrido[3,4-b]indol-9(2H)-yl)acetate. Following treatment of VI with base the acid (VIII) 2-(2,6-dimethyl-3,4-dihydro-1H-pyrido[3,4-b]indol-9(2H)-yl)acetic acid is obtained. The treatment of this acid with DCC or other standard coupling reagents with 3-methylbutan-1-ol gives compound 19 isopentyl 2-(2,6-dimethyl-3,4-dihydro-1H-pyrido[3,4-b]indol-9(2H)-yl)acetate. After the successful synthesis of the compound, purification can be achieved using standard normal phase or reverse phase methods.

Example 38

Preparation of 4-fluorophenyl 2-(1,2,3,4-tetrahydro-2,6-dimethylpyrido[3,4-b]indol-9-yl)acetate (Compound 20, Scheme V)

The title compound is prepared by following General Methods 1, 3, 4, 5 and 6 by using p-tolylhydrazine hydrochloride, ethyl bromoacetate, and triethylamine (General Method 1), ethyl 2-(1-(4-methylphenyl)hydrazinyl)acetate and 4,4-diethoxy-N-methylbutan-1-amine (General Method 3), ethyl 2-(5-methyl-3-(2-(methylamino)ethyl)-1H-indol-1-yl)acetate, formaldehyde and TFA in acetonitrile (General Method 4), ethyl 2-(6-methyl-1,2,3,4-tetrahydro-2-methylpyrido[3,4-b]indol-9-yl)acetate and NaOH (General Method 5), and 2-(6-methyl-1,2,3,4-tetrahydro-2-methylpyrido[3,4-b]indol-9-yl)acetic acid, 4-fluorophenol and EDCI (General Method 6).

Example 39a

Preparation of methyl 2-(1,2,3,4-tetrahydro-2,6-dimethylpyrido[3,4-b]indol-9-yl)acetate (Compound 21, Scheme V)

The title compound is prepared by following General Methods 1, 3, and 4 by using p-tolylhydrazine hydrochloride, methyl bromoacetate, and triethylamine (General Method 1), methyl 2-(1-(4-methylphenyl)hydrazinyl)acetate and 4,4-diethoxy-N-methylbutan-1-amine (General Method 3), and methyl 2-(5-methyl-3-(2-(methylamino)ethyl)-1H-indol-1-yl)acetate, formaldehyde and TFA in acetonitrile (General Method 4).

Example 39b

Preparation of Compound 21

2-(2,6-dimethyl-3,4-dihydro-1H-pyrido[3,4-b]indol-9(2H)-yl)acetic acid (50 mg, 0.19 mmol) was dissolved in dichloromethane (3 mL) and cooled to 0° C. Oxalyl chloride (0.03 mL, 0.23 mmol) was added drop-wise followed by catalytic amount of N,N-dimethylformamide, and the reaction mixture was stirred at RT for 1 h. Oxalyl chloride was evaporated under reduced pressure to obtain the corresponding acid chloride. A solution of isoamyl alcohol (0.02 g, 0.23 mmol) and 4-dimethylaminopyridine (26 mg, 0.21 mmol) in dichloromethane (previously stirred at RT for 1 h) was added drop-wise to the acid chloride. The progress of the reaction was monitored by LCMS. After completion of the reaction, the reaction mixture was quenched with ice water and extracted with dichloromethane. The organic layer was washed with aq. sodium bicarbonate solution, dilute HCl solution, dried over anhydrous sodium sulfate, evaporated under reduced pressure and purified by reverse phase chromatography to yield methyl 2-(2,6-dimethyl-3,4-dihydro-1H-pyrido[3,4-b]indol-9(2H)-yl)acetate as TFA salt (2 mg). $^1$H NMR (CD$_3$OD): 7.3 (s, 1H), 7.2 (d, 1H), 7.0 (d, 1H), 5.0 (m, 2H), 4.5 (s, 2H), 4.1 (m, 1H), 3.9 (m, 1H), 3.8 (s, 3H), 3.5 (s, 3H), 3.2 (m, 2H), 2.5 (s, 3H).

Example 40

Preparation of cyclohexyl 2-(1,2,3,4-tetrahydro-2,6-dimethylpyrido[3,4-b]indol-9-yl)acetate (Compound 22, Scheme V)

The title compound is prepared by following General Methods 1, 3, 4, 5 and 6 by using p-tolylhydrazine hydrochloride, ethyl bromoacetate, and triethylamine (General Method 1), ethyl 2-(1-(4-methylphenyl)hydrazinyl)acetate and 4,4-diethoxy-N-methylbutan-1-amine (General Method 3), ethyl 2-(5-methyl-3-(2-(methylamino)ethyl)-1H-indol-1-yl)acetate, formaldehyde and TFA in acetonitrile (General Method 4), ethyl 2-(6-methyl-1,2,3,4-tetrahydro-2-methylpyrido[3, 4-b]indol-9-yl)acetate and NaOH (General Method 5), and 2-(6-methyl-1,2,3,4-tetrahydro-2-methylpyrido[3,4-b]indol-9-yl)acetic acid, cyclohexanol and EDCI (General Method 6).

Example 41

Preparation of isopropyl 2-(1,2,3,4-tetrahydro-2,6-dimethylpyrido[3,4-b]indol-9-yl)acetate (Compound 23, Scheme V)

The title compound is prepared by following General Methods 1, 3, 4, 5 and 6 by using p-tolylhydrazine hydrochloride, ethyl bromoacetate, and triethylamine (General Method 1), ethyl 2-(1-(4-methylphenyl)hydrazinyl)acetate and 4,4-diethoxy-N-methylbutan-1-amine (General Method 3), ethyl 2-(5-methyl-3-(2-(methylamino)ethyl)-1H-indol-1-yl)acetate, formaldehyde and TFA in acetonitrile (General Method 4), ethyl 2-(6-methyl-1,2,3,4-tetrahydro-2-methylpyrido[3,4-b]indol-9-yl)acetate and NaOH (General Method 5), and 2-(6-methyl-1,2,3,4-tetrahydro-2-methylpyrido[3,4-b]indol-9-yl)acetic acid, isopropanol and EDCI (General Method 6).

Example 42

Preparation of 2-(7-chloro-1,2,3,4-tetrahydro-2-methylpyrido[3,4-b]indol-9-yl)-N-isopentyl-N-methylacetamide (Compound 24, Scheme IV)

The title compound is prepared by following General Methods 1, 3, 4, 5 and 7 by using 3-chlorophenylhydrazine hydrochloride, ethyl bromoacetate, and triethylamine (General Method 1), ethyl 2-(1-(3-chlorophenyl)hydrazinyl)acetate and 4,4-diethoxy-N-methylbutan-1-amine (General Method 3), ethyl 2-(6-chloro-3-(2-(methylamino)ethyl)-1H-indol-1-yl)acetate, formaldehyde and TFA in acetonitrile (General Method 4), ethyl 2-(7-chloro-1,2,3,4-tetrahydro-2-methylpyrido[3,4-b]indol-9-yl)acetate and NaOH (General Method 5), and 2-(7-chloro-1,2,3,4-tetrahydro-2-methylpyrido[3,4-b]indol-9-yl)acetic acid, N,3-dimethylbutan-1-amine and EDCI (General Method 7).

Example 43

Preparation of 2-(5-chloro-1,2,3,4-tetrahydro-2-methylpyrido[3,4-b]indol-9-yl)-N-(4-fluorophenyl)acetamide (Compound 25, Scheme IV)

The title compound is prepared by following General Methods 1, 3, 4, 5 and 7 by using 3-chlorophenylhydrazine hydrochloride, ethyl bromoacetate, and triethylamine (General Method 1), ethyl 2-(1-(3-chlorophenyl)hydrazinyl)acetate and 4,4-diethoxy-N-methylbutan-1-amine (General Method 3), ethyl 2-(4-chloro-3-(2-(methylamino)ethyl)-1H-indol-1-yl)acetate, formaldehyde and TFA in acetonitrile (General Method 4), ethyl 2-(5-chloro-1,2,3,4-tetrahydro-2-methylpyrido[3,4-b]indol-9-yl)acetate and NaOH (General Method 5), and 2-(5-chloro-1,2,3,4-tetrahydro-2-methylpyrido[3,4-b]indol-9-yl)acetic acid, 4-fluoroaniline and EDCI (General Method 7).

Example 44

Preparation of cyclohexyl 7-aza-2-(1,2,3,4-tetrahydro-2-methylpyrido[3,4-b]indol-9-yl)acetate (Compound 26, Scheme V)

The title compound is prepared by following General Methods 1, 3, 4, 5 and 6 by using 1-(pyridin-3-yl)hydrazine hydrochloride and ethyl bromoacetate (General Method 1), ethyl 2-(1-(pyridin-3-yl)hydrazinyl)acetate and 4,4-diethoxy-N-methylbutan-1-amine (General Method 3), ethyl 2-(3-(2-(methylamino)ethyl)-1H-pyrrolo[2,3-c]pyridin-1-yl)acetate, formaldehyde and TFA in acetonitrile (General Method 4), ethyl 7-aza-2-(1,2,3,4-tetrahydro-2-methylpyrido[3,4-b]indol-9-yl)acetate and NaOH (General Method 5), and 7-aza-2-(1,2,3,4-tetrahydro-2-methylpyrido[3,4-b]indol-9-yl)acetic acid, cyclohexanol and EDCI (General Method 6).

Example 45

Preparation of isopropyl 8-aza-2-(1,2,3,4-tetrahydro-2-methylpyrido[3,4-b]indol-9-yl)acetate (Compound 27, Scheme V)

The title compound is prepared by following General Methods 1, 3, 4, 5 and 6 by using 1-(pyridin-2-yl)hydrazine hydrochloride and ethyl bromoacetate (General Method 1), ethyl 2-(1-(pyridin-2-yl)hydrazinyl)acetate and 4,4-diethoxy-N-methylbutan-1-amine (General Method 3), ethyl 2-(3-(2-(methylamino)ethyl)-1H-pyrrolo[2,3-b]pyridin-1-yl)acetate, formaldehyde and TFA in acetonitrile (General Method 4), ethyl 8-aza-2-(1,2,3,4-tetrahydro-2-methylpyrido[3,4-b]indol-9-yl)acetate and NaOH (General Method 5), and 8-aza-2-(1,2,3,4-tetrahydro-2-methylpyrido[3,4-b]indol-9-yl)acetic acid, isopropanol and EDCI (General Method 6).

Example 46

Preparation of 5-aza-N-cyclohexyl-2-(1,2,3,4-tetrahydro-2-methylpyrido[3,4-b]indol-9-yl)-N-methylacetamide (Compound 28, Scheme IV)

The title compound is prepared by following General Methods 1, 3, 4, 5 and 7 by using 1-(pyridin-3-yl)hydrazine hydrochloride and ethyl bromoacetate (General Method 1), ethyl 2-(1-(pyridin-3-yl)hydrazinyl)acetate and 4,4-diethoxy-N-methylbutan-1-amine (General Method 3), ethyl 2-(3-(2-(methylamino)ethyl)-1H-pyrrolo[3,2-b]pyridin-1-yl)acetate, formaldehyde and TFA in acetonitrile (General Method 4), ethyl 5-aza-2-(1,2,3,4-tetrahydro-2-methylpyrido[3,4-b]indol-9-yl)acetate and NaOH (General Method 5), and 5-aza-2-(1,2,3,4-tetrahydro-2-methylpyrido[3,4-b]indol-9-yl)acetic acid, N-methylcyclohexylamine and EDCI (General Method 7).

Example 47a

Preparation of 6-chloro-2,3,4,9-tetrahydro-2-methyl-9-(3-phenylpropyl)-1H-pyrido[3,4-b]indole (Compound 29, Scheme I)

The title compound was prepared by following General Methods 2, 3 and 4 using 4-chlorophenylhydrazine hydrochloride, 1-(3-bromopropyl)benzene, and tetra-n-butylammonium chloride (General Method 2), 1-(4-chlorophenyl)-1-(3-phenylpropyl)hydrazine (Example 9) and 4,4-diethoxy-N-methylbutan-1-amine (General Method 3) and 2-(5-chloro-1-(3-phenylpropyl)-1H-indol-3-yl)-N-methylethanamine (Example 18), formaldehyde and TFA in acetonitrile (General Method 4).

(A) N-(4-Chloro-phenyl)-N-(3-phenyl-propyl)-hydrazine

4-Chlorophenylhydrazine hydrochloride (550 mg, 3 mmol) was added to a vigorously stirred mixture of tetra-n- butylammonium chloride (42 mg, 0.15 mmol) in 50% aqueous sodium hydroxide (3 mL) followed by 1-bromo-3-phenylpropane (670 mg, 3.3 mmol). The reaction was heated to 60° C. (oil bath temperature) for 6 h. The reaction was cooled and diluted with water (30 mL) and extracted with chloroform (3×10 mL). The combined organic layer was dried (Na$_2$SO$_4$), filtered and concentrated under reduced pressure to a dark red oil (690 mg). The oil was subjected to column chromatography (silica gel, eluent: 50% dichloromethane in hexane followed by 100% dichloromethane) to give a dark yellow oil (154 mg, 20%).

(B) {2-[5-Chloro-1-(3-phenyl-propyl)-1H-indol-3-yl]-ethyl}-methyl-amine

28% aqueous HCl (0.07 mL, 0.54 mmol) was added to a solution of N-(4-Chloro-phenyl)-N-(3-phenyl-propyl)-hydrazine (261 mg, 1 mmol) in ethanol (1 mL) and water (0.5 mL) under a nitrogen atmosphere. The reaction was heated to 60° C. (oil bath temperature) and 4,4-diethoxy-N-methylbutan-1-amine (175 mg, 1 mmol) was added. The reaction was heated to 90° C. and 28% aqueous HCl (0.08 mL, 0.61 mmol) was added. The reaction was heated at reflux for 6 h. More 4,4-diethoxy-N-methylbutan-1-amine (90 mg, 0.51 mmol) was added at 60° C. and more 28% aqueous HCl (0.19 mL, 1.46 mmol) was added at 90° C. The reaction was heated to reflux for a further 8 h. The reaction was cooled and concentrated under reduced pressure. The red-brown residue was subjected to column chromatography (silica gel, eluent: EtOAc followed by EtOAc:EtOH:NH$_4$OH 90:10:1) to give a brown oil (243 mg, 74%).

(C) 6-chloro-2,3,4,9-tetrahydro-2-methyl-9-(3-phenylpropyl)-1H-pyrido[3,4-b]indole 37% aqueous formaldehyde (59 mg, 0.73 mmol) in acetonitrile (1 mL) was added to a refluxing solution of 2-[5-Chloro-1-(3-phenyl-propyl)-1H-indol-3-yl]-ethyl}-methyl-amine (216 mg, 0.66 mmol) in 5% trifluoroacetic acid in acetonitrile (6.6 mL) under a nitrogen atmosphere. The reaction was refluxed for 2 h. The reaction was cooled and concentrated under reduced pressure. The resulting dark red residue was azeotroped with heptane, then dissolved in ethyl acetate (50 mL) and washed with saturated aqueous sodium hydrogen carbonate (10 mL). The organic layer was dried (Na$_2$SO$_4$), filtered and concentrated under reduced pressure to a dark brown gum (220 mg). The gum was purified by column chromatography (silica gel, eluent: EtOAc followed by EtOAc:EtOH:NH$_4$OH 98:2:0.2) to give a brown oil (136 mg, 61%). The free base was converted to the hydrochloride by dissolving the solid in anhydrous diethyl ether (~30 mL) under a nitrogen atmosphere and filtering, 2M hydrochloride in diethyl ether (0.25 mL, 0.5 mmol) was added to the filtrate under a nitrogen atmosphere to form a precipitate. The solvent was removed under reduced pressure. The residue was triturated with anhydrous diethyl ether which was removed under a reduced pressure to give the resulting hydrochloride (151 mg, 100%) as a pink-buff solid.

Example 47b

Preparation of Compound 29

37% aqueous formaldehyde (59 mg, 0.73 mmol) in acetonitrile (1 mL) was added to a refluxing solution of 2-[5-Chloro-1-(3-phenyl-propyl)-1H-indol-3-yl]-ethyl}-methyl-amine (216 mg, 0.66 mmol) in 5% trifluoroacetic acid in acetonitrile (6.6 mL) under a nitrogen atmosphere and refluxed for an additional 2 h. The reaction was cooled and concentrated under reduced pressure. The resulting dark red residue was azeotroped with heptane, dissolved in ethyl acetate (50 mL) and washed with saturated aqueous sodium hydrogen carbonate (10 mL). The organic layer was dried (Na$_2$SO$_4$), filtered and concentrated under reduced pressure to a dark brown gum (220 mg). The gum was purified by column chromatography (silica gel, eluent: EtOAc followed by EtOAc: EtOH: NH$_4$OH 98:2:0.2) to yield a brown oil (136 mg, 61%). The free base was converted to the hydrochloride by dissolving the solid in anhydrous diethyl ether (~30 mL) under a nitrogen atmosphere and filtering. 2 M HCl solution in diethyl ether (0.25 mL, 0.5 mmol) was added to the filtrate under a nitrogen atmosphere to form a precipitate. The solvent was removed under reduced pressure. The residue was triturated with anhydrous diethyl ether which was removed under a reduced pressure to yield the resulting hydrochloride (151 mg, 100%) as a pink-buff solid. $^1$H NMR (DMSO): 11.4 (bs, 1H), 7.6 (s, 1H), 7.5 (d, 1H), 7.15-7.45 (m, 6H), 4.7-4.6 (bs, 1H), 4.4-4.3 (bs, 1H), 4.1 (m, 2H), 3.7 (bs, 1H), 3.3 (bs, 1H), 3.1-3.0 (m, 2H), 2.9 (s, 3H), 2.6 (t, 2H), 2.0 (t, 2H).

Example 48

Preparation of 6-chloro-2,3,4,9-tetrahydro-2-methyl-9-(3-(pyridin-3-yl)propyl)-1H-pyrido[3,4-b]indole (Compound 30, Scheme I)

The title compound is prepared by following General Methods 1, 3 and 4 using 4-chlorophenylhydrazine hydrochloride, 3-(3-bromopropyl)pyridine, and triethylamine (General Method 1), 1-(4-chlorophenyl)-1-(3-(pyridin-3-yl)propyl)hydrazine and 4,4-diethoxy-N-methylbutan-1-amine (General Method 3) and 2-(5-chloro-1-(3-(pyridin-3-yl)propyl)-1H-indol-3-yl)-N-methylethanamine, formaldehyde and TFA in acetonitrile (General Method 4).

Example 49

Preparation of 6-chloro-9-(3-(4-fluorophenyl)propyl)-2,3,4,9-tetrahydro-2-methyl-1H-pyrido[3,4-b]indole (Compound 31, Scheme I)

The title compound is prepared by following General Methods 1, 3 and 4 using 4-chlorophenylhydrazine hydrochloride, 1-(3-bromopropyl)-4-fluorobenzene, and triethylamine (General Method 1), 1-(4-chlorophenyl)-1-(3-(4-fluorophenyl)propyl)hydrazine and 4,4-diethoxy-N-methylbutan-1-amine (General Method 3) and 2-(5-chloro-1-(3-(4-fluorophenyl)propyl)-1H-indol-3-yl)-N-methylethanamine, formaldehyde and TFA in acetonitrile (General Method 4).

Example 50

Preparation of 6-chloro-9-(3-(6-(trifluoromethyl)pyridin-3-yl)propyl)-2,3,4,9-tetrahydro-2-methyl-1H-pyrido[3,4-b]indole (Compound 32, Scheme I)

The title compound is prepared by following General Methods 1, 3 and 4 using 4-chlorophenylhydrazine hydrochloride, 5-(3-bromopropyl)-2-(trifluoromethyl)pyridine, and triethylamine (General Method 1), 1-(4-chlorophenyl)-1-(3-(6-(trifluoromethyl)pyridin-3-yl)propyl)hydrazine and 4,4-diethoxy-N-methylbutan-1-amine (General Method 3) and 2-(5-chloro-1-(3-(6-(trifluoromethyl)pyridin-3-yl)propyl)-1H-indol-3-yl)-N-methylethanamine, formaldehyde and TFA in acetonitrile (General Method 4).

Example 51

Preparation of 2,3,4,9-tetrahydro-2,6-dimethyl-9-(3-(6-methylpyridin-3-yl)propyl)-1H-pyrido[3,4-b]indole (Compound 33, Scheme I)

The title compound is prepared by following General Methods 1, 3 and 4 using 4-chlorophenylhydrazine hydrochloride, 5-(3-bromopropyl)-2-methylpyridine, and triethylamine (General Method 1), 1-(3-(6-methylpyridin-3-yl)propyl)-1-p-tolylhydrazine and 4,4-diethoxy-N-methylbutan-1-amine (General Method 3) and N-methyl-2-(5-methyl-1-(3-(6-methylpyridin-3-yl)propyl)-1H-indol-3-yl)ethanamine, formaldehyde and TFA in acetonitrile (General Method 4).

Example 52a

Preparation of 6-chloro-2,3,4,9-tetrahydro-2-methyl-9-(2-(piperidin-1-yl)ethyl)-1H-pyrido[3,4-b]indole (Compound 34, Scheme I)

The title compound was prepared by following General Methods 2, 3 and 4 using 4-chlorophenylhydrazine hydrochloride, 1-(2-chloroethyl)piperidine hydrochloride, and tetra-n-butylammonium chloride (General Method 2), 1-(4-chlorophenyl)-1-(2-(piperidin-1-yl)ethyl)hydrazine (Example 3) and 4,4-diethoxy-N-methylbutan-1-amine (General Method 3) and 2-(5-chloro-1-(2-(piperidin-1-yl)ethyl)-1H-indol-3-yl)-N-methylethanamine (Example 12), formaldehyde and TFA in acetonitrile (General Method 4).

(A) N-(4-Chloro-phenyl)-N-(2-piperidin-1-yl-ethyl)-hydrazine 1-(2-Chloro-ethyl)piperidine (5 g, 27.9 mmol) was added to a vigorously stirred mixture of 4-chlorophenyl hydrazine hydrochloride (5 g, 27.9 mmol) and tetra-n-butylammonium chloride (0.40 g) in 50% aqueous sodium hydroxide (30 mL). The reaction was heated to 80° C. (oil bath temperature) for 3.5 h. The reaction was cooled, diluted with water and extracted with chloroform. The organic layer was washed with brine, dried (MgSO$_4$), filtered and concentrated under reduced pressure to give a red oil. The oil was subjected to column chromatography (silica gel, eluent: 10% methanol in chloroform) to give a red oil (~3 g). This was purified again by column chromatography (silica gel, eluent: 510% methanol in chloroform) to give a red oil (1.77 g, 25%).

(B) {2-[5-Chloro-1-(2-piperidin-1-yl-ethyl)-1H-indol-3-yl]-ethyl}-methyl-amine N-(4-Chloro-phenyl)-N-(2-piperidin-1-yl-ethyl)-hydrazine (1 g, 3.94 mmol) was dissolved in ethyl acetate (3 mL) and 4M hydrochloride in dioxane (23 equiv) was added. The mixture was concentrated under reduced pressure to a brown foam. This was dissolved in a mixture of ethanol (2 mL) and water (4 mL) and heated to 70° C. The 4,4-diethoxy-N-methylbutan-1-amine (0.67 g, 3.94 mmol) was added and then heated to 8090° C. 28% aqueous HCl (0.51 mL, 3.94 mmol) was added and the reaction heated at 80° C. for 4 h. The reaction was concentrated under reduced pressure. The residue was subjected to column chromatography (silica gel, eluent: EtOAc:EtOH:NH$_4$OH 7:3:1) to give a residue (0.80 g). The residue was subjected to column chromatography (silica gel, eluent: EtOAc:EtOH:NH$_4$OH 7:3:1) to give a red oil (0.440 g). The red oil was purified again by column chromatography (silica gel, eluent: EtOAc:EtOH:NH$_4$OH 7:3:1) to give the product (0.30 g, 23%).

(C) 6-chloro-2,3,4,9-tetrahydro-2-methyl-9-(2-(piperidin-1-yl)ethyl)-1H-pyrido[3,4-b]indole {2-[5-Chloro-1-(2-piperidin-1-yl-ethyl)-1H-indol-3-yl]-ethyl}-methyl-amine (0.30 g, 0.93 mmol) in 5% trifluoroacetic acid in acetonitrile (4 mL) was heated to reflux. 37% aqueous formaldehyde (0.1 mL) was added. The reaction was refluxed for 1 h. The reaction was cooled and concentrated under reduced pressure. The resulting oil was dissolved in ethyl acetate and washed with saturated aqueous sodium hydrogen carbonate and brine. The organic layer was dried (MgSO$_4$), filtered and concentrated under reduced pressure to a brown oily solid. The solid was purified by column chromatography (silica gel, eluent: 10% methanol in chloroform) to give the product (0.08 g, 25%). The free base was converted to the hydrochloride by dissolving the product in ethanol (2 mL) and 2M hydrochloride in diethyl ether was added. The solution was concentrated under reduced pressure to an oil. The oil was dissolved in chloroform and a few drops of methanol. The solution was concentrated under reduced pressure to give a solid (0.1 g) as the dihydrochloride salt.

Example 52b

Preparation of Compound 34

{2-[5-Chloro-1-(2-piperidin-1-yl-ethyl)-1H-indol-3-yl]-ethyl}-methyl-amine (0.30 g, 0.93 mmol) in 5% trifluoroacetic acid in acetonitrile (4 mL) was refluxed. 37% aqueous formaldehyde (0.1 mL) was added to the reaction mixture and refluxed for an additional 1 h, cooled and concentrated under reduced pressure. The resulting oil was dissolved in ethyl acetate and washed with saturated sodium hydrogen carbonate and brine solution. The organic layer was dried (MgSO$_4$), filtered and concentrated under reduced pressure to obtain a brown oily solid. The solid was purified by column chromatography (silica gel, eluent: 10% methanol in chloroform) to give the product (0.08 g, 25%). The free base was converted to the hydrochloride by dissolving the product in ethanol (2 mL) and 2M hydrochloride in diethyl ether was added. The solution was concentrated under reduced pressure to oil. The oil was dissolved in chloroform and a few drops of methanol and concentrated under reduced pressure to yield a solid (0.1 g) as the dihydrochloride salt. $^1$H NMR (CD$_3$OD): 7.5 (d, 2H), 7.2 (d, 1H), 4.9 (d, 1H), 4.5 (m, 3H), 3.8 (bs, 1H), 3.5-3.3 (bs, 5H), 3.4 (s, 3H), 3.0 (m, 4H), 1.8 (m, 5H), 1.5 (m, 1H).

Example 53a

Preparation of 6-chloro-9-(2-cyclopentylethyl)-2,3,4,9-tetrahydro-2-methyl-1H-pyrido[3,4-b]indole (Compound 35, Scheme I)

The title compound was prepared by following General Methods 2, 3 and 4 using 4-chlorophenylhydrazine hydrochloride, (2-bromoethyl)cyclopentane, and tetra-n-butylammonium chloride (General Method 2), 1-(4-chlorophenyl)-1-(2-cyclopentylethyl)hydrazine (Example 4) and 4,4-diethoxy-N-methylbutan-1-amine (General Method 3) and 2-(5-chloro-1-(2-cyclopentylethyl)-1H-indol-3-yl)-N-methylethanamine (Example 13), formaldehyde and TFA in acetonitrile (General Method 4).

(A) N-(4-Chloro-phenyl)-N-(2-cyclopentyl-ethyl)-hydrazine

4-Chlorophenylhydrazine hydrochloride (1.65 g, 9 mmol) was added to a vigorously stirred mixture of tetra-n-butylammonium chloride (0.126 g, 0.45 mmol) in 50% aqueous sodium hydroxide (9 mL) followed by (2-bromo-ethyl)-cyclopentane (1.74 g, 9.9 mmol). The reaction was heated to 60° C. (oil bath temperature) for 8 h. The reaction was cooled, diluted with water (75 mL) and extracted with chloroform (3×30 mL). The combined organic layer was dried ($Na_2SO_4$), filtered and concentrated under reduced pressure to an orange oil (0.69 g). The oil was subjected to column chromatography (silica gel, eluent: 50% dichloromethane in hexane followed by 70% dichloromethane in hexane) to give a yellow oil (1.17 g, 55%).

(B) {2-[5-Chloro-1-(2-cyclopentyl-ethyl)-1H-indol-3-yl]-ethyl}-methyl-amine

28% aqueous HCl (0.3 mL, 2.26 mmol) was added to a solution of N-(4-Chloro-phenyl)-N-(2-cyclopentyl-ethyl)-hydrazine (0.54 g, 2.26 mmol) in ethanol (2.5 mL) and water (1 mL) under a nitrogen atmosphere. The reaction was heated to 60° C. (oil bath temperature) and 4,4-diethoxy-N-methylbutan-1-amine (0.32 g, 1.84 mmol) was added. The reaction was heated to reflux and 28% aqueous HCl (0.15 mL, 1.13 mmol) was added. The reaction was heated at reflux for 2.5 h. The reaction was cooled to 60° C. and then more 4,4-diethoxy-N-methylbutan-1-amine (0.32 g, 1.84 mmol) was added. The reaction was heated to reflux and then more 28% aqueous HCl (0.15 mL, 1.13 mmol) was added. The reaction was heated to reflux for a further 3.5 h. The reaction was cooled and concentrated under reduced pressure. The red brown residue was subjected to column chromatography (silica gel, eluent: EtOAc followed by EtOAc:EtOH:$NH_4OH$ 90:10:1) to give the product (0.318 g, 46%).

(C) 6-chloro-9-(2-cyclopentylethyl)-2,3,4,9-tetrahydro-2-methyl-1H-pyrido[3,4-b]indole 37% aqueous formaldehyde (69 mg, 0.85 mmol) in acetonitrile (1 mL) was added to a refluxing solution of {2-[5-Chloro-1-(2-cyclopentyl-ethyl)-1H-indol-3-yl]-ethyl}-methyl-amine (283 mg, 0.77 mmol) in 5% trifluoroacetic acid in acetonitrile (5 mL) under a nitrogen atmosphere. The reaction was refluxed for 1.5 h. The reaction was cooled and concentrated under reduced pressure. The resulting dark red residue azeotroped with acetonitrile then dissolved in ethyl acetate (50 mL) and washed with saturated aqueous sodium hydrogen carbonate (20 mL). The organic layer was dried ($Na_2SO_4$), filtered and concentrated under reduced pressure to a dark residue (~400 mg). The residue was purified by column chromatography (silica gel, eluent: EtOAc followed by EtOAc:EtOH:$NH_4OH$ 98:2:0.2) to give a brown oil (198 mg, 81%). The free base was converted to the hydrochloride by dissolving the solid in anhydrous diethyl ether (~30 mL) under a nitrogen atmosphere and filtering, 2M hydrochloride in diethyl ether (0.35 mL, 0.7 mmol) was added to the filtrate under a nitrogen atmosphere to form a precipitate. The solvent was removed under reduced pressure and the residue triturated with anhydrous diethyl ether which was removed under a reduced pressure and dried in vacuo over $P_2O_5$ to give the hydrochloride (183 mg) as an off-white solid.

Example 53b

Preparation of Compound 35

37% aqueous formaldehyde (69 mg, 0.85 mmol) in acetonitrile (1 mL) was added to a refluxing solution of {2-[5-Chloro-1-(2-cyclopentyl-ethyl)-1H-indol-3-yl]-ethyl}-methyl-amine (283 mg, 0.77 mmol) in 5% trifluoroacetic acid in acetonitrile (5 mL) under a nitrogen atmosphere. The reaction mixture was refluxed for 1.5 h, cooled and concentrated under reduced pressure. The resulting dark red residue was azeotroped with acetonitrile and dissolved in ethyl acetate (50 mL) and washed with saturated aqueous sodium hydrogen carbonate (20 mL). The organic layer was dried ($Na_2SO_4$), filtered and concentrated under reduced pressure to a dark residue (~400 mg). The residue was purified by column chromatography (silica gel, eluent: EtOAc followed by EtOAc:EtOH:$NH_4OH$ 98:2:0.2) to give a brown oil (198 mg, 81%). The free base was converted to the hydrochloride by dissolving the solid in anhydrous diethyl ether (approx. 30 mL) under a nitrogen atmosphere and filtered. 2M HCl solution in diethyl ether (0.35 mL, 0.7 mmol) was added to the filtrate under a nitrogen atmosphere to form a precipitate. The solvent was removed under reduced pressure and the residue triturated with anhydrous diethyl ether which was removed under a reduced pressure and dried in vacuo over $P_2O_5$ to give the hydrochloride (183 mg) as an off-white solid. $^1$H NMR (DMSO): 10.84 (bs, 1H), 7.6 (s, 1H), 7.55 (d, 1H), 7.2 (d, 1H) 4.7 (bs, 1H), 4.4 (bs, 1H), 4.1 (bs, 2H), 3.8-3.4 (m, 4H), 3.0 (s, 3H), 1.1-1.8 (m, 11H).

Example 54

Preparation of 6-chloro-2,3,4,9-tetrahydro-2-methyl-9-(2-(3,3-dimethylcyclopentyl)ethyl)-1H-pyrido[3,4-b]indole (Compound 36, Scheme I)

The title compound is prepared by following General Methods 1, 3 and 4 using 4-chlorophenylhydrazine hydrochloride, 3-(2-bromoethyl)-1,1-dimethylcyclopentane, and triethylamine (General Method 1), 1-(4-chlorophenyl)-1-(2-(3,3-dimethylcyclopentyl)ethyl)hydrazine and 4,4-diethoxy-N-methylbutan-1-amine (General Method 3) and 2-(5-chloro-1-(2-(3,3-dimethylcyclopentyl)ethyl)-1H-indol-3-yl)-N-methylethanamine (Example 14), formaldehyde and TFA in acetonitrile (General Method 4).

Example 55

Preparation of 6-chloro-2,3,4,9-tetrahydro-2-methyl-9-(2-(piperazin-1-yl)ethyl)-1H-pyrido[3,4-b]indole (Compound 37, Scheme I)

The title compound is prepared by following General Methods 1, 3 and 4 using 4-chlorophenylhydrazine hydrochloride, tert-butyl 4-(2-bromoethyl)piperazine-1-carboxylate, and triethylamine (General Method 1), N-Boc-1-(4-chlorophenyl)-1-(2-(piperazin-1-yl)ethyl)hydrazine and 4,4-diethoxy-N-methylbutan-1-amine (General Method 3), tert-butyl 4-(2-(5-chloro-3-(2-(methylamino)ethyl)-1H-indol-1-yl)ethyl)piperazine-1-carboxylate, formaldehyde and TFA in acetonitrile (General Method 4), and Boc deprotection by using TFA/dichloromethane.

Example 56a

Preparation of 2-(6-chloro-1,2,3,4-tetrahydro-2-methylpyrido[3,4-b]indol-9-yl)-1-(4-methylpiperidin-1-yl)ethanone (Compound 38, Scheme IV)

The title compound is prepared by following General Methods 1, 3, and 4 by using 4-chlorophenylhydrazine hydrochloride, 1-(N-bromoacetyl)-4-methyl piperidine, and triethylamine (General Method 1), 2-(1-(4-chlorophenyl)hydrazinyl)-1-(4-methylpiperidin-1-yl)ethanone and 4,4-diethoxy-N-methylbutan-1-amine (General Method 3), 2-(5-chloro-3-(2-(methylamino)ethyl)-1H-indol-1-yl)-1-(4-methylpiperidin-1-yl)ethanone, formaldehyde and TFA in acetonitrile (General Method 4).

(A) 2-[N-(4-Chloro-phenyl)-hydrazino]-1-(4-methyl-piperidin-1-yl)-ethanone

Triethylamine (1.8 ml, 12.91 mmol) was added to a suspension of 4-chlorophenyl hydrazine hydrochloride (0.8 g, 4.54 mmol) in ethanol (7 mL). The reaction mixture was stirred for 10 min. 1-(N-Bromoacetyl)-4-methyl piperidine (1 g, 4.54 mmol) was added and the reaction was heated to reflux for 5 h. The reaction mixture was concentrated under reduced pressure and the residue partitioned between chloroform and water. The organic layer was separated, dried ($MgSO_4$), filtered and concentrated to an orange oil. Purification of the product by column chromatography (silica gel, eluent: 2% methanol in chloroform) gave of the correct isomer (0.5 g, 39%).

(B) 2-[5-Chloro-3-(2-methylamino-ethyl)-indol-1-yl]-1-(4-methyl-piperidin-1-yl)-ethanone 2-[N-(4-Chloro-phenyl)-hydrazino]-1-(methyl-piperidin-1-yl)-ethanone (0.75 g, 2.66 mmol) was dissolved in ethyl acetate (3 mL) and 4M hydrochloride in dioxane (0.7 mL) was added. The mixture was concentrated under reduced pressure to a glassy oil/foam. This was dissolved in a mixture of ethanol (4 mL) and water (2 mL) and heated to 60° C. The 4,4-diethoxy-N-methylbutan-1-amine (0.47 g, 2.68 mmol) was added and then heated to 7080° C. 28% aqueous HCl (0.35 mL, 2.66 mmol) was added and the reaction heated at 80° C. for 1 h. More 4,4-diethoxy-N-methylbutan-1-amine (0.2 g, 1.14 mmol) and 28% aqueous HCl (0.3 mL, 2.30 mmol) was added and heated for a further 3 h. Further 4,4-diethoxy-N-methylbutan-1-amine (0.3 g, 1.71 mmol) was added and heated for a further 6 h. The reaction was concentrated under reduced pressure to give a dark brown oil. The oil was subjected to column chromatography (silica gel, eluent: EtOAc:EtOH:$NH_4OH$ 7:3:1) to give a brown oil (0.29 g). Further purification of the brown oil by column chromatography (silica gel, eluent: EtOAc:EtOH:$NH_4OH$ 7:3:1) gave pure product (179 mg, 19%).

(C)-2-(6-Chloro-2-methyl-1,2,3,4-tetrahydro-β-carbolin-9-yl)-1-(4-methyl-piperidin-1-yl)-ethanone 2-[5-Chloro-3-(2-methylamino-ethyl)-indol-1-yl]-1-(4-methyl-piperidin-1-yl)-ethanone (160 mg, 0.46 mmol) in 5% trifluoroacetic acid in acetonitrile (3 mL) was heated to reflux. 37% aqueous formaldehyde (0.06 mL) was added. The reaction was refluxed for 10 min. The reaction was cooled and concentrated under reduced pressure. The resulting oil was dissolved in ethyl acetate and washed with saturated aqueous sodium hydrogen carbonate and brine. The organic layer was dried ($MgSO_4$), filtered and concentrated under reduced pressure to give a yellow solid. The solid was purified using the Waters Preparative LC-MS to give the product (50 mg, 30%). The free base was converted to the hydrochloride by dissolving the product in methanol (4 mL) and 2M hydrochloride in diethyl ether was added. The solution was concentrated under reduced pressure to give a buff solid (50 mg). Further drying under high vacuum gave the hydrochloride salt (25 mg, 13.7%).

Example 56b

Preparation of Compound 38

2-[5-Chloro-3-(2-methylamino-ethyl)-indol-1-yl]-1-(4-methyl-piperidin-1-yl)-ethanone (160 mg, 0.46 mmol) in 5% trifluoroacetic acid in acetonitrile (3 mL) was refluxed. 37% aqueous formaldehyde (0.06 mL) was added to the reaction and refluxed for additional 10 min, cooled and concentrated under reduced pressure. The resulting oil was dissolved in ethyl acetate and washed with saturated aqueous sodium hydrogen carbonate and brine. The organic layer was dried ($MgSO_4$), filtered and concentrated under reduced pressure to give a yellow solid. The solid was purified using the Water s Preparative HPLC to yield the product (50 mg, 30%). The free base was converted to the hydrochloride by dissolving the product in methanol (4 mL) and 2M hydrochloride in diethyl ether was added. The solution was concentrated under reduced pressure to give a buff solid (50 mg). Further drying under high vacuum gave the hydrochloride salt (25 mg, 13.7%). $^1$H NMR ($CD_3OD$): 7.6 (s, 1H), 7.39-7.46 (d, 1H), 7.2-7.3 (d, 1H), 5.2-5.35 (q, 2H), 4.5-4.6 (d, 3H), 4.1-4.2 (d, 1H), 3.7-3.85 (bs, 2H), 3.18-3.3 (m, 6H), 2.72-2.84 (t, 1H), 1.85-1.95 (q, 4H), 1.1-1.4 (m, 1H), 1.1 (d, 3H).

Example 57

Preparation of 2-(6-chloro-1,2,3,4-tetrahydro-2-methylpyrido[3,4-b]indol-9-yl)-1-(4-methylpiperazin-1-yl)ethanone (Compound 39, Scheme IV)

The title compound is prepared by following General Methods 1, 3, 4, 5 and 7 by using 4-chlorophenylhydrazine hydrochloride, ethyl bromoacetate, and triethylamine (General Method 1), ethyl 2-(1-(4-chlorophenyl)hydrazinyl)acetate and 4,4-diethoxy-N-methylbutan-1-amine (General Method 3), ethyl 2-(5-chloro-3-(2-(methylamino)ethyl)-1H-indol-1-yl)acetate, formaldehyde and TFA in acetonitrile (General Method 4), ethyl 2-(6-chloro-1,2,3,4-tetrahydro-2-methylpyrido[3,4-b]indol-9-yl)acetate and NaOH (General Method 5), and 2-(6-chloro-1,2,3,4-tetrahydro-2-methylpyrido[3,4-b]indol-9-yl)acetic acid, N-methylpiperazine and EDCI (General Method 7).

Example 58a

Preparation of 2-(6-chloro-1,2,3,4-tetrahydro-2-methylpyrido[3,4-b]indol-9-yl)-1-(pyrrolidin-1-yl)ethanone (Compound 40, Scheme IV)

The title compound is prepared by following General Methods 1, 3, 4, 5 and 7 by using 4-chlorophenylhydrazine hydrochloride, ethyl bromoacetate, and triethylamine (General Method 1), ethyl 2-(1-(4-chlorophenyl)hydrazinyl)acetate and 4,4-diethoxy-N-methylbutan-1-amine (General Method 3), ethyl 2-(5-chloro-3-(2-(methylamino)ethyl)-1H-indol-1-yl)acetate, formaldehyde and TFA in acetonitrile (General Method 4), ethyl 2-(6-chloro-1,2,3,4-tetrahydro-2-methylpyrido[3,4-b]indol-9-yl)acetate and NaOH (General Method 5), and 2-(6-chloro-1,2,3,4-tetrahydro-2-methylpyrido[3,4-b]indol-9-yl)acetic acid, pyrrolidine and EDCI (General Method 7).

Example 58b

Preparation of Compound 40

2-(6-chloro-2-methyl-3,4-dihydro-1H-pyrido[3,4-b]indol-9(2H)-yl)acetic acid (0.1 g, 0.35 mmol) was dissolved in dichloromethane (4 mL) and cooled to 0° C., using an ice-bath; followed by drop-wise addition of oxalyl chloride (0.054 g, 0.43 mmol) to the reaction mixture. A catalytic amount (1 drop) of dimethyl formamide was added and the reaction mixture was stirred for 1 h at room temperature. Excess oxalyl chloride was distilled away under reduced pressure. A solution of pyrrolidine (0.031 g, 0.43 mmol) in dichloromethane (2 mL) and 4-dimethylaminopyridine (0.044 g, 0.35 mmol) was added to this residue, under nitrogen at room temperature and stirred for 30 min. The reaction mixture was quenched with water and extracted with dichloromethane (2×10 mL). The combined organic layer was washed with NaHCO$_3$ solution followed by HCl, dried over sodium sulfate and concentrated under reduced pressure to yield 2-(6-chloro-2-methyl-3,4-dihydro-1H-pyrido[3,4-b]indol-9(2H)-yl)-1-(pyrrolidin-1-yl)ethanone as a TFA salt (10 mg) after purification by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL). 1 H NMR (CD$_3$OD): 7.5 (s, 1H), 7.3 (d, 1H), 7.19 (d, 1H), 5.2-5.1 (m, 1H), 5.0-4.9 (m, 1H), 4.4 (s, 2H), 4.3-4.2 (m, 2H), 4.0-3.9 (m, 2H), 3.5 (s, 3H), 3.4 (t, 2H), 3.2-3.1 (bs, 2H), 2.05-1.9 (m, 4H).

Example 59

Preparation of 2-(6-chloro-1,2,3,4-tetrahydro-2-methylpyrido[3,4-b]indol-9-yl)-1-(3,3,4-trimethylpiperazin-1-yl)ethanone (Compound 41, Scheme IV)

The title compound is prepared by following General Methods 1, 3, 4, 5 and 7 by using 4-chlorophenylhydrazine hydrochloride, ethyl bromoacetate, and triethylamine (General Method 1), ethyl 2-(1-(4-chlorophenyl)hydrazinyl)acetate and 4,4-diethoxy-N-methylbutan-1-amine (General Method 3), ethyl 2-(5-chloro-3-(2-(methylamino)ethyl)-1H-indol-1-yl)acetate, formaldehyde and TFA in acetonitrile (General Method 4), ethyl 2-(6-chloro-1,2,3,4-tetrahydro-2-methylpyrido[3,4-b]indol-9-yl)acetate and NaOH (General Method 5), and 2-(6-chloro-1,2,3,4-tetrahydro-2-methylpyrido[3,4-b]indol-9-yl)acetic acid, 1,2,2-trimethylpiperazine and EDCI (General Method 7).

Example 60

Preparation of 2-(1,2,3,4-tetrahydro-2,5-dimethylpyrido[3,4-b]indol-9-yl)-1-(piperidin-1-yl)ethanone (Compound 42, Scheme IV)

The title compound is prepared by following General Methods 1, 3, 4, 5 and 7 by using m-tolylhydrazine hydrochloride, ethyl bromoacetate, and triethylamine (General Method 1), ethyl 2-(1-m-tolylhydrazinyl)acetate and 4,4-diethoxy-N-methylbutan-1-amine (General Method 3), ethyl 2-(4-methyl-3-(2-(methylamino)ethyl)-1H-indol-1-yl)acetate, formaldehyde and TFA in acetonitrile (General Method 4), ethyl 2-(1,2,3,4-tetrahydro-2,5-dimethylpyrido[3,4-b]indol-9-yl)acetate and NaOH (General Method 5), and 2-(1,2,3,4-tetrahydro-2,5-dimethylpyrido[3,4-b]indol-9-yl)acetic acid, piperidine and EDCI (General Method 7).

Example 61a

Preparation of 3-(1,2,3,4-tetrahydro-2,6-dimethylpyrido[3,4-b]indol-9-yl)-1-(piperidin-1-yl)propan-1-one (Compound 43, Scheme IV)

The title compound is prepared by following General Methods 1, 3, 4, 5 and 7 by using p-tolylhydrazine hydrochloride, ethyl 3-bromopropionate, and triethylamine (General Method 1), ethyl 3-(1-p-tolylhydrazinyl)propanoate and 4,4-diethoxy-N-methylbutan-1-amine (General Method 3), ethyl 3-(5-methyl-3-(2-(methylamino)ethyl)-1H-indol-1-yl)propanoate, formaldehyde and TFA in acetonitrile (General Method 4), ethyl 3-(1,2,3,4-tetrahydro-2,6-dimethylpyrido[3,4-b]indol-9-yl)propanoate and NaOH (General Method 5), and 3-(1,2,3,4-tetrahydro-2,6-dimethylpyrido[3,4-b]indol-9-yl)propanoic acid, piperidine and EDCI (General Method 7).

Example 61b

Preparation of Compound 43

2,6-dimethyl-2,3,4,9-tetrahydro-1H-pyrido[3,4-b]indole (100 mg, 0.5 mmol), tetra n-butyl ammonium chloride (7 mg, 0.0025 mmol) and 1-(piperidin-1-yl)prop-2-en-1-one (76 mg, 0.55 mmol) was dissolved in 50% NaOH (3 mL) and the reaction mixture was heated overnight at 90° C. The reaction was monitored by TLC. After completion, the reaction mixture was extracted with ethyl acetate and water. The organic layer was separated, dried over Na$_2$SO$_4$, and concentrated under reduced pressure to obtain 3-(6-chloro-2-methyl-3,4-dihydro-1H-pyrido[3,4-b]indol-9(2H)-yl)-1-(piperidin-1-yl)propan-1-one as TFA salt (16 mg) after purification by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL). 1 H NMR (CD$_3$OD): 1.25-1.3 (m, 4H), 1.41-1.6 (m, 2H), 2.4 (s, 3H), 2.63-2.8 (m, 3H), 2.91-3.1 (m, 5H), 3.2-3.3 (m, 3H), 3.69-3.8 (m, 2H), 4.25 (t, 2H), 4.42-4.5 (m, 1H), 4.8-4.9 (m, 1H), 7.0 (d, 1H), 7.25 (s, 1H), 7.39 (d, 1H), 10.2 (bs, 1H).

Example 62a

Preparation of 4-(6-chloro-1,2,3,4-tetrahydro-2-methylpyrido[3,4-b]indol-9-yl)-1-(piperidin-1-yl)butan-1-one (Compound 44, Scheme IV)

The title compound is prepared by following General Methods 1, 3, 4, 5 and 7 by using 4-chlorophenylhydrazine hydrochloride, ethyl 4-bromobutyrate, and triethylamine (General Method 1), ethyl 4-(1-(4-chlorophenyl)hydrazinyl)butanoate and 4,4-diethoxy-N-methylbutan-1-amine (General Method 3), ethyl 4-(5-chloro-3-(2-(methylamino)ethyl)-1H-indol-1-yl)butanoate, formaldehyde and TFA in acetonitrile (General Method 4), ethyl 4-(6-chloro-1,2,3,4-tetrahydro-2-methylpyrido[3,4-b]indol-9-yl)butanoate and NaOH (General Method 5), and 4-(6-chloro-1,2,3,4-tetrahydro-2-methylpyrido[3,4-b]indol-9-yl)butanoic acid, piperidine and EDCI (General Method 7).

Example 62b

Preparation of Compound 44

Sodium hydride (0.027 g, 1.14 mmol) was dissolved in N,N-dimethylformamide. 6-chloro-2-methyl-2,3,4,9-tetrahydro-1H-pyrido[3,4-b]indole (0.1 g, 05 mmol) in N,N-dimethylformamide was added at 0° C. to the NaH solution and stirred for 0.5 h. 4-chloro-1-(piperidin-1-yl)butan-1-one (0.104 g, 0.54 mmol) in N,N-dimethylformamide was added to the reaction mixture drop-wise and stirred for 3 h. The reaction mixture was quenched with water (2 mL) and N,N-dimethylformamide was evaporated under reduced pressure to yield 4-(6-chloro-2-methyl-3,4-dihydro-1H-pyrido[3,4-b]indol-9(2H)-yl)-1-(piperidin-1-yl)butan-1-one as TFA salt (5 mg) after purification by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL). $^1$H NMR (CD$_3$OD): 7.49 (s, 1H), 7.42 (d, 1H), 7.2 (d, 1H), 4.4-4.6 (m, 2H), 4.12-4.2 (m, 2H), 3.8-3.94 (m, 2H), 3.4-3.6 (m, 2H), 3.35-3.4 (m, 2H), 3.10-3.2 (m, 5H), 2.35-2.42 (m, 2H), 1.95-2.1 (m, 2H), 1.6-1.7 (m, 2H), 1.4-1.5 (m, 4H).

Example 63

Preparation of 2-(7-chloro-1,2,3,4-tetrahydro-2-methylpyrido[3,4-b]indol-9-yl)-1-(piperidin-1-yl)ethanone (Compound 45, Scheme IV)

The title compound is prepared by following General Methods 1, 3, 4, 5 and 7 by using 3-chlorophenylhydrazine hydrochloride, ethyl bromoacetate, and triethylamine (General Method 1), ethyl 2-(1-(3-chlorophenyl)hydrazinyl)acetate and 4,4-diethoxy-N-methylbutan-1-amine (General Method 3), ethyl 2-(6-chloro-3-(2-(methylamino)ethyl)-1H-indol-1-yl)acetate, formaldehyde and TFA in acetonitrile (General Method 4), ethyl 2-(7-chloro-1,2,3,4-tetrahydro-2-methylpyrido[3,4-b]indol-9-yl)acetate and NaOH (General Method 5), and 2-(7-chloro-1,2,3,4-tetrahydro-2-methylpyrido[3,4-b]indol-9-yl)acetic acid, piperidine and EDCI (General Method 7).

Example 64

Preparation of 8-aza-2-(1,2,3,4-tetrahydro-2-methylpyrido[3,4-b]indol-9-yl)-1-(piperidin-1-yl)ethanone (Compound 46, Scheme IV)

The title compound is prepared by following General Methods 1, 3, 4, 5 and 7 by using 1-(pyridin-2-yl)hydrazine hydrochloride and ethyl bromoacetate (General Method 1), ethyl 2-(1-(pyridin-2-yl)hydrazinyl)acetate and 4,4-diethoxy-N-methylbutan-1-amine (General Method 3), ethyl 2-(3-(2-(methylamino)ethyl)-1H-pyrrolo[2,3-b]pyridin-1-yl)acetate, formaldehyde and TFA in acetonitrile (General Method 4), ethyl 8-aza-2-(1,2,3,4-tetrahydro-2-methylpyrido[3,4-b]indol-9-yl)acetate and NaOH (General Method 5), and 8-aza-2-(1,2,3,4-tetrahydro-2-methylpyrido[3,4-b]indol-9-yl)acetic acid, piperidine and EDCI (General Method 7).

Example 65

Preparation of 6-chloro-2,3,4,9-tetrahydro-2-methyl-9-(prop-2-ynyl)-1H-pyrido[3,4-b]indole (Compound 125, Scheme I)

The title compound was prepared by following General Methods 2, 3 and 4 using 4-chlorophenylhydrazine hydrochloride, propargyl bromide, and tetra-n-butylammonium chloride (General Method 2), 1-(4-chlorophenyl)-1-(prop-2-ynyl)hydrazine (Example 8) and 4,4-diethoxy-N-methylbutan-1-amine (General Method 3) and 2-(5-chloro-1-(prop-2-ynyl)-1H-indol-3-yl)-N-methylethanamine (Example 17), formaldehyde and TFA in acetonitrile (General Method 4).

(A) N-(4-Chloro-phenyl)-N-prop-2-ynyl-hydrazine

4-Chlorophenylhydrazine hydrochloride (550 mg, 3 mmol) was added to a vigorously stirred mixture of tetra-n-butylammonium chloride (42 mg, 0.15 mmol) in 50% aqueous sodium hydroxide (3 mL) followed by 80% propargyl bromide in toluene (490 mg, 3.3 mmol). The reaction was stirred at room temperature for 20 h. The reaction was diluted with water (30 mL) and extracted with chloroform (3×10 mL). The combined organic layer was dried (Na$_2$SO$_4$), filtered and concentrated under reduced pressure to a dark brown oil (530 mg). The oil was subjected to column chromatography (silica gel, eluent: 50% dichloromethane in hexanes) to give an orange solid (260 mg, 48%).

(B) [2-(5-Chloro-1-prop-2-ynyl-1H-indol-3-yl)-ethyl]-methyl-amine

28% aqueous HCl (0.13 mL, 1 mmol) was added to a solution of N-(4-Chloro-phenyl)-N-prop-2-ynyl-hydrazine (180 mg, 1 mmol) in ethanol (2 mL) under a nitrogen atmosphere. The reaction was heated to 60° C. (oil bath temperature) and 4,4-diethoxy-N-methylbutan-1-amine (175 mg, 1 mmol) was added. The reaction was heated to 90° C. and 28% aqueous HCl (0.26 mL, 2 mmol) was added. The reaction heated at reflux for 6 h. The reaction was cooled and stirred for 3 days. 28% aqueous HCl (0.26 mL, 2 mmol) was added and then heated to reflux. 4,4-diethoxy-N-methylbutan-1-amine (90 mg, 0.51 mmol) was added. The reaction was reflux for a further 6 h. The reaction was cooled and concentrated under reduced pressure. The residue was subjected to column chromatography (silica gel, eluent: EtOAc followed by EtOAc:EtOH:NH$_4$OH 90:10:1) to give a yellow orange oil (88 mg, 36%).

(C) 6-chloro-2,3,4,9-tetrahydro-2-methyl-9-(prop-2-ynyl)-1H-pyrido[3,4-b]indole

37% aqueous formaldehyde (31 mg, 0.38 mmol) in acetonitrile (0.6 mL) was added to a refluxing solution of [2-(5-Chloro-1-prop-2-ynyl-1H-indol-3-yl)-ethyl]-methyl-amine (88 mg, 0.30 mmol) in 5% trifluoroacetic acid in acetonitrile (3 mL) under a nitrogen atmosphere. The reaction was refluxed for 1.5 h. The reaction was cooled and concentrated under reduced pressure. The resulting oil was dissolved in ethyl acetate (50 mL) and washed with saturated aqueous sodium hydrogen carbonate (10 mL). The organic layer was dried (Na$_2$SO$_4$), filtered and concentrated under reduced pressure to a dark buff solid (120 mg). The solid was purified by column chromatography (silica gel, eluent: EtOAc followed by EtOAc:EtOH:NH$_4$OH 90:10:1) to give a buff solid (63 mg, 68%). The free base was converted to the hydrochloride by dissolving the solid in anhydrous diethyl ether (~20 mL) under a nitrogen atmosphere and filtering, 2M hydrochloride in diethyl ether (0.15 mL, 0.3 mmol) was added to the filtrate under a nitrogen atmosphere to form a precipitate. The solvent was removed under reduced pressure and the residue triturated with anhydrous diethyl ether which was removed under a reduced pressure. The resulting buff solid was dried in vacuo over P$_2$O$_5$ to give the hydrochloride (66 mg, 93%).

Example 66

Preparation of Compound 92

2-(2,6-dimethyl-3,4-dihydro-1H-pyrido[3,4-b]indol-9(2H)-yl)-1-phenylethyl methanesulfonate (220 mg, 0.55 mmol) was dissolved in N-methyl-2-pyrrolidone (1.5 mL), KOH powder (216 mg, 3.8 mmol) was added at RT and heated overnight at 100° C. The reaction was monitored by LCMS.

Water was added to the reaction mixture, extracted with ethyl acetate, dried over anhydrous sodium sulfate and evaporated under reduced pressure and purified by reverse phase chromatography to yield TFA salt (33 mg). $^1$H NMR (CDCl$_3$): 7.58-7.35 (m, 5H), 7.30-7.25 (m, 2H), 7.13-7.10 (d, 1H), 6.65-6.61 (d, 1H), 3.85-3.75 (m, 2H), 3.65-3.6 (m, 4H), 2.87 (s, 3H), 2.45 (s, 3H).

Example 67

Preparation of Compound 81

6-chloro-1,2-dimethyl-2,3,4,9-tetrahydro-1H-pyrido[3,4-b]indole (0.1 g, 0.43 mmol) was dissolved in 50% NaOH (6 mL); 4-fluorophenethyl methanesulfonate (0.11 g, 0.51 mmol) and tetrabutylammonium bromide (7 mg, 0.021 mmol) were added to the reaction mixture and heated overnight at 100° C. The reaction was monitored by LCMS, after completion, the reaction mixture was extracted with ethyl acetate and water, the organic layer dried over sodium sulfate and concentrated under reduced pressure. The crude compound was purified by column chromatography to yield the desired compound as a free base (0.060 g). 1 H NMR (CDCl$_3$): 7.47 (s, 1H), 7.20 (d, 1H), 7.13 (d, 1H), 6.99-6.92 (m, 4H), 4.32-4.24 (m, 1H), 4.12-4.03 (m, 1H), 3.43-3.38 (m, 1H), 3.28-3.0 (m, 2H), 3.0-3.90 (m, 1H), 2.60-2.53 (m, 1H), 2.34 (s, 3H), 1.33 (d, 3H).

Example 68

Preparation of Compound 79

6-chloro-1-ethyl-2-methyl-2,3,4,9-tetrahydro-1H-pyrido[3,4-b]indole (200 mg, 0.806 mmol) was dissolved in N-methyl-2-pyrrolidone (1.5 mL); KOH powder (452 mg, 8.06 mmol) and 2-(4-fluorophenyl)-2-methyloxirane (147 mg, 0.967 mmol) was added at RT and heated at 90° C. for 14 h. The reaction was monitored by LCMS. Upon completion, the reaction mixture was filtered and the product was purified by reverse phase chromatography to yield the title compound as the TFA salt (150 mg). 1 H NMR (CDCl$_3$): 7.37 (s, 1 h), 7.04-6.94 (m, 2H), 6.80-6.72 (m, 3H), 6.27 (d, 1H), 4.28-4.13 (m, 2H), 3.81-3.70 (m, 1H), 3.64-3.56 (m, 2H), 3.08 (s, 3H), 2.67-2.46 (m, 2H), 2.20-2.09 (m, 1H), 2.08-1.94 (m, 1H), 1.82 (s, 3H), 1.27-1.20 (m, 3H).

Example 69

Preparation of Compound 55

6-chloro-2-methyl-2,3,4,9-tetrahydro-1H-pyrido[3,4-b]indole (100 mg, 0.45 mmol), was dissolved in N,N-dimethylformamide. CuI (9 mg, 0.045 mmol), L-proline (11 mg, 0.091 mmol), and K$_3$PO$_4$ (194 mg, 0.91 mmol) was added to the reaction mixture and stirred for 10 min at room temperature, followed by drop-wise addition of tert-butyl 4-(2-chloroacetyl)piperazine-1-carboxylate (143 mg, 0.54 mmol) and stirred at 90° C. for 12 h. After completion of the reaction, the reaction mixture was filtered through Celite, N,N-dimethylformamide was evaporated under reduced pressure and extracted with ethyl acetate. The combined organic layer was dried over Na$_2$SO$_4$, and concentrated under reduced pressure. The crude compound was purified by Column chromatography to give Boc-protected compound (0.150 mg). The compound was dissolved in HCl in ethanol (4 mL). The ethanol was evaporated to obtain 2-(6-chloro-2-methyl-3,4-dihydro-1H-pyrido[3,4-b]indol-9(2H)-yl)-1-(piperazin-1-yl)ethanone as HCl salt (80 mg). 1 H NMR (CD$_3$OD): 7.52 (s, 1H), 7.24 (d, 1H), 7.15 (dd, 1H), 5.19-5.23 (m, 2H), 4.71-4.79 (m, 2H), 4.25-4.30 (m, 2H), 3.85-4.00 (m, 4H), 3.70-3.79 (m, 2H), 3.52 (s, 3H), 3.15-3.23 (m, 4H).

Example 70

Preparation of Compound 71

Sodium hydride (64 mg, 2.7 mmol) in N,N-dimethylformamide (10 mL) was charged and stirred for 10 min at RT. 6-chloro-2-methyl-2,3,4,9-tetrahydro-1H-pyrido[3,4-b]indole (0.2 g, 0.9 mmol) was added to the reaction mixture and stirred for 10 min, followed by addition of 2-phenyloxirane (163 mg, 1.3 mmol) and stirred at RT overnight. The reaction mixture was quenched with ice water, and extracted with ethyl acetate. The combined organic layer was dried over anhydrous sodium sulfate and evaporated under reduced pressure. The crude product was purified by reverse phase chromatography to yield TFA salt (60 mg), which was converted to free base (15 mg). 1 H NMR (CDCl$_3$): 7.50-7.40 (m, 1H), 7.38-7.22 (m, 5H), 7.20-7.05 (m, 2H), 4.98-4.90 (m, 1H), 4.15-4.10 (m, 2H), 3.90-3.80 (d, 1H), 3.50-3.42 (d, 1H), 2.95-2.80 (m, 4H), 2.55 (s, 3H).

Example 71

Preparation of Compound 70

Sodium hydride (64 mg, 2.7 mmol) in N,N-dimethylformamide (10 mL) was charged and stirred for 10 min at RT. 6-chloro-2-methyl-2,3,4,9-tetrahydro-1H-pyrido[3,4-b]indole (200 mg, 0.9 mmol) was added to the reaction mixture and stirred for 10 min, followed by addition of 2-(3,4-dimethoxyphenyl)oxirane (245 mg, 1.3 mmol) and stirred at RT overnight. The reaction mixture was quenched with ice water and extracted with ethyl acetate. The combined organic layer was dried over anhydrous sodium sulfate and evaporated under reduced pressure. The crude product was purified by reverse phase chromatography to yield TFA salt (70 mg), which was converted to free base (30 mg). 1 H NMR (CDCl$_3$): 7.47 (s, 1H), 7.22-7.10 (m, 2H), 6.85-6.80 (m, 2H), 6.70-6.65 (d, 1H), 4.90-4.85 (t, 1H), 4.15-4.10 (d, 2H), 3.90 (s, 3H), 3.78 (s, 3H), 3.75-3.70 (d, 1H), 3.50-3.40 (d, 1H), 2.95-2.70 (m, 4H), 2.55 (s, 3H).

Example 72

Preparation of Compound 72

Sodium hydride (72 mg, 3.0 mmol) in N,N-dimethylformamide (10 mL) was charged and stirred for 10 min at RT. 2,6-dimethyl-2,3,4,9-tetrahydro-1H-pyrido[3,4-b]indole (200 mg, 1.0 mmol) was added to the solution and stirred for 10 min, followed by addition of 2-p-tolyloxirane (201 mg, 1.5 mmol) and stirred at RT overnight. The reaction mixture was quenched with ice water and extracted with ethyl acetate. The combined organic layer was dried over anhydrous sodium sulfate and evaporated under reduced pressure. The crude product was purified by reverse phase chromatography to yield TFA salt (70 mg), which was converted to free base (40 mg). $^1$H NMR (CDCl$_3$): 7.40-7.18 (m, 6H), 7.05-7.00 9d, 1H), 5.00-4.95 (m, 1H), 4.10-4.05 (m, 2H), 3.85-3.80 (d, 1H), 3.40-3.35 (d, 1H), 2.90-2.75 (m, 4H), 2.55 (s, 3H), 2.50 (s, 3H), 2.35 (s, 3H).

Example 73

Preparation of Compound 125

37% aqueous formaldehyde (31 mg, 0.38 mmol) in acetonitrile (0.6 mL) was added to a refluxing solution of [2-(5-Chloro-1-prop-2-ynyl-1H-indol-3-yl)-ethyl]-methyl-amine (88 mg, 0.30 mmol) in 5% trifluoroacetic acid in acetonitrile (3 mL) under a nitrogen atmosphere and refluxed for an additional 1.5 h. The reaction was cooled and concentrated under reduced pressure. The resulting oil was dissolved in ethyl acetate (50 mL) and washed with saturated aqueous sodium hydrogen carbonate (10 mL). The organic layer was dried ($Na_2SO_4$), filtered and concentrated under reduced pressure to a dark buff solid (120 mg). The solid was purified by column chromatography (silica gel, eluent: EtOAc followed by EtOAc:EtOH:$NH_4OH$ 90:10:1) to yield a buff solid (63 mg, 68%). The free base was converted to the hydrochloride by dissolving the solid in anhydrous diethyl ether (~20 mL) under a nitrogen atmosphere and filtering. 2M hydrochloride in diethyl ether (0.15 mL, 0.3 mmol) was added to the filtrate under a nitrogen atmosphere to form a precipitate. The solvent was removed under reduced pressure and the residue triturated with anhydrous diethyl ether which was removed under a reduced pressure. The resulting buff solid was dried in vacuo over $P_2O_5$ to yield the hydrochloride (66 mg, 93%). $^1$H NMR (DMSO): 11.4 (bs, 1H), 7.6 (d, 2H), 7.25 (d, 1H), 5.1 (s, 2H), 4.7 (bs, 1H), 4.35 (bs, 1H), 3.7 (bs, 1H), 3.4 (bs, 3H), 3.0 (bs, 1H), 2.9 (s, 3H).

Example 74

Preparation of Compound 90

1-(6-chloro-2-methyl-3,4-dihydro-1H-pyrido[3,4-b]indol-9(2H)-yl)-2-(4-fluorophenyl) propan-2-ol (30 mg, 0.0806 mmol) was dissolved in 25% sulfuric acid, and the reaction mixture was heated overnight at 60° C. The reaction was monitored by TLC. After completion of the reaction, pH of the reaction mixture was adjusted to 10-12 and extracted with ethyl acetate. The organic layer was dried over $Na_2SO_4$, and concentrated under reduced pressure. The crude compound was purified by preparative TLC. The pure compound was stirred in ethanolic HCl to yield HCl salt of (E)-6-chloro-9-(2-(4-fluorophenyl)prop-1-enyl)-2-methyl-2,3,4,9-tetrahydro-1H-pyrido[3,4-b]indole (8 mg). $^1$H NMR ($CD_3OD$):—7.63-7.70 (m, 2H), 7.60 (s, 1H), 7.10-7.20 (m, 3H), 7.0 (s, 1H), 4.65 (d, 1H), 4.43 (d, 1H), 3.78-3.90 (m, 1H), 3.52-3.60 (m, 2H), 3.10-3.25 (m, 5H), 1.96 (s, 3H).

Example 75

Preparation of Compound 57

Sodium hydride (0.120 g, 60%, 5.0 mmol) was washed with hexane for removal of oil, dried under vacuum and dissolved in N,N-dimethylformamide. 2,6-dimethyl-2,3,4,9-tetrahydro-1H-pyrido[3,4-b]indole (0.5 g, 2.5 mmol) in N,N-dimethylformamide was added drop-wise to the reaction mixture at 0° C. and stirred for 0.5 h. The solution of 2-chloro-1-(piperidin-1-yl)ethanone (0.483 g, 3.0 mmol) in N,N-dimethylformamide was added drop-wise and the reaction mixture was stirred at RT for 2 h. The reaction was monitored by TLC. After completion of the reaction, the reaction mixture quench with ice-water, the solid compound was filtered, the crude compound was washed with hexane and diethyl ether for removal of color impurities then recrystallized by using methanol to yield the desired compound (0.4 g). The crude product was stirred with ethanolic HCl to give HCl salt of 2-(2,6-dimethyl-3,4-dihydro-1H-pyrido[3,4-b]indol-9(2H)-yl)-1-(piperidin-1-yl)ethanone. $^1$H NMR (DMSO): 11.22 (bs, 1H), 7.23-7.33 (m, 2H), 6.97 (d, 1H), 5.14 (d, 1H), 5.0 (d, 1H), 4.57 (d, 1H), 4.13-4.22 (m, 1H), 3.61-3.69 (m, 1H), 3.32-3.58 (m, 5H), 2.97-3.10 (m, 2H), 2.90 (s, 3H), 2.39 (s, 3H), 1.51-1.67 (m, 4H), 1.35-1.48 (m, 2H).

Example 76

Preparation of Compound 64

Sodium hydride (54 mg, 2.2 mmol) was dissolved in N,N-dimethylformamide (7.5 mL) and stirred for 10 min. 2,6-dimethyl-2,3,4,9-tetrahydro-1H-pyrido[3,4-b]indole (150 mg, 0.75 mmol) was added to the solution and stirred for 10 min, followed by addition of 2-(oxiran-2-yl)pyridine (133 mg, 1.1 mmol) and stirred overnight at RT. The progress of the reaction was monitored by TLC and LCMS. The reaction mixture was quenched with ice water, extracted with ethyl acetate. The organic layer was washed with brine, dried over anhydrous sodium sulfate and evaporated under reduced pressure. The crude product was purified by reverse phase chromatography to get pure title compound as TFA salt (27 mg). $^1$H NMR (DMSO): 10.30-10.10 (m, 1H), 8.70-8.55 (m, 1H), 7.95-7.50 (m, 2H), 7.45-7.05 (m, 2H), 7.00-6.75 (m, 2H), 4.95-4.70 (m, 1H), 4.60-4.40 (m, 2H), 4.20-3.60 (m, 4H), 3.55-3.35 (m, 2H), 3.00 (s, 3H), 2.38 (s, 3H).

Example 77

Preparation of Compound 65

Sodium hydride (48 mg, 2.0 mmol) was dissolved in N,N-dimethylformamide (7.5 mL) and stirred for 10 min. 6-chloro-2-methyl-2,3,4,9-tetrahydro-1H-pyrido[3,4-b]indole (150 mg, 0.68 mmol) was added to the solution and stirred for 10 min, followed by addition of 2-(oxiran-2-yl)pyridine (123 mg, 1.02 mmol) and stirred overnight at RT. The progress of the reaction was monitored by TLC and LCMS. The reaction mixture was quenched with ice water and extracted with ethyl acetate. The organic layer was washed with brine, dried over anhydrous sodium sulfate and evaporated under reduced pressure. The crude product was purified by reverse phase chromatography to get pure title compound as TFA salt (60 mg). $^1$H NMR (DMSO): 10.50-10.2 (m, 1H), 8.70-8.50 (m, 1H), 7.90-7.75 (m, 1H), 7.70-7.45 (m, 2H), 7.40-7.20 (m, 2H), 7.15-6.95 (m, 2H), 4.95-4.75 (m, 1H), 4.65-4.50 (m, 2H), 4.40-4.20 (m, 2H), 4.10-3.75 (m, 2H), 3.55-3.40 (m, 2H), 3.05 (s, 3H).

Example 78

Preparation of Compound 66

Sodium hydride (72 mg, 3.0 mmol) was dissolved in N,N-dimethylformamide (10 mL) and stirred for 10 min. 2,6-dimethyl-2,3,4,9-tetrahydro-1H-pyrido[3,4-b]indole (200 mg, 1.0 mmol) was added to the reaction mixture and stirred for 10 min, followed by addition of 2-(3,4-dimethoxyphenyl) oxirane (270 mg, 1.5 mmol) and stirred overnight at RT. The progress of the reaction was monitored by TLC and LCMS. The reaction mixture was quenched with ice water and extracted with ethyl acetate. The organic layer was washed with brine, dried over anhydrous sodium sulfate and evaporated under reduced pressure. The crude product was purified

Example 79

Preparation of Compound 67

Sodium hydride (72 mg, 3.0 mmol) was dissolved in N,N-dimethylformamide (10 mL) and stirred for 10 min. 2,6-dimethyl-2,3,4,9-tetrahydro-1H-pyrido[3,4-b]indole (200 mg, 1.0 mmol) was added to the reaction mixture and stirred for 10 min, followed by addition of 2-phenyloxirane (180 mg, 1.5 mmol) and stirred overnight at RT. The progress of the reaction was monitored by TLC and LCMS. The reaction mixture was quenched with ice water and extracted with ethyl acetate. The organic layer was washed with brine, dried over anhydrous sodium sulfate and evaporated under reduced pressure. The crude product was purified by reverse phase chromatography to get pure title compound as TFA salt (3 mg). $^1$H NMR (DMSO): 7.55-7.25 (m, 6H), 7.05-6.95 (m, 2H), 5.70-5.65 (m, 1H), 4.85-4.80 (m, 2H), 4.30-4.10 (m, 3H), 3.75-3.65 (m, 2H), 3.10-2.90 (m, 5H), 2.38 (s, 3H).

Example 80

Preparation of Compound 91

1-(2,6-dimethyl-3,4-dihydro-1H-pyrido[3,4-b]indol-9 (2H)-yl)-2-(4-fluorophenyl)propan-2-ol (70 mg, 0.198 mmol) was dissolved in 25% sulfuric acid and heated overnight at 60° C. The progress of the reaction was monitored by TLC. After completion of the reaction, the pH was adjusted to 10-12 and extracted with ethyl acetate. The organic layer was dried over Na$_2$SO$_4$, and concentrated under reduced pressure. The crude compound was purified by preparative TLC. The pure compound was stirred in ethanolic HCl to yield HCl salt of (E)-9-(2-(4-fluorophenyl)prop-1-enyl)-2,6-dimethyl-2,3,4,9-tetrahydro-1H-pyrido[3,4-b]indole (10 mg). $^1$H NMR (CD$_3$OD): 7.60-7.70 (m, 2H), 7.36 (s, 1H), 7.06-7.22 (m, 3H), 6.96 (s, 1H), 4.65 (d, 1H), 4.40 (d, 1H), 3.84-3.96 (m, 1H), 3.50-3.60 (m, 2H), 3.06-3.20 (m, 5H), 2.43 (s, 3H), 2.0 (s, 1H).

Example 81

Preparation of Compound 54

2-(6-chloro-2-methyl-3,4-dihydro-1H-pyrido[3,4-b]indol-9(2H)-yl)acetic acid (100 mg, 0.35 mmol) was dissolved in dichloromethane (4 mL) and cooled to 0° C. Oxalyl chloride (0.055 g, 0.43 mmol) was added drop-wise under dry conditions, a catalytic amount of N,N-dimethylformamide was added and the reaction mixture was stirred at RT for 1 h. Oxalyl chloride was evaporated under reduced pressure to obtain the corresponding acid chloride. The acid chloride was quenched with methanol; the excess methanol was evaporated under reduced pressure; and the residue was purified by reversed phase chromatography to yield methyl 2-(6-chloro-2-methyl-3,4-dihydro-1H-pyrido[3,4-b]indol-9(2H)-yl)acetate as TFA salt (3.0 mg). $^1$H NMR (CD$_3$OD): 7.5 (s, 1H), 7.4 (d, 1H), 7.2 (d, 1H), 5.0-4.9 (m, 2H), 4.5 (s, 2H), 4.1 (m, 1H), 3.90 (m, 1H), 3.8 (s, 3H), 3.5 (s, 3H), 3.2 (m, 2H).

Example 82

Preparation of Compound 56

6-chloro-2-methyl-2,3,4,9-tetrahydro-1H-pyrido[3,4-b]indole (100 mg, 0.45 mmol), was dissolved in N,N-dimethylformamide. CuI (9 mg, 0.045 mmol), L-proline (11 mg, 0.091 mmol) and K$_3$PO$_4$ (194 mg, 0.91 mmol) was added to the reaction mixture and stirred for 10 min. at room temperature. 5-(3-bromopropyl)-2-methylpyridine (116 mg, 0.54 mmol) was added drop-wise and the reaction mixture was heated at 90° C. for 12 h. After completion of the reaction, the reaction mixture was filtered through Celite. N,N-dimethylformamide was evaporated under reduced pressure and extracted with ethyl acetate. The organic layer was dried over Na$_2$SO$_4$, and concentrated under reduced pressure to obtain 6-chloro-2-methyl-9-(3-(6-methylpyridin-3-yl)propyl)-2,3,4,9-tetrahydro-1H-pyrido[3,4-b]indole as TFA salt (35 mg) after purification by reverse-phase chromatography (C-18, 500 mm×50 mm, Mobile Phase A=0.05% TFA in water, B=0.05% TFA in acetonitrile, Gradient: 10% B to 80% B in 30 min, injection volume 5 mL). $^1$H NMR (DMSO): 11.40 (bs, 1H), 8.62 (s, 1H), 8.17 (d, 1H), 7.69 (d, 1H), 7.58 (s, 1H), 7.45 (d, 1H), 7.17 (d, 1H), 4.64-4.79 (m, 2H), 3.43-3.48 (t, 4H), 3.18 (s, 3H), 3.03-3.10 (m, 2H), 2.71-2.79 (m, 2H), 2.60 (s, 3H), 2.10-2.25 (m, 2H).

Example 83

Preparation of Compound 59

Sodium hydride (31 mg, 1.3 mmol) was dissolved in THF. 6-chloro-2-methyl-2,3,4,9-tetrahydro-1H-pyrido[3,4-b]indole (100 mg, 0.045 mmol) in THF was added drop-wise at 0° C. to the NaH solution and stirred for 0.5 h. The solution of 2-(2-fluorophenyl)oxirane (94 mg, 0.08 mmol) in THF was added drop-wise to the reaction mixture and stirred at RT for 2 h. The progress of the reaction was monitored by TLC. After completion of the reaction, the reaction mixture was quenched with ice-water, THF was evaporated and the aqueous layer was extracted with ethyl acetate. The organic layer was dried over anhydrous sodium sulfate. The crude compound was purified by column chromatography to yield desired compound (20 mg). The product was stirred in ethanolic HCl to yield 2-(6-chloro-2-methyl-3,4-dihydro-1H-pyrido[3,4-b]indol-9(2H)-yl)-1-(2-fluorophenyl)ethanol hydrochloride salt. $^1$H NMR (CD$_3$OD): 7.44-7.60 (m, 2H), 7.20-7.28 (dd, 2H), 7.14-7.22 (m, 3H), 5.30 (dd, 2H), 4.39-4.60 (m, 2H), 4.1-4.3 (m, 2H), 3.8-3.83 (m, 1H), 3.42-3.54 (m, 2H), 3.18 (s, 3H).

Example 84

Preparation of Compound 60

Sodium hydride (36 mg, 1.5 mmol) was dissolved in THF. 2,6-dimethyl-2,3,4,9-tetrahydro-1H-pyrido[3,4-b]indole (100 mg, 0.05 mmol) in THF was added drop-wise at 0° C. to the NaH solution and the reaction mixture stirred for 0.5 h. The solution of 2-(2-fluorophenyl)oxirane (103 mg, 0.075 mmol) in THF was added drop-wise to the reaction mixture and stirred at RT for 2 h. The progress of the reaction was monitored by TLC. After completion of the reaction, the reaction mixture was quenched with ice-water, THF was evaporated and aqueous layer was extracted with ethyl acetate. The organic layer was dried over anhydrous sodium sulfate. The crude compound was purified by column chromatography to yield desired compound (30 mg) which was stirred in ethanolic HCl to yield 2-(2,6-dimethyl-3,4-dihydro-1H-pyrido[3,4-b]indol-9(2H)-yl)-1-(2-fluorophenyl)ethanol hydrochloride salt. $^1$H NMR (CD$_3$OD): 7.55 (m, 1H), 7.30 (m, 2H), 7.25 (d, 1H), 7.12 (m, 2H), 7.05 (d, 1H), 5.30 (m, 1H), 4.40 (d, 2H), 4.10 (m, 2H), 3.10 (s, 3H), 3.0 (m, 2H), 2.80 (m, 2H), 2.40 (s, 3H).

Example 85

Preparation of Compound 61

Sodium hydride (120 mg, 60%, 3.0 mmol) was washed with hexane for removal of oil, dried under vacuum and dissolved in N,N-dimethylformamide. 2,6-dimethyl-2,3,4,9-tetrahydro-1H-pyrido[3,4-b]indole (200 mg, 1.0 mmol) in N,N-dimethylformamide was added drop-wise at 0° C. to the NaH solution and stirred for 0.5 h. The solution of 2-(4-fluorophenyl)-2-methyloxirane (182 mg, 1.2 mmol) in N,N-dimethylformamide was added drop-wise to the reaction mixture and stirred at RT for 2 h. The progress of the reaction was monitored by TLC. After completion of the reaction, the reaction mixture was quenched with ice-water, N,N-dimethylformamide was evaporated and aqueous layer was extracted with ethyl acetate. The organic layer was dried over anhydrous sodium sulfate. The crude compound was purified by preparative TLC, to yield the desired compound (72 mg), which was stirred in ethanolic HCl to yield 1-(2,6-dimethyl-3,4-dihydro-1H-pyrido[3,4-b]indol-9(2H)-yl)-2-(4-fluorophenyl)propan-2-ol hydrochloride salt. $^1$H NMR (CD$_3$OD): 7.44-7.57 (m, 1H), 7.55-7.43 (m, 1H), 7.20-7.26 (m, 1H), 7.11-7.19 (m, 1H), 6.83-7.03 (m, 3H), 4.22-4.38 (m, 2H), 4.10-4.18 (m, 1H), 3.99-4.06 (m, 1H), 3.70-3.81 (m, 2H), 3.40-3.50 (m, 2H), 3.10 (s, 3H), 2.30-2.34 (m, 3H), 1.62 (d, 1.5H), 1.51 (d, 1.5H).

Example 86

Preparation of Compound 62

Sodium hydride (62 mg, 2.58 mmol) was dissolved in N,N-dimethylformamide. 6-chloro-2-methyl-2,3,4,9-tetrahydro-1H-pyrido[3,4-b]indole (200 mg, 0.90 mmol) in N,N-dimethylformamide was added drop-wise at 0° C. to the NaH solution and stirred for 0.5 h. The solution of 2-(4-fluorophenyl)-2-methyloxirane (165 mg, 2.7 mmol) in N,N-dimethylformamide was added drop-wise to the reaction mixture and stirred at RT for 2 h. The progress of the reaction was monitored by TLC. After completion of the reaction, the reaction mixture was quenched with ice-water, N,N-dimethylformamide was evaporated and the aqueous layer was extracted with ethyl acetate. The organic layer was dried over anhydrous sodium sulfate. The crude compound was purified by preparative TLC, to yield the desired compound as free base (35 mg) which was stirred in ethanolic HCl to yield 1-(6-chloro-2-methyl-3,4-dihydro-1H-pyrido[3,4-b]indol-9 (2H)-yl)-2-(4-fluorophenyl) propan-2-ol hydrochloride salt. $^1$H NMR (CD$_3$OD): 7.36-7.52 (m, 3H), 7.14-7.22 (m, 1H), 6.84-7.07 (m, 3H), 4.42-4.52 (d, 1H), 4.20-4.37 (m, 3H), 4.04-4.10 (d, 1H), 3.76-3.84 (m, 1H), 3.40-3.58 (m, 2H), 3.10 (s, 3H), 1.62 (s, 1.5H), 1.57 (s, 1.5H).

Example 87

Preparation of Compound 58

Sodium hydride (26 mg, 1.1 mmol) was dissolved in THF. 6-chloro-2-methyl-2,3,4,9-tetrahydro-1H-pyrido[3,4-b]indole (100 mg, 0.45 mmol) in THF was added drop-wise at 0° C. to the NaH solution and stirred for 0.5 h. The solution of 2-chloro-1-(piperidin-1-yl)ethanone (88 mg, 0.54 mmol) in THF was added drop-wise to the reaction mixture and stirred at RT for 2 h. The progress of the reaction was monitored by TLC. After completion of the reaction, the reaction mixture was quenched with ice-water, THF was evaporated and the aqueous layer was extracted with ethyl acetate. The organic layer was dried over anhydrous sodium sulfate. The crude compound was purified by column chromatography to yield desired compound as free base (75 mg). The free base was stirred with ethanolic HCl to give HCl salt of 2-(6-chloro-2-methyl-3,4-dihydro-1 H-pyrido[3,4-b]indol-9(2H)-yl)-1-(piperidin-1-yl)ethanone. $^1$H NMR (DMSO): 10.98 (bs, 1H), 7.58 (s, 1H), 7.44 (d, 1H), 7.15 (d, 1H), 5.05-5.23 (m, 2H), 4.51-4.63 (m, 1H), 4.18-4.27 (m, 1H), 3.63-3.73 (m, 2H), 3.50-3.60 (m, 4H), 3.00-3.07 (m, 2H), 2.97 (s, 3H), 1.60-1.69 (m, 4H), 1.40-1.45 (m, 2H).

Example 88

Preparation of Compound 83

Sodium hydride (0.040 g, 60%, 1.0 mmol) was washed with hexane for removal of oil, dried under vacuum and dissolved in THF. 6-chloro-1-ethyl-2-methyl-2,3,4,9-tetrahydro-1H-pyrido[3,4-b]indole (0.1 g, 0.40 mmol) in THF was added drop-wise at 0° C. to the NaH solution and stirred for 0.5 h. The solution of 2-chloro-1-(piperidin-1-yl)ethanone (0.078 g, 0.48 mmol) in THF was added drop-wise to the reaction mixture and stirred at RT for 2 h. The progress of the reaction was monitored by TLC. After completion of the reaction, the reaction mixture was quenched with ice-water, extracted with ethyl acetate and brine, and the crude compound was purified by column chromatography to yield the desired compound as a free base (50 mg). $^1$H NMR (CDCl$_3$): 7.42 (s, 1H), 7.10-7.01 (m, 2H), 4.81 (d, 1H), 4.61 (d, 1H), 3.61-3.38 (m, 4H), 3.28-3.18 (m, 1H), 2.99-2.83 (m, 2H), 2.48 (s, 3H), 1.80-1.48 (m, 10H), 1.08 (t, 3H).

Example 89

Preparation of Compound 82

Sodium hydride (0.043 g, 60%, 1.0 mmol) was washed with hexane for removal of oil, dried under vacuum and dissolved in THF. 6-chloro-1,2-dimethyl-2,3,4,9-tetrahydro-1H-pyrido[3,4-b]indole (0.1 g, 0.43 mmol) in THF was added drop-wise at 0° C. to the NaH solution and stirred for 0.5 h. The solution of 2-chloro-1-(piperidin-1-yl)ethanone (0.083 g, 0.51 mmol) in THF was added drop-wise to the reaction mixture and stirred at RT for 2 h. The progress of the reaction was monitored by TLC. After completion of the reaction, the reaction mixture was quenched with ice-water, extracted with ethyl acetate and brine, and the crude compound was purified by column chromatography to yield the desired compound as a free base (40 mg). $^1$H NMR (CDCl$_3$): 7.42 (s, 1H), 7.18 (d, 1H), 7.06 (d, 1H), 4.82 (d, 1H), 4.62 (d, 1H), 3.9-3.82 (m, 1H), 3.6-3.4 (m, 2H), 3.3-3.2 (m, 1H), 3.0-2.8 (m, 2H), 2.7-2.6 (m, 1H), 2.58 (s, 3H), 1.75-1.50 (m, 4H), 1.4 (d, 3H), 1.3-1.2 (m, 4H).

Example 90

Preparation of Compound 77

Tetrabutylammonium bromide (13 mg, 0.04 mmol) was dissolved in 50% aqueous sodium hydroxide (6 ml), and stirred for 10 min at RT. 6-chloro-1-ethyl-2-methyl-2,3,4,9-tetrahydro-1H-pyrido[3,4-b]indole (200 mg, 0.8 mmol) was added and stirred for 10 min at RT followed by addition of 2-(6-methylpyridin-3-yl)ethyl methanesulfonate (200 mg, 0.97 mmol). The reaction mixture was stirred overnight at 90° C. The progress of the reaction was monitored by TLC and LCMS. The reaction mixture was cooled to RT, extracted with ethyl acetate, the organic layer was dried over anhydrous sodium sulfate and concentrated. The crude product was purified by column chromatography to yield the title compound as free base (30 mg). $^1$H NMR (CDCl$_3$): 8.20-7.80 (m, 2H), 7.50 (s, 1H), 7.23 (s, 1H), 7.20-7.00 (m, 2H), 4.45-4.38 (m, 1H), 4.10-4.00 (m, 1H), 3.30-2.80 (m, 8H), 2.50 (s, 3H), 2.23 (s, 3H), 1.39-1.25 (m, 1H), 1.20-1.00 (m, 3H).

Example 91

Preparation of Compound 78

Tetrabutylammonium bromide (6 mg, 0.02 mmol) was dissolved in 50% aqueous sodium hydroxide (5 ml), stirred for 10 min at RT. 6-chloro-1-ethyl-2-methyl-2,3,4,9-tetrahydro-1H-pyrido[3,4-b]indole (100 mg, 0.4 mmol) was added and stirred for 10 min at RT, followed by addition of 4-fluorophenethyl methanesulfonate (105 mg, 0.48 mmol). The reaction mixture was stirred overnight at 100° C. The progress of the reaction was monitored by TLC and LCMS. The reaction mixture was cooled to RT, extracted with ethyl acetate, the organic layer was dried over anhydrous sodium sulfate and concentrated. The crude product was purified by column chromatography to yield the title compound as free base (57 mg). $^1$H NMR (CDCl$_3$): 7.50 (s, 1H), 7.22 (d, 1H), 7.18 (d, 1H), 7.00-6.90 (m, 4H), 4.40-4.30 (m, 1H), 4.19-4.00 (m, 1H), 3.20-3.02 (m, 2H), 3.00-2.90 (m, 2H), 2.87-2.80 (m, 2H), 2.50-2.41 (m, 1H), 2.22 (s, 3H), 1.70-1.60 (m, 2H), 1.05 (t, 3H).

Example 92

Preparation of Compound 80

Tetrabutylammonium bromide (6 mg, 0.02 mmol) was dissolved in 50% aqueous sodium hydroxide (6 ml) and stirred for 10 min at RT. 6-chloro-1,2-dimethyl-2,3,4,9-tetrahydro-1H-pyrido[3,4-b]indole (100 mg, 0.4 mmol) was added and stirred for 10 min at RT, followed by addition of 2-(6-methylpyridin-3-yl)ethyl methanesulfonate (110 mg, 0.51 mmol). The reaction mixture was stirred overnight at 100° C. The progress of the reaction was monitored by TLC and LCMS. The reaction mixture was cooled to RT, extracted with ethyl acetate, the organic layer was dried over anhydrous sodium sulfate and concentrated. The crude product was purified by column chromatography to yield the title compound as free base (40 mg). $^1$H NMR (CDCl$_3$): 8.14 (s, 1H), 7.15 (s, 1H), 7.20 (d, 1H), 7.15-7.06 (m, 2H), 7.00 (d, 1H), 4.36-4.28 (m, 1H), 4.08-4.00 (m, 1H), 3.40-3.38 (q, 1H), 3.38-3.22 (m, 2H), 3.17-3.00 (m, 2H0, 2.97-2.77 (m, 2H), 2.48 (s, 3H), 2.24 (s, 3H), 1.36 (d, 3H).

Example 93

Preparation of Compound 86

Tetrabutylammonium bromide (6.5 mg, 0.02 mmol) was dissolved in 50% aqueous sodium hydroxide (5 ml) and stirred for 10 min at RT. 6-chloro-1-ethyl-2-methyl-2,3,4,9-tetrahydro-1H-pyrido[3,4-b]indole (100 mg, 0.403 mmol) was added and stirred for 10 min at RT, followed by addition of 2-(trifluoromethyl)-5-vinylpyridine (84 mg, 0.48 mmol). The reaction mixture was stirred overnight at 110° C. The progress of the reaction was monitored by TLC and LCMS. The reaction mixture was cooled to RT, extracted with ethyl acetate; the organic layer was dried over anhydrous sodium sulfate and concentrated. The crude product was purified by column chromatography to yield the title compound (50 mg). $^1$H NMR (CDCl$_3$): 8.28 (s, 1HO, 7.52-7.42 (m, 2H), 7.28-7.10 (m, 3H), 4.48-4.38 (m, 1H), 4.15-4.00 (m, 1H), 3.30-3.20 (m, 1H), 3.17-3.00 (m, 2H), 2.86-2.56 (m, 3H), 2.47-2.40 (m, 1H), 2.10 (s, 3H), 1.70-1.50 (m, 2H), 1.02 (t, 3H).

Example 94

Preparation of Compound 52

Ethyl 2-(6-chloro-1,2,3,4-tetrahydro-2-methylpyrido[3,4-b]indol-9-yl)acetate (0.3 g, 2.9 mmol) in THF (10 mL) was added to a solution of sodium hydroxide (0.177 g, 2.9 mmol) in water (3 mL) and heated at 75° C. for 1 h. The progress of the reaction was monitored by TLC. After completion of the reaction, the solvent was removed; water (10 mL) was added to the residue and the aqueous layer was washed with ethyl acetate (2×10 mL). The pH of aqueous layer was adjusted to 2-3, and the aqueous layer was washed with ethyl acetate. The aqueous layer was evaporated, the residue was extracted with methanol, filtered, the filtrate was concentrated under reduced pressure to yield 2-(6-chloro-1,2,3,4-tetrahydro-2-methylpyrido[3,4-b]indol-9-yl)acetic acid (175 mg). $^1$H NMR (CD$_3$OD): 7.50 (s, 1H) 7.30 (d, 1H), 7.10 (d, 1H), 5.1 (d, 1H), 5.0 (d, 1H), 4.4 (s, 2H), 4.2 (m, 1H), 4.0 (m, 1H), 3.4 (s, 3H), 3.2 (m, 2H).

Example 95

Preparation of Compound 53

Ethyl 2-(1,2,3,4-tetrahydro-2,6-dimethylpyrido[3,4-b]indol-9-yl)acetate (0.35 g, 1.2 mmol) in THF (10 mL) was added to a solution of sodium hydroxide (0.146 g, 3.6 mmol) in water (3 mL) and heated at 75° C. for 1 h. The progress of the reaction was monitored by TLC. After completion of the reaction, the solvent was removed; water (10 mL) was added to the residue and the aqueous layer was washed with ethyl acetate (2×10 mL). The pH of aqueous layer was adjusted to 2-3, and the aqueous layer was washed with ethyl acetate. The aqueous layer was evaporated, the residue was extracted with methanol, filtered, the filtrate was concentrated under reduced pressure to yield 2-(1,2,3,4-tetrahydro-2,6-dimethylpyrido[3,4-b]indol-9-yl)acetic acid (65 mg). $^1$H NMR (CD$_3$OD): 7.30 (s, 1H) 7.20 (d, 1H), 7.0 (d, 1H), 5.1 (d, 1H), 4.8 (d, 1H), 4.18 (m, 1H), 4.0 (s, 2H), 3.81 (m, 1H), 3.42 (s, 3H), 3.15 (bs, 2H), 2.4 (s, 3H).

Example 96

Preparation of Compound 114

6-chloro-2-methyl-2,3,4,9-tetrahydro-1H-pyrido[3,4-b]indole (69 mg, 0.31 mmol) was dissolved in DMF (6 mL). To this solution was added CuI (6 mg, 0.031 mmol), L-proline (7 mg, 0.063 mmol), K$_3$PO$_4$ (134 mg, 0.63 mmol). The reaction mixture was stirred for 10 min at room temperature followed by addition of 4-(1-bromoprop-1-en-2-yl)-1,2-dichlorobenzene (100 mg, 0.378 mmol). The reaction mixture was heated at 80° C. overnight. Solvent was evaporated under reduced pressure; the residue was diluted with brine and extracted with ethyl acetate. Organic layer was dried over Na$_2$SO$_4$, and concentrated under reduced pressure. The crude product was purified by silica gel chromatography to obtain 28 mg of 6-chloro-9-(2-(3,4-dichlorophenyl)prop-1-enyl)-2-methyl-2,3,4,9-tetrahydro-1H-pyrido[3,4-b]indole. $^1$H NMR (DMSO) OXALATE SALT 7.95 (s, 1H), 7.62 (m, 3H), 7.30 (d, 1H), 7.20 (m, 2H), 4.30 (m, 2H), 3.40 (m, 2H), 3.0 (m, 2H), 2.82 (s, 3H), 1.90 (s, 3H).

Example 97

Preparation of Compound 112

6-chloro-1-ethyl-2-methyl-2,3,4,9-tetrahydro-1H-pyrido[3,4-b]indole (89 mg, 0.36 mmol) was dissolved in DMF (6 mL). To this solution was added CuI (8 mg, 0.035 mmol), L-proline (9 mg, 0.086 mmol), K$_3$PO$_4$ (183 mg, 0.862 mmol). The reaction mixture was stirred for 10 min at room temperature followed by addition of 4-(1-bromoprop-1-en-2-yl)-1,2-difluorobenzene (100 mg, 0.431 mmol). The reaction mixture was heated at 80° C. overnight. Solvent was evaporated under reduced pressure; the residue was diluted with brine and extracted with ethyl acetate. Organic layer was dried over Na$_2$SO$_4$, and concentrated under reduced pressure. The crude product was purified by silica gel chromatography to obtain 19 mg of 6-chloro-9-(2-(3,4-difluorophenyl)prop-1-enyl)-1-ethyl-2-methyl-2,3,4,9-tetrahydro-1H-pyrido[3,4-b]indole. $^1$H NMR (CD$_3$OD) OXALATE SALT 7.60 (t, 2H), 7.42 (m, 1H), 7.38 (m, 1H), 7.22 (m, 2H), 7.10 (s, 1H), 4.60 (m, 1H), 3.80 (m, 2H), 3.60 (m, 1H), 3.20 (m, 1H), 3.05 (s, 3H), 2.10 (m, 2H), 1.90 (s, 3H), 1.10 (t, 3H).

Example 98

Preparation of Compound 111

6-chloro-1,2-dimethyl-2,3,4,9-tetrahydro-1H-pyrido[3,4-b]indole (84 mg, 0.36 mmol) was dissolved in DMF (6 mL). To this solution was added CuI (8 mg, 0.035 mmol), L-proline (9 mg, 0.086 mmol), K$_3$PO$_4$ (183 mg, 0.862 mmol). The reaction mixture was stirred for 10 min at room temperature followed by addition of 4-(1-bromoprop-1-en-2-yl)-1,2-difluorobenzene (100 mg, 0.431 mmol). The reaction mixture was heated at 80° C. overnight. Solvent was evaporated under reduced pressure, the residue was diluted with brine and extracted with ethyl acetate. Organic layer was dried over Na$_2$SO$_4$, and concentrated under reduced pressure. The crude product was purified by silica gel chromatography to obtain 43 mg of 6-chloro-9-(2-(3,4-difluorophenyl)prop-1-enyl)-1,2-dimethyl-2,3,4,9-tetrahydro-1H-pyrido[3,4-b]indole. $^1$H NMR (CD$_3$OD) OXALATE SALT 7.62 (m, 1H), 7.60 (s, 1H), 7.50 (m, 1H), 7.36 (m, 1H), 7.22 (m, 2H), 7.05 (s, 1H), 4.80 (m, 2H), 3.60 (m, 1H), 3.10 (m, 2H), 3.0 (s, 3H), 1.90 (s, 3H), 1.60 (d, 3H).

Example 99

Preparation of Compound 121

2,6-dimethyl-2,3,4,9-tetrahydro-1H-pyrido[3,4-b]indole (68 mg, 0.34 mmol) was dissolved in DMF (5 mL). To this solution was added CuI (6 mg, 0.034 mmol), L-proline (8 mg, 0.068 mmol), K$_3$PO$_4$ (145 mg, 0.68 mmol). The reaction mixture was stirred for 10 min at room temperature followed by addition of 4-(1-bromoprop-1-en-2-yl)-2-fluoro-1-methoxybenzene (100 mg, 0.408 mmol). The reaction mixture was heated at 80° C. overnight. Solvent was evaporated under reduced pressure, the residue was diluted with brine and extracted with ethyl acetate. Organic layer was dried over Na$_2$SO$_4$, and concentrated under reduced pressure. The crude product was purified by silica gel chromatography to obtain 35 mg of 9-(2-(3-fluoro-4-methoxyphenyl)prop-1-enyl)-2,6-dimethyl-2,3,4,9-tetrahydro-1H-pyrido[3,4-b]indole. $^1$H NMR (DMSO) OXALATE SALT 7.58 (d, 1H), 7.42 (d, 1H), 7.30 (s, 1H), 7.20 (t, 1H), 7.10 (m, 2H), 6.98 (d, 1H), 4.20 (m, 2H), 3.90 (s, 3H), 3.60 (m, 2H), 2.95 (m, 2H), 2.80 (s, 3H), 2.40 (s, 3H), 1.85 (s, 3H).

Example 100

Preparation of Compound 122

6-chloro-2-methyl-2,3,4,9-tetrahydro-1H-pyrido[3,4-b]indole (75 mg, 0.34 mmol) was dissolved in DMF (5 mL). To this solution was added CuI (6 mg, 0.034 mmol), L-proline (8 mg, 0.068 mmol), K$_3$PO$_4$ (145 mg, 0.68 mmol). The reaction mixture was stirred for 10 min at room temperature followed by addition of 4-(1-bromoprop-1-en-2-yl)-2-fluoro-1-methoxybenzene (100 mg, 0.408 mmol). The reaction mixture was heated at 80° C. overnight. Solvent was evaporated under reduced pressure, the residue was diluted with brine and extracted with ethyl acetate. Organic layer was dried over Na$_2$SO$_4$, and concentrated under reduced pressure. The crude product was purified by silica gel chromatography to obtain 40 mg of 6-chloro-9-(2-(3-fluoro-4-methoxyphenyl)prop-1-enyl)-2-methyl-2,3,4,9-tetrahydro-1H-pyrido[3,4-b]indole. $^1$H NMR (DMSO) OXALATE SALT 7.60 (m, 2H), 7.42 (d, 1H), 7.25 (d, 2H), 7.18 (t, 1H), 7.10 (s, 1H), 4.10 (m, 2H), 3.90 (s, 3H), 3.50 (m, 2H), 2.95 (m, 2H), 2.78 (s, 3H), 1.82 (s, 3H).

Example 101

Preparation of Compound 129

6-chloro-1-ethyl-2-methyl-2,3,4,9-tetrahydro-1H-pyrido[3,4-b]indole (248 mg, 1.00 mmol) was dissolved in toluene (4 mL) and K$_2$CO$_3$ (276 mg, 0.2 mmol), CuSO$_4$.5H$_2$O (249 mg, 0.01 mmol) and 1,10-phenanthroline (36 mg, 0.2 mmol) were added. The reaction mixture was stirred for 10 min and a solution of 1-(bromoethynyl)-4-fluorobenzene (220 mg, 1.1 mmol) toluene (2 mL) was added. The reaction mixture was purged with nitrogen and heated at 80-85° C. overnight. Solvent was evaporated under reduced pressure and the residue was purified by silica gel column chromatography (100-200 mesh) using 0-25% ethyl acetate-hexane as eluent. $^1$H NMR (DMSO) OXALATE SALT 7.62 (m, 4H), 7.30 (m, 3H), 4.10 (m, 2H), 3.12 (m, 2H), 2.85 (m, 1H), 2.60 (s, 3H), 2.0 (m, 2H), 1.10 (t, 3H).

Example 102

Preparation of Compound 109

2,6-dimethyl-2,3,4,9-tetrahydro-1H-pyrido[3,4-b]indole (72 mg, 0.359 mmol) was dissolved in DMF (5 mL). To this solution was added CuI (8 mg, 0.035 mmol), L-proline (9 mg, 0.086 mmol), K$_3$PO$_4$ (183 mg, 0.862 mmol). The reaction mixture was stirred for 10 min at room temperature followed by addition of 4-(1-bromoprop-1-en-2-yl)-1,2-difluorobenzene (100 mg, 0.431 mmol). The reaction mixture was heated at 80° C. overnight. Solvent was evaporated under reduced pressure; the residue was diluted with brine and extracted with ethyl acetate. Organic layer was dried over Na$_2$SO$_4$, and concentrated under reduced pressure. The crude product was purified by silica gel chromatography to obtain 74 mg of 9-(2-(3,4-difluorophenyl)prop-1-enyl)-2,6-dimethyl-2,3,4,9-tetrahydro-1H-pyrido[3,4-b]indole. $^1$H NMR (DMSO) OXALATE SALT 7.80 (m, 1H), 7.50 (m, 2H), 7.30 (s, 1H), 7.20 (s, 1H), 7.15 (d, 1H), 7.0 (d, 1H), 4.22 (m, 2H), 3.40 (m, 2H), 2.90 (m, 2H), 2.82 (s, 3H), 2.40 (s, 3H), 1.90 (s, 3H).

Example 103

Preparation of Compound 110

6-chloro-2-methyl-2,3,4,9-tetrahydro-1H-pyrido[3,4-b]indole (79 mg, 0.35 mmol) was dissolved in DMF (6 mL). To this solution was added CuI (8 mg, 0.035 mmol), L-proline (9 mg, 0.086 mmol), $K_3PO_4$ (183 mg, 0.862 mmol). The reaction mixture was stirred for 10 min at room temperature followed by addition of 4-(1-bromoprop-1-en-2-yl)-1,2-difluorobenzene (100 mg, 0.431 mmol). The reaction mixture was heated at 80° C. overnight. Solvent was evaporated under reduced pressure, the residue was diluted with brine and extracted with ethyl acetate. Organic layer was dried over $Na_2SO_4$, and concentrated under reduced pressure. The crude product was purified by silica gel chromatography to obtain 60 mg of 6-chloro-9-(2-(3,4-difluorophenyl)prop-1-enyl)-2-methyl-2,3,4,9-tetrahydro-1H-pyrido[3,4-b]indole. $^1$H NMR (DMSO) OXALATE SALT 7.80 (m, 1H), 7.60 (s, 1H), 7.50 (m, 2H), 7.25 (d, 1H), 7.15 (s, 2H), 4.10 (m, 2H), 3.30 (m, 2H), 2.95 (m, 2H), 2.78 (s, 3H), 1.82 (s, 3H).

Example 104

Preparation of Compound 116

6-chloro-1-ethyl-2-methyl-2,3,4,9-tetrahydro-1H-pyrido[3,4-b]indole (78 mg, 0.31 mmol) was dissolved in DMF (5 mL). To this solution was added CuI (6 mg, 0.031 mmol), L-proline (7 mg, 0.063 mmol), $K_3PO_4$ (134 mg, 0.63 mmol). The reaction mixture was stirred for 10 min at room temperature followed by addition of 4-(1-bromoprop-1-en-2-yl)-1,2-dichlorobenzene (100 mg, 0.378 mmol). The reaction mixture was heated at 80° C. overnight. Solvent was evaporated under reduced pressure, the residue was diluted with brine and extracted with ethyl acetate. Organic layer was dried over $Na_2SO_4$, and concentrated under reduced pressure. The crude product was purified by silica gel chromatography to obtain 36 mg of 6-chloro-9-(2-(3,4-dichlorophenyl)prop-1-enyl)-1-ethyl-2-methyl-2,3,4,9-tetrahydro-1H-pyrido[3,4-b]indole. $^1$H NMR (DMSO) OXALATE SALT 7.95 (s, 1H), 7.76 (d, 1H), 7.65 (m, 2H), 7.30 (s, 1H), 7.20 (m, 2H), 3.40 (m, 3H), 2.90 (m, 4H), 2.70 (s, 3H), 1.90 (s, 3H), 0.9 (t, 3H).

Example 105

Preparation of Compound 115

6-chloro-1,2-dimethyl-2,3,4,9-tetrahydro-1H-pyrido[3,4-b]indole (74 mg, 0.31 mmol) was dissolved in DMF (5 mL). To this solution was added CuI (6 mg, 0.031 mmol), L-proline (7 mg, 0.063 mmol), $K_3PO_4$ (134 mg, 0.63 mmol). The reaction mixture was stirred for 10 min at room temperature followed by addition of 4-(1-bromoprop-1-en-2-yl)-1,2-dichlorobenzene (100 mg, 0.378 mmol). The reaction mixture was heated at 80° C. overnight. Solvent was evaporated under reduced pressure, the residue was diluted with brine and extracted with ethyl acetate. Organic layer was dried over $Na_2SO_4$, and concentrated under reduced pressure. The crude product was purified by silica gel chromatography to obtain 48 mg of 6-chloro-9-(2-(3,4-dichlorophenyl)prop-1-enyl)-1,2-dimethyl-2,3,4,9-tetrahydro-1H-pyrido[3,4-b]indole. $^1$H NMR (DMSO) OXALATE SALT 8.0 (d, 1H), 7.76 (d, 1H), 7.65 (m, 2H), 7.25 (m, 2H), 7.18 (d, 1H), 4.50 (m, 1H), 3.60 (m, 2H), 2.90 (m, 2H), 2.75 (s, 3H), 1.90 (s, 3H), 1.40 (d, 3H).

Example 106

Preparation of Compound 128

6-chloro-1-ethyl-2-methyl-2,3,4,9-tetrahydro-1H-pyrido[3,4-b]indole (248 mg, 1.00 mmol) was dissolved in toluene (4 mL) and $K_2CO_3$ (276 mg, 0.2 mmol), $CuSO_4.5H_2O$ (249 mg, 0.01 mmol) and 1,10-phenanthroline (36 mg, 0.2 mmol) were added to it. The reaction mixture was stirred for 10 min and a solution of 1-(bromoethynyl)-4-fluorobenzene (220 mg, 1.1 mmol) in toluene (2 mL) was added. The reaction mixture was purged with nitrogen and heated at 80-85° C. for 12 h. Solvent was evaporated under reduced pressure and the residue was purified by silica gel chromatography (100-200 mesh) using 0-3% Methanol: DCM as eluent followed by reverse phase chromatography. $^1$H NMR (CDCl$_3$) TFA SALT 7.50 (m, 4H), 7.35 (d, 1H), 7.10 (m, 2H), 4.60 (m, 1H), 3.70 (m, 1H), 3.60 (m, 1H), 3.10 (m, 1H), 3.0 (s, 3H), 2.95 (m, 1H), 1.90 (d, 3H).

Example 107

Preparation of Compound 130

2,6-dimethyl-2,3,4,9-tetrahydro-1H-pyrido[3,4-b]indole (200 mg, 1 mmol) was mixed with $CuSO_4.5H_2O$ (50 mg, 0.2 mmol), 1,10-phenanthroline (72 mg, 0.4 mmol), $K_3PO_4$ (425 mg, 2 mmol) and 1-(bromoethynyl)-4-chlorobenzene (237 mg, 1.1 mmol) in toluene (8-10 ml). The reaction mixture was flushed with nitrogen and heated at 80° C. for 16 h. The reaction mixture was filtered through Celite, and the Celite bed was rinsed with dichloromethane. Combined organic layer was concentrated under reduced pressure and the residue was purified by silica gel chromatography (100-200 mesh) eluting with 60-80% ethyl acetate in hexane to obtain 9-((4-chlorophenyl)ethynyl)-2,6-dimethyl-2,3,4,9-tetrahydro-1H-pyrido[3,4-b]indole (24 mg) as brown semi solid. $^1$H NMR (CDCl$_3$) FREE BASE 7.42 (m, 3H), 7.36 (m, 3H), 7.10 (d, 1H), 3.70 (s, 2H), 2.80 (m, 4H), 2.60 (s, 3H), 2.42 (s, 3H).

Example 108

Preparation of Compound 132

6-chloro-1,2-dimethyl-2,3,4,9-tetrahydro-1H-pyrido[3,4-b]indole (220 mg, μmol) was mixed with $CuSO_4.5H_2O$ (50 mg, 0.2 mmol), 1,10-phenanthroline (72 mg, 0.4 mmol), $K_3PO_4$ (425 mg, 2 mmol) and 1-(bromoethynyl)-4-chlorobenzene (237 mg, 1.1 mmol) in toluene (8-10 ml). The reaction mixture was flushed with nitrogen and heated at 80° C. for 16 h. The reaction mixture was filtered through Celite and Celite bed was rinsed with dichloromethane. Combined organic layer was concentrated under reduced pressure and the residue was purified by silica gel chromatography (100-200 mesh) eluting with 60-80% ethyl acetate in hexane to obtain 6-chloro-9-((4-chlorophenyl)ethynyl)-1,2-dimethyl-2,3,4,9-tetrahydro-1H-pyrido[3,4-b]indole as brown semi solid (88 mg). $^1$H NMR (CDCl$_3$) FREE BASE 7.51-7.43 (m, 4H), 7.39-7.36 (d, 1H), 7.30-7.22 (m, 2H), 4.05-3.97 (q, 1H), 3.24-2.80 (m, 4H), 2.60 (s, 3H), 1.68-1.58 (d, 3H).

Example 109

Preparation of Compound 155

6-chloro-2-methyl-2,3,4,9-tetrahydro-1H-pyrido[3,4-b]indole (100 mg, 0.45 mmol) was mixed with $CuSO_4.5H_2O$ (23 mg, 0.090 mmol), 1,10-phenanthroline (33 mg, 0.18 mmol), $K_3PO_4$ (192 mg, 0.90 mmol) and 4-(bromoethynyl)-2-fluoro-1-methoxybenzene (113 mg, 0.49 mmol) in toluene (5 ml). The reaction mixture was purged with nitrogen and heated at 80° C. for 16 h. Product was detected by LCMS. The reaction mixture was filtered through Celite and Celite bed was rinsed with dichloromethane. Combined organic layer was concentrated under reduced pressure and the residue was purified by silica gel chromatography (100-200 mesh) eluting with 60-80% ethyl acetate in hexane to obtain 6-chloro-9-((3-fluoro-4-methoxyphenyl)ethynyl)-2-methyl-2,3,4,9-tetrahydro-1H-pyrido[3,4-b]indole (30 mg). $^1H$ NMR ($CDCl_3$) FREE BASE 7.42 (d, 2H), 7.25 (m, 3H), 6.95 (t, 1H), 3.90 (s, 3H), 3.70 (s, 2H), 2.80 (m, 4H), 2.56 (s, 3H).

Example 110

Preparation of Compound 97

2,6-dimethyl-2,3,4,9-tetrahydro-1H-pyrido[3,4-b]indole (72 mg, 0.362 mmol) was dissolved in DMF (5 mL). To this solution was added CuI (6 mg, 0.0362 mmol), L-proline (8 mg, 0.072 mmol), and $K_3PO_4$ (154 mg, 0.724 mmol). The reaction mixture was stirred for 10 min at room temperature followed by addition of 1-(1-bromoprop-1-en-2-yl)-4-chlorobenzene (100 mg, 0.434 mmol). The reaction mixture was heated at 80° C. overnight. Solvent was evaporated under reduced pressure, the residue was diluted with brine and extracted with ethyl acetate. Organic layer was dried over $Na_2SO_4$, and concentrated under reduced pressure. The crude product was purified by silica gel chromatography to obtain 85 mg of 9-(2-(4-chlorophenyl)prop-1-enyl)-2,6-dimethyl-2,3,4,9-tetrahydro-1H-pyrido[3,4-b]indole. $^1H$ NMR ($CDCl_3$) FREE BASE 7.48 (d, 1H), 7.39 (d, 1H), 7.29 (s, 1H), 7.18-7.10 (m, 1H), 7.09-7.0 (m, 2H), 6.93 (d, 1H), 6.86 (s, 1H), 3.78-3.68 (m, 2H), 3.43-3.35 (m, 1H), 3.16-2.70 (m, 3H), 2.64 (s, 3H), 2.47 (s, 3H), 1.99 (s, 3H).

Example 111

Preparation of Compound 98

6-chloro-2-methyl-2,3,4,9-tetrahydro-1H-pyrido[3,4-b]indole (79 mg, 0.36 mmol) was dissolved in DMF (5 mL). To this solution was added CuI (6 mg, 0.0362 mmol), L-proline (8 mg, 0.072 mmol), and $K_3PO_4$ (154 mg, 0.724 mmol). The reaction mixture was stirred for 10 min at room temperature followed by addition of 1-(1-bromoprop-1-en-2-yl)-4-chlorobenzene (100 mg, 0.434 mmol). The reaction mixture was heated at 80° C. overnight. Solvent was evaporated under reduced pressure, the residue was diluted with brine and extracted with ethyl acetate. Organic layer was dried over $Na_2SO_4$, and concentrated under reduced pressure. The crude product was purified by silica gel chromatography to obtain 85 mg of 6-chloro-9-(2-(4-chlorophenyl)prop-1-enyl)-2-methyl-2,3,4,9-tetrahydro-1H-pyrido[3,4-b]indole. $^1H$ NMR ($CDCl_3$) FREE BASE 7.53-7.44 (m, 2H), 7.43-7.38 (m, 2H), 7.18-7.03 (m, 2H), 6.93 (d, 1H), 6.84 (s, 1H), 3.63-3.58 (m, 2H), 3.32-3.26 (m, 1H), 2.88 (s, 3H), 2.83-2.80 (m, 1H), 2.60 (s, 2H), 1.99 (s, 3H).

Example 112

Preparation of Compound 99

6-chloro-1,2-dimethyl-2,3,4,9-tetrahydro-1H-pyrido[3,4-b]indole (42 mg, 0.180 mmol) was dissolved in DMF (3 mL). To this solution was added CuI (3 mg, 0.018 mmol), L-proline (4 mg, 0.036 mmol), $K_3PO_4$ (77 mg, 0.36 mmol). The reaction mixture was stirred for 10 min at room temperature followed by addition of 1-(1-bromoprop-1-en-2-yl)-4-chlorobenzene (50 mg, 0.217 mmol). The reaction mixture was heated at 80° C. overnight. Solvent was evaporated under reduced pressure, the residue was diluted with brine and extracted with ethyl acetate. Organic layer was dried over $Na_2SO_4$, and concentrated under reduced pressure. The crude product was purified by silica gel chromatography to obtain 17 mg, of 6-chloro-9-(2-(4-chlorophenyl)prop-1-enyl)-1,2-dimethyl-2,3,4,9-tetrahydro-1H-pyrido[3,4-b]indole. $^1H$ NMR ($CDCl_3$) FREE BASE 7.53-7.47 (m, 2H), 7.43-7.38 (m, 2H), 7.15-7.10 (m, 1H), 7.06-7.00 (m, 2H), 6.84 (s, 1H), 3.83-3.75 (m, 1H), 3.22-3.10 (m, 1H), 2.97-2.83 (m, 2H), 2.73-2.64 (m, 1H), 2.54 (s, 3H), 1.93 (s, 3H), 1.73 (d, 3H), 1.28 (s, 3H).

Example 113

Preparation of Compound 100

6-chloro-1-ethyl-2-methyl-2,3,4,9-tetrahydro-1H-pyrido[3,4-b]indole (45 mg, 0.180 mmol) was dissolved in DMF (3 mL). To this solution was added CuI (3 mg, 0.018 mmol), L-proline (4 mg, 0.036 mmol), $K_3PO_4$ (77 mg, 0.36 mmol). The reaction mixture was stirred for 10 min at room temperature followed by addition of 1-(1-bromoprop-1-en-2-yl)-4-chlorobenzene (50 mg, 0.217 mmol). The reaction mixture was heated at 80° C. overnight. Solvent was evaporated under reduced pressure, the residue was diluted with brine and extracted with ethyl acetate. Organic layer was dried over $Na_2SO_4$, and concentrated under reduced pressure. The crude product was purified by silica gel chromatography to obtain 18 mg, of 6-chloro-9-(2-(4-chlorophenyl)prop-1-enyl)-1-ethyl-2-methyl-2,3,4,9-tetrahydro-1H-pyrido[3,4-b]indole $^1H$ NMR ($CDCl_3$) FREE BASE 7.53-7.40 (m, 4H), 7.19-7.10 (m, 2H), 7.03 (d, 1H), 6.85 (s, 1H), 3.55-3.48 (m, 1H), 3.35-3.20 (m, 2H), 3.10-2.83 (m, 2H), 2.60 (s, 3H), 1.93 (s, 3H), 1.88-1.75 (m, 2H), 1.03 (t, 3H).

Example 114

Preparation of Compound 108

6-chloro-1-ethyl-2-methyl-2,3,4,9-tetrahydro-1H-pyrido[3,4-b]indole (150 mg, 0.604 mmol) was dissolved in DMF (4 mL). To this solution was added CuI (11 mg, 0.06 mmol), L-proline (14 mg, 0.12 mmol), $K_3PO_4$ (257 mg, 1.2 mmol). The reaction mixture was stirred for 10 min at room temperature followed by addition of 3-(1-bromoprop-1-en-2-yl)pyridine (143 mg, 0.725 mmol). The reaction mixture was heated at 80° C. overnight. Solvent was evaporated under reduced pressure; the residue was diluted with brine and extracted with ethyl acetate. Organic layer was dried over $Na_2SO_4$, and concentrated under reduced pressure. The crude product was purified by silica gel chromatography to obtain 70 mg of title compound. ¹H NMR (CD₃OD) TFA SALT 9.10 (s, 1H), 8.80 (s, 1H), 8.62 (d, 1H), 7.95 (s, 1H), 7.60 (s, 1H), 7.40 (s, 1H), 7.22 (m, 2H), 4.70 (m, 1H), 3.80 (m, 1H), 3.60 (m, 1H), 3.20 (m, 2H), 3.05 (s, 3H), 2.18 (m, 2H), 2.05 (s, 3H), 1.10 (t, 3H).

Example 115

Preparation of Compound 113

2,6-dimethyl-2,3,4,9-tetrahydro-1H-pyrido[3,4-b]indole (63 mg, 0.31 mmol) was dissolved in DMF (5 mL). To this solution was added CuI (6 mg, 0.032 mmol), L-proline (7 mg, 0.063 mmol), K₃PO₄ (134 mg, 0.63 mmol). The reaction mixture was stirred for 10 min at room temperature followed by addition of 4-(1-bromoprop-1-en-2-yl)-1,2-dichlorobenzene (100 mg, 0.378 mmol). The reaction mixture was heated at 80° C. overnight. Solvent was evaporated under reduced pressure, the residue was diluted with brine and extracted with ethyl acetate. Organic layer was dried over Na₂SO₄, and concentrated under reduced pressure. The crude product was purified by silica gel chromatography to obtain 45 mg of 9-(2-(3,4-dichlorophenyl)prop-1-enyl)-2,6-dimethyl-2,3,4,9-tetrahydro-1H-pyrido[3,4-b]indole. ¹H NMR (CD₃OD) TFA SALT 7.82 (d, 1H), 7.58 (d, 2H), 7.36 (d, 1H), 7.15 (m, 2H), 7.0 (s, 1H), 4.65 (m, 1H), 4.40 (m, 1H), 3.85 (m, 1H), 3.60 (m, 1H), 3.20 (m, 2H), 3.10 (s, 3H), 2.42 (s, 3H), 2.0 (s, 3H).

Example 116

Preparation of Compound 106

6-chloro-2-methyl-2,3,4,9-tetrahydro-1H-pyrido[3,4-b]indole (200 mg, 0.9 mmol) was dissolved in DMF (5 mL). To this solution was added CuI (17 mg, 0.09 mmol), L-proline (20 mg, 0.18 mmol), K₃PO₄ (387 mg, 1.8 mmol). The reaction mixture was stirred for 10 min at room temperature followed by addition of 3-(1-bromoprop-1-en-2-yl)pyridine (215 mg, 1.09 mmol). The reaction mixture was heated at 90° C. overnight. Solvent was evaporated under reduced pressure, the residue was diluted with brine and extracted with ethyl acetate. Organic layer was dried over Na₂SO₄, and concentrated under reduced pressure. The crude product was purified by silica gel chromatography to obtain 180 mg of title compound. ¹H NMR (CD₃OD) TFA SALT 9.10 (m, 1H), 8.80 (m, 1H), 8.50 (d, 1H), 7.82 (s, 1H), 7.60 (s, 1H), 7.30 (m, 3H), 4.60 (m, 2H), 3.70 (m, 2H), 3.20 (m, 2H), 3.15 (s, 3H), 2.05 (s, 3H).

Example 117

Preparation of Compound 107

6-chloro-1,2-dimethyl-2,3,4,9-tetrahydro-1H-pyrido[3,4-b]indole (100 mg, 0.42 mmol) was dissolved in DMF (4 mL). To this solution was added CuI (8 mg, 0.04 mmol), L-proline (9 mg, 0.08 mmol), K₃PO₄ (182 mg, 0.85 mmol). The reaction mixture was stirred for 10 min at room temperature followed by addition of 3-(1-bromoprop-1-en-2-yl)pyridine (101 mg, 0.51 mmol). The reaction mixture was heated at 90° C. for 18 h. Solvent was evaporated under reduced pressure, the residue was diluted with brine and extracted with ethyl acetate. Organic layer was dried over Na₂SO₄, and concentrated under reduced pressure. The crude product was purified by silica gel chromatography to obtain 80 mg of title compound. MS m/z observed 352 (M+1).

Example 118

Preparation of Compound 117

2,6-dimethyl-2,3,4,9-tetrahydro-1H-pyrido[3,4-b]indole (73 mg, 0.36 mmol) was dissolved in DMF (6 mL). To this solution was added CuI (7 mg, 0.036 mmol), L-proline (8 mg, 0.073 mmol), K₃PO₄ (156 mg, 0.734 mmol). The reaction mixture was stirred for 10 min at room temperature followed by addition of 1-(1-bromoprop-1-en-2-yl)-4-methoxybenzene (100 mg, 0.44 mmol). The reaction mixture was heated at 80° C. for 18 h. Solvent was evaporated under reduced pressure, the residue was diluted with brine and extracted with ethyl acetate. Organic layer was dried over Na₂SO₄, and concentrated under reduced pressure. The crude product was purified by silica gel chromatography to obtain 22 mg of 9-(2-(4-methoxyphenyl)prop-1-enyl)-2,6-dimethyl-2,3,4,9-tetrahydro-1H-pyrido[3,4-b]indole. ¹H NMR (DMSO) OXALATE SALT 7.60 (d, 2H), 7.30 (d, 1H), 7.10 (d, 1H), 7.0 (m, 4H), 4.20 (m, 2H), 3.80 (s, 3H), 3.40 (m, 2H), 2.95 (m, 2H), 2.82 (s, 3H), 2.40 (s, 3H), 1.82 (s, 3H).

Example 119

Preparation of Compound 118

6-chloro-2-methyl-2,3,4,9-tetrahydro-1H-pyrido[3,4-b]indole (80 mg, 0.36 mmol) was dissolved in DMF (6 mL). To this solution was added CuI (7 mg, 0.036 mmol), L-proline (8 mg, 0.073 mmol), K₃PO₄ (156 mg, 0.734 mmol). The reaction mixture was stirred for 10 min at room temperature followed by addition of 1-(1-bromoprop-1-en-2-yl)-4-methoxybenzene (100 mg, 0.44 mmol). The reaction mixture was heated at 80° C. for 18 h. Solvent was evaporated under reduced pressure, the residue was diluted with brine and extracted with ethyl acetate. Organic layer was dried over Na₂SO₄, and concentrated under reduced pressure. The crude product was purified by silica gel chromatography to obtain 67 mg of 6-chloro-9-(2-(4-methoxyphenyl)prop-1-enyl)-2-methyl-2,3,4,9-tetrahydro-1H-pyrido[3,4-b]indole. ¹H NMR (DMSO) OXALATE SALT 7.60 (m, 3H), 7.25 (d, 1H), 7.18 (d, 1H), 7.0 (m, 3H), 4.20 (m, 2H), 3.80 (s, 3H), 3.38 (m, 2H), 2.95 (m, 2H), 2.80 (s, 3H), 1.82 (s, 3H).

Example 120

Preparation of Compound 119

6-chloro-1,2-dimethyl-2,3,4,9-tetrahydro-1H-pyrido[3,4-b]indole (85 mg, 0.36 mmol) was dissolved in DMF (6 mL). To this solution was added CuI (7 mg, 0.036 mmol), L-proline (8 mg, 0.073 mmol), K₃PO₄ (156 mg, 0.734 mmol). The reaction mixture was stirred for 10 min at room temperature followed by addition of 1-(1-bromoprop-1-en-2-yl)-4-methoxybenzene (100 mg, 0.44 mmol). The reaction mixture was heated at 80° C. for 18 h. Solvent was evaporated under reduced pressure, the residue was diluted with brine and extracted with ethyl acetate. Organic layer was dried over Na₂SO₄, and concentrated under reduced pressure. The crude product was purified by silica gel chromatography to obtain 18 mg of 6-chloro-9-(2-(4-methoxyphenyl)prop-1-enyl)-1,2-dimethyl-2,3,4,9-tetrahydro-1H-pyrido[3,4-b]indole. ¹H NMR (DMSO) OXALATE SALT 7.60 (m, 3H), 7.18 (s, 2H), 7.05 (s, 1H), 7.0 (d, 2H), 3.80 (s, 3H), 3.50 (m, 2H), 2.85 (m, 4H), 2.70 (m, 2H), 1.80 (s, 3H), 1.20 (d, 3H).

Example 121

Preparation of Compound 120

6-chloro-1-ethyl-2-methyl-2,3,4,9-tetrahydro-1H-pyrido[3,4-b]indole (91 mg, 0.36 mmol) was dissolved in DMF (5 mL). To this solution was added CuI (7 mg, 0.036 mmol), L-proline (8 mg, 0.073 mmol), $K_3PO_4$ (156 mg, 0.734 mmol). The reaction mixture was stirred for 10 min at room temperature followed by addition of 1-(1-bromoprop-1-en-2-yl)-4-methoxybenzene (100 mg, 0.44 mmol). The reaction mixture was heated at 80° C. for 18 h. Solvent was evaporated under reduced pressure, the residue was diluted with brine and extracted with ethyl acetate. Organic layer was dried over $Na_2SO_4$, and concentrated under reduced pressure. The crude product was purified by silica gel chromatography to obtain 12 mg of 6-chloro-1-ethyl-9-(2-(4-methoxyphenyl)prop-1-enyl)-2-methyl-2,3,4,9-tetrahydro-1H-pyrido[3,4-b]indole. $^1$H NMR (DMSO) OXALATE SALT 7.60 (m, 3H), 7.18 (s, 2H), 7.05 (s, 1H), 7.0 (d, 2H), 3.80 (s, 3H), 3.70 (m, 1H), 2.90 (m, 4H), 2.70 (m, 3H), 1.80 (m, 5H), 0.95 (t, 3H).

Example 122

Preparation of Compound 123

6-chloro-1,2-dimethyl-2,3,4,9-tetrahydro-1H-pyrido[3,4-b]indole (80 mg, 0.34 mmol) was dissolved in DMF (6 mL). To this solution was added CuI (6 mg, 0.034 mmol), L-proline (8 mg, 0.068 mmol), $K_3PO_4$ (145 mg, 0.68 mmol). The reaction mixture was stirred for 10 min at room temperature followed by addition of 4-(1-bromoprop-1-en-2-yl)-2-fluoro-1-methoxybenzene (100 mg, 0.40 mmol). The reaction mixture was heated at 80° C. for 18 h. Solvent was evaporated under reduced pressure, the residue was diluted with brine and extracted with ethyl acetate. Organic layer was dried over $Na_2SO_4$, and concentrated under reduced pressure. The crude product was purified by silica gel chromatography to obtain 17 mg of 6-chloro-9-(2-(3-fluoro-4-methoxyphenyl)prop-1-enyl)-1,2-dimethyl-2,3,4,9-tetrahydro-1H-pyrido[3,4-b]indole. $^1$H NMR (DMSO) OXALATE SALT 7.65 (d, 2H), 7.47 (dd, 1H), 7.25 (d, 2H), 7.20 (s, 1H), 7.12 (s, 1H), 3.90 (s, 3H), 3.40 (m, 3H), 2.96 (m, 2H), 2.80 (s, 3H), 1.80 (s, 3H), 1.50 (d, 3H).

Example 123

Preparation of Compound 124

6-chloro-1-ethyl-2-methyl-2,3,4,9-tetrahydro-1H-pyrido[3,4-b]indole (84 mg, 0.34 mmol) was dissolved in DMF (5 mL). To this solution was added CuI (6 mg, 0.034 mmol), L-proline (8 mg, 0.068 mmol), $K_3PO_4$ (145 mg, 0.68 mmol). The reaction mixture was stirred for 10 min at room temperature followed by addition of 4-(1-bromoprop-1-en-2-yl)-2-fluoro-1-methoxybenzene (100 mg, 0.408 mmol). The reaction mixture was heated at 80° C. for 18 h. Solvent was evaporated under reduced pressure, the residue was diluted with brine and extracted with ethyl acetate. Organic layer was dried over $Na_2SO_4$, and concentrated under reduced pressure. The crude product was purified by silica gel chromatography to obtain 21 mg of 6-chloro-1-ethyl-9-(2-(3-fluoro-4-methoxyphenyl)prop-1-enyl)-2-methyl-2,3,4,9-tetrahydro-1H-pyrido[3,4-b]indole. $^1$H NMR (CD$_3$OD) TFA SALT 7.60 (d, 1H), 7.42 (m, 2H), 7.20 (m, 3H), 7.0 (s, 1H), 4.60 (m, 1H), 3.90 (s, 3H), 3.8 (m, 1H), 3.60 (m, 1H), 3.20 (m, 2H), 3.05 (s, 3H), 2.10 (m, 2H), 1.90 (s, 3H), 1.10 (t, 3H).

Example 124

Preparation of Compound 159

1-Ethyl-2,6-dimethyl-2,3,4,9-tetrahydro-1H-pyrido[3,4-b]indole (228 mg, 1 mmol) was mixed with $CuSO_4.5H_2O$ (249 mg, 1 mmol), 1,10-phenanthroline (36 mg, 0.2 mmol), $K_2CO_3$ (276 mg, 0.2 mmol) and 1-(bromoethynyl)-4-fluorobenzene compound (220 mg, 1.1 mmol) in toluene (8-10 ml). The reaction mixture was flushed with nitrogen and heated at 80-85° C. for 16 h. The reaction mixture was filtered through Celite, and the Celite bed was rinsed with dichloromethane. Combined organic layer was concentrated under reduced pressure and the residue was purified by silica gel chromatography (100-200 mesh) eluting with 5% MeOH/DCM as eluent followed by reverse phase chromatography. $^1$H NMR (CD$_3$OD) TFA SALT 7.80 (d, 1H), 7.40 (d, 1H), 7.30 (m, 3H), 7.05 (m, 2H), 5.0 (m, 1H), 4.50 (m, 2H), 3.80 (m, 1H), 3.55 (m, 1H), 3.10 (m, 2H), 3.0 (s, 3H), 2.42 (s, 3H), 1.80 (q, 2H), 1.18 (t, 3H).

Example 125

Preparation of Compound 160

1-ethyl-2,6-dimethyl-2,3,4,9-tetrahydro-1H-pyrido[3,4-b]indole (42 mg, 0.180 mmol) was dissolved in DMF (4 mL). To this solution was added CuI (3 mg, 0.0180 mmol), L-proline (4 mg, 0.036 mmol), $K_3PO_4$ (77 mg, 0.360 mmol). The reaction mixture was stirred for 10 min at room temperature followed by addition of 1-(1-bromoprop-1-en-2-yl)-4-chlorobenzene (50 mg, 0.217 mmol). The reaction mixture was heated at 80° C. for 18 h. Solvent was evaporated under reduced pressure, the residue was diluted with brine and extracted with ethyl acetate. Organic layer was dried over $Na_2SO_4$, and concentrated under reduced pressure. The crude product was purified by silica gel chromatography to obtain 20 mg, of 9-(2-(4-chlorophenyl)prop-1-enyl)-1-ethyl-2,6-dimethyl-2,3,4,9-tetrahydro-1H-pyrido[3,4-b]indole. $^1$H NMR (CDCl$_3$) FREE BASE-7.5 (d, 2H), 7.4 (d, 2H), 7.33 (s, 1H), 7.02 (s, 2H), 6.85 (s, 1H), 3.40-3.24 (m, 1H), 3.14-2.90 (m, 1H), 2.82-2.7 (m, 1H), 2.68-2.53 (m, 2H), 2.43 (s, 3H), 2.06-2.02 (m, 1H), 1.93 (s, 3H), 1.90-1.72 (m, 1H), 1.30 (s, 3H), 1.1-0.98 (m, 3H).

Example 126

Preparation of Compound 161

1,2,6-trimethyl-2,3,4,9-tetrahydro-1H-pyrido[3,4-b]indole (39 mg, 0.180 mmol) was dissolved in DMF (4 mL). To this solution was added CuI (3 mg, 0.0180 mmol), L-proline (4 mg, 0.036 mmol), $K_3PO_4$ (77 mg, 0.360 mmol). The reaction mixture was stirred for 10 min at room temperature followed by addition of 1-(1-bromoprop-1-en-2-yl)-4-chlorobenzene (50 mg, 0.217 mmol). The reaction mixture was heated at 80° C. for 18 h. Solvent was evaporated under reduced pressure, the residue was diluted with brine and extracted with ethyl acetate. Organic layer was dried over $Na_2SO_4$, and concentrated under reduced pressure. The crude product was purified by silica gel chromatography to obtain 25 mg, of 9-(2-(4-chlorophenyl)prop-1-enyl)-1,2,6-trimethyl-2,3,4,9-tetrahydro-1H-pyrido[3,4-b]indole. $^1$H NMR (CDCl$_3$) FREE BASE-7.48 (d, 2H), 7.4 (d, 2H), 7.32 (s, 1H), 7.04 (s, 2H), 6.87 (s, 1H), 4.03-3.94 (m, 1H), 3.4-3.3 (m, 1H), 3.18-3.08 (m, 1H), 2.9-2.8 (m, 1H), 2.72-2.63 (m, 1H), 2.48 (s, 3H), 1.95 (s, 3H), 1.33-1.20 (m, 6H).

Example 127

Preparation of Compound 162

1-ethyl-2,6-dimethyl-2,3,4,9-tetrahydro-1H-pyrido[3,4-b]indole (228 mg, µmol) was mixed with CuSO$_4$.5H$_2$O (50 mg, 0.2 mmol), 1,10-phenanthroline (72 mg, 0.4 mmol), K$_3$PO$_4$ (425 mg, 2 mmol) and 1-(bromoethynyl)-4-chlorobenzene (237 mg, 1.1 mmol) in toluene (8-10 ml). The reaction mixture was flushed with nitrogen and heated at 80° C. for 16 h. The reaction mixture was filtered through Celite, and the Celite bed was rinsed with dichloromethane. Combined organic layer was concentrated under reduced pressure and the residue was purified by silica gel chromatography (100-200 mesh) eluting with 60-80% ethyl acetate in hexane to obtain 9-((4-chlorophenyl)ethynyl)-1-ethyl-2,6-dimethyl-2,3,4,9-tetrahydro-1H-pyrido[3,4-b]indole as brown semi solid (30 mg). $^1$H NMR (CDCl$_3$) FREE BASE 7.50-7.40 (m, 3H), 7.37-7.33 (m, 2H), 7.28 (s, 1H), 7.20-7.15 (d, 1H), 5.25-5.20 (t, 1H), 3.06 (s, 3H), 3.02 (s, 3H), 2.98-2.88 (m, 2H), 2.80-2.60 (m, 2H), 1.20-1.18 (m, 2H), 1.10-1.07 (t, 3H).

Example 128

Preparation of Compound 163

2,6-dimethyl-1-phenyl-2,3,4,9-tetrahydro-1H-pyrido[3,4-b]indole (276 mg, µmol) was mixed with CuSO$_4$.5H$_2$O (50 mg, 0.2 mmol), 1,10-phenanthroline (72 mg, 0.4 mmol), K$_3$PO$_4$ (425 mg, 2 mmol) and 1-(bromoethynyl)-4-chlorobenzene (237 mg, 1.1 mmol) in toluene (8-10 ml). The reaction mixture was flushed with nitrogen and heated at 80° C. for 16 h. The reaction mixture was filtered through Celite, and the Celite bed was rinsed with dichloromethane. Combined organic layer was concentrated under reduced pressure and the residue was purified by silica gel chromatography (100-200 mesh) eluting with 60-80% ethyl acetate in hexane to obtain 9-((4-chlorophenyl)ethynyl)-1-ethyl-2,6-dimethyl-2,3,4,9-tetrahydro-1H-pyrido[3,4-b]indole as brown semi solid (90 mg). The product was dissolved in 50% aqueous TFA:acetonitrile (1:1) and stirred at 50° C. to obtain the title compound as TFA salt (off white solid). $^1$H NMR (CD$_3$OD) TFA SALT 7.65 (d, 1H), 7.45-7.3 (m, 4H), 7.2 (m, 3H), 7.05 (m, 2H), 6.7 (d, 2H), 6.25 (s, 1H), 4.25 (d, 1H), 4.15 (d, 1H), 3.4 (m, 2H), 3.2 (m, 2H), 2.9 (bs, 3), 2.4 (s, 3H).

Example 129

Preparation of Compound 164

2,6-dimethyl-1-phenyl-2,3,4,9-tetrahydro-1H-pyrido[3,4-b]indole (99 mg, 0.362 mmol) was dissolved in DMF (5 mL). To this solution was added CuI (6 mg, 0.0362 mmol), L-proline (8 mg, 0.072 mmol), K$_3$PO$_4$ (154 mg, 0.724 mmol). The reaction mixture was stirred for 10 min at room temperature followed by addition of 1-(1-bromoprop-1-en-2-yl)-4-chlorobenzene (100 mg, 0.434 mmol). The reaction mixture was heated at 80° C. for 18 h. Solvent was evaporated under reduced pressure, the residue was diluted with brine and extracted with ethyl acetate. Organic layer was dried over Na$_2$SO$_4$, and concentrated under reduced pressure. The crude product was purified by silica gel chromatography to obtain 35 mg, of 9-(2-(4-chlorophenyl)prop-1-enyl)-2,6-dimethyl-1-phenyl-2,3,4,9-tetrahydro-1H-pyrido[3,4-b]indole. $^1$H NMR (CDCl$_3$) TFA SALT-7.42 (s, 1H), 7.25-7.2 (m, 5H), 7.2-7.16 (m, 2H), 7.10-7.0 (m, 3H), 6.96 (d, 1H), 6.2 (s, 1H), 4.45 (bs, 1H), 3.22-3.28 (m, 1H), 3.17-3.08 (m, 4H), 2.9-2.8 (m, 1H), 2.5 (s, 3H), 2.45-2.4 (m, 4H).

Example 130

Preparation of Compound 165

1,2,6-trimethyl-2,3,4,9-tetrahydro-1H-pyrido[3,4-b]indole (213 mg, 1 mmol) was dissolved in DMF (5 mL). To this solution was added CuI (19 mg, 0.1 mmol), L-proline (0.2 mmol), K$_3$PO$_4$ (424 mg, 2 mmol). The reaction mixture was stirred for 10 min at room temperature followed by addition of 1-(1-bromoprop-1-en-2-yl)-2-fluorobenzene (260 mg, 1.2 mmol). The reaction mixture was heated at 85° C. for 18 h. Solvent was evaporated under reduced pressure, the residue was diluted with brine and extracted with ethyl acetate. Organic layer was dried over Na$_2$SO$_4$, and concentrated under reduced pressure. The crude product was purified by silica gel chromatography followed by reverse phase chromatography. $^1$H NMR (CDCl$_3$) TFA SALT 7.25-7.00 (m, 4H), 6.90 (m, 2H), 6.70 (s, 1H), 4.05 (m, 1H), 3.60 (m, 1H), 3.40 (m, 1H), 3.0 (m, 3H), 2.45 (s, 3H), 2.30 (s, 3H), 2.22 (s, 3H), 1.60 (d, 3H).

Example 131

Preparation of Compound 166

1,2,6-trimethyl-2,3,4,9-tetrahydro-1H-pyrido[3,4-b]indole (213 mg, 1 mmol) was dissolved in DMF (5 mL). To this solution was added CuI (19 mg, 0.1 mmol), L-proline (0.2 mmol), K$_3$PO$_4$ (424 mg, 2 mmol). The reaction mixture was stirred for 10 min at room temperature followed by addition of 1-(1-bromoprop-1-en-2-yl)-2-fluorobenzene (260 mg, 1.2 mmol). The reaction mixture was heated at 85° C. for 18 h. Solvent was evaporated under reduced pressure, the residue was diluted with brine and extracted with ethyl acetate. Organic layer was dried over Na$_2$SO$_4$, and concentrated under reduced pressure. The crude product was purified by silica gel chromatography followed by reverse phase chromatography. $^1$H NMR (CDCl$_3$) TFA SALT 7.40 (m, 3H), 7.20 (m, 4H), 6.70 (s, 1H), 4.42 (m, 1H), 3.70 (m, 1H), 3.60 (m, 1H), 3.10 (m, 2H), 3.0 (s, 3H), 2.42 (s, 3H), 1.90 (s, 3H), 1.70 (d, 3H).

Example 132

Preparation of Compound 167

6-chloro-1,2-dimethyl-2,3,4,9-tetrahydro-1H-pyrido[3,4-b]indole (213 mg, 1 mmol) was dissolved in DMF (5 mL). To this solution was added CuI (19 mg, 0.1 mmol), L-proline (0.2 mmol), K$_3$PO$_4$ (424 mg, 2 mmol). The reaction mixture was stirred for 10 min at room temperature followed by addition of 1-(1-bromoprop-1-en-2-yl)-2-fluorobenzene (260 mg, 1.2 mmol). The reaction mixture was heated at 85° C. for 18 h. Solvent was evaporated under reduced pressure, the residue was diluted with brine and extracted with ethyl acetate. Organic layer was dried over Na$_2$SO$_4$, and concentrated under reduced pressure. The crude product was purified by silica gel chromatography followed by reverse phase chromatography. $^1$H NMR (CDCl$_3$) TFA SALT 7.40 (s, 1H), 7.15

(m, 3H), 6.95-6.80 (m, 3H), 6.70 (s, 1H), 4.10 (m, 1H), 3.58 (m, 1H), 3.40 (m, 1H), 2.80 (m, 2H), 2.42 (s, 3H), 2.30 (s, 3H), 1.65 (d, 3H).

Example 133

Preparation of Compound 168

6-chloro-1,2-dimethyl-2,3,4,9-tetrahydro-1H-pyrido[3,4-b]indole (213 mg, 1 mmol) was dissolved in DMF (5 mL). To this solution was added CuI (19 mg, 0.1 mmol), L-proline (0.2 mmol), $K_3PO_4$ (424 mg, 2 mmol). The reaction mixture was stirred for 10 min at room temperature followed by addition of 1-(1-bromoprop-1-en-2-yl)-2-fluorobenzene (260 mg, 1.2 mmol). The reaction mixture was heated at 85° C. for 18 h. Solvent was evaporated under reduced pressure, the residue was diluted with brine and extracted with ethyl acetate. Organic layer was dried over $Na_2SO_4$, and concentrated under reduced pressure. The crude product was purified by silica gel chromatography followed by reverse phase chromatography. $^1H$ NMR ($CDCl_3$) TFA SALT 7.55 (s, 1H), 7.38 (m, 2H), 7.22-7.10 (m, 4H), 6.70 (s, 1H), 4.55 (m, 1H), 3.70 (m, 1H), 3.60 (m, 1H), 3.10 (m, 2H), 3.0 (s, 3H), 2.0 (s, 3H), 1.78 (d, 3H).

Example 134

Preparation of Compound 169

1,2,6-trimethyl-2,3,4,9-tetrahydro-1H-pyrido[3,4-b]indole (235 mg, 1 mmol) was dissolved in DMF (5 mL). To this solution was added CuI (19 mg, 0.1 mmol), L-proline (0.2 mmol), $K_3PO_4$ (424 mg, 2 mmol). The reaction mixture was stirred for 10 min at room temperature followed by addition of 1-(1-bromoprop-1-en-2-yl)-2,4-dichlorobenzene (318 mg, 1.2 mmol). The reaction mixture was heated at 85° C. for 18 h. Solvent was evaporated under reduced pressure; the residue was diluted with brine and extracted with ethyl acetate. Organic layer was dried over $Na_2SO_4$, and concentrated under reduced pressure. The crude product was purified by silica gel chromatography followed by reverse phase chromatography. $^1H$ NMR ($CDCl_3$) TFA SALT 7.38 (s, 1H), 7.20 (m, 2H), 7.10 (d, 1H), 6.98 (d, 1H), 7.82 (d, 1H), 6.70 (s, 1H), 4.25 (m, 1H), 3.60 (m, 1H), 3.40 (m, 1H), 2.90 (m, 2H), 2.60 (s, 3H), 2.42 (s, 3H), 2.30 (s, 3H), 1.70 (d, 3H).

Example 135

Preparation of Compound 170

1-ethyl-2,6-dimethyl-2,3,4,9-tetrahydro-1H-pyrido[3,4-b]indole (235 mg, 1 mmol) was dissolved in DMF (5 mL). To this solution was added CuI (19 mg, 0.1 mmol), L-proline (0.2 mmol), $K_3PO_4$ (424 mg, 2 mmol). The reaction mixture was stirred for 10 min at room temperature followed by addition of 1-(1-bromoprop-1-en-2-yl)-2,4-dichlorobenzene (318 mg, 1.2 mmol). The reaction mixture was heated at 85° C. for 18 h. Solvent was evaporated under reduced pressure, the residue was diluted with brine and extracted with ethyl acetate. Organic layer was dried over $Na_2SO_4$, and concentrated under reduced pressure. The crude product was purified by silica gel chromatography followed by reverse phase chromatography. $^1H$ NMR ($CD_3OD$) TFA SALT 7.62 (s, 1H), 7.55 (d, 1H), 7.45 (d, 1H), 7.40 (s, 1H), 7.30 (d, 1H), 7.18 (d, 1H), 6.70 (s, 1H), 4.60 (m, 1H), 3.80 (m, 1H), 3.60 (m, 1H), 3.20 (m, 2H), 3.0 (s, 3H), 2.42 (s, 3H), 2.20 (m, 2H), 1.90 (s, 3H), 1.20 (t, 3H).

Example 136

Preparation of Compound 171

6-chloro-1-ethyl-9-((4-fluorophenyl)ethynyl)-2-methyl-2,3,4,9-tetrahydro-1H-pyrido[3,4-b]indole (50 mg) was dissolved in acetonitrile and water (1:1, 5 mL) followed by addition of TFA (0.1 mL). The reaction mixture was heated at 55° C. for 1 h. Solvent was evaporated under reduced pressure and the residue was basified with 10% KOH solution and extracted in DCM. Organic layer was washed with water, dried over anhydrous sodium sulphate and concentrated. The residue was purified by silica gel chromatography (100-200 mesh) using 0-1% methanol: DCM as eluant followed by reverse phase chromatography. $^1H$ NMR ($CD_3OD$) TFA SALT 7.90 (d, 1H), 7.50 (s, 1H), 7.30 (m, 3H), 7.05 (t, 2H), 4.50 (m, 2H), 4.10 (m, 1H), 3.25 (m, 1H), 2.90 (m, 2H), 2.58 (m, 1H), 2.42 (s, 3H), 1.78 (m, 1H), 1.60 (m, 1H), 1.05 (t, 3H).

Example 137

Preparation of Compound 172

1,2,6-trimethyl-2,3,4,9-tetrahydro-1H-pyrido[3,4-b]indole (214 mg, μmol) was mixed with $CuSO_4.5H_2O$ (50 mg, 0.2 mmol), 1,10-phenanthroline (72 mg, 0.4 mmol), $K_3PO_4$ (425 mg, 2 mmol) and 1-(bromoethynyl)-4-chlorobenzene (237 mg, 1.1 mmol) in toluene (8-10 ml). The reaction mixture was flushed with nitrogen and heated at 80° C. for 16 h. The reaction mixture was filtered through Celite, and the Celite bed was rinsed with dichloromethane. Combined organic layer was concentrated under reduced pressure and the residue was purified by silica gel chromatography (100-200 mesh) eluting with 60-80% ethyl acetate in hexane to obtain 9-((4-chlorophenyl)ethynyl)-1,2,6-trimethyl-2,3,4,9-tetrahydro-1H-pyrido[3,4-b]indole (67 mg) as brown semi solid. $^1H$ NMR ($CDCl_3$) FREE BASE 7.42 (d, 2H), 7.38 (d, 2H), 7.30 (m, 2H), 7.10 (d, 1H), 3.90 (m, 1H), 3.20 (m, 1H), 2.90 (m, 2H), 2.62 (m, 1H), 2.58 (s, 3H), 2.42 (s, 3H), 1.30 (d, 3H).

Example 138

Preparation of Compound 173

9-((4-chlorophenyl)ethynyl)-2,6-dimethyl-2,3,4,9-tetrahydro-1H-pyrido[3,4-b]indole (50 mg) was dissolved in acetonitrile and water (1:1, 5 mL) followed by addition of TFA (0.1 mL). The reaction mixture was heated at 55° C. for 1 h. Solvent was evaporated under reduced pressure and the residue was basified with 10% KOH solution and extracted in DCM. Organic layer was washed with water, dried over anhydrous sodium sulphate and concentrated. The residue was purified by silica gel chromatography (100-200 mesh) using 0-1% methanol: DCM as eluant followed by reverse phase chromatography. TFA SALT-BATCH1 $^1H$ NMR ($CDCl_3$) TFA SALT 7.60 (d, 1H), 7.36 (d, 2H), 7.30 (s, 1H), 7.22 (m, 3H), 5.0 (m, 1H), 4.35 (m, 3H), 3.90 (m, 1H), 3.30 (m, 1H), 3.15 (m, 1H), 3.05 (s, 3H), 2.95 (m, 1H), 2.45 (s, 3H).

Example 139

Preparation of Compound 174

1,2,6-trimethyl-2,3,4,9-tetrahydro-1H-pyrido[3,4-b]indole (67 mg, 0.31 mmol) was dissolved in DMF (5 mL). To this solution was added CuI (6 mg, 0.032 mmol), L-proline (7 mg, 0.063 mmol), K$_3$PO$_4$ (134 mg, 0.63 mmol). The reaction mixture was stirred for 10 min at room temperature followed by addition of 4-(1-bromoprop-1-en-2-yl)-1,2-dichlorobenzene (100 mg, 0.378 mmol). The reaction mixture was heated at 80° C. for 18 h. Solvent was evaporated under reduced pressure, the residue was diluted with brine and extracted with ethyl acetate. Organic layer was dried over Na$_2$SO$_4$, and concentrated under reduced pressure. The crude product was purified by silica gel chromatography followed by reverse phase chromatography to afford 70 mg of 9-(2-(3,4-difluorophenyl)prop-1-enyl)-1,2,6-trimethyl-2,3,4,9-tetrahydro-1H-pyrido[3,4-b]indole. $^1$H NMR FREE BASE (CDCl$_3$): 7.62 (s, 1H), 7.48 (d, 1H), 7.40 (dd, 1H), 7.33 (s, 1H), 7.08-7.0 (m, 2H), 6.90 (s, 1H), 3.83-3.78 (m, 1H), 3.25-3.15 (m, 1H), 2.98-2.90 (m, 2H), 2.73-2.68 (m, 1H), 2.58 (s, 3H), 2.45 (s, 3H), 1.98 (s, 3H), 1.38 (d, 3H).

Example 140

Preparation of Compound 175

1,2,6-trimethyl-2,3,4,9-tetrahydro-1H-pyrido[3,4-b]indole (77 mg, 0.359 mmol) was dissolved in DMF (5 mL). To this solution was added CuI (8 mg, 0.0359 mmol), L-proline (9 mg, 0.086 mmol), K$_3$PO$_4$ (183 mg, 0.862 mmol). The reaction mixture was stirred for 10 min at room temperature followed by addition of 4-(1-bromoprop-1-en-2-yl)-1,2-difluorobenzene (100 mg, 0.431 mmol). The reaction mixture was heated at 80° C. for 18 h. Solvent was evaporated under reduced pressure, the residue was diluted with brine and extracted with ethyl acetate. Organic layer was dried over Na$_2$SO$_4$, and concentrated under reduced pressure. The crude product was purified by silica gel chromatography 5 mg of 9-(2-(3,4-difluorophenyl)prop-1-enyl)-1,2,6-trimethyl-2,3,4,9-tetrahydro-1H-pyrido[3,4-b]indole. $^1$H NMR (CDCl$_3$) FREE BASE 7.38 (m, 2H), 7.20 (m, 2H), 7.0 (d, 2H), 6.80 (s, 1H), 3.80 (m, 1H), 3.20 (m, 1H), 2.90 (m, 2H), 2.70 (m, 1H), 2.60 (s, 3H), 2.42 (s, 3H), 1.90 (s, 3H), 1.30 (d, 3H).

Example 141

Preparation of Compound 176

1-ethyl-2,6-dimethyl-2,3,4,9-tetrahydro-1H-pyrido[3,4-b]indole (82 mg, 0.36 mmol) was dissolved in DMF (6 mL). To this solution was added CuI (8 mg, 0.036 mmol), L-proline (9 mg, 0.086 mmol), K$_3$PO$_4$ (183 mg, 0.86 mmol). The reaction mixture was stirred for 10 min at room temperature followed by addition of 4-(1-bromoprop-1-en-2-yl)-1,2-difluorobenzene (100 mg, 0.43 mmol). The reaction mixture was heated at 80° C. for 18 h. Solvent was evaporated under reduced pressure, the residue was diluted with brine and extracted with ethyl acetate. Organic layer was dried over Na$_2$SO$_4$, and concentrated under reduced pressure. The crude product was purified by silica gel chromatography to obtain 25 mg of (E)-9-(2-(3,4-difluorophenyl)prop-1-enyl)-1-ethyl-2,6-dimethyl-2,3,4,9-tetrahydro-1H-pyrido[3,4-b]indole. $^1$H NMR (DMSO) OXALATE SALT 7.80 (m, 1H), 7.56 (m, 2H), 7.38 (s, 1H), 7.20 (s, 1H), 7.05 (m, 2H), 3.80 (m, 3H), 3.18 (s, 3H), 3.0 (m, 2H), 2.80 (m, 2H), 2.40 (s, 3H), 1.82 (s, 3H), 0.95 (t, 3H).

Example 142

Preparation of Compound 177

1-ethyl-2,6-dimethyl-2,3,4,9-tetrahydro-1H-pyrido[3,4-b]indole (72 mg, 0.31 mmol) was dissolved in DMF (5 mL). To this solution was added CuI (6 mg, 0.032 mmol), L-proline (7 mg, 0.063 mmol), K$_3$PO$_4$ (134 mg, 0.63 mmol). The reaction mixture was stirred for 10 min at room temperature followed by addition of 4-(1-bromoprop-1-en-2-yl)-1,2-dichlorobenzene (100 mg, 0.378 mmol). The reaction mixture was heated at 80° C. for 18 h. Solvent was evaporated under reduced pressure, the residue was diluted with brine and extracted with ethyl acetate. Organic layer was dried over Na$_2$SO$_4$, and concentrated under reduced pressure. The crude product was purified by silica gel chromatography to obtain 70 mg of 9-(2-(3,4-dichlorophenyl)prop-1-enyl)-1-ethyl-2,6-dimethyl-2,3,4,9-tetrahydro-1H-pyrido[3,4-b]indole. $^1$H NMR FREE BASE (CDCl$_3$): 7.63 (s, 1H), 7.49 (d, 1H), 7.39 (d, 1H), 7.34 (s, 1H), 7.05-7.0 (m, 2H), 6.94 (s, 1H), 3.44-3.38 (m, 1H), 3.24-3.15 (m, 1H), 2.95-2.84 (m, 2H), 2.68-2.6 (m, 1H), 2.53 (s, 2H), 2.46 (s, 3H), 1.97 (s, 3H), 1.75-1.65 (m, 2H), 0.98 (t, 3H).

Example 143

Preparation of Compound 178

1,2,6-trimethyl-2,3,4,9-tetrahydro-1H-pyrido[3,4-b]indole (235 mg, 1 mmol) was dissolved in DMF (5 mL). To this solution was added CuI (19 mg, 0.1 mmol), L-proline (23 mg, 0.2 mmol), K$_3$PO$_4$ ((424 mg, 2 mmol). The reaction mixture was stirred for 10 min at room temperature followed by addition of 1-(1-bromoprop-1-en-2-yl)-2,4-dichlorobenzene (318 mg, 1.2 mmol). The reaction mixture was heated at 85° C. for 18 h. Solvent was evaporated under reduced pressure; the residue was diluted with brine and extracted with ethyl acetate. Organic layer was dried over Na$_2$SO$_4$, and concentrated under reduced pressure. The crude product was purified by silica gel chromatography using 0-5% MeOH: DCM as eluant followed by reverse phase chromatography. $^1$H NMR (CD$_3$OD) TFA SALT 7.60 (s, 1H), 7.50 (d, 1H), 7.42 (d, 1H), 7.38 (s, 1H), 4.25 (d, 1H), 7.16 (d, 1H), 6.70 (s, 1H), 3.85 (m, 1H), 3.60 (m, 2H), 3.18 (m, 2H), 3.05 (s, 3H), 2.42 (s, 3H), 1.90 (s, 3H), 1.70 (d, 3H).

Example 144

Preparation of Compound 184

2,6-dimethyl-1-phenyl-2,3,4,9-tetrahydro-1H-pyrido[3,4-b]indole (276 mg, μmol) was mixed with CuSO$_4$.5H$_2$O (50 mg, 0.2 mmol), 1,10-phenanthroline (72 mg, 0.4 mmol), K$_3$PO$_4$ (425 mg, 2 mmol) and 1-(bromoethynyl)-4-chlorobenzene (237 mg, 1.1 mmol) in toluene (8-10 ml). The reaction mixture was flushed with nitrogen and heated at 80° C. for 16 h. The reaction mixture was filtered through Celite, and the Celite bed was rinsed with dichloromethane. Combined organic layer was concentrated under reduced pressure and the residue was purified by silica gel chromatography (100-200 mesh) eluting with 60-80% ethyl acetate in hexane to obtain 9-((4-chlorophenyl)ethynyl)-1-ethyl-2,6-dimethyl-2,3,4,9-tetrahydro-1H-pyrido[3,4-b]indole as brown semi solid (90 mg). $^1$H NMR (CDCl$_3$) FREE BASE 7.40-7.20 (m, 9H), 7.16-7.12 (d, 1H), 7.08-7.04 (d, 2H), 4.73 (s, 1H), 3.22-3.16 (m, 1H), 3.0-2.80 (m, 3H), 2.50 (s, 3H), 2.45 (s, 3H).

Example 145

Preparation of Compounds 47, 48, 49, 50, 51, 63, 68, 69, 73, 74, 75, 76, 84, 85, 87, 88, 89, 93, 94, 95, 96, 101, 102, 103, 104, 105, 126, 127, 131, 133, 134, 135, 136, 137, 138, 139, 140, 141, 142, 143, 144, 145, 146, 147, 148, 149, 150, 151, 152, 153, 154, 156, 157, 158, 179, 180, 181, 182 and 183.

Compounds 63, 74, 75, 76, 84, 85, 87, 88, 89 and 158 are synthesized using appropriate starting materials according to General Methods 1, 3 and 4. Compounds 50, 51, 68, 69, 73 and 179 are synthesized using appropriate starting materials according to General Method 8. Compounds 47, 48 and 49 are synthesized using appropriate starting materials according to General Method 9. Compounds 93, 94, 95, 96, 101, 102, 103, 104, 105 and 180 are synthesized using appropriate starting materials according to General Method 16. Compounds 126, 127, 131, 133, 134, 135, 136, 137, 138, 139, 140, 141, 142, 143, 144, 145, 146, 147, 148, 149, 150, 151, 152, 153, 154, 156, 157, 181, 182 and 183 are synthesized using appropriate starting materials according to General Method 17.

Example B1

Determination of the Ability of Compounds of the Invention to Bind a Histamine Receptor Histamine H1

To evaluate in radioligand binding assays the activity of compounds of the invention, human recombinant histamine H1 receptor expressed in Chinese hamster ovary (CHO) cells (De Backer, M. D. et al., Biochem. Biophys. Res. Comm. 197(3):1601, 1993) in a modified Tris-HCl buffer (50 mM Tris-HCl, pH 7.4, 2 mM $MgCl_2$, 100 mM NaCl, 250 mM Sucrose) was used. Compounds of the invention were incubated with 1.2 nM [$^3$H]Pyrilamine for 180 minutes at 25° C. Non-specific binding was estimated in the presence of 1 µM pyrilamine. Receptor proteins were filtered and washed, the filters were then counted to determine [$^3$H]Pyrilamine specifically bound. Compounds were screened at 1 µM or lower, using 1% DMSO as vehicle. Biochemical assay results are presented as the percent inhibition of specific binding in Table 3.

Histamine H2

To evaluate in radioligand binding assays the activity of compounds of the invention, human recombinant histamine H2 receptor expressed in Chinese hamster ovary (CHO) K1 cells (Ruat, M., Proc. Natl. Acad. Sci. USA. 87(5):1658, 1990) in a 50 mM Phosphate buffer, pH 7.4 was used. Compounds of the invention were incubated with 0.1 nM [$^{125}$I] Aminopotentidine for 120 minutes at 25° C. Non-specific binding was estimated in the presence of 3 µM Tiotidine. Receptor proteins were filtered and washed, the filters were then counted to determine [$^{125}$I]Aminopotentidine specifically bound. Compounds were screened at 1 µM or lower, using 1% DMSO as vehicle. Biochemical assay results are presented as the percent inhibition of specific binding in Table 3.

Histamine H3

To evaluate in radioligand binding assays the activity of compounds of the invention, human recombinant histamine $H_3$ receptor expressed in Chinese hamster ovary (CHO-K1) cells (Yanai K et al. Jpn J. Pharmacol. 65(2): 107, 1994; Zhu Y et al. Mol. Pharmacol. 59(3): 434, 2001) in a modified Tris-HCl buffer (50 mM Tris-HCl, pH 7.4, 5 mM $MgCl_2$, 0.04% BSA) is used. Compounds of invention are incubated with 3 nM [$^3$H]R(−)-α-Methylhistamine for 90 minutes at 25° C. Non-specific binding is estimated in the presence of 1 µM R(−)-α-Methylhistamine. Receptor proteins are filtered and washed, the filters are counted to determine [$^3$H]R(−)-α-Methylhistamine specifically bound. Compounds are screened at 1 µM or lower, using 1% DMSO as vehicle. Compounds of the invention are tested in this biochemical assay and percent inhibition of specific binding is determined.

Example B2

Determination of the Ability of Compounds of the Invention to Bind a Imidazoline $I_2$ Receptor Central Imidazoline $I_2$ To evaluate in radioligand binding assays the activity of compounds of the invention, rat central imidazoline $I_2$ receptor obtained from Wistar Rat cerebral cortex (Brown, C. M. et al., Br. J. Pharmacol. 99:803, 1990) in a modified Tris-HCl buffer (50 mM Tris-HCl buffer, pH 7.4, 0.5 mM EDTA) was used. Compounds of the invention were incubated with 2 nM [$^3$H]Idazoxan for 30 minutes at 25° C. Non-specific binding was estimated in the presence of 1 µM Idazoxan. Receptor proteins were filtered and washed, the filters were then counted to determine [$^3$H]Idazoxan specifically bound. Compounds were screened at 1 µM or lower, using 1% DMSO as vehicle. Compounds of the invention were tested in this biochemical assay and percent inhibition of specific binding was determined. Certain compounds showed inhibition of specific binding by at least about 80%.

TABLE 3

Binding data (Percentage Inhibition)

| Example No. | Compound No. | Imidazoline $I_2$ Central (1 µM) | Histamine Binding (1 µM) | |
|---|---|---|---|---|
| | | | H1 | H2 |
| 19 | 1 | 40 | 77 | 5 |
| 20 | 2 | 18 | 95 | 71 |
| 21 | 3 | 20 | 83 | 51 |
| 23 | 5 | | 35 | 36 |
| 32 | 14 | | 0 | 12 |
| 33 | 15 | | 0 | −3 |
| 34 | 16 | | 16 | 1 |
| 35 | 17 | | 54 | −6 |
| 36 | 18 | | 10 | 7 |
| 39 | 21 | | 3 | 2 |
| 47 | 29 | | 98 | 60 |
| 52 | 34 | | 56 | 20 |
| 53 | 35 | | 98 | 67 |
| 56 | 38 | 33 | 16 | 3 |
| 58 | 40 | | 7 | 4 |
| 61 | 43 | | 30 | 6 |
| 62 | 44 | | 62 | 9 |
| 94 | 52 | | 3 | −5 |
| 95 | 53 | | 5 | 0 |
| 81 | 54 | | 5 | 21 |
| 69 | 55 | | 90 | 2 |
| 82 | 56 | | 30 | 20 |
| 75 | 57 | | 0 | 10 |
| 87 | 58 | | 2 | 11 |
| 83 | 59 | | 13 | 28 |
| 84 | 60 | | 19 | 15 |
| 85 | 61 | | 49 | 17 |
| 86 | 62 | | 48 | 48 |
| 78 | 66 | | 19 | 1 |
| 79 | 67 | | 35 | 8 |
| 71 | 70 | | 39 | 1 |
| 70 | 71 | | 54 | 11 |
| 72 | 72 | | 55 | 19 |
| 91 | 78 | | 71 | 33 |
| 68 | 79 | | 50 | 20 |
| 92 | 80 | | 66 | 18 |
| 67 | 81 | | 80 | 67 |
| 74 | 90 | | 29/48 | 64 |
| 80 | 91 | | 28/42 | 68 |
| 66 | 92 | | 99 | 50 |
| 110 | 97 | | 20 | 89 |
| 111 | 98 | | 40 | 94 |
| 112 | 99 | | 65 | 62 |
| 113 | 100 | | 33 | 39 |
| 114 | 108 | | 30 | 12 |

TABLE 3-continued

Binding data (Percentage Inhibition)

| Example No. | Compound No. | Imidazoline $I_2$ Central (1 μM) | Histamine Binding (1 μM) H1 | H2 |
|---|---|---|---|---|
| 102 | 109 |  | 20 | 67 |
| 103 | 110 |  | 25 | 64 |
| 98 | 111 |  | 60 | 61 |
| 97 | 112 |  | 33 | 38 |
| 115 | 113 |  | 26 | 81 |
| 96 | 114 |  | 30 | 75 |
| 105 | 115 |  | 50 | 71 |
| 104 | 116 |  | 8 | 50 |
| 99 | 121 |  | 9 | 50 |
| 100 | 122 |  | 13 | 56 |
| 73 | 125 | 60 | 83 | 9 |
| 106 | 128 |  | 32 | 53 |
| 101 | 129 |  | 8 | 26 |
| 107 | 130 |  | 5 | 51 |
| 108 | 132 |  | 14 | 57 |
| 109 | 155 |  | 2 | 49 |
| 124 | 159 |  | 5 | 20 |
| 125 | 160 |  | 31 | 67 |
| 126 | 161 |  | 51 | 82 |
| 127 | 162 |  | 15 | 33 |
| 128 | 163 |  | 13 | 27 |
| 129 | 164 |  | 12 | 25 |
| 130 | 165 |  | 21 | 22 |
| 131 | 166 |  | 79 | 90 |
| 132 | 167 |  | 64 | 51 |
| 133 | 168 |  | 85 | 64 |
| 134 | 169 |  | 20 | 50 |
| 135 | 170 |  | 27 | 60 |
| 136 | 171 |  | 15 | 17 |
| 137 | 172 |  | 11 | 45 |
| 138 | 173 |  | 12 | 49 |
| 139 | 174 |  | 43 | 75 |
| 140 | 175 |  | 25 | 60 |
| 141 | 176 |  | 17 | 26 |
| 142 | 177 |  | 11 | 39 |
| 143 | 178 |  | 44 | 54 |

Example B3

Determination of the Ability of Compounds of the Invention to Bind an Adrenergic Receptor Adrenergic $\alpha_{1A}$ To evaluate in radioligand binding assays the activity of compounds of the invention, rat adrenergic $\alpha_{1A}$ receptor obtained from Wistar Rat submaxillary glands (Michel, A. D. et al., Br. J. Pharmacol. 98:883, 1989) in a modified Tris-HCl buffer (50 mM Tris-HCl buffer, pH 7.4, 0.5 mM EDTA) is used. Compounds of the invention are incubated with 0.25 nM [$^3$H]Prozosin for 60 minutes at 25° C. Non-specific binding is estimated in the presence of 10 μM phentolamine. Receptor proteins are filtered and washed, the filters are then counted to determine [$^3$H]Prozosin specifically bound. Compounds of the invention are screened at 1 μM or lower, using 1% DMSO as vehicle. Compounds of the invention are tested in this biochemical assay and percent inhibition of specific binding is determined.

Adrenergic $\alpha_{1B}$

To evaluate in radioligand binding assays the activity of compounds of the invention, rat adrenergic $\alpha_{1B}$ receptor obtained from Wistar Rat liver (Garcia-S'ainz, J. A. et al., Biochem. Biophys. Res. Commun. 186:760, 1992; Michel A. D. et al., Br. J. Pharmacol. 98:883, 1989) in a modified Tris-HCl buffer (50 mM Tris-HCl buffer, pH 7.4, 0.5 mM EDTA) is used. Compounds of the invention are incubated with 0.25 nM [$^3$H]Prozosin for 60 minutes at 25° C. Non-specific binding is estimated in the presence of 10 μM phentolamine. Receptor proteins are filtered and washed, the filters are then counted to determine [$^3$H]Prozosin specifically bound. Compounds are screened at 1 μM or lower, using 1% DMSO as vehicle. Compounds of the invention are tested in this biochemical assay and percent inhibition of specific binding is determined.

Adrenergic $\alpha_{1D}$

To evaluate in radioligand binding assays the activity of compounds of the invention, human recombinant adrenergic $\alpha_{1D}$ receptor expressed in human embryonic kidney (HEK-293) cells (Kenny, B. A. et al. Br. J. Pharmacol. 115(6):981, 1995) in a 50 mM Tris-HCl buffer, pH 7.4, was used. Compounds of invention were incubated with 0.6 nM [$^3$H]Prozosin for 60 minutes at 25° C. Non-specific binding was estimated in the presence of 10 μM phentolamine. Receptor proteins were filtered and washed, the filters were then counted to determine [$^3$H]Prozosin specifically bound. Compounds were screened at 1 μM or lower, using 1% DMSO as vehicle. Biochemical assay results are presented as the percent inhibition of specific binding in Table 4.

Adrenergic $\alpha_{2A}$

To evaluate in radioligand binding assays the activity of compounds of the invention, human recombinant adrenergic ($X^2A$ receptor expressed in insect Sf9 cells (Uhlen S et al. J Pharmacol Exp Ther. 271:1558, 1994) in a modified Tris-HCl buffer (50 mM Tris-HCl, pH 7.4, 12.5 mM $MgCl_2$, 2 mM EDTA) was used. Compounds of invention were incubated with 1 nM [$^3$H]MK-912 for 60 minutes at 25° C. MK912 is (2S-trans)-1,3,4,5',6,6',7,12b-octahydro-1',3'-dimethyl-spiro [2H-benzofuro[2,3-a]quinolizine-2,4'(1'H)-pyrimidin]-2' (3'H)-one hydrochloride Non-specific binding was estimated in the presence of 10 μM WB-4101 (2-(2,6-Dimethoxyphenoxyethyl)aminomethyl-1,4-benzodioxane hydrochloride). Receptor proteins were filtered and washed, the filters were then counted to determine [$^3$H]MK-912 specifically bound. Compounds were screened at 1 μM or lower, using 1% DMSO as vehicle. Biochemical assay results are presented as the percent inhibition of specific binding in Table 4.

Adrenergic $\alpha_{2B}$

To evaluate in radioligand binding assays the activity of compounds of the invention, human recombinant adrenergic $\alpha_{2B}$ receptor expressed in Chinese hamster ovary (CHO-K1) cells (Uhlen S et al. Eur J. Pharmacol. 343(1):93, 1998) in a modified Tris-HCl buffer (50 mM Tris-HCl, pH 7.4, 12.5 mM $MgCl_2$, 1 mM EDTA, 0.2% BSA) was used. Compounds of the invention were incubated with 2.5 nM [$^3$H]Rauwolscine for 60 minutes at 25° C. Non-specific binding was estimated in the presence of 10 μM Prozosin. Receptor proteins were filtered and washed, the filters were then counted to determine [$^3$H]Rauwolscine specifically bound. Compounds were screened at 1 μM or lower, using 1% DMSO as vehicle. Biochemical assay results are presented as the percent inhibition of specific binding in Table 4.

Adrenergic $\alpha_{2C}$

To evaluate in radioligand binding assays the activity of compounds of the invention, human recombinant α2c receptor expressed in insect Sf9 cells (Uhlen S et al. J Pharmacol Exp Ther. 271:1558, 1994) in a modified Tris-HCl buffer (50 mM Tris-HCl, pH 7.4, 12.5 mM $MgCl_2$, 2 mM EDTA) is used. Compounds of the invention are incubated with 1 nM [$^3$H]MK-912 for 60 minutes at 25° C. Non-specific binding is estimated in the presence of 10 μM WB-4101. Receptor proteins are filtered and washed, the filters are then counted to determine [$^3$H]MK-912 specifically bound. Compounds are screened at 1 μM or lower, using 1% DMSO as vehicle. Compounds of the invention are tested in this biochemical assay and percent inhibition of specific binding is determined.

Example B4

Determination of the Ability of Compounds of the Invention to Bind a Dopamine Receptor Dopamine $D_{2L}$ To evaluate in radioligand binding assays the activity of compounds of the invention, human recombinant dopamine D2L receptor expressed in Chinese hamster ovary (CHO) cells (Grandy, D. K. et al. Proc. Natl. Acad. Sci. USA. 86:9762, 1989; Hayes, G. et al., Mol. Endocrinol. 6:920, 1992) in a modified Tris-HCl buffer (50 mM Tris-HCl, pH 7.4, 1.4 mM Ascorbic Acid, 0.001% BSA, 150 mM NaCl) was used. Compounds of the invention were incubated with 0.16 nM [$^3$H]Spiperone for 120 minutes at 25° C. Non-specific binding was estimated in the presence of 10 μM Haloperidol. Receptor proteins were filtered and washed, the filters were then counted to determine [$^3$H]Spiperone specifically bound. Compounds were screened at 1 μM or lower, using 1% DMSO as vehicle. Biochemical assay results are presented as the percent inhibition of specific binding in Table 4.

TABLE 4

Percent Inhibition of ligand binding to aminergic G protein-coupled receptors by compounds of the invention:

| Example No. | Compound No. | Adrenergic (1 μM ligand conc.) | | | Dopamine (1 μM ligand conc.) |
|---|---|---|---|---|---|
| | | $\alpha_{1D}$ | $\alpha_{2A}$ | $\alpha_{2B}$ | $D_{2L}$ |
| 19 | 1 | 65 | 74 | 99 | 6 |
| 20 | 2 | 42 | 81 | 81 | −7 |
| 21 | 3 | 77 | 99 | 108 | 47 |
| 23 | 5 | 64 | 74 | 83 | 0 |
| 32 | 14 | 33 | 19 | −16 | 6 |
| 33 | 15 | 5 | 15 | 8 | −5 |
| 34 | 16 | 2 | −4 | −7 | −7 |
| 35 | 17 | 18 | 17 | 14 | −3 |
| 36 | 18 | 21 | 4 | 19 | 0 |
| 39 | 21 | −7 | 0 | 11 | −1 |
| 47 | 29 | 84 | 96 | 79 | 24 |
| 52 | 34 | 56 | 66 | 38 | 9 |
| 53 | 35 | 60 | 88 | 65 | 3 |
| 56 | 38 | 25 | 15 | 15 | −8 |
| 58 | 40 | 3 | 1 | 18 | −11 |
| 61 | 43 | 58 | 42 | −14 | −8 |
| 62 | 44 | 61 | 77 | 20 | 8 |
| 94 | 52 | −11 | 4 | 9 | 1 |
| 95 | 53 | 6 | 5 | 6 | 6 |
| 81 | 54 | 11 | 4 | 18 | −16 |
| 69 | 55 | 10 | 10 | −21 | −6 |
| 82 | 56 | 16 | 7 | −10 | 9 |
| 75 | 57 | 77 | 4 | 29 | 6 |
| 87 | 58 | 19 | −12 | −15 | −5 |
| 83 | 59 | 30 | 91 | 97 | 35 |
| 84 | 60 | 29 | 79 | −5 | 18 |
| 85 | 61 | 49 | 83 | 101 | 41 |
| 86 | 62 | 44 | 90 | 102 | 81 |
| 78 | 66 | 74 | 55 | 74 | 9 |
| 79 | 67 | 85 | 85 | 106 | 21 |
| 71 | 70 | 44 | 81 | 77 | 0 |
| 70 | 71 | 58 | 88 | 95 | 21 |
| 72 | 72 | 86 | 93 | 105 | 24 |
| 91 | 78 | 42 | 93 | 102 | 11 |
| 68 | 79 | 17 | 92 | 89 | 2 |
| 92 | 80 | 89 | 82 | 100 | 5 |
| 67 | 81 | 64 | 92 | 102 | 21 |
| 74 | 90 | 62 | 88 | 97 | 36/39 |

TABLE 4-continued

Percent Inhibition of ligand binding to aminergic G protein-coupled receptors by compounds of the invention:

| Example No. | Compound No. | Adrenergic (1 μM ligand conc.) | | | Dopamine (1 μM ligand conc.) |
|---|---|---|---|---|---|
| | | $\alpha_{1D}$ | $\alpha_{2A}$ | $\alpha_{2B}$ | $D_{2L}$ |
| 80 | 91 | 73 | 95 | 94 | 27/44 |
| 66 | 92 | 97 | 96 | 104 | 47 |
| 110 | 97 | 66 | 91 | 96 | 15 |
| 111 | 98 | 57 | 74 | 87 | 32 |
| 112 | 99 | 20 | 59 | 77 | −7 |
| 113 | 100 | 8 | 56 | 53 | −11 |
| 114 | 108 | | | | −4 |
| 102 | 109 | | | | 12 |
| 103 | 110 | | | | 10 |
| 98 | 111 | | | | 5 |
| 97 | 112 | | | | 12 |
| 115 | 113 | | | | 9 |
| 96 | 114 | | | | 8 |
| 105 | 115 | | | | 0 |
| 104 | 116 | | | | 0 |
| 99 | 121 | | | | 21 |
| 100 | 122 | | | | 21 |
| 73 | 125 | 93 | 89 | 67 | 19 |
| 106 | 128 | 25 | 81 | 94 | 14 |
| 101 | 129 | 10 | 75 | 81 | −8 |
| 107 | 130 | | | | −3 |
| 108 | 132 | −8 | 13 | 84 | −6 |
| 109 | 155 | | | | 12 |
| 124 | 159 | 25 | 71 | 78 | −9 |
| 125 | 160 | 25 | 51 | 75 | −1 |
| 126 | 161 | 32 | 52 | 92 | 0 |
| 127 | 162 | 19 | 76 | 85 | 4 |
| 128 | 163 | 78 | 96 | 37 | −12 |
| 129 | 164 | 10 | 58 | 15 | −2 |
| 130 | 165 | 26 | 86 | 91 | 6 |
| 131 | 166 | 69 | 95 | 106 | 21 |
| 132 | 167 | 36 | 92 | 94 | 22 |
| 133 | 168 | 38 | 74 | 82 | 9 |
| 134 | 169 | | | | 5 |
| 135 | 170 | | | | 1 |
| 136 | 171 | | | | 5 |
| 137 | 172 | | | | 1 |
| 138 | 173 | | | | 22 |
| 139 | 174 | | | | 29 |
| 140 | 175 | | | | 0 |
| 141 | 176 | | | | −2 |
| 142 | 177 | | | | 9 |
| 143 | 178 | | | | 3 |

Example B5

Determination of the Ability of Compounds of the Invention to Bind a Serotonin Receptor Serotonin (5-Hydroxytryptamine) 5-$HT_{1A}$ To evaluate in radioligand binding assays the activity of compounds of the invention, human recombinant serotonin (5-Hydroxytryptamine) 5-HT1A receptor expressed in Chinese hamster ovary (CHO-K1) cells (Martin G R and Humphrey P P A. Neuropharmacol. 33:261, 1994; May J A, et al. J Pharmacol Exp Ther. 306(1): 301, 2003) in a modified Tris-HCl buffer (50 mM Tris-HCl, pH 7.4, 0.1% Ascorbic Acid, 0.5 mM EDTA, 10 mM MgSO$_4$) is used. Compounds of invention are incubated with 1.5 nM [$^3$H]8-OH-DPAT for 60 minutes at 25° C. Non-specific binding is estimated in the presence of 10 μM Metergoline. Receptor proteins are filtered and washed, the filters are then counted to determine [3H] 8-OH-DPAT specifically bound. Compounds are screened at 1 μM or lower, using 1% DMSO as vehicle. Compounds of the invention are tested in this biochemical assay and percent inhibition of specific binding is determined.

Serotonin (5-Hydroxytryptamine) 5-HT1B

To evaluate in radioligand binding assays the activity of compounds of the invention, serotonin (5-Hydroxytryptamine) 5-$HT_{1B}$ receptor from Wistar Rat cerebral cortex (Hoyer et al. Eur J Pharmaco. 118: 1, 1985; Pazos et al. Eur J. Pharmacol. 106: 531, 1985) in a modified Tris-HCl buffer (50 mM Tris-HCl, pH 7.4, 154 mM NaCl, 10 µM Pargyline, 30 µM Isoprenaline) is used. Compounds of invention are incubated with 10 pM [$^{125}$I]Cyanopindolol for 90 minutes at 37° C. Non-specific binding is estimated in the presence of 10 µM Serotonin (5-HT). Receptor proteins are filtered and washed, the filters are then counted to determine [$^{125}$I]Cyanopindolol specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-$HT_{2A}$

To evaluate in radioligand binding assays the activity of compounds of the invention, human recombinant serotonin (5-Hydroxytryptamine) 5-$HT_{2A}$ receptor expressed in Chinese hamster ovary (CHO-K1) cells (Bonhaus, D. W. et al. Br. J. Pharmacol. 115:622, 1995; Saucier, C. and Albert, P. R., J. Neurochem. 68:1998, 1997) in a 50 mM Tris-HCl buffer, pH 7.4, was used. Compounds of the invention were incubated with 0.5 nM [$^3$H]Ketanserin for 60 minutes at 25° C. Non-specific binding was estimated in the presence of 1 µM Mianserin. Receptor proteins were filtered and washed, the filters were then counted to determine [$^3$H] Ketanserin specifically bound. Compounds were screened at 1 µM or lower, using 1% DMSO as vehicle. Biochemical assay results are presented as the percent inhibition of specific binding in Table 5.

Serotonin (5-Hydroxytryptamine) 5-$HT_{2B}$

To evaluate in radioligand binding assays the activity of compounds of the invention, human recombinant serotonin (5-Hydroxytryptamine) 5-$HT_{2B}$ receptor expressed in Chinese hamster ovary (CHO-K1) cells (Bonhaus, D. W. et al., Br. J. Pharmacol. 115:622, 1995) in a modified Tris-HCl buffer (50 mM Tris-HCl, pH 7.4, 4 mM $CaCl_2$, 0.1% Ascorbic Acid) is used. Compounds of invention are incubated with 1.2 nM [$^3$H]Lysergic acid diethylamide (LSD) for 60 minutes at 37° C. Non-specific binding is estimated in the presence of 10 µM Serotonin (5-HT). Receptor proteins are filtered and washed, the filters are then counted to determine [$^3$H]LSD specifically bound. Compounds are screened at 1 µM or lower, using 1% DMSO as vehicle. Compounds of the invention are tested in this biochemical assay and percent inhibition of specific binding is determined. Biochemical assay results may be presented as the percent inhibition of specific binding.

Serotonin (5-Hydroxytryptamine) 5-$HT_{2C}$

To evaluate in radioligand binding assays the activity of compounds of the invention, human recombinant serotonin (5-Hydroxytryptamine) 5-$HT_{2C}$ receptor expressed in Chinese hamster ovary (CHO-K1) cells (Wolf, W. A. and Schutz, J. S., J. Neurochem. 69:1449, 1997) in a modified Tris-HCl buffer (50 mM Tris-HCl, pH 7.4, 0.1% Ascorbic Acid, 10 µM Pargyline) was used. Compounds of the invention were incubated with 1 nM [$^3$H]Mesulergine for 60 minutes at 25° C. Non-specific binding was estimated in the presence of 1 µM Mianserin. Receptor proteins were filtered and washed, the filters were then counted to determine [$^3$H]Mesulergine specifically bound. Compounds were screened at 1 µM or lower, using 1% DMSO as vehicle. Biochemical assay results are presented as the percent inhibition of specific binding in Table 5.

Serotonin (5-Hydroxytryptamine) 5-$HT_3$

To evaluate in radioligand binding assays the activity of compounds of the invention, human recombinant serotonin (5-Hydroxytryptamine) 5-$HT_3$ receptor expressed in human embryonic kidney (HEK-293) cells (Miller K et al. Synapase. 11:58, 1992; Boess F G et al. Neuropharmacology. 36:637, 1997) in a modified Tris-HCl buffer (50 mM Tris-HCl, pH 7.4, 1 mM EDTA, 5 mM $MgCl_2$) is used. Compounds of invention are incubated with 0.69 nM [$^3$H]GR-65630 for 60 minutes at 25° C. Non-specific binding is estimated in the presence of 10 µM MDL-72222. Receptor proteins are filtered and washed, the filters are then counted to determine [$^3$H]GR-65630 specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-$HT_4$

To evaluate in radioligand binding assays the activity of compounds of the invention, serotonin (5-Hydroxytryptamine) 5-$HT_4$ receptor from Duncan Hartley derived Guinea pig striatum (Grossman C J et al. Br J. Pharmacol. 109:618, 1993) in a 50 mM Tris-HCl, pH 7.4, is used. Compounds of invention are incubated with 0.7 nM [$^3$H]GR-113808 for 30 minutes at 25° C. Non-specific binding is estimated in the presence of 30 µM Serotonin (5-HT). Receptor proteins are filtered and washed, the filters are then counted to determine [$^3$H]GR-113808 specifically bound. Compounds are screened at 1 µM or lower, using 1% DMSO as vehicle. Compounds of the invention are tested in this biochemical assay and percent inhibition of specific binding is determined.

Serotonin (5-Hydroxytryptamine) 5-$HT_{5A}$

To evaluate in radioligand binding assays the activity of compounds of the invention, human recombinant serotonin (5-Hydroxytryptamine) 5-$HT_{5A}$ receptor expressed in Chinese hamster ovary (CHO-K1) cells (Rees, S. et al., FEBS Lett. 355:242, 1994) in a modified Tris-HCl buffer (50 mM Tris-HCl, pH 7.4, 10 mM $MgCl_2$, 0.5 mM EDTA) was used. Compounds of the invention were incubated with 1.7 nM [$^3$H]Lysergic acid diethylamide (LSD) for 60 minutes at 37° C. Non-specific binding was estimated in the presence of 100 µM Serotonin (5-HT). Receptor proteins were filtered and washed, the filters were then counted to determine [$^3$H]LSD specifically bound. Compounds were screened at 1 µM or lower, using 1% DMSO as vehicle. Compounds of the invention were tested in this biochemical assay and percent inhibition of specific binding was determined. Biochemical assay results are presented as the percent inhibition of specific binding in Table 5.

Serotonin (5-Hydroxytryptamine) 5-$HT_6$

To evaluate in radioligand binding assays the activity of compounds of the invention, human recombinant serotonin (5-Hydroxytryptamine) 5-HT6 receptor expressed in human HeLa cells (Monsma, F. J. Jr. et al., Mol. Pharmacol. 43:320, 1993) in a modified Tris-HCl buffer (50 mM Tris-HCl, pH 7.4, 150 mM NaCl, 2 mM Ascorbic Acid, 0.001% BSA) was used. Compounds of the invention were incubated with 1.5 nM [3H]Lysergic acid diethylamide (LSD) for 120 minutes at 37° C. Non-specific binding was estimated in the presence of 5 µM Serotonin (5-HT). Receptor proteins were filtered and washed, the filters were then counted to determine [3H]LSD specifically bound. Compounds were screened at 1 µM or lower, using 1% DMSO as vehicle. Biochemical assay results are presented as the percent inhibition of specific binding in Table 5.

Serotonin (5-Hydroxytryptamine) 5-HT$_7$

To evaluate in radioligand binding assays the activity of compounds of the invention, human recombinant serotonin (5-Hydroxytryptamine) 5-HT$_7$ receptor expressed in Chinese hamster ovary (CHO) cells (Roth, B. L. et al., J. Pharmacol. Exp. Ther. 268:1403, 1994; Shen, Y. et al., J. Biol. Chem. 268:18200, 1993) in a modified Tris-HCl buffer (50 mM Tris-HCl, pH 7.4, 10 mM MgCl$_2$, 0.5 mM EDTA) was used. Compounds of invention were incubated with 5.5 nM [$^3$H] Lysergic acid diethylamide (LSD) for 2 hours at 25° C. Non-specific binding was estimated in the presence of 10 μM Serotonin (5-HT). Receptor proteins were filtered and washed, the filters were then counted to determine [$^3$H]LSD specifically bound. Compounds were screened at 1 μM or lower, using 1% DMSO as vehicle. Biochemical assay results are presented as the percent inhibition of specific binding in Table 5.

TABLE 5

Percent Inhibition of ligand binding to aminergic G protein-coupled receptors by compounds of the invention:

| Example No. | Compound No. | Serotonin (1 μM ligand concentration) | | | |
|---|---|---|---|---|---|
| | | 5-HT$_{2A}$ | 5-HT$_{2C}$ | 5-HT$_6$ | 5-HT$_7$ |
| 19 | 1 | | 25 | 5 | |
| 20 | 2 | | 84 | 58 | |
| 21 | 3 | | 90 | 100 | |
| 23 | 5 | 51 | 39 | 6 | |
| 32 | 14 | 27 | 20 | 12 | |
| 33 | 15 | 6 | 15 | −2 | |
| 34 | 16 | 10 | −18 | 9 | |
| 35 | 17 | 17 | 3 | 3 | |
| 36 | 18 | −1 | 3 | 1 | |
| 39 | 21 | 4 | 16 | 6 | |
| 47 | 29 | 83 | 90 | 62 | |
| 52 | 34 | 31 | 37 | 16 | |
| 53 | 35 | 69 | 87 | 67 | |
| 56 | 38 | | 14 | −2 | |
| 58 | 40 | 5 | 12 | 6 | |
| 61 | 43 | 69 | 31 | 3 | |
| 62 | 44 | 73 | 54 | 12 | |
| 94 | 52 | −11 | −4 | −4 | |
| 95 | 53 | −6 | −3 | −8 | |
| 81 | 54 | 0 | −1 | 8 | |
| 69 | 55 | 17 | 13 | 0 | |
| 82 | 56 | 12 | −3 | −3 | |
| 75 | 57 | 28 | 14 | 6 | |
| 87 | 58 | −10 | 30 | −7 | |
| 83 | 59 | 80 | 74 | 60 | |
| 84 | 60 | 74 | 5 | 62 | |
| 85 | 61 | 86 | 81 | 61 | |
| 86 | 62 | 88 | 95 | 77 | |
| 78 | 66 | 51 | 48 | 5 | |
| 79 | 67 | 77 | 85 | 51 | |
| 71 | 70 | 56 | 63 | 21 | |
| 70 | 71 | 87 | 81 | 66 | |
| 72 | 72 | 96 | 89 | 61 | |
| 91 | 78 | 80 | 101 | 48 | 99 |
| 68 | 79 | 62 | 77 | 27 | 85 |
| 92 | 80 | 56 | 79 | 23 | 82 |
| 67 | 81 | 93 | 88 | 96 | 82 |
| 74 | 90 | 97 | 99 | 98 | |
| 80 | 91 | 97 | 104 | 100 | |
| 66 | 92 | 97 | 96 | 96 | |
| 110 | 97 | 97 | 99 | 72 | 98 |
| 111 | 98 | 98 | 103 | 79 | 94 |
| 112 | 99 | 86 | 97 | 69 | 68 |
| 113 | 100 | 87 | 98 | 23 | 42 |
| 114 | 108 | 45 | 60 | 6 | 62 |
| 102 | 109 | 96 | 97 | 72 | 96 |
| 103 | 110 | 93 | 97 | 73 | 87 |
| 98 | 111 | 79 | 93 | 88 | 78 |
| 97 | 112 | 82 | 94 | 61 | 67 |
| 115 | 113 | 99 | 91 | 49 | 84 |
| 96 | 114 | 93 | 95 | 42 | 87 |
| 105 | 115 | 85 | 86 | 40 | 74 |
| 104 | 116 | 83 | 85 | 38 | 51 |
| 99 | 121 | 96 | 102 | 33 | 94 |
| 100 | 122 | 95 | 102 | 36 | 95 |
| 73 | 125 | | | 74 | 66 |
| 106 | 128 | 95 | 101 | 90 | 24 |
| 101 | 129 | 85 | 107 | 22 | 15 |
| 107 | 130 | 91 | 95 | 7 | 22 |
| 108 | 132 | 80 | 94 | 17 | 35 |
| 109 | 155 | 85 | 95 | 14 | 19 |
| 124 | 159 | 89 | 103 | 46 | 49 |
| 125 | 160 | 95 | 103 | 24 | 84 |
| 126 | 161 | 96 | 99 | 75 | 93 |
| 127 | 162 | 98 | 101 | 12 | 27 |
| 128 | 163 | 98 | 96 | 89 | 29 |
| 129 | 164 | 95 | 98 | 16 | 8 |
| 130 | 165 | 85 | 93 | 46 | 91 |
| 131 | 166 | 102 | 96 | 95 | 92 |
| 132 | 167 | 88 | 95 | 55 | 97 |
| 133 | 168 | 94 | 96 | 71 | 84 |
| 134 | 169 | 80 | 91 | 24 | 78 |
| 135 | 170 | 96 | 98 | 36 | 74 |
| 136 | 171 | 80 | 92 | 36 | 13 |
| 137 | 172 | 96 | 100 | 10 | 1 |
| 138 | 173 | 95 | 90 | 48 | 81 |
| 139 | 174 | 98 | 89 | 33 | 74 |
| 140 | 175 | 86 | 97 | 77 | 82 |
| 141 | 176 | 81 | 94 | 26 | 53 |
| 142 | 177 | 83 | 88 | 6 | 57 |
| 143 | 178 | 97 | 101 | 25 | 59 |

Example B6

Determination of Serotonin (5-Hydroxytryptamine) 5-HT$_{2A}$ Agonist/Antagonist Activity of Compounds of the Invention To determine for agonist or antagonist activity of compounds of the invention in functional assays, human recombinant serotonin 5-HT$_{2A}$ receptor expressed in human embryonic kidney (HEK-293) cells (Jerman J C, Brough S J, Gager T, Wood M, Coldwell M C, Smart D and Middlemiss D N. Eur J Pharmacol, 414: 23-30, 2001) is used. Cells are suspended in DMEM buffer, and distributed in microplates. A cytoplasmic calcium fluorescent indicator which varies proportionally to the free cytosolic Ca$^{2+}$ ion concentration is mixed with probenicid in HBSS buffer complemented with 20 mM Hepes (pH 7.4), added into each well and equilibrated with the cells for 30 min at 37° C. followed by 30 min at 22° C.

To measure agonist effects, compounds of the invention, reference agonist or HBSS buffer (basal control) is added to the cells and changes in fluorescence intensity are measured using a microplate reader. For stimulated control measurements, 5-HT at 100 nM is added in separate assay wells.

The results are expressed as a percent of the control response to 100 nM 5-HT. The standard reference agonist is 5-HT, which is tested in each experiment at several concentrations to generate a concentration-response curve from which its EC$_{50}$ value is calculated.

To measure antagonist effects, the addition of the compounds of the invention, reference antagonist or HBSS buffer is followed by the addition of 3 nM 5-HT or HBSS buffer (basal control) prior the fluorescence measurements. The results are expressed as a percent inhibition of the control response to 3 nM 5-HT. The standard reference antagonist is ketanserin, which is tested in each experiment at several concentrations to generate a concentration-response curve from which its $IC_{50}$ value is calculated. Compounds are screened at 3 μM or lower, using DMSO as vehicle.

Example B7

Determination of Serotonin (5-Hydroxytryptamine) 5-HT$_6$ Agonist/Antagonist Activity of Compounds of the Invention To determine for agonist or antagonist activity of compounds of the invention in functional assays, human recombinant 5-HT$_6$ receptor is transfected in CHO cells (Kohen, R., Metcalf, M. A., Khan, N., Druck, T., Huebner, K., Lachowicz, J. E., Meltzer, H. Y., Sibley, D. R., Roth, B. L. And Hamblin, M. W. Cloning, characterisation and chromosomal localization of a human 5-HT6 serotonin receptor, J. Neurochem., 66: 47, 1996) and the activity of compounds of the invention is determined by measuring their effects on cAMP production using the Homogeneous Time Resolved Fluorescence (HTRF) detection method. Cells are suspended in HBSS buffer complemented with HEPES 20 mM (pH 7.4) and 500 μM IBMX, and then distributed in microplates and incubated for 45 min at 37° C. in the absence (control) or presence of compounds of the invention or the reference agonist or antagonist.

For agonist determinations, stimulated control measurement, separate assay wells contain 10 μM 5-HT. Following incubation, the cells are lysed and the fluorescence acceptor (D2-labeled cAMP) and fluorescence donor (anti-cAMP antibody labeled with europium cryptate) are added. After 60 min at room temperature, the fluorescence transfer is measured at lex=337 nm and lem=620 and 665 nm using a microplate reader. The cAMP concentration is determined by dividing the signal measured at 665 nm by that measured at 620 nm (ratio).

The results are expressed as a percent of the control response to 10 μM 5-HT. The standard reference agonist is 5-HT, which is tested in each experiment at several concentrations to generate a concentration-response curve from which its $EC_{50}$ value is calculated.

For antagonist determinations, the reference agonist 5-HT is added at a final concentration of 100 nM. For basal control measurements, separate assay wells do not contain 5-HT. Following 45 min incubation at 37° C., the cells are lysed and the fluorescence acceptor (D2-labeled cAMP) and fluorescence donor (anti-cAMP antibody labeled with europium cryptate) are added.

After 60 min at room temperature, the fluorescence transfer is measured as mentioned above. The results are expressed as a percent inhibition of the control response to 100 nM 5-HT. The standard reference antagonist is methiothepin Example B8

Determination of Dopamine D$_{2L}$ Antagonist Activity of Compounds

To determine for agonist or antagonist activity of compounds of the invention in functional assays, human recombinant dopamine D2L receptor stably expressed in Chinese hamster ovary (CHO) cells (Senogles S E et al. J Biol. Chem. 265(8): 4507, 1990) is used. Compounds of invention are pre-incubated with the membranes (0.1 mg/ml) and 10 mM GDP in modified HEPES buffer (20 mM HEPES, pH 7.4, 100 mM NaCl, 10 mM MgCl$_2$, 1 mM DTT, 1 mM EDTA) for 20 minutes and Scintillation Proximity Assay (SPA) beads are added for another 60 minutes at 30° C. The reaction is initiated by 0.3 nM [$^{35}$S]GTPγS for an additional 15 minute incubation period. Increase of [$^{35}$S]GTPγS binding by 50 percent or more (350%) relative to the 1 mM dopamine response by compounds of the invention indicates possible dopamine D2L receptor agonists activity. Inhibition of a 10 μM dopamine-induced increase of [$^{35}$S]GTPγS binding response by 50 percent or more (350%) by compounds of the invention indicates receptor antagonist activity. Compounds are screened at 3 μM or lower, using 0.4% DMSO as vehicle. Assay results are presented as the percent response of specific binding.

Example B9

Determination of Dopamine D$_{2S}$ Antagonist Activity of Compounds of the Invention To determine for agonist or antagonist activity of compounds of the invention in functional assays, human recombinant dopamine D2s receptor stably expressed in Chinese hamster ovary (CHO) cells (Gilliland S L and Alper R H. Naunyn-Schmiedeberg's Archives of Pharmacology. 361: 498, 2000) is used. Compounds of invention are pre-incubated with the membranes (0.05 mg/ml) and 3 μM GDP in modified HEPES buffer (20 mM HEPES, pH 7.4, 100 mM NaCl, 10 mM MgCl$_2$, 1 mM DTT, 1 mM EDTA) for 20 minutes and Scintillation Proximity Assay (SPA) beads are then added for another 60 minutes at 30° C. The reaction is initiated by 0.3 nM [$^{35}$S]GTPγS for an additional 30 minute incubation period. Increase of [$^{35}$S]GTPγS binding by 50 percent or more (350%) relative to the 100 μM dopamine response by compounds of the invention indicates possible dopamine D$_{2S}$ receptor agonists activity. Inhibition of a 3 μM dopamine-induced increase of [$^{35}$S]GTPγS binding response by 50 percent or more (350%) by compounds of the invention indicates receptor antagonist activity. Compounds are screened at 3 μM or lower, using 0.4% DMSO as vehicle. Assay results are presented as the percent response of specific binding.

Example B10

Determination for Agonist or Antagonist Activity of Compounds of the Invention in a Histamine H1 Functional Assay To determine for agonist or antagonist activity of compounds of the invention in functional assays, human recombinant Histamine H1 receptor expressed in human embryonic kidney (HEK-293) cells (Miller, T. R., Witte, D. G., Ireland, L. M., Kang, C. H., Roch, J. M., Masters, J. N., Esbenshade, T. A And Hancock, A. A. J. Biomol. Screen., 4: 249-258, 1999) is used. Cells are suspended in DMEM buffer, and then distributed in microplates. A cytoplasmic calcium fluorescent indicator-which varies proportionally to the free cytosolic $Ca^{2+}$ ion concentration—is mixed with probenicid in HBSS buffer complemented with 20 mM Hepes (pH 7.4) and is then added into each well and equilibrated with the cells for 30 min at 37° C. and then for another 30 min at 22° C. To measure agonist effects, compounds of the invention, reference agonist or HBSS buffer (basal control) are added to the cells and changes in fluorescence intensity are measured using a microplate reader. For stimulated control measurements, histamine at 10 µM is added in separate assay wells.

The results are expressed as a percent of the control response to 10 µM histamine. The standard reference agonist is histamine, which is tested in each experiment at several concentrations to generate a concentration-response curve from which its $EC_{50}$ value is calculated.

To measure antagonist effects, the addition of the compounds of the invention, reference antagonist or HBSS buffer is followed by the addition of 300 nM histamine or HBSS buffer (basal control) prior the fluorescence measurements. The results are expressed as percent inhibition of the control response to 300 nM histamine. The standard reference antagonist is ketanserin, which is tested in each experiment at several concentrations to generate a concentration-response curve from which its $IC_{50}$ value is calculated. Compounds are screened at 3 µM or lower, using DMSO as vehicle.

Example B11

Increase of Neurite Outgrowth

Neurite Outgrowth in Cortical Neurons

Compounds are tested to determine their ability to stimulate neurite outgrowth of cortical neurons. Standard methods are used to isolate cortical neurons. For the isolation of primary rat cortical neurons, the fetal brain from a pregnant rat at 17 days of gestation was prepared in Leibovitz's medium (L15; Gibco). The cortex is dissected out, and the meninges were removed. Trypsin (Gibco) is used to dissociate cortical C with DNAse I. The cells are triturated for 30 minutes with a pipette in Dulbecco's Modified Eagle Media ("DMEM"; Gibco) with 10% Fetal Bovine Serum ("FBS") (Gibco) and centrifuged at 350×g for 10 minutes at room temperature. The cells are suspended in Neurobasal medium supplemented with 2% B27 (Gibco) and 0.5 mM L-glutamine (Gibco). The cells are maintained at 30,000 cells per well of poly-L-lysine coated plates at 37° C. in 5% $CO_2$-95% air atmosphere. After adhesion, a vehicle control or compounds of the invention are added at different concentrations to the medium. BDNF (50 ng/mL) is used as a positive control for neurite growth. After treatment, cultures are washed in phosphate-buffered saline ("PBS"; Gibco) and fixed in glutaraldehyde 2.5% in PBS. Cells are fixed after 3 days growth. Several pictures (~80) of cells with neurites are taken per condition with a camera. The length measurements are made by analysis of the pictures using software from Image-Pro Plus (France). The results are expressed as mean (s.e.m.). Statistical analysis of the data is performed using one way analysis of variance (ANOVA).

Neurite Outgrowth in Rat Mixed Cortical Cultures

Cortical mixed cultures are prepared from E18 Wistar rat embryos. The cortices are dissected out and the tissue was cut to small pieces. The cells are separated by 15-min incubation with DNase and papain. The cells are collected by centrifugation (1500 rpm, 5 min). The tissue is triturated with a pipette and the cells are plated using the micro-islet protocol (20 000 cells in 25 µl medium) on poly-L-lysine coated 48 wells, in MEM supplemented with 2 mM glutamine, 0.1 µg/ml gentamicin, 10% heat-inactivated fetal bovine serum (FBS-HI) and 10% heat-inactivated horse serum (HS-HI). After the cells attach to the well, 250 µl medium is added to the wells. Four hours after plating the medium is changed to fresh medium (MEM with supplements and 5% HS-HI) containing test compound at 0.5, 5 and 50 nM concentrations. As positive controls BDNF (50, 100 and/or 150 ng/ml), and/or NGF (50 ng/ml and/or 100 ng/ml) are used. After 2 days in vitro, the cell's conditioned media are collected from plates before fixing the cells. The media samples are centrifuged 13 000 rpm 3 min to get rid of cell debris. The samples are stored at −20° C. for later analysis. Cells are formaldehyde-fixed and processed for immunocytochemistry. BDNF levels in the conditioned media are determined with a BDNF ELISA using the manufacturers (Promega, BDNF Emax® ImmunoAssay System, catalog number: G7610) instructions.

The cultures are fixed with 4% formaldehyde in 0.01 M PBS for 30 min and washed once with PBS. The fixed cells are first permeabilized and non-specific binding is blocked by a 30-min incubation with blocking buffer containing 1% bovine serum albumin and 0.3% Triton X-100 in PBS. Rabbit anti-MAP-2 (dilution 1:1000, AB5622, Chemicon, in blocking buffer) is used as a primary antibody. The cells are incubated with the primary antibody for 48 h at +4° C., washed with PBS and incubated with secondary antibody goat anti-rabbit IgG conjugated to Alexa Fluor568 (1:200, A11036, Molecular Probes) for 2 h at RT. The immunopositive cells are visualized by a fluorescence microscope equipped with appropriate filter set, and documented by a high resolution image capturing. The number of cells per field (4 field per well) are counted, and the neurite outgrowth is quantified using Image Pro Plus software.

The number of wells per compound concentration used is 6 (n=6). All data are presented as mean±standard deviation (SD) or standard error of mean (SEM), and differences are considered to be statistically significant at the $p<0.05$ level. Statistical analysis is performed using StatsDirect statistical software. Differences between group means are analyzed by using 1-way-ANOVA followed by Dunnet's test (comparison to the vehicle treated group).

Example B12

Use of an In Vivo Model to Evaluate the Ability of Compounds to Enhance Cognition, Learning and Memory in Scopolamine Treated Rats The two-trial object recognition paradigm developed by Ennaceur and Delacour in the rat is used as a model of episodic/short-term memory. Ennaceur, A., and Delacour, J. (1988), *Behav. Brain Res.* 31:47-59. The paradigm is based on spontaneous exploratory activity of rodents and does not involve rule learning or reinforcement. The novel object recognition paradigm is sensitive to the effects of ageing and cholinergic dysfunction. See, e.g., Scali, C., et al., (1994), *Neurosci. Letts.* 170:117-120; and Bartolini, L., et al., (1996), *Biochem. Behav.* 53:277-283.

Male Sprague-Dawley rats between six and seven weeks old, weighing between 220-300 grams are obtained, e.g., from Centre d'Elevage (Rue Janvier, B. P. 55, Le Genest-Saint-Isle 53940, France). The animals are housed in groups of 2 to 4 in polypropylene cages (with a floor area of 1032 $cm^2$) under standard conditions: at room temperature (22±2° C.), under a 12 hour light/12 hour dark cycle, with food and water provided ad libitum. Animals are permitted to acclimate to environmental conditions for at least 5 days before the experiment begins, and are numbered on their tails with indelible marker.

The experimental arena is a square wooden box (60 cm×60 cm×40 cm) painted dark blue, with 15 cm×15 cm black squares under a clear plexiglass floor. The arena and objects placed inside the arena are cleaned with water between each trial to eliminate any odor trails left by rats. The arena is placed in a dark room illuminated only by halogen lamps directed towards the ceiling in order to produce a uniformly dim light in the box of approximately 60 lux. The day before testing, animals are allowed to freely explore the experimental arena for three minutes in the presence of two objects (habituation). Animals to be tested are placed in the experimental room at least 30 minutes before testing.

Novel object recognition test is comprised of two trials separated by an interval of 120 minutes or 24 hours. When agents that disrupt memory such as the cholinergic antagonist scopolamine are used an inter-trial interval of 120 minutes is preferred. Alternatively a 24 hours inter-trial interval is used when studying effect of natural forgetting on novel object recognition task. During the first, or acquisition, trial ($T_1$), rats are placed in the arena, where two identical objects have been previously placed. The time required for each animal to complete 15 seconds of object exploration is determined, with a cut-off time of four minutes. Exploration is considered to be directing the nose at a distance less than 2 centimeters ("cm") from the object and/or touching the object. During the second, or testing, trial ($T_2$), one of the objects presented in the first trial is replaced with an unknown or novel object, while the second, familiar object is left in place. Rats are placed back in the arena for three minutes, and exploration of both objects is determined. Locomotor activity of rats (number of times rats cross grid lines visible under the clear plexiglass floor) is scored for during $T_1$ and $T_2$. At the conclusion of the experiments, the rats are sacrificed by an overdose of pentobarbital given intraperitoneally.

The following parameters are measured as part of the novel object recognition task: (1) time required to achieve 15 seconds of object exploration during $T_1$; (2) locomotor activity during $T_1$ (number of crossed lines); (3) time spent in active exploration of the familiar object during $T_2$ ($T_{Familiar}$); (4) time spent in active exploration of the novel object during $T_2$ ($T_{Novel}$); and (5) locomotor activity during $T_2$ (number of crossed lines). The difference between time spent in active exploration of the novel object during $T_2$ and time spent in active exploration of the familiar object during $T_2$ ($\Delta T_{Novel} - T_{Familiar}$) is evaluated. The % of animals in each group with $T_{Novel} - T_{Familiar}$ greater than or equal to 5 seconds is also derived; described as % of good learners.

Animals not meeting a minimal level of object exploration are excluded from the study as having naturally low levels of spontaneous exploration. Thus, only rats exploring the objects for at least five seconds ($T_{Novel} + T_{Familiar} > 5$ seconds) are included in the study.

Animals are randomly assigned to groups of 14. Compounds of the invention and controls are administered to animals the groups as follows: Solutions of compounds are prepared freshly each day at a concentration of 0.25 mg/ml using purified water or saline as vehicle. Donepezil, used as a positive control, and scopolamine are administered simultaneously in a single solution of saline (5 mL/kg) prepared freshly each day. Scopolamine is purchased from Sigma Chemical Co. (Catalog No. S-1875; St. Quentin Fallavier, France) is dissolved in saline to a concentration of 0.06 mg/mL.

Donepezil or its vehicle and scopolamine are administered intraperitoneally forty minutes before the acquisition trial ($T_1$). Compounds or their vehicle are administered by gavage twenty-five minutes before the acquisition trial ($T_1$), i.e., five minutes after administration of scopolamine. The volume of administration is 5 ml/kg body weight for compounds administered intraperitoneally, and 10 ml/kg for compounds administered orally. Recognition scores and % of good learners for compounds are determined.

Example B13

Use of an In Vivo Model to Determine the Ability of Compounds to Treat, Prevent and/or Delay the Onset and/or the Development of Schizophrenia in PCP Treated Animals In vivo models of schizophrenia can be used to determine the ability of the compounds described herein to treat and/or prevent and/or delay the onset and/or the development of schizophrenia.

One exemplary model for testing the activity of one or more compounds described herein to treat and/or prevent and/or delay the onset and/or development of schizophrenia employs phencyclidine (PCP), which is administered to the animal (e.g., non-primate (rat) or primate (monkey)), resulting in dysfunctions similar to those seen in schizophrenic humans. See Jentsch et al., 1997, Science 277:953-955 and Piercey et al., 1988, Life Sci. 43(4):375-385). Standard experimental protocols may be employed in this or in other animal models. One protocol involves PCP-induced hyperactivity.

Male mice (various strains, e.g., C57Bl/6J) from appropriate vendor (for example, Jackson Laboratories (Bar Harbor, Me.) are used. Mice are received at 6-weeks of age. Upon receipt, mice are assigned unique identification numbers (tail marked) and are group housed with 4 mice/cage in OPTI mouse ventilated cages. All animals remain housed in groups of four during the remainder of the study. All mice are acclimated to the colony room for at least two weeks prior to testing and are subsequently tested at an average age of 8 weeks. During the period of acclimation, mice are examined on a regular basis, handled, and weighed to assure adequate health and suitability. Animals are maintained on a 12/12 light/dark cycle. The room temperature is maintained between 20 and 23° C. with a relative humidity maintained between 30% and 70%. Food and water are provided ad libitum for the duration of the study. In each test, animals are randomly assigned across treatment groups.

The open filed (OF) test assesses locomotor behavior, i.e. to measure mouse locomotor activity at baseline and in response to pharmacological agents. The open field chambers are Plexiglas square chambers (27.3×27.3×20.3 cm; Med Associates Inc., St Albans, Vt.) surrounded by infrared photobeams (16×16×16) to measure horizontal and vertical activity. The analysis is configured to divide the open field into a center and periphery zone such that the infrared photobeams allow measurement of activity in the center and periphery of the field. Distance traveled is measured from horizontal beam breaks as the mouse moved whereas rearing activity is measured from vertical beam breaks.

Mice (10 to 12 animals per treatment group) are brought to the activity experimental room for at least 1 hr acclimation to the experimental room conditions prior to testing. Eight animals are tested in each run. Mice are administered vehicle (e.g. 10% DMSO or 5% PEG200 and 1% Tween 80), compound of the invention, clozapine (positive control, 1 mg/kg ip) and placed in the OF chambers for 30 min following which they are injected with either water or PCP and placed back in the OF chambers for a 60-minute session. At the end of each OF test session the OF chambers are thoroughly cleaned.

PCP Hyperactivity Mouse Model of Schizophrenia

The test compound at the desired dose is dissolved in appropriate vehicle, e.g., 5% PEG200, 1% Tween80 and administered orally 30 min prior to PCP injection. Clozapine (1 mg/kg) is dissolved in 10% DMSO and administered i.p.

30 min prior to PCP injection. PCP (5 mg/kg) is dissolved in sterile injectable saline solution and administered i.p.

Data are analyzed by analysis of variance (ANOVA) followed by post-hoc comparisons with Fisher Tests when appropriate. Baseline activity is measured during the first 30 min of the test prior to PCP injection. PCP-induced activity is measured during the 60 min following PCP injection. Statistical outliers that fell above or below 2 standard deviations from the mean are removed from the final analyses. An effect is considered significant if $p<0.05$. Total distances traveled and total rearing following PCP administration are compared between groups treated with compounds and groups treated with vehicle and positive control clozapine.

PCP Hyperactivity Mouse Model of Schizophrenia

Protocol is as described above with the exception of the treatment groups which are as follows: All injections are at a dose volume of 10 ml/kg. The test compound at the desired dose is dissolved in Phosphate Buffered Saline (PBS) and administered orally 30 min prior to PCP injection. Clozapine (0.5 and 1.0 mg/kg) is dissolved in 10% DMSO and administered i.p. 30 min prior to Phencyclidine (PCP) injection. PCP (5.0 mg/kg) is dissolved in sterile injectable saline and administered i.p. Total distances traveled for is determined.

Example B14

Use of an In Vivo Model to Determine the Ability of Compounds to Treat, Prevent and/or Delay the Onset and/or the Development of Schizophrenia in Amphetamine Treated Animals Male mice (various strains e.g., C57B1/6J) from appropriate supplier (for example Jackson Laboratories, Bar Harbor, Me.) are used. Mice typically are received at 6-weeks of age. Mice are acclimated to the colony room for at least two weeks prior to testing. During the period of acclimation, mice are examined on a regular basis, handled, and weighed to assure adequate health and suitability and maintained on a 12/12 light/dark cycle. The room temperature is maintained between 20 and 23° C. with a relative humidity maintained between 30% and 70%. Food and water are provided ad libitum for the duration of the study. In each test, animals are randomly assigned between treatment groups.

The open field test (OF) is used to assess motor activity. The open field chambers are plexiglass square chambers (e.g., 27.3×27.3×20.3 cm; Med Associates Inc., St Albans, Vt.) surrounded by infrared photobeam sources (16×16×16). The enclosure is configured to split the open field into a center and periphery zone and the photocell beams are set to measure activity in the center and in the periphery of the OF chambers. Horizontal activity (distance traveled) and vertical activity (rearing) are measured from consecutive beam breaks.

On the day of testing, animals are brought to the experimental room for at least 1 hr acclimation prior to start of treatment. Animals are administered with vehicle, haloperidol (positive control, 0.1 mg/kg ip) or test compound and placed in the OF. The time of administration of client compound to each animal is recorded. Baseline activity is recorded for 30 min following which mice receive amphetamine (4 mg/kg) or water and are placed back in the OF chambers for a 60-minute session. At the end of each open field test session the OF chambers are thoroughly cleaned. Typically ten to twelve mice are tested in each group. Test compound doses typically range from 0.01 mg/kg to 60 mg/kg.

Data are analyzed by analysis of variance (ANOVA) followed by post-hoc comparisons with Fisher Tests when appropriate. Baseline activity is measured during the first 30 min of the test prior to amphetamine injection. Amphetamine-induced activity is measured during the 60 min following amphetamine injection. Statistical outliers that fall above or below 2 standard deviations from the mean are removed from the final analyses. An effect is considered significant if $p<0.05$. Total distance traveled and total rearing following amphetamine administration are compared between groups treated with compound and groups treated with vehicle and positive control haloperidol.

Example B15

Use of the In Vivo Conditioned Avoidance Response (Car) Model to Determine the Ability of Compounds to Treat, Prevent and/or Delay the Onset and/or the Development of Schizophrenia All currently approved antipsychotic agents (typical and atypical) are known to have the ability to selectively suppress conditioned avoidance response (CAR) behavior in the rat. This evidence makes CAR one of the primary tests to assess antipsychotic activity of novel compounds.

Rats (various strains, 2 months of age) are trained and tested in a computer-assisted, two-way active avoidance apparatus (shuttle box). This box consists of two compartments of equal size divided by a stainless steel partition containing an opening of 7×7 cm. Each compartment is equipped with an electrified grid floor made of stainless steel rods spaced 1 cm apart. Rats trained to avoid the foot shock are placed each day in the shuttle box for a 4 minutes habituation period followed by 30 trials spaced by inter-trial interval varying at random between 20 and 30 seconds. Each trial consists of a 10-second stimulus light (conditioned stimulus, CS) followed by a 10-second foot shock (unconditioned stimulus, US) in presence of the light presented in the compartment where the rat is located. If the animal leaves the compartment prior to the delivery of the foot shock, the response is considered an avoidance response. If the rat does not change compartment during the 10-second light period and during the 10-second shock+light period, an escape failure is recorded. This test requires animals to be trained 5 days/week. On each training day, rats are submitted to one training session of 30-trials. Treatment with test compound is initiated only when rats reach an avoidance performance of at least 80% on at least two consecutive training sessions. The test compound is administered orally at various doses and various pre-treatment times (depending upon specific pharmacokinetic properties).

Compounds with antipsychotic profile inhibit conditioned avoidance responses with or without increases in escape failures. Statistical analysis is performed using a Friedman two-way ANOVA by ranks followed by the Wilcoxon matched-pairs signed-ranks test to test each dose of the test compound administered versus vehicle control treated rats.

The ability of compounds of the invention to bind receptors detailed hereinabove is evaluated in multiple concentrations. Examples of assay results are shown in Table 6.

TABLE 6

Percentage inhibition of ligand binding to receptors by compounds of the invention:

| Receptor | Compound Concentration | Compound No. 90 | Compound No. 91 | Compound No. 92 | Compound No. 166 |
|---|---|---|---|---|---|
| Adrenergic $\alpha_{1D}$ | 1 μM | 62 | 73 | 97 | 69 |
| Adrenergic $\alpha_{2A}$ | 1 μM | 88 | 95 | 96 | 95 |
| Adrenergic $\alpha_{2B}$ | 1 μM | 97 | 94 | 104 | 106 |
| $D_{2L}$ | 10 μM | 91 | 91 | | 50 |
| | 1 μM | 39 | 44 | 47 | 21 |
| | 3 μM | 70 | 64 | 72 | 12 |
| H1 | 0.03 μM | | | 67 | |
| | 0.1 μM | | | 91 | |
| | 0.3 μM | | | 96 | 23 |
| | 10 μM | 94 | 95 | | |
| | 1 μM | 48 | 42 | 99 | 79 |
| | 3 μM | 76 | 75 | | 77 |
| H2 | 1 μM | 64 | 68 | 50 | 90 |
| 5-HT$_{2A}$ | 0.03 μM | 31 | 54 | 37 | 46 |
| | 0.1 μM | 64 | 79 | 65 | 74 |
| | 0.3 μM | 87 | 92 | 83 | 81 |
| | 10 nM | 9 | 21 | 13 | 15 |
| | 1 μM | 97 | 97 | 97 | 102 |
| | 3 nM | 1 | 2 | | |
| 5-HT$_{2C}$ | 0.03 μM | 65 | 77 | | 62 |
| | 0.1 μM | 82 | 87 | | 87 |
| | 0.3 μM | 93 | 93 | | 93 |
| | 10 nM | 37 | 58 | | 33 |
| | 1 μM | 99 | 104 | 96 | 96 |
| | 3 nM | 22 | 22 | | |
| 5-HT$_6$ | 0.03 μM | 58 | 68 | 28 | 16 |
| | 0.1 μM | 81 | 84 | 60 | 38 |
| | 0.3 μM | 94 | 96 | 81 | 55 |
| | 10 nM | 32 | 42 | 14 | 13 |
| | 1 μM | 98 | 100 | 96 | 95 |
| | 3 nM | 16 | 15 | | |
| 5-HT$_7$ | 0.03 μM | 29 | 53 | | |
| | 0.1 μM | 63 | 83 | | |
| | 0.3 μM | 86 | 87 | | |
| | 10 nM | 15 | 36 | | |
| | 1 μM | | | | 92 |
| | 3 nM | −2 | 19 | | |

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A compound of the formula (E-2):

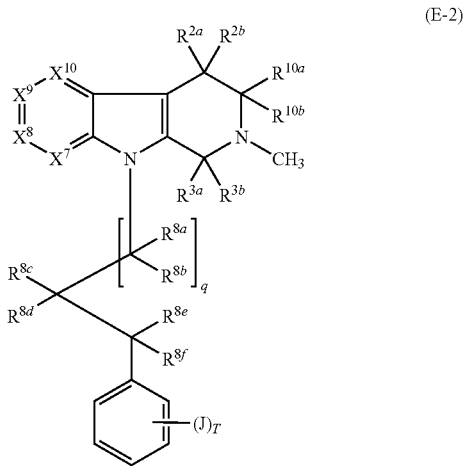

(E-2)

wherein:
each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;

each $R^{3a}$ and $R^{3b}$ is independently H, substituted or unsubstituted $C_1$-$C_8$ alkyl, halo, cyano, nitro, hydroxyl, alkoxy, amino, substituted amino, cycloalkyl, acylamino or acyloxy or $R^{3a}$ and $R^{3b}$ are taken together with the carbon to which they are attached to form a cycloalkyl moiety or a carbonyl moiety;

each $X^7$, $X^8$, $X^9$ and $X^{10}$ is independently $CR^4$;

q is 0;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, or is taken together with the carbon to which it is attached and a geminal $R^{8c}$, $R^{8d}$, $R^{8e}$ or $R^{8f}$ to form a cycloalkyl moiety or a carbonyl moiety, provided that at least one of $R^{8c}$, $R^{8d}$, $R^{8e}$ and $R^{8f}$ is other than H;

each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety;

J is halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl and aminocarbonylamino moiety; and T is an integer from 0 to 5, or a pharmaceutically acceptable salt thereof.

2. The compound of claim 1, or a pharmaceutically acceptable salt thereof, wherein any one or more of provisions (i)-(v) apply
(i) $R^{8c}$ and $R^{8d}$ are both H; $R^{8e}$ is H, hydroxyl or methyl; and $R^{8f}$ is hydroxyl or methyl;
(ii) $X^9$ is $CR^4$ where $R^4$ is halo or substituted or unsubstituted $C_1$-$C_8$alkyl;
(iii) $X^7$, $X^8$ and $X^{10}$ are each $CR^4$ where $R^4$ is H;
(iv) $R^{2a}$ and $R^{2b}$ are both H; and
(v) $R^{10a}$ and $R^{10b}$ are both H.

3. A compound of the formula (E-3):

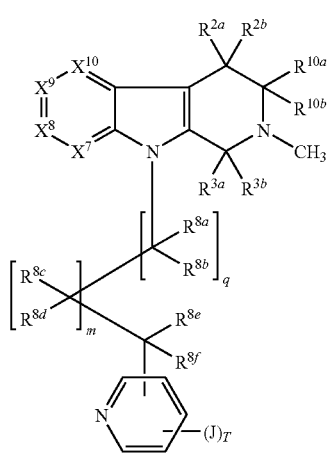

(E-3)

wherein:
each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;
each $R^{3a}$ and $R^{3b}$ is independently H, substituted or unsubstituted $C_1$-$C_8$ alkyl, halo, cyano, nitro, hydroxyl, alkoxy, amino, substituted amino, cycloalkyl, acylamino or acyloxy or $R^{3a}$ and $R^{3b}$ are taken together with the carbon to which they are attached to form a cycloalkyl moiety or a carbonyl moiety;
each $X^7$, $X^8$, $X^9$ and $X^{10}$ is independently $CR^4$;
m is 1;
q is 0;
each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;
each $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, or is taken together with the carbon to which it is attached and a geminal $R^{8c}$, $R^{8d}$, $R^{8e}$ or $R^{8f}$ to form a cycloalkyl moiety or a carbonyl moiety, provided that at least one of $R^{8c}$, $R^{8d}$, $R^{8e}$ and $R^{8f}$ is other than H;
each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety;
J is halo, cyano, nitro, perhaloalkyl, perhaloalkoxy, substituted or unsubstituted $C_1$-$C_8$ alkyl, substituted or unsubstituted $C_2$-$C_8$ alkenyl, substituted or unsubstituted $C_2$-$C_8$ alkynyl, acyl, acyloxy, carbonylalkoxy, thioalkyl, substituted or unsubstituted heterocyclyl, alkoxy, substituted or unsubstituted amino, acylamino, sulfonylamino, sulfonyl, carbonyl, aminoacyl and aminocarbonylamino moiety; and T is an integer from 0 to 4, or a pharmaceutically acceptable salt thereof.

4. The compound of claim 3, or a pharmaceutically acceptable salt thereof, wherein any one or more of provisions (i)-(v) apply:
(i) $R^{8c}$ and $R^{8d}$ are both H; $R^{8e}$ is H, hydroxyl or methyl; and $R^{8f}$ is hydroxyl or methyl;
(ii) $X^9$ is $CR^4$ where $R^4$ is halo or substituted or unsubstituted $C_1$-$C_8$ alkyl;
(iii) $X^7$, $X^8$ and $X^{10}$ are each $CR^4$ where $R^4$ is H;
(iv) $R^{2a}$ and $R^{2b}$ are both H; and
(v) $R^{10a}$ and $R^{10b}$ are both H.

5. A compound of the formula (E-4):

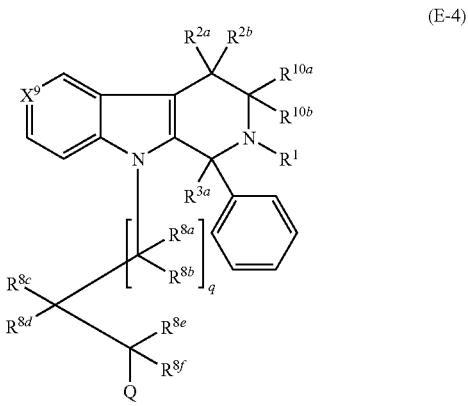

(E-4)

wherein:
$R^1$ is H, hydroxyl, substituted or unsubstituted $C_1$-$C_8$ alkyl, substituted or unsubstituted $C_2$-$C_8$ alkenyl, substituted or unsubstituted $C_2$-$C_8$ alkynyl, perhaloalkyl, acyl, acyloxy, carbonylalkoxy, substituted or unsubstituted heterocyclyl, substituted or unsubstituted aryl, substituted or unsubstituted heteroaryl, substituted or unsubstituted aralkyl, $C_1$-$C_8$ perhaloalkoxy, alkoxy, aryloxy, carboxyl, thioalkyl, substituted or unsubstituted amino, acylamino, aminoacyl, aminocarbonylamino, aminocarbonyloxy, aminosulfonyl, sulfonylamino, sulfonyl or carbonylalkylenealkoxy;
each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;
each $R^{3a}$ is H, substituted or unsubstituted $C_1$-$C_8$ alkyl, halo, cyano, nitro, hydroxyl, alkoxy, amino, substituted amino, cycloalkyl, acylamino or acyloxy;

289

$X^9$ is $CR^4$;

q is 0;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, or is taken together with the carbon to which it is attached and a geminal $R^{8c}$, $R^{8d}$, $R^{8e}$ or $R^{8f}$ to form a cycloalkyl moiety or a carbonyl moiety, provided that at least one of $R^{8c}$, $R^{8d}$, $R^{8e}$ and $R^{8f}$ is other than H;

each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety; and Q is a substituted or unsubstituted aryl, substituted or unsubstituted heteroaryl, substituted or unsubstituted cycloalkyl, substituted or unsubstituted cycloalkenyl, substituted or a unsubstituted heterocyclyl, or a pharmaceutically acceptable salt thereof.

6. A compound of the formula (E-5):

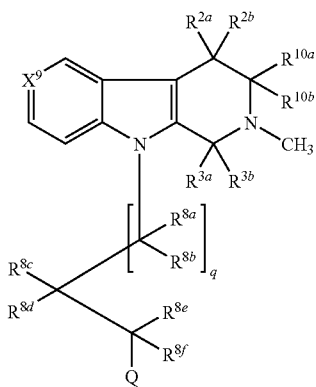

(E-5)

wherein:

each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;

$R^{3a}$ and $R^{3b}$ are independently H, substituted or unsubstituted $C_1$-$C_8$ alkyl, halo, cyano, nitro, hydroxyl, alkoxy, amino, substituted amino, cycloalkyl, acylamino, phenyl or acyloxy or $R^{3a}$ and $R^{3b}$ are taken together with the carbon to which they are attached to form a cycloalkyl moiety;

$X^9$ is $CR^4$ where $R^4$ is a substituted or unsubstituted $C_1$-$C_8$ alkyl or halo;

q is 0;

each $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonyla-

290 lkoxy, or is taken together with the carbon to which it is attached and a geminal $R^{8c}$, $R^{8d}$, $R^{8e}$ or $R^{8f}$ to form a cycloalkyl moiety or a carbonyl moiety, provided that at least one of $R^{8c}$, $R^{8d}$, $R^{8e}$ and $R^{8f}$ is other than H;

each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety; and Q is a substituted or unsubstituted aryl, substituted or unsubstituted heteroaryl, substituted or unsubstituted cycloalkyl, substituted or unsubstituted cycloalkenyl, substituted or a unsubstituted heterocyclyl, or a pharmaceutically acceptable salt thereof.

7. The compound of claim 6, or a pharmaceutically acceptable salt thereof, wherein any one or more of provisions (i)-(v) apply:
   (i) $X^9$ is $CR^4$ where $R^4$ is an unsubstituted $C_1$-$C_8$ alkyl or halo;
   (ii) $R^{3a}$ and $R^{3b}$ are independently H or unsubstituted $C_1$-$C_8$ alkyl;
   (iii) $R^{2a}$, $R^{2b}$, $R^{10a}$ and $R^{10b}$ are each H;
   (iv) $R^{8c}$ and $R^{8d}$ are both H; $R^{8e}$ is H, hydroxyl or methyl; and $R^{8f}$ is hydroxyl or methyl;
   (v) Q is a substituted or unsubstituted aryl or substituted or unsubstituted heteroaryl.

8. A compound of the formula (E-6):

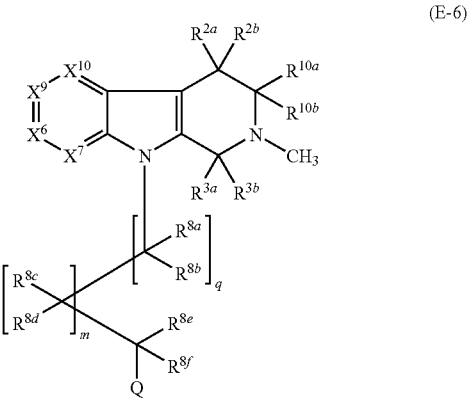

(E-6)

wherein:

each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;

$R^{3a}$ and $R^{3b}$ are independently H, substituted or unsubstituted $C_1$-$C_8$ alkyl, halo, cyano, nitro, hydroxyl, alkoxy, amino, substituted amino, cycloalkyl, phenyl, acylamino or acyloxy or $R^{3a}$ and $R^{3b}$ are taken together with the carbon to which they are attached to form a cycloalkyl moiety;

each $X^7$, $X^8$ and $X^{10}$ is independently $CR^4$, wherein each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_7$-$C_8$ alkenyl, substituted or unsubstituted $C_2$-$C_8$ alkenyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

$X^9$ is $CR^{4a}$, wherein $R^{4a}$ is halo or a substituted or unsubstituted $C_1$-$C_8$ alkyl;

m is 1;

q is 0;

each $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, or is taken together with the carbon to which it is attached and a geminal $R^{8c}$, $R^{8d}$, $R^{8e}$ or $R^{8f}$ to form a cycloalkyl moiety or a carbonyl moiety, provided that at least one of $R^{8c}$, $R^{8d}$, $R^{8e}$ and $R^{8f}$ is other than H;

each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety;

Q is a substituted phenyl, unsubstituted phenyl, substituted pyridyl or unsubstituted pyridyl moiety, or a pharmaceutically acceptable salt thereof.

9. The compound of claim 8, or a pharmaceutically acceptable salt thereof, wherein any one or more of provisions (i)-(vi) apply:
(i) $X^9$ is $CR^4$ where $R^4$ is an unsubstituted $C_1$-$C_8$ alkyl or halo;
(ii) $R^{3a}$ and $R^{3b}$ are independently H, phenyl or unsubstituted $C_1$-$C_8$ alkyl;
(iii) $R^{2a}$, $R^{2b}$, $R^{10a}$ and $R^{10b}$ are each H;
(iv) $R^{8c}$ and $R^{8d}$ are both H; $R^{8e}$ is H, hydroxyl or methyl; and $R^{8f}$ is hydroxyl or methyl;
(v) $X^7$, $X^8$ and $X^{10}$ are each $CR^4$ where $R^4$ is H; and
(vi) Q is a substituted or unsubstituted phenyl or pyridyl moiety.

10. A compound of the formula (E-7):

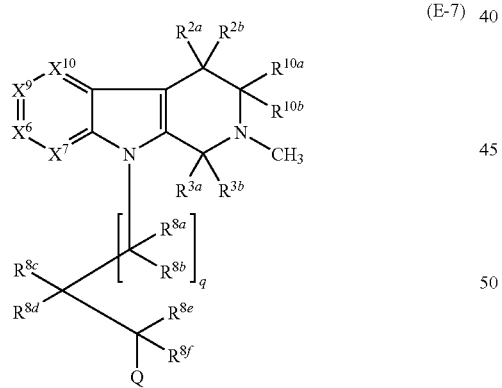

(E-7)

wherein:
each $R^{2a}$ and $R^{2b}$ is independently H, substituted or unsubstituted $C_1$-$C_8$ alkyl, halo, cyano, hydroxyl, alkoxy or nitro, or $R^{2a}$ and $R^{2b}$ are taken together with the carbon to which they are attached to form a cycloalkyl moiety or a carbonyl moiety;

$R^{3a}$ and $R^{3b}$ are independently H, substituted or unsubstituted $C_1$-$C_8$ alkyl, halo, cyano, nitro, hydroxyl, alkoxy, amino, substituted amino, cycloalkyl, phenyl, acylamino or acyloxy or $R^{3a}$ and $R^{3b}$ are taken together with the carbon to which they are attached to form a cycloalkyl moiety;

each $X^7$, $X^8$, $X^9$ and $X^{10}$ is independently $CR^4$;

q is 0;

each $R^4$ is independently H, hydroxyl, nitro, cyano, halo, $C_1$-$C_8$ perhaloalkyl, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted aryl, substituted or unsubstituted heteroaryl, $C_1$-$C_8$ perhaloalkoxy, $C_1$-$C_8$ alkoxy, aryloxy, carboxyl, thiol, carbonylalkoxy, substituted or unsubstituted heterocyclyl, substituted or unsubstituted aralkyl, thioalkyl, substituted or unsubstituted amino, acylamino, aminoacyl, aminocarbonylamino, aminocarbonyloxy, aminosulfonyl, sulfonylamino, sulfonyl, carbonylalkylenealkoxy, alkylsulfonylamino or acyl;

each $R^{8c}$, $R^{8d}$, $R^{8e}$ and $R^{8f}$ is independently H, hydroxyl, $C_1$-$C_8$ alkyl, $C_1$-$C_8$ perhaloalkyl, carboxy, carbonylalkoxy, is taken together with the carbon to which it is attached and a geminal $R^{8c}$, $R^{8d}$, $R^{8e}$ or $R^{8f}$ to form a cycloalkyl moiety or a carbonyl moiety, each $R^{10a}$ and $R^{10b}$ is independently H, halo, a substituted or unsubstituted $C_1$-$C_8$ alkyl, hydroxyl, alkoxyl, cyano or nitro, or $R^{10a}$ and $R^{10b}$ are taken together with the carbon to which they are attached to form a cycloalkyl moiety or a carbonyl moiety;

Q is an unsubstituted cycloalkyl, substituted cycloalkyl, unsubstituted heterocyclyl or substituted heterocyclyl moiety, or a pharmaceutically acceptable salt thereof.

11. The compound of claim 10, or a pharmaceutically acceptable salt thereof, wherein any one or more of provisions (i)-(vi) applies:
(i) $X^9$ is $CR^4$ where $R^4$ is H, an unsubstituted $C_1$-$C_8$ alkyl or halo;
(ii) $R^{3a}$ and $R^{3b}$ are each H;
(iii) $R^{2a}$, $R^{2b}$, $R^{10a}$ and $R^{10b}$ are each H;
(iv) $R^{8c}$ and $R^{8d}$ are both H; $R^{8e}$ is H, hydroxyl or methyl; and $R^{8f}$ is hydroxyl or methyl;
(v) $X^7$, $X^8$ and $X^{10}$ are each $CR^4$ where $R^4$ is H; and
(vi) Q is a substituted or unsubstituted cyclopentyl, cyclohexyl, piperidinyl or piperazinyl moiety.

12. A compound of the formula (G):

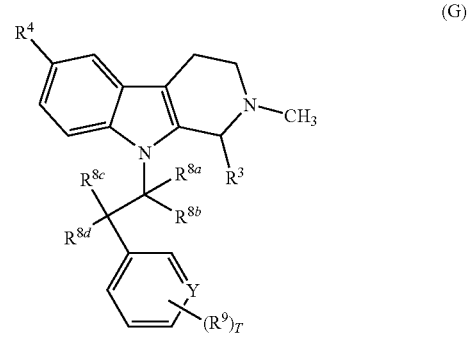

(G)

wherein:
$R^3$ is H, methyl, ethyl or phenyl;
$R^4$ is methyl or chloro;
Y is CH or N;
$R^9$ is fluoro, chloro or methoxy;
T is 0, 1 or 2; and
each $R^{8a}$, $R^{8b}$, $R^{8c}$ and $R^{8d}$ is independently H, hydroxyl, methyl, or is taken together with the carbon to which it is attached and a geminal $R^{8a}$, $R^{8b}$, $R^{8c}$ or $R^{8d}$ to form a carbonyl moiety, provided that at least one of $R^{8a}$, $R^{8b}$, $R^{8c}$ and $R^{8d}$ is other than H;
or a pharmaceutically acceptable salt thereof.
13. A compound selected from the group consisting of compounds
5
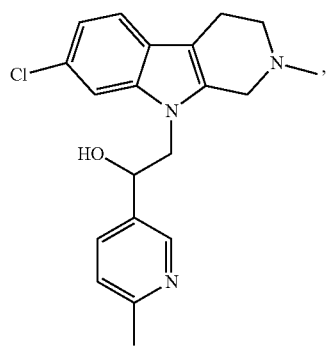
7
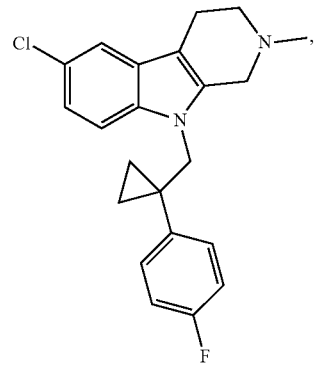
10
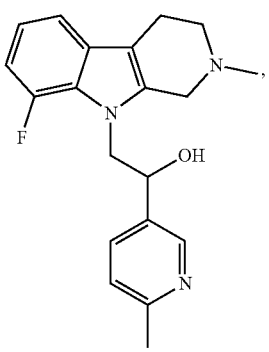
13
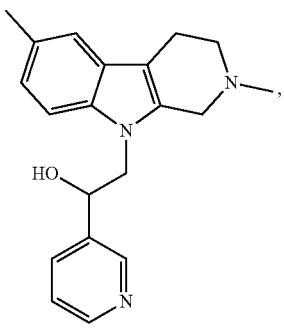
50
-continued
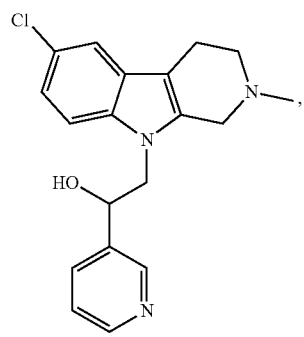
51
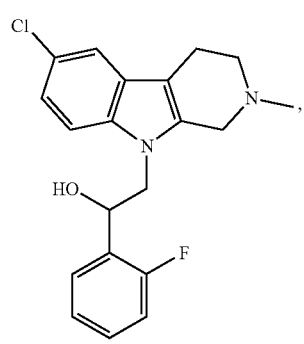
59
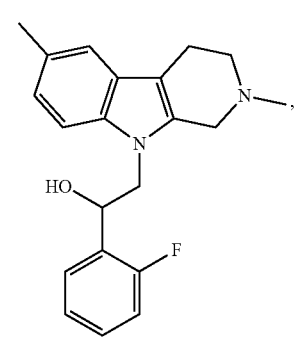
60
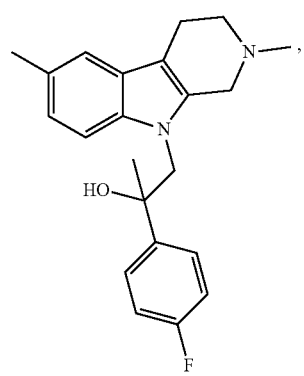
61

-continued
62 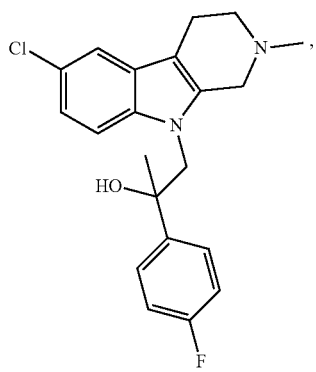
64 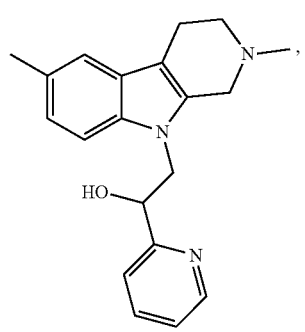
65 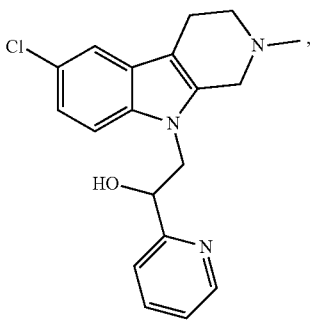
66 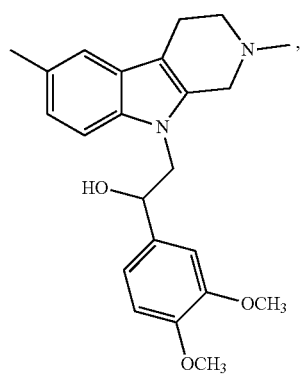
-continued
67 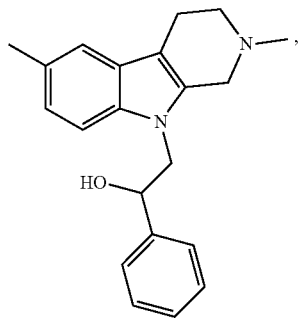
68 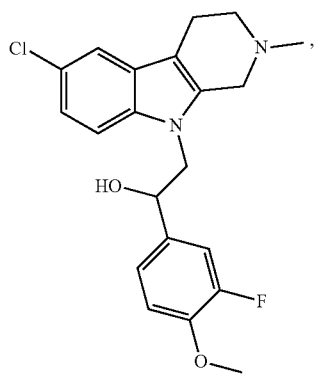
69 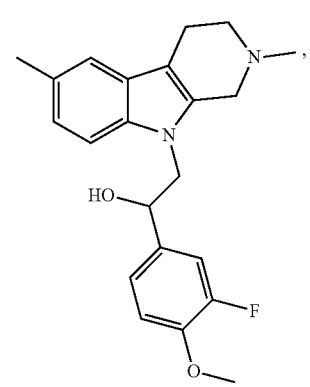
70 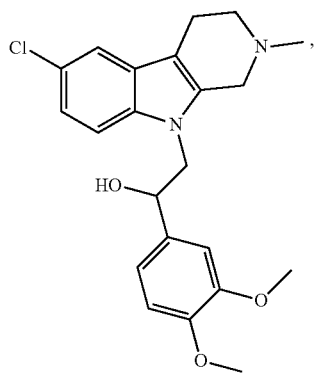

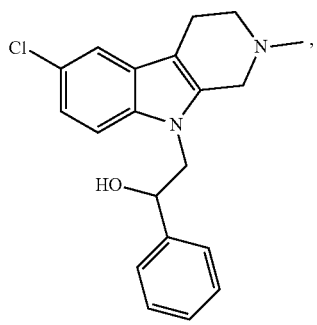
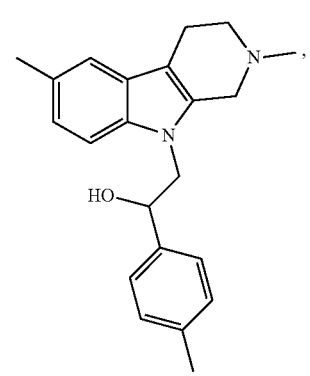
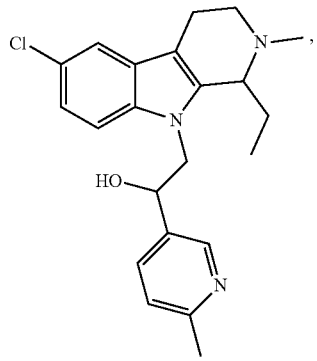
or a pharmaceutically acceptable salt thereof.
14. The compound of claim 13, wherein the compound is selected from the group consisting of compounds
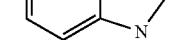
or a pharmaceutically acceptable salt thereof.

15. The compound of claim 13, wherein the compound is selected from the group consisting of compounds
50 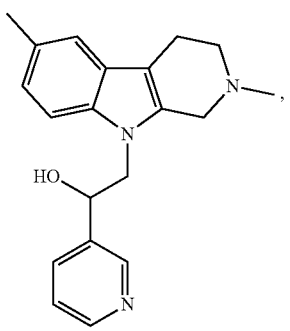
51 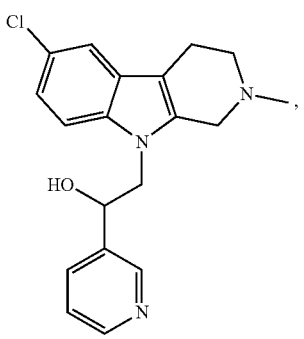
59 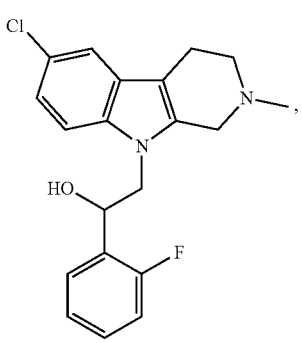
60 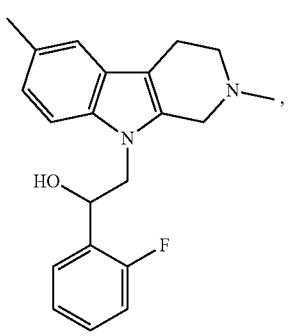
-continued
61 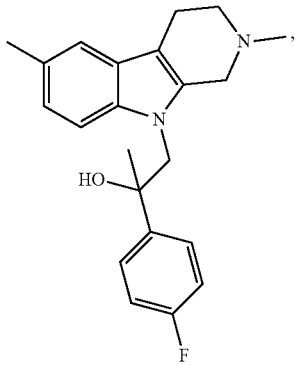
62 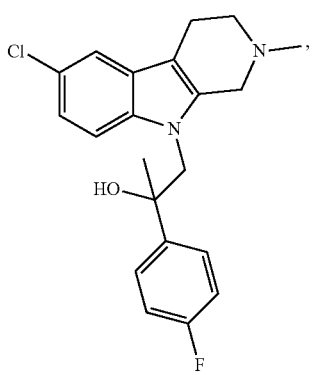
64 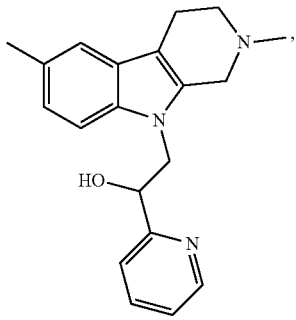
65 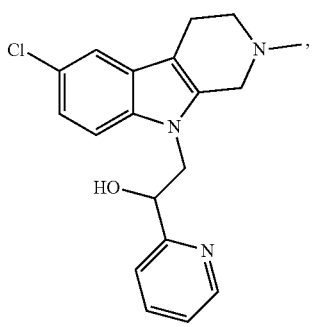

| 66 | 70 |
|---|---|
| 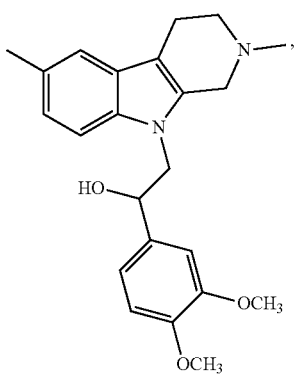 | 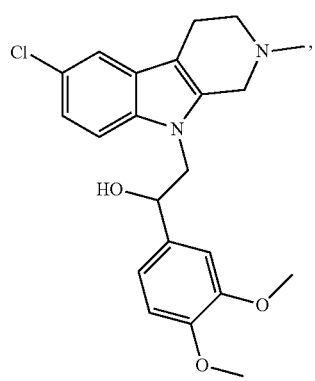 |
| 67 | 71 |
| 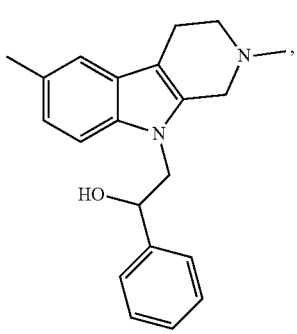 | 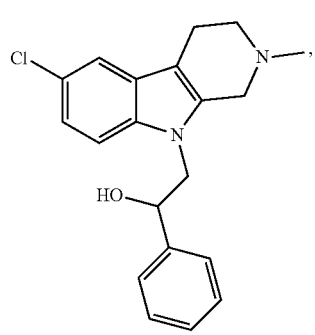 |
| | 72 |
| 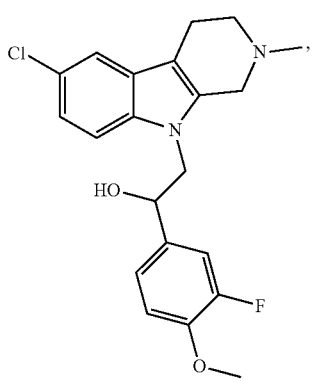 | 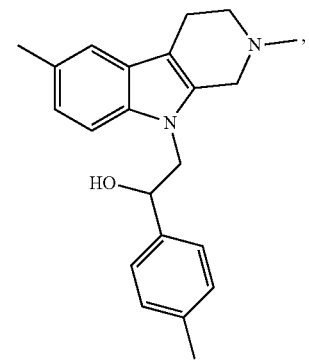 |
| 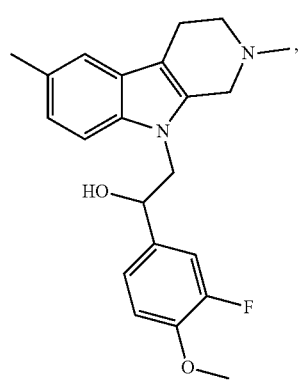 | |

-continued

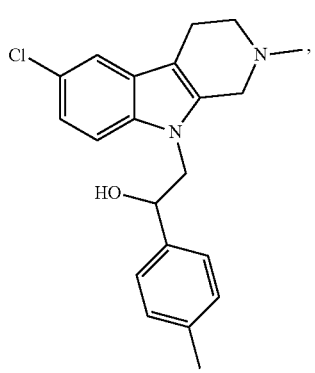
73 and

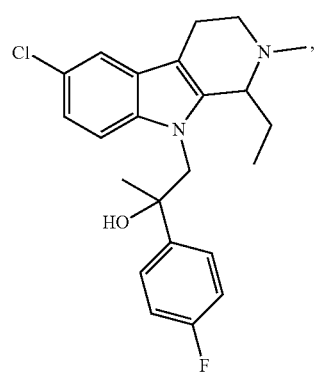
79 or a pharmaceutically acceptable salt thereof.

16. The compound of claim 13, wherein the compound is

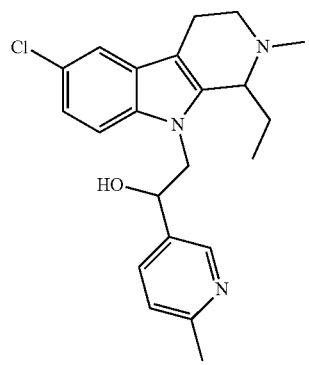
179 or a pharmaceutically acceptable salt thereof.

17. A pharmaceutical composition comprising (a) a compound of claim 12 or a pharmaceutically acceptable salt thereof and (b) a pharmaceutically acceptable carrier.

18. A kit comprising a compound according to claim 12 or a pharmaceutically acceptable salt thereof.

19. A kit comprising a compound according to claim 8 or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,338,447 B2 | Page 1 of 1 |
| APPLICATION NO. | : 12/410407 | |
| DATED | : December 25, 2012 | |
| INVENTOR(S) | : Hung et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 739 days.

Signed and Sealed this
Eighteenth Day of November, 2014

Michelle K. Lee
*Deputy Director of the United States Patent and Trademark Office*